US012435374B2

(12) United States Patent
Koumbaris et al.

(10) Patent No.: US 12,435,374 B2
(45) **Date of Patent: *Oct. 7, 2025**

(54) TARGET-ENRICHED MULTIPLEXED PARALLEL ANALYSIS FOR ASSESSMENT OF TUMOR BIOMARKERS

(71) Applicant: NIPD GENETICS PUBLIC COMPANY LIMITED, Nicosia (CY)

(72) Inventors: George Koumbaris, Lithrodontas (CY); Marios Ioannides, Nicosia (CY); Elena Kypri, Nicosia (CY); Acilleas Achilleos, Limassol (CY); Petros Mina, Nicosia (CY); Alexia Eliades, Nicosia (CY); Charalambos Loizides, Nicosia (CY); Philippos Patsalis, Nicosia (CY)

(73) Assignee: NIPD GENETICS PUBLIC COMPANY LIMITED, Nicosia (CY)

( * ) Notice: Subject to any disclaimer, the term of this patent is extended or adjusted under 35 U.S.C. 154(b) by 827 days.

This patent is subject to a terminal disclaimer.

(21) Appl. No.: 16/625,447

(22) PCT Filed: Jul. 6, 2018

(86) PCT No.: PCT/EP2018/068441

§ 371 (c)(1),
(2) Date: Dec. 20, 2019

(87) PCT Pub. No.: WO2019/008172

PCT Pub. Date: Jan. 10, 2019

(65) Prior Publication Data

US 2022/0228219 A1 Jul. 21, 2022

Related U.S. Application Data

(60) Provisional application No. 62/529,779, filed on Jul. 7, 2017.

(51) Int. Cl.
*C12Q 1/6886* (2018.01)
*C12Q 1/6806* (2018.01)

(52) U.S. Cl.
CPC ......... *C12Q 1/6886* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 7,888,017 | B2 | 2/2011 | Quake et al. |
| 8,008,018 | B2 | 8/2011 | Quake et al. |
| 8,195,415 | B2 | 6/2012 | Fan et al. |
| 8,296,076 | B2 | 10/2012 | Fan et al. |
| 8,682,594 | B2 | 3/2014 | Fan et al. |
| 2008/0194414 | A1 | 8/2008 | Albert et al. |
| 2011/0039304 | A1 | 2/2011 | Church et al. |
| 2011/0201507 | A1 | 8/2011 | Rava et al. |
| 2012/0270739 | A1 | 10/2012 | Rava et al. |
| 2015/0203907 | A1 | 7/2015 | Gilbert et al. |
| 2016/0068889 | A1 | 3/2016 | Gole et al. |
| 2016/0340733 | A1 | 11/2016 | Koumbaris et al. |
| 2017/0051355 | A1 | 2/2017 | Zimmermann et al. |

FOREIGN PATENT DOCUMENTS

| | | | | |
|---|---|---|---|---|
| EP | 2902500 | A1 | 8/2015 | |
| EP | 3298166 | B1 | 2/2020 | |
| WO | WO-2012092426 | A1 * | 7/2012 | ............... C12Q 1/68 |
| WO | WO-2014/130890 | A1 | 8/2014 | |
| WO | WO-2016/024134 | A2 | 2/2016 | |
| WO | WO-2016/189388 | A1 | 12/2016 | |
| WO | WO-2019/008148 | A1 | 1/2019 | |
| WO | WO-2019/008153 | A1 | 1/2019 | |

OTHER PUBLICATIONS

Samorodnitsky et al.(J.Mol.Diag.,2015,17(1):64-75)(Year:2015) (Year: 2015).*
Agilent (2009) "The Agilent Technologies SureSelect Platform for Target Enrichment" https:/Avww.agilent.com/cs/library/posters/public/SureSelect_Platform_for_Target_Enrichment.pdf; accessed on Feb. 9, 2023 (Year: 2009).*
Life Technologies. (2011). "Accurate and sensitive mutation detection and quantitation using taqman . . . " TaqMan Mutation Detection Assays. Retrieved Feb. 9, 2023, from https://tools.thermofisher.com/content/sfs/brochures/ap-mutation-detection-quantitation-taqman-md-assays.pdf (Year: 2011).*
Bianchi, D.W. et al. (2012) "Genome-wide Fetal Aneuploidy Detection by Maternal Plasma DNA Sequencing", Obstet. Gynecol. 119:890-901.
Chan, K.C. (2004) "Size Distributions of Maternal and Fetal DNA in Maternal Plasma", Clin. Chem. 50:88-92.
Chen, E.Z. et al. (2011) "Noninvasive Prenatal Diagnosis of Fetal Trisomy 18 and Trisomy 13 by Maternal Plasma DNA Sequencing", PLoS One 6:e21791.
Chiu, R. W. et al.(2008) "Noninvasive Prenatal Diagnosis of Fetal Chromosomal Aneuploidy by Massively Parallel Genomic Sequencing of DNA in Maternal Plasma", Proc. Natl. Acad. Sci. USA 105:20458-20463.
Duncavage et al: "Targeted next generation sequencing of clinically significant gene mutations and translocations in leukemia", Modern Pathology, vol. 25, No. 6, (2012), pp. 795-804.

(Continued)

*Primary Examiner* — Nancy J Leith
*Assistant Examiner* — Jessica D Parisi
(74) *Attorney, Agent, or Firm* — BALLARD SPAHR LLP

(57) ABSTRACT

The invention provides methods for assessment of tumor biomarkers using target-enriched multiplexed parallel analysis. The methods of the invention utilize Target Capture Sequences (TACS) to thereby enrich for target sequences of interest, followed by massive parallel sequencing and statistical analysis of the enriched population. The methods can be used with DNA samples from a patient, such as a tissue biopsy or plasma sample (liquid biopsy), for detection of the presence of tumor biomarkers, e.g., for purposes of diagnosis, screening, therapy selection and/or treatment monitoring. Kits for carrying out the methods of the invention are also provided.

14 Claims, 93 Drawing Sheets

Specification includes a Sequence Listing.

(56) References Cited

OTHER PUBLICATIONS

Ehrich, M. et al. (2011) "Noninvasive detection of fetal Trisomy 21 by sequencing of DNA in maternal blood: a study in a clinical setting", Am. J. Obstet. Gynecol. 204:205e1-11.
Forbes, S.A. et al. (2017) "COSMIC: somatic cancer genetics at high-resolution", Nucl. Acids Res. 45:D777-D783.
Jiang et al, (2015), "Lengthening and shortening of plasma DNA in hepatocellular carcinoma patients", Proceedings of the National Academy of Sciences, 112(11), pp. E1317-E1325.
Koumbaris, G. et al. (2015) "Cell-Free DNA Analysis of Targeted Genomic Regions in Maternal Plasma for Non-Invasive Prenatal Testing of Trisomy 21, Trisomy 18, Trisomy 13, and Fetal Sex", Clinical chemistry, 62(6):848-855.
Li, H. and Durbin, R. (2009) "Fast and Accurate Short Read Alignment With Burrows-Wheeler Transform", Bioinformatics 25:1754-1760.
Li, H. et al. (2009) "The Sequence Alignment/Map Format and SAMtools ", Bioinformatics 25:2078-2079.
Liang, L. et al. (2013) "Identification of Chromosomal Errors in Human Preimplantation Embryos with Oligonucleotide DNA Microarray", PLoS One 8(4):e61838.
Liao, G.J. et al. (2012) "Noninvasive Prenatal Diagnosis of Fetal Trisomy 21 by Allelic Ratio Analysis Using Targeted Massively Parallel Sequencing of Maternal Plasma DNA", PLoS One 7:e38154.
Lin et al: "Applications of targeted gene capture and next-generation sequencing technologies in studies of human deafness and other genetic disabilities", Hearing Research, vol. 288, No. 1, (2012), pp. 67-76.
Maricic, T. et al. (2010) "Multiplexed DNA Sequence Capture of Mitochondrial Genomes Using PCR Products", PLoS One 5:e14004.
Nicolaides, K.H. et al. (2013) "Validation of Targeted Sequencing of Single-Nucleotide Polymorphisms for Non-Invasive Prenatal Detection of Aneuploidy of Chromosomes 13, 18, 21, X, and Y ", Prenat. Diagn. 33:575-579.
Palomaki, G.E. et al. (2011) "DNA Sequencing of Maternal Plasma to Detect Down Syndrome: An International Clinical Validation Study", Genet. Med. 13:913-920.
Palomaki, G.E. et al. (2012); "DNA Sequencing of Maternal Plasma Reliably Identifies Trisomy 18 and Trisomy 13 as Well as Down Syndrome: An International Collaborative Study", Genet. Med. 14:296-305.
Prior et al. (2012) "A Comprehensive Survey of Ras Mutations in Cancer", Cancer Res. 72:2457-2467.
Sehnert, A.J. et al. (2011) "Optimal Detection of Fetal Chromosomal Abnormalities by Massively Parallel DNA Sequencing of Cell-Free Fetal DNA From Maternal Blood ", Clin. Chem. 57:1042-1049.
Shar, N.A et al. (2016) "Cancer somatic mutations cluster in a subset of regulatory sites predicted from the ENCODE data", Mol. Canc. 15:76.
Sparks, A.B. et al. (2012) "Selective Analysis of Cell-Free DNA in Maternal Blood for Evaluation of Fetal Trisomy", Prenat. Diagn. 32:3-9.
Tarasov, Artem, et al. "Sambamba: fast processing of NGS alignment formats." Bioinformatics 31.12 (2015): 2032-2034.
Tewhey, R. et al. (2009) "Enrichment of sequencing targets from the human genome by solution hybridization", Genome Biol. 10:R116.
Treangen et al. (2012) "Repetitive DNA and Next-Generation Sequencing: Computational Challenges and Solutions", Nature Reviews Genet. 13:36-46.
Tsangaras, K. et al. (2014) "Hybridization Capture Using Short PCR Products Enriches Small Genomes by Capturing Flanking Sequences (CapFlank)", PLoS One 9:e109101.
Zimmerman, B. et al. (2012) "Noninvasive Prenatal Aneuploidy Testing of Chromosomes 13, 18, 21, X, and Y, Using Targeted Sequencing of Polymorphic Loci", Prenat. Diag. 32:1233-1241.
International Search Report and Written Opinion were mailed on Oct. 23, 2018 by the International Searching Authority for International Application No. PCT/EP2018/068402, filed on Jul. 6, 2018 and published as WO 2019/008148 on Jan. 10, 2019 (Applicant-NIPD Genetics Public Company Limited) (12 Pages).
International Preliminary Report on Patentability was mailed on Jan. 7, 2020 by the International Searching Authority for International Application No. PCT/EP2018/068402, filed on Jul. 6, 2018 and published as WO 2019/008148 on Jan. 10, 2019 (Applicant-NIPD Genetics Public Company Limited) (8 Pages).
International Search Report and Written Opinion were mailed on Oct. 11, 2018 by the International Searching Authority for International Application No. PCT/EP2018/068414, filed on Jul. 6, 2018 and published as WO 2019/008153 on Jan. 10, 2019 (Applicant-NIPD Genetics Public Company Limited ) (13 Pages).
International Preliminary Report on Patentability was mailed on Jan. 7, 2020 by the International Searching Authority for International Application No. PCT/EP2018/068414, filed on Jul. 6, 2018 and published as WO 2019/008153 on Jan. 10, 2019 (Applicant-NIPD Genetics Public Company Limited ) (9 Pages).
International Search Report and Written Opinion were mailed on Oct. 1, 2019 by the International Searching Authority for International Application No. PCT/EP2018/068431, filed on Jul. 6, 2018 and published as WO/2019/008167 on Jan. 10, 2019 (Applicant-NIPD Genetics Public Company Limited) (13 Pages).
International Preliminary Report on Patentability was mailed on Jan. 7, 2020 by the International Searching Authority for International Application No. PCT/EP2018/068431, filed on Jul. 6, 2018 and published as WO/2019/008167 on Jan. 10, 2019 (Applicant-NIPD Genetics Public Company Limited) (9 Pages).
International Preliminary Report on Patentability was mailed on Oct. 1, 2019 by the International Searching Authority for International Application No. PCT/EP2018/068441, filed on Jul. 6, 2018 and published as WO2019008172 on Jan. 10, 2019 (Applicant-NIPD Genetics Public Company Limited) (24 Pages).

* cited by examiner

| chromosome | start | stop | forward primer | reverse primer | SEQ ID NOs: |
|---|---|---|---|---|---|
| chr13 | 91049752 | 91050001 | TCT TCT CGT TCA AGA TGC CG | AAG GGT GGA AGC ACA TTG AC | 1, 2 |
| chr13 | 92177139 | 92177388 | AAA TTA CAT GCA AGG CTA CCA C | ATA GAG GAA CAA GCT GCA CA | 3, 4 |
| chr13 | 93071049 | 93071298 | ACA GGA AGA AAG GGG AGT TAC | CTC GTC CCT TGC ACA TCT TA | 5, 6 |
| chr13 | 94326973 | 94327222 | TTC AGG TTG TGT GAT GTG TC | AGG TGG GGA AGA ACA AAA CA | 7, 8 |
| chr13 | 94415507 | 94415756 | TAA GCA GAG GTT TTG TTG CC | GAG AGT AGG TGC AGG GAA AC | 9, 10 |
| chr13 | 95600034 | 95600283 | GTG AAG TAT TTG CTG CCA CC | ATC CCG CAT TCT TAA CCA CA | 11, 12 |
| chr13 | 112910529 | 112910778 | ATG GTC ATC TCA ACA GCA CA | GAC TAA GCA AAA GCA TCT CCC | 13, 14 |
| chr13 | 53328405 | 53328654 | TCC ACT GAC GTT GAG ATT CG | TTC TTA CAG GCT CAG GGT AT | 15, 16 |
| chr13 | 20533985 | 20534234 | CGA ACC TCC TTG ACC TCT TA | CCC ATA GCT TAA CCC CTA CAA | 17, 18 |
| chr13 | 20535728 | 20535977 | GTT ATG TTG ATA GGG GAA GCT T | TCT TCA TCT TAC TGT CTA GCA C | 19, 20 |
| chr13 | 20544227 | 20544476 | AAG CCC TCT ACT CCA TCT GT | TCA TAC CCT ATC CCT GTG ATC | 21, 22 |
| chr13 | 20567359 | 20567607 | TCA GAA CTC GTC AGT GGA AG | TCT TGC CCT TGA TTT GTT TCC | 23, 24 |
| chr13 | 20577159 | 20577407 | GAA GGG CCA GAC AGC TTA T | GCC TTT TAT CCA TAT GCC ACC | 25, 26 |
| chr13 | 20598772 | 20599021 | ATT TGC TTT GTT TTT GTC CCT | GCC CTC AAC TTT GCT TTT CA | 27, 28 |
| chr13 | 20600556 | 20600804 | GAT CAT TGC TTT GTT TGG ACC | AAA AAC CTG CAC TGT GTT CG | 29, 30 |
| chr13 | 20610779 | 20611027 | AGG AGA GGA AAA ATC TTG ACC | TTT TTA CAG CAA TCT TCA CTG C | 31, 32 |

FIG. 2A

| chromosome | start | stop | forward primer | reverse primer | SEQ ID NOs: |
|---|---|---|---|---|---|
| chr13 | 20621336 | 20621585 | CTG CCT GCA GCC ATT ATT GT | TAA GCC GGA ATG ATT TGT AAG G | 33, 34 |
| chr13 | 20624392 | 20624641 | CCT TGG GGT ATG TTT GTT ATG T | TAC CCT TTG GCT TAA CAG CT | 35, 36 |
| chr13 | 20625461 | 20625710 | ACT TTT TCT GTA TCA GTC ACG G | AGT TGT CAT GTT GGG CTC AT | 37, 38 |
| chr13 | 20632609 | 20632857 | CTG CTT TTG TGT GTT CCC TT | TGT CCT AAG TTA CCT GTC TGA C | 39, 40 |
| chr13 | 20635196 | 20635444 | CCA GTT CCT GTT TTT CTG CC | GCC CTG GAA AGT ACT GTA ACA | 41, 42 |
| chr13 | 21127405 | 21127653 | GCC TTC ACT GAT CCT ACT TTC | TGT TAC AGC CAG GCT TTC AT | 43, 44 |
| chr13 | 21163998 | 21164247 | GGA TAT GGG GTA GGT TTT TGT | CAA CGA ACA CAG GGT TTA CA | 45, 46 |
| chr13 | 21170950 | 21171199 | ACT CAT AGA ACT GGG GCT TT | CCA GGA CTC TCT CTT TTC TTC | 47, 48 |
| chr13 | 21172515 | 21172764 | CTT TGT AGG TCC TCC AGA GA | GAC ACA TAA GAC CAC TTT AGG C | 49, 50 |
| chr13 | 21173774 | 21174022 | CCT GTT TTC AGT GGG TTG AA | GAT ATG TTC TGG AGG ACT GCT | 51, 52 |
| chr13 | 21182580 | 21182828 | CCA CGT TGT ACC TTT CCA TG | TGA TTC TCA CAG GCT CCT TG | 53, 54 |
| chr13 | 21203385 | 21203634 | GAG ATT CAA AAC AGT GGT GGC | TGA TGG AAG TTT CTA GGT CAG T | 55, 56 |
| chr13 | 21217173 | 21217422 | ACA ACA CTG TCC TTG GGT T | AAC ACT CTT GCT CCC TAT GT | 57, 58 |
| chr13 | 21228403 | 21228652 | TAA ATG TCC TGT GTG CTC GG | TTT CTC TCC CAG CTT GAT CTT | 59, 60 |
| chr13 | 21237418 | 21237666 | GAC AGG ACA CAT GGA GAG AG | CTG TGC AGA GAC GAA CTA AG | 61, 62 |
| chr13 | 21239719 | 21239968 | AAC TGA TGG TGA TTT GCA TGT | CTC TCG GAG CAA AGA CCT T | 63, 64 |

FIG. 2B

| chromosome | start | stop | forward primer | reverse primer | SEQ ID NOs: |
|---|---|---|---|---|---|
| chr13 | 21245232 | 21245481 | GGC TTC TGG AAA CAT CTT GC | ACC TCA TAA GTA CGC CCA TC | 65, 66 |
| chr13 | 21251423 | 21251672 | CAA TAG AAG TAG GGG GTG AGG | TGA TCT TCC TTT GCT CCT GT | 67, 68 |
| chr13 | 21276601 | 21276850 | AGC TGG GAT GGG TTG TTT AT | ATG ACG ACG ATG TTG GAG AG | 69, 70 |
| chr13 | 21296989 | 21297237 | GCC AGT TGT CAG AAG AAT CC | TCC TTC AGC AAG CCT CTT TT | 71, 72 |
| chr13 | 21321012 | 21321261 | CAA CTG CAT TCC AAA ACA GC | TGA GGG TGA TAA CCT GTG AG | 73, 74 |
| chr13 | 21330138 | 21330386 | GAA GGG AAA CAG TGA GAA AGA | GGC TTG AAG TTT GTC TGT GA | 75, 76 |
| chr13 | 21348854 | 21349102 | TCA AGC GCC GTA AGT ATG TA | GGA TTT TCA CAT TGC TCA GC | 77, 78 |
| chr13 | 21351692 | 21351941 | TAA CCA TAA CAT CCA GGG CA | TAG CAT GAG AGT GAA CTG AGG | 79, 80 |
| chr13 | 21356527 | 21356775 | TTG TAA GCT GGC ACA CTG AA | CAG CCA CAT AGC CCA TAT CT | 81, 82 |
| chr13 | 21361621 | 21361869 | TTA AGA AAG TGC CGT GTT GC | TGC CCA TGA GTC TAC TTG TG | 83, 84 |
| chr13 | 21396343 | 21396591 | ATG GGT CCA TGA AGA GAA GC | AAG TGG ACT GAG GGA CAA TT | 85, 86 |
| chr13 | 21399744 | 21399992 | AGT TGT TTC CAG TAC TGC CA | TCA GAC TGA GCA TTA AAT CAC C | 87, 88 |
| chr13 | 21417352 | 21417601 | GTA TGC TTT CAA GTG ACG CC | TAG GTC TGG AAG AAT GCC AG | 89, 90 |
| chr13 | 21422981 | 21423229 | GAA GAC AAT GCA ATG AGG TGT | AGT ATC TTG GGC TTG TGA CA | 91, 92 |
| chr13 | 21607075 | 21607324 | AGA CCC AAT GAG AAC AGG AA | GCT CCA CTT CCA GTC TTT CT | 93, 94 |
| chr13 | 21631007 | 21631256 | TGA TGG AGG AAG TGT GAA GC | TTG GAA TAG TGA GCC TCC CT | 95, 96 |

FIG. 2C

| chromosome | start | stop | forward primer | reverse primer | SEQ ID NOs: |
|---|---|---|---|---|---|
| chr13 | 22114658 | 22114907 | TGG CTT TTC TGT AGT TTG GG | TCT GGG GCT CTT TGT CTT TG | 97, 98 |
| chr13 | 22130956 | 22131205 | AGC AGC AAG AGT TGA GAA GA | ATT TTT CCT CCC CTG TAG CT | 99, 100 |
| chr13 | 22189915 | 22190164 | CGC TTT GAA AAA TCA CCA TGG | CTG GGC ACA CTG TAT TAC CA | 101, 102 |
| chr13 | 22270443 | 22270692 | AGA GGT TTC CAT CGT TGC TA | CAC CAC GTT TCT AAT GCA GA | 103, 104 |
| chr13 | 22396225 | 22396474 | AAC AGC CCC AAA CTT CCT AC | GAG TTG AAA AAG GTC CAC GC | 105, 106 |
| chr13 | 22609278 | 22609527 | ATC ACT GCC AAC AAG CCA TT | CAG AGG AAA GAC ACA GTG CT | 107, 108 |
| chr13 | 22691882 | 22692131 | TGA GTT GTG GGG GAT AAA GG | TCT TGG TTT TGA GGC TGT CA | 109, 110 |
| chr13 | 22765144 | 22765393 | TCT GGG CAC TTT CCT TAT GA | ATC AGC CTA ATT CTC CCC AC | 111, 112 |
| chr13 | 27175379 | 27175628 | GCA GTT TTG AGG GGA GAA GA | ATC CCC CAT CAT CCA TAC TC | 113, 114 |
| chr13 | 27405837 | 27406086 | TTC ATG ATG CCA CCT CCT C | CAT AGC TAG GCC TGT GAG TG | 115, 116 |
| chr13 | 27646720 | 27646969 | GCC CAA ATA CCC CTT CAG TA | TCA GCT TGC TCC TTC TCT G | 117, 118 |
| chr13 | 27674747 | 27674996 | GCA CCT CAA TCC CGT ACA AT | CTA GGT CCT CAG CAG TGT TT | 119, 120 |
| chr13 | 27969360 | 27969609 | GCG TTT TAA GCA GCT GTG TA | TCC CAG AGT TAA CAA TAC CCC | 121, 122 |
| chr13 | 27978231 | 27978480 | TCT CCA GAT CGA AAC AGC AT | CCA TTT GCA CTG CCG ATT TC | 123, 124 |
| chr13 | 28003481 | 28003730 | TCA TTC AAA GCC AAG ATG CC | ACT AGT CCC AAA AGC CTA CAC | 125, 126 |
| chr13 | 28073180 | 28073429 | ACA CGC TAC ATA GAC ACT GG | AAC AGC AGC GTC AGA ATA AC | 127, 128 |

FIG. 2D

| chromosome | start | stop | forward primer | reverse primer | SEQ ID NOs: |
|---|---|---|---|---|---|
| chr13 | 28077809 | 28078058 | CAA TCG AGG TCA CAT TCA CC | AGG TCT TTA CGG GAA GGA AA | 129, 130 |
| chr13 | 28212786 | 28213035 | TGA CAC GCT GAA GAA AAT AGC | TGA GGG AGA AGT TTG GTA GG | 131, 132 |
| chr13 | 28302961 | 28303210 | GGA GGG AAT GGC AGA AGT AA | CCC TGT CTA AAG AGC CAT GT | 133, 134 |
| chr13 | 28325874 | 28326123 | GGA TTT TCA GAG CAG AGG TTG | GTT TGG AGT TTC GAT GCC TT | 135, 136 |
| chr13 | 28395893 | 28396142 | AAG AGT TGC CTG TAC CCT TC | ATG TTT TGG TCC TGG GAG AA | 137, 138 |
| chr13 | 28549591 | 28549840 | GTC TCT TTA CTG GGA GCG T | GGA AGT GGT TAG GGC AGA TT | 139, 140 |
| chr13 | 28592602 | 28592851 | ACA TTG CCC CTG ACA ACA TA | AGC CCA GTA AAG ATA AGA GGC | 141, 142 |
| chr13 | 28608293 | 28608542 | TCA TTA TCT GAG GAG CCG G | CCC TTC CCT TTC ATC CAA GA | 143, 144 |
| chr13 | 28617043 | 28617292 | GGC TCC ATA ATC TTC TGC AAT | CTG AAA CCT TCT CCT TAG CC | 145, 146 |
| chr13 | 28622471 | 28622720 | CGT ACA TCT GAT TTG TGG GT | ATT ATC CAA CCT GAC CTG CA | 147, 148 |
| chr13 | 28623594 | 28623843 | TGC CAC TGA TGA TAC AAA AGC | AGG TGC AAA GCT GTT CAT G | 149, 150 |
| chr13 | 28941450 | 28941699 | GAA ACG TGT GGT GTC CTC TA | AAT GCC AAG ATT GTC CTT CA | 151, 152 |
| chr13 | 28958898 | 28959147 | AGT GTT TGG GGC TCT ATC AG | TGC GAA ACC TCA GTG ATC A | 153, 154 |
| chr13 | 28960375 | 28960624 | CTT TCC CTT TTG AGT CCT GC | CAC TTC CTT CAG CAC ACT TT | 155, 156 |
| chr13 | 29003985 | 29004234 | TCT CGC TTA CCT TGC TAC AT | CCG GCT CTC TAT GAA AGT GA | 157, 158 |
| chr13 | 29052686 | 29052935 | AAA GCG GGA ATT GGA ACT TT | ACT TGT CTG TCT GCC TGT TT | 159, 160 |

FIG. 2E

| chromosome | start | stop | forward primer | reverse primer | SEQ ID NOs: |
|---|---|---|---|---|---|
| chr13 | 52293092 | 52293341 | GGG GAA CAT TGG GAA GAG AT | CTG ATG CGC TGA AAA CCA A | 161, 162 |
| chr13 | 52302656 | 52302905 | TCT ACC AGC TAC AAA CCC AT | TTC CAT GTG TTC TTC CTC CC | 163, 164 |
| chr13 | 53286404 | 53286653 | TCA GCC AAT ACC CAT AGC AG | AGC AGT AGG GTT AAC AGG AG | 165, 166 |
| chr13 | 53306303 | 53306552 | AAT CAG AGG AAG ATG GGT CG | GCA GCA ATG TTT CGG TGT A | 167, 168 |
| chr13 | 53497224 | 53497473 | GAG AAC TCC ACC CTG TCT TT | TAC TAA TGG CTG GGG GTA AC | 169, 170 |
| chr13 | 53548644 | 53548893 | GGG AGT GTG TGA ATG TGT CT | CTG ATG AGG CTA AAG GAC CA | 171, 172 |
| chr13 | 53652715 | 53652964 | AAG CTT TAC ATC ATG GCA CTG | CAG AGT TCT CCA TCC CAG AC | 173, 174 |
| chr13 | 53861872 | 53862121 | AAA GGT CCA TAG GCT CAC AT | CTG AGT TCC TCC TTT TGC CT | 175, 176 |
| chr13 | 53897429 | 53897678 | TTG ACC AAT GCC ATT AAG CC | GCA AAA GGT GGT GTT AGC TG | 177, 178 |
| chr13 | 53938205 | 53938454 | ACC AGG GAA ATG TTA GCT TCT | ATC CAC ATC CCA TGC CTA AG | 179, 180 |
| chr13 | 54626806 | 54627055 | TGC TCT GTT ATG GTT GGA GTT | TCT ATT CCT TTG GCA CCT CC | 181, 182 |
| chr13 | 54740174 | 54740423 | GAA GCG GCA GTA ATT CAG GA | AGG AAA CGA GAG CTT TGT CC | 183, 184 |
| chr13 | 54753834 | 54754083 | AAC TGT GTC CTA AGC AGT GA | CCT TTC AGC TTC CAA GTC CT | 185, 186 |
| chr13 | 54768238 | 54768487 | GTC ACC TCC AGA GCT TTC AT | GCT CTC TTC CTC CCA CTA AAA | 187, 188 |
| chr13 | 54773333 | 54773582 | GAA CAA TGC AAC CTG AGA ACT | ACT GCC TGT GTT TTC TTC CT | 189, 190 |
| chr13 | 54910969 | 54911218 | TGA TTG TCC TCT ACC ATG CAT | AAA GCA ATT TCT TCC CCA GC | 191, 192 |

FIG. 2F

| chromosome | start | stop | forward primer | reverse primer | SEQ ID NOs: |
|---|---|---|---|---|---|
| chr13 | 54917347 | 54917596 | AGG CTT GAA ACA CCA CCT TTA | TGT CTG TTG CCA TTC CTT CT | 193, 194 |
| chr13 | 54926251 | 54926500 | TTG ATT TGT TGG GTG GTT GG | TGA CTG TGA CTT GTG CTT TC | 195, 196 |
| chr13 | 55009732 | 55009981 | TGC CAA TCT GAG GTT TTT CC | GAA TTA CAT TTC CCT GGG CG | 197, 198 |
| chr13 | 59785342 | 59785591 | ACT CTG CTT TAG GGC TTC TG | TGA AAC CGT CTT CCT TGT CT | 199, 200 |
| chr13 | 60086302 | 60086551 | GCA GAA AAG CTC CCA AAC AA | TTT AAA GCA GAG CAG GAC CT | 201, 202 |
| chr13 | 60668020 | 60668269 | GAA AAG AGG TGG AGA GGG AG | TTT ATG ACA CAC AGA GCA GC | 203, 204 |
| chr13 | 60707747 | 60707996 | AGG ACC CTT TTG CTG ATT TC | ATG TGT TTG ACC CTT TCC CT | 205, 206 |
| chr13 | 60975949 | 60976198 | CTG GCC CAA GTG CAT ACA TA | ATC CTG AAG TTG TTC CAC ATC | 207, 208 |
| chr13 | 61177164 | 61177413 | AAC CAG AGA GAC ACC TTG AC | GAC CCT GCT TTG TTA CTA GGA | 209, 210 |
| chr13 | 61495655 | 61495904 | TCC TCC CTA TCT CCT GTG AC | TGG ACA TGG ACA TTT CAA CG | 211, 212 |
| chr13 | 67720914 | 67721163 | ACT CTG CCA GAA AAG CCT AC | AAA AAT GCT TCC ACT TGC CT | 213, 214 |
| chr13 | 67799557 | 67799806 | CCT TTG TCT TGA AGC CTC CT | GCA CCT CCA ACA ACA TTC AA | 215, 216 |
| chr13 | 70101783 | 70102032 | TTG ACT GAG CAG AGT AGA GC | TTG GAA ATG GGG CTG GAG | 217, 218 |
| chr13 | 71512697 | 71512946 | TTC TAC CTA CAA GCA AAG AGA G | ACT GGT CTA TTG GGG GAA AAT | 219, 220 |
| chr13 | 71821654 | 71821903 | TCA CCA ACA GAG GAT CAA ACT | AGT GTT AGG AAA GCA GAG TG | 221, 222 |
| chr13 | 72405844 | 72406093 | CCG AGG GAT AAC ATA CAG CT | TGG ACA GGG TTT CAC AAG AT | 223, 224 |

FIG. 2G

| chromosome | start | stop | forward primer | reverse primer | SEQ ID NOs: |
|---|---|---|---|---|---|
| chr13 | 74087455 | 74087704 | CAC TAG TCA CAG AAG CAG GT | CTC CTC TCC ATC TTT CCA GG | 225, 226 |
| chr13 | 74192477 | 74192726 | GTA GAA ACC CCG AGA CAA CT | ATA GGC TGA CTT CCA CAT CTC | 227, 228 |
| chr13 | 74260893 | 74261142 | CAA TTT GCT GTT CAG AGG CT | TGT GGG GGT CAA TTC TAA CG | 229, 230 |
| chr13 | 78218064 | 78218313 | TCA TGA TGT GGC TTA GTG GG | CCA ACG GGT AGT GGT AGA TT | 231, 232 |
| chr13 | 88033439 | 88033688 | TAC ACC CAC ATG CAT ACA CA | CTT ACC CCA CTT CTT CCT GA | 233, 234 |
| chr13 | 90954378 | 90954627 | GAA GTG TGC ATG GGA GAG T | CCT GTC ACA ACT GCC TTT G | 235, 236 |
| chr13 | 91290109 | 91290358 | TTT GGG TGG CTC TAT GTT AGG | TTT GCC ATT TTG TGA TGC CA | 237, 238 |
| chr13 | 91874767 | 91875016 | CTC CTT GAC TCA TTT CCC GT | GGA GTT TCA GGT TGG CAG AA | 239, 240 |
| chr13 | 92125914 | 92126163 | AGA GTA CCA CTG CCA AGA AA | ACA GCT TGC TTC AAA CTA CA | 241, 242 |
| chr13 | 92308079 | 92308328 | CTG CTA GTC TGT CAG GAG AG | TTG AAG GGG CAA AAT ACA GC | 243, 244 |
| chr13 | 92971372 | 92971621 | GGG CAG CAG TAT AAA CAT CC | GCC CCA AAT TGT AAC AAA GC | 245, 246 |
| chr13 | 94063232 | 94063481 | GAC ATT CCC TTC CAT TGA GC | TGA CGA AGA CTC CAA CAC AA | 247, 248 |
| chr13 | 94453836 | 94454085 | TTC CTG GTA AAT GTG CTG GT | AAG TCA GGG AAA TGA AGC TG | 249, 250 |
| chr13 | 94713643 | 94713892 | GGC CAG ATT TGC AGT GAT TT | GTA ACA CAG TGC TCC TTC TC | 251, 252 |
| chr13 | 95766126 | 95766375 | AGA ATC AAC AAC AAT GGC AGG | GGC CCC AAT TAG CTG ATT TC | 253, 254 |
| chr13 | 95814599 | 95814848 | CTC TGA GGA AAG CTT GTA GGA | CTG AGC AGG GAA AAA TCC AG | 255, 256 |

FIG. 2H

| chromosome | start | stop | forward primer | reverse primer | SEQ ID NOs: |
|---|---|---|---|---|---|
| chr13 | 111956688 | 111956937 | AGG TTT TGG TTC TGC TTC AG | ACA AAG GAT TCA GGT GCA GT | 257, 258 |
| chr13 | 112517966 | 112518215 | CGG GTC AGT GAT TCT AGC T | ACA GGT TTT GCT CTT CAG GA | 259, 260 |
| chr13 | 112531519 | 112531768 | GTC ACT ATG GAA TGG GGG TT | GGC AAG TTT GTC TGG TTC ATT | 261, 262 |
| chr13 | 112986709 | 112986958 | GCT TCT TCC CCG CAA TAT GA | CCA TCT GCA TCT GTC TCC TT | 263, 264 |
| chr13 | 113000054 | 113000303 | CGG TTC AGA GTC AAT GCC TA | GCT CCT CTC CTT CTC CCT T | 265, 266 |
| chr13 | 21391429 | 21391678 | TAC CCA ACA AGC CAG AGA AAT | TGT ATA AGG GCA ATC GTG GT | 267, 268 |
| chr13 | 21394616 | 21394865 | AGA GGG AAA GTG CAA GGA AT | AAG GAA CCA GGT CAG ACA AG | 269, 270 |
| chr13 | 21404268 | 21404516 | GTT TTT CAG CAC ACT GTC CC | GTT AGA AGG CAA ACA TCA TGC | 271, 272 |
| chr13 | 21618233 | 21618482 | ACC ACA TTA CTC ACA ACC CT | TGC AGT CAT AGG AAA AGG CT | 273, 274 |
| chr13 | 21619521 | 21619769 | AAG CCC TTT TCA TCT CCA CA | GCA GTC AGA ATG GTT TGG C | 275, 276 |
| chr13 | 21629602 | 21629851 | CCA GAG CTG AGA CAA CTA CT | AGA CAT TGG TTT GGT TGG TTC | 277, 278 |
| chr13 | 21654127 | 21654376 | GAA GCA ATT CCT CAC ACC AC | ACA CAA ATG AAA GCC CGT AC | 279, 280 |
| chr13 | 22215795 | 22216044 | TTC AGT CAG AAT GAG GAG CC | GGT CTG CTG TTT CTC TTT GC | 281, 282 |
| chr13 | 22227261 | 22227510 | CTC CTC TCC CCT CTG ATT TT | AGA GCC TTA CCA AGC TGA AG | 283, 284 |
| chr13 | 22243011 | 22243260 | TTT TAA AGC GAC AGT CAC ACG | GGG ATG GTT ACT TAG TGG GG | 285, 286 |
| chr13 | 22255153 | 22255402 | TCC TCT GCC TTC TAC CCT TT | TTA CAC TCG CCT TCC AAA CA | 287, 288 |

FIG. 21

| chromosome | start | stop | forward primer | reverse primer | SEQ ID NOs: |
|---|---|---|---|---|---|
| chr13 | 22639387 | 22639636 | TGT TGT GCC TTT TGT TCT GG | GAG AGA GGA GGA GTT GGA AG | 289, 290 |
| chr13 | 27183101 | 27183350 | TTA GGA GGT AAG GCT GGA AAA A | ATC CAC GAC ATC CAA AAT CA | 291, 292 |
| chr13 | 27387690 | 27387939 | CTG TCA GCA ATT TCA GGT CAG | TTG TGC AAG AAG AAA CCT GC | 293, 294 |
| chr13 | 30466189 | 30466438 | AGA CAA AGG CTT CAC GGA AC | GGC CTT GCA TAA ACC ACA TT | 295, 296 |
| chr13 | 30977198 | 30977447 | TTC CTC TGT GTC TTG AAG GT | TTT GTA ATT GGT CCT CGC CT | 297, 298 |
| chr13 | 31061235 | 31061484 | ATC AAT GCA GGT GAG TGT GA | CAA GTA TTT CAT GGC GCT CC | 299, 300 |
| chr13 | 31205037 | 31205286 | CAC TCC ACA TAA GCC TCA GA | GTC AAC AGT ATC AGC TTC CAA | 301, 302 |
| chr13 | 32625308 | 32625557 | AGG ATG TAG TTG GGT GAG GA | TGG GCT TCT TTT TCA TTC CG | 303, 304 |
| chr13 | 34428102 | 34428351 | CAG TCA TCA CGG GGA GAT AC | TCA ACA AGC TCT CTG TTC AC | 305, 306 |
| chr13 | 36054899 | 36055148 | GAC AGA TAT TTG TGC AGG GT | GTG CAA ACA GTG ACC TCA AT | 307, 308 |
| chr13 | 36105686 | 36105935 | TCC TAG CCC TTA CCT TTC CT | GCT GGG CTG CTT TAA TTT CT | 309, 310 |
| chr13 | 40676702 | 40676951 | AGC CTG AAT GTC ACT GAT CA | GGA ATT GTG GGG TCA AAT GG | 311, 312 |
| chr13 | 40745383 | 40745632 | ACT CAT CAC TTC TGG CTG C | CTA GTG CTT CTA CCT CCA GAC | 313, 314 |
| chr13 | 49281723 | 49281972 | TCT TGT GTT TCC TGC CCT AT | AAC CAC ACA CTA ACA GGG AA | 315, 316 |
| chr13 | 53624527 | 53624776 | TTG CTG TGG ATG AGA ATG GA | TCT AGT TTG CCC TCT TTC CC | 317, 318 |
| chr13 | 60069277 | 60069526 | TGA GGG CAG AAA GAA ACA GA | CGA ATT GCT TCC TTG CTC TG | 319, 320 |

FIG. 2J

| chromosome | start | stop | forward primer | reverse primer | SEQ ID NOs: |
|---|---|---|---|---|---|
| chr13 | 60654975 | 60655224 | GGG GTC ACA CAT CAC TTT TC | TCT ATC ACA GCA GGA AAT CAC T | 321, 322 |
| chr13 | 61151386 | 61151635 | ATA GGG TCA CAA TCC ACT GC | TCT TCG TGT TTC TCT AGC CC | 323, 324 |
| chr13 | 62064603 | 62064852 | ATA TTG AGC CCC GCA TGT TA | TTG AAG AGC TAA AGG GGG AG | 325, 326 |
| chr13 | 71479359 | 71479608 | GGT TGC AGG AGA AAG AAC AT | TGT CAC CGT ACT ACC TAA GC | 327, 328 |
| chr13 | 39233534 | 39233783 | TGC CAT GTA ATT GCC AAG AT | AGT ACG CTC CTT TGC AGA G | 329, 330 |
| chr13 | 39281667 | 39281916 | CCT GTT CTC CAT CCC TCT G | TTA CGG GGA CAC AAA ATG GT | 331, 332 |
| chr13 | 39343524 | 39343773 | TCA CAA ACT ACC CAA CAC CTA | CTG TGC TTT GCC CTT GAA G | 333, 334 |
| chr13 | 39444897 | 39445146 | CAG AAT TAG TTG GGG AGC TGT | AAG TCA ACC CAT ATG CCA CT | 335, 336 |
| chr13 | 39469458 | 39469707 | GCC ATC TCC TGA AAT AGT GC | ACA TTC AGG CTG TCA CAC AT | 337, 338 |
| chr13 | 39486237 | 39486486 | GCA AGT GTT CCC ATC TAG AA | TTC ATG TCA CTA GTT TTA TAA GGC | 339, 340 |
| chr13 | 39541262 | 39541511 | ATT GAT ACC CCT CTC CCC AG | AGT AGT GAG GCT CCA AAG TG | 341, 342 |
| chr13 | 39597307 | 39597556 | AAG TAA GCT GTC TCC TGG C | TGG GAG GAG TTT GCT GTT TA | 343, 344 |
| chr13 | 39662550 | 39662799 | AGG TTG GTT GGC ATG AAG AA | TTC TAA GCC TGT GAC TGA CA | 345, 346 |
| chr13 | 39681445 | 39681694 | AGC AGA GTT TCA AGA CAA GC | TGA ACC TGA CTT TGC TTG GG | 347, 348 |
| chr13 | 39707053 | 39707302 | TTT TAC ACA GCA GGC CTC TT | GCC ATT CTA TCA TCT CGG GA | 349, 350 |
| chr13 | 39791099 | 39791348 | GCA ACT CCA AAT TAT CAG GGC | AGT CTC TCC CTG AAA CCC A | 351, 352 |

FIG. 2K

| chromosome | start | stop | forward primer | reverse primer | SEQ ID NOs: |
|---|---|---|---|---|---|
| chr13 | 39882804 | 39883053 | CAG CAC CTT GCC TTA GCA AA | AAG AGT TGG CTT GGA GTT GA | 353, 354 |
| chr13 | 39887397 | 39887646 | CTT GTT GTC TTG TAG CCC TG | CCC ACA ATT ATG AAA GGA GGT | 355, 356 |
| chr13 | 40023278 | 40023527 | CAC AGA TAC AGA CGT CCA CA | TTG ACC AGG ACA AAT GAG GA | 357, 358 |
| chr13 | 40038277 | 40038526 | AGC TCA GCA ATT AAA CAG TCC | CAC TTT GTT GGT CTG GGT CA | 359, 360 |
| chr13 | 40071926 | 40072175 | TGT TGA GAG TGC CAG AGA TG | GGG ACT CTA GGT GGG GTT AA | 361, 362 |
| chr13 | 40138914 | 40139163 | CTT CCA CCT TCT GCC AAT GA | GTT TAT GCC TTG GGA TTG CC | 363, 364 |
| chr13 | 40171414 | 40171663 | TTC TGA CAT TTG CAA GCA CC | GTG TGG TAA GGA TGC TAG GA | 365, 366 |
| chr13 | 40405751 | 40406000 | CTG TTG CTA GTT TCT TGG GC | GAA AGT GAC TCC TCC CTG AC | 367, 368 |
| chr13 | 40483291 | 40483540 | TTT TCC AGT CCC AGC ACA T | CCA GGT TCT GTT CTC TGT CA | 369, 370 |
| chr13 | 40562330 | 40562579 | TCT CTC TCT TCC TGA AAC AGC | GTG AGA CAT GGT TGC TGT TC | 371, 372 |
| chr13 | 40590631 | 40590880 | AAC CTC TGC TTT GTG TAG TGA | CTT TCT CCT GCT CCA CCT AT | 373, 374 |
| chr13 | 40633944 | 40634193 | GAG AGA ATG CAA GGT TCA GC | CTA TGT GTG TTC CAA CCC GA | 375, 376 |
| chr13 | 40644042 | 40644291 | TAC AGC ATC AAA GAG GAA GC | GGG ACC TTC TAA CCA TGT GT | 377, 378 |
| chr13 | 40661582 | 40661831 | GAG GGG ATG AGG GGA AAA AG | CGG GAT TTT GAA AAG GCA GA | 379, 380 |
| chr13 | 40667939 | 40668188 | CAT GAC CTC TGA CGG ATC TG | GTG TTG TCT CTC AGC TCC TC | 381, 382 |
| chr13 | 40684306 | 40684555 | AGG CAA TGA GGT CAA GGA C | GTT CTC TGG TTA AGG CCC TT | 383, 384 |

FIG. 2L

| chromosome | start | stop | forward primer | reverse primer | SEQ ID NOs: |
|---|---|---|---|---|---|
| chr13 | 40747946 | 40748195 | ATG ATG GCC CCA ACT TCT TC | CCT CTT CAC CTA TAA GCC CC | 385, 386 |
| chr13 | 40767281 | 40767530 | TTC TAG ACA CTG AGG GAG CA | TAG GGG ACA GTA AGC CAG AT | 387, 388 |
| chr13 | 41165017 | 41165266 | AAC GCT ACA CTT TAC GAG CT | ACG ATG GAC CTC TGT TGA AC | 389, 390 |
| chr13 | 41176869 | 41177118 | TCA ACA CTA CCT GCC AAT CA | ATT CCC ATC CAT CCA TCA CTC | 391, 392 |
| chr13 | 41573543 | 41573792 | TGC CGA CAC AAA AGA ATG C | TCG TTT TTG GAT GGT GGT TG | 393, 394 |
| chr13 | 41581284 | 41581533 | AAA GTG TTC CTC CCT GCT G | GAA GTT CCT CCA GTA GAC TCA | 395, 396 |
| chr13 | 41588844 | 41589093 | AGG AGC AAA ATA GTC TGG CT | TTG TTT GAG TCT GGG AGG AA | 397, 398 |
| chr13 | 41628316 | 41628565 | ACC ACT CTT GAA TCA TTG CAG | AAT ACT GTG AGA CTG CCA CC | 399, 400 |
| chr13 | 41633944 | 41634193 | CCA GCC AAT TTT CTC TTT CCC | CAG TCA CGG AAA GTA CCC TC | 401, 402 |
| chr13 | 41827812 | 41828061 | ACT GTC CCT ACT GCC AAT TT | ACC ATG TTT CCC TCT GTC AC | 403, 404 |
| chr13 | 42280338 | 42280587 | ATC TGG TTT GAA CTT GCC AAC | TTA CCA AGG GAC AGG ATG GA | 405, 406 |
| chr13 | 42349979 | 42350228 | CAC TCT GAA TAG CTC TCC CC | CCC TAG AGG TCA AGG TAT GG | 407, 408 |
| chr13 | 42589616 | 42589865 | TTA TCC GGG ACA GTT TCA GG | ATA GGC CCT GTG TGT TAG TT | 409, 410 |
| chr13 | 42773088 | 42773337 | GAA TCT TTT GGC CCA CAC TC | AGA AAG TCC CCT CCA TTT CT | 411, 412 |
| chr13 | 42811933 | 42812182 | GTC AGA CAC ACT TAG CTG GT | GCC AAT GCC AAA GTC AGT TA | 413, 414 |
| chr13 | 44211957 | 44212206 | ACA CAT TTC ACC TTC ACC CT | GAG GAC GAG TTG AAC AAA GC | 415, 416 |

FIG. 2M

| chromosome | start | stop | forward primer | reverse primer | SEQ ID NOs: |
|---|---|---|---|---|---|
| chr13 | 44239246 | 44239495 | GCA CTA ATC CAG GGG CTT AA | ATA CTG GTC TCA AGG TAG CAC | 417, 418 |
| chr13 | 44247433 | 44247682 | CCC CTT ACC ACC ACT TCT AC | ACC AAG TGA AGC TGA GTT AAT G | 419, 420 |
| chr13 | 44359516 | 44359765 | TTC AGA TCC CTT AAG CAC GC | CCC AGA TAC ACT CCT GCT TC | 421, 422 |
| chr13 | 44388992 | 44389241 | ACC TAA GGC CTC AAA TTC CA | CAA ACA TGA GAG GGG GAG AA | 423, 424 |
| chr13 | 44493443 | 44493692 | CAG ACC ACG GGC ATA AGA AA | AAA CAC AGC AAT GAG GAA GG | 425, 426 |
| chr13 | 44557886 | 44558135 | TGG ATG TGT GGA TTT GGA GA | GAT ACT CCC CTG TGT TGC TT | 427, 428 |
| chr13 | 44959162 | 44959411 | CTG GCT GTC TTC TGG GAA A | GCT CTT ACT AGG ATG GCA GG | 429, 430 |
| chr13 | 45043950 | 45044199 | CAA GCA GAA CTG AGA AGA GTC | GTT TCC AGC AGC AAT CCT TT | 431, 432 |
| chr13 | 45115235 | 45115484 | AGT GGA ACG AGG ATT GTG TT | CTG TGC AGA AGG GTT AGC T | 433, 434 |
| chr13 | 45147386 | 45147635 | CTC CCA TCT GAA ACT GCT GA | AAA CCC CTG CTA CCC AAA AT | 435, 436 |
| chr13 | 47067063 | 47067312 | ACA TCA CAA CCA CCC TGA C | AAT GCC CAG ATG CTG TTT TC | 437, 438 |
| chr13 | 47120595 | 47120844 | GTG TTG ACC TGA TTT GCC AA | GAG TGG TTG TTC TCT CCA GAT | 439, 440 |
| chr13 | 47154937 | 47155186 | GAA CAA AGA GGA ACA GAG CC | CAG TCT AGA AGC TCA CCC AG | 441, 442 |
| chr13 | 47258834 | 47259083 | TTC ATG ATT CCA GGG TCC TC | TCT CCT CTA CCC CTA CAC TG | 443, 444 |
| chr13 | 47261849 | 47262098 | GGA CGG ATT TAG TGT ACA TTG G | GGT GTA AAT GTG GCC TCT CC | 445, 446 |
| chr13 | 47286641 | 47286890 | TTT CCT TCC AAC ACC ACA GA | ACA AAG CTA CAA ACT CTG GC | 447, 448 |

FIG. 2N

| chromosome | start | stop | forward primer | reverse primer | SEQ ID NOs: |
|---|---|---|---|---|---|
| chr13 | 47314093 | 47314342 | TCC TTA GGG TTC TGC GAA AT | TTT CAC TGG GAG ACT GAT GC | 449, 450 |
| chr13 | 47623498 | 47623747 | GGA AAC TCC CTG CCT TCT AC | CTG TTC TGT TCC TGA GGC TA | 451, 452 |
| chr13 | 48562058 | 48562307 | TCT TCC AAA CAC CAG GTC TA | TGT GTA TCC ATT GCC TCA TCT | 453, 454 |
| chr13 | 48698166 | 48698415 | ACT CAA TGG AAG GAA GGG C | GAA GAG GGT GTG TGT AGG AC | 455, 456 |
| chr13 | 48762184 | 48762433 | AAG GAC TTG TGC TGT ATT GC | TGG TTG CTC TTC CTA GTT CC | 457, 458 |
| chr13 | 48806515 | 48806764 | GAC GGG AGC CAG TAT TCT AC | CAA TGT GGA GGA AGC TCT TG | 459, 460 |
| chr13 | 48811339 | 48811588 | GGG ATT GAG AGC TTG GTT CT | TTG CAC ACC CAA TAT GCT AC | 461, 462 |
| chr13 | 49119202 | 49119451 | CTC CCC ACC AAG ATG TTC AA | TCC AAG GTT TCT CTA GCG AC | 463, 464 |
| chr13 | 49479756 | 49480005 | GTT TTG GGT CAT GCA GTG TT | TCG CTA TTC TCC TTG CCA TA | 465, 466 |
| chr13 | 49505070 | 49505319 | GAC AAA AAC ACT TGC CAG AC | AAC AGC CTC TTT CCT TAG CA | 467, 468 |
| chr13 | 49530727 | 49530976 | AAC CAT GGC TTT GCA AGT AC | TTT TTG GCT CAG TGG GAT GT | 469, 470 |
| chr13 | 50387096 | 50387317 | GGA ACC CTC TGC TAT TTT GC | CTG TTC ATT CTT CTT CAG GGC | 471, 472 |
| chr13 | 50960526 | 50960775 | TAC TCC TTG TGT GAA CCC CT | TTC CCG AGC CCA TAA ACT AC | 473, 474 |
| chr13 | 51783208 | 51783457 | ACC TTT ACC CCA TAC CAT CC | TGC TCA GAT TTC AGC TTC CT | 475, 476 |
| chr13 | 51816719 | 51816968 | CAT TCC TTT GGT TGG TGT CC | GTC AGC GAT GTG GAT GTC TA | 477, 478 |
| chr13 | 51825241 | 51825490 | CTA ATG GGC CTG TTG TTC CT | AAC TGA CTC CAT GAC CTG TG | 479, 480 |

FIG. 2O

| chromosome | start | stop | forward primer | reverse primer | SEQ ID NOs: |
|---|---|---|---|---|---|
| chr13 | 52025153 | 52025402 | CAA CCT ACC TGC CCA TAG TT | GAA GCT GCT ACT TGG TGA AC | 481, 482 |
| chr13 | 52249504 | 52249753 | CGT AGC AAA TTA TGG CGA GG | TTT TCC TCC TGT TCT GTT GC | 483, 484 |
| chr13 | 29111011 | 29111260 | GGT CAG AAG GGA AAG GGT TC | TTC TCA AAT GCA ACC ACT CC | 485, 486 |
| chr13 | 29192994 | 29193243 | CCA GAT TAA AAC GTG GTG CC | CTG GCC CTT CAA TTT CAT GC | 487, 488 |
| chr13 | 29233772 | 29234021 | CCC ACA ACT ATA GGT CGC AT | CCA GCA GTA CCG ATA TCA GAG | 489, 490 |
| chr13 | 29310139 | 29310388 | AGT TGT TCC ATT TGT ACC AGC | CAG AAG GCA GGA GAT GGA TT | 491, 492 |
| chr13 | 29563140 | 29563389 | TTG GCT GCA CTT TGA GTC A | AAG CAA CCA TTT TCC TGA GC | 493, 494 |
| chr13 | 29580073 | 29580322 | CAG ATG GCC CAT TGT AAC AA | TCA CCC TTC ATC TAC CCA CT | 495, 496 |
| chr13 | 29929175 | 29929424 | TAT TGA GGT TCC CGT GCT G | AAC CTG GTG ACC TTC TAC AG | 497, 498 |
| chr13 | 29934475 | 29934724 | AGA ATG TGA AGT GGC TCC AT | AAA ATT CTG GTT GGG GAG GA | 499, 500 |
| chr13 | 29939640 | 29939889 | TTT GGG TTT GTG TGT GTG TG | CCA TAC CTC ATC TGC TCT GT | 501, 502 |
| chr13 | 29957853 | 29958102 | AGG AAT CTC TCT CTG CCA AG | GGC TGT CCC TGA ACT ACT TT | 503, 504 |
| chr13 | 29995732 | 29995981 | TCT TCA AGG CAG GTC ATA GG | CTT GGC TTA AAC TCT GCT CC | 505, 506 |
| chr13 | 30003375 | 30003624 | GAA ACC TAA GAC GTT CCA CTG | GAC TTG AAC ACA CCC TCA GA | 507, 508 |
| chr13 | 30014954 | 30015203 | GAG TGA AGG GAT TGG AGC AA | AGG AGA AGA GAC CAT TGC AG | 509, 510 |
| chr13 | 30114022 | 30114271 | ATG TCT CAG GCT AGG TGT TC | TTA GCT AAG TCT GTG CGG AG | 511, 512 |

FIG. 2P

| chromosome | start | stop | forward primer | reverse primer | SEQ ID NOs: |
|---|---|---|---|---|---|
| chr13 | 30145894 | 30146143 | ACA CTC ACA AAG CCC AGT TA | GAA GCA ACA CTG TAC AGG C | 513, 514 |
| chr13 | 30187253 | 30187502 | GTG CAG ACT CAT GTT ATG GC | TCT GAT AAA GGC TGG CTC AT | 515, 516 |
| chr13 | 30421518 | 30421767 | AGG ATC TCA AAG CAC CAC AG | TAA AAC AGT GCC GCT ACT TC | 517, 518 |
| chr13 | 30531947 | 30532196 | AAC GGG AAG AGG GAA ACT TT | AGT GCT ATG AGT CTT GGT CC | 519, 520 |
| chr13 | 30778718 | 30778967 | ATG TTC AAC AGA GTC AGG CT | GGA AAA CAT GCG GTG GTC TA | 521, 522 |
| chr13 | 30905760 | 30906009 | CAG TAA CAG TCC AGG GTC TT | GCA GAG AAA TGG GTT AAG GG | 523, 524 |
| chr13 | 31011560 | 31011809 | AGT CTG GGA GCC TAG AAT CA | GGT AGA GGT GGG TTA TCT GT | 525, 526 |
| chr13 | 31089936 | 31090185 | CAT TGT AGT TTC AGG ACA CCA A | CTG TAA ATC TCC GGG GGT G | 527, 528 |
| chr13 | 31227324 | 31227573 | ACC ACA GAA TGA CTT GCA GC | GGC GAG AAT GGA GAG AGA AA | 529, 530 |
| chr13 | 31430437 | 31430686 | TTT CAC GTG TAA CAG GAG CA | TCC CAA GCC AGG ATT CTT TT | 531, 532 |
| chr13 | 31575060 | 31575309 | TGC TAC AGG GAA AAT GGT CT | GAA CAA GTA CAA CCG TGC AG | 533, 534 |
| chr13 | 31641685 | 31641934 | TCC ACT GCT TAG TTT GCC TT | ACA AAT GCC CCA TAT CAA CC | 535, 536 |
| chr13 | 31718167 | 31718416 | ACA GGT GGG GAG AAA AGG TA | GGA AAG AGG CCT GGA GTA AT | 537, 538 |
| chr13 | 31723797 | 31724044 | CTG CCA CTA CTA CAC AGC TA | TTT CCA CTG GAT GTC GTC AT | 539, 540 |
| chr13 | 32249897 | 32250146 | ATG GGT CTC TGG AAT GCA TG | AGG ACA AAG TTT CAG CCT CT | 541, 542 |
| chr13 | 32296888 | 32297137 | AGT TCT CCA CAG CAC ATC AT | ACT CAG GAC ACG ACT TCA TAC | 543, 544 |

FIG. 2Q

| chromosome | start | stop | forward primer | reverse primer | SEQ ID NOs: |
|---|---|---|---|---|---|
| chr13 | 32311823 | 32312072 | TCT TTC ATC TCA GCT CTG CA | ACA TCT TTG GCT CAC TGG TT | 545, 546 |
| chr13 | 32316395 | 32316644 | CCG AAC AGT ATT TTG AGG GG | TCA CAG TGG GCT TCA TTC AG | 547, 548 |
| chr13 | 32321163 | 32321412 | TTT GGC TGT TTC CTG TTT CC | ACC TGG AAT CTA TCT AGG ATG G | 549, 550 |
| chr13 | 32348262 | 32348511 | ACC TAA CTT GCC TTG TCC TT | CTG CGG AAG GAT CTA GTC TT | 551, 552 |
| chr13 | 32565108 | 32565357 | ACA GGA GAA CAA GCA GCA TA | TGA GAA GTA TTC AGC ATT TCC C | 553, 554 |
| chr13 | 32578964 | 32579213 | CAG CCT AGT ATA TGG GAA CGT | CAC TCA CGG ACT TTT AGG C | 555, 556 |
| chr13 | 32584041 | 32584290 | ACC CAT ATG TAG TAT CGC TCT TG | | 557, 558 |
| chr13 | 32596887 | 32597136 | TAT GGG TTT TTC TGC TCC ACT | TCA CAC GCC AGG TTA TTA CA | 559, 560 |
| chr13 | 32651705 | 32651954 | AAA TGT GAG GGA GAG TCG TC | AAG TGG GTT TGC AGT TTG GA | 561, 562 |
| chr13 | 32760468 | 32760717 | GCA GGA CCC TTC AGC ATT A | ATG TAC GTG TGT GTC CAT GT | 563, 564 |
| chr13 | 32829312 | 32829561 | GAC TGG ATG ATG CAA AGG TG | AGG CGG GTT GGT CAA TAA TA | 565, 566 |
| chr13 | 32852622 | 32852871 | AAC ATT TGC AGG GGG ATC AA | CCA CAA ATC CCA TCA ACA CA | 567, 568 |
| chr13 | 32872003 | 32872252 | AAA GAT GCC TCC TTG TGT CT | TTT CAC AGT AAC ATC GGC AC | 569, 570 |
| chr13 | 33535420 | 33535669 | AAG TTA TCT GCC CAG GGA AA | CTG ACA GCC TGC ATT TGA TT | 571, 572 |
| chr13 | 33634729 | 33634978 | TCC TGG CTA GTT TTG CTG AA | TTT CCT GGA GTA AAG CGA TCT | 573, 574 |
| chr13 | 33660366 | 33660615 | CTC CTT GCT TGC CTT TAC AC | CCC ACA ATC ACC CAT CTC TA | 575, 576 |

FIG. 2R

| chromosome | start | stop | forward primer | reverse primer | SEQ ID NOs: |
|---|---|---|---|---|---|
| chr13 | 33742309 | 33742558 | AGC CTT AAT TCC CCA TGC AT | TAT CTC ACT CCA GAG CTT CC | 577, 578 |
| chr13 | 33760763 | 33761012 | TTT TTC TGT GGA GTG TGG CT | ACA GGT AGT TTG GTG GTG TC | 579, 580 |
| chr13 | 33787480 | 33787729 | AAA GAG TCA ACC ATG CAC TG | GCT GTT GAA TGC CAG AAC TT | 581, 582 |
| chr13 | 33803219 | 33803468 | GGT GAA GCA GCC TGA ATA AA | ATA GGG TCG GTT TTG GTC TG | 583, 584 |
| chr13 | 33925858 | 33926107 | TCT TTG TAC CAA GCT GCC A | CAT CAT CCC TGT CAT TCC CA | 585, 586 |
| chr13 | 34286418 | 34286667 | GCT TCT ACT TTC CCC TCC AG | GTG GGC TAA GAA AAC ACC TC | 587, 588 |
| chr13 | 34301780 | 34302029 | AGA AAA GCC AAC CTC CTC TT | ATT GTG GTT TGT GGC ATG TG | 589, 590 |
| chr13 | 34380783 | 34381032 | CCA GGG TAC TAA AAG GGG AC | CCA GAT TCA GCC TGT ATT CC | 591, 592 |
| chr13 | 35504924 | 35505173 | TTG TGG GTC AAT GTC AAC AC | GCC CAT GGA AGT AAA CAG TC | 593, 594 |
| chr13 | 35532835 | 35533084 | AGA AAA GGT GGA GGA AGG GA | AGG TTT GAC ATA ATA GTG CTG C | 595, 596 |
| chr13 | 35538772 | 35539021 | GGA GTT GTT TAC AGG TGG ACT | AAT CCT TTC CCC ACT CAC TG | 597, 598 |
| chr13 | 36233165 | 36233414 | TAG CTT CCA ATT CAC AGG TCA | CAC AAA GCA GTT CCA TGT CC | 599, 600 |
| chr13 | 36343466 | 36343715 | TTA AAT GCG CCA AGT CCC TA | GGA CAA TTT CTC ACT TGC CA | 601, 602 |
| chr13 | 36348003 | 36348252 | ATT TCC TGG GTC AAG CTC TT | AAG GGG TGT TGT TAG ATG CT | 603, 604 |
| chr13 | 36380590 | 36380839 | CTT GGA CCA GGA ATG CTC TA | GCA TCA CAC ACA GCA GAT AC | 605, 606 |
| chr13 | 36386774 | 36387023 | AGG CAG TCA GAT CCA CCT AT | AAA ATG TCC GTC CCA GAT GA | 607, 608 |

FIG. 2S

| chromosome | start | stop | forward primer | reverse primer | SEQ ID NOs: |
|---|---|---|---|---|---|
| chr13 | 36410707 | 36410956 | AAA ATT GCC TGC TGT TTG GA | GGG GGA AAA TGT GTT GTG TT | 609, 610 |
| chr13 | 36427833 | 36428082 | GCA CCA TCA TGA AAC CTC CT | AAC TGT TAG CTT CTC CAC CC | 611, 612 |
| chr13 | 36445018 | 36445267 | ATA GGC CAG TCT CAG GTA GA | CGA GTG TAG GTT CCG GTT TA | 613, 614 |
| chr13 | 36451093 | 36451342 | AGA TTG CAG CCT ACC CAA AG | AGA ATG CCC ATT TCA GGA GT | 615, 616 |
| chr13 | 36568336 | 36568585 | TTG ACT GAA GTG TTC CAG GT | ATA TGT GGT TTG AGG TCA GCT | 617, 618 |
| chr13 | 36576882 | 36577131 | GCT TCT TTC AAC CAT CCA CC | GGC TTT GGT CAC ATG GAG A | 619, 620 |
| chr13 | 36663599 | 36663848 | GCA GCA CTC AAC TAT TCC AC | TGA GGC AAG ATT CAG TGA CT | 621, 622 |
| chr13 | 37595672 | 37595921 | CAG GAG TTA TGG CAC CAG TG | ACT TCA TCT TGA CAG CAG CT | 623, 624 |
| chr13 | 38283224 | 38283473 | GAG AGT GTG GAG GCA GAA AA | CAC TTC CTC ATG ATG TTT TGG A | 625, 626 |
| chr13 | 38320894 | 38321143 | GCC CAA CTT ATT TTC CAG CT | GGC CAG CCC ACT TAT TTT TG | 627, 628 |
| chr13 | 38361974 | 38362223 | TCA AGC CCC TTA GAT TGA ACA | CTC AGG GTG GAG TTT CAA AC | 629, 630 |
| chr13 | 38380696 | 38380945 | GCT GGG CAT GTA GAA CTC AA | GAT CTT TCT TCC CCT CCT CC | 631, 632 |
| chr13 | 38789453 | 38789702 | GGG AAA TTG TCA AGG GCT TT | TGT ACA TCC ACC ACT TGT TTG | 633, 634 |
| chr13 | 39009512 | 39009761 | CTT AGT TGC TGT TGT GCT TCT | AGC GGT AGT AAG AAG GCA AA | 635, 636 |
| chr13 | 39096011 | 39096260 | AGT TGT AGC TGT ATC TGG GT | AGA CAG GTG ACC ATT TTC CC | 637, 638 |
| chr13 | 39202882 | 39203131 | AGC TGA GTC ATG TTT AAG GC | TGT GGA ACT TTT GAG CCA GA | 639, 640 |

FIG. 2T

| chromosome | start | stop | forward primer | reverse primer | SEQ ID NOs: |
|---|---|---|---|---|---|
| chrX | 44004660 | 44004909 | CAA TTC AGA CTT TGC CCA AAC | CAT AAC GAA ATA GGG CCT TCC | 641, 642 |
| chrX | 44005572 | 44005821 | CAA TCA TTC CCA CAG TTC CAA | ATT TCT GCC TCT TCT CTT CCC | 643, 644 |
| chrX | 80622102 | 80622351 | CTG TGA TGG TCC ATT CAA GG | TCA TCA AGT CAC CTC TCC AC | 645, 646 |
| chrX | 81576088 | 81576337 | TAG CTG GAA ATT GCA AGG AG | TGG AAA ACT AGA CAG CAG CC | 647, 648 |
| chrX | 83458870 | 83459119 | TCT GTT CAC CTG AGC CTT T | GGA AAG GGG AAA AGG TGA CA | 649, 650 |
| chrX | 83461989 | 83462238 | TAA CTT GGA CTG TGA ACC CA | CTG TCC TCT GTC CCA CAT AA | 651, 652 |
| chrX | 83972195 | 83972444 | CGC AAC AGG ATG AAG GAA AT | TTT CTG AGT CCA TTC CCC AT | 653, 654 |
| chrX | 83973091 | 83973340 | GAC TCA CAC TCT GAA AGC CT | GGC CAT CCT GAT ATC TTC CA | 655, 656 |
| chrX | 84308155 | 84308404 | AAT TTA GGT AGC ACT GAC CCC | CAG AGA GAT GCA GAG GTT CA | 657, 658 |
| chrX | 84412933 | 84413182 | CTG GGG AAT TAG GAA GCA CA | TGT GTG TGA GCT AGC TGA AT | 659, 660 |
| chrX | 84530826 | 84531075 | ATG ACA AGG CTG GCT CAT C | GGT TTC CCA TCC TAC CAC AT | 661, 662 |
| chrX | 84531356 | 84531605 | TTA GTT TTG GCA TGT GGT GG | GGT GCT TTT GTT GCC TTA CT | 663, 664 |
| chrX | 84561384 | 84561633 | TGG TGA GGG AGT GTT CTT TT | ACT AGA AAG CAG GGT ACA GT | 665, 666 |
| chrX | 85583338 | 85583587 | TCA TTG GGG GAG TCA TTC AC | GCT TTT TCC AAC TTC TGC TG | 667, 668 |
| chrX | 85584098 | 85584347 | GAA GTG GTG TGA TGA GGG TG | CAA CAG ACA AGT CAC CTC CT | 669, 670 |
| chrX | 85643367 | 85643616 | AAG TTA GGC CCT GTT AAG CA | GGT TCT TCC TGG ACT TCA AA | 671, 672 |

FIG. 2U

| chromosome | start | stop | forward primer | reverse primer | SEQ ID NOs: |
|---|---|---|---|---|---|
| chrX | 85643847 | 85644096 | TGT TGG TCG GAG TCA GAA AT | GAA AGC AGT AGT TTC AGG TGT | 673, 674 |
| chrX | 85644765 | 85645014 | GTA AAA GAG GTT GGG ATG CC | TGA AAG ACT CTG TTG CCA TG | 675, 676 |
| chrX | 85682212 | 85682461 | CGT TGG ACA TGG ATC ATA CC | CAC TAC ACG CTC AGA ACA AA | 677, 678 |
| chrX | 85715710 | 85715959 | TCA CAA CAA GGG AAA TAG CCT A | AAG GCA AGC AAT AAT GAG GC | 679, 680 |
| chrX | 85764768 | 85765017 | TAG TCA GGT AAA CAA CGC CT | GGA CAG TCT GTG AAA ATT GCT | 681, 682 |
| chrX | 85988749 | 85988998 | TCT GTT TCT TGT TTG GCT GAG | ACA AAC AAC CCT TAA TGC CC | 683, 684 |
| chrX | 85989214 | 85989463 | ACA TAG GTC ACA CAA AGG GT | TGA AAC AGT GAA TCC GCA AT | 685, 686 |
| chrX | 85997574 | 85997823 | GTG TGA CAC TTT TCT GCC TT | AAG GGA AAT GTG GAT GCA GTA | 687, 688 |
| chrX | 87225841 | 87226090 | CTG GAA ATA GAA GGC CTT TGC | TTG AAG GGA AGC GGA AAG T | 689, 690 |
| chrX | 91517109 | 91517358 | TCT TGG TCT GGG AAT AAG CC | ATT TCC AGC TAA TGA TGC TCC | 691, 692 |
| chrX | 91517578 | 91517827 | TGC CCC TAT GAA CAA CAG AA | GCT CAC TTA CGC ATT AAC CA | 693, 694 |
| chrX | 94601042 | 94601291 | TGA ACG TCT TGC TTA CCC AC | ACA GGC AAA ATT CAG TTG GA | 695, 696 |
| chrX | 95282210 | 95282459 | GAA GGA AGG CAG AGG TCA A | AGG CTG AAT CAC GTC AAA AC | 697, 698 |
| chrX | 95700693 | 95700942 | CTT CCA CAA AGT CCT GCA AC | CCT CGT TCA CAT TTG ACG C | 699, 700 |
| chrX | 96016317 | 96016566 | ATG TGA ACC ATT GAG AGG CA | TGT CTG GGT TCA ACT GTT TG | 701, 702 |
| chrX | 96474722 | 96474971 | AAG AGA AAC TAC CCT GGC AA | ATT TTG CAT GCC TGT TGA GA | 703, 704 |

FIG. 2V

| chromosome | start | stop | forward primer | reverse primer | SEQ ID NOs: |
|---|---|---|---|---|---|
| chrX | 96475190 | 96475439 | GCA TGT AGT TCA GTT CAG GC | GCT CTC CTC AAA ACC CAA GT | 705, 706 |
| chrX | 96522258 | 96522507 | ATG AAA TGT AAT GGG GTG CG | CTT AAT GAG GGG GCA CAA AG | 707, 708 |
| chrX | 96685785 | 96686034 | TTT TGG CAG TGA TGA CCT TG | TTT TCG TCC AGT CTT CCA CC | 709, 710 |
| chrX | 98226881 | 98227130 | TTC TTG GCT TTT CTG ACC CT | TAC AGG ACC GTC AGT GAG AG | 711, 712 |
| chrX | 98227467 | 98227716 | TTG AGA AAG ACC CCA ACA GAA | TTA GCT ACT GAC GCT TCA CC | 713, 714 |
| chrX | 98314697 | 98314946 | GAA AAT AAC ACA GTA GGG ATG C | GCA CAG ACA ACA TGC TAG TT | 715, 716 |
| chrX | 98331718 | 98331967 | GAA TGG AGA GGC AGT TTT CA | TTA GTC TGT TCA CTG GCA CA | 717, 718 |
| chrX | 102986351 | 102986600 | CAC CCT TTT CCT GTT TTG CA | CTT ATC AGC AGG GCA CAG T | 719, 720 |
| chrX | 112117885 | 112118134 | AGA AGA AAC TTG CAG TGT TGG | TTG CAT CAA ACA AAG CCA CA | 721, 722 |
| chrX | 116461543 | 116461792 | TGC AGC ATT ATT CTT TCT GGG | GAG AGA CAA GTC ACC CCT TC | 723, 724 |
| chrX | 116746667 | 116746916 | ACA CAC ATA TTA GGG AAC AGC | AGT CAA CTA CAA ATG GGG GA | 725, 726 |
| chrX | 117121287 | 117121536 | GAG TGT AGG TGC TTG GGT AT | GTG CCA AAA TCA ACG AAA GC | 727, 728 |
| chrX | 117494627 | 117494876 | CCT TAG AAT CCT AGC GCC TT | AAG GAG GGA GTA CAA AGT GAG | 729, 730 |
| chrX | 118400460 | 118400709 | TCA TGA GGT TGC CAG TGT TT | ATC ACA TTT TCA GCA CGA GG | 731, 732 |
| chrX | 119760145 | 119760394 | CCC CAT ACA TCA TCA CAT GC | CAG GGA GGG ATG ATT TGG AA | 733, 734 |
| chrX | 120436725 | 120436974 | GGG TAA TGC TTT CTT GGG GA | AGA ACT GAG AGG GGA GCA TA | 735, 736 |

FIG. 2W

| chromosome | start | stop | forward primer | reverse primer | SEQ ID NOs: |
|---|---|---|---|---|---|
| chrX | 120437307 | 120437556 | AGT TGA GAA GGG AAG GCA AG | CAC TCA CCA ACA AAG GCT TT | 737, 738 |
| chrX | 121854317 | 121854566 | CTC CTG GTG GCT TAT TTT TGA | TCC CCA TCT CCC TAA CTC AT | 739, 740 |
| chrX | 121855104 | 121855353 | TCT GGA TTT TGG CTA CTC ATG A | TTT TTC TGC TGC ATC CAA GG | 741, 742 |
| chrX | 122863038 | 122863287 | GTA GTC CTC CTT TGC CCT TC | ACT GTA CGC CAT GAA AAA CA | 743, 744 |
| chrX | 123203756 | 123204005 | GAC ATG CAC AGA TCG AAA CC | GGC AAA TCA AGT GAG CTG AC | 745, 746 |
| chrX | 123989030 | 123989279 | CGC ATT TGA CAA CAG GGA TC | CGT GGG TGG AGA ATT TCA CA | 747, 748 |
| chrX | 124394967 | 124395216 | AAG CCA CCT GTT CTC TCT CA | ACT TAG GTC AGT TGC TTG GT | 749, 750 |
| chrX | 125455385 | 125455634 | ATT CCA ACC ATT CCG ACA CC | GAC TTC ATC AGC ACG TAC TT | 751, 752 |
| chrX | 125500101 | 125500350 | AAA GAA AAT GGT GAA CGT GC | TGC AGG CAA AAT TAG CAT GG | 753, 754 |
| chrX | 125500582 | 125500831 | TGA TCA GGG CTT TAG AGG TC | GAC TTA TCT GCT TTC ACC CC | 755, 756 |
| chrX | 127973758 | 127974007 | ACT CCC TAT TGT TCT CCC CT | CCC CAT GAA CCT AAG ACC AT | 757, 758 |
| chrX | 128274367 | 128274616 | CTC CTT GAC AGA TGT GAC CC | TCT GGA CAT GTC TTT GCG TA | 759, 760 |
| chrX | 128274689 | 128274938 | TTT TGG AGT CTG AGC CAC AA | CTC CAG GAC ATC TCA GCA AT | 761, 762 |
| chrX | 128275238 | 128275487 | TTG AAG TCC CGT TGC TGA T | CCT CTC GTG TGG GAA ATG TA | 763, 764 |
| chrX | 128694864 | 128695113 | TTG GGG TCA GTT CTA ACA GT | TAT CTC TGG CTA CCT CCT GT | 765, 766 |
| chrX | 131201343 | 131201592 | TTT TCA CCA CCT CTT CCC TC | CCC CAT CCC TGT ACC AAA G | 767, 768 |

FIG. 2X

| chromosome | start | stop | forward primer | reverse primer | SEQ ID NOs: |
|---|---|---|---|---|---|
| chrX | 132160888 | 132161137 | ACC TGA CCA CAA GCT TTA CA | CTG CAG AGA TAT TCC ATG GC | 769, 770 |
| chrX | 133560531 | 133560780 | CAC ATA TTG GCG CAC AGT AC | AAA GCT GGG TTC TTA GGC TT | 771, 772 |
| chrX | 133847304 | 133847553 | GCC ATG CAC CGA TGA AAA AT | GCT GTT TTA GGG GCA CAT TT | 773, 774 |
| chrX | 133886077 | 133886326 | TTG TGA GGA GAT TTC TGG GC | AAG AGG CAA TGT GGA GGT TA | 775, 776 |
| chrX | 133886778 | 133887027 | CAC ACT AAG AGC ACT GGG AA | GCC CAA ACA ATC TGC CTT TTA | 777, 778 |
| chrX | 135279738 | 135279987 | ATG ACC TAG CAC ATC TTC CC | TGG CTT CAA ATA ACT GGG CT | 779, 780 |
| chrX | 135581031 | 135581280 | ACA TTT TCC CCA TTC CAT GC | AGA GCA CAC AGA ACA GAA CT | 781, 782 |
| chrX | 136941543 | 136941792 | GTC TGT CAA CCA CAC TTT GC | CTG GTG GAT TTC TCG TCA GA | 783, 784 |
| chrX | 138913313 | 138913562 | CTG TCT CTC CTT TTG CCA AA | TAG GTG TTT GTG TGA GGC TT | 785, 786 |
| chrX | 138913920 | 138914169 | AGT AAC CTG CGA CTC TCA GT | GCC TCA CTG CTC CTA TCT TT | 787, 788 |
| chrX | 139857034 | 139857283 | TAG CAT TTA AGG AGT GGG CT | CTC TAG CAG CTG TTC CTC C | 789, 790 |
| chrX | 139857318 | 139857567 | GGC CTC CTC AGT GAT TTG AA | CGT CGT ATC TCT GGC TTT GT | 791, 792 |
| chrX | 141400062 | 141400311 | CTT TCT TTG CCT CCC CTG TA | GTC CCC AAC CTC ATC TTT CA | 793, 794 |
| chrX | 141408144 | 141408393 | ACT TCC ATT TGT GTC AAC GC | TCT TCA AAG ATG GCT GCA AA | 795, 796 |
| chrX | 141408548 | 141408797 | TCT TGC TTT GGG TTA GAG GG | AGT ATA ACC AGA TAG CCG TGC | 797, 798 |
| chrX | 142517923 | 142518172 | AAC CAC ACC TCC ACA AGA AA | TGT CCT CAG GGC AAT AAA GT | 799, 800 |

FIG. 2Y

| chromosome | start | stop | forward primer | reverse primer | SEQ ID NOs: |
|---|---|---|---|---|---|
| chrX | 143466384 | 143466633 | CAA GAT ATG AGG GAG GGG AA | TTT GCT GCT TGA AGT GGA AC | 801, 802 |
| chrX | 147766073 | 147766322 | TCT AAC CTG GGC CCT TTC TT | GCT GCA ATG ACC TGA TTT CT | 803, 804 |
| chrX | 147869477 | 147869726 | TGC CCT TCC AGA ACT GTA AA | TCC CTC TCT CCT CCA AAT GA | 805, 806 |
| chrX | 147880766 | 147881015 | GCC AGG TCA CTT AAC AAA GC | TGC CAC AGT AGG TAT AGG TTG | 807, 808 |
| chrX | 147881811 | 147882060 | CAA TAA GGC GCC AAG TTC G | CCC TCG CCC TAA AGA AAC TA | 809, 810 |
| chrX | 151796091 | 151796340 | GTC ATC AGG GGA GCA AAT GT | CCC CTG AAT CCC TAC CTC AT | 811, 812 |
| chrX | 104102171 | 104102420 | AAC ATG CAA TCC CTG GAA TTC | TGT TGT ACA AGT GAG CCA TTC | 813, 814 |
| chrX | 104124449 | 104124698 | AGT TGT TTC AGG ACA GGA TCT | ACC AAG CAA TCA ACT CAC TCT | 815, 816 |
| chrX | 104234605 | 104234854 | TCC TCC TGC CTT TAA TAA GCT | GCC CAA TTT GTC TAG CCA ATA | 817, 818 |
| chrX | 104235195 | 104235444 | TTA CAA GGC ATC TGA CAG GAA | CTA CTG ATC CCA AAG AAG GCA | 819, 820 |
| chrX | 104291380 | 104291629 | TTA CTG GTA GGT TTG AGC ACA | GTG AAA GGT TCT ATC TGC CAA | 821, 822 |
| chrX | 104291786 | 104292035 | GAG CTA CGT TCT TTC TCA TCA C | GGC ATA CCG AGC ATA CAT AGA | 823, 824 |
| chrX | 104647680 | 104647929 | CAC CAA TTA AAG TGT GCT GCA | CAC CTG TTT CAC CAA ATC ACT | 825, 826 |
| chrX | 104648691 | 104648940 | TCC CTT CCA AAG TGC CTT ATA | TCT CAT GCT CTG ACA GAC AAG | 827, 828 |
| chrX | 106886942 | 106887191 | TGG TTG GTT TGG GAT ACT TGA | TTG TCC TGT TTC TCT TGT GAC | 829, 830 |
| chrX | 3343487 | 3343736 | GAA CCC AAA TCG ATC ATG CAT | CAC AGG ACT GCA TGC CTA TTA | 831, 832 |

FIG. 2Z

| chromosome | start | stop | forward primer | reverse primer | SEQ ID NOs: |
|---|---|---|---|---|---|
| chrX | 4013011 | 4013260 | AGA GTT AAA CGT GCA ATG TGG | GAC TCT CTC AGC ATC GAG TTT | 833, 834 |
| chrX | 5008870 | 5009119 | GTT CGT TGG TCA TAG TTG TTG T | CTG ATG GAA GGG CAT TAT CCA | 835, 836 |
| chrX | 5687782 | 5688031 | AGT TTA GCC AAA GGA TTC AGC | TTC TGG TTC CAT AAA TCC ATG C | 837, 838 |
| chrX | 5717003 | 5717252 | TCA ACC ATT TAG AAC CAC CTT G | GGG ATT ATT GTT GGC TAC TGA G | 839, 840 |
| chrX | 5808998 | 5809247 | AAT GTC CAC TTT AGC GGA GAG | AAT TGG TGA CCT AGG GAT CAG | 841, 842 |
| chrX | 5814187 | 5814436 | GGA GTA TTC TGT TCA TGT TGG G | GGG TTT CGT AAG GGA GAA TGA | 843, 844 |
| chrX | 5836574 | 5836823 | TTT CTA GAA TTG AGG AAG GGC A | AA GAC ATC CCA GTT ATG CAT TGT | 845, 846 |
| chrX | 5849776 | 5850025 | AGG ATA AGA CGA GGC ATC AAT | AGA TGG GAG GGA GAT TAG ACA | 847, 848 |
| chrX | 6895474 | 6895723 | TTC TGT GTT GAC ATG TAC CTC T | GAG TAG CAA CAA CAC ATG GAG | 849, 850 |
| chrX | 6965226 | 6965475 | TCC AAC ATT TCT CTC TGT CCC | TTC TCC TTC ATT AGC CAC ACA | 851, 852 |
| chrX | 6965573 | 6965822 | ATA ACG TGT ACT CCT CAG CC | AGT CTG CAC TGT ACT CTT CTG | 853, 854 |
| chrX | 7152743 | 7152992 | GCA CTT GGA GGA TGT AAA GAC | ACA AAT GGT TCA TGA TGG TGG | 855, 856 |
| chrX | 9529739 | 9529988 | TGT ATG CTT TAG GAC CCA GTT | GGT ACT CAC GTT TCA GTT TCC | 857, 858 |
| chrX | 9605323 | 9605572 | AAC TCC ACA GGA ATC TTT CTG A | GTT CAT TTC TAC AGT CCA GGC | 859, 860 |
| chrX | 9615158 | 9615407 | CAT TTC TCC TGG GAC CGA AT | CTC TCA CTG TGC TGC TTA AAG | 861, 862 |
| chrX | 9766329 | 9766578 | TTC TGA AGC TGA CGA AAT TCC | CAA AGA ATT CCA CAG AGA TGG G | 863, 864 |

FIG. 2AA

| chromosome | start | stop | forward primer | reverse primer | SEQ ID NOs: |
|---|---|---|---|---|---|
| chrX | 9793372 | 9793621 | GTT GCT TAG TCC TTG CTT CAC | TGA GCT ACA GAC AAG ATT GCA | 865, 866 |
| chrX | 9849298 | 9849547 | AGG TCA TTG GTC TGC AGT TAT | TCA CAT GGG ATC GAC ATA TGC | 867, 868 |
| chrX | 9850182 | 9850431 | AGC ATT TAG AGA ACA GCA GTC | CCA CAC AAT TTC CTG GCT ATG | 869, 870 |
| chrX | 10002581 | 10002830 | GTG TAA GAA GTG GTT GGG TTT | TCT TGC TTC TGG AGA GTT CTT | 871, 872 |
| chrX | 10301512 | 10301761 | AAA GGC AGA GCA GTG TAT TTA G | AGG TTA TGC AGA CTT CAG GAA | 873, 874 |
| chrX | 10354762 | 10355011 | AGA CAA GAG AAC AAT CAG GTG A | AAG CCA ATT CTG CCT CTC TAG | 875, 876 |
| chrX | 10375361 | 10375610 | CAA AGA AGC TCT AGG ACA GGA | TCC CTT CCT TAT TCT GGC AAC | 877, 878 |
| chrX | 10384260 | 10384509 | TGG TGG AGG AAA TCA ATG TTG | GCT TCA AAC ACT CTA AAG GGC | 879, 880 |
| chrX | 10398645 | 10398894 | CAC AAG GGA GGA AAC GTT CT | TGC CAT TAA TGA GAA GTG CTG | 881, 882 |
| chrX | 10572719 | 10572968 | TGA GAT TTA GTG CCA GCT AGA | TGG CAA TCC TGT TAA ACA ACT C | 883, 884 |
| chrX | 10579800 | 10580049 | AGG ATT AGT TTG GCT CCT CAG | CCC GAA CAT TGA TAA CAG AAG A | 885, 886 |
| chrX | 10580482 | 10580731 | CCT GCA CTA TTT CCT CAA AGC | GCA ACT CAG GAA AGA CTA CAT C | 887, 888 |
| chrX | 10627502 | 10627751 | CAA TTT CCT TCT CAC TGA GCC | TTA AGA AAG TAC CCA TCC TCC C | 889, 890 |
| chrX | 10645064 | 10645313 | ACG CTT CCC AAA TCT ATC TGG | GTC ATG CCT TAC AAC TTA GCA | 891, 892 |
| chrX | 10669664 | 10669913 | CTT ATT TGT GTG CCC AAT ACC A | AAT CTT TGC CAA GGT ATG AGC | 893, 894 |
| chrX | 10709674 | 10709923 | TTG CAG CAG GAA CAC CAT AAA | GCC ACT TAT ACC TCC AGA CAT | 895, 896 |

FIG. 2AB

| chromosome | start | stop | forward primer | reverse primer | SEQ ID NOs: |
|---|---|---|---|---|---|
| chrX | 10710087 | 10710336 | CTG TTC ATG TTG CTA CCA CAG | CCA CAA TCC TGA ATG CCA TG | 897, 898 |
| chrX | 11139863 | 11140112 | CTG CCT TAG ATT CAC TTT CGG | CTG CAA GGT ACA ACA CAA GTC | 899, 900 |
| chrX | 11658912 | 11659161 | CCA TCT GTG AGG TCT TCT TTG | ATC TCT GTG CCA GCA AGT ATT | 901, 902 |
| chrX | 11681358 | 11681607 | TCC TTG GTT GTG TAT TTA GCC | ATT GGG AAA CTG TCA CTG ATG | 903, 904 |
| chrX | 11686196 | 11686445 | AGA CTC AAC TCA CAT TGG CC | GCC CTA ATA GAG AAG CAA AGC | 905, 906 |
| chrX | 11686913 | 11687162 | GGT CTG ACT CTG TGG TTT GG | GGG AGC CAA TCA GAT AGA AGT | 907, 908 |
| chrX | 11687182 | 11687431 | TTT CAT TTC ATC CTG CCC ATG | GGG AAG TTG GGC TAT TTA ATG C | 909, 910 |
| chrX | 11917847 | 11918096 | TTC TGT TAT TCG CCA TCA GTC | AAC TGT GTA GAG CGA CCA AAT | 911, 912 |
| chrX | 12016474 | 12016723 | GAA TTG GGA ACT TGG GAA GC | CAG TAA GGC CAT GGT CTA GAT | 913, 914 |
| chrX | 12158815 | 12159064 | GAA CTT TGG AGA GGA CAG TGT | CTC AGA ACA TTT GCA CCT TCT | 915, 916 |
| chrX | 12485152 | 12485401 | AAC TGT CAT GTG TGT CTG CTA | ACC TGA TAC AAT GGA GCA TGT | 917, 918 |
| chrX | 12608017 | 12608266 | TGA TTC CTT CCA CCT ACC AAA | GGG ACC TAA ACT CCT TTG GAA | 919, 920 |
| chrX | 12724960 | 12725209 | GCC AAG GTC CAT TAT CTC AAG | TCT GCA GTG GTG TTA TCT AGT | 921, 922 |
| chrX | 12841791 | 12842040 | GAA CCT GCA TTG TCA TTC TCT | CAC TTA AGT TTC CAC GCC AG | 923, 924 |
| chrX | 12904558 | 12904807 | AAG AAC ATC AAC AAA CTC CAG G | GTA ATG GCG AGA GGT TAA AGC | 925, 926 |
| chrX | 12937788 | 12938037 | TCA ATT CTC TTT CAC ACG TGC | TTT AGG TAT CGA AGT TGG GTC A | 927, 928 |

FIG. 2AC

| chromosome | start | stop | forward primer | reverse primer | SEQ ID NOs: |
|---|---|---|---|---|---|
| chrX | 12938100 | 12938349 | AGG TGC TGG ATC TTG AAT TCA | GAT AAG TTT GGA AGC TGC ATC A | 929, 930 |
| chrX | 12992266 | 12992515 | TCC CTC TAC CCG AAT CTC TTA | AAG CTC TGC CAT TGA CTT TAC | 931, 932 |
| chrX | 12995926 | 12996175 | TGG GTT TAA AGG ACA CTA GCA | CCC TAC AGA ACC GAG GAA TC | 933, 934 |
| chrX | 12997273 | 12997522 | CGA AGG TCA CAC AGT TTA GTC | TCA ATC TTT GCA TAC ACA GCC | 935, 936 |
| chrX | 13293562 | 13293811 | ATG TGC CTT GTT GAT TGA TGG | GTA GGT TTA CAT GGA CAG ATG C | 937, 938 |
| chrX | 13338207 | 13338456 | AGA TGG TAT GTC ACA AAG CAC | TCT TCT GTT TAG TGC TGT GGT | 939, 940 |
| chrX | 13340422 | 13340671 | ACA CTT TGG AGA GCT TCA GAT | CAA GTT CAT TTC TTC CCT GCA | 941, 942 |
| chrX | 13351532 | 13351781 | GTG CCC AGA ATT ATT TGT GTC T | TGC AGG AAT ACA TGG TAG ACA | 943, 944 |
| chrX | 13624857 | 13625106 | GCT CTC TTG TGG AAA CGA TTA | CAT AGG CCT TCA TGT CTC TCA | 945, 946 |
| chrX | 15525635 | 15525884 | AGT TTG TTT CTC TGG CCT ACT | TAT GAG GGT GCA CTA ACA GAT | 947, 948 |
| chrX | 15543469 | 15543718 | ACC ACC TCA AAG ATT TCA TGG | GGT GCT ACT ACT GGT GTA TGT | 949, 950 |
| chrX | 15543853 | 15544102 | GTC TTC ATC TAT TTC GTG AGC C | GCC ATG CAA TAT CAA ATC CCA | 951, 952 |
| chrX | 15844810 | 15845059 | TCA TCC CAG ATT CAG AAT GCC | GAA ACC AAA GAC TAG TGC AGC | 953, 954 |
| chrX | 16860721 | 16860970 | CGT TCA ATG AAG TCC CTT GTC | ATG ACT AAC ACT CTG CCA AGT | 955, 956 |
| chrX | 16861729 | 16861978 | TTC ACA AGA ACT CTG CTG GAT | AAC AAA TGC ATC CCA GAC AGA | 957, 958 |
| chrX | 18307677 | 18307926 | GAA GCC TTC TAG TGG GAC TAA | GCA GAG AGG AGT ATG TGG TAT | 959, 960 |

FIG. 2AD

| chromosome | start | stop | forward primer | reverse primer | SEQ ID NOs: |
|---|---|---|---|---|---|
| chrX | 18600682 | 18600931 | GTT AGG GTC ATG GGT CAC TTT | ATG GGT CAT TCT ACG AAG CAA | 961, 962 |
| chrX | 19376384 | 19376633 | GCC TTT GTA GAG TGG ACT TCT | TGG TGT GTG TGG TGA TAA TTA G | 963, 964 |
| chrX | 20026004 | 20026253 | GGC TTC TTG ATA CTG CTT TCC | AGT GAC CCT CTG AAT AAC CTG | 965, 966 |
| chrX | 20627108 | 20627357 | AGG TGT GCA ATA CTC AAG GAA | TCA GCA AGT AAA CCT GAG ACC | 967, 968 |
| chrX | 21537202 | 21537451 | AAG GTC TTA GGA GTG AGG ACA | GTA CCT TCA CCC TCC AGA TC | 969, 970 |
| chrX | 21629967 | 21630216 | TCG TGC TAT TTC AGT CAG ATC T | TCA TCA AAT TGC CCA CTC CTA | 971, 972 |
| chrX | 21887062 | 21887311 | TGT CCA GCC GTA ACA TTT CAT | CAT CAG ACT GTC TTG CCT TTC | 973, 974 |
| chrX | 22202443 | 22202692 | AAT GGA CAT CTT TCA GGT CTG | CAT TCT TGC TGA CAT TTC CCA | 975, 976 |
| chrX | 23018625 | 23018874 | TCA AAT TGG GAT CGC ATT AGG | GAA GAT CAG GGT ATT GCT GAA A | 977, 978 |
| chrX | 23019006 | 23019255 | ATG CCT GGG TTT ATT CAT CTT G | TTT GTA GGT CAT TCA GCC TCC | 979, 980 |
| chrX | 24521525 | 24521774 | GGA GAA GTT TGG GTT TGA TCC | TGG CTA GGA TTC ACT TAG GAA A | 981, 982 |
| chrX | 24522047 | 24522296 | TGA TAG GAG CCA TCA GTT CTT | GCA AAC AGG GTG AAT TAT GCT | 983, 984 |
| chrX | 25401534 | 25401783 | AGC AGA TGT TGT TAG CTT TCC | AGA AGT CTG GGA AAC GAA GAG | 985, 986 |
| chrX | 25403300 | 25403549 | TTC TCT GTC ACT TCC ATG AGG | CAG ATG CTC CAT TAC TAG GTG | 987, 988 |
| chrX | 28689766 | 28690015 | CCA GTA ACT TAT TCT GCC AGA G | CAC ATG GAG AAA GGT GAA TCA | 989, 990 |
| chrX | 28693600 | 28693849 | TGA GAG ACA AGC TGC ATT ACA | TCC CAT CCA ATA CTG CCT TC | 991, 992 |

FIG. 2AE

| chromosome | start | stop | forward primer | reverse primer | SEQ ID NOs: |
|---|---|---|---|---|---|
| chrX | 28717026 | 28717275 | GCA CAG AAA TTA GAG TTC ATG G | TCT GGC TCA AAG GAT CAC ATG | 993, 994 |
| chrX | 28720131 | 28720380 | GCT GTC GTA TCT GAC AGT GAA | AAG ATC CCA TTG ACC CTG AAT | 995, 996 |
| chrX | 28808128 | 28808377 | CAG GCA TCT TGG TTT GTA GTG | CCA CAG GCT CTC TAG AAC TAA | 997, 998 |
| chrX | 28824813 | 28825062 | CGT GAT GAA CAG TGA TGA CTT | TTG AGA GGG TTT ACA AGG TCC | 999, 1000 |
| chrX | 28825844 | 28826093 | CGC CAT TTG TTC TCC TAT TCA | CTT CTC CTA CTC TGC ATT CTC A | 1001, 1002 |
| chrX | 29487025 | 29487274 | TTC GTT AGC TAC TGG GTA CTC | GAC ATT AGT GGA TTC AGG CCA | 1003, 1004 |
| chrX | 30847194 | 30847443 | CCA CCC TTT ACA CCT ATC CAA | GCT GAA GTG GAG GCA ATT AAC | 1005, 1006 |
| chrX | 32660941 | 32661190 | AGA GTG CAC AAA GGA GAA GAC | TAT AAC TGT TGA GTC TGC CCA | 1007, 1008 |
| chrX | 32949975 | 32950224 | TCT ACT GTG TCA AAG CAG ATT G | ACT GAG CTT ACA TTC ATG CAC | 1009, 1010 |
| chrX | 35971182 | 35971431 | TTC TTC CTA GCC TTC CTT TCC | GCC ACT TTC TCT GCA AAG AAT | 1011, 1012 |
| chrX | 35971544 | 35971793 | TCT CTG GCT GTG CAG TAA ATT | ACT TCC TAC GGA CTC AAA TCT | 1013, 1014 |
| chrX | 43599991 | 43600240 | AAA CTC CCA GCT TTA ATC CCT | GGC TCT CAT TAC AAT TGG CTG | 1015, 1016 |
| chrX | 43600262 | 43600511 | AAG AAT GGG TGA GTT GGG TTC | ATT GCT TTC AGT GGT GGA TTG | 1017, 1018 |
| chrX | 43807492 | 43807741 | GGA AAC TGA ATT GCC AAG TCT | GGA ATG AAA CAG AGG AGT CCC | 1019, 1020 |
| chrX | 63137429 | 63137678 | CTC CCA ACT TTT ATG CAG CC | AAG ATG CTA GAA ACC CAC AAG | 1021, 1022 |
| chrX | 63137928 | 63138177 | GCT CAG GGA ATA TCT TGG GAA | AAT GGG TGG GTT ACA GAG AG | 1023, 1024 |

FIG. 2AF

| chromosome | start | stop | forward primer | reverse primer | SEQ ID NOs: |
|---|---|---|---|---|---|
| chrX | 74269728 | 74269977 | ACA TTC AGC AAG TAG GAA GGA | GCA TTT GGA CAT GAA CAA GC | 1025, 1026 |
| chrX | 74270926 | 74271175 | CCC AGA AGA GCA GTA ACA AC | CAT TGG TGG GTG GAT AGC TG | 1027, 1028 |
| chrX | 74282022 | 74282271 | GAA AAA GGG GGA TAG GCA TT | ACC AGG AGG AGA AAA GCA AA | 1029, 1030 |
| chrX | 74329664 | 74329913 | CCC AAC AAC TGC AAT AAA AGG | CGG AAA ACA AAC CCT GAA GT | 1031, 1032 |
| chrX | 74344769 | 74345018 | ACC GAA ATT GCT TGC TCT TA | ACC TGC ATA TTG AGC CAT AC | 1033, 1034 |
| chrX | 74741441 | 74741690 | CCT TAG TGT GAC AGG ACA GG | TGT TCT TTC ACT TTT AGC CCC | 1035, 1036 |
| chrX | 76192017 | 76192266 | CCA AGA CAA CTA GGC CAA TG | TTT CTA GAA CCC TCA GCA ACT | 1037, 1038 |
| chrX | 76194203 | 76194452 | GAA GAG ATG ATG CAA AAG AGC | CCC CCA ACA GTT TTT AGT GGT | 1039, 1040 |
| chrX | 76221949 | 76222198 | TCC AAG CAA GGG ATC TCT TC | AAG GCA AAA CAC TCC CTT TT | 1041, 1042 |
| chrX | 76226569 | 76226818 | GAA TGG TCA GGG AAG GGT TT | CAG TGA TTG CCT CTA GAA AAG G | 1043, 1044 |
| chrX | 76234682 | 76234931 | AGT CTT CAG CCA TCT TCC TG | CTA AGC AGA TTG AAG CAG CT | 1045, 1046 |
| chrX | 76308591 | 76308840 | GCA TTT CCA GGC TTT ACA AGT | TGT CCC CAG GCT TAA GAA TC | 1047, 1048 |
| chrX | 76647025 | 76647274 | CTC TCT CTC CCT GGT CAG AT | AGC CAG AAT AAG CAA CTG TC | 1049, 1050 |
| chrX | 76711476 | 76711725 | CAG CAA TTC TCA GGC TCA GA | TTT CTC CTA TCC CAG CTT GC | 1051, 1052 |
| chrX | 76759387 | 76759636 | TCT GAA ACA AAG CCT CCT TAG | AGT ACA GAG GAT AAC AAG GGT | 1053, 1054 |
| chrX | 76778190 | 76778439 | AGG ATA AGG TTT CCC ATG CTC | CTC CCA TCA GTA CCC TCT CT | 1055, 1056 |

FIG. 2AG

| chromosome | start | stop | forward primer | reverse primer | SEQ ID NOs: |
|---|---|---|---|---|---|
| chrX | 76778847 | 76779096 | ATG TAT CTG AAG GAG CTC TGC | GGA ATG CCT AAA CCA TAG TGT | 1057, 1058 |
| chrX | 76875971 | 76876220 | GGC CTT CAT CAC AAA CAA CA | AGT GGT ATT TCA ATG CTC TAC C | 1059, 1060 |
| chrX | 76923678 | 76923927 | TGT GTC CCA TCT ACA AAG CC | GCA GTA CAT CGT CCT GGA A | 1061, 1062 |
| chrX | 76937441 | 76937690 | TCC TTG AAC TCT TTC CAA GC | CCT GAG CGA GAA GAA ATT TGT | 1063, 1064 |
| chrX | 76938848 | 76939097 | TGT TTT CCT GTC CAA GTC CA | GGA ACT GAA CAA GAA GTG GAG | 1065, 1066 |
| chrX | 76939481 | 76939730 | CAG CAT CCA TCG CTC GAA A | ACC TAC TCT TAT TCC GCA CT | 1067, 1068 |
| chrX | 76949897 | 76950146 | GGT ATT GGT GGG GGA AAT GA | TGA CAG CCT CTC TCT TCA AT | 1069, 1070 |
| chrX | 76951314 | 76951563 | GCA CTG CTG TAA AAG ATC TAT GAG | | 1071, 1072 |
| chrX | 77040328 | 77040577 | ACT CAA AGG CAC ATT TCG C | GCT GTT TTT CTG TGT GCT TC | 1073, 1074 |
| chrX | 77168344 | 77168593 | ATT CTA TTC CGA TCA CAG CCT T | ATG TAT TTC CTT TAG CGC CC | 1075, 1076 |
| chrX | 77634270 | 77634519 | CTA CCT GAC AAA TGG AGC TT | AAT TTT GCA AGA CTT CCG GT | 1077, 1078 |
| chrX | 78176076 | 78176325 | GAA ATG GCC ATG TGT ACT GAG | TCC CAG TTG TGA ACA TTT GC | 1079, 1080 |
| chrX | 78176555 | 78176804 | GAA GCC TCT CAA GCT ACA AG | ATG GGT TTT TGC ACA GAT GAC | 1081, 1082 |
| chrX | 78178901 | 78179150 | GAA TGA GAT TAG GGA GCA AAG T | GGG AGT CAG AAG GAG GTC A | 1083, 1084 |
| chrX | 78208245 | 78208494 | GGA AGT AAG AAG AGT GCT GC | CCT CTT TTT GCA TGA ACC TGA | 1085, 1086 |
| chrX | 78290291 | 78290540 | GCT CCT GAT TGA AGA AGT GT | CCT TAC CCT TTC CAC TCA GA | 1087, 1088 |

FIG. 2AH

| chromosome | start | stop | forward primer | reverse primer | SEQ ID NOs: |
|---|---|---|---|---|---|
| chrX | 78401753 | 78402002 | CTG CTC CTT TGT CTC CTG T | GAC TGG TAT AAT CTT GCC GTG | 1089, 1090 |
| chrX | 78403248 | 78403497 | TAA GGT GAG AGT GTG AGG AAG | TGT CTG CAT CTT GAT CTC TGG | 1091, 1092 |
| chrX | 78405536 | 78405785 | CCA GGG GAA CAT TTA CTC AGA | CGT TCC ACA GCA TTT GAG C | 1093, 1094 |
| chrX | 78411791 | 78412040 | AGG GTA CAT GTA AGG CAG CT | AGG AGC CCT TAA CTA TGG TG | 1095, 1096 |
| chrX | 78427326 | 78427575 | TTC TGT GGC ATT GTG TCT TG | TGG CTT GGG TAT TGC AGA TA | 1097, 1098 |
| chrX | 78430991 | 78431240 | CCC CAA ATT TAC CCC ACT CT | GGG GAC AGT AGA AGA TGA GT | 1099, 1100 |
| chrX | 78431372 | 78431621 | ATC CCT AGC ACT TTC AGG AC | AGT TGT TTC TGG ACG GAC TT | 1101, 1102 |
| chrX | 78437851 | 78438100 | TTA CCA ATC CAT CCA GCC TG | AGA ATT TCC CTG TCC ATA CCA | 1103, 1104 |
| chrX | 78526539 | 78526788 | AGA AGC TAA ACA GGT TGC CC | AGT GAG TGA ACT TGC CAT CA | 1105, 1106 |
| chrX | 78531686 | 78531935 | CAT AAG AGC ACA GCC AAG AT | GGC TTT TCT CTG CAC TGA TT | 1107, 1108 |
| chrX | 78996675 | 78996924 | TGT CCT GCC ACT TTT ACA TC | GCA AAG GAA ACA GGC TAA CTA | 1109, 1110 |
| chrX | 107682036 | 107682285 | GAG CTA AGC AGA ACC TAA GGA | ATG GCA GCT GAA TCG ATA TCT | 1111, 1112 |
| chrX | 107683930 | 107684179 | TTA AGC AAC AGG AAC CTA CCC | TAG GTG ATG GGC AAA TTC TCA | 1113, 1114 |
| chrX | 110366745 | 110366994 | GCC AAG GGT AAT CAT AGC AAC | GAA ATG CCT TCC CAC TTA CAA T | 1115, 1116 |
| chrX | 110367927 | 110368176 | TCA TAA TGA AAC CCT TGC TGC | ATT GGC AAA TGT ACC TGA AGC | 1117, 1118 |
| chrX | 110368330 | 110368579 | AAT CCT AGT GCA TGA GAC TCC | CAA TGA TTG CTC TTG TGC CAA | 1119, 1120 |

FIG. 2AI

| chromosome | start | stop | forward primer | reverse primer | SEQ ID NOs: |
|---|---|---|---|---|---|
| chrX | 110443307 | 110443556 | TAC TGC CTG CAT CAT TAC CAC | AGC TGT CCT CCT CTC CAT ATA | 1121, 1122 |
| chrX | 110466084 | 110466333 | ATT AAC AAT GAG GAG CCA GGT | GCC GTT CAA GTT ACT CGA TTG | 1123, 1124 |
| chrX | 110537791 | 110538040 | GAG AGA TGG TTG AGA AAT GCC | TAG TGA CTA GCT TTG GAG AGT | 1125, 1126 |
| chrX | 110538060 | 110538309 | ACT ACA ACC ACC AAT TAC AGC | AGC CAA TGA TCC CTT ATG ACT T | 1127, 1128 |
| chrX | 110538444 | 110538693 | AGT GAC ATT TCC AAG GGC TTT | AAC TAA ACT GGT AGG CAA TCG | 1129, 1130 |
| chrX | 110575740 | 110575989 | GGA GAT GGG AAG ACG ATT AGA | CAA TCA GAC CAC AGG AAG GAA | 1131, 1132 |
| chrX | 110576099 | 110576348 | AGT CTT TCA GTC TTA CAT GGG T | GAT GTG TTT ATT GCC TGT GGT | 1133, 1134 |
| chrX | 110950649 | 110950898 | TAG TTT CTG TGA TCC TGG CAG | GCT CCT TTC ATA GTT TCA GGG | 1135, 1136 |
| chrX | 110971144 | 110971393 | TTT CTC CCA GCT GTT CCT AG | ACA CAC TGC AGT TCT CAC TAT A | 1137, 1138 |
| chrX | 121597454 | 121597703 | TAC GGA ACT TCG AAT CAA CTC | TGA ATC AAG TGA CAT GAC AGC | 1139, 1140 |
| chrX | 135558463 | 135558712 | TCA AGT CAC CCT CAT TGT AGG | TTC TTA CAG TCC TCA GCA CTT | 1141, 1142 |
| chrX | 135570815 | 135571064 | TGT AAC GTG GAT GTG AGA TTG | CCA CTA GGC TGC ACT AAT GTA | 1143, 1144 |
| chrX | 135760826 | 135761075 | TTG AGC TAA GTC TGC ATC ACT | CAC TAG CTT CTG TAA CTG TGT G | 1145, 1146 |
| chrX | 135831981 | 135832230 | CTA GAG AAA GCA ACG CCT AAG | GTC TCA CAC TGC TCA TTT CCA | 1147, 1148 |
| chrX | 136044394 | 136044643 | AGC ACC TTC CAT AGC TTC TTT | CAC TAG GGT TCA TCA GCT GTT | 1149, 1150 |
| chrX | 136318161 | 136318410 | GTG TCT TCT GAT GGC CAA ATG | CAA CCA ACA TTA GAG TGA CCC | 1151, 1152 |

FIG. 2AJ

| chromosome | start | stop | forward primer | reverse primer | SEQ ID NOs: |
|---|---|---|---|---|---|
| chrX | 136320360 | 136320609 | AAT CAG GTG AAA GGT ACC TCC | GCT GGT TGA GAG AGA GAG AGA | 1153, 1154 |
| chrX | 139380500 | 139380749 | CCT TCA CAA TTC AGG GAA CAA | ACA CCA GCC GAA TAC AGA TTT | 1155, 1156 |
| chrX | 139381074 | 139381323 | TGG ACC CAG TTC TAT GCA ATT | TGC TTC ATA CCT TTC TGC TTC | 1157, 1158 |
| chrX | 144897923 | 144898172 | AAT GAC CCT TAC AAC TCC GAA | ATT TCC CAT GCC TTT CAA CTC | 1159, 1160 |
| chrX | 144908837 | 144909086 | TTT GGG AAG TGA TTG TGA AGG | TCT CTC AGT AGG CGT CTT TAA | 1161, 1162 |
| chrX | 144958353 | 144958602 | TCA GCT GCA TAG ACC TTG TTT | TGA CTG CTA CGC TAG ACT TG | 1163, 1164 |
| chrX | 144959377 | 144959626 | TCA TTT GTT CTC ATT ACG GGC | GGA TAG AGG AAA CCC AGG TG | 1165, 1166 |
| chrX | 145799354 | 145799603 | TTC TAC CTG GGT TCT CTT GG | GGC TCT TTC AAA GTA TCC AGG | 1167, 1168 |
| chrX | 145922717 | 145922966 | TAA CTT CCT GAG CAC ACA TCA | AGA CTT TCT TTG TTG CCT TCA G | 1169, 1170 |
| chrX | 146994477 | 146994726 | GGG TAA ATT CAG GAA TGC ACA | GCC TCA ACA ATT CAG TCC AC | 1171, 1172 |
| chrX | 146995311 | 146995560 | ATT TCT TCT GGT GAG TTT GCG | CAT AAG TTG CTG GAA GAG AAC A | 1173, 1174 |
| chrX | 147540977 | 147541226 | CCT CTT CCT GAC ATG TTG TTG | TCG ACT GCT TTA AGT GAA GGA | 1175, 1176 |
| chrX | 149764787 | 149765036 | GTT GGT GCC AGA TTG TAA CTT | ACC AGT GAT TAG TGT TTC TCC T | 1177, 1178 |
| chrX | 150808513 | 150808762 | GCC TGG CTC AAT AAT AGT CCT | CAA CAC ACA CAC AAA CAC ACA | 1179, 1180 |
| chrX | 150809248 | 150809497 | ATG TTG CCT TCT CTA CGT TTG | GGT AAG AGT TGC CCT AAT GTC | 1181, 1182 |
| chrX | 150942801 | 150943050 | GAG TGG AGC GCT ACC TTT AT | GCT TGG CTT CTC ACA AAT GT | 1183, 1184 |

FIG. 2AK

| chromosome | start | stop | forward primer | reverse primer | SEQ ID NOs: |
|---|---|---|---|---|---|
| chrX | 79712826 | 79713075 | AGA ATG GGA AAT GGG AAG GA | GTT TGC CAG TAG AAA TGG GA | 1185, 1186 |
| chrX | 80374192 | 80374441 | CAC AAT ACA TGG GCT GCT TT | GTA AAG TGT TCA GAG GAC GG | 1187, 1188 |
| chrX | 80491243 | 80491492 | CCA CTC CAA CTC TGC TTT TAC | ACT AGG GAG AAG AAT TGG CAG | 1189, 1190 |
| chrX | 80514786 | 80515035 | GAT GTG GAT TGT CTT TGT TGC | CCA GTT CAT TCC AGC TTC CA | 1191, 1192 |
| chrX | 80553311 | 80553560 | AGC CTT TCA TTG CAC ATT TCA G | GAT CGC CAA CCT GTT TTA TAA G | 1193, 1194 |
| chrX | 104028154 | 104028403 | TCC CAC CAC AAG ACC AAT TT | GCT GTC AAA GTG GAG ATA ACC | 1195, 1196 |
| chrX | 104039199 | 104039448 | GAA GAT AGG TGG TGG AGT TCA | AAC GCT TCC ATC CAC CTA ATT | 1197, 1198 |
| chrX | 104101675 | 104101924 | CTG TTT GAA TGA AGT TGG CTG | ACC TGC CTG TCT TAC CAT TAA | 1199, 1200 |
| chr21 | 17021878 | 17022127 | TAT ACA TGG GTG GGA TTT GTC | GAT ACT TTC CTT TCT CCA GAT CT | 1201, 1202 |
| chr21 | 17046718 | 17046967 | TTT GTG ATG GAC CAT CTA ACC | GGC CGC AGT TTT TGA TTT AG | 1203, 1204 |
| chr21 | 17088576 | 17088825 | GAA GAT CTG GTG TCC CAC TA | TGG GAA GGA CGG TTT GTT A | 1205, 1206 |
| chr21 | 17134784 | 17135033 | ATC TGA AGA TCT CCG TGG TA | TGA ATC ATG CTG TGG AGA AC | 1207, 1208 |
| chr21 | 17161709 | 17161958 | ATG TAT GAA CCA TTT CCT GCT | ATA GAA GAG GTA CCC AGC AA | 1209, 1210 |
| chr21 | 17183683 | 17183932 | AGC ACA GAA TTG AAT GAA GGA A | CCC TGA CTA TGC TAA GTT GC | 1211, 1212 |
| chr21 | 17301983 | 17302232 | GCA TGA GTA AGG CTG AAG TG | TGC AAG CAA AAT GAA ACC AG | 1213, 1214 |
| chr21 | 17302814 | 17303063 | AAA GGC TTA TAT TGC TTT TGA ATC A | | 1215, 1216 |

FIG. 2AL

| chromosome | start | stop | forward primer | reverse primer | SEQ ID NOs: |
|---|---|---|---|---|---|
| chr21 | 17336649 | 17336898 | TTG CTG TTG TTG GGA TCA AG | CAG CTG CTC CTT CTT TAG C | 1217, 1218 |
| chr21 | 17346228 | 17346477 | GCT TCT GGA TCC ACC TAT CT | TAT ACT GCC AAA GGT GAC CT | 1219, 1220 |
| chr21 | 17348050 | 17348299 | AAA AGC TGC CTA AAA TGC CA | GAA GCA TAA TGA GAA CCT CCA | 1221, 1222 |
| chr21 | 17351309 | 17351558 | AGT CAG CAA GTT AGC AGA AA | AAC CCA ACT TGC AGA CAA TC | 1223, 1224 |
| chr21 | 17362239 | 17362488 | CCC ACA TTT ATC CCT TGT CC | ATC TGT TTG CTG TGT CAG AA | 1225, 1226 |
| chr21 | 17367713 | 17367962 | TGT CTG ATT CCA TCT TTC CC | TCC AGA TAT ATT CAA AAG GGA GA | 1227, 1228 |
| chr21 | 17506670 | 17506919 | CAG CCA CCA AAA CAC AAT G | AGG TTT TTA TCA AAG CCC CA | 1229, 1230 |
| chr21 | 17548792 | 17549041 | AAG GCC TGT TTT GTG TGT AG | GGG ACT TGA TGT TCT AAG CAA | 1231, 1232 |
| chr21 | 17591325 | 17591574 | ACA GCT CAC AGA TCT TTA AGC | CCT ACA TGA TAC GCA CAG TC | 1233, 1234 |
| chr21 | 17695933 | 17696182 | GGC ATT ATA AAG AGA TAG CTC CA | | 1235, 1236 |
| chr21 | 19087043 | 19087292 | TGT TTT TCC TTG CCC TGT AA | GTT TTT CTC TAC CCA GCA CA | 1237, 1238 |
| chr21 | 19178365 | 19178614 | TAA CCA GAT GAA TGA GGG CA | CTC TAA TTT GCC ACC CTC TTT | 1239, 1240 |
| chr21 | 22579319 | 22579568 | CAA CAA GCC AAA ACC ACA TC | GAA CGC TAA AGC TTT TCC CA | 1241, 1242 |
| chr21 | 22605212 | 22605461 | GTT GGT TCT TGA AGA CCT GA | TCT TTC TCC TGC CAA GTA GA | 1243, 1244 |
| chr21 | 22964667 | 22964916 | TGT GGT AAG TAG TCT CTA AAG A | ATA ACA CTG TCC TTC TGG GC | 1245, 1246 |
| chr21 | 22984832 | 22985081 | ACC AAA TTT CCA GAT CAC GG | GAG CCT ACT CTC TGA TAC GA | 1247, 1248 |

FIG. 2AM

| chromosome | start | stop | forward primer | reverse primer | SEQ ID NOs: |
|---|---|---|---|---|---|
| chr21 | 22985386 | 22985635 | AAT GAA TGG TCA TGG CTC AC | CCA GTT GTT CAC TTC TCT GAT | 1249, 1250 |
| chr21 | 36076596 | 36076845 | GCC CTG AAG CAC ATT AAA GT | GCC TTA AAA CCA AAC TGT GT | 1251, 1252 |
| chr21 | 36169368 | 36169617 | GCC TCC AGG TTT ATG ACA AC | CTC GAC TTC AAT CAC CCA AG | 1253, 1254 |
| chr21 | 36789088 | 36789337 | CAG CTC TAT TCC CCT TCT GA | TGA ACA AAT TGC TGT GCT GA | 1255, 1256 |
| chr21 | 37939587 | 37939836 | CCT TGG AAG GGA AAG TTG AT | CCC CCT AAA TGA AAG TGG TC | 1257, 1258 |
| chr21 | 37959766 | 37960015 | GTC CCA CCC TGC TCT TAG | | 1259, 1260 |
| chr21 | 37983316 | 37983565 | CAG AGT AAG ACA GTG GGA CA | TGA GTG CTT GGA ATT TTG CA | 1261, 1262 |
| chr21 | 38559539 | 38559788 | AAG TGT GGT GCA TAA AGG AT | GGT TGG CTA CTT CAT GGT AC | 1263, 1264 |
| chr21 | 38751525 | 38751774 | CTC TAA GAA GGA GGG TTT GG | TCA CTG CAT TCC TAG AAC CT | 1265, 1266 |
| chr21 | 39173262 | 39173511 | GAG GTT GAT GAG AGG TAG GG | ATA ACT CAG GCA AAA TGG GG | 1267, 1268 |
| chr21 | 39285267 | 39285516 | AGC CAG GGA TAT TGT TGA AG | CCT TCT GCT CTC ACT TTA CG | 1269, 1270 |
| chr21 | 39330340 | 39330589 | CAG GTA AGT GTG TGT TCC AG | GGA TAC TAG CAG AGG TGG AG | 1271, 1272 |
| chr21 | 39442392 | 39442641 | TTG ATT TCC ATG CAG AAG GG | TGT ACA CAA TAT GCC AGG AAC | 1273, 1274 |
| chr21 | 39499219 | 39499468 | TAA TTT GGC CTT AGG GGT TG | GCA CTT GAG TTA TGG GAC TT | 1275, 1276 |
| chr21 | 39541298 | 39541547 | TCC ATA AAA GGT GCT TAA AGC | TGT GAT ATG TAG TGT GTA TCA GT | 1277, 1278 |
| chr21 | 39563720 | 39563969 | TTG TAT CAC ACC ATC GTG GA | GAA TGT GTT CAA AGG AGG GT | 1279, 1280 |

FIG. 2AN

| chromosome | start | stop | forward primer | reverse primer | SEQ ID NOs: |
|---|---|---|---|---|---|
| chr21 | 39584873 | 39585122 | ACT GCT GAG AAC AAT CAT GC | GAT GAA GGG GAT TAC GGG AA | 1281, 1282 |
| chr21 | 46530377 | 46530731 | GGT GTG GAG AAT TTG TTT GC | TTT AGG AAG CAG CAC AAG AA | 1283, 1284 |
| chr21 | 46534043 | 46534292 | TGA TAT TAG GCG GTG GCT TA | GAG GGT GCT GGG GTT ATC | 1285, 1286 |
| chr21 | 46535763 | 46536012 | TCT CAC CTA AAA TCT GGG GC | CCC GAA AGC ACT TAC CTT TT | 1287, 1288 |
| chr21 | 46537454 | 46537703 | AGG ACT GTG ACA CTT TAT CTT T | TTC ATG AGC TGC AAT GTG TT | 1289, 1290 |
| chr21 | 46542089 | 46542338 | ATG CGA GGT AGA AAA TGA GAG | TGC TAT GAA AAG AGG GAC CA | 1291, 1292 |
| chr21 | 46556856 | 46557105 | TGT GGC TTT AAG GTT CTG AAG | GTC CTG GAT CTA CAC GTG AA | 1293, 1294 |
| chr21 | 46564465 | 46564714 | TCG TTG CTA TTC TGC TTT GA | GTA AAT CTG TGT GCC AGC AA | 1295, 1296 |
| chr21 | 46567255 | 46567504 | TCC CTT TTG TGG TTT CTT GG | TAA AAG AGG CGT GTG GAA AA | 1297, 1298 |
| chr21 | 46572969 | 46573218 | TTG CCG CAC TCT TCA TTA AT | CCA GTA GCT TGT GAT GTG TA | 1299, 1300 |
| chr21 | 46605329 | 46605578 | ACT GGC TTC TCC TCA TTA GT | TAC AGG CCT CTG AAA GAT GA | 1301, 1302 |
| chr21 | 32134809 | 32135058 | ACT GAT TTG CCA TGT AGA GC | AGA GCA TGC TAG ACG TCT TT | 1303, 1304 |
| chr21 | 32148136 | 32148385 | GAA TGT CAT ATT GCC TGC CA | CTG GGC TGT AAT TAA GGC TC | 1305, 1306 |
| chr21 | 32165994 | 32166243 | TCA CTC GCT TAG AAT GTT GC | AAC ACC TGC ACA CTT TGA AA | 1307, 1308 |
| chr21 | 32174173 | 32174422 | ACC ATT AAC TTC CTG CAA ACT | AAT GAA CTT TGT GGG CTG AA | 1309, 1310 |
| chr21 | 32179882 | 32180131 | TAA AGC CCC ATA CCA GGA TT | CCA CAC TCT CAC TGG TTC TA | 1311, 1312 |

FIG. 2AO

| chromosome | start | stop | forward primer | reverse primer | SEQ ID NOs: |
|---|---|---|---|---|---|
| chr21 | 32181384 | 32181633 | CCA AAA ATC ACC CAT ATG CG | CAC AGT GGA TAC CTC AGG AA | 1313, 1314 |
| chr21 | 32184463 | 32184712 | ATA ACC CAG GTG CTT CAA AG | CCA ACA CAG GAG GAA CTT TT | 1315, 1316 |
| chr21 | 32201994 | 32202243 | TCC ACA GCA GAA GTA ACG A | GAG AAA AGC CAA CAA AAA TGT G | 1317, 1318 |
| chr21 | 32208609 | 32208858 | AGG AAA GCT ATG AAG AAA GGG | TGT CAT TAC TAG AAG CAC CTT T | 1319, 1320 |
| chr21 | 32319600 | 32319849 | AGC TCC AGA GTG TCA GTA TT | TGG TGT GAG TTC AGG AGG GTT TA | 1321, 1322 |
| chr21 | 35034581 | 35034830 | TTG ATT TCC AGC ACT GAA CTT T | ACC ATT TCT GAC AGA ACA GA | 1323, 1324 |
| chr21 | 35060177 | 35060426 | TGT TTG ATT TTT CAG GCT GA | TGA TGC TTA AAC ACA TGC CT | 1325, 1326 |
| chr21 | 35070605 | 35070854 | CTG GTC ATT CCT GAG TGT CT | AAG GGA TAT GCA GCT TGT TC | 1327, 1328 |
| chr21 | 35093305 | 35093554 | TCC TGT TTT ACA CTT TTC TAA CTT T | | 1329, 1330 |
| chr21 | 35094930 | 35095179 | ACC TCA ACC TGT TTT AGC AC | GTT GTC ATT CAA ATG TCA CCA C | 1331, 1332 |
| chr21 | 35099418 | 35099667 | CAG TGT GTG TCA TGC CAA AT | CTC AGA TTC CAG AGC CCT C | 1333, 1334 |
| chr21 | 35138457 | 35138706 | GGT CTA TGT TAA TCT TGG GCC | ACA TTG CTA GCA GCT TTT GT | 1335, 1336 |
| chr21 | 35152877 | 35153126 | AGC CAG TCT GTA TCT AAA GGT | ACT TGC CAA GAA CAG TAT CTG | 1337, 1338 |
| chr21 | 35157173 | 35157422 | ACT CTT GGG GTT TCT TCA GT | TTC CTT CTT CCA GGT GAA CA | 1339, 1340 |
| chr21 | 35161795 | 35162044 | CGA ACC AAA AGC AAA ATC CTT | TGT TTC TCC TTC ATC TGG TC | 1341, 1342 |
| chr21 | 35296082 | 35296331 | AAT CTA TGG AGG TCA CTG GG | TGT CAC CTT GCA GAT ACA GG | 1343, 1344 |

FIG. 2AP

| chromosome | start | stop | forward primer | reverse primer | SEQ ID NOs: |
|---|---|---|---|---|---|
| chr21 | 35450331 | 35450580 | AGG TCC TTG TAG TTT GCT TG | ATT GTT CAC AGG GTC AAG TC | 1345, 1346 |
| chr21 | 35473022 | 35473271 | GTG AGA GCC AAT AGA GTG TG | ATG AGC CAG GAG AAT CAT CA | 1347, 1348 |
| chr21 | 35473971 | 35474220 | GCA TGG TGT GTG AAA GTG AT | CAT CAT TTC AAA GGG GCT CA | 1349, 1350 |
| chr21 | 35498164 | 35498413 | ATG CTG CTT TTG ACT GAT GT | TCT TCT CTA ACA CCC ACT CC | 1351, 1352 |
| chr21 | 35540943 | 35541192 | CGA AGC TGT ATT CCT GTC TC | ACC CTT ACC AAA GTA GCA TC | 1353, 1354 |
| chr21 | 35702965 | 35703214 | ATG GAC TAA CTG GAG AGC G | ATC ACG ACG CCT TGT TTA TT | 1355, 1356 |
| chr21 | 28574819 | 28575068 | ATG TCC TGC CAG TAA ACA CA | ACT TTC CTG CCA ACA ATC TC | 1357, 1358 |
| chr21 | 28586377 | 28586626 | TGC CAC TAA ACA CCT AAG GA | TTG ATA GTT GCA TCT GGG GA | 1359, 1360 |
| chr21 | 28597009 | 28597258 | TTG GAA ATT TTG GGG TCA GG | TTT GTT AAC TAA CGT GAT TCC A | 1361, 1362 |
| chr21 | 28616121 | 28616370 | TTC TGA CCT CCC TTA CTG AG | CCC ACT CTC CAT GTG TTC TT | 1363, 1364 |
| chr21 | 28631408 | 28631657 | TAT GTG CTT GCG ATG TGT T | TCC TGC TTC AAC TCA ATA CG | 1365, 1366 |
| chr21 | 28891355 | 28891604 | GAA CCT TAG GGC CAG TCT AT | ACC CCT CAT TTT CGT ATG TC | 1367, 1368 |
| chr21 | 28892223 | 28892472 | AGA ACC TGA TGT GTT TTC CTC | ACA GTT ATG GAG GAA TTG CG | 1369, 1370 |
| chr21 | 28919446 | 28919695 | ATG TGA GAG AAG CAA AAC CC | TCA AAC CTC TTT TAT CTG TCC C | 1371, 1372 |
| chr21 | 29012106 | 29012355 | GTA GTT GTC TTG AGG GCT TT | ATT TCA CGT AAC ACT CTG GT | 1373, 1374 |
| chr21 | 29021007 | 29021256 | CCT GGT CAA CAA CAT ATG GG | CTC TGG CAA AAC TTT CTG GAT | 1375, 1376 |

FIG. 2AQ

| chromosome | start | stop | forward primer | reverse primer | SEQ ID NOs: |
|---|---|---|---|---|---|
| chr21 | 29753618 | 29753867 | AGA ATA TTG CAT TTG GCC AGA | GCT TCT CAT GCT CAC ACT G | 1377, 1378 |
| chr21 | 29796479 | 29796728 | AAA GCT ATG CAA ATA GTG GCA | AAT ATG ACT TGC CCT TTT GAA | 1379, 1380 |
| chr21 | 29812165 | 29812414 | AGT TCC CAA CAG AGG CTA AT | TCA CAG CCA GTT ACA CAG A | 1381, 1382 |
| chr21 | 29813966 | 29814215 | AGT TAT AGG TGA GGA AGG GC | CTA CAG TGC AGA AGA GTC CC | 1383, 1384 |
| chr21 | 29814951 | 29815200 | CAC TGC AAA AGA AGG AGG TT | TTG GTT TCA TGT GGC TTT GA | 1385, 1386 |
| chr21 | 29820028 | 29820277 | TCT CAA CAT CGC TGA TCT AGT | TCC TTC TCC CCA ACT TTC TT | 1387, 1388 |
| chr21 | 29825992 | 29826241 | AGG TAG CTG GAA AAG GAG AA | CTT TAG ATT CCA GGG CTC TTG | 1389, 1390 |
| chr21 | 29827616 | 29827865 | TGA AAT TGC CCA GAA TTG AGT | TGA AAG CGT GAA AAT CAG CT | 1391, 1392 |
| chr21 | 29841662 | 29841911 | ATT TTC CTG GAC TTC TGA CA | ACT CGA TCC CTA GGT AAT GT | 1393, 1394 |
| chr21 | 29884231 | 29884480 | TGT TAT TCC TCT TCC TGT CCA | ACA AGT GGG TAG GGA TGT TC | 1395, 1396 |
| chr21 | 29898255 | 29898504 | TAA CCA CAC AAC TAC AGC TT | GCA CAA GTT TTC AGG GAA TG | 1397, 1398 |
| chr21 | 30368230 | 30368479 | ATT CAA AAT GGG GAC GAG AG | GTG GAA AGT CTC GTC AGA AT | 1399, 1400 |
| chr21 | 30413906 | 30414155 | TCC CAG TTT GCT ACT CTG G | TCC ACC TCT GAG CAT AAC AT | 1401, 1402 |
| chr21 | 30415555 | 30415804 | TCT CAT TAT GTG AAG ATT GCT TTC | | 1403, 1404 |
| chr21 | 30428953 | 30429202 | TTA AGA TTA AGC AGT CTT CTT GG | | 1405, 1406 |
| chr21 | 30477650 | 30477899 | CAA CAG ATC TGA TTC TGC CC | CCA TCC CAC TTC TCC AGA TA | 1407, 1408 |

FIG. 2AR

| chromosome | start | stop | forward primer | reverse primer | SEQ ID NOs: |
|---|---|---|---|---|---|
| chr21 | 30528161 | 30528410 | CAT GTG TTT CAA AGT TGG CT | CCA CCT TCC TGC TTA AAG AA | 1409, 1410 |
| chr21 | 30550132 | 30550381 | ACT ATA GCA TTA GGG TGA GGG | CTC CTT ACT TGC ACT GAG TT | 1411, 1412 |
| chr21 | 30580738 | 30580987 | GAG ATT TGG ACA TGC TTT CA | GGG AAA ACT TAC GGC AAC TT | 1413, 1414 |
| chr21 | 30600446 | 30600695 | CCC ACC ACC AGT TGT CAT C | TAG AAA TGT TTA GGG TGC ATG A | 1415, 1416 |
| chr21 | 30628668 | 30628917 | GCC ACT CAC TTC CTA GAT AAT | TAC CCC TCT TTT CCA TCT GC | 1417, 1418 |
| chr21 | 30660609 | 30660858 | ACA GTA TCT CAG GCC CTT AT | GCA TTT TGA CAG GAA AGT GG | 1419, 1420 |
| chr21 | 30680391 | 30680640 | TCA GTA GTT CCT CAG ATG CTA | TAG GGC CAC AGT TTC TCA AT | 1421, 1422 |
| chr21 | 30720214 | 30720463 | AAT GCA TGA AAG TCC AGG AA | GAA TGA GAA ATC TGG CAG GA | 1423, 1424 |
| chr21 | 30782462 | 30782711 | ACA TGC ACT CTT GTC TTA TGC | TCA GAT GCC TGA TGA CCA TA | 1425, 1426 |
| chr21 | 30810199 | 30810448 | CAC ATA TAC TGG CTT TCT GGT C | AAT ATG CAG TGG GTA GGA GC | 1427, 1428 |
| chr21 | 30849402 | 30849651 | GCA CAT GTC ATT AGC AGG G | GAC AAC AGC TGA CTT CCA TT | 1429, 1430 |
| chr21 | 30868525 | 30868774 | ACA TGC TCA ATT ATG GAG CC | CAC TCT CTG GAA CAA ACA CA | 1431, 1432 |
| chr21 | 30988776 | 30989025 | ACA AAG ACA GGA ATA GGG CT | GTT TTG AGG CGG TTT CAT GA | 1433, 1434 |
| chr21 | 31012406 | 31012655 | CAA TCT GCT GAC TTG CTT CTT TTC A | | 1435, 1436 |
| chr21 | 31032720 | 31032969 | CTT TGG CTC AGA ATC TTC CAA | GAA CAC CTC AAA GTT GCT CA | 1437, 1438 |
| chr21 | 31085356 | 31085605 | TGT ATG AGG ACC AGC AGT AAA | AAG AAG CAA GGA CAA GGA TG | 1439, 1440 |

FIG. 2AS

| chromosome | start | stop | forward primer | reverse primer | SEQ ID NOs: |
|---|---|---|---|---|---|
| chr21 | 31494755 | 31495004 | TCT TTT CCC CTT GTG CAT AG | GAA ACA ACC ACC ACA ACA AA | 1441, 1442 |
| chr21 | 31560667 | 31560916 | GCT TAG TGT GTG TGA TCC GT | CCA CCA TGT TTA CAC CGT TT | 1443, 1444 |
| chr21 | 31605973 | 31606222 | ACT CAC CTT TCC CAA GAA GA | TTT ACC CAT GAA TTG CTG CA | 1445, 1446 |
| chr21 | 31621826 | 31622075 | TGG TAG TGG GAA GAG GTT GA | AGT TTG CAT TTG TTC AGG GA | 1447, 1448 |
| chr21 | 31653822 | 31654071 | GCA TGG AGA ACA AAA GCT GA | TTC GGA TGG CTT TGA TTG TC | 1449, 1450 |
| chr21 | 31670830 | 31671079 | TGT GAG CAA GAA ACT GAA GG | CAT TGT AAA TTA AAC GGC CTC | 1451, 1452 |
| chr21 | 31691347 | 31691596 | AGT ATC ACT TGT CCA GCT CA | CTA ATG CAA GCT GCT TCT CT | 1453, 1454 |
| chr21 | 31708936 | 31709185 | CAC AGG ACT AGG TAG GCT TT | TGT CTA GTG GTA ATC TGG GG | 1455, 1456 |
| chr21 | 31733443 | 31733692 | GTG TTA ACA GCT TTC CCT TCA | TCT GGA CAG TGG AGT TGA AA | 1457, 1458 |
| chr21 | 31768996 | 31769245 | TCA TGT ACA GAA AGA ATT AGC CT | | 1459, 1460 |
| chr21 | 31886189 | 31886438 | AGA GGC CAA GTG ACC AAA TA | AGG AGA GAC ATA ACT GGT CT | 1461, 1462 |
| chr21 | 31886808 | 31887057 | AAG CCA GTA ATT CAT CTT CCC | ATT GCA ATG TCT GTG GAT GT | 1463, 1464 |
| chr21 | 32119833 | 32120082 | CCA TGA CAT AAC ACA TCA CCA | AAG AAG TTG AGG TAG CAC G | 1465, 1466 |
| chr21 | 32125263 | 32125512 | ATA GAT TTC CTC CTG GGC TC | AGT GTC CTT TCC TCC AGT TC | 1467, 1468 |
| chr21 | 25795207 | 25795456 | CCA CCT CTG TAC CCA CTA TC | TTG AAC CTG AAA GGA ACT GTG | 1469, 1470 |
| chr21 | 25802273 | 25802522 | TTC CCT GGA AGA TAG CCA AT | GCT CAA TCA CCT GTT CCC TT | 1471, 1472 |

FIG. 2AT

| chromosome | start | stop | forward primer | reverse primer | SEQ ID NOs: |
|---|---|---|---|---|---|
| chr21 | 26355452 | 26355702 | TGG ACA CGT AAA AGA AGG TG | CAT TGA AGC TCA CTC TAA GGG | 1473, 1474 |
| chr21 | 26365770 | 26366019 | CTG AGA ACC TTG TCC AAC TG | CTA AAG TTT GGG TTA GGG GT | 1475, 1476 |
| chr21 | 26373440 | 26373689 | TTT CGC TAG TCT TTG CAC TT | TGC CTT ACA TTT TCT GTG GG | 1477, 1478 |
| chr21 | 26374774 | 26375023 | GCG GCA ATA ATT GTC ACA AA | GCC ATA AGA TTT CCC CAC TC | 1479, 1480 |
| chr21 | 26390279 | 26390528 | CAG AAA TGT GTC AGG CTA CA | ACA AAG CAA GAG GAT GAA ACA | 1481, 1482 |
| chr21 | 26390951 | 26391200 | AAC TCT TCA TTT TGA CGG GG | CAA AGC ACC ATC AAC ACT TA | 1483, 1484 |
| chr21 | 26402802 | 26403051 | TGG GTT GTG CTG TTG TTT AG | CAC TGC AAC TCC TAG AAT GA | 1485, 1486 |
| chr21 | 26496769 | 26497018 | GCT CAG CTC CTT TCA TCT G | TGT GGG GAA ATT GCT GTT TA | 1487, 1488 |
| chr21 | 26515400 | 26515649 | AGG ACA TTC AGC CTA TTT GC | GTA TGG GCA GCT GTA ACT TG | 1489, 1490 |
| chr21 | 26571662 | 26571911 | ACA CAG TAT CAA GGT CAA CA | TCA CAA GCC ACT GAA AAT GT | 1491, 1492 |
| chr21 | 26589786 | 26590035 | GCA GAA CCA CAG TCT ATG AG | TGT ATG TTA AGC TAG CCA ACA | 1493, 1494 |
| chr21 | 26604824 | 26605073 | AAT GCT CCA AGT TAT TCC AGA | TGT GTT ATT GAA CTT TGC CA | 1495, 1496 |
| chr21 | 26933670 | 26933919 | AAG AGA GAA GCG ACA AAA CC | TTC ATC CCT ACC TCA TCA CC | 1497, 1498 |
| chr21 | 26950703 | 26950952 | AAT GAG AAG GAA TTG GGT GC | AGA TCA CTT TTG GCT GTA ACC | 1499, 1500 |
| chr21 | 27045134 | 27045383 | AAT GAA GTG TTA GGG CCA TC | CAA GTG ACA ATC TCA GCC AA | 1501, 1502 |
| chr21 | 27398390 | 27398639 | GCT CAT CAC AGT TTA AGG AGT | GCA TTT TCA GAT GGT TCC CT | 1503, 1504 |

FIG. 2AU

| chromosome | start | stop | forward primer | reverse primer | SEQ ID NOs: |
|---|---|---|---|---|---|
| chr21 | 27441346 | 27441595 | ATG TGG AAG CAA GAG AAA GG | ATG GAG AGT TTG AGT GGA GT | 1505, 1506 |
| chr21 | 27465490 | 27465739 | TGA AAG GTG AAG TGG CTT TT | CTG CCA CTG GGT TTA TAG AAA A | 1507, 1508 |
| chr21 | 27485182 | 27485431 | GTA AGT AAG GGG TCC TAG CT | ACA CCT TTA CTC CTG TGG AT | 1509, 1510 |
| chr21 | 27486006 | 27486255 | TGT GAC TTC CAT GAA ACT GG | GAT GTA GGG CCT TAT CCA CA | 1511, 1512 |
| chr21 | 27502429 | 27502678 | GCT GAC AAA CTA ACC TTC CA | AGC TTG GTG ATC TTC AAA CA | 1513, 1514 |
| chr21 | 27520192 | 27520441 | AAA ACC TCC CAA AAC AGA CT | TGA AAT GGT GGG TAA TGC TC | 1515, 1516 |
| chr21 | 27539803 | 27540052 | AGT TTA GTG GCC ACG TGA AA | CAT GCA AGT TCA CGA GGT TA | 1517, 1518 |
| chr21 | 27623130 | 27623379 | GGC AGA AGT TTC AAT TCC CT | AGT CTG AGG AAG AAG CAA CT | 1519, 1520 |
| chr21 | 27623692 | 27623941 | AAA GCC TCT GTT TGC ACT TT | GAG TCC AAT CTT TTC CCA CA | 1521, 1522 |
| chr21 | 27763679 | 27763928 | TCA GTC AGC TTC TTG AGT CA | TCC ACT GCG TTC TTA TCC TT | 1523, 1524 |
| chr21 | 27894000 | 27894249 | TGT TTC ATT TGG GTC ATG GA | GGA CAG AAC AGC TAC AAA GG | 1525, 1526 |
| chr21 | 27926498 | 27926747 | TAC AGC ACT AGG ATC ACT CTG | CTG GCT TGT GAA TTA GAG GG | 1527, 1528 |
| chr21 | 28077177 | 28077426 | ATG CAT GTT TCT TGC AAA GG | GTA AGA TGG TGG GCA GGA T | 1529, 1530 |
| chr21 | 28122462 | 28122711 | GTA GGA TTC AGG GCA TTT CA | AGA AGG GCT CAA AAC ACA TC | 1531, 1532 |
| chr21 | 28161337 | 28161586 | AAC TGG AAC TGA GCG TGA G | TCA TGT AGG CTT TCT GAT TTT | 1533, 1534 |
| chr21 | 28180925 | 28181174 | TGT ATG CAG TTA CCT CCA GA | TGT AGC TCT TGA CCT AGC AA | 1535, 1536 |

FIG. 2AV

| chromosome | start | stop | forward primer | reverse primer | SEQ ID NOs: |
|---|---|---|---|---|---|
| chr21 | 28275754 | 28276003 | GGA TGT ATA CCA GAC CCC TT | TAA GTT CAC GGT GAA GTG AAC | 1537, 1538 |
| chr21 | 28291449 | 28291698 | CGA AAG ATG TTA GCA CCT CA | GTG GCT TCA ACT AAC TGG AC | 1539, 1540 |
| chr21 | 28294820 | 28295069 | AAT TGG CTT TGC AGT GTT TC | ACC CGT AAG TGT TTG AGT GA | 1541, 1542 |
| chr21 | 28295351 | 28295600 | GCT TGC TGG TAG GAG GTA TA | TGT AGA AGT AGG GTT TGC GT | 1543, 1544 |
| chr21 | 28295857 | 28296106 | CTG GAA ACG GAA GGA AGT TG | CAG GGG ACA TTT GAA GAT GG | 1545, 1546 |
| chr21 | 28311866 | 28312115 | CTG TGT TCA GTA AGT GGC TG | GAA ATT GTG CAG TGA AAG CA | 1547, 1548 |
| chr21 | 28334784 | 28335033 | GAC AGT GAA GTG TGA TCG TT | ATG TAA GAA GTG CGT TGC TTA | 1549, 1550 |
| chr21 | 28354814 | 28355063 | TGG TGA TGC TGT TTT GGA AA | AGA TCT GGA ATC TGA GAC TCC | 1551, 1552 |
| chr21 | 28415341 | 28415590 | TTC TTT CAG GCA GAA GAA ATC A | TAT AGG ATA AGG TCA AGC AGG T | 1553, 1554 |
| chr21 | 28433186 | 28433435 | AAG TTC CAT TAC TGT ATT GAA AAT T | | 1555, 1556 |
| chr21 | 28450226 | 28450475 | GGA CGT ACG TGC TTA TTT CA | TCA GTG AAT GAG GAA TCA TGC | 1557, 1558 |
| chr21 | 28474083 | 28474332 | CAG CCT GAT ATT CCC ATT GAG | TTC TCA GGA GTA CCA CAA GC | 1559, 1560 |
| chr21 | 28491062 | 28491311 | TCA TGA GGC TGA GTG AGT AT | GGA TGA AAC ACA GAA CCA TG | 1561, 1562 |
| chr21 | 28509439 | 28509688 | AAA GCT CTC CTA TCT CCA GT | CAG ATC CCT TTC ATT TTG CA | 1563, 1564 |
| chr21 | 28534176 | 28534425 | ACA AAG AGT CTG GAC TAT CCT | GGA AAA GTG CTC AAT TAG GC | 1565, 1566 |
| chr21 | 40042441 | 40042690 | TGC CTA AAA ATA CCC AAA GCT | CTG GCA GTT ATA GTC ACC AA | 1567, 1568 |

FIG. 2AW

| chromosome | start | stop | forward primer | reverse primer | SEQ ID NOs: |
|---|---|---|---|---|---|
| chr21 | 40427338 | 40427587 | CCA AGA CAC TCA CTC CAA AG | AGC AAG TCC TTA TGA TGC CA | 1569, 1570 |
| chr21 | 40509976 | 40510225 | CCA GGA AAA GGA GCA GTT TT | GCT GGT GAA GTT GGA GTT TT | 1571, 1572 |
| chr21 | 40531291 | 40531540 | GTT CAA CTC TTT CTG CGA AC | GCT GGG TTT AAG CCA CAT AT | 1573, 1574 |
| chr21 | 40578323 | 40578572 | CCA CTT CTT CTG TTT CCA AC | TGT AGC CTA AAT AGC AGC CT | 1575, 1576 |
| chr21 | 40601158 | 40601407 | GGG AAG GGC ATG CTA ATC A | AGG AAT TGC TTT TAT TTT AAC CA | 1577, 1578 |
| chr21 | 40630577 | 40630826 | TGT TCA ATC ACC TCT CCA TC | GCT GCT TTC AGG TTT TTG TG | 1579, 1580 |
| chr21 | 41280723 | 41280972 | AGA GGA GAG GCT AAG CTT TG | ATG GTG CAG AAA AGA GCA AT | 1581, 1582 |
| chr21 | 41607273 | 41607522 | ACA AGA GAG GAA GCT GTC AG | GTG TGG TGC CAT TTT CTT TC | 1583, 1584 |
| chr21 | 41629820 | 41630069 | AGC CCC TTT CTC CTT ATT CT | GAA CAA TAC TTT CTC CCC GG | 1585, 1586 |
| chr21 | 41703462 | 41703711 | AGG GAA GCA GGA TTT TAA CG | GAA ATG GCC ATG CTA GGA AT | 1587, 1588 |
| chr21 | 41729089 | 41729338 | AAG TTT CAC AAT ACC CAG GT | ACT TCC AGT AAC ATG GAT GC | 1589, 1590 |
| chr21 | 41761636 | 41761885 | TCG CAG AAT GGA CAA GTA CT | GAA ACA CCC AGA CTT GTA GC | 1591, 1592 |
| chr21 | 41839021 | 41839270 | GGC TCC CAG ATT TTG ATC AT | TTA AAT CTT TGT GTG CGT GT | 1593, 1594 |
| chr21 | 41908902 | 41909151 | CCT AGA ACT GCA AAA CAC CT | CCT CCA GGA ACT TTG TTC AG | 1595, 1596 |
| chr21 | 41933321 | 41933570 | TTC CAT TAT TTT CTC ACC GGC | AAA AAC CTT CAC AAA CCC CA | 1597, 1598 |
| chr21 | 41981868 | 41982117 | CAG TCC AAC AAA GAG GTC AC | GAG TGG ATA TTG TCT CGC TG | 1599, 1600 |

FIG. 2AX

| chromosome | start | stop | forward primer | reverse primer | SEQ ID NOs: |
|---|---|---|---|---|---|
| chr21 | 42029142 | 42029391 | TTG TGT GTG TTG AAG CCT AG | ACT AGC CCA CTA ATG TTG CT | 1601, 1602 |
| chr21 | 42030642 | 42030891 | AGT GGG GGT AGG AAG AAA AA | CGA TTA TCA GAA CAG ATG AGG T | 1603, 1604 |
| chr21 | 42080190 | 42080439 | GTT CCA ACA ATG TAA GGC AC | ATT GCA CAG CTG AAA ATC CT | 1605, 1606 |
| chr21 | 42251219 | 42251468 | GGA ACC CTC TAT GGT CAA AG | GGC ACA CTG ACC GTA TTT AT | 1607, 1608 |
| chr21 | 42559559 | 42559808 | ATT GCT GTG TAG TTC CTT GA | TGG TAG TGG GTC AGG AAT TT | 1609, 1610 |
| chr21 | 42601828 | 42602077 | TTT CTT GCC ACC ATT CTG AC | TCT CTT GAA AAG AAA GGC GG | 1611, 1612 |
| chr21 | 42851340 | 42851589 | CAC ACG TTC TAA CCA AGT GC | TGA ATT ACA CAG CAA AGC CC | 1613, 1614 |
| chr21 | 42872713 | 42872962 | TAG CCA CAT CTT AAC AGA CCT | CTG CCA ATG GGA TCG AAT TT | 1615, 1616 |
| chr21 | 43032728 | 43032977 | ATT CCT GAG GGT GAC ATG AA | GAG TGA CGC TGT TCA TTC TT | 1617, 1618 |
| chr21 | 43406661 | 43406910 | CCT GCC CCA TCA ACT TAA AA | GAT AGT AAC CGG GTG TAG CA | 1619, 1620 |
| chr21 | 46521300 | 46521549 | CTG GGT GCA GAG GAT CTC | | 1621, 1622 |
| chr21 | 16323548 | 16323797 | TTG AGT TGA ACT TTG CTT TAG A | TCT AAT AAG GGA TTG ATG GAG TT | 1623, 1624 |
| chr21 | 16330249 | 16330498 | GAA CTA GGA GAC ACT GGG TT | GGG AGA TTT CCT GCT TGT AG | 1625, 1626 |
| chr21 | 16332622 | 16332871 | CAA GAA TAG CTA ACT GGT GCT | AAT CCA TGC AGC TTC TCT CT | 1627, 1628 |
| chr21 | 16333315 | 16333564 | AGT TAC ACA CTG AAT CAT GGG | TGC ATT GTC TCT GGT TTG AA | 1629, 1630 |
| chr21 | 16335355 | 16335604 | CCC ATG TGG CTT CAC TAA TA | TCC TGA ATG CAT CCT TAA CC | 1631, 1632 |

FIG. 2AY

| chromosome | start | stop | forward primer | reverse primer | SEQ ID NOs: |
|---|---|---|---|---|---|
| chr21 | 16344361 | 16344610 | GAT TGT GGT CAC GTG GAG AG | TGG GAA AGG TGA GAA GGA TT | 1633, 1634 |
| chr21 | 16349606 | 16349855 | CAG ATC CAG GTA TTC GGA GA | TTC GGG ACC CAT ACC TAA AA | 1635, 1636 |
| chr21 | 16358650 | 16358899 | ACA ACA ACA ACC ATT ACC CA | TCT TTT CTG GAC CCA CAT GA | 1637, 1638 |
| chr21 | 15713251 | 15713500 | TGG CCA TAG TAC TGC TTG TA | GAC CTC TAC ATC TGT ATC TTC C | 1639, 1640 |
| chr21 | 15714357 | 15714606 | TGT CTC ACT GTT GGG AAC TT | CCC TTC ATT TTC TGT CCC AT | 1641, 1642 |
| chr21 | 15725977 | 15726226 | TTT GTC TGT ATC CTA TGC CC | TCA GCC TTG AGT ATT AGC CTA | 1643, 1644 |
| chr21 | 15731366 | 15731615 | GCT GAC AAA ATT GGA TCC CA | AAG TTT GCC ATG AAG GTC AT | 1645, 1646 |
| chr21 | 15816232 | 15816481 | AAA ATC CTC CTG AGT CCT CT | GAC TTC TGG TTG TTT CCT CA | 1647, 1648 |
| chr21 | 15843963 | 15844212 | TTC ACT GGG CTC TTC AGC TA | ATG TGT CTA TTG CCC TAC CT | 1649, 1650 |
| chr21 | 15858450 | 15858699 | AAA GGG CAG GAG TTA GGT AA | TGC GGG AAG TTC ACA TGA A | 1651, 1652 |
| chr21 | 15859015 | 15859264 | AGG CAT AAG AAA CCA GGT TG | GTG AAC TTC AGG CTG CTT A | 1653, 1654 |
| chr21 | 16002625 | 16002874 | GTA GTT CGG TCC AAT GTC AG | TGG TTT CGT CCC GTA AAT AG | 1655, 1656 |
| chr21 | 16030414 | 16030663 | GAT GGT CAC AAT TGC AGG TT | AAT TCC TTT CAA TGC TGG CT | 1657, 1658 |
| chr21 | 16063119 | 16063368 | GCC AAA GAT CTC AAT TGC CA | AGA AAG ACA CAT ATG CCA TGG | 1659, 1660 |
| chr21 | 16068358 | 16068607 | GAC CAA GAC TGT CTC TCC TT | TTG TTG GTG TCA GTT CTG AA | 1661, 1662 |
| chr21 | 16071495 | 16071744 | TAA TGG TCA AAT CCC TCT CAA A | TGT AGG AAC AGA TTA GGG CA | 1663, 1664 |

FIG. 2AZ

| chromosome | start | stop | forward primer | reverse primer | SEQ ID NOs: |
|---|---|---|---|---|---|
| chr21 | 16081282 | 16081531 | CAT GTA GGC TGA AGA CTC CT | CTC CAA GCT GAT ATG CCA TC | 1665, 1666 |
| chr21 | 16115078 | 16115327 | TTT CTC TCC AAA CTG GTT GC | CCA CCC CTC ATT TCT TCC TT | 1667, 1668 |
| chr21 | 16122085 | 16122334 | TAC AGG CAA GAA ATA GTG TCT | GGG TCC TTC GTT TTC TGT TT | 1669, 1670 |
| chr21 | 16130688 | 16130937 | TTC AGC AAG AAT GGG GAT TC | TAG GAA ACA GGC TAA AAG GGA | 1671, 1672 |
| chr21 | 16133865 | 16134114 | CAA AGA GAG AGC CAT CAC AG | TAC TGT GTA GAA GGC AGT GT | 1673, 1674 |
| chr21 | 16139969 | 16140218 | TGA GAA CAC TGC TAT TTC TGC | GCT AAG GAC AAA GAA CCA CT | 1675, 1676 |
| chr21 | 16141592 | 16141841 | GCA TGG TCA GGA CAT TGG | | 1677, 1678 |
| chr21 | 16160517 | 16160766 | GAT TGA ATC AGG AGG GAA GC | TGG CTA AGA CCA GGA TTG TT | 1679, 1680 |
| chr21 | 16165861 | 16166110 | AGC TTA AAT GAT GAA GTG CTT TC | | 1681, 1682 |
| chr21 | 16189746 | 16189995 | TTC TCC TAC GTA TCT TGG CA | TGA TAG GCA GAT CAT TCC CC | 1683, 1684 |
| chr21 | 16190806 | 16191055 | ACC TGG GAC ATA ACC TTG AT | GCA AAT GGC AAA GGG AAA AC | 1685, 1686 |
| chr21 | 16192618 | 16192867 | CCA TTT TCC TAC TGC GTG TC | CAC GGC TAG TGC TCA TTT T | 1687, 1688 |
| chr21 | 16195809 | 16196058 | GAA CAT ACC AAA CCC ACT GG | CCG TAA TAC CCA AGT CAT CTG | 1689, 1690 |
| chr21 | 16198337 | 16198586 | ACC CAA TGA TGT ACA GTT CC | AGC AAA CTA AAA CAG CAA CTT C | 1691, 1692 |
| chr21 | 16203731 | 16203980 | ACC TAT TCG ACT TGA AAC TCA G | AGC CTG CTA TCT TCA CTG G | 1693, 1694 |
| chr21 | 16207035 | 16207284 | ATT TCT GCA CAA CTG TTC CA | ACC ACA TAT ATA GAG ACT TTG AA( | 1695, 1696 |

FIG. 2BA

| chromosome | start | stop | forward primer | reverse primer | SEQ ID NOs: |
|---|---|---|---|---|---|
| chr21 | 16209341 | 16209590 | GCT GTA ATG TGA CTA ACC CT | CTC CAG ACT CTG CAA GGA T | 1697, 1698 |
| chr21 | 16211270 | 16211519 | TTT CCC GAG GTT CAC AGA TA | TTT CCT GTT GCT CTT GAT CA | 1699, 1700 |
| chr21 | 16219907 | 16220156 | GAA CTT GTG TGA CCC AAA AC | CCA CAA AGA TGA AGG CCA AG | 1701, 1702 |
| chr21 | 16230785 | 16231034 | CAT TGC ACT GTG ATG TCA TG | CCA TAC CTT AGT TCT CAG GGT | 1703, 1704 |
| chr21 | 16236026 | 16236275 | GCA CTG GAA ATT GAC ATC AC | GTA AGA GAG AGC TGG GAC AA | 1705, 1706 |
| chr21 | 16241139 | 16241388 | GGG AGA GGC TGA AAG AAG AA | TGT GAC CAT CCT ATC CAC AA | 1707, 1708 |
| chr21 | 16242812 | 16243061 | TGT ATC ACT TCC TCA TGC CA | AGA ACC AGT TGT ACG AGT TC | 1709, 1710 |
| chr21 | 16246944 | 16247193 | CCA AGA GTT TCC TGT TTC CA | AGT CTT CTC CCT TCC TTG TC | 1711, 1712 |
| chr21 | 16265484 | 16265733 | ATG ACA CAT ACA TCC ATT TAC A | GCC CTT TTC TCT CTT TGA CC | 1713, 1714 |
| chr21 | 16273734 | 16273983 | CTC AAA CTG CCC AGT GAT TT | TCT TGT TCC AAG TAT TCC TGG | 1715, 1716 |
| chr21 | 16275865 | 16276114 | TCC TAG CTT GCC AAA GAA AT | ACC ACT TTA GCC CAT CTC TT | 1717, 1718 |
| chr21 | 16290234 | 16290483 | CCT CCT CTC CAG GCA TTT TA | GTG GTG GAT TAT TGA GCT GG | 1719, 1720 |
| chr21 | 16295877 | 16296126 | AAC AGA GTA GCA CAG AGA GT | TGC TTA ATG GGA TCA TTG ACC | 1721, 1722 |
| chr21 | 16296687 | 16296936 | TTC AGA GAG ACA GAC AGC AT | CCC ACA TAG TGC AAA AGA CA | 1723, 1724 |
| chr21 | 16298842 | 16299091 | AGA GGA AAA TCA CAA GCA GT | GTA TGT GTG AAG TAG CCG AG | 1725, 1726 |
| chr21 | 16316213 | 16316462 | TTT GAA AAC CCA ACA GAC CT | TGG TCC TAA CTC AGA CCT TT | 1727, 1728 |

FIG. 2BB

| chromosome | start | stop | forward primer | reverse primer | SEQ ID NOs: |
|---|---|---|---|---|---|
| chr21 | 16319836 | 16320085 | AAT CCA CAC ACC AAC AGA GG | AAC ATG AAG GGA AGG TTG TG | 1729, 1730 |
| chr18 | 64634331 | 64634580 | TGT TCA CAT CTG TTG GTT TGC | TAT ACT TCA ACT TGC AGG CAG | 1731, 1732 |
| chr18 | 64645925 | 64646174 | CTT ACT CGG TGG GTG ATA TTT | GCC AAA GAC AAT GAG AGA GTC | 1733, 1734 |
| chr18 | 64975938 | 64976187 | AAG AAA CAC CAG CAT CAG TTC | ATT TAG CAG CCA TGA CCA GTA | 1735, 1736 |
| chr18 | 64996573 | 64996822 | AGC TTT AGA GGT GAG TGA ACA | TGG GCC AAT TCC TAA TCC ATT | 1737, 1738 |
| chr18 | 65066425 | 65066674 | AGA AAC TTC ACT GTC TTC CAC T | CGA TCT CAT GAA TAA GTC TGA CC | 1739, 1740 |
| chr18 | 65073729 | 65073978 | TGT GAT GGA CAT TGG TAC CTG | TGG AAA GCA GAC TAA CAG TGA | 1741, 1742 |
| chr18 | 65074170 | 65074419 | ATA TCA TCT GCC TGT CCC AAC | GGG ACC CTA TGT AGA GAT TGT | 1743, 1744 |
| chr18 | 66343957 | 66344206 | GAG TGC TCT GTG TTT GTT TCA | GGA GCC CAA GGA TGT ATT AGA | 1745, 1746 |
| chr18 | 66344406 | 66344655 | TCA GTG GTG AGC TCT TGA ATA T | CTA ATA GCT GGT TCT GCA CAC | 1747, 1748 |
| chr18 | 66585247 | 66585496 | ACT CTC TCT TCA CAC ATG CAA | GAT GAA ATG AAT GCT GAC TCT C | 1749, 1750 |
| chr18 | 66596489 | 66596738 | GTG TTG AAG TCA GTA AAG CCT | AAA CTG AAG CTT CGA GAA CCC | 1751, 1752 |
| chr18 | 66601231 | 66601480 | TGC TTT CAC ATG GCA CTA GAT | TGC CGA CAA CTA CTT TAG GTA | 1753, 1754 |
| chr18 | 69966208 | 69966457 | GGA GAG AGA AAT CCC AAC TGA | TGT ATC CAA TCA CCT GTC AGA | 1755, 1756 |
| chr18 | 70088939 | 70089188 | GGG AGA TGT CAA CAC TAG GTC | CAG CAC CTT AAG CAG AAA TCA | 1757, 1758 |
| chr18 | 70093364 | 70093613 | ATA TGA CAT GGT GGC TCT CC | AAG CCC TTC ATC CAT TTC TCT | 1759, 1760 |

FIG. 2BC

| chromosome | start | stop | forward primer | reverse primer | SEQ ID NOs: |
|---|---|---|---|---|---|
| chr18 | 70107935 | 70108184 | AAC ATA GAG CCA TGG GAG GTA | ATC TTG GTG CCA TCT TAA GGT | 1761, 1762 |
| chr18 | 70198868 | 70199117 | GAT AGC CTT CAA ATC ATG CCT | AGC AAA CCA ATC GCA AAC TAG | 1763, 1764 |
| chr18 | 70200128 | 70200377 | GAA AGC GGG TGA ACA ACA ATA | AAT CAT CAT CTT CAT CAG CTC G | 1765, 1766 |
| chr18 | 70200907 | 70201156 | GAT AGA GAG CAC AAA GAG CAT | CCT TTC GCC TTG CTT ATA TGG | 1767, 1768 |
| chr18 | 70674976 | 70675225 | AAC AAG AGG AAT AGG AGC CAG | ACT ACT CAA CAG CCT ACC AAA | 1769, 1770 |
| chr18 | 70682967 | 70683216 | TGG GTG CTG ATA GTA ACA AAG | TGG AGC TGG GAA CTT TAA TGT | 1771, 1772 |
| chr18 | 73541191 | 73541440 | ACT ATT GAA CTG TTG GCT TCG | GAA GAG AGA GAG AAT GCG TGT | 1773, 1774 |
| chr18 | 73548315 | 73548564 | TCC ACT AAA GAG CAA CCA AAC | GAC ATG GAT ATT CTG GTG CCA | 1775, 1776 |
| chr18 | 73605288 | 73605537 | TGA AGT GGT CAG TAA CAA TGG | CTG TTG CAA GAT GAC CCA AAT | 1777, 1778 |
| chr18 | 73704485 | 73704734 | ATT TCA GAG CTC CTT TGT CCT | AGA TAC ACA CAC GTT CAC AAA C | 1779, 1780 |
| chr18 | 73752546 | 73752795 | GGC AAA GAA ATC TGG TGT TCA | GAT GGC AAT GCT TGA TAA CGA | 1781, 1782 |
| chr18 | 73764755 | 73765004 | TTG CTG GTT GAT AGG CAT TTG | TTC CAT GAA GTT CCT CAA GAC T | 1783, 1784 |
| chr18 | 73768420 | 73768669 | ATT CCC GCA ATT GTG AGA TTC | CCA CCC ACA TAC CCT GAA ATT | 1785, 1786 |
| chr18 | 73775027 | 73775276 | AAA GAG GTA CAG AAC TCA GAC C | GTA ACA CAC GGA TGC TGA AG | 1787, 1788 |
| chr18 | 73788751 | 73789000 | GTC TTC ATG AAC GTT GCC AAT | TGG ACA CGA GGC TAT TTG TAG | 1789, 1790 |
| chr18 | 73851108 | 73851357 | CTT CTC AGG GCT CTT TGT GTA | GGC TTA AGA AGG AGA GTG GTT | 1791, 1792 |

FIG. 2BD

| chromosome | start | stop | forward primer | reverse primer | SEQ ID NOs: |
|---|---|---|---|---|---|
| chr18 | 73854713 | 73854962 | GCA ACA GAA ACC AAG ATT CCT | TAG TTT CCT TTG GCC TTC TCC | 1793, 1794 |
| chr18 | 73871422 | 73871671 | TCA TTG TCT ACC TCA AAG AGC A | CTA GGG TTC CCA GTT CAC AAA | 1795, 1796 |
| chr18 | 73876103 | 73876352 | CTC TGA AGG AAC AAA GGA TGG | GAA ACA ACA TTG AGG GCA TTG | 1797, 1798 |
| chr18 | 73879805 | 73880054 | CAT TAG AAT GCG GTG GTT TCA | GAG CTC TTT GAA GTA GAA GCA | 1799, 1800 |
| chr18 | 73884248 | 73884497 | CAT GTC TGG GCT GAG GTT TAA | CCA TTC CAA CAA AGC TTC CG | 1801, 1802 |
| chr18 | 73931865 | 73932114 | TTC CTC TTG AAG ATG CAC TGG | CTA CTT GCC CTA TTG TGT CGA | 1803, 1804 |
| chr18 | 73938014 | 73938263 | CCA GCA TGT GAG GAA TTG AAC | CCA GGG TGT TTG AAG GTA GAA | 1805, 1806 |
| chr18 | 73943212 | 73943461 | CCC ACT TAG TCA TCC ACA CAT | CTG GAG GTA AGA AGG AAT GCA | 1807, 1808 |
| chr18 | 73947628 | 73947877 | GTT TCA CAC ACC AGA AGA GAG | ATG TGG GAC TCT TTG CTC TC | 1809, 1810 |
| chr18 | 73964168 | 73964417 | CCA TAC ACC TGC TCT GAC ATT | ATG AAT ACA GCT TTG CAT GGC | 1811, 1812 |
| chr18 | 73966321 | 73966570 | ATC AGT AAC AGT CCC ATT GCT | GTT AAA GCA TTC ACA GCC CTC | 1813, 1814 |
| chr18 | 73974071 | 73974320 | CAT GAG GCA TTT GAT CCA TGG | CTG GGA CTT GTC TAT CCT CCT | 1815, 1816 |
| chr18 | 73985549 | 73985798 | ACC CTG TTT CAC TGA ACA ACT | ATG TCT GTC CAA GTG AAC AGT | 1817, 1818 |
| chr18 | 73987174 | 73987423 | CCC TGT AAT GAG AGC GTT ATT | AAA GTA TCC AGA CCC AGA ACC | 1819, 1820 |
| chr18 | 48466086 | 48466335 | GAG AGA ATG GGT TAA ATC TGC C | ATA GGC CAG CAC TCC AAA TAA | 1821, 1822 |
| chr18 | 48928528 | 48928777 | CTG CCT GAC TTA GCC TTA AAT | CAA ATC AAG TCC CAT GGT AGG | 1823, 1824 |

FIG. 2BE

| chromosome | start | stop | forward primer | reverse primer | SEQ ID NOs: |
|---|---|---|---|---|---|
| chr18 | 48929078 | 48929327 | AAC CAG AAT GTT ACT AGC CCA | CTT TCC GTC TTT ATA GGC AGC | 1825, 1826 |
| chr18 | 48951524 | 48951773 | CAA TCC TGT GTG TTT AGT GGA | AGA AAT CGT GTT CAC AGC CTA | 1827, 1828 |
| chr18 | 48951856 | 48952105 | TGT GGG AAG CAT TGA CTC TT | CCG TAA ATG AAG TGG CTT GAA | 1829, 1830 |
| chr18 | 48959882 | 48960131 | TCC TGT GAG AAA TGG AGC TTT | CCT TTC TTG CAA CCT TGA GAT | 1831, 1832 |
| chr18 | 48960304 | 48960553 | GTT GCC AAG CTT AAA TAC CTG T | CTC TAG ATG CTC AAC CTC AGG | 1833, 1834 |
| chr18 | 49004516 | 49004765 | CCA CAA CAA CAT AAA CAC TGC | AAT AAC AGT CCA CCA GAA CCA | 1835, 1836 |
| chr18 | 49006425 | 49006674 | TCT TCC AGG CAT ATT CAT TGC | TCC AAG GAC CTG CAA ATG TTA | 1837, 1838 |
| chr18 | 49017695 | 49017944 | ATC CAT TCT CTC TAC TTG GGA | AGG TTA CAT CAT TCA CCC ACA | 1839, 1840 |
| chr18 | 49148010 | 49148259 | GGC TAG AGG GTG ATT ATA AGC T | ATG AAG ACA ATG ACA TCT GCG | 1841, 1842 |
| chr18 | 49149627 | 49149876 | TAC TCA TCC CGA TTT CTT CCC | CAC TTG TCA TGG TTT AGG GAC | 1843, 1844 |
| chr18 | 49149933 | 49150182 | TTC TCT TTC TCT TCT GGG CAG | ACC TCC ACC TTA TTG CTT CAA | 1845, 1846 |
| chr18 | 49150459 | 49150708 | TTG TGA GAC TCA AGG CCA TTT | GAA TTG CAA AGG ATG GGT AGG | 1847, 1848 |
| chr18 | 50239403 | 50239652 | TTG GTA GAG AGA GGC CAT TTG | CTG CAT TGT GAG TCC ATG TAA | 1849, 1850 |
| chr18 | 50242789 | 50243038 | GGA GGA AGC TCT TGA AGA CAT | TCC TAT CTT CAT CCC TCT TCC | 1851, 1852 |
| chr18 | 50243069 | 50243318 | AGC ATC TTC CGT TTA ACT CCA | TTC CAT TTA GCC TCC CAT CTG | 1853, 1854 |
| chr18 | 50243367 | 50243616 | CTG CCT GCC AAG TAT GTT CT | TAG CTT TAT GGG CCT TGT TCT | 1855, 1856 |

FIG. 2BF

| chromosome | start | stop | forward primer | reverse primer | SEQ ID NOs: |
|---|---|---|---|---|---|
| chr18 | 50247229 | 50247478 | CTA CTC CTT GTG TCA TTG GCT | CCA CCT CTC AAA CCC AGA TTT | 1857, 1858 |
| chr18 | 50308727 | 50308976 | TGA TTC TGA GAC ACG TGC TTA | GTC AGC GTA TTT GGG ATT GAA T | 1859, 1860 |
| chr18 | 50309031 | 50309280 | CTT GAG GAC CTT TCA TGC TTG | AAA TCT GCC ACC CAT TTC TTC | 1861, 1862 |
| chr18 | 50338747 | 50338996 | TTG TGA TTT CAG GTA GGA GGG | TAT TCT GAG TTC TAC CCA GGT | 1863, 1864 |
| chr18 | 50423284 | 50423533 | TTC CCT CAG AGA CAG TAT CCT | TAC ATG AGA CCC AGA AAC AGA | 1865, 1866 |
| chr18 | 50424422 | 50424671 | AAA GGA GGT CTG GCT TTG AA | CTT CTT GGC AGA CTA TCA GGA | 1867, 1868 |
| chr18 | 50424789 | 50425038 | GCA TAA ACC TGG ACT GTG AAA | AAG CTG CTA AAT CTG TAG GGA | 1869, 1870 |
| chr18 | 50448837 | 50449086 | CAC TCA GCG ATT CTC CTC AC | CTG ACC AGA CCT GTT GAC TAA | 1871, 1872 |
| chr18 | 50449492 | 50449741 | AAA GCC AGA CAC AGA CTA GTT | TGA TAT GTT CAG TTT GCC TAC C | 1873, 1874 |
| chr18 | 50514079 | 50514328 | ATT CCT GGG ACC ACA AGC AT | AGC TTG AGT TTC TTG CTG GG | 1875, 1876 |
| chr18 | 50519889 | 50520138 | TAT TGC CTC ATG TGG TTG TG | TTC CCG CAA AGT AGA AGC TAT | 1877, 1878 |
| chr18 | 56064244 | 56064493 | GTG TTG ACT TGA AAG GAA TCA C | AAA CGC ATA CAA ACA GGA GAC | 1879, 1880 |
| chr18 | 56148666 | 56148915 | CAG GTT AGG AAT GAC AGT GGG | CTT CTA AAC CCA TCA CCT GCT | 1881, 1882 |
| chr18 | 56149037 | 56149286 | TTA GGT TAC CCA GGG ACG TTA | CAC CCA AAC TCA CAG GTA CAA | 1883, 1884 |
| chr18 | 56244171 | 56244420 | CGG TTT GCT TTC TGA ACA ACA | TGA ATT CTG AGA TCG AGA GCC | 1885, 1886 |
| chr18 | 56245242 | 56245491 | CAT TTG GGA CCC TTT GAA ACT | AGA TTA ACT GTT GCC TCA CTG | 1887, 1888 |

FIG. 2BG

| chromosome | start | stop | forward primer | reverse primer | SEQ ID NOs: |
|---|---|---|---|---|---|
| chr18 | 56247063 | 56247312 | GGT TAT CTC TGG GCA AAG TTC | CAA GAC AGT GCA TTC CAT GG | 1889, 1890 |
| chr18 | 56527049 | 56527298 | TAG AGA GCA GAG AAC AAA CCC | CCA AGG AAA GAG TTG AGA AGG | 1891, 1892 |
| chr18 | 56528011 | 56528260 | ATA AGG GCA TTT GGA GGG AAA | TGA CTG CAG TCG ATA AGG AAG | 1893, 1894 |
| chr18 | 56532190 | 56532439 | AAT GCA CAC TTA GAC ACC ACA | AAC ACC GAG AAA GAG AGA GAG | 1895, 1896 |
| chr18 | 56532882 | 56533131 | CGA TTG CTA CCC AGG AGA TAA | TCT ACT GCT TTC GTC TTA TGC | 1897, 1898 |
| chr18 | 56534208 | 56534457 | AGA GGT TCT GTG TAT GAG TGT | CAT ATT CGC ACT GTA TAG CCG | 1899, 1900 |
| chr18 | 56601487 | 56601736 | TAG AGA ATT GTA CGC TGG ACA | CTG ATG GAT TCT CTG GTG TGA | 1901, 1902 |
| chr18 | 56633131 | 56633380 | TCT GGA GAA ATG CAC AAG AGA | TCA AGG AGA AGA GAG AGG GTA | 1903, 1904 |
| chr18 | 56635259 | 56635508 | TGG GTT AGA ACA TGG TGC TTA | TCT CCC AAA GCA GAC AAA GAC | 1905, 1906 |
| chr18 | 56719296 | 56719545 | ATC GCA TCA CAC CCT TAC TAT | AGT CAG TTG TTA CGT GCA AAG | 1907, 1908 |
| chr18 | 58037828 | 58038077 | GGA AAT TTA GCT TGA CAT GGC | AAA GGT TTG TTC ATC CTC CCT | 1909, 1910 |
| chr18 | 58038328 | 58038577 | TTT GTA AAT CCA CAG TGC CTA C | ACA GAG CAC GCA ATA TAG GAA | 1911, 1912 |
| chr18 | 58039111 | 58039360 | GGT ACT GGA GAG CAT AGA AGA | CTG CAT TCA CCC ATG TAC TTT | 1913, 1914 |
| chr18 | 58040290 | 58040539 | AAA CAA GCT ATC TTC AGG CAG | TCC AGC CAT ACC ATG TCT ATC | 1915, 1916 |
| chr18 | 59424085 | 59424334 | CGA ACA ATC AGA GAC TCG ACT | CTC ACT AGG GAA GAA CAG CAG | 1917, 1918 |
| chr18 | 59424765 | 59425014 | CTG GTT GAC AAT CTG CAA GTT | TGC TGG GTC TGA GTG TTA TAA A | 1919, 1920 |

FIG. 2BH

| chromosome | start | stop | forward primer | reverse primer | SEQ ID NOs: |
|---|---|---|---|---|---|
| chr18 | 59441324 | 59441573 | ACC ATC CAA GTC GTC TTC ATA | GTT CTG TGA ATG GTG CTG TTA | 1921, 1922 |
| chr18 | 59499718 | 59499967 | ATA GCT ACG CAT ACC CTG TAG | GGC CCA GAA GAC TCT TGT AAT | 1923, 1924 |
| chr18 | 59500226 | 59500475 | AGC AGA AGA AAC AGT AAG GCA | CGA CCT ACA TCA GCT AAT GGT | 1925, 1926 |
| chr18 | 59507920 | 59508169 | ACC CAG GGA CCT ATT TGT TC | AAG GGA AGA ATA ACA ATG GTG C | 1927, 1928 |
| chr18 | 59543044 | 59543293 | CAA GGG CTC AGG TCT TCA TTA | ATG GGA GTA TGG GAG TAG GAA | 1929, 1930 |
| chr18 | 59556453 | 59556702 | TCA CTG TGA CTT GGA GAC TAA | TTG GTG GCT TGC AGA GAT TT | 1931, 1932 |
| chr18 | 59614976 | 59615225 | TGC TCT GCT TCA CTG TGA TTA | TCA CAC GAT CAT CAT ACT CAC A | 1933, 1934 |
| chr18 | 59625553 | 59625802 | GAT GAA TGA CTA ATA GCC CAC G | GGT AGC AGA TGA CTA GAC GAT | 1935, 1936 |
| chr18 | 59631090 | 59631339 | CCA TGT TTA GTT TGG TGC TGT | ACG CCT CTG TCA TTT CCT AAC | 1937, 1938 |
| chr18 | 59631779 | 59632028 | AGC CAA GTG AGG TGC TAA AT | CAG TTG ACT CAA TGG TGC AAT | 1939, 1940 |
| chr18 | 59632388 | 59632637 | TCA GGG AGA AAT GAT GTC ACC | ATA GGT TAC AGA TTG CCA CGT | 1941, 1942 |
| chr18 | 59695718 | 59695967 | CAG TAG CTG GCA AGA ATC ATC | GAT GCT GCT ATC AAA GGA ACA | 1943, 1944 |
| chr18 | 59696087 | 59696336 | CAA CAC TGC TAG AAT TCC CAA | AAG ACA AAG AGA TGG AAG GCA | 1945, 1946 |
| chr18 | 59696563 | 59696812 | CCT GAG AAG CAC CTG ATT GTA | AAT ACC CTC TTC CCT TCC TCA | 1947, 1948 |
| chr18 | 59712419 | 59712668 | TGT TGT CAG AAA TCC CAG GAA | CCA CCG TCA ATA TTT ATC AGC T | 1949, 1950 |
| chr18 | 59756979 | 59757228 | AAC TGG AGC CAT ATA ACG ATG | GCC TCA GTC CAA ATC TTA GAT | 1951, 1952 |

FIG. 2BI

| chromosome | start | stop | forward primer | reverse primer | SEQ ID NOs: |
|---|---|---|---|---|---|
| chr18 | 59770789 | 59771038 | GAA ATG GTG CCC TAT TGT TGA | CCT TAG GAT TCT CAA AGA GTG T | 1953, 1954 |
| chr18 | 59805993 | 59806242 | TCT TAC ATG CAG TCA TAC TCC T | GCA GTA CAG ATT CTT GAA CAG T | 1955, 1956 |
| chr18 | 59813876 | 59814125 | GTC CCT CAG TAA CAC CAT CTT A | AGA GGA TTA GAT GTC TTG CTG T | 1957, 1958 |
| chr18 | 59855411 | 59855660 | GAA GCA AGA GGA TCA GGC AAT | TAC TGC AGG CAA TTC AGG TAA | 1959, 1960 |
| chr18 | 59909054 | 59909303 | AGT GTT TCA GAG GCT TGA AAG | GAA CAG GTC CAG TAA GTG AGG | 1961, 1962 |
| chr18 | 59909336 | 59909585 | ATC CGG CAT CCT TTA AAC TCT | TTG TGA GTC CTT GTC TCC TTG | 1963, 1964 |
| chr18 | 59910140 | 59910389 | AGG CTA GGA AGA AAT GGG AAA | GAC GAC TAA GAC ATT GCA TCA | 1965, 1966 |
| chr18 | 59910602 | 59910851 | ACA CAT ATG CTC TGT CTC TCA | AGA AGT CTC TCT CCG TTG TTT | 1967, 1968 |
| chr18 | 59973803 | 59974052 | AGT TAG TTA TCA CCT CGT CCC | CTT ATG TGC ATC AAC TGT GCT | 1969, 1970 |
| chr18 | 59996728 | 59996977 | TGT GTA TTT CCC TCT AGT TGC A | AGT GTC TCT CAG AAT CAG GAC | 1971, 1972 |
| chr18 | 60010541 | 60010790 | AGC CTC TTT CTA CAT CGT TCG | TTT ATT TCC CTA CGC AAA GCC | 1973, 1974 |
| chr18 | 60011381 | 60011630 | TTA CCT GTG CAG AAG AGT GAC | AGC CTT TGA TGA CTG AGT TGA | 1975, 1976 |
| chr18 | 60240694 | 60240943 | TCT TGT GTT CTA GCG TGT TTG | TTG GTT TCT ATT CTG CAC TGC | 1977, 1978 |
| chr18 | 60378353 | 60378602 | TGT GGT TAG TCA GAA ATG TGG | TTA GAG CTT GCT AGT ATC GGG | 1979, 1980 |
| chr18 | 60384593 | 60384842 | GGG TCC TGA TGA GTC TTT GTC | GAA ATC CCA AAC TGC CTG AAA | 1981, 1982 |
| chr18 | 60384979 | 60385228 | TGG TGC CTT TGT TTA TTC AGC | ATC CTT CTT GTG AAC CTT CCT | 1983, 1984 |

FIG. 2BJ

| chromosome | start | stop | forward primer | reverse primer | SEQ ID NOs: |
|---|---|---|---|---|---|
| chr18 | 60389544 | 60389793 | TGT TAT GTG CCA GGG TTT AAC | ACC AGA TGC ATG TGA TTA AAG G | 1985, 1986 |
| chr18 | 60401084 | 60401333 | ATT GGT TCC AGA TAC AGT CGA | GTG TAC TCT AGG CTA CTG TCA | 1987, 1988 |
| chr18 | 60412199 | 60412448 | GGA AGG AAG TAC AGC ATG GAT | GTC AGC AGC AAG TAA AGG TTC | 1989, 1990 |
| chr18 | 60420053 | 60420302 | CCT TAT TGA AGC TGA CCA TGC | CAT CTA GTC AAG GGT TCC ACA | 1991, 1992 |
| chr18 | 60434561 | 60434810 | CAG TGG GAA ATG TGC TTA CAT | CAA GTC ATG CTC CAA ACT GTT | 1993, 1994 |
| chr18 | 60449047 | 60449296 | AAA GGG CCT ATA TTC ACC AGA | AGG ACT TAG GAC AAC AGA GAA | 1995, 1996 |
| chr18 | 60452471 | 60452720 | AGA GCC ATT TAA GAC TCT CTG T | TGC CCA ACA CCA TCT CTA ATA | 1997, 1998 |
| chr18 | 60456757 | 60457006 | TAC CTT GTT CTC TGC CTC AAT | GCC TTC ATC ACT CAG AAC TTC | 1999, 2000 |
| chr18 | 60467147 | 60467396 | TTT AGA AGG ATG TGG ACA GGG | AGG GTA TCT ATT CTC CGG ACA | 2001, 2002 |
| chr18 | 60469757 | 60470006 | AGC AGG ACA TGG ACT TCA AA | ATT TGC CCA AGT AAG TTC CAC | 2003, 2004 |
| chr18 | 60514168 | 60514417 | GCG GCT CTT GTT TCT GAA ATC | TGG AAG TAC ATG GGA TGC ATT | 2005, 2006 |
| chr18 | 60537888 | 60538137 | ACA GGT AGG AGT TCA GAG ACA | CTT GAA GAG TTC CAA TGC CAA | 2007, 2008 |
| chr18 | 60544380 | 60544629 | TTT CCT ATT CTG CTC TTC TGC T | CGC TGC TGT TTA AAT CGA TCA | 2009, 2010 |
| chr18 | 60544742 | 60544991 | AAA TGC TGC TCA GGG TTA GAG | GCT CTG CTT TGC TCA AAT TCT | 2011, 2012 |
| chr18 | 60545407 | 60545656 | CAA CTT TAC TCT GCA CAG CTC | TGA GCT CCA GAA TTA GAT GTG T | 2013, 2014 |
| chr18 | 60611934 | 60612183 | CAG TGC CAC TAC AAA GAA ATC A | AAC ACC TCC TTT CTC ACT ACA G | 2015, 2016 |

FIG. 2BK

| chromosome | start | stop | forward primer | reverse primer | SEQ ID NOs: |
|---|---|---|---|---|---|
| chr18 | 60617081 | 60617330 | AGA AGC AGA GGT TGG ATA TGG | ACA AAC TTC ATT CAC CGC AG | 2017, 2018 |
| chr18 | 60617641 | 60617890 | CCA CAA TCC CAT AGT CAC CAT | AAC TAC GCC ACC CAA CTA AA | 2019, 2020 |
| chr18 | 60630438 | 60630687 | GCT GGT TCT TGT TGC TGA TAA | GCT TCA GTG TAA CCA TGA CTC | 2021, 2022 |
| chr18 | 60630849 | 60631098 | TCC CTC ACG ACT TAT GTT TGA | TGC ACA ATT AAG CTA CTT CTC C | 2023, 2024 |
| chr18 | 60639840 | 60640089 | CTA CCT TCT CCA GTG CAC TAT | CAA CAC CAA ACT TGC CTG AAT | 2025, 2026 |
| chr18 | 60640300 | 60640549 | GGA CCT CTC TTT GAA ATG GAC | TCC ACA ATT TCT ACA GCA ACC | 2027, 2028 |
| chr18 | 60776944 | 60777193 | TGG GTT GTG TTT CTC TGA CTT | GTG TCA TTT GAT TGG TGC TCT | 2029, 2030 |
| chr18 | 60813738 | 60813987 | TAC AAG CCT CCT TTA ACC CTT | GGG TGT TTC AGT AGG TTA GGA T | 2031, 2032 |
| chr18 | 60814585 | 60814834 | AAA GGG TTT GAT ACA GTT GGG | TGG GAT TCT AAT GTC TGG TGC | 2033, 2034 |
| chr18 | 60938666 | 60938915 | AGG TAT TGG AGA GCA AGA AAG A | AGA GGT GGT TGG TTG GTT | 2035, 2036 |
| chr18 | 60939202 | 60939451 | GCA AAC TGG AGC TAA AGT CAT | GGG CAT CCT GTC TGA AAT ATG | 2037, 2038 |
| chr18 | 60950541 | 60950790 | TTG GTT GCT AGC TCT CAA ATG | AAG AAG CGC AGA TAC AGT ACA | 2039, 2040 |
| chr18 | 60953225 | 60953474 | TTC AAT GCC CTT ACT TCT CCT | CAC AGC AAG TTT GAA CCT AGT | 2041, 2042 |
| chr18 | 60958474 | 60958723 | GCT TGA GGC GGA TAT GAT TG | AGT GCA AAT GAT GAC CTG TTG | 2043, 2044 |
| chr18 | 60960879 | 60961128 | CAT ATG GTG CTT GTT CTG GG | GAA CTG TTG CAT GAG AGG TAC | 2045, 2046 |
| chr18 | 60965583 | 60965832 | CAA ACT CAC CAC CCT TCA TTC | CTT TGT CCT TCT CTG TTG TGT | 2047, 2048 |

FIG. 2BL

| chromosome | start | stop | forward primer | reverse primer | SEQ ID NOs: |
|---|---|---|---|---|---|
| chr18 | 60970051 | 60970300 | CCT TAG CCC TGC AAA TAA CAC | TTT CTT CTA GAG TCC AGA GGT G | 2049, 2050 |
| chr18 | 60974839 | 60975088 | TCA CAG ATA GGG ACA AGC TC | ATT CTC TTC TCT CTT CCA GCC | 2051, 2052 |
| chr18 | 60984378 | 60984627 | GCC ACA GGT ATC AAT CAC TTC | TAT GGC TTT GCT ACC TTG TCA | 2053, 2054 |
| chr18 | 61055997 | 61056246 | GCT TCT GTG GCA CTA ATC AAG | CTA TTT CTC TGG CTC TTG ACC | 2055, 2056 |
| chr18 | 61088669 | 61088918 | GCC TTA TTG ACT TAC TGG ACT G | TTC TTA AAC CTC TGT GTG GCT | 2057, 2058 |
| chr18 | 61090462 | 61090711 | GTC AGG GAT TAG AGG CAG AAC | TGG ACA AAC AAG AAC TGG GTA | 2059, 2060 |
| chr18 | 61100325 | 61100574 | CAA TCA CTT GGT CAG ATA GTG T | CCA TGA TCA CTG AAA CCA ACA | 2061, 2062 |
| chr18 | 61154459 | 61154708 | AGT GGA GAG GTT GAG TAT AGT G | CCA TAT GCC CTG CTC TTT AAG | 2063, 2064 |
| chr18 | 61162901 | 61163150 | TGA GAA GGG AGG AAG AAT GTG | GGG TGG ACA AAG CAA TTC AAA | 2065, 2066 |
| chr18 | 61170629 | 61170878 | AAG GTC AAA CTC TCC ATT CCA | CAG CAT TCA ATT CAT CCT TGT G | 2067, 2068 |
| chr18 | 61197492 | 61197741 | GGA GAT GTC TTT GCC CTG ATT | AAG TAG AAG CAA GCC CTG AAT | 2069, 2070 |
| chr18 | 61213452 | 61213701 | GGT CCT CGT TTG TCC TTA AGA | GTG TGG TAG GGA TGA GAA TTA T | 2071, 2072 |
| chr18 | 61213900 | 61214149 | AGT ATT GCT TTG AGG GCT CTA | TCA GGT AAG CTT CCC TCC AC | 2073, 2074 |
| chr18 | 61216749 | 61216998 | AGC TAT CAT GTA AGT CAC TCC C | ACT GGT TGT AGA AAG GAC CTC | 2075, 2076 |
| chr18 | 61232928 | 61233177 | AGG AAA TTC AGT ACC TCA GCT | AGT AAG AGG CCA GAA GTC AGA | 2077, 2078 |
| chr18 | 61236079 | 61236328 | CAA CCT TCT CAT TGT TGA AGC T | GCA GTG CAG GCC TAT ATA TAG | 2079, 2080 |

FIG. 2BM

| chromosome | start | stop | forward primer | reverse primer | SEQ ID NOs: |
|---|---|---|---|---|---|
| chr18 | 61253277 | 61253526 | GGT GAC TTT GCT TTC CCA AG | AAA TCT CTG AGT CGG CCA TAA | 2081, 2082 |
| chr18 | 61259478 | 61259727 | GCT GAC AAA CGG AGG GAG AG | AGG CAT GGC AAA CTT ACT TG | 2083, 2084 |
| chr18 | 61264533 | 61264782 | TGT TCT TCA TCA GGC ACA ATG | CAT TTC ACT TTC GAG GAT GGT | 2085, 2086 |
| chr18 | 61289440 | 61289689 | ACC ATT TGT GTG ATC CAG AAC | GTC AGA CTA AAG TGA GGA CCA | 2087, 2088 |
| chr18 | 61368889 | 61369138 | CTT GTC TTG AGT GCG GTA CA | CCA GCC CTA CCT AAA GTG AAT | 2089, 2090 |
| chr18 | 61370663 | 61370912 | GCC TCT CAG TTT CCT CTT ATA G | CCC TTT CAC AAG ACT CTT CTC | 2091, 2092 |
| chr18 | 63685629 | 63685878 | CCT AGA TCA GTG CAG AGA ATT TAG T | | 2093, 2094 |
| chr18 | 63711583 | 63711832 | CTT TAG TTT GGA GGC CTC ATT C | CCA AAT GTA GAA CAG GAT CAG C | 2095, 2096 |
| chr18 | 63721183 | 63721432 | CTG ACA TCG ATG GAA TTC TGG | TAG CAG TAG GTG TGG CTT TC | 2097, 2098 |
| chr18 | 64379625 | 64379874 | ACA CTG CAC GAA TGG AAG ATC | TTG GAT TCT CTT GGT TGT GAG | 2099, 2100 |
| chr18 | 64398368 | 64398617 | ATA AAC TTG GTG CTC AGT GGT | CAA CGC TTT GGT ATA GTT TGT G | 2101, 2102 |
| chr18 | 64410092 | 64410341 | ACA AGC ATT ACA GAA TTC GGC | CCA GGT GCC ATC GTT AAA GAA | 2103, 2104 |
| chr18 | 64412606 | 64412855 | ACT GAC AGA TTC TCA CCT ATA TCA G | | 2105, 2106 |
| chr18 | 64417267 | 64417516 | GGA TCA AAG CCA CTC TAG ACT | GGA TAA GTC AAC TAC CAT GGT T | 2107, 2108 |
| chr18 | 64421562 | 64421811 | TTG AGA TGG CAT CAA GTT CAA G | AAT GGA ATT ACT CAG CTG TGG | 2109, 2110 |
| chr18 | 64426871 | 64427120 | ACT GGA TTC ATG CGT TAT CAA G | GGC AGA AAC TGA TAG AGA CTG | 2111, 2112 |

FIG. 2BN

| chromosome | start | stop | forward primer | reverse primer | SEQ ID NOs: |
|---|---|---|---|---|---|
| chr18 | 64436287 | 64436536 | TAT TCT TGT GTG GAC CCT GTG | ACC ATG TTC TGA GTA CCT CTT | 2113, 2114 |
| chr18 | 64593727 | 64593976 | TGA TAT TGC ATG AAA GTC CCT G | AG TCC TGA ATC AAT GTC TAA CAC | 2115, 2116 |
| chr18 | 24962594 | 24962843 | TCA CAC ATG AGG AGT AGA CA | TGG TCC CTG TGC TTT GAT AT | 2117, 2118 |
| chr18 | 24964748 | 24964997 | CAC AGC AGG AGA CAT GAG AA | TGG CTT TTC TTT CCT CGG TA | 2119, 2120 |
| chr18 | 25003553 | 25003802 | TTT CCT CCT GGC TTG ATC AC | CCA AGG CTG CTT TAA TTC CA | 2121, 2122 |
| chr18 | 25033345 | 25033594 | CAA AGG AGA GAA GTG ACC CA | CAA ACT ATC GCT GAG GAC CT | 2123, 2124 |
| chr18 | 25037434 | 25037683 | CTA CGA GTG AAA CAG AGT GC | GTC TGC TGC CAT TGA GTT AT | 2125, 2126 |
| chr18 | 25052992 | 25053241 | AGA CTA AAA GCC TCC AAG CC | GCT CAC CCT CTC TTC TCT CT | 2127, 2128 |
| chr18 | 25080042 | 25080291 | TAG AAT ATG TCA CCC AGC CC | ACC TGT TTC TCC CAG TTA CA | 2129, 2130 |
| chr18 | 25124915 | 25125164 | ACA GAA TCA TCC CAT AGC CA | GCC CAT GAA AGA GAA ACC AG | 2131, 2132 |
| chr18 | 25128057 | 25128306 | CGC CAT TCT GTG CTT AAT TTG | CTC CAT CAG TGC AGA AGT CC | 2133, 2134 |
| chr18 | 25140257 | 25140506 | GTG AAG CAA GAG AAA GCA AGA | ACA GTC AGC AGC CCT AAA AT | 2135, 2136 |
| chr18 | 25140722 | 25140971 | TGA TTC GGC TGC AGG TTA TT | GCC TCC TTC ACA TAA TGC AG | 2137, 2138 |
| chr18 | 25147759 | 25148008 | CTG GCT TCA AAT GCA TCT GA | TTG TCA ACA GAG AGT CAG CT | 2139, 2140 |
| chr18 | 25157828 | 25158077 | ACT GGG AAA TTG GAA TTC GC | CTG AAA TGG TCT GGG AGT CT | 2141, 2142 |
| chr18 | 25160244 | 25160493 | GGT AAA ACT GCC TGG AAA CT | TCA AAG ACA GAG TGA GTG GA | 2143, 2144 |

FIG. 2BO

| chromosome | start | stop | forward primer | reverse primer | SEQ ID NOs: |
|---|---|---|---|---|---|
| chr18 | 25166354 | 25166603 | AGA CCA CGG GCT CTA TCT AT | TTT GGG GGT TAC ACT TCA TAG | 2145, 2146 |
| chr18 | 25172986 | 25173235 | CAT CTT GCT TAT TGG CTT ACG A | AGC CAG CAG AAT AAT ACC AGG | 2147, 2148 |
| chr18 | 25174972 | 25175221 | GAG GTA GAG GCA GTG TCT TG | ACC TCA TCT TTT GTC AGC CT | 2149, 2150 |
| chr18 | 25175640 | 25175889 | TAG TCC TTG AAC TCC CTG GT | ACA GTT CCA TAG GCA GGT TT | 2151, 2152 |
| chr18 | 25182855 | 25183104 | CCA GCT TAG GGT CTG TTT TT | GCA GTT CCA GAT CCA ATA TGC | 2153, 2154 |
| chr18 | 25198531 | 25198780 | GAC CAC AAC TAT CAA GAG CAC | TTT GGG AAA GAT GGG AGA GC | 2155, 2156 |
| chr18 | 25201886 | 25202135 | CCA AAG AAA GGT TGA AGC CC | TTG CAG GTA AGG TAC AGA AGA | 2157, 2158 |
| chr18 | 25209395 | 25209644 | AAT AAT GTG CAC TGT GAT GGC | CTT CAG CTG CAT CTT GAG C | 2159, 2160 |
| chr18 | 25213880 | 25214129 | TTT AAG GGT CTG ATG GTT GC | GGC ACT TCA AAA ACA AAC CC | 2161, 2162 |
| chr18 | 25216888 | 25217137 | GAA AAT GCC CAT CGT CTC AA | AGG GTT TTA TGG TCT CCT GG | 2163, 2164 |
| chr18 | 25228617 | 25228866 | ATT CCT TGT CTT TCC CCC TC | TCA ACA CGG AGA ACT GAA AAC | 2165, 2166 |
| chr18 | 25231535 | 25231784 | TCA TTT CTC TAG CCC AAA GAT G | TCC GTG TAA ATG AAC AAA GCA C | 2167, 2168 |
| chr18 | 25245662 | 25245911 | TTG GTT TGT TGA CTT CAG CC | TTC AGG GAA TGG TTT GCA TT | 2169, 2170 |
| chr18 | 25246300 | 25246549 | GCT CAG TGA CAG TTG GGA TT | GAG ATG CCA TTC CCA AAA GG | 2171, 2172 |
| chr18 | 25254843 | 25255092 | GTC TTG TCT CTC TTC TTC CAC T | CCC TAC CAT AGT GCC AGA TG | 2173, 2174 |
| chr18 | 25265476 | 25265725 | TTT AGA GCA GGT GGA AAC GA | CAG CTT TCA GTG ACA GAG GA | 2175, 2176 |

FIG. 2BP

| chromosome | start | stop | forward primer | reverse primer | SEQ ID NOs: |
|---|---|---|---|---|---|
| chr18 | 25278532 | 25278781 | CTT GGG TTT TTA TCG GTT GCT | CCA AAG GCA GAT GAG TGT TT | 2177, 2178 |
| chr18 | 25279010 | 25279259 | GTT GCC TGG ATT GCT CTA AA | GCC TGG GAT AGA AAT GGG AA | 2179, 2180 |
| chr18 | 25283817 | 25284066 | AAA TCA CGA CGT AGG AAA CC | GGA AAG GAA AGG AAG CTG TG | 2181, 2182 |
| chr18 | 25292042 | 25292291 | TCA CCT TGG AGC AGG TCA TA | TCA GAG AGG TCT TGC TGA AG | 2183, 2184 |
| chr18 | 25295429 | 25295678 | CGA AGA AGG TCT GGG AGA TG | TCT CTC TGT TGC TTG TTT CCT | 2185, 2186 |
| chr18 | 25330345 | 25330594 | CAC CAT TGT TTC ATC AGG ACT | CGC ATG TGG TAG ATC ATC AG | 2187, 2188 |
| chr18 | 25332963 | 25333212 | TTG CAT CAT CAG CTC ACA TAC | TAT AAC ACC CTC ACC TCC CA | 2189, 2190 |
| chr18 | 25333284 | 25333533 | AGA CCT GGA AAA TGA TGG GT | CAC CCA AAT CAC CTT GCT ATG | 2191, 2192 |
| chr18 | 25345252 | 25345501 | CCT GGA AGT GTG TAA CAA GC | CAA CTA CCG TGG ATT CCG TT | 2193, 2194 |
| chr18 | 25384702 | 25384951 | CTC CCT AGC AAA AAC TTC TCA | TCT ATC ATG AGT CGC TTC CA | 2195, 2196 |
| chr18 | 25510767 | 25511016 | TGC CTT ATT CAC TGT GCA AC | TTT CTG TCA CTT TCT GGG CT | 2197, 2198 |
| chr18 | 25519108 | 25519357 | TGA TGG CCT AGT GAG TTT CC | CGT GTG TTT CTA GTG CAT TGT | 2199, 2200 |
| chr18 | 25531724 | 25531973 | TGC AAT GTA ACA AAA GCG TG | GGG CTC AGA GGG AAT ATC AG | 2201, 2202 |
| chr18 | 25543168 | 25543417 | GCC ACA TTT GCT TTC ACA CA | CCG ACG AAT GGA TGA AAG AC | 2203, 2204 |
| chr18 | 25547425 | 25547674 | ACG TCA TTG GGT TCA TGG C | ACC CAA ATT CCA TGC CTA CT | 2205, 2206 |
| chr18 | 25557343 | 25557592 | ATT TTA CCC CCT TAG GCA CC | TGT ACA GCA GTC TCC AGA AA | 2207, 2208 |

FIG. 2BQ

| chromosome | start | stop | forward primer | reverse primer | SEQ ID NOs: |
|---|---|---|---|---|---|
| chr18 | 25564483 | 25564732 | TCT TCT ACA CAG CCC TTC AG | GCC CTC TTA CCC TTT CTC AT | 2209, 2210 |
| chr18 | 25583087 | 25583336 | ATT GGG ATC GTC AGC ATC AA | CAT TCA AAG ATC CAG ACC AGG | 2211, 2212 |
| chr18 | 25585083 | 25585332 | TGA TTG TCT TGT CCA CTG GT | ATC TGT GAT TGC TGC CCT C | 2213, 2214 |
| chr18 | 25589902 | 25590151 | ACA TCA CAC TTC ATG CCC TT | CTA GAA ACT CCC AGG ACA GA | 2215, 2216 |
| chr18 | 25601966 | 25602215 | ATG AAG GCA TTA GGA GGG AG | CAT GTG TGG AAA GGA TTG GT | 2217, 2218 |
| chr18 | 25611986 | 25612235 | AAA GTG GAG AAG TGG CAG AT | TAT GAA TGA ACC GTG GCT CA | 2219, 2220 |
| chr18 | 25617498 | 25617747 | CCT TAG GAT TCT GAG AGG TGA G | AAG TTG AGT CGT TTG TCC CA | 2221, 2222 |
| chr18 | 25629105 | 25629354 | AGG GCT TCT GAT TGA TTT GC | TAG TGT TTC AGG AGC GTG TT | 2223, 2224 |
| chr18 | 25631180 | 25631429 | CAG GGT AGT CGG GAT TTC TC | CCA GGA CAA GCA GAC ATT TT | 2225, 2226 |
| chr18 | 25643639 | 25643888 | CCC GGT AAT GAT CTA CAG CA | GCT GCT GGT GAT TTT TGA AGA | 2227, 2228 |
| chr18 | 25645371 | 25645620 | AAC GGC ACT TGG TTC ACT A | CTC TGG GCA AAC AAG AAA CC | 2229, 2230 |
| chr18 | 25665025 | 25665274 | ACT CTG AAC TCC TCC TCC TG | GTG TGT GTT TGT GGA AGT GT | 2231, 2232 |
| chr18 | 25666614 | 25666863 | TTT GCT CAC ACA CAA GAC AC | AAA GCC CAA TCT CTC TGG TTA | 2233, 2234 |
| chr18 | 25667057 | 25667306 | ACG ACT GCA TCC TTT TCA TC | TAG GCG GGC TTA TTG TGT TT | 2235, 2236 |
| chr18 | 25670741 | 25670990 | CCA TCA TAG CCT ACA AAT ACC C | TCA ATG TAA ACT GCC CGG AG | 2237, 2238 |
| chr18 | 25673208 | 25673457 | AGA GAG TTG AAA ATA TCC CCC A | ATG GGA GTC GAA TGG TGT AAA | 2239, 2240 |

FIG. 2BR

| chromosome | start | stop | forward primer | reverse primer | SEQ ID NOs: |
|---|---|---|---|---|---|
| chr18 | 25681018 | 25681267 | ACT TTC TTG AAC ACC CCA GT | TAA CAT TTG AGG GCA TGG GA | 2241, 2242 |
| chr18 | 25682079 | 25682328 | TGC CTG TGT CCT ACT TTT CC | CAG AAT ACC CTC ACT GTG CT | 2243, 2244 |
| chr18 | 25689906 | 25690155 | TGA CTG CCC AAG AAT GTA CA | GGA GAT AAC AGC AGA GGT CC | 2245, 2246 |
| chr18 | 25700540 | 25700789 | CCG AAC ACG CTG TAT GTA TT | TGT GGG TGA TAT CTG TGT CT | 2247, 2248 |
| chr18 | 25703648 | 25703897 | GGA AGG GAA TTG AAG CAC AG | GCC ATC CTG TAA CTG AAT GC | 2249, 2250 |
| chr18 | 25707188 | 25707437 | TCA TCC TAT CCA CCA ACC TG | GTA TTT TCC CTT TGC CGC AG | 2251, 2252 |
| chr18 | 25716100 | 25716349 | AAT GAA CTG GCC CTG ACT TA | ATT ACA GCA AAG AAC GTG GC | 2253, 2254 |
| chr18 | 25722951 | 25723200 | TAA GAT ACC ATA CCG CAG CT | TCT GTG TGT TTT GCA TTG GT | 2255, 2256 |
| chr18 | 25725055 | 25725304 | TCA GCG TTC ATG GTA CCA ATA | GTG ACA GTT TTC CAA GGC AT | 2257, 2258 |
| chr18 | 25748105 | 25748354 | GTT TCC CAA CCA ACA AAC AAG | GCA TTA CTT TTT CGC ACA CT | 2259, 2260 |
| chr18 | 26214441 | 26214690 | TCT ATC GGG ATG GAG AGT GA | GGG GAT TGT TTT AAG CAG GC | 2261, 2262 |
| chr18 | 26236788 | 26237037 | GTT CAG ACA GGT GGA CTA GG | CCA TTG TTC TCA CCA ACT CT | 2263, 2264 |
| chr18 | 26261336 | 26261585 | AAG CAA CCT GGG AAA TTG TG | CCT GAA ACA CAA GCA GCA G | 2265, 2266 |
| chr18 | 26265937 | 26266186 | GGG TTA AGG TTG CTG GGT TA | AGC TGC CTA TTT GAT TGG TG | 2267, 2268 |
| chr18 | 26285286 | 26285535 | GTG AAA TGT GGT TGT AGT GCA | CAG TAC AGT CAG CCT TCC TT | 2269, 2270 |
| chr18 | 26289006 | 26289255 | GTG ACT GCC TTG CTT CAT TT | TGC ATT CAA ACT ACC CCA AG | 2271, 2272 |

FIG. 2BS

| chromosome | start | stop | forward primer | reverse primer | SEQ ID NOs: |
|---|---|---|---|---|---|
| chr18 | 26308405 | 26308654 | CAG TTC TGG AGC CTT CTA CT | CCG AAA AGA GGC AAG CAA TT | 2273, 2274 |
| chr18 | 26308962 | 26309211 | TTA GGG CAG GAT GTA CAG AA | GTC ACC TCA ACC TAA CTC CA | 2275, 2276 |
| chr18 | 26312054 | 26312303 | GCT GGT GAC CTT CAT TCA AG | GCA ACA GTC TAC CCG TCT AG | 2277, 2278 |
| chr18 | 26316149 | 26316398 | TAA AAC CAT GTT CGG GGC A | ATC AAT GCT CTG ACC TCC TG | 2279, 2280 |
| chr18 | 47100905 | 47101154 | CTA CCT GTC CGT TTC CCT TAC | ATA CAT CAG GCC TCC AGA ATT | 2281, 2282 |
| chr18 | 47130278 | 47130527 | GAC AAA GAT GAC TGG AGG TGA | CAC ATC TTT AGA GCT CAG GTG A | 2283, 2284 |
| chr18 | 47366936 | 47367185 | GGG TGG ATG GTG AGA TAT GTG | CCA TCA CTT CAC AAT CCA CAC | 2285, 2286 |
| chr18 | 47371131 | 47371380 | CTT CAA ACC TGA TCC ATG TGC | AAT CCT GCA GTC ATC TTC CC | 2287, 2288 |
| chr18 | 47689868 | 47690117 | GCA GAA ACA GCA TGA ATC TCC | CAA GTC TGG TTT GTG AGA AGC | 2289, 2290 |
| chr18 | 47690267 | 47690516 | TGA CTT CAA ACA TCC CAT CCA | GGG AGC TTC TGT AGT CTT TGA | 2291, 2292 |
| chr18 | 47703689 | 47703938 | GTG GGA TGA GTT CTA GAG GAA | TAA GGA GAG CAG GAC TTA CAG | 2293, 2294 |
| chr18 | 47708139 | 47708388 | AGT CAC ACA CAT ACA CAC AGT | CCA ACG GTT CAT TTG TCG TAT | 2295, 2296 |
| chr18 | 47717445 | 47717694 | ACG ACT TCC CTG TGT AAC TTA | CCT TGC TCT GTT AAT GGG TTT | 2297, 2298 |
| chr18 | 47738531 | 47738780 | CCT TCT CTT GTC TCT AGT GCC | AAC AAT GCT TAA CGG GAA TCC | 2299, 2300 |
| chr18 | 47777438 | 47777687 | CTG GAA ATA CAC ACA CAC CTG | GCA GAG TTC ATA GAA GGG TCA | 2301, 2302 |
| chr18 | 47794212 | 47794461 | ATT TGT AAA CCA CCC ACT TCG | AAA CCG AGA CGA CCA CCT AAT | 2303, 2304 |

FIG. 2BT

| chromosome | start | stop | forward primer | reverse primer | SEQ ID NOs: |
|---|---|---|---|---|---|
| chr18 | 47799400 | 47799649 | TCA CTG TGC TGA CAA ATC CTA | GAG TGA TGA TGA GCC ATG ATG | 2305, 2306 |
| chr18 | 47802662 | 47802911 | CCC ATC ATC ATC CCT TCA GAC | GGA TAT TGG AGA TAG CAG GCA | 2307, 2308 |
| chr18 | 39874986 | 39875235 | TCA TCA CTT TAT CCT CCC AGT | GTT TGG CAC TGC AAC TAG ATA | 2309, 2310 |
| chr18 | 39891490 | 39891739 | ATG GGC ACA GGT AAA GAG TTT | TGA AAT AAG GGA AGC CAC ACA | 2311, 2312 |
| chr18 | 42204240 | 42204489 | TTT GTA AGC TGA GTG TGA GGT | TCC TTA GTG TGC CAA TTA GCC | 2313, 2314 |
| chr18 | 42313146 | 42313395 | TTA CTG TTT GAA TGC CAG CTC | TTA ATG TGG AGA GAC AGG CC | 2315, 2316 |
| chr18 | 42313939 | 42314188 | TCC CTT CTC CCA TCA CAA TTC | CAA TGC ATC TTA CTC ACC CTT | 2317, 2318 |
| chr18 | 42314302 | 42314551 | GAA GAC TGC ATG TGT GTC CTA | AGT ATG GAA GTG GGA ATT GGA | 2319, 2320 |
| chr18 | 42349923 | 42350172 | TTC TCA CTC TCA ACT GAA CCA | TTG CTT CCA CAG AAA CTC TTC | 2321, 2322 |
| chr18 | 42407165 | 42407414 | TCA GGG AGC TTC TAA TTA AGG A | AAC CGA CCT ATT CCA AAG TCT | 2323, 2324 |
| chr18 | 42418033 | 42418282 | AAG ATG ATC CCA GGC TTA AGG | TGT GAA GCG AAT ACA GCT CAA | 2325, 2326 |
| chr18 | 42449702 | 42449951 | GTT GAG GTT TGC TGA TCT TGG | GTT CTA ACT ACA CCA GGC TCT | 2327, 2328 |
| chr18 | 42450400 | 42450649 | CAA AGA TAG ATT CGC ACA CCA | GTA TGA GTG TAG GTG TGG AGG | 2329, 2330 |
| chr18 | 42461427 | 42461676 | GAG CTG GAC AAA TTA AAT GGC | AAT CTG GAT CTA GCG AAG GAC | 2331, 2332 |
| chr18 | 42462834 | 42463083 | CCA GTG CAT TTG GTT TGA CA | TAA TGA GAA GGC AGG ATG AGG | 2333, 2334 |
| chr18 | 42468595 | 42468844 | TAT GTG AAT CCT CTG TGT GGC | AAG ACA ACT CTC TAG GCC TCA | 2335, 2336 |

FIG. 2BU

| chromosome | start | stop | forward primer | reverse primer | SEQ ID NOs: |
|---|---|---|---|---|---|
| chr18 | 42468938 | 42469187 | AGC TTG TCT CTC ATT CTG CTT | GTT TAT GGT TGT CCC TGG AGA | 2337, 2338 |
| chr18 | 42644003 | 42644252 | GAC TCC CGA TTT CAT TTG CTG | TCC ACC TTC TGA TCA CAC AAT | 2339, 2340 |
| chr18 | 42644494 | 42644743 | TCC CAA TCG TTG TGA AAC ATA C | AAG ATC AGG TAC CAA GGC ATT | 2341, 2342 |
| chr18 | 42645387 | 42645636 | TCT TTA CAG GAA GTT GGG ACC | ATG ATG TGA AGT CCA TGG TGA | 2343, 2344 |
| chr18 | 42741059 | 42741308 | TAA GTT CAG ATC AGG GAG CAG | TCC AAA TTG ACT TCC ATG AGC | 2345, 2346 |
| chr18 | 42745733 | 42745982 | GTT GAA AGT CTT ACA GAA CGC T | GTG GTT TCA GGA ATT TGG AGG | 2347, 2348 |
| chr18 | 42746460 | 42746709 | CAA CAT AGG CAC ATT GTC CTC | TAT TTG CTG CTT CAT TCT TCC C | 2349, 2350 |
| chr18 | 42746911 | 42747160 | GTC AGG CCT CAT AAC TCT CTT | AAG TCA TTA CGT CCC ACA CTG | 2351, 2352 |
| chr18 | 42747473 | 42747722 | GTT GTG TGG CTT TCC TTA TCA | AAA GTC ATC AGA AGG GTA GCA | 2353, 2354 |
| chr18 | 43796659 | 43796908 | CCT GCA GCT CTG TGT AAA TTT | AAT GAT GCC GAA CAG TGA GTA | 2355, 2356 |
| chr18 | 43820471 | 43820720 | CTT TGG CCA GTT CTT TCT CTC | AAT GTA AGA CAG GGA CAG AGA | 2357, 2358 |
| chr18 | 43841913 | 43842162 | GTG GCC CAG CAT TAT TTG TT | TGA ATT CCA CAG TCC AGT CAA | 2359, 2360 |
| chr18 | 43842202 | 43842451 | TCT TGG TGT GAC TTG CTA ACA | AAT GCC TTC AAA GAC AGT GAC | 2361, 2362 |
| chr18 | 43842647 | 43842896 | TTT CTG GCT GAG ATA AGA CCC | CAC ACC TGC AAT TGA GAT GAA | 2363, 2364 |
| chr18 | 43845701 | 43845950 | ACA ATT CCG TGG TAT ACA GCT | GTC ATG ATG ATG CAA CAG CTA | 2365, 2366 |
| chr18 | 43846353 | 43846602 | TGA TTG TGC CCT AAC CAA ACT | TTT CAC GGT AAG AGG AGC AAA | 2367, 2368 |

FIG. 2BV

| chromosome | start | stop | forward primer | reverse primer | SEQ ID NOs: |
|---|---|---|---|---|---|
| chr18 | 43917652 | 43917901 | TGT CGT ATC CTG CTG TTT AGA | TTC TCT CTA GGC AGG TGA ACT | 2369, 2370 |
| chr18 | 43918519 | 43918768 | TCA GGA GTA AAG TCA GGA CCT | ACC CTT TGA AAG AAC CAG GAA | 2371, 2372 |
| chr18 | 43918998 | 43919247 | TGA GCT GAT TTA CTG TGA CAC | AAT GAG CCA CTG TTC TCT AGG | 2373, 2374 |
| chr18 | 43919544 | 43919793 | TAG CAC CTT GAC TTC AGG ATT | ATT TGC ACA TTA GGG CCT CAA | 2375, 2376 |
| chr18 | 44086123 | 44086372 | TGA GGT TGG AAA GGG TCA ATT | GAA CTT CCC TGC TTC CTT CT | 2377, 2378 |
| chr18 | 44094299 | 44094548 | CAG CTT TCC TTC CTC TTC TCT | AAA TAC TTG GCT GTG ACC ATG | 2379, 2380 |
| chr18 | 44167214 | 44167463 | ACA GTG AGA GGA AAG AAC AGC | AAG ACC CTT GAG AAC TTC CAA | 2381, 2382 |
| chr18 | 44167791 | 44168040 | GGA AAT AAA TTG TGA GCT GGC | ATG TGT AAA GAC GTC CTG GAA | 2383, 2384 |
| chr18 | 44168296 | 44168545 | AGA CAG CCC TTC AAT CCA TAC | TCT ATG TGG AGG GAT TTG ACA | 2385, 2386 |
| chr18 | 44173512 | 44173761 | CCT ACA TCC CTT CCT CCT TTC | TTC CTG AAG TTT ATG GTG CAA C | 2387, 2388 |
| chr18 | 44174626 | 44174875 | TCA CCC ATC TTC CAA TTA GCT | AAG GTT GAA TGA GGA TCA AGC | 2389, 2390 |
| chr18 | 44857765 | 44858014 | TTT CTA AGC ACA AAC TGA CAC C | GAG GGA AGA ACA CAA CAC ATG | 2391, 2392 |
| chr18 | 45110525 | 45110774 | GAT GTT TGC ACT GGA GGG ATA | CAG ACT AGC CTA CAA TCC TCC | 2393, 2394 |
| chr18 | 45197621 | 45197870 | GAA GAC TAA ATG TTG GCC GAA | CAT TCA GGT TCT TAA GGG CTG | 2395, 2396 |
| chr18 | 45197871 | 45198120 | GTA GAG AGA GGG AGG ATC ACA | GAA AGG CAG ACG ATG AAA GAG | 2397, 2398 |
| chr18 | 45198760 | 45199009 | CTT GCC ATG AAG TTT GAC CAG | ATC TCC ATC AGC ACA GGA ATT | 2399, 2400 |

FIG. 2BW

| chromosome | start | stop | forward primer | reverse primer | SEQ ID NOs: |
|---|---|---|---|---|---|
| chr18 | 45234886 | 45235135 | AGG ATG AGC ATT TGT AAC CTG | GCA GTG TGA GAT CTG TGA ATG | 2401, 2402 |
| chr18 | 45235523 | 45235772 | TGT CGC TTT CAA ATT ACC CAC | AGA CTT TCC TGT TCC TCT TCA | 2403, 2404 |
| chr18 | 45238370 | 45238619 | CAT ACA AGT GCT CTG TTA GGC | TTT ACA ATG AAC TAG CCA GGC | 2405, 2406 |
| chr18 | 45335896 | 45336145 | AGG ACT TGG AAC CAG AAA GAC | TAA CAT CTG CCT GAA AGC TTC | 2407, 2408 |
| chr18 | 45336353 | 45336602 | AAA GAG GGC TGA TAT CGT CTG | CTC GTG TGT GCA ATT TGG AAT | 2409, 2410 |
| chr18 | 45357461 | 45357710 | CTC ACT GCA AAC TAT GGA ACC | GGA GAG ATG GAG AAG ACC TTT | 2411, 2412 |
| chr18 | 45357745 | 45357994 | TAT TCT GCC CAT CTT CTT CCT | AAT GTA TTA CTG TGC TCC CGT | 2413, 2414 |
| chr18 | 45358502 | 45358751 | GGA GAC AGC CCA AAC ATA GA | ACC ACC TGC CAC TGT ATA AAT | 2415, 2416 |
| chr18 | 45362379 | 45362628 | AGC AAT GGT GAA GTT CTG GAT | AAT TCT TCT TCT GGT GCA AGG | 2417, 2418 |
| chr18 | 45397588 | 45397837 | CTG GTC AGT GAG AGA AGG GAA | TTG CCC TTT GAA CTG TTG ATC | 2419, 2420 |
| chr18 | 45864183 | 45864432 | TTT CTC CAC TGG CAT GAA CT | AAG CAC ACT AAG GCC TGA TAA | 2421, 2422 |
| chr18 | 46464382 | 46464631 | CAT GAT CAC AAT TCC AAG CCA | TCA GTA TCC ATT CAG CAT CCA | 2423, 2424 |
| chr18 | 46473428 | 46473677 | ACC CAG TCA AGT TAC AGT CTT | TAA CCG AAG CCC ATA CTC TG | 2425, 2426 |
| chr18 | 46474545 | 46474794 | TGT AAA GCA TAT CAA GGG AAC G | TCC TTA CTC CAG ATA CCC GAT | 2427, 2428 |
| chr18 | 46481797 | 46482046 | TGC AGA GAT ATG TTC CCG TAT | TCT GGC TTC TTT CTT GGA GAG | 2429, 2430 |
| chr18 | 46483016 | 46483265 | AGA AGA CAG TAC AAG GAA GGC | GCA ACA TTC ATT TCA TCC TGC | 2431, 2432 |

FIG. 2BX

| chromosome | start | stop | forward primer | reverse primer | SEQ ID NOs: |
|---|---|---|---|---|---|
| chr18 | 46589014 | 46589263 | TGT TTG CCA TTT GTT CTC CTC | CAT CAC GAC ATC CAT TTC CAC | 2433, 2434 |
| chr18 | 46599847 | 46600096 | TTG AAG GCA AGA GAA GTT TGG | GTG GTT ATT ATC GGT GGG TGA | 2435, 2436 |
| chr18 | 46601866 | 46602115 | GCC AAG GAA ATG TAG GGA AAG | CTG CCA TTC CTT GTT TCC AA | 2437, 2438 |
| chr18 | 46983278 | 46983527 | AAC CTT CAC ACC TAG AGA CAG | ATT TGG ACT TGA AGC AGC CT | 2439, 2440 |
| chr18 | 47013103 | 47013352 | GCA TAA CAG GGA AAG TCA CCT | CTG TAT TCT TTG TCC ACC ACC | 2441, 2442 |
| chr18 | 47016802 | 47017051 | AGG ATG TTA GTG GTT TGG GTA | GAC AGG ACA CCT TGG ATT GAT | 2443, 2444 |
| chr18 | 286722 | 286971 | TCT GAC ACT GAC CTT CAA CT | GAG TAA TTC CCC CGA TGC AG | 2445, 2446 |
| chr18 | 298393 | 298642 | GAA ACA TTG CTT TCC CTC CA | TGA GAA TCA TTG AGC CAA ACC | 2447, 2448 |
| chr18 | 338127 | 338376 | TTC CAC ACA TCT CTT CTC CG | AAT TGT GAG CGT TAG AGT GC | 2449, 2450 |
| chr18 | 340427 | 340676 | GGG AGC CTT GAA AAC CTG AA | CCA GTG GGT CTT AAC ATT GAG | 2451, 2452 |
| chr18 | 387135 | 387384 | ATT GGT AGC GTT GTC AGC A | AAA AGG CTA GTA GAG GGT GC | 2453, 2454 |
| chr18 | 391175 | 391424 | TTC CTG CAT CTT GTA GAC CC | TCG CTG AAG AAC TGA GAC AC | 2455, 2456 |
| chr18 | 434440 | 434689 | GGG CTA ATG TTT TGC TTC CA | GGG AAG TGA TTG GAG AGA GG | 2457, 2458 |
| chr18 | 457527 | 457776 | TGT TGA TTA GAG CTT CCC CC | CCG CTT GGT ATA GAG TGC TG | 2459, 2460 |
| chr18 | 460384 | 460633 | AGA GGT TTT CTT CCC CGT G | TTG AGG TTG TCA GGA AAG CT | 2461, 2462 |
| chr18 | 469281 | 469530 | TAG TGC CCT CTA TTG TGC CT | TCT TGG GAA AGG GTC ATT CT | 2463, 2464 |

FIG. 2BY

| chromosome | start | stop | forward primer | reverse primer | SEQ ID NOs: |
|---|---|---|---|---|---|
| chr18 | 572716 | 572965 | ACT GCT GGA CTT TGA AAT GC | TCT CTT CCA TGC ACT CCA C | 2465, 2466 |
| chr18 | 598352 | 598601 | CAA ACA GTG AGA TGT GGC TG | GAT CTG ACC CTC TGC TCA C | 2467, 2468 |
| chr18 | 615413 | 615662 | TTG CTT CCT GAA AAC TGG TTC | CCT GAA AGA TGC ATG GTT GG | 2469, 2470 |
| chr18 | 618280 | 618529 | ATT CCA ATC ACG TCT CTG CA | GCC ACA GAA CAA CCA GAT TC | 2471, 2472 |
| chr18 | 901111 | 901360 | ACA ATC TCA CAG CCT GGA AA | TGG GGT TAA GAG CTC AAG AG | 2473, 2474 |
| chr18 | 939383 | 939632 | TCA GAT GGG TGA GGT TCT TG | AGT GTG GAT GAC TTC TGC AA | 2475, 2476 |
| chr18 | 26321283 | 26321532 | CTG CTC CTT CCC TCC AAT TA | GCC CCA TTA TCC TCC TTT GT | 2477, 2478 |
| chr18 | 26337865 | 26338114 | AAA TGC CAG TCC TGT AAA GG | CAA ATC AGA CCC ACT AAG CAC | 2479, 2480 |
| chr18 | 26345717 | 26345966 | TGT CCC ATT GCT TAG GAA GT | TGT TTT GGA CTG CTT CAC TC | 2481, 2482 |
| chr18 | 26365387 | 26365636 | TGT GTG ATC CAG AGA CCC TA | ATT ATC ATG CTC ACT CCT CCA | 2483, 2484 |
| chr18 | 26367518 | 26367767 | ACC AAT GTA GAC TTA GCG GG | GAC ATA GCA CGG GAG GAG TA | 2485, 2486 |
| chr18 | 26392500 | 26392749 | ACT CTC ATA TTG CCC CAC TT | GCT AGT GGC GTT TTA GGA AA | 2487, 2488 |
| chr18 | 26406499 | 26406748 | CCA GGG ATT GAT GTA CTG GT | TCG CTT GGA AGT CAT AGC C | 2489, 2490 |
| chr18 | 26711590 | 26711839 | AAT TCT GGT CTA TCT GGC GT | CAG AGC TGC TTT GAA GAT AAT CC | 2491, 2492 |
| chr18 | 26729342 | 26729591 | GCC AGC CCT TTT CAC ATA TT | GAA GCC TGA TAG ATG TGC CT | 2493, 2494 |
| chr18 | 26733981 | 26734230 | AAC TAC ACC ATC CCC TGT TT | TAC CTC TGC CTC CAA TTG TC | 2495, 2496 |

FIG. 2BZ

| chromosome | start | stop | forward primer | reverse primer | SEQ ID NOs: |
|---|---|---|---|---|---|
| chr18 | 26739336 | 26739585 | CCA TTT CAA ACA TGC TGG TC | CCC ATG TAG ACA AAG TGC TT | 2497, 2498 |
| chr18 | 26750685 | 26750934 | AGA TTA TAA GAA GGC AGG GAA C | GGC AGG TTT GTC TTA CAG TT | 2499, 2500 |
| chr18 | 26752487 | 26752736 | GTA GAG GGC TTA AAA CAT GTC C | TGT GAG ATT GCA TTC CCC TT | 2501, 2502 |
| chr18 | 26757573 | 26757822 | ACA AGA ACA CAG TCG TTA AGC | CGG GTC AGA GAA AGA TCA GG | 2503, 2504 |
| chr18 | 27244230 | 27244479 | TCT CTC CTT CAC TCC CTT CA | AAA CAT TTG TAA CCA CTC CCT G | 2505, 2506 |
| chr18 | 35076347 | 35076596 | TGT CCA CCC CTC TTT GAT TG | CCT GTA ATA TGG GAC TCC TGG | 2507, 2508 |
| chr18 | 35147912 | 35148161 | TTT AGC TTC TCC TGC CTT TG | CCA AAC CAC ACA CAC AAA CT | 2509, 2510 |
| chr18 | 35282655 | 35282904 | AGA AGC AAT TCA CCA GGT CA | AGG AGA AGG ACA TTT CAC AGG | 2511, 2512 |
| chr18 | 35292141 | 35292390 | TGG AGT CAG AAG TGT GTG TT | AGG CCG ATA AGA CAA GGT TC | 2513, 2514 |
| chr18 | 35304247 | 35304496 | TCT GGT GTC AAA GCT TAG GG | GTT TCC CAT AGA GCC CTG G | 2515, 2516 |
| chr18 | 35311302 | 35311551 | TGC CGA TGA TGT GTG TTT TG | CTC CAC TCT CTC CAA CCA AC | 2517, 2518 |
| chr18 | 36463709 | 36463958 | TGT CCC TTC CTA ATC CCA AA | AAA CTG TGA AAG GAC GAG GA | 2519, 2520 |
| chr18 | 36473033 | 36473282 | AGG ATG TTT AAG TTG CAG CA | TCC CTT GCT TTT GTA CCA GG | 2521, 2522 |
| chr18 | 36475403 | 36475652 | TAT GCA GTT TTA CCC CCT CC | CAT GTG TGT ACT GTG CCT CA | 2523, 2524 |
| chr18 | 36479145 | 36479394 | TTC TGT GTG GTC TCC TCT TG | TCT TTC ACT GTC ACT ATG GGG | 2525, 2526 |
| chr18 | 36482038 | 36482287 | ATG GAG GGA CAA GTG AGA CA | AAA TGC AGC TTC CCA ACA TC | 2527, 2528 |

FIG. 2CA

| chromosome | start | stop | forward primer | reverse primer | SEQ ID NOs: |
|---|---|---|---|---|---|
| chr18 | 36483959 | 36484208 | GGG GAA CAT GGA GCT GTA AA | GAG ACT TTC TGG AGG ACG AA | 2529, 2530 |
| chr18 | 36485761 | 36486010 | GGA CCC CCT ACC ACA TTT AC | GAA ACG TAA TTT AGT GAC TGG C | 2531, 2532 |
| chr18 | 36487627 | 36487876 | AGA TGG AGA AAT GTG CAG AGA | ATG TGT CTA TTG CTA CCT GTG A | 2533, 2534 |
| chr18 | 36489135 | 36489384 | ATG ACT GCA TCC AAG AGC A | CTC CTT CAT TTT GCT GGT GG | 2535, 2536 |
| chr18 | 36531244 | 36531493 | CAG AAT TTC CAG GCA GTT GT | GGT GAT CAT TTG TCT GCA CA | 2537, 2538 |
| chr18 | 36554006 | 36554255 | GAA TCC AGA AGC TCA GTC CTT | TGA AGG GAT GAA GGC AGA AG | 2539, 2540 |
| chr18 | 36558050 | 36558299 | AGC CCT GGA ATC TTG ACA TT | ATT GTG TTG TCC TTC CGT TT | 2541, 2542 |
| chr18 | 36569619 | 36569868 | GTG CAT TAT ACG GAT GGC C | CTG AAG CAT CAC TGG CAT TG | 2543, 2544 |
| chr18 | 1017928 | 1018177 | GGT AGA GGG TCC TGT GAT TC | AAG CTT GTA GTC TGG GTA GC | 2545, 2546 |
| chr18 | 241538 | 241787 | GTA ACT GCT AGC CAC TGA GT | TCC CTC TGT ACT ATG TAG CAT G | 2547, 2548 |
| chr18 | 242831 | 243080 | GCC TTT TTG GGA ATC CTA GT | TTC ATT TCC CTT TGT TGC CC | 2549, 2550 |

FIG. 2CB

Fig 10

| chromosome | start | stop | gene |
|---|---|---|---|
| chr1 | 115256347 | 115256588 | NRAS |
| chr1 | 115256398 | 115256647 | NRAS |
| chr1 | 115256410 | 115256649 | NRAS |
| chr1 | 115256442 | 115256691 | NRAS |
| chr1 | 115256467 | 115256726 | NRAS |
| chr1 | 115256470 | 115256715 | NRAS |
| chr1 | 115258538 | 115258778 | NRAS |
| chr1 | 115258570 | 115258813 | NRAS |
| chr1 | 115258607 | 115258846 | NRAS |
| chr1 | 115258659 | 115258901 | NRAS |
| chr3 | 178916725 | 178916970 | PI3KCA |
| chr3 | 178916766 | 178917010 | PI3KCA |
| chr3 | 178916782 | 178917028 | PI3KCA |
| chr3 | 178916822 | 178917068 | PI3KCA |
| chr3 | 178917417 | 178917566 | PI3KCA |
| chr3 | 178917417 | 178917618 | PI3KCA |
| chr3 | 178917420 | 178917590 | PI3KCA |
| chr3 | 178917420 | 178917604 | PI3KCA |
| chr3 | 178921331 | 178921578 | PI3KCA |
| chr3 | 178921339 | 178921585 | PI3KCA |
| chr3 | 178921347 | 178921596 | PI3KCA |
| chr3 | 178921364 | 178921608 | PI3KCA |
| chr3 | 178927888 | 178928114 | PI3KCA |
| chr3 | 178927898 | 178928114 | PI3KCA |
| chr3 | 178927974 | 178928182 | PI3KCA |
| chr3 | 178935873 | 178936102 | PI3KCA |
| chr3 | 178935930 | 178936133 | PI3KCA |
| chr3 | 178935944 | 178936197 | PIK3CA |
| chr3 | 178935995 | 178936197 | PI3KCA |
| chr3 | 178936030 | 178936279 | PI3KCA |
| chr3 | 178951914 | 178952159 | PI3KCA |
| chr3 | 178951915 | 178952140 | PI3KCA |
| chr3 | 178951921 | 178952140 | PI3KCA |
| chr3 | 178951921 | 178952159 | PI3KCA |
| chr3 | 178951948 | 178952109 | PIK3CA |
| chr3 | 178952004 | 178952152 | PIK3CA |
| chr3 | 178952010 | 178952109 | PIK3CA |
| chr3 | 178952109 | 178952152 | PIK3CA |

Fig. 10 cont

| chromosome | start | stop | gene |
|---|---|---|---|
| chr7 | 55241468 | 55241710 | EGFR |
| chr7 | 55241542 | 55241789 | EGFR |
| chr7 | 55241576 | 55241746 | EGFR |
| chr7 | 55242269 | 55242500 | EGFR |
| chr7 | 55242272 | 55242520 | EGFR |
| chr7 | 55242280 | 55242532 | EGFR |
| chr7 | 55242319 | 55242558 | EGFR |
| chr7 | 55242332 | 55242584 | EGFR |
| chr7 | 55242505 | 55242271 | EGFR |
| chr7 | 55248852 | 55249080 | EGFR |
| chr7 | 55248896 | 55249120 | EGFR |
| chr7 | 55248933 | 55249182 | EGFR |
| chr7 | 55248937 | 55249187 | EGFR |
| chr7 | 55248961 | 55249208 | EGFR |
| chr7 | 55259335 | 55259571 | EGFR |
| chr7 | 55259337 | 55259586 | EGFR |
| chr7 | 55259356 | 55259602 | EGFR |
| chr7 | 55259368 | 55259570 | EGFR |
| chr7 | 55259391 | 55259640 | EGFR |
| chr12 | 25378488 | 25378688 | KRAS |
| chr12 | 25378503 | 25378751 | KRAS |
| chr12 | 25378546 | 25378778 | KRAS |
| chr12 | 25378554 | 25378783 | KRAS |
| chr12 | 25380153 | 25380359 | KRAS |
| chr12 | 25380166 | 25380337 | KRAS |
| chr12 | 25380167 | 25380326 | KRAS |
| chr12 | 25380167 | 25380359 | KRAS |
| chr12 | 25398080 | 25398329 | KRAS |
| chr12 | 25398145 | 25398394 | KRAS |
| chr12 | 25398153 | 25398397 | KRAS |
| chr12 | 25398159 | 25398408 | KRAS |
| chr12 | 25398186 | 25398433 | KRAS |

SEQUENCE LISTING

<160> NUMBER OF SEQ ID NOS: 2550

<210> SEQ ID NO 1
<211> LENGTH: 20
<212> TYPE: DNA
<213> ORGANISM: Homo sapiens

<400> SEQUENCE: 1
tcttctcgtt caagatgccg 20

<210> SEQ ID NO 2
<211> LENGTH: 22
<212> TYPE: DNA
<213> ORGANISM: Homo sapiens

<400> SEQUENCE: 2
aaattacatg caaggctacc ac 22

<210> SEQ ID NO 3
<211> LENGTH: 21
<212> TYPE: DNA
<213> ORGANISM: Homo sapiens

<400> SEQUENCE: 3
acaggaagaa aggggagtta c 21

<210> SEQ ID NO 4
<211> LENGTH: 20
<212> TYPE: DNA
<213> ORGANISM: Homo sapiens

<400> SEQUENCE: 4
ttcaggttgt gtgatgtgtc 20

<210> SEQ ID NO 5
<211> LENGTH: 20
<212> TYPE: DNA
<213> ORGANISM: Homo sapiens

<400> SEQUENCE: 5
taagcagagg ttttgttgcc 20

<210> SEQ ID NO 6
<211> LENGTH: 20
<212> TYPE: DNA
<213> ORGANISM: Homo sapiens

<400> SEQUENCE: 6
gtgaagtatt tgctgccacc 20

<210> SEQ ID NO 7
<211> LENGTH: 20
<212> TYPE: DNA
<213> ORGANISM: Homo sapiens

<400> SEQUENCE: 7
atggtcatct caacagcaca 20

<210> SEQ ID NO 8
<211> LENGTH: 20
<212> TYPE: DNA
<213> ORGANISM: Homo sapiens

<400> SEQUENCE: 8
tccactgacg ttgagattcg 20

<210> SEQ ID NO 9
<211> LENGTH: 20
<212> TYPE: DNA
<213> ORGANISM: Homo sapiens

<400> SEQUENCE: 9
cgaacctcct tgacctctta 20

<210> SEQ ID NO 10
<211> LENGTH: 22
<212> TYPE: DNA
<213> ORGANISM: Homo sapiens

<400> SEQUENCE: 10
gttatgttga taggggaagc tt 22

<210> SEQ ID NO 11
<211> LENGTH: 20
<212> TYPE: DNA
<213> ORGANISM: Homo sapiens

<400> SEQUENCE: 11
aagccctcta ctccatctgt 20

<210> SEQ ID NO 12
<211> LENGTH: 20
<212> TYPE: DNA
<213> ORGANISM: Homo sapiens

<400> SEQUENCE: 12
tcagaactcg tcagtggaag 20

<210> SEQ ID NO 13
<211> LENGTH: 19
<212> TYPE: DNA
<213> ORGANISM: Homo sapiens

<400> SEQUENCE: 13
gaagggccag acagcttat 19

<210> SEQ ID NO 14
<211> LENGTH: 21
<212> TYPE: DNA
<213> ORGANISM: Homo sapiens

<400> SEQUENCE: 14
atttgctttg tttttgtccc t 21

<210> SEQ ID NO 15
<211> LENGTH: 21
<212> TYPE: DNA
<213> ORGANISM: Homo sapiens

<400> SEQUENCE: 15
gatcattgct ttgtttggac c 21

<210> SEQ ID NO 16
<211> LENGTH: 21
<212> TYPE: DNA
<213> ORGANISM: Homo sapiens

<400> SEQUENCE: 16
aggagaggaa aaatcttgac c 21

<210> SEQ ID NO 17
<211> LENGTH: 20
<212> TYPE: DNA
<213> ORGANISM: Homo sapiens

<400> SEQUENCE: 17
ctgcctgcag ccattattgt 20

<210> SEQ ID NO 18
<211> LENGTH: 22
<212> TYPE: DNA
<213> ORGANISM: Homo sapiens

<400> SEQUENCE: 18
ccttggggta tgtttgttat gt 22

<210> SEQ ID NO 19
<211> LENGTH: 22
<212> TYPE: DNA
<213> ORGANISM: Homo sapiens

<400> SEQUENCE: 19
actttttctg tatcagtcac gg 22

<210> SEQ ID NO 20
<211> LENGTH: 20
<212> TYPE: DNA
<213> ORGANISM: Homo sapiens

<400> SEQUENCE: 20
ctgcttttgt gtgttccctt 20

<210> SEQ ID NO 21
<211> LENGTH: 20
<212> TYPE: DNA
<213> ORGANISM: Homo sapiens

<400> SEQUENCE: 21
ccagttcctg tttttctgcc 20

<210> SEQ ID NO 22
<211> LENGTH: 21
<212> TYPE: DNA
<213> ORGANISM: Homo sapiens

<400> SEQUENCE: 22
gccttcactg atcctacttt c 21

<210> SEQ ID NO 23
<211> LENGTH: 21
<212> TYPE: DNA
<213> ORGANISM: Homo sapiens

<400> SEQUENCE: 23
ggatatgggg taggtttttg t 21

<210> SEQ ID NO 24
<211> LENGTH: 20
<212> TYPE: DNA
<213> ORGANISM: Homo sapiens

<400> SEQUENCE: 24
actcatagaa ctggggcttt 20

<210> SEQ ID NO 25
<211> LENGTH: 20
<212> TYPE: DNA
<213> ORGANISM: Homo sapiens

<400> SEQUENCE: 25
ctttgtaggt cctccagaga 20

<210> SEQ ID NO 26
<211> LENGTH: 20
<212> TYPE: DNA
<213> ORGANISM: Homo sapiens

<400> SEQUENCE: 26
cctgttttca gtgggttgaa 20

<210> SEQ ID NO 27
<211> LENGTH: 20
<212> TYPE: DNA
<213> ORGANISM: Homo sapiens

<400> SEQUENCE: 27
ccacgttgta cctttccatg 20

<210> SEQ ID NO 28
<211> LENGTH: 21
<212> TYPE: DNA
<213> ORGANISM: Homo sapiens

<400> SEQUENCE: 28
gagattcaaa acagtggtgg c 21

<210> SEQ ID NO 29
<211> LENGTH: 19
<212> TYPE: DNA
<213> ORGANISM: Homo sapiens

<400> SEQUENCE: 29
acaacactgt ccttgggtt 19

<210> SEQ ID NO 30
<211> LENGTH: 20
<212> TYPE: DNA
<213> ORGANISM: Homo sapiens

<400> SEQUENCE: 30
taaatgtcct gtgtgctcgg 20

<210> SEQ ID NO 31
<211> LENGTH: 20
<212> TYPE: DNA
<213> ORGANISM: Homo sapiens

<400> SEQUENCE: 31
gacaggacac atggagagag 20

<210> SEQ ID NO 32
<211> LENGTH: 21
<212> TYPE: DNA

<213> ORGANISM: Homo sapiens

<400> SEQUENCE: 32
aactgatggt gatttgcatg t 21

<210> SEQ ID NO 33
<211> LENGTH: 20
<212> TYPE: DNA
<213> ORGANISM: Homo sapiens

<400> SEQUENCE: 33
ggcttctgga aacatcttgc 20

<210> SEQ ID NO 34
<211> LENGTH: 21
<212> TYPE: DNA
<213> ORGANISM: Homo sapiens

<400> SEQUENCE: 34
caatagaagt agggggtgag g 21

<210> SEQ ID NO 35
<211> LENGTH: 20
<212> TYPE: DNA
<213> ORGANISM: Homo sapiens

<400> SEQUENCE: 35
agctgggatg ggttgtttat 20

<210> SEQ ID NO 36
<211> LENGTH: 20
<212> TYPE: DNA
<213> ORGANISM: Homo sapiens

<400> SEQUENCE: 36
gccagttgtc agaagaatcc 20

<210> SEQ ID NO 37
<211> LENGTH: 20
<212> TYPE: DNA
<213> ORGANISM: Homo sapiens

<400> SEQUENCE: 37
caactgcatt ccaaaacagc 20

<210> SEQ ID NO 38
<211> LENGTH: 21
<212> TYPE: DNA
<213> ORGANISM: Homo sapiens

<400> SEQUENCE: 38
gaagggaaac agtgagaaag a 21

<210> SEQ ID NO 39
<211> LENGTH: 20
<212> TYPE: DNA
<213> ORGANISM: Homo sapiens

<400> SEQUENCE: 39
tcaagcgccg taagtatgta 20

<210> SEQ ID NO 40
<211> LENGTH: 20

<212> TYPE: DNA
<213> ORGANISM: Homo sapiens

<400> SEQUENCE: 40
taaccataac atccagggca 20

<210> SEQ ID NO 41
<211> LENGTH: 20
<212> TYPE: DNA
<213> ORGANISM: Homo sapiens

<400> SEQUENCE: 41
ttgtaagctg gcacactgaa 20

<210> SEQ ID NO 42
<211> LENGTH: 20
<212> TYPE: DNA
<213> ORGANISM: Homo sapiens

<400> SEQUENCE: 42
ttaagaaagt gccgtgttgc 20

<210> SEQ ID NO 43
<211> LENGTH: 20
<212> TYPE: DNA
<213> ORGANISM: Homo sapiens

<400> SEQUENCE: 43
atgggtccat gaagagaagc 20

<210> SEQ ID NO 44
<211> LENGTH: 20
<212> TYPE: DNA
<213> ORGANISM: Homo sapiens

<400> SEQUENCE: 44
agttgtttcc agtactgcca 20

<210> SEQ ID NO 45
<211> LENGTH: 20
<212> TYPE: DNA
<213> ORGANISM: Homo sapiens

<400> SEQUENCE: 45
gtatgctttc aagtgacgcc 20

<210> SEQ ID NO 46
<211> LENGTH: 21
<212> TYPE: DNA
<213> ORGANISM: Homo sapiens

<400> SEQUENCE: 46
gaagacaatg caatgaggtg t 21

<210> SEQ ID NO 47
<211> LENGTH: 20
<212> TYPE: DNA
<213> ORGANISM: Homo sapiens

<400> SEQUENCE: 47
agacccaatg agaacaggaa 20

<210> SEQ ID NO 48

<211> LENGTH: 20
<212> TYPE: DNA
<213> ORGANISM: Homo sapiens

<400> SEQUENCE: 48
tgatggagga agtgtgaagc 20

<210> SEQ ID NO 49
<211> LENGTH: 20
<212> TYPE: DNA
<213> ORGANISM: Homo sapiens

<400> SEQUENCE: 49
tggcttttct gtagtttggg 20

<210> SEQ ID NO 50
<211> LENGTH: 20
<212> TYPE: DNA
<213> ORGANISM: Homo sapiens

<400> SEQUENCE: 50
agcagcaaga gttgagaaga 20

<210> SEQ ID NO 51
<211> LENGTH: 21
<212> TYPE: DNA
<213> ORGANISM: Homo sapiens

<400> SEQUENCE: 51
ggctttgaaa aatcaccatg g 21

<210> SEQ ID NO 52
<211> LENGTH: 20
<212> TYPE: DNA
<213> ORGANISM: Homo sapiens

<400> SEQUENCE: 52
agaggtttcc atcgttgcta 20

<210> SEQ ID NO 53
<211> LENGTH: 20
<212> TYPE: DNA
<213> ORGANISM: Homo sapiens

<400> SEQUENCE: 53
aacagcccca aacttcctac 20

<210> SEQ ID NO 54
<211> LENGTH: 20
<212> TYPE: DNA
<213> ORGANISM: Homo sapiens

<400> SEQUENCE: 54
atcactgcca acaagccatt 20

<210> SEQ ID NO 55
<211> LENGTH: 20
<212> TYPE: DNA
<213> ORGANISM: Homo sapiens

<400> SEQUENCE: 55
tgagttgtgg gggataaagg 20

<210> SEQ ID NO 56
<211> LENGTH: 20
<212> TYPE: DNA
<213> ORGANISM: Homo sapiens

<400> SEQUENCE: 56
tctgggcact ttccttatga 20

<210> SEQ ID NO 57
<211> LENGTH: 20
<212> TYPE: DNA
<213> ORGANISM: Homo sapiens

<400> SEQUENCE: 57
gcagttttga ggggagaaga 20

<210> SEQ ID NO 58
<211> LENGTH: 19
<212> TYPE: DNA
<213> ORGANISM: Homo sapiens

<400> SEQUENCE: 58
ttcatgatgc cacctcctc 19

<210> SEQ ID NO 59
<211> LENGTH: 20
<212> TYPE: DNA
<213> ORGANISM: Homo sapiens

<400> SEQUENCE: 59
gcccaaatac cccttcagta 20

<210> SEQ ID NO 60
<211> LENGTH: 20
<212> TYPE: DNA
<213> ORGANISM: Homo sapiens

<400> SEQUENCE: 60
gcacctcaat cccgtacaat 20

<210> SEQ ID NO 61
<211> LENGTH: 20
<212> TYPE: DNA
<213> ORGANISM: Homo sapiens

<400> SEQUENCE: 61
gcgttttaag cagctgtgta 20

<210> SEQ ID NO 62
<211> LENGTH: 20
<212> TYPE: DNA
<213> ORGANISM: Homo sapiens

<400> SEQUENCE: 62
tctccagatc gaaacagcat 20

<210> SEQ ID NO 63
<211> LENGTH: 20
<212> TYPE: DNA
<213> ORGANISM: Homo sapiens

<400> SEQUENCE: 63
tcattcaaag ccaagatgcc 20

<210> SEQ ID NO 64
<211> LENGTH: 20
<212> TYPE: DNA
<213> ORGANISM: Homo sapiens

<400> SEQUENCE: 64
acacgctaca tagacactgg 20

<210> SEQ ID NO 65
<211> LENGTH: 20
<212> TYPE: DNA
<213> ORGANISM: Homo sapiens

<400> SEQUENCE: 65
caatcgaggt cacattcacc 20

<210> SEQ ID NO 66
<211> LENGTH: 21
<212> TYPE: DNA
<213> ORGANISM: Homo sapiens

<400> SEQUENCE: 66
tgacacgctg aagaaaatag c 21

<210> SEQ ID NO 67
<211> LENGTH: 20
<212> TYPE: DNA
<213> ORGANISM: Homo sapiens

<400> SEQUENCE: 67
ggagggaatg gcagaagtaa 20

<210> SEQ ID NO 68
<211> LENGTH: 21
<212> TYPE: DNA
<213> ORGANISM: Homo sapiens

<400> SEQUENCE: 68
ggattttcag agcagaggtt g 21

<210> SEQ ID NO 69
<211> LENGTH: 20
<212> TYPE: DNA
<213> ORGANISM: Homo sapiens

<400> SEQUENCE: 69
aagagttgcc tgtacccttc 20

<210> SEQ ID NO 70
<211> LENGTH: 19
<212> TYPE: DNA
<213> ORGANISM: Homo sapiens

<400> SEQUENCE: 70
gtctctttac tgggagcgt 19

<210> SEQ ID NO 71
<211> LENGTH: 20
<212> TYPE: DNA
<213> ORGANISM: Homo sapiens

<400> SEQUENCE: 71
acattgcccc tgacaacata 20

<210> SEQ ID NO 72
<211> LENGTH: 19
<212> TYPE: DNA
<213> ORGANISM: Homo sapiens

<400> SEQUENCE: 72
tcattatctg aggagccgg 19

<210> SEQ ID NO 73
<211> LENGTH: 21
<212> TYPE: DNA
<213> ORGANISM: Homo sapiens

<400> SEQUENCE: 73
ggctccataa tcttctgcaa t 21

<210> SEQ ID NO 74
<211> LENGTH: 20
<212> TYPE: DNA
<213> ORGANISM: Homo sapiens

<400> SEQUENCE: 74
cgtacatctg atttgtgggt 20

<210> SEQ ID NO 75
<211> LENGTH: 21
<212> TYPE: DNA
<213> ORGANISM: Homo sapiens

<400> SEQUENCE: 75
tgccactgat gatacaaaag c 21

<210> SEQ ID NO 76
<211> LENGTH: 20
<212> TYPE: DNA
<213> ORGANISM: Homo sapiens

<400> SEQUENCE: 76
gaaacgtgtg gtgtcctcta 20

<210> SEQ ID NO 77
<211> LENGTH: 20
<212> TYPE: DNA
<213> ORGANISM: Homo sapiens

<400> SEQUENCE: 77
agtgtttggg gctctatcag 20

<210> SEQ ID NO 78
<211> LENGTH: 20
<212> TYPE: DNA
<213> ORGANISM: Homo sapiens

<400> SEQUENCE: 78
ctttcccttt tgagtcctgc 20

<210> SEQ ID NO 79
<211> LENGTH: 20
<212> TYPE: DNA
<213> ORGANISM: Homo sapiens

<400> SEQUENCE: 79
tctcgcttac cttgctacat 20

<210> SEQ ID NO 80
<211> LENGTH: 20
<212> TYPE: DNA
<213> ORGANISM: Homo sapiens

<400> SEQUENCE: 80
aaagcgggaa ttggaacttt 20

<210> SEQ ID NO 81
<211> LENGTH: 20
<212> TYPE: DNA
<213> ORGANISM: Homo sapiens

<400> SEQUENCE: 81
ggggaacatt gggaagagat 20

<210> SEQ ID NO 82
<211> LENGTH: 20
<212> TYPE: DNA
<213> ORGANISM: Homo sapiens

<400> SEQUENCE: 82
tctaccagct acaaacccat 20

<210> SEQ ID NO 83
<211> LENGTH: 20
<212> TYPE: DNA
<213> ORGANISM: Homo sapiens

<400> SEQUENCE: 83
tcagccaata cccatagcag 20

<210> SEQ ID NO 84
<211> LENGTH: 20
<212> TYPE: DNA
<213> ORGANISM: Homo sapiens

<400> SEQUENCE: 84
aatcagagga agatgggtcg 20

<210> SEQ ID NO 85
<211> LENGTH: 20
<212> TYPE: DNA
<213> ORGANISM: Homo sapiens

<400> SEQUENCE: 85
gagaactcca ccctgtcttt 20

<210> SEQ ID NO 86
<211> LENGTH: 20
<212> TYPE: DNA
<213> ORGANISM: Homo sapiens

<400> SEQUENCE: 86
gggagtgtgt gaatgtgtct 20

<210> SEQ ID NO 87
<211> LENGTH: 21
<212> TYPE: DNA
<213> ORGANISM: Homo sapiens

<400> SEQUENCE: 87
aagctttaca tcatggcact g 21

<210> SEQ ID NO 88
<211> LENGTH: 20
<212> TYPE: DNA
<213> ORGANISM: Homo sapiens

<400> SEQUENCE: 88
aaaggtccat aggctcacat 20

<210> SEQ ID NO 89
<211> LENGTH: 20
<212> TYPE: DNA
<213> ORGANISM: Homo sapiens

<400> SEQUENCE: 89
ttgaccaatg ccattaagcc 20

<210> SEQ ID NO 90
<211> LENGTH: 21
<212> TYPE: DNA
<213> ORGANISM: Homo sapiens

<400> SEQUENCE: 90
accagggaaa tgttagcttc t 21

<210> SEQ ID NO 91
<211> LENGTH: 21
<212> TYPE: DNA
<213> ORGANISM: Homo sapiens

<400> SEQUENCE: 91
tgctctgtta tggttggagt t 21

<210> SEQ ID NO 92
<211> LENGTH: 20
<212> TYPE: DNA
<213> ORGANISM: Homo sapiens

<400> SEQUENCE: 92
gaagcggcag taattcagga 20

<210> SEQ ID NO 93
<211> LENGTH: 20
<212> TYPE: DNA
<213> ORGANISM: Homo sapiens

<400> SEQUENCE: 93
aactgtgtcc taagcagtga 20

<210> SEQ ID NO 94
<211> LENGTH: 20
<212> TYPE: DNA
<213> ORGANISM: Homo sapiens

<400> SEQUENCE: 94
gtcacctcca gagctttcat 20

<210> SEQ ID NO 95
<211> LENGTH: 21
<212> TYPE: DNA
<213> ORGANISM: Homo sapiens

<400> SEQUENCE: 95
gaacaatgca acctgagaac t 21

<210> SEQ ID NO 96
<211> LENGTH: 21
<212> TYPE: DNA
<213> ORGANISM: Homo sapiens

<400> SEQUENCE: 96
tgattgtcct ctaccatgca t 21

<210> SEQ ID NO 97
<211> LENGTH: 21
<212> TYPE: DNA
<213> ORGANISM: Homo sapiens

<400> SEQUENCE: 97
aggcttgaaa caccaccttt a 21

<210> SEQ ID NO 98
<211> LENGTH: 20
<212> TYPE: DNA
<213> ORGANISM: Homo sapiens

<400> SEQUENCE: 98
ttgatttgtt gggtggttgg 20

<210> SEQ ID NO 99
<211> LENGTH: 20
<212> TYPE: DNA
<213> ORGANISM: Homo sapiens

<400> SEQUENCE: 99
tgccaatctg aggtttttcc 20

<210> SEQ ID NO 100
<211> LENGTH: 20
<212> TYPE: DNA
<213> ORGANISM: Homo sapiens

<400> SEQUENCE: 100
actctgcttt agggcttctg 20

<210> SEQ ID NO 101
<211> LENGTH: 20
<212> TYPE: DNA
<213> ORGANISM: Homo sapiens

<400> SEQUENCE: 101
gcagaaaagc tcccaaacaa 20

<210> SEQ ID NO 102
<211> LENGTH: 20
<212> TYPE: DNA
<213> ORGANISM: Homo sapiens

<400> SEQUENCE: 102
gaaaagaggt ggagagggag 20

<210> SEQ ID NO 103
<211> LENGTH: 20
<212> TYPE: DNA
<213> ORGANISM: Homo sapiens

<400> SEQUENCE: 103 aggaccctttt tgctgatttc 20

<210> SEQ ID NO 104
<211> LENGTH: 20
<212> TYPE: DNA
<213> ORGANISM: Homo sapiens

<400> SEQUENCE: 104
ctggcccaag tgcatacata 20

<210> SEQ ID NO 105
<211> LENGTH: 20
<212> TYPE: DNA
<213> ORGANISM: Homo sapiens

<400> SEQUENCE: 105
aaccagagag acaccttgac 20

<210> SEQ ID NO 106
<211> LENGTH: 20
<212> TYPE: DNA
<213> ORGANISM: Homo sapiens

<400> SEQUENCE: 106
tcctccctat ctcctgtgac 20

<210> SEQ ID NO 107
<211> LENGTH: 20
<212> TYPE: DNA
<213> ORGANISM: Homo sapiens

<400> SEQUENCE: 107
actctgccag aaaagcctac 20

<210> SEQ ID NO 108
<211> LENGTH: 20
<212> TYPE: DNA
<213> ORGANISM: Homo sapiens

<400> SEQUENCE: 108
cctttgtctt gaagcctcct 20

<210> SEQ ID NO 109
<211> LENGTH: 20
<212> TYPE: DNA
<213> ORGANISM: Homo sapiens

<400> SEQUENCE: 109
ttgactgagc agagtagagc 20

<210> SEQ ID NO 110
<211> LENGTH: 22
<212> TYPE: DNA
<213> ORGANISM: Homo sapiens

<400> SEQUENCE: 110
ttctacctac aagcaaagag ag 22

<210> SEQ ID NO 111
<211> LENGTH: 21
<212> TYPE: DNA

<213> ORGANISM: Homo sapiens

<400> SEQUENCE: 111
tcaccaacag aggatcaaac t 21

<210> SEQ ID NO 112
<211> LENGTH: 20
<212> TYPE: DNA
<213> ORGANISM: Homo sapiens

<400> SEQUENCE: 112
ccgagggata acatacagct 20

<210> SEQ ID NO 113
<211> LENGTH: 20
<212> TYPE: DNA
<213> ORGANISM: Homo sapiens

<400> SEQUENCE: 113
cactagtcac agaagcaggt 20

<210> SEQ ID NO 114
<211> LENGTH: 20
<212> TYPE: DNA
<213> ORGANISM: Homo sapiens

<400> SEQUENCE: 114
gtagaaaccc cgagacaact 20

<210> SEQ ID NO 115
<211> LENGTH: 20
<212> TYPE: DNA
<213> ORGANISM: Homo sapiens

<400> SEQUENCE: 115
caatttgctg ttcagaggct 20

<210> SEQ ID NO 116
<211> LENGTH: 20
<212> TYPE: DNA
<213> ORGANISM: Homo sapiens

<400> SEQUENCE: 116
tcatgatgtg gcttagtggg 20

<210> SEQ ID NO 117
<211> LENGTH: 20
<212> TYPE: DNA
<213> ORGANISM: Homo sapiens

<400> SEQUENCE: 117
tacacccaca tgcatacaca 20

<210> SEQ ID NO 118
<211> LENGTH: 19
<212> TYPE: DNA
<213> ORGANISM: Homo sapiens

<400> SEQUENCE: 118
gaagtgtgca tgggagagt 19

<210> SEQ ID NO 119
<211> LENGTH: 21

<212> TYPE: DNA
<213> ORGANISM: Homo sapiens

<400> SEQUENCE: 119
tttgggtggc tctatgttag g 21

<210> SEQ ID NO 120
<211> LENGTH: 20
<212> TYPE: DNA
<213> ORGANISM: Homo sapiens

<400> SEQUENCE: 120
ctccttgact catttcccgt 20

<210> SEQ ID NO 121
<211> LENGTH: 20
<212> TYPE: DNA
<213> ORGANISM: Homo sapiens

<400> SEQUENCE: 121
agagtaccac tgccaagaaa 20

<210> SEQ ID NO 122
<211> LENGTH: 20
<212> TYPE: DNA
<213> ORGANISM: Homo sapiens

<400> SEQUENCE: 122
ctgctagtct gtcaggagag 20

<210> SEQ ID NO 123
<211> LENGTH: 20
<212> TYPE: DNA
<213> ORGANISM: Homo sapiens

<400> SEQUENCE: 123
gggcagcagt ataaacatcc 20

<210> SEQ ID NO 124
<211> LENGTH: 20
<212> TYPE: DNA
<213> ORGANISM: Homo sapiens

<400> SEQUENCE: 124
gacattccct tccattgagc 20

<210> SEQ ID NO 125
<211> LENGTH: 20
<212> TYPE: DNA
<213> ORGANISM: Homo sapiens

<400> SEQUENCE: 125
ttcctggtaa atgtgctggt 20

<210> SEQ ID NO 126
<211> LENGTH: 20
<212> TYPE: DNA
<213> ORGANISM: Homo sapiens

<400> SEQUENCE: 126
ggccagattt gcagtgattt 20

<210> SEQ ID NO 127

<211> LENGTH: 21
<212> TYPE: DNA
<213> ORGANISM: Homo sapiens

<400> SEQUENCE: 127
agaatcaaca acaatggcag g 21

<210> SEQ ID NO 128
<211> LENGTH: 21
<212> TYPE: DNA
<213> ORGANISM: Homo sapiens

<400> SEQUENCE: 128
ctctgaggaa agcttgtagg a 21

<210> SEQ ID NO 129
<211> LENGTH: 20
<212> TYPE: DNA
<213> ORGANISM: Homo sapiens

<400> SEQUENCE: 129
aggttttcgt tctgcttcag 20

<210> SEQ ID NO 130
<211> LENGTH: 19
<212> TYPE: DNA
<213> ORGANISM: Homo sapiens

<400> SEQUENCE: 130
cgggtcagtg attctagct 19

<210> SEQ ID NO 131
<211> LENGTH: 20
<212> TYPE: DNA
<213> ORGANISM: Homo sapiens

<400> SEQUENCE: 131
gtcactatgg aatgggggtt 20

<210> SEQ ID NO 132
<211> LENGTH: 20
<212> TYPE: DNA
<213> ORGANISM: Homo sapiens

<400> SEQUENCE: 132
gcttcttccc cgcaatatga 20

<210> SEQ ID NO 133
<211> LENGTH: 20
<212> TYPE: DNA
<213> ORGANISM: Homo sapiens

<400> SEQUENCE: 133
cggttcagag tcaatgccta 20

<210> SEQ ID NO 134
<211> LENGTH: 21
<212> TYPE: DNA
<213> ORGANISM: Homo sapiens

<400> SEQUENCE: 134
tacccaacaa gccagagaaa t 21

<210> SEQ ID NO 135
<211> LENGTH: 20
<212> TYPE: DNA
<213> ORGANISM: Homo sapiens

<400> SEQUENCE: 135
agagggaaag tgcaaggaat 20

<210> SEQ ID NO 136
<211> LENGTH: 20
<212> TYPE: DNA
<213> ORGANISM: Homo sapiens

<400> SEQUENCE: 136
gtttttcagc acactgtccc 20

<210> SEQ ID NO 137
<211> LENGTH: 20
<212> TYPE: DNA
<213> ORGANISM: Homo sapiens

<400> SEQUENCE: 137
accacattac tcacaaccct 20

<210> SEQ ID NO 138
<211> LENGTH: 20
<212> TYPE: DNA
<213> ORGANISM: Homo sapiens

<400> SEQUENCE: 138
aagccctttt catctccaca 20

<210> SEQ ID NO 139
<211> LENGTH: 20
<212> TYPE: DNA
<213> ORGANISM: Homo sapiens

<400> SEQUENCE: 139
ccagagctga gacaactact 20

<210> SEQ ID NO 140
<211> LENGTH: 20
<212> TYPE: DNA
<213> ORGANISM: Homo sapiens

<400> SEQUENCE: 140
gaagcaattc ctcacaccac 20

<210> SEQ ID NO 141
<211> LENGTH: 20
<212> TYPE: DNA
<213> ORGANISM: Homo sapiens

<400> SEQUENCE: 141
ttcagtcaga atgaggagcc 20

<210> SEQ ID NO 142
<211> LENGTH: 20
<212> TYPE: DNA
<213> ORGANISM: Homo sapiens

<400> SEQUENCE: 142
ctcctctccc ctctgatttt 20

<210> SEQ ID NO 143
<211> LENGTH: 21
<212> TYPE: DNA
<213> ORGANISM: Homo sapiens

<400> SEQUENCE: 143
ttttaaagcg acagtcacac g 21

<210> SEQ ID NO 144
<211> LENGTH: 20
<212> TYPE: DNA
<213> ORGANISM: Homo sapiens

<400> SEQUENCE: 144
tcctctgcct tctacccttt 20

<210> SEQ ID NO 145
<211> LENGTH: 20
<212> TYPE: DNA
<213> ORGANISM: Homo sapiens

<400> SEQUENCE: 145
tgttgtgcct tttgttctgg 20

<210> SEQ ID NO 146
<211> LENGTH: 22
<212> TYPE: DNA
<213> ORGANISM: Homo sapiens

<400> SEQUENCE: 146
ttaggaggta aggctggaaa aa 22

<210> SEQ ID NO 147
<211> LENGTH: 21
<212> TYPE: DNA
<213> ORGANISM: Homo sapiens

<400> SEQUENCE: 147
ctgtcagcaa tttcaggtca g 21

<210> SEQ ID NO 148
<211> LENGTH: 20
<212> TYPE: DNA
<213> ORGANISM: Homo sapiens

<400> SEQUENCE: 148
agacaaaggc ttcacggaac 20

<210> SEQ ID NO 149
<211> LENGTH: 20
<212> TYPE: DNA
<213> ORGANISM: Homo sapiens

<400> SEQUENCE: 149
ttcctctgtg tcttgaaggt 20

<210> SEQ ID NO 150
<211> LENGTH: 20
<212> TYPE: DNA
<213> ORGANISM: Homo sapiens

<400> SEQUENCE: 150
atcaatgcag gtgagtgtga 20

<210> SEQ ID NO 151
<211> LENGTH: 20
<212> TYPE: DNA
<213> ORGANISM: Homo sapiens

<400> SEQUENCE: 151
cactccacat aagcctcaga 20

<210> SEQ ID NO 152
<211> LENGTH: 20
<212> TYPE: DNA
<213> ORGANISM: Homo sapiens

<400> SEQUENCE: 152
aggatgtagt tgggtgagga 20

<210> SEQ ID NO 153
<211> LENGTH: 20
<212> TYPE: DNA
<213> ORGANISM: Homo sapiens

<400> SEQUENCE: 153
cagtcatcac ggggagatac 20

<210> SEQ ID NO 154
<211> LENGTH: 20
<212> TYPE: DNA
<213> ORGANISM: Homo sapiens

<400> SEQUENCE: 154
gacagatatt tgtgcagggt 20

<210> SEQ ID NO 155
<211> LENGTH: 20
<212> TYPE: DNA
<213> ORGANISM: Homo sapiens

<400> SEQUENCE: 155
tcctagccct tacctttcct 20

<210> SEQ ID NO 156
<211> LENGTH: 20
<212> TYPE: DNA
<213> ORGANISM: Homo sapiens

<400> SEQUENCE: 156
agcctgaatg tcactgatca 20

<210> SEQ ID NO 157
<211> LENGTH: 19
<212> TYPE: DNA
<213> ORGANISM: Homo sapiens

<400> SEQUENCE: 157
actcatcact tctggctgc 19

<210> SEQ ID NO 158
<211> LENGTH: 20
<212> TYPE: DNA
<213> ORGANISM: Homo sapiens

<400> SEQUENCE: 158
tcttgtgttt cctgccctat 20

<210> SEQ ID NO 159
<211> LENGTH: 20
<212> TYPE: DNA
<213> ORGANISM: Homo sapiens

<400> SEQUENCE: 159
ttgctgtgga tgagaatgga 20

<210> SEQ ID NO 160
<211> LENGTH: 20
<212> TYPE: DNA
<213> ORGANISM: Homo sapiens

<400> SEQUENCE: 160
tgagggcaga aagaaacaga 20

<210> SEQ ID NO 161
<211> LENGTH: 20
<212> TYPE: DNA
<213> ORGANISM: Homo sapiens

<400> SEQUENCE: 161
ggggtcacac atcacttttc 20

<210> SEQ ID NO 162
<211> LENGTH: 20
<212> TYPE: DNA
<213> ORGANISM: Homo sapiens

<400> SEQUENCE: 162
atagggtcac aatccactgc 20

<210> SEQ ID NO 163
<211> LENGTH: 20
<212> TYPE: DNA
<213> ORGANISM: Homo sapiens

<400> SEQUENCE: 163
atattgagcc ccgcatgtta 20

<210> SEQ ID NO 164
<211> LENGTH: 20
<212> TYPE: DNA
<213> ORGANISM: Homo sapiens

<400> SEQUENCE: 164
ggttgcagga gaaagaacat 20

<210> SEQ ID NO 165
<211> LENGTH: 20
<212> TYPE: DNA
<213> ORGANISM: Homo sapiens

<400> SEQUENCE: 165
tgccatgtaa ttgccaagat 20

<210> SEQ ID NO 166
<211> LENGTH: 19
<212> TYPE: DNA
<213> ORGANISM: Homo sapiens

<400> SEQUENCE: 166
cctgttctcc atccctctg 19

<210> SEQ ID NO 167
<211> LENGTH: 21
<212> TYPE: DNA
<213> ORGANISM: Homo sapiens

<400> SEQUENCE: 167
tcacaaacta cccaacacct a 21

<210> SEQ ID NO 168
<211> LENGTH: 21
<212> TYPE: DNA
<213> ORGANISM: Homo sapiens

<400> SEQUENCE: 168
cagaattagt tggggagctg t 21

<210> SEQ ID NO 169
<211> LENGTH: 20
<212> TYPE: DNA
<213> ORGANISM: Homo sapiens

<400> SEQUENCE: 169
gccatctcct gaaatagtgc 20

<210> SEQ ID NO 170
<211> LENGTH: 20
<212> TYPE: DNA
<213> ORGANISM: Homo sapiens

<400> SEQUENCE: 170
gcaagtgttc ccatctagaa 20

<210> SEQ ID NO 171
<211> LENGTH: 20
<212> TYPE: DNA
<213> ORGANISM: Homo sapiens

<400> SEQUENCE: 171
attgataccc ctctccccag 20

<210> SEQ ID NO 172
<211> LENGTH: 19
<212> TYPE: DNA
<213> ORGANISM: Homo sapiens

<400> SEQUENCE: 172
aagtaagctg tctcctggc 19

<210> SEQ ID NO 173
<211> LENGTH: 20
<212> TYPE: DNA
<213> ORGANISM: Homo sapiens

<400> SEQUENCE: 173
aggttggttg gcatgaagaa 20

<210> SEQ ID NO 174
<211> LENGTH: 20
<212> TYPE: DNA
<213> ORGANISM: Homo sapiens

<400> SEQUENCE: 174
agcagagttt caagacaagc 20

<210> SEQ ID NO 175
<211> LENGTH: 20
<212> TYPE: DNA
<213> ORGANISM: Homo sapiens

<400> SEQUENCE: 175
ttttacacag caggcctctt 20

<210> SEQ ID NO 176
<211> LENGTH: 21
<212> TYPE: DNA
<213> ORGANISM: Homo sapiens

<400> SEQUENCE: 176
gcaactccaa attatcaggg c 21

<210> SEQ ID NO 177
<211> LENGTH: 20
<212> TYPE: DNA
<213> ORGANISM: Homo sapiens

<400> SEQUENCE: 177
cagcaccttc ccttagcaaa 20

<210> SEQ ID NO 178
<211> LENGTH: 20
<212> TYPE: DNA
<213> ORGANISM: Homo sapiens

<400> SEQUENCE: 178
cttgttgtct tgtagccctg 20

<210> SEQ ID NO 179
<211> LENGTH: 20
<212> TYPE: DNA
<213> ORGANISM: Homo sapiens

<400> SEQUENCE: 179
cacagataca gacgtccaca 20

<210> SEQ ID NO 180
<211> LENGTH: 21
<212> TYPE: DNA
<213> ORGANISM: Homo sapiens

<400> SEQUENCE: 180
agctcagcaa ttaaacagtc c 21

<210> SEQ ID NO 181
<211> LENGTH: 20
<212> TYPE: DNA
<213> ORGANISM: Homo sapiens

<400> SEQUENCE: 181
tgttgagagt gccagagatg 20

<210> SEQ ID NO 182
<211> LENGTH: 20
<212> TYPE: DNA
<213> ORGANISM: Homo sapiens

<400> SEQUENCE: 182
cttccacctt ctgccaatga 20

<210> SEQ ID NO 183
<211> LENGTH: 20
<212> TYPE: DNA
<213> ORGANISM: Homo sapiens

<400> SEQUENCE: 183
ttctgacatt tgcaagcacc 20

<210> SEQ ID NO 184
<211> LENGTH: 20
<212> TYPE: DNA
<213> ORGANISM: Homo sapiens

<400> SEQUENCE: 184
ctgttgctag tttcttgggc 20

<210> SEQ ID NO 185
<211> LENGTH: 19
<212> TYPE: DNA
<213> ORGANISM: Homo sapiens

<400> SEQUENCE: 185
ttttccagtc ccagcacat 19

<210> SEQ ID NO 186
<211> LENGTH: 21
<212> TYPE: DNA
<213> ORGANISM: Homo sapiens

<400> SEQUENCE: 186
tctctctctt cctgaaacag c 21

<210> SEQ ID NO 187
<211> LENGTH: 21
<212> TYPE: DNA
<213> ORGANISM: Homo sapiens

<400> SEQUENCE: 187
aacctctgct ttgtgtagtg a 21

<210> SEQ ID NO 188
<211> LENGTH: 20
<212> TYPE: DNA
<213> ORGANISM: Homo sapiens

<400> SEQUENCE: 188
gagagaatgc aaggttcagc 20

<210> SEQ ID NO 189
<211> LENGTH: 20
<212> TYPE: DNA
<213> ORGANISM: Homo sapiens

<400> SEQUENCE: 189
tacagcatca aagaggaagc 20

<210> SEQ ID NO 190
<211> LENGTH: 20
<212> TYPE: DNA

<213> ORGANISM: Homo sapiens

<400> SEQUENCE: 190
gaggggatga ggggaaaaag 20

<210> SEQ ID NO 191
<211> LENGTH: 20
<212> TYPE: DNA
<213> ORGANISM: Homo sapiens

<400> SEQUENCE: 191
catgacctct gacggatctg 20

<210> SEQ ID NO 192
<211> LENGTH: 19
<212> TYPE: DNA
<213> ORGANISM: Homo sapiens

<400> SEQUENCE: 192
aggcaatgag gtcaaggac 19

<210> SEQ ID NO 193
<211> LENGTH: 20
<212> TYPE: DNA
<213> ORGANISM: Homo sapiens

<400> SEQUENCE: 193
atgatggccc caacttcttc 20

<210> SEQ ID NO 194
<211> LENGTH: 20
<212> TYPE: DNA
<213> ORGANISM: Homo sapiens

<400> SEQUENCE: 194
ttctagacac tgagggagca 20

<210> SEQ ID NO 195
<211> LENGTH: 20
<212> TYPE: DNA
<213> ORGANISM: Homo sapiens

<400> SEQUENCE: 195
aacgctacac tttacgagct 20

<210> SEQ ID NO 196
<211> LENGTH: 20
<212> TYPE: DNA
<213> ORGANISM: Homo sapiens

<400> SEQUENCE: 196
tcaacactac ctgccaatca 20

<210> SEQ ID NO 197
<211> LENGTH: 19
<212> TYPE: DNA
<213> ORGANISM: Homo sapiens

<400> SEQUENCE: 197
tgccgacaca aaagaatgc 19

<210> SEQ ID NO 198
<211> LENGTH: 19

<212> TYPE: DNA
<213> ORGANISM: Homo sapiens

<400> SEQUENCE: 198
aaagtgttcc tccctgctg 19

<210> SEQ ID NO 199
<211> LENGTH: 20
<212> TYPE: DNA
<213> ORGANISM: Homo sapiens

<400> SEQUENCE: 199
aggagcaaaa tagtctggct 20

<210> SEQ ID NO 200
<211> LENGTH: 21
<212> TYPE: DNA
<213> ORGANISM: Homo sapiens

<400> SEQUENCE: 200
accactcttg aatcattgca g 21

<210> SEQ ID NO 201
<211> LENGTH: 21
<212> TYPE: DNA
<213> ORGANISM: Homo sapiens

<400> SEQUENCE: 201
ccagccaatt ttctctttcc c 21

<210> SEQ ID NO 202
<211> LENGTH: 20
<212> TYPE: DNA
<213> ORGANISM: Homo sapiens

<400> SEQUENCE: 202
actgtcccta ctgccaattt 20

<210> SEQ ID NO 203
<211> LENGTH: 21
<212> TYPE: DNA
<213> ORGANISM: Homo sapiens

<400> SEQUENCE: 203
atctggtttg aacttgccaa c 21

<210> SEQ ID NO 204
<211> LENGTH: 20
<212> TYPE: DNA
<213> ORGANISM: Homo sapiens

<400> SEQUENCE: 204
cactctgaat agctctcccc 20

<210> SEQ ID NO 205
<211> LENGTH: 20
<212> TYPE: DNA
<213> ORGANISM: Homo sapiens

<400> SEQUENCE: 205
ttatccggga cagtttcagg 20

<210> SEQ ID NO 206

<211> LENGTH: 20
<212> TYPE: DNA
<213> ORGANISM: Homo sapiens

<400> SEQUENCE: 206
gaatcttttg gcccacactg 20

<210> SEQ ID NO 207
<211> LENGTH: 20
<212> TYPE: DNA
<213> ORGANISM: Homo sapiens

<400> SEQUENCE: 207
gtcagacaca cttagctggt 20

<210> SEQ ID NO 208
<211> LENGTH: 20
<212> TYPE: DNA
<213> ORGANISM: Homo sapiens

<400> SEQUENCE: 208
acacatttca ccttcaccct 20

<210> SEQ ID NO 209
<211> LENGTH: 20
<212> TYPE: DNA
<213> ORGANISM: Homo sapiens

<400> SEQUENCE: 209
gcactaatcc aggggcttaa 20

<210> SEQ ID NO 210
<211> LENGTH: 20
<212> TYPE: DNA
<213> ORGANISM: Homo sapiens

<400> SEQUENCE: 210
ccccttacca ccacttctac 20

<210> SEQ ID NO 211
<211> LENGTH: 20
<212> TYPE: DNA
<213> ORGANISM: Homo sapiens

<400> SEQUENCE: 211
ttcagatccc ttaagcacgc 20

<210> SEQ ID NO 212
<211> LENGTH: 20
<212> TYPE: DNA
<213> ORGANISM: Homo sapiens

<400> SEQUENCE: 212
acctaaggcc tcaaattcca 20

<210> SEQ ID NO 213
<211> LENGTH: 20
<212> TYPE: DNA
<213> ORGANISM: Homo sapiens

<400> SEQUENCE: 213
cagaccacgg gcataagaaa 20

<210> SEQ ID NO 214
<211> LENGTH: 20
<212> TYPE: DNA
<213> ORGANISM: Homo sapiens

<400> SEQUENCE: 214
tggatgtgtg gatttggaga 20

<210> SEQ ID NO 215
<211> LENGTH: 19
<212> TYPE: DNA
<213> ORGANISM: Homo sapiens

<400> SEQUENCE: 215
ctggctgtct tctgggaaa 19

<210> SEQ ID NO 216
<211> LENGTH: 21
<212> TYPE: DNA
<213> ORGANISM: Homo sapiens

<400> SEQUENCE: 216
caagcagaac tgagaagagt c 21

<210> SEQ ID NO 217
<211> LENGTH: 20
<212> TYPE: DNA
<213> ORGANISM: Homo sapiens

<400> SEQUENCE: 217
agtggaacga ggattgtgtt 20

<210> SEQ ID NO 218
<211> LENGTH: 20
<212> TYPE: DNA
<213> ORGANISM: Homo sapiens

<400> SEQUENCE: 218
ctcccatctg aaactgctga 20

<210> SEQ ID NO 219
<211> LENGTH: 19
<212> TYPE: DNA
<213> ORGANISM: Homo sapiens

<400> SEQUENCE: 219
acatcacaac caccctgac 19

<210> SEQ ID NO 220
<211> LENGTH: 20
<212> TYPE: DNA
<213> ORGANISM: Homo sapiens

<400> SEQUENCE: 220
gtgttgacct gatttgccaa 20

<210> SEQ ID NO 221
<211> LENGTH: 20
<212> TYPE: DNA
<213> ORGANISM: Homo sapiens

<400> SEQUENCE: 221
gaacaaagag gaacagagcc 20

<210> SEQ ID NO 222
<211> LENGTH: 20
<212> TYPE: DNA
<213> ORGANISM: Homo sapiens

<400> SEQUENCE: 222
ttcatgattc cagggtcctc 20

<210> SEQ ID NO 223
<211> LENGTH: 22
<212> TYPE: DNA
<213> ORGANISM: Homo sapiens

<400> SEQUENCE: 223
ggacggattt agtgtacatt gg 22

<210> SEQ ID NO 224
<211> LENGTH: 20
<212> TYPE: DNA
<213> ORGANISM: Homo sapiens

<400> SEQUENCE: 224
tttccttcca acaccacaga 20

<210> SEQ ID NO 225
<211> LENGTH: 20
<212> TYPE: DNA
<213> ORGANISM: Homo sapiens

<400> SEQUENCE: 225
tccttagggt tctgcgaaat 20

<210> SEQ ID NO 226
<211> LENGTH: 20
<212> TYPE: DNA
<213> ORGANISM: Homo sapiens

<400> SEQUENCE: 226
ggaaactccc tgccttctac 20

<210> SEQ ID NO 227
<211> LENGTH: 20
<212> TYPE: DNA
<213> ORGANISM: Homo sapiens

<400> SEQUENCE: 227
tcttccaaac accaggtcta 20

<210> SEQ ID NO 228
<211> LENGTH: 19
<212> TYPE: DNA
<213> ORGANISM: Homo sapiens

<400> SEQUENCE: 228
actcaatgga aggaagggc 19

<210> SEQ ID NO 229
<211> LENGTH: 20
<212> TYPE: DNA
<213> ORGANISM: Homo sapiens

<400> SEQUENCE: 229
aaggacttgt gctgtattgc 20

<210> SEQ ID NO 230
<211> LENGTH: 20
<212> TYPE: DNA
<213> ORGANISM: Homo sapiens

<400> SEQUENCE: 230
gacgggagcc agtattctac 20

<210> SEQ ID NO 231
<211> LENGTH: 20
<212> TYPE: DNA
<213> ORGANISM: Homo sapiens

<400> SEQUENCE: 231
gggattgaga gcttggttct 20

<210> SEQ ID NO 232
<211> LENGTH: 20
<212> TYPE: DNA
<213> ORGANISM: Homo sapiens

<400> SEQUENCE: 232
ctccccacca agatgttcaa 20

<210> SEQ ID NO 233
<211> LENGTH: 20
<212> TYPE: DNA
<213> ORGANISM: Homo sapiens

<400> SEQUENCE: 233
gttttgggtc atgcagtgtt 20

<210> SEQ ID NO 234
<211> LENGTH: 20
<212> TYPE: DNA
<213> ORGANISM: Homo sapiens

<400> SEQUENCE: 234
gacaaaaaca cttgccagac 20

<210> SEQ ID NO 235
<211> LENGTH: 20
<212> TYPE: DNA
<213> ORGANISM: Homo sapiens

<400> SEQUENCE: 235
aaccatggct ttgcaagtac 20

<210> SEQ ID NO 236
<211> LENGTH: 20
<212> TYPE: DNA
<213> ORGANISM: Homo sapiens

<400> SEQUENCE: 236
ggaaccctct gctattttgc 20

<210> SEQ ID NO 237
<211> LENGTH: 20
<212> TYPE: DNA
<213> ORGANISM: Homo sapiens

<400> SEQUENCE: 237
tactccttgt gtgaacccct 20

<210> SEQ ID NO 238
<211> LENGTH: 20
<212> TYPE: DNA
<213> ORGANISM: Homo sapiens

<400> SEQUENCE: 238
acctttaccc cataccatcc 20

<210> SEQ ID NO 239
<211> LENGTH: 20
<212> TYPE: DNA
<213> ORGANISM: Homo sapiens

<400> SEQUENCE: 239
cattcctttg gttggtgtcc 20

<210> SEQ ID NO 240
<211> LENGTH: 20
<212> TYPE: DNA
<213> ORGANISM: Homo sapiens

<400> SEQUENCE: 240
ctaatgggcc tgttgttcct 20

<210> SEQ ID NO 241
<211> LENGTH: 20
<212> TYPE: DNA
<213> ORGANISM: Homo sapiens

<400> SEQUENCE: 241
caacctacct gcccatagtt 20

<210> SEQ ID NO 242
<211> LENGTH: 20
<212> TYPE: DNA
<213> ORGANISM: Homo sapiens

<400> SEQUENCE: 242
cgtagcaaat tatggcgagg 20

<210> SEQ ID NO 243
<211> LENGTH: 20
<212> TYPE: DNA
<213> ORGANISM: Homo sapiens

<400> SEQUENCE: 243
ggtcagaagg gaaagggttc 20

<210> SEQ ID NO 244
<211> LENGTH: 20
<212> TYPE: DNA
<213> ORGANISM: Homo sapiens

<400> SEQUENCE: 244
ccagattaaa acgtggtgcc 20

<210> SEQ ID NO 245
<211> LENGTH: 20
<212> TYPE: DNA
<213> ORGANISM: Homo sapiens

<400> SEQUENCE: 245
cccacaacta taggtcgcat 20

<210> SEQ ID NO 246
<211> LENGTH: 21
<212> TYPE: DNA
<213> ORGANISM: Homo sapiens

<400> SEQUENCE: 246
agttgttcca tttgtaccag c 21

<210> SEQ ID NO 247
<211> LENGTH: 19
<212> TYPE: DNA
<213> ORGANISM: Homo sapiens

<400> SEQUENCE: 247
ttggctgcac tttgagtca 19

<210> SEQ ID NO 248
<211> LENGTH: 20
<212> TYPE: DNA
<213> ORGANISM: Homo sapiens

<400> SEQUENCE: 248
cagatggccc attgtaacaa 20

<210> SEQ ID NO 249
<211> LENGTH: 19
<212> TYPE: DNA
<213> ORGANISM: Homo sapiens

<400> SEQUENCE: 249
tattgaggtt cccgtgctg 19

<210> SEQ ID NO 250
<211> LENGTH: 20
<212> TYPE: DNA
<213> ORGANISM: Homo sapiens

<400> SEQUENCE: 250
agaatgtgaa gtggctccat 20

<210> SEQ ID NO 251
<211> LENGTH: 20
<212> TYPE: DNA
<213> ORGANISM: Homo sapiens

<400> SEQUENCE: 251
tttgggtttg tgtgtgtgtg 20

<210> SEQ ID NO 252
<211> LENGTH: 20
<212> TYPE: DNA
<213> ORGANISM: Homo sapiens

<400> SEQUENCE: 252
aggaatctct ctctgccaag 20

<210> SEQ ID NO 253
<211> LENGTH: 20
<212> TYPE: DNA
<213> ORGANISM: Homo sapiens

<400> SEQUENCE: 253
tcttcaaggc aggtcatagg 20

<210> SEQ ID NO 254
<211> LENGTH: 21
<212> TYPE: DNA
<213> ORGANISM: Homo sapiens

<400> SEQUENCE: 254
gaaacctaag acgttccact g 21

<210> SEQ ID NO 255
<211> LENGTH: 20
<212> TYPE: DNA
<213> ORGANISM: Homo sapiens

<400> SEQUENCE: 255
gagtgaaggg attggagcaa 20

<210> SEQ ID NO 256
<211> LENGTH: 20
<212> TYPE: DNA
<213> ORGANISM: Homo sapiens

<400> SEQUENCE: 256
atgtctcagg ctaggtgttc 20

<210> SEQ ID NO 257
<211> LENGTH: 20
<212> TYPE: DNA
<213> ORGANISM: Homo sapiens

<400> SEQUENCE: 257
acactcacaa agcccagtta 20

<210> SEQ ID NO 258
<211> LENGTH: 20
<212> TYPE: DNA
<213> ORGANISM: Homo sapiens

<400> SEQUENCE: 258
gtgcagactc atgttatggc 20

<210> SEQ ID NO 259
<211> LENGTH: 20
<212> TYPE: DNA
<213> ORGANISM: Homo sapiens

<400> SEQUENCE: 259
aggatctcaa agcaccacag 20

<210> SEQ ID NO 260
<211> LENGTH: 20
<212> TYPE: DNA
<213> ORGANISM: Homo sapiens

<400> SEQUENCE: 260
aacgggaaga gggaaacttt 20

<210> SEQ ID NO 261
<211> LENGTH: 20
<212> TYPE: DNA
<213> ORGANISM: Homo sapiens

<400> SEQUENCE: 261
atgttcaaca gagtcaggct 20

<210> SEQ ID NO 262
<211> LENGTH: 20
<212> TYPE: DNA
<213> ORGANISM: Homo sapiens

<400> SEQUENCE: 262
cagtaacagt ccagggtctt 20

<210> SEQ ID NO 263
<211> LENGTH: 20
<212> TYPE: DNA
<213> ORGANISM: Homo sapiens

<400> SEQUENCE: 263
agtctgggag cctagaatca 20

<210> SEQ ID NO 264
<211> LENGTH: 22
<212> TYPE: DNA
<213> ORGANISM: Homo sapiens

<400> SEQUENCE: 264
cattgtagtt tcaggacacc aa 22

<210> SEQ ID NO 265
<211> LENGTH: 20
<212> TYPE: DNA
<213> ORGANISM: Homo sapiens

<400> SEQUENCE: 265
accacagaat gacttgcagc 20

<210> SEQ ID NO 266
<211> LENGTH: 20
<212> TYPE: DNA
<213> ORGANISM: Homo sapiens

<400> SEQUENCE: 266
tttcacgtgt aacaggagca 20

<210> SEQ ID NO 267
<211> LENGTH: 20
<212> TYPE: DNA
<213> ORGANISM: Homo sapiens

<400> SEQUENCE: 267
tgctacaggg aaaatggtct 20

<210> SEQ ID NO 268
<211> LENGTH: 20
<212> TYPE: DNA
<213> ORGANISM: Homo sapiens

<400> SEQUENCE: 268
tccactgctt agtttgcctt 20

<210> SEQ ID NO 269
<211> LENGTH: 20
<212> TYPE: DNA

<213> ORGANISM: Homo sapiens

<400> SEQUENCE: 269
acaggtgggg agaaaaggta 20

<210> SEQ ID NO 270
<211> LENGTH: 20
<212> TYPE: DNA
<213> ORGANISM: Homo sapiens

<400> SEQUENCE: 270
ctgccactac tacacagcta 20

<210> SEQ ID NO 271
<211> LENGTH: 20
<212> TYPE: DNA
<213> ORGANISM: Homo sapiens

<400> SEQUENCE: 271
atgggtctct ggaatgcatg 20

<210> SEQ ID NO 272
<211> LENGTH: 20
<212> TYPE: DNA
<213> ORGANISM: Homo sapiens

<400> SEQUENCE: 272
agttctccac agcacatcat 20

<210> SEQ ID NO 273
<211> LENGTH: 20
<212> TYPE: DNA
<213> ORGANISM: Homo sapiens

<400> SEQUENCE: 273
tctttcatct cagctctgca 20

<210> SEQ ID NO 274
<211> LENGTH: 20
<212> TYPE: DNA
<213> ORGANISM: Homo sapiens

<400> SEQUENCE: 274
ccgaacagta ttttgagggg 20

<210> SEQ ID NO 275
<211> LENGTH: 20
<212> TYPE: DNA
<213> ORGANISM: Homo sapiens

<400> SEQUENCE: 275
tttggctgtt tcctgtttcc 20

<210> SEQ ID NO 276
<211> LENGTH: 20
<212> TYPE: DNA
<213> ORGANISM: Homo sapiens

<400> SEQUENCE: 276
acctaacttg ccttgtcctt 20

<210> SEQ ID NO 277
<211> LENGTH: 20

<212> TYPE: DNA
<213> ORGANISM: Homo sapiens

<400> SEQUENCE: 277
acaggagaac aagcagcata 20

<210> SEQ ID NO 278
<211> LENGTH: 21
<212> TYPE: DNA
<213> ORGANISM: Homo sapiens

<400> SEQUENCE: 278
cagcctagta tatgggaacg t 21

<210> SEQ ID NO 279
<211> LENGTH: 23
<212> TYPE: DNA
<213> ORGANISM: Homo sapiens

<400> SEQUENCE: 279
acccatatgt agtatcgctc ttg 23

<210> SEQ ID NO 280
<211> LENGTH: 21
<212> TYPE: DNA
<213> ORGANISM: Homo sapiens

<400> SEQUENCE: 280
tatgggtttt tctgctccac t 21

<210> SEQ ID NO 281
<211> LENGTH: 20
<212> TYPE: DNA
<213> ORGANISM: Homo sapiens

<400> SEQUENCE: 281
aaatgtgagg gagagtcgtc 20

<210> SEQ ID NO 282
<211> LENGTH: 19
<212> TYPE: DNA
<213> ORGANISM: Homo sapiens

<400> SEQUENCE: 282
gcaggaccct tcagcatta 19

<210> SEQ ID NO 283
<211> LENGTH: 20
<212> TYPE: DNA
<213> ORGANISM: Homo sapiens

<400> SEQUENCE: 283
gactggatga tgcaaaggtg 20

<210> SEQ ID NO 284
<211> LENGTH: 20
<212> TYPE: DNA
<213> ORGANISM: Homo sapiens

<400> SEQUENCE: 284
aacatttgca gggggatcaa 20

<210> SEQ ID NO 285

<211> LENGTH: 20
<212> TYPE: DNA
<213> ORGANISM: Homo sapiens

<400> SEQUENCE: 285
aaagatgcct ccttgtgtct 20

<210> SEQ ID NO 286
<211> LENGTH: 20
<212> TYPE: DNA
<213> ORGANISM: Homo sapiens

<400> SEQUENCE: 286
aagttatctg cccagggaaa 20

<210> SEQ ID NO 287
<211> LENGTH: 20
<212> TYPE: DNA
<213> ORGANISM: Homo sapiens

<400> SEQUENCE: 287
tcctggctag ttttgctgaa 20

<210> SEQ ID NO 288
<211> LENGTH: 20
<212> TYPE: DNA
<213> ORGANISM: Homo sapiens

<400> SEQUENCE: 288
ctccttgctt gcctttacac 20

<210> SEQ ID NO 289
<211> LENGTH: 20
<212> TYPE: DNA
<213> ORGANISM: Homo sapiens

<400> SEQUENCE: 289
agccttaatt ccccatgcat 20

<210> SEQ ID NO 290
<211> LENGTH: 20
<212> TYPE: DNA
<213> ORGANISM: Homo sapiens

<400> SEQUENCE: 290
tttttctgtg gagtgtggct 20

<210> SEQ ID NO 291
<211> LENGTH: 20
<212> TYPE: DNA
<213> ORGANISM: Homo sapiens

<400> SEQUENCE: 291
aaagagtcaa ccatgcactg 20

<210> SEQ ID NO 292
<211> LENGTH: 20
<212> TYPE: DNA
<213> ORGANISM: Homo sapiens

<400> SEQUENCE: 292
ggtgaagcag cctgaataaa 20

<210> SEQ ID NO 293
<211> LENGTH: 19
<212> TYPE: DNA
<213> ORGANISM: Homo sapiens

<400> SEQUENCE: 293
tctttgtacc aagctgcca 19

<210> SEQ ID NO 294
<211> LENGTH: 20
<212> TYPE: DNA
<213> ORGANISM: Homo sapiens

<400> SEQUENCE: 294
gcttctactt tcccctccag 20

<210> SEQ ID NO 295
<211> LENGTH: 20
<212> TYPE: DNA
<213> ORGANISM: Homo sapiens

<400> SEQUENCE: 295
agaaaagcca acctcctctt 20

<210> SEQ ID NO 296
<211> LENGTH: 20
<212> TYPE: DNA
<213> ORGANISM: Homo sapiens

<400> SEQUENCE: 296
ccagggtact aaaaggggac 20

<210> SEQ ID NO 297
<211> LENGTH: 20
<212> TYPE: DNA
<213> ORGANISM: Homo sapiens

<400> SEQUENCE: 297
ttgtgggtca atgtcaacac 20

<210> SEQ ID NO 298
<211> LENGTH: 20
<212> TYPE: DNA
<213> ORGANISM: Homo sapiens

<400> SEQUENCE: 298
agaaaaggtg gaggaaggga 20

<210> SEQ ID NO 299
<211> LENGTH: 21
<212> TYPE: DNA
<213> ORGANISM: Homo sapiens

<400> SEQUENCE: 299
ggagttgttt acaggtggac t 21

<210> SEQ ID NO 300
<211> LENGTH: 21
<212> TYPE: DNA
<213> ORGANISM: Homo sapiens

<400> SEQUENCE: 300
tagcttccaa ttcacaggtc a 21

<210> SEQ ID NO 301
<211> LENGTH: 20
<212> TYPE: DNA
<213> ORGANISM: Homo sapiens

<400> SEQUENCE: 301
ttaaatgcgc caagtcccta 20

<210> SEQ ID NO 302
<211> LENGTH: 20
<212> TYPE: DNA
<213> ORGANISM: Homo sapiens

<400> SEQUENCE: 302
atttcctggg tcaagctctt 20

<210> SEQ ID NO 303
<211> LENGTH: 20
<212> TYPE: DNA
<213> ORGANISM: Homo sapiens

<400> SEQUENCE: 303
cttggaccag gaatgctcta 20

<210> SEQ ID NO 304
<211> LENGTH: 20
<212> TYPE: DNA
<213> ORGANISM: Homo sapiens

<400> SEQUENCE: 304
aggcagtcag atccacctat 20

<210> SEQ ID NO 305
<211> LENGTH: 20
<212> TYPE: DNA
<213> ORGANISM: Homo sapiens

<400> SEQUENCE: 305
aaaattgcct gctgtttgga 20

<210> SEQ ID NO 306
<211> LENGTH: 20
<212> TYPE: DNA
<213> ORGANISM: Homo sapiens

<400> SEQUENCE: 306
gcaccatcat gaaacctcct 20

<210> SEQ ID NO 307
<211> LENGTH: 20
<212> TYPE: DNA
<213> ORGANISM: Homo sapiens

<400> SEQUENCE: 307
ataggccagt ctcaggtaga 20

<210> SEQ ID NO 308
<211> LENGTH: 20
<212> TYPE: DNA
<213> ORGANISM: Homo sapiens

<400> SEQUENCE: 308
agattgcagc ctacccaaag 20

<210> SEQ ID NO 309
<211> LENGTH: 20
<212> TYPE: DNA
<213> ORGANISM: Homo sapiens

<400> SEQUENCE: 309
ttgactgaag tgttccaggt 20

<210> SEQ ID NO 310
<211> LENGTH: 20
<212> TYPE: DNA
<213> ORGANISM: Homo sapiens

<400> SEQUENCE: 310
gcttctttca accatccacc 20

<210> SEQ ID NO 311
<211> LENGTH: 20
<212> TYPE: DNA
<213> ORGANISM: Homo sapiens

<400> SEQUENCE: 311
gcagcactca actattccac 20

<210> SEQ ID NO 312
<211> LENGTH: 20
<212> TYPE: DNA
<213> ORGANISM: Homo sapiens

<400> SEQUENCE: 312
caggagttat ggcaccagtg 20

<210> SEQ ID NO 313
<211> LENGTH: 20
<212> TYPE: DNA
<213> ORGANISM: Homo sapiens

<400> SEQUENCE: 313
gagagtgtgg aggcagaaaa 20

<210> SEQ ID NO 314
<211> LENGTH: 20
<212> TYPE: DNA
<213> ORGANISM: Homo sapiens

<400> SEQUENCE: 314
gcccaactta ttttccagct 20

<210> SEQ ID NO 315
<211> LENGTH: 21
<212> TYPE: DNA
<213> ORGANISM: Homo sapiens

<400> SEQUENCE: 315
tcaagcccct tagattgaac a 21

<210> SEQ ID NO 316
<211> LENGTH: 20
<212> TYPE: DNA
<213> ORGANISM: Homo sapiens

<400> SEQUENCE: 316
gctgggcatg tagaactcaa 20

<210> SEQ ID NO 317
<211> LENGTH: 20
<212> TYPE: DNA
<213> ORGANISM: Homo sapiens

<400> SEQUENCE: 317
gggaaattgt caagggcttt 20

<210> SEQ ID NO 318
<211> LENGTH: 21
<212> TYPE: DNA
<213> ORGANISM: Homo sapiens

<400> SEQUENCE: 318
cttagttgct gttgtgcttc t 21

<210> SEQ ID NO 319
<211> LENGTH: 20
<212> TYPE: DNA
<213> ORGANISM: Homo sapiens

<400> SEQUENCE: 319
agttgtagct gtatctgggt 20

<210> SEQ ID NO 320
<211> LENGTH: 20
<212> TYPE: DNA
<213> ORGANISM: Homo sapiens

<400> SEQUENCE: 320
agctgagtca tgtttaaggc 20

<210> SEQ ID NO 321
<211> LENGTH: 21
<212> TYPE: DNA
<213> ORGANISM: Homo sapiens

<400> SEQUENCE: 321
caattcagac tttgcccaaa c 21

<210> SEQ ID NO 322
<211> LENGTH: 21
<212> TYPE: DNA
<213> ORGANISM: Homo sapiens

<400> SEQUENCE: 322
caatcattcc cacagttcca a 21

<210> SEQ ID NO 323
<211> LENGTH: 20
<212> TYPE: DNA
<213> ORGANISM: Homo sapiens

<400> SEQUENCE: 323
ctgtgatggt ccattcaagg 20

<210> SEQ ID NO 324
<211> LENGTH: 20
<212> TYPE: DNA
<213> ORGANISM: Homo sapiens

<400> SEQUENCE: 324
tagctggaaa ttgcaaggag 20

<210> SEQ ID NO 325
<211> LENGTH: 19
<212> TYPE: DNA
<213> ORGANISM: Homo sapiens

<400> SEQUENCE: 325
tctgttcacc tgagccttt 19

<210> SEQ ID NO 326
<211> LENGTH: 20
<212> TYPE: DNA
<213> ORGANISM: Homo sapiens

<400> SEQUENCE: 326
taacttggac tgtgaaccca 20

<210> SEQ ID NO 327
<211> LENGTH: 20
<212> TYPE: DNA
<213> ORGANISM: Homo sapiens

<400> SEQUENCE: 327
cgcaacagga tgaaggaaat 20

<210> SEQ ID NO 328
<211> LENGTH: 20
<212> TYPE: DNA
<213> ORGANISM: Homo sapiens

<400> SEQUENCE: 328
gactcacact ctgaaagcct 20

<210> SEQ ID NO 329
<211> LENGTH: 21
<212> TYPE: DNA
<213> ORGANISM: Homo sapiens

<400> SEQUENCE: 329
aatttaggta gcactgaccc c 21

<210> SEQ ID NO 330
<211> LENGTH: 20
<212> TYPE: DNA
<213> ORGANISM: Homo sapiens

<400> SEQUENCE: 330
ctggggaatt aggaagcaga 20

<210> SEQ ID NO 331
<211> LENGTH: 19
<212> TYPE: DNA
<213> ORGANISM: Homo sapiens

<400> SEQUENCE: 331
atgacaaggc tggctcatc 19

<210> SEQ ID NO 332
<211> LENGTH: 20
<212> TYPE: DNA
<213> ORGANISM: Homo sapiens

<400> SEQUENCE: 332
ttagttttgg catgtggtgg 20

<210> SEQ ID NO 333
<211> LENGTH: 20
<212> TYPE: DNA
<213> ORGANISM: Homo sapiens

<400> SEQUENCE: 333
tggtgaggga gtgttctttt 20

<210> SEQ ID NO 334
<211> LENGTH: 20
<212> TYPE: DNA
<213> ORGANISM: Homo sapiens

<400> SEQUENCE: 334
tcattggggg agtcattcac 20

<210> SEQ ID NO 335
<211> LENGTH: 20
<212> TYPE: DNA
<213> ORGANISM: Homo sapiens

<400> SEQUENCE: 335
gaagtggtgt gatgagggtg 20

<210> SEQ ID NO 336
<211> LENGTH: 20
<212> TYPE: DNA
<213> ORGANISM: Homo sapiens

<400> SEQUENCE: 336
aagttaggcc ctgttaagca 20

<210> SEQ ID NO 337
<211> LENGTH: 20
<212> TYPE: DNA
<213> ORGANISM: Homo sapiens

<400> SEQUENCE: 337
tgttggtcgg agtcagaaat 20

<210> SEQ ID NO 338
<211> LENGTH: 20
<212> TYPE: DNA
<213> ORGANISM: Homo sapiens

<400> SEQUENCE: 338
gtaaaagagg ttgggatgcc 20

<210> SEQ ID NO 339
<211> LENGTH: 20
<212> TYPE: DNA
<213> ORGANISM: Homo sapiens

<400> SEQUENCE: 339
cgttggacat ggatcatacc 20

<210> SEQ ID NO 340
<211> LENGTH: 22
<212> TYPE: DNA
<213> ORGANISM: Homo sapiens

<400> SEQUENCE: 340
tcacaacaag ggaaatagcc ta 22

<210> SEQ ID NO 341
<211> LENGTH: 20
<212> TYPE: DNA
<213> ORGANISM: Homo sapiens

<400> SEQUENCE: 341
tagtcaggta aacaacgcct 20

<210> SEQ ID NO 342
<211> LENGTH: 21
<212> TYPE: DNA
<213> ORGANISM: Homo sapiens

<400> SEQUENCE: 342
tctgtttctt gtttggctga g 21

<210> SEQ ID NO 343
<211> LENGTH: 20
<212> TYPE: DNA
<213> ORGANISM: Homo sapiens

<400> SEQUENCE: 343
acataggtca cacaaagggt 20

<210> SEQ ID NO 344
<211> LENGTH: 20
<212> TYPE: DNA
<213> ORGANISM: Homo sapiens

<400> SEQUENCE: 344
gtgtgacact tttctgcctt 20

<210> SEQ ID NO 345
<211> LENGTH: 21
<212> TYPE: DNA
<213> ORGANISM: Homo sapiens

<400> SEQUENCE: 345
ctggaaatag aaggcctttg c 21

<210> SEQ ID NO 346
<211> LENGTH: 20
<212> TYPE: DNA
<213> ORGANISM: Homo sapiens

<400> SEQUENCE: 346
tcttggtctg ggaataagcc 20

<210> SEQ ID NO 347
<211> LENGTH: 20
<212> TYPE: DNA
<213> ORGANISM: Homo sapiens

<400> SEQUENCE: 347
tgcccctatg aacaacagaa 20

<210> SEQ ID NO 348
<211> LENGTH: 20
<212> TYPE: DNA

<213> ORGANISM: Homo sapiens

<400> SEQUENCE: 348
tgaacgtctt gcttacccac 20

<210> SEQ ID NO 349
<211> LENGTH: 19
<212> TYPE: DNA
<213> ORGANISM: Homo sapiens

<400> SEQUENCE: 349
gaaggaaggc agaggtcaa 19

<210> SEQ ID NO 350
<211> LENGTH: 20
<212> TYPE: DNA
<213> ORGANISM: Homo sapiens

<400> SEQUENCE: 350
cttccacaaa gtcctgcaac 20

<210> SEQ ID NO 351
<211> LENGTH: 20
<212> TYPE: DNA
<213> ORGANISM: Homo sapiens

<400> SEQUENCE: 351
atgtgaacca ttgagaggca 20

<210> SEQ ID NO 352
<211> LENGTH: 20
<212> TYPE: DNA
<213> ORGANISM: Homo sapiens

<400> SEQUENCE: 352
aagagaaact accctggcaa 20

<210> SEQ ID NO 353
<211> LENGTH: 20
<212> TYPE: DNA
<213> ORGANISM: Homo sapiens

<400> SEQUENCE: 353
gcatgtagtt cagttcaggc 20

<210> SEQ ID NO 354
<211> LENGTH: 20
<212> TYPE: DNA
<213> ORGANISM: Homo sapiens

<400> SEQUENCE: 354
atgaaatgta atggggtgcg 20

<210> SEQ ID NO 355
<211> LENGTH: 20
<212> TYPE: DNA
<213> ORGANISM: Homo sapiens

<400> SEQUENCE: 355
ttttggcagt gatgaccttg 20

<210> SEQ ID NO 356
<211> LENGTH: 20

<212> TYPE: DNA
<213> ORGANISM: Homo sapiens

<400> SEQUENCE: 356
ttcttggctt ttctgaccct 20

<210> SEQ ID NO 357
<211> LENGTH: 21
<212> TYPE: DNA
<213> ORGANISM: Homo sapiens

<400> SEQUENCE: 357
ttgagaaaga ccccaacaga a 21

<210> SEQ ID NO 358
<211> LENGTH: 22
<212> TYPE: DNA
<213> ORGANISM: Homo sapiens

<400> SEQUENCE: 358
gaaaataaca cagtagggat gc 22

<210> SEQ ID NO 359
<211> LENGTH: 20
<212> TYPE: DNA
<213> ORGANISM: Homo sapiens

<400> SEQUENCE: 359
gaatggagag gcagttttca 20

<210> SEQ ID NO 360
<211> LENGTH: 20
<212> TYPE: DNA
<213> ORGANISM: Homo sapiens

<400> SEQUENCE: 360
cacccttttc ctgttttgca 20

<210> SEQ ID NO 361
<211> LENGTH: 21
<212> TYPE: DNA
<213> ORGANISM: Homo sapiens

<400> SEQUENCE: 361
agaagaaact tgcagtgttg g 21

<210> SEQ ID NO 362
<211> LENGTH: 21
<212> TYPE: DNA
<213> ORGANISM: Homo sapiens

<400> SEQUENCE: 362
tgcagcatta ttctttctgg g 21

<210> SEQ ID NO 363
<211> LENGTH: 21
<212> TYPE: DNA
<213> ORGANISM: Homo sapiens

<400> SEQUENCE: 363
acacacatat tagggaacag c 21

<210> SEQ ID NO 364

<211> LENGTH: 20
<212> TYPE: DNA
<213> ORGANISM: Homo sapiens

<400> SEQUENCE: 364
gagtgtaggt gcttgggtat 20

<210> SEQ ID NO 365
<211> LENGTH: 20
<212> TYPE: DNA
<213> ORGANISM: Homo sapiens

<400> SEQUENCE: 365
ccttagaatc ctagcgcctt 20

<210> SEQ ID NO 366
<211> LENGTH: 20
<212> TYPE: DNA
<213> ORGANISM: Homo sapiens

<400> SEQUENCE: 366
tcatgaggtt gccagtgttt 20

<210> SEQ ID NO 367
<211> LENGTH: 20
<212> TYPE: DNA
<213> ORGANISM: Homo sapiens

<400> SEQUENCE: 367
ccccatacat catcacatgc 20

<210> SEQ ID NO 368
<211> LENGTH: 20
<212> TYPE: DNA
<213> ORGANISM: Homo sapiens

<400> SEQUENCE: 368
gggtaatgct ttcttgggga 20

<210> SEQ ID NO 369
<211> LENGTH: 20
<212> TYPE: DNA
<213> ORGANISM: Homo sapiens

<400> SEQUENCE: 369
agttgagaag ggaaggcaag 20

<210> SEQ ID NO 370
<211> LENGTH: 21
<212> TYPE: DNA
<213> ORGANISM: Homo sapiens

<400> SEQUENCE: 370
ctcctggtgg cttatttttg a 21

<210> SEQ ID NO 371
<211> LENGTH: 22
<212> TYPE: DNA
<213> ORGANISM: Homo sapiens

<400> SEQUENCE: 371
tctggatttt ggctactcat ga 22

<210> SEQ ID NO 372
<211> LENGTH: 20
<212> TYPE: DNA
<213> ORGANISM: Homo sapiens

<400> SEQUENCE: 372
gtagtcctcc tttgcccttc 20

<210> SEQ ID NO 373
<211> LENGTH: 20
<212> TYPE: DNA
<213> ORGANISM: Homo sapiens

<400> SEQUENCE: 373
gacatgcaca gatcgaaacc 20

<210> SEQ ID NO 374
<211> LENGTH: 20
<212> TYPE: DNA
<213> ORGANISM: Homo sapiens

<400> SEQUENCE: 374
cgcatttgac aacagggatc 20

<210> SEQ ID NO 375
<211> LENGTH: 20
<212> TYPE: DNA
<213> ORGANISM: Homo sapiens

<400> SEQUENCE: 375
aagccacctg ttctctctca 20

<210> SEQ ID NO 376
<211> LENGTH: 20
<212> TYPE: DNA
<213> ORGANISM: Homo sapiens

<400> SEQUENCE: 376
attccaacca ttccgacacc 20

<210> SEQ ID NO 377
<211> LENGTH: 20
<212> TYPE: DNA
<213> ORGANISM: Homo sapiens

<400> SEQUENCE: 377
aaagaaaatg gtgaacgtgc 20

<210> SEQ ID NO 378
<211> LENGTH: 20
<212> TYPE: DNA
<213> ORGANISM: Homo sapiens

<400> SEQUENCE: 378
tgatcagggc tttagaggtc 20

<210> SEQ ID NO 379
<211> LENGTH: 20
<212> TYPE: DNA
<213> ORGANISM: Homo sapiens

<400> SEQUENCE: 379
actccctatt gttctcccct 20

<210> SEQ ID NO 380
<211> LENGTH: 20
<212> TYPE: DNA
<213> ORGANISM: Homo sapiens

<400> SEQUENCE: 380
ctccttgaca gatgtgaccc 20

<210> SEQ ID NO 381
<211> LENGTH: 20
<212> TYPE: DNA
<213> ORGANISM: Homo sapiens

<400> SEQUENCE: 381
ttttggagtc tgagccacaa 20

<210> SEQ ID NO 382
<211> LENGTH: 19
<212> TYPE: DNA
<213> ORGANISM: Homo sapiens

<400> SEQUENCE: 382
ttgaagtccc gttgctgat 19

<210> SEQ ID NO 383
<211> LENGTH: 20
<212> TYPE: DNA
<213> ORGANISM: Homo sapiens

<400> SEQUENCE: 383
ttggggtcag ttctaacagt 20

<210> SEQ ID NO 384
<211> LENGTH: 20
<212> TYPE: DNA
<213> ORGANISM: Homo sapiens

<400> SEQUENCE: 384
ttttcaccac ctcttccctc 20

<210> SEQ ID NO 385
<211> LENGTH: 20
<212> TYPE: DNA
<213> ORGANISM: Homo sapiens

<400> SEQUENCE: 385
acctgaccac aagctttaca 20

<210> SEQ ID NO 386
<211> LENGTH: 20
<212> TYPE: DNA
<213> ORGANISM: Homo sapiens

<400> SEQUENCE: 386
cacatattgg cgcacagtac 20

<210> SEQ ID NO 387
<211> LENGTH: 20
<212> TYPE: DNA
<213> ORGANISM: Homo sapiens

<400> SEQUENCE: 387
gccatgcacc gatgaaaaat 20

<210> SEQ ID NO 388
<211> LENGTH: 20
<212> TYPE: DNA
<213> ORGANISM: Homo sapiens

<400> SEQUENCE: 388
ttgtgaggag atttctgggc 20

<210> SEQ ID NO 389
<211> LENGTH: 20
<212> TYPE: DNA
<213> ORGANISM: Homo sapiens

<400> SEQUENCE: 389
cacactaaga gcactgggaa 20

<210> SEQ ID NO 390
<211> LENGTH: 20
<212> TYPE: DNA
<213> ORGANISM: Homo sapiens

<400> SEQUENCE: 390
atgacctagc acatcttccc 20

<210> SEQ ID NO 391
<211> LENGTH: 20
<212> TYPE: DNA
<213> ORGANISM: Homo sapiens

<400> SEQUENCE: 391
acattttccc cattccatgc 20

<210> SEQ ID NO 392
<211> LENGTH: 20
<212> TYPE: DNA
<213> ORGANISM: Homo sapiens

<400> SEQUENCE: 392
gtctgtcaac cacactttgc 20

<210> SEQ ID NO 393
<211> LENGTH: 20
<212> TYPE: DNA
<213> ORGANISM: Homo sapiens

<400> SEQUENCE: 393
ctgtctctcc ttttgccaaa 20

<210> SEQ ID NO 394
<211> LENGTH: 20
<212> TYPE: DNA
<213> ORGANISM: Homo sapiens

<400> SEQUENCE: 394
agtaacctgc gactctcagt 20

<210> SEQ ID NO 395
<211> LENGTH: 20
<212> TYPE: DNA
<213> ORGANISM: Homo sapiens

<400> SEQUENCE: 395
tagcatttaa ggagtgggct 20

<210> SEQ ID NO 396
<211> LENGTH: 20
<212> TYPE: DNA
<213> ORGANISM: Homo sapiens

<400> SEQUENCE: 396
ggcctcctca gtgatttgaa 20

<210> SEQ ID NO 397
<211> LENGTH: 20
<212> TYPE: DNA
<213> ORGANISM: Homo sapiens

<400> SEQUENCE: 397
ctttctttgc ctcccctgta 20

<210> SEQ ID NO 398
<211> LENGTH: 20
<212> TYPE: DNA
<213> ORGANISM: Homo sapiens

<400> SEQUENCE: 398
acttccattt gtgtcaacgg 20

<210> SEQ ID NO 399
<211> LENGTH: 20
<212> TYPE: DNA
<213> ORGANISM: Homo sapiens

<400> SEQUENCE: 399
tcttgctttg ggttagaggg 20

<210> SEQ ID NO 400
<211> LENGTH: 20
<212> TYPE: DNA
<213> ORGANISM: Homo sapiens

<400> SEQUENCE: 400
aaccacacct ccacaagaaa 20

<210> SEQ ID NO 401
<211> LENGTH: 20
<212> TYPE: DNA
<213> ORGANISM: Homo sapiens

<400> SEQUENCE: 401
caagatatga gggaggggaa 20

<210> SEQ ID NO 402
<211> LENGTH: 20
<212> TYPE: DNA
<213> ORGANISM: Homo sapiens

<400> SEQUENCE: 402
tctaacctgg gccctttctt 20

<210> SEQ ID NO 403
<211> LENGTH: 20
<212> TYPE: DNA
<213> ORGANISM: Homo sapiens

<400> SEQUENCE: 403
tgcccttcca gaactgtaaa 20

<210> SEQ ID NO 404
<211> LENGTH: 20
<212> TYPE: DNA
<213> ORGANISM: Homo sapiens

<400> SEQUENCE: 404
gccaggtcac ttaacaaagc 20

<210> SEQ ID NO 405
<211> LENGTH: 19
<212> TYPE: DNA
<213> ORGANISM: Homo sapiens

<400> SEQUENCE: 405
caataaggcg ccaagttcg 19

<210> SEQ ID NO 406
<211> LENGTH: 20
<212> TYPE: DNA
<213> ORGANISM: Homo sapiens

<400> SEQUENCE: 406
gtcatcaggg gagcaaatgt 20

<210> SEQ ID NO 407
<211> LENGTH: 21
<212> TYPE: DNA
<213> ORGANISM: Homo sapiens

<400> SEQUENCE: 407
aacatgcaat ccctggaatt c 21

<210> SEQ ID NO 408
<211> LENGTH: 21
<212> TYPE: DNA
<213> ORGANISM: Homo sapiens

<400> SEQUENCE: 408
agttgtttca ggacaggatc t 21

<210> SEQ ID NO 409
<211> LENGTH: 21
<212> TYPE: DNA
<213> ORGANISM: Homo sapiens

<400> SEQUENCE: 409
tcctcctgcc tttaataagc t 21

<210> SEQ ID NO 410
<211> LENGTH: 21
<212> TYPE: DNA
<213> ORGANISM: Homo sapiens

<400> SEQUENCE: 410
ttacaaggca tctgacagga a 21

<210> SEQ ID NO 411
<211> LENGTH: 21
<212> TYPE: DNA
<213> ORGANISM: Homo sapiens

<400> SEQUENCE: 411
ttactggtag gtttgagcac a 21

<210> SEQ ID NO 412
<211> LENGTH: 22
<212> TYPE: DNA
<213> ORGANISM: Homo sapiens

<400> SEQUENCE: 412
gagctacgtt ctttctcatc ac 22

<210> SEQ ID NO 413
<211> LENGTH: 21
<212> TYPE: DNA
<213> ORGANISM: Homo sapiens

<400> SEQUENCE: 413
caccaattaa agtgtgctgc a 21

<210> SEQ ID NO 414
<211> LENGTH: 21
<212> TYPE: DNA
<213> ORGANISM: Homo sapiens

<400> SEQUENCE: 414
tcccttccaa agtgccttat a 21

<210> SEQ ID NO 415
<211> LENGTH: 21
<212> TYPE: DNA
<213> ORGANISM: Homo sapiens

<400> SEQUENCE: 415
tggttggttt gggatacttg a 21

<210> SEQ ID NO 416
<211> LENGTH: 21
<212> TYPE: DNA
<213> ORGANISM: Homo sapiens

<400> SEQUENCE: 416
gaacccaaat cgatcatgca t 21

<210> SEQ ID NO 417
<211> LENGTH: 21
<212> TYPE: DNA
<213> ORGANISM: Homo sapiens

<400> SEQUENCE: 417
agagttaaac gtgcaatgtg g 21

<210> SEQ ID NO 418
<211> LENGTH: 22
<212> TYPE: DNA
<213> ORGANISM: Homo sapiens

<400> SEQUENCE: 418
gttcgttggt catagttgtt gt 22

<210> SEQ ID NO 419
<211> LENGTH: 21
<212> TYPE: DNA
<213> ORGANISM: Homo sapiens

<400> SEQUENCE: 419
agtttagcca aaggattcag c 21

<210> SEQ ID NO 420
<211> LENGTH: 22
<212> TYPE: DNA
<213> ORGANISM: Homo sapiens

<400> SEQUENCE: 420
tcaaccattt agaaccacct tg 22

<210> SEQ ID NO 421
<211> LENGTH: 21
<212> TYPE: DNA
<213> ORGANISM: Homo sapiens

<400> SEQUENCE: 421
aatgtccact ttagcggaga g 21

<210> SEQ ID NO 422
<211> LENGTH: 22
<212> TYPE: DNA
<213> ORGANISM: Homo sapiens

<400> SEQUENCE: 422
ggagtattct gttcatgttg gg 22

<210> SEQ ID NO 423
<211> LENGTH: 22
<212> TYPE: DNA
<213> ORGANISM: Homo sapiens

<400> SEQUENCE: 423
tttctagaat tgaggaaggg ca 22

<210> SEQ ID NO 424
<211> LENGTH: 21
<212> TYPE: DNA
<213> ORGANISM: Homo sapiens

<400> SEQUENCE: 424
aggataagac gaggcatcaa t 21

<210> SEQ ID NO 425
<211> LENGTH: 22
<212> TYPE: DNA
<213> ORGANISM: Homo sapiens

<400> SEQUENCE: 425
ttctgtgttg acatgtacct ct 22

<210> SEQ ID NO 426
<211> LENGTH: 21
<212> TYPE: DNA
<213> ORGANISM: Homo sapiens

<400> SEQUENCE: 426
tccaacattt ctctctgtcc c 21

<210> SEQ ID NO 427
<211> LENGTH: 20
<212> TYPE: DNA

<213> ORGANISM: Homo sapiens

<400> SEQUENCE: 427
ataacgtgta ctcctcagcc 20

<210> SEQ ID NO 428
<211> LENGTH: 21
<212> TYPE: DNA
<213> ORGANISM: Homo sapiens

<400> SEQUENCE: 428
gcacttggag gatgtaaaga c 21

<210> SEQ ID NO 429
<211> LENGTH: 21
<212> TYPE: DNA
<213> ORGANISM: Homo sapiens

<400> SEQUENCE: 429
tgtatgcttt aggacccagt t 21

<210> SEQ ID NO 430
<211> LENGTH: 22
<212> TYPE: DNA
<213> ORGANISM: Homo sapiens

<400> SEQUENCE: 430
aactccacag gaatctttct ga 22

<210> SEQ ID NO 431
<211> LENGTH: 20
<212> TYPE: DNA
<213> ORGANISM: Homo sapiens

<400> SEQUENCE: 431
catttctcct gggaccgaat 20

<210> SEQ ID NO 432
<211> LENGTH: 21
<212> TYPE: DNA
<213> ORGANISM: Homo sapiens

<400> SEQUENCE: 432
ttctgaagct gacgaaattc c 21

<210> SEQ ID NO 433
<211> LENGTH: 21
<212> TYPE: DNA
<213> ORGANISM: Homo sapiens

<400> SEQUENCE: 433
gttgcttagt ccttgcttca c 21

<210> SEQ ID NO 434
<211> LENGTH: 21
<212> TYPE: DNA
<213> ORGANISM: Homo sapiens

<400> SEQUENCE: 434
aggtcattgg tctgcagtta t 21

<210> SEQ ID NO 435
<211> LENGTH: 21

<212> TYPE: DNA
<213> ORGANISM: Homo sapiens

<400> SEQUENCE: 435
agcatttaga gaacagcagt c 21

<210> SEQ ID NO 436
<211> LENGTH: 21
<212> TYPE: DNA
<213> ORGANISM: Homo sapiens

<400> SEQUENCE: 436
gtgtaagaag tggttgggtt t 21

<210> SEQ ID NO 437
<211> LENGTH: 22
<212> TYPE: DNA
<213> ORGANISM: Homo sapiens

<400> SEQUENCE: 437
aaaggcagag cagtgtattt ag 22

<210> SEQ ID NO 438
<211> LENGTH: 22
<212> TYPE: DNA
<213> ORGANISM: Homo sapiens

<400> SEQUENCE: 438
agacaagaga acaatcaggt ga 22

<210> SEQ ID NO 439
<211> LENGTH: 21
<212> TYPE: DNA
<213> ORGANISM: Homo sapiens

<400> SEQUENCE: 439
caaagaagct ctaggacagg a 21

<210> SEQ ID NO 440
<211> LENGTH: 21
<212> TYPE: DNA
<213> ORGANISM: Homo sapiens

<400> SEQUENCE: 440
tggtggagga aatcaatgtt g 21

<210> SEQ ID NO 441
<211> LENGTH: 20
<212> TYPE: DNA
<213> ORGANISM: Homo sapiens

<400> SEQUENCE: 441
cacaagggag gaaacgttct 20

<210> SEQ ID NO 442
<211> LENGTH: 21
<212> TYPE: DNA
<213> ORGANISM: Homo sapiens

<400> SEQUENCE: 442
tgagatttag tgccagctag a 21

<210> SEQ ID NO 443

<211> LENGTH: 21
<212> TYPE: DNA
<213> ORGANISM: Homo sapiens

<400> SEQUENCE: 443
aggattagtt tggctcctca g 21

<210> SEQ ID NO 444
<211> LENGTH: 21
<212> TYPE: DNA
<213> ORGANISM: Homo sapiens

<400> SEQUENCE: 444
cctgcactat ttcctcaaag c 21

<210> SEQ ID NO 445
<211> LENGTH: 21
<212> TYPE: DNA
<213> ORGANISM: Homo sapiens

<400> SEQUENCE: 445
caatttcctt ctcactgagc c 21

<210> SEQ ID NO 446
<211> LENGTH: 21
<212> TYPE: DNA
<213> ORGANISM: Homo sapiens

<400> SEQUENCE: 446
acgcttccca aatctatctg g 21

<210> SEQ ID NO 447
<211> LENGTH: 22
<212> TYPE: DNA
<213> ORGANISM: Homo sapiens

<400> SEQUENCE: 447
cttatttgtg tgcccaatac ca 22

<210> SEQ ID NO 448
<211> LENGTH: 21
<212> TYPE: DNA
<213> ORGANISM: Homo sapiens

<400> SEQUENCE: 448
ttgcagcagg aacaccataa a 21

<210> SEQ ID NO 449
<211> LENGTH: 21
<212> TYPE: DNA
<213> ORGANISM: Homo sapiens

<400> SEQUENCE: 449
ctgttcatgt tgctaccaca g 21

<210> SEQ ID NO 450
<211> LENGTH: 21
<212> TYPE: DNA
<213> ORGANISM: Homo sapiens

<400> SEQUENCE: 450
ctgccttaga ttcactttcg g 21

<210> SEQ ID NO 451
<211> LENGTH: 21
<212> TYPE: DNA
<213> ORGANISM: Homo sapiens

<400> SEQUENCE: 451
ccatctgtga ggtcttcttt g 21

<210> SEQ ID NO 452
<211> LENGTH: 21
<212> TYPE: DNA
<213> ORGANISM: Homo sapiens

<400> SEQUENCE: 452
tccttggttg tgtatttagc c 21

<210> SEQ ID NO 453
<211> LENGTH: 20
<212> TYPE: DNA
<213> ORGANISM: Homo sapiens

<400> SEQUENCE: 453
agactcaact cacattggcc 20

<210> SEQ ID NO 454
<211> LENGTH: 20
<212> TYPE: DNA
<213> ORGANISM: Homo sapiens

<400> SEQUENCE: 454
ggtctgactc tgtggtttgg 20

<210> SEQ ID NO 455
<211> LENGTH: 21
<212> TYPE: DNA
<213> ORGANISM: Homo sapiens

<400> SEQUENCE: 455
tttcatttca tcctgcccat g 21

<210> SEQ ID NO 456
<211> LENGTH: 21
<212> TYPE: DNA
<213> ORGANISM: Homo sapiens

<400> SEQUENCE: 456
ttctgttatt cgccatcagt c 21

<210> SEQ ID NO 457
<211> LENGTH: 20
<212> TYPE: DNA
<213> ORGANISM: Homo sapiens

<400> SEQUENCE: 457
gaattgggaa cttgggaagc 20

<210> SEQ ID NO 458
<211> LENGTH: 21
<212> TYPE: DNA
<213> ORGANISM: Homo sapiens

<400> SEQUENCE: 458
gaactttgga gaggacagtg t 21

<210> SEQ ID NO 459
<211> LENGTH: 21
<212> TYPE: DNA
<213> ORGANISM: Homo sapiens

<400> SEQUENCE: 459
aactgtcatg tgtgtctgct a 21

<210> SEQ ID NO 460
<211> LENGTH: 21
<212> TYPE: DNA
<213> ORGANISM: Homo sapiens

<400> SEQUENCE: 460
tgattccttc cacctaccaa a 21

<210> SEQ ID NO 461
<211> LENGTH: 21
<212> TYPE: DNA
<213> ORGANISM: Homo sapiens

<400> SEQUENCE: 461
gccaaggtcc attatctcaa g 21

<210> SEQ ID NO 462
<211> LENGTH: 21
<212> TYPE: DNA
<213> ORGANISM: Homo sapiens

<400> SEQUENCE: 462
gaacctgcat tgtcattctc t 21

<210> SEQ ID NO 463
<211> LENGTH: 22
<212> TYPE: DNA
<213> ORGANISM: Homo sapiens

<400> SEQUENCE: 463
aagaacatca acaaactcca gg 22

<210> SEQ ID NO 464
<211> LENGTH: 21
<212> TYPE: DNA
<213> ORGANISM: Homo sapiens

<400> SEQUENCE: 464
tcaattctct ttcacacgtg c 21

<210> SEQ ID NO 465
<211> LENGTH: 21
<212> TYPE: DNA
<213> ORGANISM: Homo sapiens

<400> SEQUENCE: 465
aggtgctgga tcttgaattc a 21

<210> SEQ ID NO 466
<211> LENGTH: 21
<212> TYPE: DNA
<213> ORGANISM: Homo sapiens

<400> SEQUENCE: 466
tccctctacc cgaatctctt a 21

<210> SEQ ID NO 467
<211> LENGTH: 21
<212> TYPE: DNA
<213> ORGANISM: Homo sapiens

<400> SEQUENCE: 467
tgggtttaaa ggacactagc a 21

<210> SEQ ID NO 468
<211> LENGTH: 21
<212> TYPE: DNA
<213> ORGANISM: Homo sapiens

<400> SEQUENCE: 468
cgaaggtcac acagtttagt c 21

<210> SEQ ID NO 469
<211> LENGTH: 21
<212> TYPE: DNA
<213> ORGANISM: Homo sapiens

<400> SEQUENCE: 469
atgtgccttg ttgattgatg g 21

<210> SEQ ID NO 470
<211> LENGTH: 21
<212> TYPE: DNA
<213> ORGANISM: Homo sapiens

<400> SEQUENCE: 470
agatggtatg tcacaaagca c 21

<210> SEQ ID NO 471
<211> LENGTH: 21
<212> TYPE: DNA
<213> ORGANISM: Homo sapiens

<400> SEQUENCE: 471
acactttgga gagcttcaga t 21

<210> SEQ ID NO 472
<211> LENGTH: 22
<212> TYPE: DNA
<213> ORGANISM: Homo sapiens

<400> SEQUENCE: 472
gtgcccagaa ttatttgtgt ct 22

<210> SEQ ID NO 473
<211> LENGTH: 21
<212> TYPE: DNA
<213> ORGANISM: Homo sapiens

<400> SEQUENCE: 473
gctctcttgt ggaaacgatt a 21

<210> SEQ ID NO 474
<211> LENGTH: 21
<212> TYPE: DNA
<213> ORGANISM: Homo sapiens

<400> SEQUENCE: 474
agtttgtttc tctggcctac t 21

<210> SEQ ID NO 475
<211> LENGTH: 21
<212> TYPE: DNA
<213> ORGANISM: Homo sapiens

<400> SEQUENCE: 475
accacctcaa agatttcatg g 21

<210> SEQ ID NO 476
<211> LENGTH: 22
<212> TYPE: DNA
<213> ORGANISM: Homo sapiens

<400> SEQUENCE: 476
gtcttcatct atttcgtgag cc 22

<210> SEQ ID NO 477
<211> LENGTH: 21
<212> TYPE: DNA
<213> ORGANISM: Homo sapiens

<400> SEQUENCE: 477
tcatcccaga ttcagaatgc c 21

<210> SEQ ID NO 478
<211> LENGTH: 21
<212> TYPE: DNA
<213> ORGANISM: Homo sapiens

<400> SEQUENCE: 478
cgttcaatga agtcccttgt c 21

<210> SEQ ID NO 479
<211> LENGTH: 21
<212> TYPE: DNA
<213> ORGANISM: Homo sapiens

<400> SEQUENCE: 479
ttcacaagaa ctctgctgga t 21

<210> SEQ ID NO 480
<211> LENGTH: 21
<212> TYPE: DNA
<213> ORGANISM: Homo sapiens

<400> SEQUENCE: 480
gaagccttct agtgggacta a 21

<210> SEQ ID NO 481
<211> LENGTH: 21
<212> TYPE: DNA
<213> ORGANISM: Homo sapiens

<400> SEQUENCE: 481
gttagggtca tgggtcactt t 21

<210> SEQ ID NO 482
<211> LENGTH: 21
<212> TYPE: DNA
<213> ORGANISM: Homo sapiens

<400> SEQUENCE: 482
gcctttgtag agtggacttc t 21

<210> SEQ ID NO 483
<211> LENGTH: 21
<212> TYPE: DNA
<213> ORGANISM: Homo sapiens

<400> SEQUENCE: 483
ggcttcttga tactgctttc c 21

<210> SEQ ID NO 484
<211> LENGTH: 21
<212> TYPE: DNA
<213> ORGANISM: Homo sapiens

<400> SEQUENCE: 484
aggtgtgcaa tactcaagga a 21

<210> SEQ ID NO 485
<211> LENGTH: 21
<212> TYPE: DNA
<213> ORGANISM: Homo sapiens

<400> SEQUENCE: 485
aaggtcttag gagtgaggac a 21

<210> SEQ ID NO 486
<211> LENGTH: 22
<212> TYPE: DNA
<213> ORGANISM: Homo sapiens

<400> SEQUENCE: 486
tcgtgctatt tcagtcagat ct 22

<210> SEQ ID NO 487
<211> LENGTH: 21
<212> TYPE: DNA
<213> ORGANISM: Homo sapiens

<400> SEQUENCE: 487
tgtccagccg taacatttca t 21

<210> SEQ ID NO 488
<211> LENGTH: 21
<212> TYPE: DNA
<213> ORGANISM: Homo sapiens

<400> SEQUENCE: 488
aatggacatc tttcaggtct g 21

<210> SEQ ID NO 489
<211> LENGTH: 21
<212> TYPE: DNA
<213> ORGANISM: Homo sapiens

<400> SEQUENCE: 489
tcaaattggg atcgcattag g 21

<210> SEQ ID NO 490
<211> LENGTH: 22
<212> TYPE: DNA
<213> ORGANISM: Homo sapiens

<400> SEQUENCE: 490
atgcctgggt ttattcatct tg 22

<210> SEQ ID NO 491
<211> LENGTH: 21
<212> TYPE: DNA
<213> ORGANISM: Homo sapiens

<400> SEQUENCE: 491
ggagaagttt gggtttgatc c 21

<210> SEQ ID NO 492
<211> LENGTH: 21
<212> TYPE: DNA
<213> ORGANISM: Homo sapiens

<400> SEQUENCE: 492
tgataggagc catcagttct t 21

<210> SEQ ID NO 493
<211> LENGTH: 21
<212> TYPE: DNA
<213> ORGANISM: Homo sapiens

<400> SEQUENCE: 493
agcagatgtt gttagctttc c 21

<210> SEQ ID NO 494
<211> LENGTH: 21
<212> TYPE: DNA
<213> ORGANISM: Homo sapiens

<400> SEQUENCE: 494
ttctctgtca cttccatgag g 21

<210> SEQ ID NO 495
<211> LENGTH: 22
<212> TYPE: DNA
<213> ORGANISM: Homo sapiens

<400> SEQUENCE: 495
ccagtaactt attctgccag ag 22

<210> SEQ ID NO 496
<211> LENGTH: 21
<212> TYPE: DNA
<213> ORGANISM: Homo sapiens

<400> SEQUENCE: 496
tgagagacaa gctgcattac a 21

<210> SEQ ID NO 497
<211> LENGTH: 22
<212> TYPE: DNA
<213> ORGANISM: Homo sapiens

<400> SEQUENCE: 497
gcacagaaat tacagttcat gg 22

<210> SEQ ID NO 498
<211> LENGTH: 21
<212> TYPE: DNA
<213> ORGANISM: Homo sapiens

<400> SEQUENCE: 498
gctctcgtat ctgacagtga a 21

<210> SEQ ID NO 499
<211> LENGTH: 21
<212> TYPE: DNA
<213> ORGANISM: Homo sapiens

<400> SEQUENCE: 499
caggcatctt ggtttgtagt g 21

<210> SEQ ID NO 500
<211> LENGTH: 21
<212> TYPE: DNA
<213> ORGANISM: Homo sapiens

<400> SEQUENCE: 500
cgtgatgaac agtgatgact t 21

<210> SEQ ID NO 501
<211> LENGTH: 21
<212> TYPE: DNA
<213> ORGANISM: Homo sapiens

<400> SEQUENCE: 501
cgccatttgt tctcctattc a 21

<210> SEQ ID NO 502
<211> LENGTH: 21
<212> TYPE: DNA
<213> ORGANISM: Homo sapiens

<400> SEQUENCE: 502
ttcgttagct actgggtact c 21

<210> SEQ ID NO 503
<211> LENGTH: 21
<212> TYPE: DNA
<213> ORGANISM: Homo sapiens

<400> SEQUENCE: 503 ccaccctta cacctatcca a 21

<210> SEQ ID NO 504
<211> LENGTH: 21
<212> TYPE: DNA
<213> ORGANISM: Homo sapiens

<400> SEQUENCE: 504
agagtgcaca aaggagaaga c 21

<210> SEQ ID NO 505
<211> LENGTH: 22
<212> TYPE: DNA
<213> ORGANISM: Homo sapiens

<400> SEQUENCE: 505
tctactgtgt caaagcagat tg 22

<210> SEQ ID NO 506
<211> LENGTH: 21
<212> TYPE: DNA

<213> ORGANISM: Homo sapiens

<400> SEQUENCE: 506
ttcttcctag ccttcctttc c 21

<210> SEQ ID NO 507
<211> LENGTH: 21
<212> TYPE: DNA
<213> ORGANISM: Homo sapiens

<400> SEQUENCE: 507
tctctggctg tgcagtaaat t 21

<210> SEQ ID NO 508
<211> LENGTH: 21
<212> TYPE: DNA
<213> ORGANISM: Homo sapiens

<400> SEQUENCE: 508
aaactcccag ctttaatccc t 21

<210> SEQ ID NO 509
<211> LENGTH: 21
<212> TYPE: DNA
<213> ORGANISM: Homo sapiens

<400> SEQUENCE: 509
aagaatgggt gagttgggtt c 21

<210> SEQ ID NO 510
<211> LENGTH: 21
<212> TYPE: DNA
<213> ORGANISM: Homo sapiens

<400> SEQUENCE: 510
ggaaactgaa ttgccaagtc t 21

<210> SEQ ID NO 511
<211> LENGTH: 20
<212> TYPE: DNA
<213> ORGANISM: Homo sapiens

<400> SEQUENCE: 511
ctcccaactt ttatgcagcc 20

<210> SEQ ID NO 512
<211> LENGTH: 21
<212> TYPE: DNA
<213> ORGANISM: Homo sapiens

<400> SEQUENCE: 512
gctcagggaa tatcttggga a 21

<210> SEQ ID NO 513
<211> LENGTH: 21
<212> TYPE: DNA
<213> ORGANISM: Homo sapiens

<400> SEQUENCE: 513
acattcagca agtaggaagg a 21

<210> SEQ ID NO 514
<211> LENGTH: 20

<212> TYPE: DNA
<213> ORGANISM: Homo sapiens

<400> SEQUENCE: 514
cccagaagag cagtaacaac 20

<210> SEQ ID NO 515
<211> LENGTH: 20
<212> TYPE: DNA
<213> ORGANISM: Homo sapiens

<400> SEQUENCE: 515
gaaaaagggg gataggcatt 20

<210> SEQ ID NO 516
<211> LENGTH: 21
<212> TYPE: DNA
<213> ORGANISM: Homo sapiens

<400> SEQUENCE: 516
cccaacaact gcaataaaag g 21

<210> SEQ ID NO 517
<211> LENGTH: 20
<212> TYPE: DNA
<213> ORGANISM: Homo sapiens

<400> SEQUENCE: 517
accgaaattg cttgctctta 20

<210> SEQ ID NO 518
<211> LENGTH: 20
<212> TYPE: DNA
<213> ORGANISM: Homo sapiens

<400> SEQUENCE: 518
ccttagtgtg acaggacagg 20

<210> SEQ ID NO 519
<211> LENGTH: 20
<212> TYPE: DNA
<213> ORGANISM: Homo sapiens

<400> SEQUENCE: 519
ccaagacaac taggccaatg 20

<210> SEQ ID NO 520
<211> LENGTH: 21
<212> TYPE: DNA
<213> ORGANISM: Homo sapiens

<400> SEQUENCE: 520
gaagagatga tgcaaaagag c 21

<210> SEQ ID NO 521
<211> LENGTH: 20
<212> TYPE: DNA
<213> ORGANISM: Homo sapiens

<400> SEQUENCE: 521
tccaagcaag ggatctcttc 20

<210> SEQ ID NO 522

<211> LENGTH: 20
<212> TYPE: DNA
<213> ORGANISM: Homo sapiens

<400> SEQUENCE: 522
gaatggtcag ggaagggttt 20

<210> SEQ ID NO 523
<211> LENGTH: 20
<212> TYPE: DNA
<213> ORGANISM: Homo sapiens

<400> SEQUENCE: 523
agtcttcagc catcttcctg 20

<210> SEQ ID NO 524
<211> LENGTH: 21
<212> TYPE: DNA
<213> ORGANISM: Homo sapiens

<400> SEQUENCE: 524
gcatttccag gctttacaag t 21

<210> SEQ ID NO 525
<211> LENGTH: 20
<212> TYPE: DNA
<213> ORGANISM: Homo sapiens

<400> SEQUENCE: 525
ctctctctcc ctggtcagat 20

<210> SEQ ID NO 526
<211> LENGTH: 20
<212> TYPE: DNA
<213> ORGANISM: Homo sapiens

<400> SEQUENCE: 526
cagcaattct caggctcaga 20

<210> SEQ ID NO 527
<211> LENGTH: 21
<212> TYPE: DNA
<213> ORGANISM: Homo sapiens

<400> SEQUENCE: 527
tctgaaacaa agcctcctta g 21

<210> SEQ ID NO 528
<211> LENGTH: 21
<212> TYPE: DNA
<213> ORGANISM: Homo sapiens

<400> SEQUENCE: 528
aggataaggt ttcccatgct c 21

<210> SEQ ID NO 529
<211> LENGTH: 21
<212> TYPE: DNA
<213> ORGANISM: Homo sapiens

<400> SEQUENCE: 529
atgtatctga aggagctctg c 21

<210> SEQ ID NO 530
<211> LENGTH: 20
<212> TYPE: DNA
<213> ORGANISM: Homo sapiens

<400> SEQUENCE: 530
ggccttcatc acaaacaaca 20

<210> SEQ ID NO 531
<211> LENGTH: 20
<212> TYPE: DNA
<213> ORGANISM: Homo sapiens

<400> SEQUENCE: 531
tgtgtcccat ctacaaagcc 20

<210> SEQ ID NO 532
<211> LENGTH: 20
<212> TYPE: DNA
<213> ORGANISM: Homo sapiens

<400> SEQUENCE: 532
tccttgaact ctttccaagc 20

<210> SEQ ID NO 533
<211> LENGTH: 20
<212> TYPE: DNA
<213> ORGANISM: Homo sapiens

<400> SEQUENCE: 533
tgttttcctg tccaagtcca 20

<210> SEQ ID NO 534
<211> LENGTH: 19
<212> TYPE: DNA
<213> ORGANISM: Homo sapiens

<400> SEQUENCE: 534
cagcatccat cgctcgaaa 19

<210> SEQ ID NO 535
<211> LENGTH: 20
<212> TYPE: DNA
<213> ORGANISM: Homo sapiens

<400> SEQUENCE: 535
ggtattggtg ggggaaatga 20

<210> SEQ ID NO 536
<211> LENGTH: 24
<212> TYPE: DNA
<213> ORGANISM: Homo sapiens

<400> SEQUENCE: 536
gcactgctgt aaaagatcta tgag 24

<210> SEQ ID NO 537
<211> LENGTH: 19
<212> TYPE: DNA
<213> ORGANISM: Homo sapiens

<400> SEQUENCE: 537
actcaaaggc acatttcgc 19

<210> SEQ ID NO 538
<211> LENGTH: 22
<212> TYPE: DNA
<213> ORGANISM: Homo sapiens

<400> SEQUENCE: 538
attctattcc gatcacagcc tt 22

<210> SEQ ID NO 539
<211> LENGTH: 20
<212> TYPE: DNA
<213> ORGANISM: Homo sapiens

<400> SEQUENCE: 539
ctacctgaca aatggagctt 20

<210> SEQ ID NO 540
<211> LENGTH: 21
<212> TYPE: DNA
<213> ORGANISM: Homo sapiens

<400> SEQUENCE: 540
gaaatggcca tgtgtactga g 21

<210> SEQ ID NO 541
<211> LENGTH: 20
<212> TYPE: DNA
<213> ORGANISM: Homo sapiens

<400> SEQUENCE: 541
gaagcctctc aagctacaag 20

<210> SEQ ID NO 542
<211> LENGTH: 22
<212> TYPE: DNA
<213> ORGANISM: Homo sapiens

<400> SEQUENCE: 542
gaatgagatt agggagcaaa gt 22

<210> SEQ ID NO 543
<211> LENGTH: 20
<212> TYPE: DNA
<213> ORGANISM: Homo sapiens

<400> SEQUENCE: 543
ggaagtaaga agagtgctgc 20

<210> SEQ ID NO 544
<211> LENGTH: 20
<212> TYPE: DNA
<213> ORGANISM: Homo sapiens

<400> SEQUENCE: 544
gctcctgatt gaagaagtgt 20

<210> SEQ ID NO 545
<211> LENGTH: 19
<212> TYPE: DNA
<213> ORGANISM: Homo sapiens

<400> SEQUENCE: 545
ctgctccttt gtctcctgt 19

<210> SEQ ID NO 546
<211> LENGTH: 21
<212> TYPE: DNA
<213> ORGANISM: Homo sapiens

<400> SEQUENCE: 546
taaggtgaga gtgtgaggaa g 21

<210> SEQ ID NO 547
<211> LENGTH: 21
<212> TYPE: DNA
<213> ORGANISM: Homo sapiens

<400> SEQUENCE: 547
ccaggggaac atttactcag a 21

<210> SEQ ID NO 548
<211> LENGTH: 20
<212> TYPE: DNA
<213> ORGANISM: Homo sapiens

<400> SEQUENCE: 548
agggtacatg taaggcagct 20

<210> SEQ ID NO 549
<211> LENGTH: 20
<212> TYPE: DNA
<213> ORGANISM: Homo sapiens

<400> SEQUENCE: 549
ttctgtggca ttgtgtcttg 20

<210> SEQ ID NO 550
<211> LENGTH: 20
<212> TYPE: DNA
<213> ORGANISM: Homo sapiens

<400> SEQUENCE: 550
ccccaaattt accccactct 20

<210> SEQ ID NO 551
<211> LENGTH: 20
<212> TYPE: DNA
<213> ORGANISM: Homo sapiens

<400> SEQUENCE: 551
atccctagca ctttcaggac 20

<210> SEQ ID NO 552
<211> LENGTH: 20
<212> TYPE: DNA
<213> ORGANISM: Homo sapiens

<400> SEQUENCE: 552
ttaccaatcc atccagcctg 20

<210> SEQ ID NO 553
<211> LENGTH: 20
<212> TYPE: DNA
<213> ORGANISM: Homo sapiens

<400> SEQUENCE: 553
agaagctaaa caggttgccc 20

<210> SEQ ID NO 554
<211> LENGTH: 20
<212> TYPE: DNA
<213> ORGANISM: Homo sapiens

<400> SEQUENCE: 554
cataagagca cagccaagat 20

<210> SEQ ID NO 555
<211> LENGTH: 20
<212> TYPE: DNA
<213> ORGANISM: Homo sapiens

<400> SEQUENCE: 555
tgtcctgcca cttttacatc 20

<210> SEQ ID NO 556
<211> LENGTH: 21
<212> TYPE: DNA
<213> ORGANISM: Homo sapiens

<400> SEQUENCE: 556
gagctaagca gaacctaagg a 21

<210> SEQ ID NO 557
<211> LENGTH: 21
<212> TYPE: DNA
<213> ORGANISM: Homo sapiens

<400> SEQUENCE: 557
ttaagcaaca ggaacctacc c 21

<210> SEQ ID NO 558
<211> LENGTH: 21
<212> TYPE: DNA
<213> ORGANISM: Homo sapiens

<400> SEQUENCE: 558
gccaagggta atcatagcaa c 21

<210> SEQ ID NO 559
<211> LENGTH: 21
<212> TYPE: DNA
<213> ORGANISM: Homo sapiens

<400> SEQUENCE: 559
tcataatgaa acccttgctg c 21

<210> SEQ ID NO 560
<211> LENGTH: 21
<212> TYPE: DNA
<213> ORGANISM: Homo sapiens

<400> SEQUENCE: 560
aatcctagtg catgagactc c 21

<210> SEQ ID NO 561
<211> LENGTH: 21
<212> TYPE: DNA
<213> ORGANISM: Homo sapiens

<400> SEQUENCE: 561
tactgcctgc atcattacca c 21

<210> SEQ ID NO 562
<211> LENGTH: 21
<212> TYPE: DNA
<213> ORGANISM: Homo sapiens

<400> SEQUENCE: 562
attaacaatg aggagccagg t 21

<210> SEQ ID NO 563
<211> LENGTH: 21
<212> TYPE: DNA
<213> ORGANISM: Homo sapiens

<400> SEQUENCE: 563
gagagatggt tgagaaatgc c 21

<210> SEQ ID NO 564
<211> LENGTH: 21
<212> TYPE: DNA
<213> ORGANISM: Homo sapiens

<400> SEQUENCE: 564
actacaacca ccaattacag c 21

<210> SEQ ID NO 565
<211> LENGTH: 21
<212> TYPE: DNA
<213> ORGANISM: Homo sapiens

<400> SEQUENCE: 565
agtgacattt ccaagggctt t 21

<210> SEQ ID NO 566
<211> LENGTH: 21
<212> TYPE: DNA
<213> ORGANISM: Homo sapiens

<400> SEQUENCE: 566
ggagatggga agacgattag a 21

<210> SEQ ID NO 567
<211> LENGTH: 22
<212> TYPE: DNA
<213> ORGANISM: Homo sapiens

<400> SEQUENCE: 567
agtctttcag tcttacatgg gt 22

<210> SEQ ID NO 568
<211> LENGTH: 21
<212> TYPE: DNA
<213> ORGANISM: Homo sapiens

<400> SEQUENCE: 568
tagtttctgt gatcctggca g 21

<210> SEQ ID NO 569
<211> LENGTH: 20
<212> TYPE: DNA
<213> ORGANISM: Homo sapiens

<400> SEQUENCE: 569
tttctcccag ctgttcctag 20

<210> SEQ ID NO 570
<211> LENGTH: 21
<212> TYPE: DNA
<213> ORGANISM: Homo sapiens

<400> SEQUENCE: 570
tacggaactt cgaatcaact c 21

<210> SEQ ID NO 571
<211> LENGTH: 21
<212> TYPE: DNA
<213> ORGANISM: Homo sapiens

<400> SEQUENCE: 571
tcaagtcacc ctcattgtag g 21

<210> SEQ ID NO 572
<211> LENGTH: 21
<212> TYPE: DNA
<213> ORGANISM: Homo sapiens

<400> SEQUENCE: 572
tgtaacgtgg atgtgagatt g 21

<210> SEQ ID NO 573
<211> LENGTH: 21
<212> TYPE: DNA
<213> ORGANISM: Homo sapiens

<400> SEQUENCE: 573
ttgagctaag tctgcatcac t 21

<210> SEQ ID NO 574
<211> LENGTH: 21
<212> TYPE: DNA
<213> ORGANISM: Homo sapiens

<400> SEQUENCE: 574
ctagagaaag caacgcctaa g 21

<210> SEQ ID NO 575
<211> LENGTH: 21
<212> TYPE: DNA
<213> ORGANISM: Homo sapiens

<400> SEQUENCE: 575
agcaccttcc atagcttctt t 21

<210> SEQ ID NO 576
<211> LENGTH: 21
<212> TYPE: DNA
<213> ORGANISM: Homo sapiens

<400> SEQUENCE: 576
gtgtcttctg atggccaaat g 21

<210> SEQ ID NO 577
<211> LENGTH: 21
<212> TYPE: DNA
<213> ORGANISM: Homo sapiens

<400> SEQUENCE: 577
aatcaggtga aaggtacctc c 21

<210> SEQ ID NO 578
<211> LENGTH: 21
<212> TYPE: DNA
<213> ORGANISM: Homo sapiens

<400> SEQUENCE: 578
ccttcacaat tcagggaaca a 21

<210> SEQ ID NO 579
<211> LENGTH: 21
<212> TYPE: DNA
<213> ORGANISM: Homo sapiens

<400> SEQUENCE: 579
tggacccagt tctatgcaat t 21

<210> SEQ ID NO 580
<211> LENGTH: 21
<212> TYPE: DNA
<213> ORGANISM: Homo sapiens

<400> SEQUENCE: 580
aatgaccctt acaactccga a 21

<210> SEQ ID NO 581
<211> LENGTH: 21
<212> TYPE: DNA
<213> ORGANISM: Homo sapiens

<400> SEQUENCE: 581
tttgggaagt gattgtgaag g 21

<210> SEQ ID NO 582
<211> LENGTH: 21
<212> TYPE: DNA
<213> ORGANISM: Homo sapiens

<400> SEQUENCE: 582
tcagctgcat agaccttgtt t 21

<210> SEQ ID NO 583
<211> LENGTH: 21
<212> TYPE: DNA
<213> ORGANISM: Homo sapiens

<400> SEQUENCE: 583
tcatttgttc tcattacggg c 21

<210> SEQ ID NO 584
<211> LENGTH: 20
<212> TYPE: DNA
<213> ORGANISM: Homo sapiens

<400> SEQUENCE: 584
ttctacctgg gttctcttgg 20

<210> SEQ ID NO 585
<211> LENGTH: 21
<212> TYPE: DNA

<213> ORGANISM: Homo sapiens

<400> SEQUENCE: 585
taacttcctg agcacacatc a 21

<210> SEQ ID NO 586
<211> LENGTH: 21
<212> TYPE: DNA
<213> ORGANISM: Homo sapiens

<400> SEQUENCE: 586
gggtaaattc aggaatgcac a 21

<210> SEQ ID NO 587
<211> LENGTH: 21
<212> TYPE: DNA
<213> ORGANISM: Homo sapiens

<400> SEQUENCE: 587
atttcttctg gtgagtttgc g 21

<210> SEQ ID NO 588
<211> LENGTH: 21
<212> TYPE: DNA
<213> ORGANISM: Homo sapiens

<400> SEQUENCE: 588
cctcttcctg acatgttgtt g 21

<210> SEQ ID NO 589
<211> LENGTH: 21
<212> TYPE: DNA
<213> ORGANISM: Homo sapiens

<400> SEQUENCE: 589
gttggtgcca gattgtaact t 21

<210> SEQ ID NO 590
<211> LENGTH: 21
<212> TYPE: DNA
<213> ORGANISM: Homo sapiens

<400> SEQUENCE: 590
gcctggctca ataatagtcc t 21

<210> SEQ ID NO 591
<211> LENGTH: 21
<212> TYPE: DNA
<213> ORGANISM: Homo sapiens

<400> SEQUENCE: 591
atgttgcctt ctctacgttt g 21

<210> SEQ ID NO 592
<211> LENGTH: 20
<212> TYPE: DNA
<213> ORGANISM: Homo sapiens

<400> SEQUENCE: 592
gagtggagcg ctacctttat 20

<210> SEQ ID NO 593
<211> LENGTH: 20

<212> TYPE: DNA
<213> ORGANISM: Homo sapiens

<400> SEQUENCE: 593
agaatgggaa atgggaagga 20

<210> SEQ ID NO 594
<211> LENGTH: 20
<212> TYPE: DNA
<213> ORGANISM: Homo sapiens

<400> SEQUENCE: 594
cacaatacat gggctgcttt 20

<210> SEQ ID NO 595
<211> LENGTH: 21
<212> TYPE: DNA
<213> ORGANISM: Homo sapiens

<400> SEQUENCE: 595
ccactccaac tctgctttta c 21

<210> SEQ ID NO 596
<211> LENGTH: 21
<212> TYPE: DNA
<213> ORGANISM: Homo sapiens

<400> SEQUENCE: 596
gatgtggatt gtctttgttg c 21

<210> SEQ ID NO 597
<211> LENGTH: 22
<212> TYPE: DNA
<213> ORGANISM: Homo sapiens

<400> SEQUENCE: 597
agcctttcat tgcacatttc ag 22

<210> SEQ ID NO 598
<211> LENGTH: 20
<212> TYPE: DNA
<213> ORGANISM: Homo sapiens

<400> SEQUENCE: 598
tcccaccaca agaccaattt 20

<210> SEQ ID NO 599
<211> LENGTH: 21
<212> TYPE: DNA
<213> ORGANISM: Homo sapiens

<400> SEQUENCE: 599
gaagataggt ggtggagttc a 21

<210> SEQ ID NO 600
<211> LENGTH: 21
<212> TYPE: DNA
<213> ORGANISM: Homo sapiens

<400> SEQUENCE: 600
ctgtttgaat gaagttggct g 21

<210> SEQ ID NO 601

<211> LENGTH: 21
<212> TYPE: DNA
<213> ORGANISM: Homo sapiens

<400> SEQUENCE: 601
tatacatggg tgggatttgt c 21

<210> SEQ ID NO 602
<211> LENGTH: 21
<212> TYPE: DNA
<213> ORGANISM: Homo sapiens

<400> SEQUENCE: 602
tttgtgatgg accatctaac c 21

<210> SEQ ID NO 603
<211> LENGTH: 20
<212> TYPE: DNA
<213> ORGANISM: Homo sapiens

<400> SEQUENCE: 603
gaagatctgg tgtcccacta 20

<210> SEQ ID NO 604
<211> LENGTH: 20
<212> TYPE: DNA
<213> ORGANISM: Homo sapiens

<400> SEQUENCE: 604
atctgaagat ctccgtggta 20

<210> SEQ ID NO 605
<211> LENGTH: 21
<212> TYPE: DNA
<213> ORGANISM: Homo sapiens

<400> SEQUENCE: 605
atgtatgaac catttcctgc t 21

<210> SEQ ID NO 606
<211> LENGTH: 22
<212> TYPE: DNA
<213> ORGANISM: Homo sapiens

<400> SEQUENCE: 606
agcacagaat tgaatgaagg aa 22

<210> SEQ ID NO 607
<211> LENGTH: 20
<212> TYPE: DNA
<213> ORGANISM: Homo sapiens

<400> SEQUENCE: 607
gcatgagtaa ggctgaagtg 20

<210> SEQ ID NO 608
<211> LENGTH: 24
<212> TYPE: DNA
<213> ORGANISM: Homo sapiens

<400> SEQUENCE: 608
aaaggcttat attgcttttg aatc 24

<210> SEQ ID NO 609
<211> LENGTH: 20
<212> TYPE: DNA
<213> ORGANISM: Homo sapiens

<400> SEQUENCE: 609
ttgctgttgt tgggatcaag 20

<210> SEQ ID NO 610
<211> LENGTH: 20
<212> TYPE: DNA
<213> ORGANISM: Homo sapiens

<400> SEQUENCE: 610
gcttctgcat ccacctatct 20

<210> SEQ ID NO 611
<211> LENGTH: 20
<212> TYPE: DNA
<213> ORGANISM: Homo sapiens

<400> SEQUENCE: 611
aaaagctgcc taaaatgcca 20

<210> SEQ ID NO 612
<211> LENGTH: 20
<212> TYPE: DNA
<213> ORGANISM: Homo sapiens

<400> SEQUENCE: 612
agtcagcaag ttagcagaaa 20

<210> SEQ ID NO 613
<211> LENGTH: 20
<212> TYPE: DNA
<213> ORGANISM: Homo sapiens

<400> SEQUENCE: 613
cccacattta tcccttgtcc 20

<210> SEQ ID NO 614
<211> LENGTH: 20
<212> TYPE: DNA
<213> ORGANISM: Homo sapiens

<400> SEQUENCE: 614
tgtctgattc catctttccc 20

<210> SEQ ID NO 615
<211> LENGTH: 19
<212> TYPE: DNA
<213> ORGANISM: Homo sapiens

<400> SEQUENCE: 615
cagccaccaa aacacaatg 19

<210> SEQ ID NO 616
<211> LENGTH: 20
<212> TYPE: DNA
<213> ORGANISM: Homo sapiens

<400> SEQUENCE: 616
aaggcctgtt ttgtgtgtag 20

<210> SEQ ID NO 617
<211> LENGTH: 21
<212> TYPE: DNA
<213> ORGANISM: Homo sapiens

<400> SEQUENCE: 617
acagctcaca gatctttaag c 21

<210> SEQ ID NO 618
<211> LENGTH: 23
<212> TYPE: DNA
<213> ORGANISM: Homo sapiens

<400> SEQUENCE: 618
ggcattataa agagatagct cca 23

<210> SEQ ID NO 619
<211> LENGTH: 20
<212> TYPE: DNA
<213> ORGANISM: Homo sapiens

<400> SEQUENCE: 619
tgtttttcct tgccctgtaa 20

<210> SEQ ID NO 620
<211> LENGTH: 20
<212> TYPE: DNA
<213> ORGANISM: Homo sapiens

<400> SEQUENCE: 620
taaccagatg aatgagggca 20

<210> SEQ ID NO 621
<211> LENGTH: 20
<212> TYPE: DNA
<213> ORGANISM: Homo sapiens

<400> SEQUENCE: 621
caacaagcca aaaccacatc 20

<210> SEQ ID NO 622
<211> LENGTH: 20
<212> TYPE: DNA
<213> ORGANISM: Homo sapiens

<400> SEQUENCE: 622
gttggttctt gaagacctga 20

<210> SEQ ID NO 623
<211> LENGTH: 22
<212> TYPE: DNA
<213> ORGANISM: Homo sapiens

<400> SEQUENCE: 623
tgtggtaagt agtctctaaa ga 22

<210> SEQ ID NO 624
<211> LENGTH: 20
<212> TYPE: DNA
<213> ORGANISM: Homo sapiens

<400> SEQUENCE: 624
accaaatttc cagatcacgg 20

<210> SEQ ID NO 625
<211> LENGTH: 20
<212> TYPE: DNA
<213> ORGANISM: Homo sapiens

<400> SEQUENCE: 625
aatgaatggt catggctcac 20

<210> SEQ ID NO 626
<211> LENGTH: 20
<212> TYPE: DNA
<213> ORGANISM: Homo sapiens

<400> SEQUENCE: 626
gccctgaagc acattaaagt 20

<210> SEQ ID NO 627
<211> LENGTH: 20
<212> TYPE: DNA
<213> ORGANISM: Homo sapiens

<400> SEQUENCE: 627
gcctccaggt ttatgacaac 20

<210> SEQ ID NO 628
<211> LENGTH: 20
<212> TYPE: DNA
<213> ORGANISM: Homo sapiens

<400> SEQUENCE: 628
cagctctatt cccccttctga 20

<210> SEQ ID NO 629
<211> LENGTH: 20
<212> TYPE: DNA
<213> ORGANISM: Homo sapiens

<400> SEQUENCE: 629
ccttggaagg gaaagttgat 20

<210> SEQ ID NO 630
<211> LENGTH: 18
<212> TYPE: DNA
<213> ORGANISM: Homo sapiens

<400> SEQUENCE: 630
gtcccaccct gctcttag 18

<210> SEQ ID NO 631
<211> LENGTH: 20
<212> TYPE: DNA
<213> ORGANISM: Homo sapiens

<400> SEQUENCE: 631
cagagtaaga cagtgggaca 20

<210> SEQ ID NO 632
<211> LENGTH: 20
<212> TYPE: DNA
<213> ORGANISM: Homo sapiens

<400> SEQUENCE: 632
aagtgtggtg cataaaggat 20

<210> SEQ ID NO 633
<211> LENGTH: 20
<212> TYPE: DNA
<213> ORGANISM: Homo sapiens

<400> SEQUENCE: 633
ctgtaagaag gagggtttgg 20

<210> SEQ ID NO 634
<211> LENGTH: 20
<212> TYPE: DNA
<213> ORGANISM: Homo sapiens

<400> SEQUENCE: 634
gaggttgatg agaggtaggg 20

<210> SEQ ID NO 635
<211> LENGTH: 20
<212> TYPE: DNA
<213> ORGANISM: Homo sapiens

<400> SEQUENCE: 635
agccagggat attgttgaag 20

<210> SEQ ID NO 636
<211> LENGTH: 20
<212> TYPE: DNA
<213> ORGANISM: Homo sapiens

<400> SEQUENCE: 636
caggtaagtg tgtgttccag 20

<210> SEQ ID NO 637
<211> LENGTH: 20
<212> TYPE: DNA
<213> ORGANISM: Homo sapiens

<400> SEQUENCE: 637
ttgatttcca tgcagaaggg 20

<210> SEQ ID NO 638
<211> LENGTH: 20
<212> TYPE: DNA
<213> ORGANISM: Homo sapiens

<400> SEQUENCE: 638
taatttggcc ttaggggttg 20

<210> SEQ ID NO 639
<211> LENGTH: 21
<212> TYPE: DNA
<213> ORGANISM: Homo sapiens

<400> SEQUENCE: 639
tccataaaag gtgcttaaag c 21

<210> SEQ ID NO 640
<211> LENGTH: 20
<212> TYPE: DNA
<213> ORGANISM: Homo sapiens

<400> SEQUENCE: 640
ttgtatcaca ccatcgtgga 20

<210> SEQ ID NO 641
<211> LENGTH: 20
<212> TYPE: DNA
<213> ORGANISM: Homo sapiens

<400> SEQUENCE: 641
actgctgaga acaatcatgc 20

<210> SEQ ID NO 642
<211> LENGTH: 20
<212> TYPE: DNA
<213> ORGANISM: Homo sapiens

<400> SEQUENCE: 642
ggtgtggaga atttgtttgc 20

<210> SEQ ID NO 643
<211> LENGTH: 20
<212> TYPE: DNA
<213> ORGANISM: Homo sapiens

<400> SEQUENCE: 643
tgatattagg cggtggctta 20

<210> SEQ ID NO 644
<211> LENGTH: 20
<212> TYPE: DNA
<213> ORGANISM: Homo sapiens

<400> SEQUENCE: 644
tctcacctaa aatctggggc 20

<210> SEQ ID NO 645
<211> LENGTH: 22
<212> TYPE: DNA
<213> ORGANISM: Homo sapiens

<400> SEQUENCE: 645
aggactgtga cactttatct tt 22

<210> SEQ ID NO 646
<211> LENGTH: 21
<212> TYPE: DNA
<213> ORGANISM: Homo sapiens

<400> SEQUENCE: 646
atgcgaggta gaaaatgaga g 21

<210> SEQ ID NO 647
<211> LENGTH: 21
<212> TYPE: DNA
<213> ORGANISM: Homo sapiens

<400> SEQUENCE: 647
tgtggcttta aggttctgaa g 21

<210> SEQ ID NO 648
<211> LENGTH: 20
<212> TYPE: DNA
<213> ORGANISM: Homo sapiens

<400> SEQUENCE: 648
tcgttgctat tctgctttga 20

<210> SEQ ID NO 649
<211> LENGTH: 20
<212> TYPE: DNA
<213> ORGANISM: Homo sapiens

<400> SEQUENCE: 649 tccctttgt ggtttcttgg 20

<210> SEQ ID NO 650
<211> LENGTH: 20
<212> TYPE: DNA
<213> ORGANISM: Homo sapiens

<400> SEQUENCE: 650
ttgccgcact cttcattaat 20

<210> SEQ ID NO 651
<211> LENGTH: 20
<212> TYPE: DNA
<213> ORGANISM: Homo sapiens

<400> SEQUENCE: 651
actggcttct cctcattagt 20

<210> SEQ ID NO 652
<211> LENGTH: 20
<212> TYPE: DNA
<213> ORGANISM: Homo sapiens

<400> SEQUENCE: 652
actgatttgc catgtagagc 20

<210> SEQ ID NO 653
<211> LENGTH: 20
<212> TYPE: DNA
<213> ORGANISM: Homo sapiens

<400> SEQUENCE: 653
gaatgtcata ttgcctgcca 20

<210> SEQ ID NO 654
<211> LENGTH: 20
<212> TYPE: DNA
<213> ORGANISM: Homo sapiens

<400> SEQUENCE: 654
tcactcgctt agaatgttgc 20

<210> SEQ ID NO 655
<211> LENGTH: 21
<212> TYPE: DNA
<213> ORGANISM: Homo sapiens

<400> SEQUENCE: 655
accattaact tcctgcaaac t 21

<210> SEQ ID NO 656
<211> LENGTH: 20
<212> TYPE: DNA
<213> ORGANISM: Homo sapiens

<400> SEQUENCE: 656
taaagcccca taccaggatt 20

<210> SEQ ID NO 657
<211> LENGTH: 20
<212> TYPE: DNA
<213> ORGANISM: Homo sapiens

<400> SEQUENCE: 657
ccaaaaatca cccatatgcg 20

<210> SEQ ID NO 658
<211> LENGTH: 20
<212> TYPE: DNA
<213> ORGANISM: Homo sapiens

<400> SEQUENCE: 658
ataacccagg tgcttcaaag 20

<210> SEQ ID NO 659
<211> LENGTH: 19
<212> TYPE: DNA
<213> ORGANISM: Homo sapiens

<400> SEQUENCE: 659
tccacagcag aagtaacga 19

<210> SEQ ID NO 660
<211> LENGTH: 21
<212> TYPE: DNA
<213> ORGANISM: Homo sapiens

<400> SEQUENCE: 660
aggaaagcta tgaagaaagg g 21

<210> SEQ ID NO 661
<211> LENGTH: 20
<212> TYPE: DNA
<213> ORGANISM: Homo sapiens

<400> SEQUENCE: 661
agctccagag tgtcagtatt 20

<210> SEQ ID NO 662
<211> LENGTH: 22
<212> TYPE: DNA
<213> ORGANISM: Homo sapiens

<400> SEQUENCE: 662
ttgatttcca gcactgaact tt 22

<210> SEQ ID NO 663
<211> LENGTH: 20
<212> TYPE: DNA
<213> ORGANISM: Homo sapiens

<400> SEQUENCE: 663
tgtttgattt ttcaggctga 20

<210> SEQ ID NO 664
<211> LENGTH: 20
<212> TYPE: DNA

<213> ORGANISM: Homo sapiens

<400> SEQUENCE: 664
ctggtcattc ctgagtgtct 20

<210> SEQ ID NO 665
<211> LENGTH: 24
<212> TYPE: DNA
<213> ORGANISM: Homo sapiens

<400> SEQUENCE: 665
tcctgtttta cacttttcta actt 24

<210> SEQ ID NO 666
<211> LENGTH: 20
<212> TYPE: DNA
<213> ORGANISM: Homo sapiens

<400> SEQUENCE: 666
acctcaacct gttttagcac 20

<210> SEQ ID NO 667
<211> LENGTH: 20
<212> TYPE: DNA
<213> ORGANISM: Homo sapiens

<400> SEQUENCE: 667
cagtgtgtgt catgccaaat 20

<210> SEQ ID NO 668
<211> LENGTH: 21
<212> TYPE: DNA
<213> ORGANISM: Homo sapiens

<400> SEQUENCE: 668
ggtctatgtt aatcttgggc c 21

<210> SEQ ID NO 669
<211> LENGTH: 21
<212> TYPE: DNA
<213> ORGANISM: Homo sapiens

<400> SEQUENCE: 669
agccagtctg tatctaaagg t 21

<210> SEQ ID NO 670
<211> LENGTH: 20
<212> TYPE: DNA
<213> ORGANISM: Homo sapiens

<400> SEQUENCE: 670
actcttgggg tttcttcagt 20

<210> SEQ ID NO 671
<211> LENGTH: 21
<212> TYPE: DNA
<213> ORGANISM: Homo sapiens

<400> SEQUENCE: 671
cgaaccaaaa gcaaaatcct t 21

<210> SEQ ID NO 672
<211> LENGTH: 20

<212> TYPE: DNA
<213> ORGANISM: Homo sapiens

<400> SEQUENCE: 672
aatctatgga ggtcactggg 20

<210> SEQ ID NO 673
<211> LENGTH: 20
<212> TYPE: DNA
<213> ORGANISM: Homo sapiens

<400> SEQUENCE: 673
aggtccttgt agtttgcttg 20

<210> SEQ ID NO 674
<211> LENGTH: 20
<212> TYPE: DNA
<213> ORGANISM: Homo sapiens

<400> SEQUENCE: 674
gtgagagcca atagagtgtg 20

<210> SEQ ID NO 675
<211> LENGTH: 20
<212> TYPE: DNA
<213> ORGANISM: Homo sapiens

<400> SEQUENCE: 675
gcatggtgtg tgaaagtgat 20

<210> SEQ ID NO 676
<211> LENGTH: 20
<212> TYPE: DNA
<213> ORGANISM: Homo sapiens

<400> SEQUENCE: 676
atgctgcttt tgactgatgt 20

<210> SEQ ID NO 677
<211> LENGTH: 20
<212> TYPE: DNA
<213> ORGANISM: Homo sapiens

<400> SEQUENCE: 677
cgaagctgta ttcctgtctc 20

<210> SEQ ID NO 678
<211> LENGTH: 19
<212> TYPE: DNA
<213> ORGANISM: Homo sapiens

<400> SEQUENCE: 678
atggactaac tggagagcg 19

<210> SEQ ID NO 679
<211> LENGTH: 20
<212> TYPE: DNA
<213> ORGANISM: Homo sapiens

<400> SEQUENCE: 679
atgtcctgcc agtaaacaca 20

<210> SEQ ID NO 680

<211> LENGTH: 20
<212> TYPE: DNA
<213> ORGANISM: Homo sapiens

<400> SEQUENCE: 680
tgccactaaa cacctaagga 20

<210> SEQ ID NO 681
<211> LENGTH: 20
<212> TYPE: DNA
<213> ORGANISM: Homo sapiens

<400> SEQUENCE: 681
ttggaaattt tggggtcagg 20

<210> SEQ ID NO 682
<211> LENGTH: 20
<212> TYPE: DNA
<213> ORGANISM: Homo sapiens

<400> SEQUENCE: 682
ttctgacctc ccttactgag 20

<210> SEQ ID NO 683
<211> LENGTH: 19
<212> TYPE: DNA
<213> ORGANISM: Homo sapiens

<400> SEQUENCE: 683
tatgtgcttg cgatgtgtt 19

<210> SEQ ID NO 684
<211> LENGTH: 20
<212> TYPE: DNA
<213> ORGANISM: Homo sapiens

<400> SEQUENCE: 684
gaaccttagg gccagtctat 20

<210> SEQ ID NO 685
<211> LENGTH: 21
<212> TYPE: DNA
<213> ORGANISM: Homo sapiens

<400> SEQUENCE: 685
agaacctgat gtgttttcct c 21

<210> SEQ ID NO 686
<211> LENGTH: 20
<212> TYPE: DNA
<213> ORGANISM: Homo sapiens

<400> SEQUENCE: 686
atgtgagaga agcaaaaccc 20

<210> SEQ ID NO 687
<211> LENGTH: 20
<212> TYPE: DNA
<213> ORGANISM: Homo sapiens

<400> SEQUENCE: 687
gtagttgtct tgagggcttt 20

<210> SEQ ID NO 688
<211> LENGTH: 20
<212> TYPE: DNA
<213> ORGANISM: Homo sapiens

<400> SEQUENCE: 688
cctggtcaac aacatatggg 20

<210> SEQ ID NO 689
<211> LENGTH: 21
<212> TYPE: DNA
<213> ORGANISM: Homo sapiens

<400> SEQUENCE: 689
agaatattgc atttggccag a 21

<210> SEQ ID NO 690
<211> LENGTH: 21
<212> TYPE: DNA
<213> ORGANISM: Homo sapiens

<400> SEQUENCE: 690
aaagctatgc aaatagtggc a 21

<210> SEQ ID NO 691
<211> LENGTH: 20
<212> TYPE: DNA
<213> ORGANISM: Homo sapiens

<400> SEQUENCE: 691
agttcccaac agaggctaat 20

<210> SEQ ID NO 692
<211> LENGTH: 20
<212> TYPE: DNA
<213> ORGANISM: Homo sapiens

<400> SEQUENCE: 692
agttataggt gaggaagggc 20

<210> SEQ ID NO 693
<211> LENGTH: 20
<212> TYPE: DNA
<213> ORGANISM: Homo sapiens

<400> SEQUENCE: 693
cactgcaaaa gaaggaggtt 20

<210> SEQ ID NO 694
<211> LENGTH: 21
<212> TYPE: DNA
<213> ORGANISM: Homo sapiens

<400> SEQUENCE: 694
tctcaacatc gctgatctag t 21

<210> SEQ ID NO 695
<211> LENGTH: 20
<212> TYPE: DNA
<213> ORGANISM: Homo sapiens

<400> SEQUENCE: 695
aggtagctgg aaaaggagaa 20

<210> SEQ ID NO 696
<211> LENGTH: 21
<212> TYPE: DNA
<213> ORGANISM: Homo sapiens

<400> SEQUENCE: 696
tgaaattgcc cagaattgag t 21

<210> SEQ ID NO 697
<211> LENGTH: 20
<212> TYPE: DNA
<213> ORGANISM: Homo sapiens

<400> SEQUENCE: 697
attttcctgg acttctgaca 20

<210> SEQ ID NO 698
<211> LENGTH: 21
<212> TYPE: DNA
<213> ORGANISM: Homo sapiens

<400> SEQUENCE: 698
tgttattcct cttcctgtcc a 21

<210> SEQ ID NO 699
<211> LENGTH: 20
<212> TYPE: DNA
<213> ORGANISM: Homo sapiens

<400> SEQUENCE: 699
taaccacaca actacagctt 20

<210> SEQ ID NO 700
<211> LENGTH: 20
<212> TYPE: DNA
<213> ORGANISM: Homo sapiens

<400> SEQUENCE: 700
attcaaaatg gggacgagag 20

<210> SEQ ID NO 701
<211> LENGTH: 19
<212> TYPE: DNA
<213> ORGANISM: Homo sapiens

<400> SEQUENCE: 701
tcccagtttg ctactctgg 19

<210> SEQ ID NO 702
<211> LENGTH: 24
<212> TYPE: DNA
<213> ORGANISM: Homo sapiens

<400> SEQUENCE: 702
tctcattatg tgaagattgc tttc 24

<210> SEQ ID NO 703
<211> LENGTH: 23
<212> TYPE: DNA
<213> ORGANISM: Homo sapiens

<400> SEQUENCE: 703
ttaagattaa gcagtcttct tgg 23

<210> SEQ ID NO 704
<211> LENGTH: 20
<212> TYPE: DNA
<213> ORGANISM: Homo sapiens

<400> SEQUENCE: 704
caacagatct gattctgccc 20

<210> SEQ ID NO 705
<211> LENGTH: 20
<212> TYPE: DNA
<213> ORGANISM: Homo sapiens

<400> SEQUENCE: 705
catgtgtttc aaagttggct 20

<210> SEQ ID NO 706
<211> LENGTH: 21
<212> TYPE: DNA
<213> ORGANISM: Homo sapiens

<400> SEQUENCE: 706
actatagcat tagggtgagg g 21

<210> SEQ ID NO 707
<211> LENGTH: 20
<212> TYPE: DNA
<213> ORGANISM: Homo sapiens

<400> SEQUENCE: 707
gagatttgga catgctttca 20

<210> SEQ ID NO 708
<211> LENGTH: 19
<212> TYPE: DNA
<213> ORGANISM: Homo sapiens

<400> SEQUENCE: 708
cccaccacca gttgtcatc 19

<210> SEQ ID NO 709
<211> LENGTH: 21
<212> TYPE: DNA
<213> ORGANISM: Homo sapiens

<400> SEQUENCE: 709
gccactcact tcctagataa t 21

<210> SEQ ID NO 710
<211> LENGTH: 20
<212> TYPE: DNA
<213> ORGANISM: Homo sapiens

<400> SEQUENCE: 710
acagtatctc agggccttat 20

<210> SEQ ID NO 711
<211> LENGTH: 21
<212> TYPE: DNA
<213> ORGANISM: Homo sapiens

<400> SEQUENCE: 711
tcagtagttc ctcagatgct a 21

<210> SEQ ID NO 712
<211> LENGTH: 20
<212> TYPE: DNA
<213> ORGANISM: Homo sapiens

<400> SEQUENCE: 712
aatgcatgaa agtccaggaa 20

<210> SEQ ID NO 713
<211> LENGTH: 21
<212> TYPE: DNA
<213> ORGANISM: Homo sapiens

<400> SEQUENCE: 713
acatgcactc ttgtcttatg c 21

<210> SEQ ID NO 714
<211> LENGTH: 22
<212> TYPE: DNA
<213> ORGANISM: Homo sapiens

<400> SEQUENCE: 714
cacatatact ggctttctgg tc 22

<210> SEQ ID NO 715
<211> LENGTH: 19
<212> TYPE: DNA
<213> ORGANISM: Homo sapiens

<400> SEQUENCE: 715
gcacatgtca ttagcaggg 19

<210> SEQ ID NO 716
<211> LENGTH: 20
<212> TYPE: DNA
<213> ORGANISM: Homo sapiens

<400> SEQUENCE: 716
acatgctcaa ttatggagcc 20

<210> SEQ ID NO 717
<211> LENGTH: 20
<212> TYPE: DNA
<213> ORGANISM: Homo sapiens

<400> SEQUENCE: 717
acaaagacag gaatagggct 20

<210> SEQ ID NO 718
<211> LENGTH: 24
<212> TYPE: DNA
<213> ORGANISM: Homo sapiens

<400> SEQUENCE: 718
caatctgctg acttgcttct tttc 24

<210> SEQ ID NO 719
<211> LENGTH: 21
<212> TYPE: DNA
<213> ORGANISM: Homo sapiens

<400> SEQUENCE: 719
ctttggctca gaatcttcca a 21

<210> SEQ ID NO 720
<211> LENGTH: 21
<212> TYPE: DNA
<213> ORGANISM: Homo sapiens

<400> SEQUENCE: 720
tgtatgagga ccagcagtaa a 21

<210> SEQ ID NO 721
<211> LENGTH: 20
<212> TYPE: DNA
<213> ORGANISM: Homo sapiens

<400> SEQUENCE: 721
tcttttcccc ttgtgcatag 20

<210> SEQ ID NO 722
<211> LENGTH: 20
<212> TYPE: DNA
<213> ORGANISM: Homo sapiens

<400> SEQUENCE: 722
gcttagtgtg tgtgatccgt 20

<210> SEQ ID NO 723
<211> LENGTH: 20
<212> TYPE: DNA
<213> ORGANISM: Homo sapiens

<400> SEQUENCE: 723
actcaccttt cccaagaaga 20

<210> SEQ ID NO 724
<211> LENGTH: 20
<212> TYPE: DNA
<213> ORGANISM: Homo sapiens

<400> SEQUENCE: 724
tggtagtggg aagaggttga 20

<210> SEQ ID NO 725
<211> LENGTH: 20
<212> TYPE: DNA
<213> ORGANISM: Homo sapiens

<400> SEQUENCE: 725
gcatggagaa caaaagctga 20

<210> SEQ ID NO 726
<211> LENGTH: 20
<212> TYPE: DNA
<213> ORGANISM: Homo sapiens

<400> SEQUENCE: 726
tgtgagcaag aaactgaagg 20

<210> SEQ ID NO 727
<211> LENGTH: 20
<212> TYPE: DNA
<213> ORGANISM: Homo sapiens

<400> SEQUENCE: 727
agtatcactt gtccagctca 20

<210> SEQ ID NO 728
<211> LENGTH: 20
<212> TYPE: DNA
<213> ORGANISM: Homo sapiens

<400> SEQUENCE: 728
cacaggacta ggtaggcttt 20

<210> SEQ ID NO 729
<211> LENGTH: 21
<212> TYPE: DNA
<213> ORGANISM: Homo sapiens

<400> SEQUENCE: 729
gtgttaacag ctttcccttc a 21

<210> SEQ ID NO 730
<211> LENGTH: 23
<212> TYPE: DNA
<213> ORGANISM: Homo sapiens

<400> SEQUENCE: 730
tcatgtacag aaagaattag cct 23

<210> SEQ ID NO 731
<211> LENGTH: 20
<212> TYPE: DNA
<213> ORGANISM: Homo sapiens

<400> SEQUENCE: 731
agaggccaag tgaccaaata 20

<210> SEQ ID NO 732
<211> LENGTH: 21
<212> TYPE: DNA
<213> ORGANISM: Homo sapiens

<400> SEQUENCE: 732
aagccagtaa ttcatcttcc c 21

<210> SEQ ID NO 733
<211> LENGTH: 21
<212> TYPE: DNA
<213> ORGANISM: Homo sapiens

<400> SEQUENCE: 733
ccatgacata acacatcacc a 21

<210> SEQ ID NO 734
<211> LENGTH: 20
<212> TYPE: DNA
<213> ORGANISM: Homo sapiens

<400> SEQUENCE: 734
atagatttcc tcctgggctg 20

<210> SEQ ID NO 735
<211> LENGTH: 20
<212> TYPE: DNA
<213> ORGANISM: Homo sapiens

<400> SEQUENCE: 735
ccacctctgt acccactatc 20

<210> SEQ ID NO 736
<211> LENGTH: 20
<212> TYPE: DNA
<213> ORGANISM: Homo sapiens

<400> SEQUENCE: 736
ttccctggaa gatagccaat 20

<210> SEQ ID NO 737
<211> LENGTH: 20
<212> TYPE: DNA
<213> ORGANISM: Homo sapiens

<400> SEQUENCE: 737
tggacacgta aaagaaggtg 20

<210> SEQ ID NO 738
<211> LENGTH: 20
<212> TYPE: DNA
<213> ORGANISM: Homo sapiens

<400> SEQUENCE: 738
ctgagaacct tgtccaactg 20

<210> SEQ ID NO 739
<211> LENGTH: 20
<212> TYPE: DNA
<213> ORGANISM: Homo sapiens

<400> SEQUENCE: 739
tttcgctagt ctttgcactt 20

<210> SEQ ID NO 740
<211> LENGTH: 20
<212> TYPE: DNA
<213> ORGANISM: Homo sapiens

<400> SEQUENCE: 740
gcggcaataa ttgtcacaaa 20

<210> SEQ ID NO 741
<211> LENGTH: 20
<212> TYPE: DNA
<213> ORGANISM: Homo sapiens

<400> SEQUENCE: 741
cagaaatgtg tcaggctaca 20

<210> SEQ ID NO 742
<211> LENGTH: 20
<212> TYPE: DNA
<213> ORGANISM: Homo sapiens

<400> SEQUENCE: 742
aactcttcat tttgacgggg 20

<210> SEQ ID NO 743
<211> LENGTH: 20
<212> TYPE: DNA

<213> ORGANISM: Homo sapiens

<400> SEQUENCE: 743
tgggttgtgc tgttgtttag 20

<210> SEQ ID NO 744
<211> LENGTH: 19
<212> TYPE: DNA
<213> ORGANISM: Homo sapiens

<400> SEQUENCE: 744
gctcagctcc tttcatctg 19

<210> SEQ ID NO 745
<211> LENGTH: 20
<212> TYPE: DNA
<213> ORGANISM: Homo sapiens

<400> SEQUENCE: 745
aggacattca gcctatttgc 20

<210> SEQ ID NO 746
<211> LENGTH: 20
<212> TYPE: DNA
<213> ORGANISM: Homo sapiens

<400> SEQUENCE: 746
acacagtatc aaggtcaaca 20

<210> SEQ ID NO 747
<211> LENGTH: 20
<212> TYPE: DNA
<213> ORGANISM: Homo sapiens

<400> SEQUENCE: 747
gcagaaccac agtctatgag 20

<210> SEQ ID NO 748
<211> LENGTH: 21
<212> TYPE: DNA
<213> ORGANISM: Homo sapiens

<400> SEQUENCE: 748
aatgctccaa gttattccag a 21

<210> SEQ ID NO 749
<211> LENGTH: 20
<212> TYPE: DNA
<213> ORGANISM: Homo sapiens

<400> SEQUENCE: 749
aagagagaag cgacaaaacc 20

<210> SEQ ID NO 750
<211> LENGTH: 20
<212> TYPE: DNA
<213> ORGANISM: Homo sapiens

<400> SEQUENCE: 750
aatgagaagg aattgggtgc 20

<210> SEQ ID NO 751
<211> LENGTH: 20

<212> TYPE: DNA
<213> ORGANISM: Homo sapiens

<400> SEQUENCE: 751
aatgaagtgt tagggccatc 20

<210> SEQ ID NO 752
<211> LENGTH: 21
<212> TYPE: DNA
<213> ORGANISM: Homo sapiens

<400> SEQUENCE: 752
gctcatcaca gtttaaggag t 21

<210> SEQ ID NO 753
<211> LENGTH: 20
<212> TYPE: DNA
<213> ORGANISM: Homo sapiens

<400> SEQUENCE: 753
atgtggaagc aagagaaagg 20

<210> SEQ ID NO 754
<211> LENGTH: 20
<212> TYPE: DNA
<213> ORGANISM: Homo sapiens

<400> SEQUENCE: 754
tgaaaggtga agtggctttt 20

<210> SEQ ID NO 755
<211> LENGTH: 20
<212> TYPE: DNA
<213> ORGANISM: Homo sapiens

<400> SEQUENCE: 755
gtaagtaagg ggtcctagct 20

<210> SEQ ID NO 756
<211> LENGTH: 20
<212> TYPE: DNA
<213> ORGANISM: Homo sapiens

<400> SEQUENCE: 756
tgtgacttcc atgaaactgg 20

<210> SEQ ID NO 757
<211> LENGTH: 20
<212> TYPE: DNA
<213> ORGANISM: Homo sapiens

<400> SEQUENCE: 757
gctgacaaac taaccttcca 20

<210> SEQ ID NO 758
<211> LENGTH: 20
<212> TYPE: DNA
<213> ORGANISM: Homo sapiens

<400> SEQUENCE: 758
aaaacctccc aaaacagact 20

<210> SEQ ID NO 759

<211> LENGTH: 20
<212> TYPE: DNA
<213> ORGANISM: Homo sapiens

<400> SEQUENCE: 759
agtttagtgg ccacgtgaaa 20

<210> SEQ ID NO 760
<211> LENGTH: 20
<212> TYPE: DNA
<213> ORGANISM: Homo sapiens

<400> SEQUENCE: 760
ggcagaagtt tcaattccct 20

<210> SEQ ID NO 761
<211> LENGTH: 20
<212> TYPE: DNA
<213> ORGANISM: Homo sapiens

<400> SEQUENCE: 761
aaagcctctg tttgcacttt 20

<210> SEQ ID NO 762
<211> LENGTH: 20
<212> TYPE: DNA
<213> ORGANISM: Homo sapiens

<400> SEQUENCE: 762
tcagtcagct tcttgagtca 20

<210> SEQ ID NO 763
<211> LENGTH: 20
<212> TYPE: DNA
<213> ORGANISM: Homo sapiens

<400> SEQUENCE: 763
tgtttcattt gggtcatgga 20

<210> SEQ ID NO 764
<211> LENGTH: 21
<212> TYPE: DNA
<213> ORGANISM: Homo sapiens

<400> SEQUENCE: 764
tacagcacta ggatcactct g 21

<210> SEQ ID NO 765
<211> LENGTH: 20
<212> TYPE: DNA
<213> ORGANISM: Homo sapiens

<400> SEQUENCE: 765
atgcatgttt cttgcaaagg 20

<210> SEQ ID NO 766
<211> LENGTH: 20
<212> TYPE: DNA
<213> ORGANISM: Homo sapiens

<400> SEQUENCE: 766
gtaggattca gggcatttca 20

<210> SEQ ID NO 767
<211> LENGTH: 19
<212> TYPE: DNA
<213> ORGANISM: Homo sapiens

<400> SEQUENCE: 767
aactggaact gagcgtgag 19

<210> SEQ ID NO 768
<211> LENGTH: 20
<212> TYPE: DNA
<213> ORGANISM: Homo sapiens

<400> SEQUENCE: 768
tgtatgcagt tacctccaga 20

<210> SEQ ID NO 769
<211> LENGTH: 20
<212> TYPE: DNA
<213> ORGANISM: Homo sapiens

<400> SEQUENCE: 769
ggatgtatac cagacccctt 20

<210> SEQ ID NO 770
<211> LENGTH: 20
<212> TYPE: DNA
<213> ORGANISM: Homo sapiens

<400> SEQUENCE: 770
cgaaagatgt tagcacctca 20

<210> SEQ ID NO 771
<211> LENGTH: 20
<212> TYPE: DNA
<213> ORGANISM: Homo sapiens

<400> SEQUENCE: 771
aattggcttt gcagtgtttc 20

<210> SEQ ID NO 772
<211> LENGTH: 20
<212> TYPE: DNA
<213> ORGANISM: Homo sapiens

<400> SEQUENCE: 772
gcttgctggt aggaggtata 20

<210> SEQ ID NO 773
<211> LENGTH: 20
<212> TYPE: DNA
<213> ORGANISM: Homo sapiens

<400> SEQUENCE: 773
ctggaaacgg aaggaagttg 20

<210> SEQ ID NO 774
<211> LENGTH: 20
<212> TYPE: DNA
<213> ORGANISM: Homo sapiens

<400> SEQUENCE: 774
ctgtgttcag taagtggctg 20

<210> SEQ ID NO 775
<211> LENGTH: 20
<212> TYPE: DNA
<213> ORGANISM: Homo sapiens

<400> SEQUENCE: 775
gacagtgaag tgtgatcgtt 20

<210> SEQ ID NO 776
<211> LENGTH: 20
<212> TYPE: DNA
<213> ORGANISM: Homo sapiens

<400> SEQUENCE: 776
tggtgatgct gttttggaaa 20

<210> SEQ ID NO 777
<211> LENGTH: 22
<212> TYPE: DNA
<213> ORGANISM: Homo sapiens

<400> SEQUENCE: 777
ttctttcagg cagaagaaat ga 22

<210> SEQ ID NO 778
<211> LENGTH: 24
<212> TYPE: DNA
<213> ORGANISM: Homo sapiens

<400> SEQUENCE: 778
aagttccatt actgtattga aaat 24

<210> SEQ ID NO 779
<211> LENGTH: 20
<212> TYPE: DNA
<213> ORGANISM: Homo sapiens

<400> SEQUENCE: 779
ggacgtacgt gcttatttca 20

<210> SEQ ID NO 780
<211> LENGTH: 21
<212> TYPE: DNA
<213> ORGANISM: Homo sapiens

<400> SEQUENCE: 780
cagcctgata ttcccattga g 21

<210> SEQ ID NO 781
<211> LENGTH: 20
<212> TYPE: DNA
<213> ORGANISM: Homo sapiens

<400> SEQUENCE: 781
tcatgaggct gagtgagtat 20

<210> SEQ ID NO 782
<211> LENGTH: 20
<212> TYPE: DNA
<213> ORGANISM: Homo sapiens

<400> SEQUENCE: 782
aaagctctcc tatctccagt 20

<210> SEQ ID NO 783
<211> LENGTH: 21
<212> TYPE: DNA
<213> ORGANISM: Homo sapiens

<400> SEQUENCE: 783
acaaagagtc tggactatcc t 21

<210> SEQ ID NO 784
<211> LENGTH: 21
<212> TYPE: DNA
<213> ORGANISM: Homo sapiens

<400> SEQUENCE: 784
tgcctaaaaa tacccaaagc t 21

<210> SEQ ID NO 785
<211> LENGTH: 20
<212> TYPE: DNA
<213> ORGANISM: Homo sapiens

<400> SEQUENCE: 785
ccaagacact cactccaaag 20

<210> SEQ ID NO 786
<211> LENGTH: 20
<212> TYPE: DNA
<213> ORGANISM: Homo sapiens

<400> SEQUENCE: 786
ccaggaaaag gagcagtttt 20

<210> SEQ ID NO 787
<211> LENGTH: 20
<212> TYPE: DNA
<213> ORGANISM: Homo sapiens

<400> SEQUENCE: 787
gttcaactct ttctgcgaac 20

<210> SEQ ID NO 788
<211> LENGTH: 20
<212> TYPE: DNA
<213> ORGANISM: Homo sapiens

<400> SEQUENCE: 788
ccacttcttc tgtttccaac 20

<210> SEQ ID NO 789
<211> LENGTH: 19
<212> TYPE: DNA
<213> ORGANISM: Homo sapiens

<400> SEQUENCE: 789
gggaagggca tgctaatca 19

<210> SEQ ID NO 790
<211> LENGTH: 20
<212> TYPE: DNA
<213> ORGANISM: Homo sapiens

<400> SEQUENCE: 790
tgttcaatca cctctccatc 20

<210> SEQ ID NO 791
<211> LENGTH: 20
<212> TYPE: DNA
<213> ORGANISM: Homo sapiens

<400> SEQUENCE: 791
agaggagagg ctaagctttg 20

<210> SEQ ID NO 792
<211> LENGTH: 20
<212> TYPE: DNA
<213> ORGANISM: Homo sapiens

<400> SEQUENCE: 792
acaagagagg aagctgtcag 20

<210> SEQ ID NO 793
<211> LENGTH: 20
<212> TYPE: DNA
<213> ORGANISM: Homo sapiens

<400> SEQUENCE: 793
agcccctttc tccttattct 20

<210> SEQ ID NO 794
<211> LENGTH: 20
<212> TYPE: DNA
<213> ORGANISM: Homo sapiens

<400> SEQUENCE: 794
agggaagcag gattttaacg 20

<210> SEQ ID NO 795
<211> LENGTH: 20
<212> TYPE: DNA
<213> ORGANISM: Homo sapiens

<400> SEQUENCE: 795
aagtttcaca atacccaggt 20

<210> SEQ ID NO 796
<211> LENGTH: 20
<212> TYPE: DNA
<213> ORGANISM: Homo sapiens

<400> SEQUENCE: 796
tcgcagaatg gacaagtact 20

<210> SEQ ID NO 797
<211> LENGTH: 20
<212> TYPE: DNA
<213> ORGANISM: Homo sapiens

<400> SEQUENCE: 797
ggctcccaga ttttgatcat 20

<210> SEQ ID NO 798
<211> LENGTH: 20
<212> TYPE: DNA
<213> ORGANISM: Homo sapiens

<400> SEQUENCE: 798
cctagaactg caaaacacct 20

<210> SEQ ID NO 799
<211> LENGTH: 21
<212> TYPE: DNA
<213> ORGANISM: Homo sapiens

<400> SEQUENCE: 799
ttccattatt ttctcaccgg c 21

<210> SEQ ID NO 800
<211> LENGTH: 20
<212> TYPE: DNA
<213> ORGANISM: Homo sapiens

<400> SEQUENCE: 800
cagtccaaca aagaggtcac 20

<210> SEQ ID NO 801
<211> LENGTH: 20
<212> TYPE: DNA
<213> ORGANISM: Homo sapiens

<400> SEQUENCE: 801
ttgtgtgtgt tgaagcctag 20

<210> SEQ ID NO 802
<211> LENGTH: 20
<212> TYPE: DNA
<213> ORGANISM: Homo sapiens

<400> SEQUENCE: 802
agtgggggta ggaagaaaaa 20

<210> SEQ ID NO 803
<211> LENGTH: 20
<212> TYPE: DNA
<213> ORGANISM: Homo sapiens

<400> SEQUENCE: 803
gttccaacaa tgtaaggcac 20

<210> SEQ ID NO 804
<211> LENGTH: 20
<212> TYPE: DNA
<213> ORGANISM: Homo sapiens

<400> SEQUENCE: 804
ggaaccctct atggtcaaag 20

<210> SEQ ID NO 805
<211> LENGTH: 20
<212> TYPE: DNA
<213> ORGANISM: Homo sapiens

<400> SEQUENCE: 805
attgctgtgt agttccttga 20

<210> SEQ ID NO 806
<211> LENGTH: 20
<212> TYPE: DNA
<213> ORGANISM: Homo sapiens

<400> SEQUENCE: 806
tttcttgcca ccattctgac 20

<210> SEQ ID NO 807
<211> LENGTH: 20
<212> TYPE: DNA
<213> ORGANISM: Homo sapiens

<400> SEQUENCE: 807
cacacgttct aaccaagtgc 20

<210> SEQ ID NO 808
<211> LENGTH: 21
<212> TYPE: DNA
<213> ORGANISM: Homo sapiens

<400> SEQUENCE: 808
tagccacatc ttaacagacc t 21

<210> SEQ ID NO 809
<211> LENGTH: 20
<212> TYPE: DNA
<213> ORGANISM: Homo sapiens

<400> SEQUENCE: 809
attcctgagg gtgacatgaa 20

<210> SEQ ID NO 810
<211> LENGTH: 20
<212> TYPE: DNA
<213> ORGANISM: Homo sapiens

<400> SEQUENCE: 810
cctgccccat caacttaaaa 20

<210> SEQ ID NO 811
<211> LENGTH: 18
<212> TYPE: DNA
<213> ORGANISM: Homo sapiens

<400> SEQUENCE: 811
ctgggtgcag aggatctc 18

<210> SEQ ID NO 812
<211> LENGTH: 22
<212> TYPE: DNA
<213> ORGANISM: Homo sapiens

<400> SEQUENCE: 812
ttgagttgaa ctttgcttta ga 22

<210> SEQ ID NO 813
<211> LENGTH: 20
<212> TYPE: DNA
<213> ORGANISM: Homo sapiens

<400> SEQUENCE: 813
gaactaggag acactgggtt 20

<210> SEQ ID NO 814
<211> LENGTH: 21
<212> TYPE: DNA
<213> ORGANISM: Homo sapiens

<400> SEQUENCE: 814
caagaatagc taactggtgc t 21

<210> SEQ ID NO 815
<211> LENGTH: 21
<212> TYPE: DNA
<213> ORGANISM: Homo sapiens

<400> SEQUENCE: 815
agttacacac tgaatcatgg g 21

<210> SEQ ID NO 816
<211> LENGTH: 20
<212> TYPE: DNA
<213> ORGANISM: Homo sapiens

<400> SEQUENCE: 816
cccatgtggc ttcactaata 20

<210> SEQ ID NO 817
<211> LENGTH: 20
<212> TYPE: DNA
<213> ORGANISM: Homo sapiens

<400> SEQUENCE: 817
gattgtggtc acgtggagag 20

<210> SEQ ID NO 818
<211> LENGTH: 20
<212> TYPE: DNA
<213> ORGANISM: Homo sapiens

<400> SEQUENCE: 818
cagatccagg tattcggaga 20

<210> SEQ ID NO 819
<211> LENGTH: 20
<212> TYPE: DNA
<213> ORGANISM: Homo sapiens

<400> SEQUENCE: 819
acaacaacaa ccattaccca 20

<210> SEQ ID NO 820
<211> LENGTH: 20
<212> TYPE: DNA
<213> ORGANISM: Homo sapiens

<400> SEQUENCE: 820
tggccatagt actgcttgta 20

<210> SEQ ID NO 821
<211> LENGTH: 20
<212> TYPE: DNA
<213> ORGANISM: Homo sapiens

<400> SEQUENCE: 821
tgtctcactg ttgggaactt 20

<210> SEQ ID NO 822
<211> LENGTH: 20
<212> TYPE: DNA

<213> ORGANISM: Homo sapiens

<400> SEQUENCE: 822
tttgtctgta tcctatgccc 20

<210> SEQ ID NO 823
<211> LENGTH: 20
<212> TYPE: DNA
<213> ORGANISM: Homo sapiens

<400> SEQUENCE: 823
gctgacaaaa ttggatccca 20

<210> SEQ ID NO 824
<211> LENGTH: 20
<212> TYPE: DNA
<213> ORGANISM: Homo sapiens

<400> SEQUENCE: 824
aaaatcctcc tgagtcctct 20

<210> SEQ ID NO 825
<211> LENGTH: 20
<212> TYPE: DNA
<213> ORGANISM: Homo sapiens

<400> SEQUENCE: 825
ttcactgggc tcttcagcta 20

<210> SEQ ID NO 826
<211> LENGTH: 20
<212> TYPE: DNA
<213> ORGANISM: Homo sapiens

<400> SEQUENCE: 826
aaagggcagg agttaggtaa 20

<210> SEQ ID NO 827
<211> LENGTH: 20
<212> TYPE: DNA
<213> ORGANISM: Homo sapiens

<400> SEQUENCE: 827
aggcataaga aaccaggttg 20

<210> SEQ ID NO 828
<211> LENGTH: 20
<212> TYPE: DNA
<213> ORGANISM: Homo sapiens

<400> SEQUENCE: 828
gtagttcggt ccaatgtcag 20

<210> SEQ ID NO 829
<211> LENGTH: 20
<212> TYPE: DNA
<213> ORGANISM: Homo sapiens

<400> SEQUENCE: 829
gatggtcaca attgcaggtt 20

<210> SEQ ID NO 830
<211> LENGTH: 20

<212> TYPE: DNA
<213> ORGANISM: Homo sapiens

<400> SEQUENCE: 830
gccaaagatc tcaattgcca 20

<210> SEQ ID NO 831
<211> LENGTH: 20
<212> TYPE: DNA
<213> ORGANISM: Homo sapiens

<400> SEQUENCE: 831
gaccaagact gtctctcctt 20

<210> SEQ ID NO 832
<211> LENGTH: 22
<212> TYPE: DNA
<213> ORGANISM: Homo sapiens

<400> SEQUENCE: 832
taatggtcaa atccctctca aa 22

<210> SEQ ID NO 833
<211> LENGTH: 20
<212> TYPE: DNA
<213> ORGANISM: Homo sapiens

<400> SEQUENCE: 833
catgtaggct gaagactcct 20

<210> SEQ ID NO 834
<211> LENGTH: 20
<212> TYPE: DNA
<213> ORGANISM: Homo sapiens

<400> SEQUENCE: 834
tttctctcca aactggttgc 20

<210> SEQ ID NO 835
<211> LENGTH: 21
<212> TYPE: DNA
<213> ORGANISM: Homo sapiens

<400> SEQUENCE: 835
tacaggcaag aaatagtgtc t 21

<210> SEQ ID NO 836
<211> LENGTH: 20
<212> TYPE: DNA
<213> ORGANISM: Homo sapiens

<400> SEQUENCE: 836
ttcagcaaga atggggattc 20

<210> SEQ ID NO 837
<211> LENGTH: 20
<212> TYPE: DNA
<213> ORGANISM: Homo sapiens

<400> SEQUENCE: 837
caaagagaga gccatcacag 20

<210> SEQ ID NO 838

<211> LENGTH: 21
<212> TYPE: DNA
<213> ORGANISM: Homo sapiens

<400> SEQUENCE: 838
tgagaacact gctatttctg c 21

<210> SEQ ID NO 839
<211> LENGTH: 18
<212> TYPE: DNA
<213> ORGANISM: Homo sapiens

<400> SEQUENCE: 839
gcatggtcag gacattgg 18

<210> SEQ ID NO 840
<211> LENGTH: 20
<212> TYPE: DNA
<213> ORGANISM: Homo sapiens

<400> SEQUENCE: 840
gattgaatca ggagggaagc 20

<210> SEQ ID NO 841
<211> LENGTH: 23
<212> TYPE: DNA
<213> ORGANISM: Homo sapiens

<400> SEQUENCE: 841
agcttaaatg atgaagtgct ttc 23

<210> SEQ ID NO 842
<211> LENGTH: 20
<212> TYPE: DNA
<213> ORGANISM: Homo sapiens

<400> SEQUENCE: 842
ttctcctacg tatcttggca 20

<210> SEQ ID NO 843
<211> LENGTH: 20
<212> TYPE: DNA
<213> ORGANISM: Homo sapiens

<400> SEQUENCE: 843
acctgggaca taaccttgat 20

<210> SEQ ID NO 844
<211> LENGTH: 20
<212> TYPE: DNA
<213> ORGANISM: Homo sapiens

<400> SEQUENCE: 844
ccattttcct actgcgtgtc 20

<210> SEQ ID NO 845
<211> LENGTH: 20
<212> TYPE: DNA
<213> ORGANISM: Homo sapiens

<400> SEQUENCE: 845
gaacatacca aacccactgg 20

<210> SEQ ID NO 846
<211> LENGTH: 20
<212> TYPE: DNA
<213> ORGANISM: Homo sapiens

<400> SEQUENCE: 846
acccaatgat gtacagttcc 20

<210> SEQ ID NO 847
<211> LENGTH: 22
<212> TYPE: DNA
<213> ORGANISM: Homo sapiens

<400> SEQUENCE: 847
acctattcga cttgaaactc ag 22

<210> SEQ ID NO 848
<211> LENGTH: 20
<212> TYPE: DNA
<213> ORGANISM: Homo sapiens

<400> SEQUENCE: 848
atttctgcac aactgttcca 20

<210> SEQ ID NO 849
<211> LENGTH: 20
<212> TYPE: DNA
<213> ORGANISM: Homo sapiens

<400> SEQUENCE: 849
gctgtaatgt gactaaccct 20

<210> SEQ ID NO 850
<211> LENGTH: 20
<212> TYPE: DNA
<213> ORGANISM: Homo sapiens

<400> SEQUENCE: 850
tttcccgagg ttcacagata 20

<210> SEQ ID NO 851
<211> LENGTH: 20
<212> TYPE: DNA
<213> ORGANISM: Homo sapiens

<400> SEQUENCE: 851
gaacttgtgt gacccaaaac 20

<210> SEQ ID NO 852
<211> LENGTH: 20
<212> TYPE: DNA
<213> ORGANISM: Homo sapiens

<400> SEQUENCE: 852
cattgcactg tgatgtcatg 20

<210> SEQ ID NO 853
<211> LENGTH: 20
<212> TYPE: DNA
<213> ORGANISM: Homo sapiens

<400> SEQUENCE: 853
gcactggaaa ttgacatcac 20

<210> SEQ ID NO 854
<211> LENGTH: 20
<212> TYPE: DNA
<213> ORGANISM: Homo sapiens

<400> SEQUENCE: 854
gggagaggct gaaagaagaa 20

<210> SEQ ID NO 855
<211> LENGTH: 20
<212> TYPE: DNA
<213> ORGANISM: Homo sapiens

<400> SEQUENCE: 855
tgtatcactt cctcatgcca 20

<210> SEQ ID NO 856
<211> LENGTH: 20
<212> TYPE: DNA
<213> ORGANISM: Homo sapiens

<400> SEQUENCE: 856
ccaagagttt cctgtttcca 20

<210> SEQ ID NO 857
<211> LENGTH: 22
<212> TYPE: DNA
<213> ORGANISM: Homo sapiens

<400> SEQUENCE: 857
atgacacata catccattta ca 22

<210> SEQ ID NO 858
<211> LENGTH: 20
<212> TYPE: DNA
<213> ORGANISM: Homo sapiens

<400> SEQUENCE: 858
ctcaaactgc ccagtgattt 20

<210> SEQ ID NO 859
<211> LENGTH: 20
<212> TYPE: DNA
<213> ORGANISM: Homo sapiens

<400> SEQUENCE: 859
tcctagcttg ccaaagaaat 20

<210> SEQ ID NO 860
<211> LENGTH: 20
<212> TYPE: DNA
<213> ORGANISM: Homo sapiens

<400> SEQUENCE: 860
cctcctctcc aggcatttta 20

<210> SEQ ID NO 861
<211> LENGTH: 20
<212> TYPE: DNA
<213> ORGANISM: Homo sapiens

<400> SEQUENCE: 861
aacagagtag cacagagagt 20

<210> SEQ ID NO 862
<211> LENGTH: 20
<212> TYPE: DNA
<213> ORGANISM: Homo sapiens

<400> SEQUENCE: 862
ttcagagaga cagacagcat 20

<210> SEQ ID NO 863
<211> LENGTH: 20
<212> TYPE: DNA
<213> ORGANISM: Homo sapiens

<400> SEQUENCE: 863
agaggaaaat cacaagcagt 20

<210> SEQ ID NO 864
<211> LENGTH: 20
<212> TYPE: DNA
<213> ORGANISM: Homo sapiens

<400> SEQUENCE: 864
tttgaaaacc caacagacct 20

<210> SEQ ID NO 865
<211> LENGTH: 20
<212> TYPE: DNA
<213> ORGANISM: Homo sapiens

<400> SEQUENCE: 865
aatccacaca ccaacagagg 20

<210> SEQ ID NO 866
<211> LENGTH: 21
<212> TYPE: DNA
<213> ORGANISM: Homo sapiens

<400> SEQUENCE: 866
tgttcacatc tgttggtttg c 21

<210> SEQ ID NO 867
<211> LENGTH: 21
<212> TYPE: DNA
<213> ORGANISM: Homo sapiens

<400> SEQUENCE: 867
gttactcggt gggtgatatt t 21

<210> SEQ ID NO 868
<211> LENGTH: 21
<212> TYPE: DNA
<213> ORGANISM: Homo sapiens

<400> SEQUENCE: 868
aagaaacacc agcatcagtt c 21

<210> SEQ ID NO 869
<211> LENGTH: 21
<212> TYPE: DNA
<213> ORGANISM: Homo sapiens

<400> SEQUENCE: 869
aggtttagag gtgagtgaac a 21

<210> SEQ ID NO 870
<211> LENGTH: 22
<212> TYPE: DNA
<213> ORGANISM: Homo sapiens

<400> SEQUENCE: 870
agaaacttca ctgtcttcca ct 22

<210> SEQ ID NO 871
<211> LENGTH: 21
<212> TYPE: DNA
<213> ORGANISM: Homo sapiens

<400> SEQUENCE: 871
tgtgatggac attggtacct g 21

<210> SEQ ID NO 872
<211> LENGTH: 21
<212> TYPE: DNA
<213> ORGANISM: Homo sapiens

<400> SEQUENCE: 872
atatcatctg cctgtcccaa c 21

<210> SEQ ID NO 873
<211> LENGTH: 21
<212> TYPE: DNA
<213> ORGANISM: Homo sapiens

<400> SEQUENCE: 873
gagtgctctg tgtttgtttc a 21

<210> SEQ ID NO 874
<211> LENGTH: 22
<212> TYPE: DNA
<213> ORGANISM: Homo sapiens

<400> SEQUENCE: 874
tcagtggtga gctcttgaat at 22

<210> SEQ ID NO 875
<211> LENGTH: 21
<212> TYPE: DNA
<213> ORGANISM: Homo sapiens

<400> SEQUENCE: 875
actctctctt cacacatgca a 21

<210> SEQ ID NO 876
<211> LENGTH: 21
<212> TYPE: DNA
<213> ORGANISM: Homo sapiens

<400> SEQUENCE: 876
gtgttgaagt cagtaaagcc t 21

<210> SEQ ID NO 877
<211> LENGTH: 21
<212> TYPE: DNA
<213> ORGANISM: Homo sapiens

<400> SEQUENCE: 877
tgctttcaca tggcactaga t 21

<210> SEQ ID NO 878
<211> LENGTH: 21
<212> TYPE: DNA
<213> ORGANISM: Homo sapiens

<400> SEQUENCE: 878
ggagagagaa atcccaactg a 21

<210> SEQ ID NO 879
<211> LENGTH: 21
<212> TYPE: DNA
<213> ORGANISM: Homo sapiens

<400> SEQUENCE: 879
gggagatgtc aacactaggt c 21

<210> SEQ ID NO 880
<211> LENGTH: 20
<212> TYPE: DNA
<213> ORGANISM: Homo sapiens

<400> SEQUENCE: 880
atatgacatg gtggctctcc 20

<210> SEQ ID NO 881
<211> LENGTH: 21
<212> TYPE: DNA
<213> ORGANISM: Homo sapiens

<400> SEQUENCE: 881
aacatagagc catgggaggt a 21

<210> SEQ ID NO 882
<211> LENGTH: 21
<212> TYPE: DNA
<213> ORGANISM: Homo sapiens

<400> SEQUENCE: 882
gatagccttc aaatcatgcc t 21

<210> SEQ ID NO 883
<211> LENGTH: 21
<212> TYPE: DNA
<213> ORGANISM: Homo sapiens

<400> SEQUENCE: 883
gaaagcgggt gaacaacaat a 21

<210> SEQ ID NO 884
<211> LENGTH: 21
<212> TYPE: DNA
<213> ORGANISM: Homo sapiens

<400> SEQUENCE: 884
gatagagagc acaaagagca t 21

<210> SEQ ID NO 885
<211> LENGTH: 21
<212> TYPE: DNA
<213> ORGANISM: Homo sapiens

<400> SEQUENCE: 885
aacaagagga ataggagcca g 21

<210> SEQ ID NO 886
<211> LENGTH: 21
<212> TYPE: DNA
<213> ORGANISM: Homo sapiens

<400> SEQUENCE: 886
tgggtgctga tagtaacaaa g 21

<210> SEQ ID NO 887
<211> LENGTH: 21
<212> TYPE: DNA
<213> ORGANISM: Homo sapiens

<400> SEQUENCE: 887
actattgaac tgttggcttc g 21

<210> SEQ ID NO 888
<211> LENGTH: 21
<212> TYPE: DNA
<213> ORGANISM: Homo sapiens

<400> SEQUENCE: 888
tccactaaag agcaaccaaa c 21

<210> SEQ ID NO 889
<211> LENGTH: 21
<212> TYPE: DNA
<213> ORGANISM: Homo sapiens

<400> SEQUENCE: 889
tgaagtggtc agtaacaatg g 21

<210> SEQ ID NO 890
<211> LENGTH: 21
<212> TYPE: DNA
<213> ORGANISM: Homo sapiens

<400> SEQUENCE: 890
atttcagagc tcctttgtcc t 21

<210> SEQ ID NO 891
<211> LENGTH: 21
<212> TYPE: DNA
<213> ORGANISM: Homo sapiens

<400> SEQUENCE: 891
ggcaaagaaa tctggtgttc a 21

<210> SEQ ID NO 892
<211> LENGTH: 21
<212> TYPE: DNA
<213> ORGANISM: Homo sapiens

<400> SEQUENCE: 892
ttgctggttg ataggcattt g 21

<210> SEQ ID NO 893
<211> LENGTH: 21
<212> TYPE: DNA
<213> ORGANISM: Homo sapiens

<400> SEQUENCE: 893
attcccgcaa ttgtgagatt c 21

<210> SEQ ID NO 894
<211> LENGTH: 22
<212> TYPE: DNA
<213> ORGANISM: Homo sapiens

<400> SEQUENCE: 894
aaagaggtac agaactcaga cc 22

<210> SEQ ID NO 895
<211> LENGTH: 21
<212> TYPE: DNA
<213> ORGANISM: Homo sapiens

<400> SEQUENCE: 895
gtcttcatga acgttgccaa t 21

<210> SEQ ID NO 896
<211> LENGTH: 21
<212> TYPE: DNA
<213> ORGANISM: Homo sapiens

<400> SEQUENCE: 896
cttctcaggg ctctttgtgt a 21

<210> SEQ ID NO 897
<211> LENGTH: 21
<212> TYPE: DNA
<213> ORGANISM: Homo sapiens

<400> SEQUENCE: 897
gcaacagaaa ccaagattcc t 21

<210> SEQ ID NO 898
<211> LENGTH: 22
<212> TYPE: DNA
<213> ORGANISM: Homo sapiens

<400> SEQUENCE: 898
tcattgtcta cctcaaagag ca 22

<210> SEQ ID NO 899
<211> LENGTH: 21
<212> TYPE: DNA
<213> ORGANISM: Homo sapiens

<400> SEQUENCE: 899
ctctgaagga acaaaggatg g 21

<210> SEQ ID NO 900
<211> LENGTH: 21
<212> TYPE: DNA
<213> ORGANISM: Homo sapiens

<400> SEQUENCE: 900
cattagaatg cggtggtttc a 21

<210> SEQ ID NO 901
<211> LENGTH: 21
<212> TYPE: DNA

<213> ORGANISM: Homo sapiens

<400> SEQUENCE: 901
gatgtctggg ctgaggttta a 21

<210> SEQ ID NO 902
<211> LENGTH: 21
<212> TYPE: DNA
<213> ORGANISM: Homo sapiens

<400> SEQUENCE: 902
ttcctcttga agatgcactg g 21

<210> SEQ ID NO 903
<211> LENGTH: 21
<212> TYPE: DNA
<213> ORGANISM: Homo sapiens

<400> SEQUENCE: 903
ccagcatgtg aggaattgaa c 21

<210> SEQ ID NO 904
<211> LENGTH: 21
<212> TYPE: DNA
<213> ORGANISM: Homo sapiens

<400> SEQUENCE: 904
cccacttagt catccacaca t 21

<210> SEQ ID NO 905
<211> LENGTH: 21
<212> TYPE: DNA
<213> ORGANISM: Homo sapiens

<400> SEQUENCE: 905
gtttcacaca ccagaagaga g 21

<210> SEQ ID NO 906
<211> LENGTH: 21
<212> TYPE: DNA
<213> ORGANISM: Homo sapiens

<400> SEQUENCE: 906
ccatacacct gctctgacat t 21

<210> SEQ ID NO 907
<211> LENGTH: 21
<212> TYPE: DNA
<213> ORGANISM: Homo sapiens

<400> SEQUENCE: 907
atcagtaaca gtcccattgc t 21

<210> SEQ ID NO 908
<211> LENGTH: 21
<212> TYPE: DNA
<213> ORGANISM: Homo sapiens

<400> SEQUENCE: 908
catgaggcat ttgatccatg g 21

<210> SEQ ID NO 909
<211> LENGTH: 21

<212> TYPE: DNA
<213> ORGANISM: Homo sapiens

<400> SEQUENCE: 909
accctgtttc actgaacaac t 21

<210> SEQ ID NO 910
<211> LENGTH: 21
<212> TYPE: DNA
<213> ORGANISM: Homo sapiens

<400> SEQUENCE: 910
ccctgtaatg agagcgttat t 21

<210> SEQ ID NO 911
<211> LENGTH: 22
<212> TYPE: DNA
<213> ORGANISM: Homo sapiens

<400> SEQUENCE: 911
gagagaatgg gttaaatctg cc 22

<210> SEQ ID NO 912
<211> LENGTH: 21
<212> TYPE: DNA
<213> ORGANISM: Homo sapiens

<400> SEQUENCE: 912
ctgcctgact tagccttaaa t 21

<210> SEQ ID NO 913
<211> LENGTH: 21
<212> TYPE: DNA
<213> ORGANISM: Homo sapiens

<400> SEQUENCE: 913
aaccagaatg ttactagccc a 21

<210> SEQ ID NO 914
<211> LENGTH: 21
<212> TYPE: DNA
<213> ORGANISM: Homo sapiens

<400> SEQUENCE: 914
caatcctgtg tgtttagtgg a 21

<210> SEQ ID NO 915
<211> LENGTH: 20
<212> TYPE: DNA
<213> ORGANISM: Homo sapiens

<400> SEQUENCE: 915
tgtgggaagc attgactctt 20

<210> SEQ ID NO 916
<211> LENGTH: 21
<212> TYPE: DNA
<213> ORGANISM: Homo sapiens

<400> SEQUENCE: 916
tcctgtgaga aatggagctt t 21

<210> SEQ ID NO 917

<211> LENGTH: 22
<212> TYPE: DNA
<213> ORGANISM: Homo sapiens

<400> SEQUENCE: 917
gttgccaagc ttaaatacct gt 22

<210> SEQ ID NO 918
<211> LENGTH: 21
<212> TYPE: DNA
<213> ORGANISM: Homo sapiens

<400> SEQUENCE: 918
ccacaacaac ataaacactg c 21

<210> SEQ ID NO 919
<211> LENGTH: 21
<212> TYPE: DNA
<213> ORGANISM: Homo sapiens

<400> SEQUENCE: 919
tcttccaggc atattcattg c 21

<210> SEQ ID NO 920
<211> LENGTH: 21
<212> TYPE: DNA
<213> ORGANISM: Homo sapiens

<400> SEQUENCE: 920
atccattctc tctacttggg a 21

<210> SEQ ID NO 921
<211> LENGTH: 22
<212> TYPE: DNA
<213> ORGANISM: Homo sapiens

<400> SEQUENCE: 921
ggctagaggg tgattataag ct 22

<210> SEQ ID NO 922
<211> LENGTH: 21
<212> TYPE: DNA
<213> ORGANISM: Homo sapiens

<400> SEQUENCE: 922
tactcatccc gatttcttcc c 21

<210> SEQ ID NO 923
<211> LENGTH: 21
<212> TYPE: DNA
<213> ORGANISM: Homo sapiens

<400> SEQUENCE: 923
ttctctttct cttctgggca g 21

<210> SEQ ID NO 924
<211> LENGTH: 21
<212> TYPE: DNA
<213> ORGANISM: Homo sapiens

<400> SEQUENCE: 924
ttgtgagact caaggccatt t 21

<210> SEQ ID NO 925
<211> LENGTH: 21
<212> TYPE: DNA
<213> ORGANISM: Homo sapiens

<400> SEQUENCE: 925
ttggtagaga gaggccattt g 21

<210> SEQ ID NO 926
<211> LENGTH: 21
<212> TYPE: DNA
<213> ORGANISM: Homo sapiens

<400> SEQUENCE: 926
ggaggaagct cttgaagaca t 21

<210> SEQ ID NO 927
<211> LENGTH: 21
<212> TYPE: DNA
<213> ORGANISM: Homo sapiens

<400> SEQUENCE: 927
agcatcttcc gtttaactcc a 21

<210> SEQ ID NO 928
<211> LENGTH: 20
<212> TYPE: DNA
<213> ORGANISM: Homo sapiens

<400> SEQUENCE: 928
ctgcctgcca agtatgttct 20

<210> SEQ ID NO 929
<211> LENGTH: 21
<212> TYPE: DNA
<213> ORGANISM: Homo sapiens

<400> SEQUENCE: 929
ctactccttg tgtcattggc t 21

<210> SEQ ID NO 930
<211> LENGTH: 21
<212> TYPE: DNA
<213> ORGANISM: Homo sapiens

<400> SEQUENCE: 930
tgattctgag acacgtgctt a 21

<210> SEQ ID NO 931
<211> LENGTH: 21
<212> TYPE: DNA
<213> ORGANISM: Homo sapiens

<400> SEQUENCE: 931
cttgaggacc tttcatgctt g 21

<210> SEQ ID NO 932
<211> LENGTH: 21
<212> TYPE: DNA
<213> ORGANISM: Homo sapiens

<400> SEQUENCE: 932
ttgtgatttc aggtaggagg g 21

<210> SEQ ID NO 933
<211> LENGTH: 21
<212> TYPE: DNA
<213> ORGANISM: Homo sapiens

<400> SEQUENCE: 933
ttccctcaga gacagtatcc t 21

<210> SEQ ID NO 934
<211> LENGTH: 20
<212> TYPE: DNA
<213> ORGANISM: Homo sapiens

<400> SEQUENCE: 934
aaaggaggtc tggctttgaa 20

<210> SEQ ID NO 935
<211> LENGTH: 21
<212> TYPE: DNA
<213> ORGANISM: Homo sapiens

<400> SEQUENCE: 935
gcataaacct ggactgtgaa a 21

<210> SEQ ID NO 936
<211> LENGTH: 20
<212> TYPE: DNA
<213> ORGANISM: Homo sapiens

<400> SEQUENCE: 936
cactcagcga ttctcctcac 20

<210> SEQ ID NO 937
<211> LENGTH: 21
<212> TYPE: DNA
<213> ORGANISM: Homo sapiens

<400> SEQUENCE: 937
aaagccagac acagactagt t 21

<210> SEQ ID NO 938
<211> LENGTH: 20
<212> TYPE: DNA
<213> ORGANISM: Homo sapiens

<400> SEQUENCE: 938
attcctggga ccacaagcat 20

<210> SEQ ID NO 939
<211> LENGTH: 20
<212> TYPE: DNA
<213> ORGANISM: Homo sapiens

<400> SEQUENCE: 939
tattgcctca tgtggttgtg 20

<210> SEQ ID NO 940
<211> LENGTH: 22
<212> TYPE: DNA
<213> ORGANISM: Homo sapiens

<400> SEQUENCE: 940
gtgttgactt gaaaggaatc ac 22

<210> SEQ ID NO 941
<211> LENGTH: 21
<212> TYPE: DNA
<213> ORGANISM: Homo sapiens

<400> SEQUENCE: 941
caggttagga atgacagtgg g 21

<210> SEQ ID NO 942
<211> LENGTH: 21
<212> TYPE: DNA
<213> ORGANISM: Homo sapiens

<400> SEQUENCE: 942
ttaggttacc cagggacgtt a 21

<210> SEQ ID NO 943
<211> LENGTH: 21
<212> TYPE: DNA
<213> ORGANISM: Homo sapiens

<400> SEQUENCE: 943
cggtttgctt tctgaacaac a 21

<210> SEQ ID NO 944
<211> LENGTH: 21
<212> TYPE: DNA
<213> ORGANISM: Homo sapiens

<400> SEQUENCE: 944
catttgggac cctttgaaac t 21

<210> SEQ ID NO 945
<211> LENGTH: 21
<212> TYPE: DNA
<213> ORGANISM: Homo sapiens

<400> SEQUENCE: 945
ggttatctct gggcaaagtt c 21

<210> SEQ ID NO 946
<211> LENGTH: 21
<212> TYPE: DNA
<213> ORGANISM: Homo sapiens

<400> SEQUENCE: 946
tagagagcag agaacaaacc c 21

<210> SEQ ID NO 947
<211> LENGTH: 21
<212> TYPE: DNA
<213> ORGANISM: Homo sapiens

<400> SEQUENCE: 947
ataagggcat ttggagggaa a 21

<210> SEQ ID NO 948
<211> LENGTH: 21
<212> TYPE: DNA
<213> ORGANISM: Homo sapiens

<400> SEQUENCE: 948
aatgcacact tagacaccac a 21

<210> SEQ ID NO 949
<211> LENGTH: 21
<212> TYPE: DNA
<213> ORGANISM: Homo sapiens

<400> SEQUENCE: 949
ggattgctac ccaggagata a 21

<210> SEQ ID NO 950
<211> LENGTH: 21
<212> TYPE: DNA
<213> ORGANISM: Homo sapiens

<400> SEQUENCE: 950
agaggttctg tgtatgagtg t 21

<210> SEQ ID NO 951
<211> LENGTH: 21
<212> TYPE: DNA
<213> ORGANISM: Homo sapiens

<400> SEQUENCE: 951
tagagaattg tacgctggac a 21

<210> SEQ ID NO 952
<211> LENGTH: 21
<212> TYPE: DNA
<213> ORGANISM: Homo sapiens

<400> SEQUENCE: 952
tctggagaaa tgcacaagag a 21

<210> SEQ ID NO 953
<211> LENGTH: 21
<212> TYPE: DNA
<213> ORGANISM: Homo sapiens

<400> SEQUENCE: 953
tgggttagaa catggtgctt a 21

<210> SEQ ID NO 954
<211> LENGTH: 21
<212> TYPE: DNA
<213> ORGANISM: Homo sapiens

<400> SEQUENCE: 954
atcgcatcac acccttacta t 21

<210> SEQ ID NO 955
<211> LENGTH: 21
<212> TYPE: DNA
<213> ORGANISM: Homo sapiens

<400> SEQUENCE: 955
ggaaatttag cttgacatgg c 21

<210> SEQ ID NO 956
<211> LENGTH: 22
<212> TYPE: DNA
<213> ORGANISM: Homo sapiens

<400> SEQUENCE: 956
tttgtaaatc cacagtgcct ac 22

<210> SEQ ID NO 957
<211> LENGTH: 21
<212> TYPE: DNA
<213> ORGANISM: Homo sapiens

<400> SEQUENCE: 957
ggtactggag agcatagaag a 21

<210> SEQ ID NO 958
<211> LENGTH: 21
<212> TYPE: DNA
<213> ORGANISM: Homo sapiens

<400> SEQUENCE: 958
aaacaagcta tcttcaggca g 21

<210> SEQ ID NO 959
<211> LENGTH: 21
<212> TYPE: DNA
<213> ORGANISM: Homo sapiens

<400> SEQUENCE: 959
cgaacaatca gagactcgac t 21

<210> SEQ ID NO 960
<211> LENGTH: 21
<212> TYPE: DNA
<213> ORGANISM: Homo sapiens

<400> SEQUENCE: 960
ctggttgaca atctgcaagt t 21

<210> SEQ ID NO 961
<211> LENGTH: 21
<212> TYPE: DNA
<213> ORGANISM: Homo sapiens

<400> SEQUENCE: 961
accatccaag tcgtcttcat a 21

<210> SEQ ID NO 962
<211> LENGTH: 21
<212> TYPE: DNA
<213> ORGANISM: Homo sapiens

<400> SEQUENCE: 962
atagctacgc ataccctgta g 21

<210> SEQ ID NO 963
<211> LENGTH: 21
<212> TYPE: DNA
<213> ORGANISM: Homo sapiens

<400> SEQUENCE: 963
agcagaagaa acagtaaggc a 21

<210> SEQ ID NO 964
<211> LENGTH: 20
<212> TYPE: DNA
<213> ORGANISM: Homo sapiens

<400> SEQUENCE: 964
acccagggac ctatttgttc 20

<210> SEQ ID NO 965
<211> LENGTH: 21
<212> TYPE: DNA
<213> ORGANISM: Homo sapiens

<400> SEQUENCE: 965
caagggctca ggtcttcatt a 21

<210> SEQ ID NO 966
<211> LENGTH: 21
<212> TYPE: DNA
<213> ORGANISM: Homo sapiens

<400> SEQUENCE: 966
tcactgtgac ttggagacta a 21

<210> SEQ ID NO 967
<211> LENGTH: 21
<212> TYPE: DNA
<213> ORGANISM: Homo sapiens

<400> SEQUENCE: 967
tgctctgctt cactgtgatt a 21

<210> SEQ ID NO 968
<211> LENGTH: 22
<212> TYPE: DNA
<213> ORGANISM: Homo sapiens

<400> SEQUENCE: 968
gatgaatgac taatagccca cg 22

<210> SEQ ID NO 969
<211> LENGTH: 21
<212> TYPE: DNA
<213> ORGANISM: Homo sapiens

<400> SEQUENCE: 969
ccatgtttag tttggtgctg t 21

<210> SEQ ID NO 970
<211> LENGTH: 20
<212> TYPE: DNA
<213> ORGANISM: Homo sapiens

<400> SEQUENCE: 970
agccaagtga ggtgctaaat 20

<210> SEQ ID NO 971
<211> LENGTH: 21
<212> TYPE: DNA
<213> ORGANISM: Homo sapiens

<400> SEQUENCE: 971
tcagggagaa atgatgtcac c 21

<210> SEQ ID NO 972
<211> LENGTH: 21
<212> TYPE: DNA
<213> ORGANISM: Homo sapiens

<400> SEQUENCE: 972
cagtagctgg caagaatcat c 21

<210> SEQ ID NO 973
<211> LENGTH: 21
<212> TYPE: DNA
<213> ORGANISM: Homo sapiens

<400> SEQUENCE: 973
caacactgct agaattccca a 21

<210> SEQ ID NO 974
<211> LENGTH: 21
<212> TYPE: DNA
<213> ORGANISM: Homo sapiens

<400> SEQUENCE: 974
cctgagaagc acctgattgt a 21

<210> SEQ ID NO 975
<211> LENGTH: 20
<212> TYPE: DNA
<213> ORGANISM: Homo sapiens

<400> SEQUENCE: 975
tgttgtcaga aatcccagga 20

<210> SEQ ID NO 976
<211> LENGTH: 21
<212> TYPE: DNA
<213> ORGANISM: Homo sapiens

<400> SEQUENCE: 976
aactggagcc atataacgat g 21

<210> SEQ ID NO 977
<211> LENGTH: 21
<212> TYPE: DNA
<213> ORGANISM: Homo sapiens

<400> SEQUENCE: 977
gaaatggtgc cctattgttg a 21

<210> SEQ ID NO 978
<211> LENGTH: 22
<212> TYPE: DNA
<213> ORGANISM: Homo sapiens

<400> SEQUENCE: 978
tcttacatgc agtcatactc ct 22

<210> SEQ ID NO 979
<211> LENGTH: 22
<212> TYPE: DNA
<213> ORGANISM: Homo sapiens

<400> SEQUENCE: 979
gtccctcagt aacaccatct ta 22

<210> SEQ ID NO 980
<211> LENGTH: 21
<212> TYPE: DNA

<213> ORGANISM: Homo sapiens

<400> SEQUENCE: 980
gaagcaagag gatcaggcaa t 21

<210> SEQ ID NO 981
<211> LENGTH: 21
<212> TYPE: DNA
<213> ORGANISM: Homo sapiens

<400> SEQUENCE: 981
agtgtttcag aggcttgaaa g 21

<210> SEQ ID NO 982
<211> LENGTH: 21
<212> TYPE: DNA
<213> ORGANISM: Homo sapiens

<400> SEQUENCE: 982
atccggcatc ctttaaactc t 21

<210> SEQ ID NO 983
<211> LENGTH: 21
<212> TYPE: DNA
<213> ORGANISM: Homo sapiens

<400> SEQUENCE: 983
aggctaggaa gaaatgggaa a 21

<210> SEQ ID NO 984
<211> LENGTH: 21
<212> TYPE: DNA
<213> ORGANISM: Homo sapiens

<400> SEQUENCE: 984
acacatatgc tctgtctctc a 21

<210> SEQ ID NO 985
<211> LENGTH: 21
<212> TYPE: DNA
<213> ORGANISM: Homo sapiens

<400> SEQUENCE: 985
agttagttat cacctcgtcc c 21

<210> SEQ ID NO 986
<211> LENGTH: 22
<212> TYPE: DNA
<213> ORGANISM: Homo sapiens

<400> SEQUENCE: 986
tgtgtatttc cctctagttg ca 22

<210> SEQ ID NO 987
<211> LENGTH: 21
<212> TYPE: DNA
<213> ORGANISM: Homo sapiens

<400> SEQUENCE: 987
agcctctttc tacatcgttc g 21

<210> SEQ ID NO 988
<211> LENGTH: 21

<212> TYPE: DNA
<213> ORGANISM: Homo sapiens

<400> SEQUENCE: 988
ttacctgtgc agaagagtga c 21

<210> SEQ ID NO 989
<211> LENGTH: 21
<212> TYPE: DNA
<213> ORGANISM: Homo sapiens

<400> SEQUENCE: 989
tcttgtgttc tagcgtgttt g 21

<210> SEQ ID NO 990
<211> LENGTH: 21
<212> TYPE: DNA
<213> ORGANISM: Homo sapiens

<400> SEQUENCE: 990
tgtggttagt cagaaatgtg g 21

<210> SEQ ID NO 991
<211> LENGTH: 21
<212> TYPE: DNA
<213> ORGANISM: Homo sapiens

<400> SEQUENCE: 991
gggtcctgat gagtctttgt c 21

<210> SEQ ID NO 992
<211> LENGTH: 21
<212> TYPE: DNA
<213> ORGANISM: Homo sapiens

<400> SEQUENCE: 992
tggtgccttt gtttattcag c 21

<210> SEQ ID NO 993
<211> LENGTH: 21
<212> TYPE: DNA
<213> ORGANISM: Homo sapiens

<400> SEQUENCE: 993
tgttatgtgc cagggtttaa c 21

<210> SEQ ID NO 994
<211> LENGTH: 21
<212> TYPE: DNA
<213> ORGANISM: Homo sapiens

<400> SEQUENCE: 994
attggttcca gatacagtcg a 21

<210> SEQ ID NO 995
<211> LENGTH: 21
<212> TYPE: DNA
<213> ORGANISM: Homo sapiens

<400> SEQUENCE: 995
ggaaggaagt acagcatgga t 21

<210> SEQ ID NO 996

<211> LENGTH: 21
<212> TYPE: DNA
<213> ORGANISM: Homo sapiens

<400> SEQUENCE: 996
ccttattgaa gctgaccatg c 21

<210> SEQ ID NO 997
<211> LENGTH: 21
<212> TYPE: DNA
<213> ORGANISM: Homo sapiens

<400> SEQUENCE: 997
cagtgggaaa tgtgcttaca t 21

<210> SEQ ID NO 998
<211> LENGTH: 21
<212> TYPE: DNA
<213> ORGANISM: Homo sapiens

<400> SEQUENCE: 998
aaagggccta tattcaccag a 21

<210> SEQ ID NO 999
<211> LENGTH: 22
<212> TYPE: DNA
<213> ORGANISM: Homo sapiens

<400> SEQUENCE: 999
agagccattt aagactctct gt 22

<210> SEQ ID NO 1000
<211> LENGTH: 21
<212> TYPE: DNA
<213> ORGANISM: Homo sapiens

<400> SEQUENCE: 1000
taccttgttc tctgcctcaa t 21

<210> SEQ ID NO 1001
<211> LENGTH: 21
<212> TYPE: DNA
<213> ORGANISM: Homo sapiens

<400> SEQUENCE: 1001
tttagaagga tgtggacagg g 21

<210> SEQ ID NO 1002
<211> LENGTH: 20
<212> TYPE: DNA
<213> ORGANISM: Homo sapiens

<400> SEQUENCE: 1002
agcaggacat ggacttcaaa 20

<210> SEQ ID NO 1003
<211> LENGTH: 21
<212> TYPE: DNA
<213> ORGANISM: Homo sapiens

<400> SEQUENCE: 1003
gcggctcttg tttctgaaat c 21

<210> SEQ ID NO 1004
<211> LENGTH: 21
<212> TYPE: DNA
<213> ORGANISM: Homo sapiens

<400> SEQUENCE: 1004
acaggtagga gttcagagac a 21

<210> SEQ ID NO 1005
<211> LENGTH: 22
<212> TYPE: DNA
<213> ORGANISM: Homo sapiens

<400> SEQUENCE: 1005
tttcctattc tgctcttctg ct 22

<210> SEQ ID NO 1006
<211> LENGTH: 21
<212> TYPE: DNA
<213> ORGANISM: Homo sapiens

<400> SEQUENCE: 1006
aaatgctgct cagggttaga g 21

<210> SEQ ID NO 1007
<211> LENGTH: 21
<212> TYPE: DNA
<213> ORGANISM: Homo sapiens

<400> SEQUENCE: 1007
caactttact ctgcacagct c 21

<210> SEQ ID NO 1008
<211> LENGTH: 22
<212> TYPE: DNA
<213> ORGANISM: Homo sapiens

<400> SEQUENCE: 1008
cagtgccact acaaagaaat ca 22

<210> SEQ ID NO 1009
<211> LENGTH: 21
<212> TYPE: DNA
<213> ORGANISM: Homo sapiens

<400> SEQUENCE: 1009
agaagcagag gttggatatg g 21

<210> SEQ ID NO 1010
<211> LENGTH: 21
<212> TYPE: DNA
<213> ORGANISM: Homo sapiens

<400> SEQUENCE: 1010
ccacaatccc atagtcacca t 21

<210> SEQ ID NO 1011
<211> LENGTH: 21
<212> TYPE: DNA
<213> ORGANISM: Homo sapiens

<400> SEQUENCE: 1011
gctggttctt gttgctgata a 21

<210> SEQ ID NO 1012
<211> LENGTH: 21
<212> TYPE: DNA
<213> ORGANISM: Homo sapiens

<400> SEQUENCE: 1012
tccctcacga cttatgtttg a 21

<210> SEQ ID NO 1013
<211> LENGTH: 21
<212> TYPE: DNA
<213> ORGANISM: Homo sapiens

<400> SEQUENCE: 1013
ctaccttctc cagtgcacta t 21

<210> SEQ ID NO 1014
<211> LENGTH: 21
<212> TYPE: DNA
<213> ORGANISM: Homo sapiens

<400> SEQUENCE: 1014
ggacctctct ttgaaatgga c 21

<210> SEQ ID NO 1015
<211> LENGTH: 21
<212> TYPE: DNA
<213> ORGANISM: Homo sapiens

<400> SEQUENCE: 1015
tgggttgtgt ttctctgact t 21

<210> SEQ ID NO 1016
<211> LENGTH: 21
<212> TYPE: DNA
<213> ORGANISM: Homo sapiens

<400> SEQUENCE: 1016
tacaagcctc ctttaaccct t 21

<210> SEQ ID NO 1017
<211> LENGTH: 21
<212> TYPE: DNA
<213> ORGANISM: Homo sapiens

<400> SEQUENCE: 1017
aaagggtttg atacagttgg g 21

<210> SEQ ID NO 1018
<211> LENGTH: 22
<212> TYPE: DNA
<213> ORGANISM: Homo sapiens

<400> SEQUENCE: 1018
aggtattgga gagcaagaaa ga 22

<210> SEQ ID NO 1019
<211> LENGTH: 21
<212> TYPE: DNA
<213> ORGANISM: Homo sapiens

<400> SEQUENCE: 1019
gcaaactgga gctaaagtca t 21

<210> SEQ ID NO 1020
<211> LENGTH: 21
<212> TYPE: DNA
<213> ORGANISM: Homo sapiens

<400> SEQUENCE: 1020
ttggttgcta gctctcaaat g 21

<210> SEQ ID NO 1021
<211> LENGTH: 21
<212> TYPE: DNA
<213> ORGANISM: Homo sapiens

<400> SEQUENCE: 1021
ttcaatgccc ttacttctcc t 21

<210> SEQ ID NO 1022
<211> LENGTH: 20
<212> TYPE: DNA
<213> ORGANISM: Homo sapiens

<400> SEQUENCE: 1022
gcttgaggcg catatgattg 20

<210> SEQ ID NO 1023
<211> LENGTH: 20
<212> TYPE: DNA
<213> ORGANISM: Homo sapiens

<400> SEQUENCE: 1023
catatggtgc ttgttctggg 20

<210> SEQ ID NO 1024
<211> LENGTH: 21
<212> TYPE: DNA
<213> ORGANISM: Homo sapiens

<400> SEQUENCE: 1024
caaactcacc acccttcatt c 21

<210> SEQ ID NO 1025
<211> LENGTH: 21
<212> TYPE: DNA
<213> ORGANISM: Homo sapiens

<400> SEQUENCE: 1025
ccttagccct gcaaataaca c 21

<210> SEQ ID NO 1026
<211> LENGTH: 20
<212> TYPE: DNA
<213> ORGANISM: Homo sapiens

<400> SEQUENCE: 1026
tcacagatac ggacaagctc 20

<210> SEQ ID NO 1027
<211> LENGTH: 21
<212> TYPE: DNA
<213> ORGANISM: Homo sapiens

<400> SEQUENCE: 1027
gccacaggta tcaatcactt c 21

<210> SEQ ID NO 1028
<211> LENGTH: 21
<212> TYPE: DNA
<213> ORGANISM: Homo sapiens

<400> SEQUENCE: 1028
gcttctgtgg cactaatcaa g 21

<210> SEQ ID NO 1029
<211> LENGTH: 22
<212> TYPE: DNA
<213> ORGANISM: Homo sapiens

<400> SEQUENCE: 1029
gccttattga cttactggac tg 22

<210> SEQ ID NO 1030
<211> LENGTH: 21
<212> TYPE: DNA
<213> ORGANISM: Homo sapiens

<400> SEQUENCE: 1030
gtcagggatt agaggcagaa c 21

<210> SEQ ID NO 1031
<211> LENGTH: 22
<212> TYPE: DNA
<213> ORGANISM: Homo sapiens

<400> SEQUENCE: 1031
caatcacttg gtcagatagt gt 22

<210> SEQ ID NO 1032
<211> LENGTH: 22
<212> TYPE: DNA
<213> ORGANISM: Homo sapiens

<400> SEQUENCE: 1032
agtggagagg ttgagtatag tg 22

<210> SEQ ID NO 1033
<211> LENGTH: 21
<212> TYPE: DNA
<213> ORGANISM: Homo sapiens

<400> SEQUENCE: 1033
tgagaaggga ggaagaatgt g 21

<210> SEQ ID NO 1034
<211> LENGTH: 21
<212> TYPE: DNA
<213> ORGANISM: Homo sapiens

<400> SEQUENCE: 1034
aaggtcaaac tctccattcc a 21

<210> SEQ ID NO 1035
<211> LENGTH: 21
<212> TYPE: DNA
<213> ORGANISM: Homo sapiens

<400> SEQUENCE: 1035
ggagatgtct ttgccctgat t 21

<210> SEQ ID NO 1036
<211> LENGTH: 21
<212> TYPE: DNA
<213> ORGANISM: Homo sapiens

<400> SEQUENCE: 1036
ggtcctcgtt tgtccttaag a 21

<210> SEQ ID NO 1037
<211> LENGTH: 21
<212> TYPE: DNA
<213> ORGANISM: Homo sapiens

<400> SEQUENCE: 1037
agtattgctt tgagggctct a 21

<210> SEQ ID NO 1038
<211> LENGTH: 22
<212> TYPE: DNA
<213> ORGANISM: Homo sapiens

<400> SEQUENCE: 1038
agctatcatg taagtcactc cc 22

<210> SEQ ID NO 1039
<211> LENGTH: 21
<212> TYPE: DNA
<213> ORGANISM: Homo sapiens

<400> SEQUENCE: 1039
aggaaattca gtacctcagc t 21

<210> SEQ ID NO 1040
<211> LENGTH: 22
<212> TYPE: DNA
<213> ORGANISM: Homo sapiens

<400> SEQUENCE: 1040
caaccttctc attgttgaag ct 22

<210> SEQ ID NO 1041
<211> LENGTH: 20
<212> TYPE: DNA
<213> ORGANISM: Homo sapiens

<400> SEQUENCE: 1041
ggtgactttg ctttcccaag 20

<210> SEQ ID NO 1042
<211> LENGTH: 20
<212> TYPE: DNA
<213> ORGANISM: Homo sapiens

<400> SEQUENCE: 1042
gctgacaaac ggagggagag 20

<210> SEQ ID NO 1043
<211> LENGTH: 21
<212> TYPE: DNA
<213> ORGANISM: Homo sapiens

<400> SEQUENCE: 1043
tgttcttcat caggcacaat g 21

<210> SEQ ID NO 1044
<211> LENGTH: 21
<212> TYPE: DNA
<213> ORGANISM: Homo sapiens

<400> SEQUENCE: 1044
accatttgtg tgatccagaa c 21

<210> SEQ ID NO 1045
<211> LENGTH: 20
<212> TYPE: DNA
<213> ORGANISM: Homo sapiens

<400> SEQUENCE: 1045
cttgtcttga gtgcggtaca 20

<210> SEQ ID NO 1046
<211> LENGTH: 22
<212> TYPE: DNA
<213> ORGANISM: Homo sapiens

<400> SEQUENCE: 1046
gcctctcagt ttcctcttat ag 22

<210> SEQ ID NO 1047
<211> LENGTH: 24
<212> TYPE: DNA
<213> ORGANISM: Homo sapiens

<400> SEQUENCE: 1047
cctagatcag tgcagagaat ttag 24

<210> SEQ ID NO 1048
<211> LENGTH: 22
<212> TYPE: DNA
<213> ORGANISM: Homo sapiens

<400> SEQUENCE: 1048
ctttagtttg gaggcctcat tc 22

<210> SEQ ID NO 1049
<211> LENGTH: 21
<212> TYPE: DNA
<213> ORGANISM: Homo sapiens

<400> SEQUENCE: 1049
ctgacatcga tggaattctg g 21

<210> SEQ ID NO 1050
<211> LENGTH: 21
<212> TYPE: DNA
<213> ORGANISM: Homo sapiens

<400> SEQUENCE: 1050
acactgcacg aatggaagat c 21

<210> SEQ ID NO 1051
<211> LENGTH: 21
<212> TYPE: DNA
<213> ORGANISM: Homo sapiens

<400> SEQUENCE: 1051
ataaacttgg tgctcagtgg t 21

<210> SEQ ID NO 1052
<211> LENGTH: 21
<212> TYPE: DNA
<213> ORGANISM: Homo sapiens

<400> SEQUENCE: 1052
acaagcatta cagaattcgg c 21

<210> SEQ ID NO 1053
<211> LENGTH: 24
<212> TYPE: DNA
<213> ORGANISM: Homo sapiens

<400> SEQUENCE: 1053
actgacagat tctcacctat atca 24

<210> SEQ ID NO 1054
<211> LENGTH: 21
<212> TYPE: DNA
<213> ORGANISM: Homo sapiens

<400> SEQUENCE: 1054
ggatcaaagc cactctagac t 21

<210> SEQ ID NO 1055
<211> LENGTH: 22
<212> TYPE: DNA
<213> ORGANISM: Homo sapiens

<400> SEQUENCE: 1055
ttgagatggc atcaagttca ag 22

<210> SEQ ID NO 1056
<211> LENGTH: 22
<212> TYPE: DNA
<213> ORGANISM: Homo sapiens

<400> SEQUENCE: 1056
actggattca tgcgttatca ag 22

<210> SEQ ID NO 1057
<211> LENGTH: 21
<212> TYPE: DNA
<213> ORGANISM: Homo sapiens

<400> SEQUENCE: 1057
tattcttgtg tggaccctgt g 21

<210> SEQ ID NO 1058
<211> LENGTH: 22
<212> TYPE: DNA
<213> ORGANISM: Homo sapiens

<400> SEQUENCE: 1058
tgatattgca tgaaagtccc tg 22

<210> SEQ ID NO 1059
<211> LENGTH: 20
<212> TYPE: DNA

<213> ORGANISM: Homo sapiens

<400> SEQUENCE: 1059
tcacacatga ggagtagaca 20

<210> SEQ ID NO 1060
<211> LENGTH: 20
<212> TYPE: DNA
<213> ORGANISM: Homo sapiens

<400> SEQUENCE: 1060
cacagcagga gacatgagaa 20

<210> SEQ ID NO 1061
<211> LENGTH: 20
<212> TYPE: DNA
<213> ORGANISM: Homo sapiens

<400> SEQUENCE: 1061
tttcctcctg gcttgatcac 20

<210> SEQ ID NO 1062
<211> LENGTH: 20
<212> TYPE: DNA
<213> ORGANISM: Homo sapiens

<400> SEQUENCE: 1062
caaaggagag aagtgaccca 20

<210> SEQ ID NO 1063
<211> LENGTH: 20
<212> TYPE: DNA
<213> ORGANISM: Homo sapiens

<400> SEQUENCE: 1063
ctacgagtga aacagagtgc 20

<210> SEQ ID NO 1064
<211> LENGTH: 20
<212> TYPE: DNA
<213> ORGANISM: Homo sapiens

<400> SEQUENCE: 1064
agactaaaag cctccaagcc 20

<210> SEQ ID NO 1065
<211> LENGTH: 20
<212> TYPE: DNA
<213> ORGANISM: Homo sapiens

<400> SEQUENCE: 1065
tagaatatgt cacccagccc 20

<210> SEQ ID NO 1066
<211> LENGTH: 20
<212> TYPE: DNA
<213> ORGANISM: Homo sapiens

<400> SEQUENCE: 1066
acagaatcat cccatagcca 20

<210> SEQ ID NO 1067
<211> LENGTH: 21

<212> TYPE: DNA
<213> ORGANISM: Homo sapiens

<400> SEQUENCE: 1067
cgccattctg tgcttaattt g 21

<210> SEQ ID NO 1068
<211> LENGTH: 21
<212> TYPE: DNA
<213> ORGANISM: Homo sapiens

<400> SEQUENCE: 1068
gtgaagcaag agaaagcaag a 21

<210> SEQ ID NO 1069
<211> LENGTH: 20
<212> TYPE: DNA
<213> ORGANISM: Homo sapiens

<400> SEQUENCE: 1069
tgattcggct gcaggttatt 20

<210> SEQ ID NO 1070
<211> LENGTH: 20
<212> TYPE: DNA
<213> ORGANISM: Homo sapiens

<400> SEQUENCE: 1070
ctggcttcaa atgcatctga 20

<210> SEQ ID NO 1071
<211> LENGTH: 20
<212> TYPE: DNA
<213> ORGANISM: Homo sapiens

<400> SEQUENCE: 1071
actgggaaat tggaattcgc 20

<210> SEQ ID NO 1072
<211> LENGTH: 20
<212> TYPE: DNA
<213> ORGANISM: Homo sapiens

<400> SEQUENCE: 1072
ggtaaaactg cctggaaact 20

<210> SEQ ID NO 1073
<211> LENGTH: 20
<212> TYPE: DNA
<213> ORGANISM: Homo sapiens

<400> SEQUENCE: 1073
agaccacggg ctctatctat 20

<210> SEQ ID NO 1074
<211> LENGTH: 22
<212> TYPE: DNA
<213> ORGANISM: Homo sapiens

<400> SEQUENCE: 1074
catcttgctt attggcttac ga 22

<210> SEQ ID NO 1075

<211> LENGTH: 20
<212> TYPE: DNA
<213> ORGANISM: Homo sapiens

<400> SEQUENCE: 1075
gaggtagagg cagtgtcttg 20

<210> SEQ ID NO 1076
<211> LENGTH: 20
<212> TYPE: DNA
<213> ORGANISM: Homo sapiens

<400> SEQUENCE: 1076
tagtccttga actccctggt 20

<210> SEQ ID NO 1077
<211> LENGTH: 20
<212> TYPE: DNA
<213> ORGANISM: Homo sapiens

<400> SEQUENCE: 1077
ccagcttagc gtctgttttt 20

<210> SEQ ID NO 1078
<211> LENGTH: 21
<212> TYPE: DNA
<213> ORGANISM: Homo sapiens

<400> SEQUENCE: 1078
gaccacaact atcaagagca c 21

<210> SEQ ID NO 1079
<211> LENGTH: 20
<212> TYPE: DNA
<213> ORGANISM: Homo sapiens

<400> SEQUENCE: 1079
ccaaagaaag gttgaagccc 20

<210> SEQ ID NO 1080
<211> LENGTH: 21
<212> TYPE: DNA
<213> ORGANISM: Homo sapiens

<400> SEQUENCE: 1080
aataatgtgc actgtgatgg c 21

<210> SEQ ID NO 1081
<211> LENGTH: 20
<212> TYPE: DNA
<213> ORGANISM: Homo sapiens

<400> SEQUENCE: 1081
tttaagggtc tgatggttgc 20

<210> SEQ ID NO 1082
<211> LENGTH: 20
<212> TYPE: DNA
<213> ORGANISM: Homo sapiens

<400> SEQUENCE: 1082
gaaaatgccc atcgtctcaa 20

<210> SEQ ID NO 1083
<211> LENGTH: 20
<212> TYPE: DNA
<213> ORGANISM: Homo sapiens

<400> SEQUENCE: 1083
attccttgtc tttcccctc 20

<210> SEQ ID NO 1084
<211> LENGTH: 22
<212> TYPE: DNA
<213> ORGANISM: Homo sapiens

<400> SEQUENCE: 1084
tcatttctct agcccaaaga tg 22

<210> SEQ ID NO 1085
<211> LENGTH: 20
<212> TYPE: DNA
<213> ORGANISM: Homo sapiens

<400> SEQUENCE: 1085
ttggtttgtt gacttcagcc 20

<210> SEQ ID NO 1086
<211> LENGTH: 20
<212> TYPE: DNA
<213> ORGANISM: Homo sapiens

<400> SEQUENCE: 1086
gctcagtgac agttgggatt 20

<210> SEQ ID NO 1087
<211> LENGTH: 22
<212> TYPE: DNA
<213> ORGANISM: Homo sapiens

<400> SEQUENCE: 1087
gtcttgtctc tcttcttcca ct 22

<210> SEQ ID NO 1088
<211> LENGTH: 20
<212> TYPE: DNA
<213> ORGANISM: Homo sapiens

<400> SEQUENCE: 1088
tttagagcag gtggaaacga 20

<210> SEQ ID NO 1089
<211> LENGTH: 21
<212> TYPE: DNA
<213> ORGANISM: Homo sapiens

<400> SEQUENCE: 1089
cttgggtttt tatcggttgc t 21

<210> SEQ ID NO 1090
<211> LENGTH: 20
<212> TYPE: DNA
<213> ORGANISM: Homo sapiens

<400> SEQUENCE: 1090
gttgcctgga ttgctctaaa 20

<210> SEQ ID NO 1091
<211> LENGTH: 20
<212> TYPE: DNA
<213> ORGANISM: Homo sapiens

<400> SEQUENCE: 1091
aaatcacgac gtaggaaacc 20

<210> SEQ ID NO 1092
<211> LENGTH: 20
<212> TYPE: DNA
<213> ORGANISM: Homo sapiens

<400> SEQUENCE: 1092
tcaccttgga gcaggtcata 20

<210> SEQ ID NO 1093
<211> LENGTH: 20
<212> TYPE: DNA
<213> ORGANISM: Homo sapiens

<400> SEQUENCE: 1093
cgaagaaggt ctgggagatg 20

<210> SEQ ID NO 1094
<211> LENGTH: 21
<212> TYPE: DNA
<213> ORGANISM: Homo sapiens

<400> SEQUENCE: 1094
caccattgtt tcatcaggac t 21

<210> SEQ ID NO 1095
<211> LENGTH: 21
<212> TYPE: DNA
<213> ORGANISM: Homo sapiens

<400> SEQUENCE: 1095
ttgcatcatc agctcacata c 21

<210> SEQ ID NO 1096
<211> LENGTH: 20
<212> TYPE: DNA
<213> ORGANISM: Homo sapiens

<400> SEQUENCE: 1096
agacctggaa aatgatgggt 20

<210> SEQ ID NO 1097
<211> LENGTH: 20
<212> TYPE: DNA
<213> ORGANISM: Homo sapiens

<400> SEQUENCE: 1097
cctggaagtg tgtaacaagc 20

<210> SEQ ID NO 1098
<211> LENGTH: 21
<212> TYPE: DNA
<213> ORGANISM: Homo sapiens

<400> SEQUENCE: 1098
ctccctagca aaaacttctc a 21

<210> SEQ ID NO 1099
<211> LENGTH: 20
<212> TYPE: DNA
<213> ORGANISM: Homo sapiens

<400> SEQUENCE: 1099
tgccttattc actgtgcaac 20

<210> SEQ ID NO 1100
<211> LENGTH: 20
<212> TYPE: DNA
<213> ORGANISM: Homo sapiens

<400> SEQUENCE: 1100
tgatggccta gtgagtttcc 20

<210> SEQ ID NO 1101
<211> LENGTH: 20
<212> TYPE: DNA
<213> ORGANISM: Homo sapiens

<400> SEQUENCE: 1101
tgcaatgtaa caaaagcgtg 20

<210> SEQ ID NO 1102
<211> LENGTH: 20
<212> TYPE: DNA
<213> ORGANISM: Homo sapiens

<400> SEQUENCE: 1102
gccacatttg ctttcacaca 20

<210> SEQ ID NO 1103
<211> LENGTH: 19
<212> TYPE: DNA
<213> ORGANISM: Homo sapiens

<400> SEQUENCE: 1103
acgtcattgg gttcatggc 19

<210> SEQ ID NO 1104
<211> LENGTH: 20
<212> TYPE: DNA
<213> ORGANISM: Homo sapiens

<400> SEQUENCE: 1104
attttacccc cttaggcacc 20

<210> SEQ ID NO 1105
<211> LENGTH: 20
<212> TYPE: DNA
<213> ORGANISM: Homo sapiens

<400> SEQUENCE: 1105
tcttctacac agcccttcag 20

<210> SEQ ID NO 1106
<211> LENGTH: 20
<212> TYPE: DNA
<213> ORGANISM: Homo sapiens

<400> SEQUENCE: 1106
attgggatcg tcagcatcaa 20

<210> SEQ ID NO 1107
<211> LENGTH: 20
<212> TYPE: DNA
<213> ORGANISM: Homo sapiens

<400> SEQUENCE: 1107
tgattgtctt gtccactggt 20

<210> SEQ ID NO 1108
<211> LENGTH: 20
<212> TYPE: DNA
<213> ORGANISM: Homo sapiens

<400> SEQUENCE: 1108
acatcacact tcatgccctt 20

<210> SEQ ID NO 1109
<211> LENGTH: 20
<212> TYPE: DNA
<213> ORGANISM: Homo sapiens

<400> SEQUENCE: 1109
atgaaggcat taggagggag 20

<210> SEQ ID NO 1110
<211> LENGTH: 20
<212> TYPE: DNA
<213> ORGANISM: Homo sapiens

<400> SEQUENCE: 1110
aaagtggaga agtggcagat 20

<210> SEQ ID NO 1111
<211> LENGTH: 22
<212> TYPE: DNA
<213> ORGANISM: Homo sapiens

<400> SEQUENCE: 1111
ccttaggatt ctgagaggtg ag 22

<210> SEQ ID NO 1112
<211> LENGTH: 20
<212> TYPE: DNA
<213> ORGANISM: Homo sapiens

<400> SEQUENCE: 1112
agggcttctg attgatttgc 20

<210> SEQ ID NO 1113
<211> LENGTH: 20
<212> TYPE: DNA
<213> ORGANISM: Homo sapiens

<400> SEQUENCE: 1113
cagggtagtc gggatttctc 20

<210> SEQ ID NO 1114
<211> LENGTH: 20
<212> TYPE: DNA
<213> ORGANISM: Homo sapiens

<400> SEQUENCE: 1114
cccggtaatg atctacagca 20

<210> SEQ ID NO 1115
<211> LENGTH: 19
<212> TYPE: DNA
<213> ORGANISM: Homo sapiens

<400> SEQUENCE: 1115
aacggcactt ggttcacta 19

<210> SEQ ID NO 1116
<211> LENGTH: 20
<212> TYPE: DNA
<213> ORGANISM: Homo sapiens

<400> SEQUENCE: 1116
actctgaact cctcctcctg 20

<210> SEQ ID NO 1117
<211> LENGTH: 20
<212> TYPE: DNA
<213> ORGANISM: Homo sapiens

<400> SEQUENCE: 1117
tttgctcaca cacaagacac 20

<210> SEQ ID NO 1118
<211> LENGTH: 20
<212> TYPE: DNA
<213> ORGANISM: Homo sapiens

<400> SEQUENCE: 1118
acgactgcat ccttttcatg 20

<210> SEQ ID NO 1119
<211> LENGTH: 22
<212> TYPE: DNA
<213> ORGANISM: Homo sapiens

<400> SEQUENCE: 1119
ccatcatagc ctacaaatac cc 22

<210> SEQ ID NO 1120
<211> LENGTH: 22
<212> TYPE: DNA
<213> ORGANISM: Homo sapiens

<400> SEQUENCE: 1120
agagagttga aaatatcccc ca 22

<210> SEQ ID NO 1121
<211> LENGTH: 20
<212> TYPE: DNA
<213> ORGANISM: Homo sapiens

<400> SEQUENCE: 1121
actttcttga acaccccagt 20

<210> SEQ ID NO 1122
<211> LENGTH: 20
<212> TYPE: DNA
<213> ORGANISM: Homo sapiens

<400> SEQUENCE: 1122
tgcctgtgtc ctacttttcc 20

<210> SEQ ID NO 1123
<211> LENGTH: 20
<212> TYPE: DNA
<213> ORGANISM: Homo sapiens

<400> SEQUENCE: 1123
tgactgccca agaatgtaca 20

<210> SEQ ID NO 1124
<211> LENGTH: 20
<212> TYPE: DNA
<213> ORGANISM: Homo sapiens

<400> SEQUENCE: 1124
ccgaacacgc tgtatgtatt 20

<210> SEQ ID NO 1125
<211> LENGTH: 20
<212> TYPE: DNA
<213> ORGANISM: Homo sapiens

<400> SEQUENCE: 1125
ggaagggaat tgaagcacag 20

<210> SEQ ID NO 1126
<211> LENGTH: 20
<212> TYPE: DNA
<213> ORGANISM: Homo sapiens

<400> SEQUENCE: 1126
tcatcctatc caccaacctg 20

<210> SEQ ID NO 1127
<211> LENGTH: 20
<212> TYPE: DNA
<213> ORGANISM: Homo sapiens

<400> SEQUENCE: 1127
aatgaactgg ccctgactta 20

<210> SEQ ID NO 1128
<211> LENGTH: 20
<212> TYPE: DNA
<213> ORGANISM: Homo sapiens

<400> SEQUENCE: 1128
taagatacca taccgcagct 20

<210> SEQ ID NO 1129
<211> LENGTH: 21
<212> TYPE: DNA
<213> ORGANISM: Homo sapiens

<400> SEQUENCE: 1129
tcagcgttca tggtaccaat a 21

<210> SEQ ID NO 1130
<211> LENGTH: 21
<212> TYPE: DNA
<213> ORGANISM: Homo sapiens

<400> SEQUENCE: 1130
gtttcccaac caacaaacaa g 21

<210> SEQ ID NO 1131
<211> LENGTH: 20
<212> TYPE: DNA
<213> ORGANISM: Homo sapiens

<400> SEQUENCE: 1131
tctatcggga tggagagtga 20

<210> SEQ ID NO 1132
<211> LENGTH: 20
<212> TYPE: DNA
<213> ORGANISM: Homo sapiens

<400> SEQUENCE: 1132
gttcagacag gtggactagg 20

<210> SEQ ID NO 1133
<211> LENGTH: 20
<212> TYPE: DNA
<213> ORGANISM: Homo sapiens

<400> SEQUENCE: 1133
aagcaacctg ggaaattgtg 20

<210> SEQ ID NO 1134
<211> LENGTH: 20
<212> TYPE: DNA
<213> ORGANISM: Homo sapiens

<400> SEQUENCE: 1134
gggttaaggt tgctgggtta 20

<210> SEQ ID NO 1135
<211> LENGTH: 21
<212> TYPE: DNA
<213> ORGANISM: Homo sapiens

<400> SEQUENCE: 1135
gtgaaatgtg gttgtagtgc a 21

<210> SEQ ID NO 1136
<211> LENGTH: 20
<212> TYPE: DNA
<213> ORGANISM: Homo sapiens

<400> SEQUENCE: 1136
gtgactgcct tgcttcattt 20

<210> SEQ ID NO 1137
<211> LENGTH: 20
<212> TYPE: DNA
<213> ORGANISM: Homo sapiens

<400> SEQUENCE: 1137
cagttctgga gccttctact 20

<210> SEQ ID NO 1138
<211> LENGTH: 20
<212> TYPE: DNA

<213> ORGANISM: Homo sapiens

<400> SEQUENCE: 1138
ttagggcagg atgtacagaa 20

<210> SEQ ID NO 1139
<211> LENGTH: 20
<212> TYPE: DNA
<213> ORGANISM: Homo sapiens

<400> SEQUENCE: 1139
gctggtgacc ttcattcaag 20

<210> SEQ ID NO 1140
<211> LENGTH: 19
<212> TYPE: DNA
<213> ORGANISM: Homo sapiens

<400> SEQUENCE: 1140
taaaaccatg ttcggggca 19

<210> SEQ ID NO 1141
<211> LENGTH: 21
<212> TYPE: DNA
<213> ORGANISM: Homo sapiens

<400> SEQUENCE: 1141
ctacctgtcc gtttccctta c 21

<210> SEQ ID NO 1142
<211> LENGTH: 21
<212> TYPE: DNA
<213> ORGANISM: Homo sapiens

<400> SEQUENCE: 1142
gacaaagatg actggaggtg a 21

<210> SEQ ID NO 1143
<211> LENGTH: 21
<212> TYPE: DNA
<213> ORGANISM: Homo sapiens

<400> SEQUENCE: 1143
gggtggatgg tgagatatgt g 21

<210> SEQ ID NO 1144
<211> LENGTH: 21
<212> TYPE: DNA
<213> ORGANISM: Homo sapiens

<400> SEQUENCE: 1144
cttcaaacct gatccatgtg c 21

<210> SEQ ID NO 1145
<211> LENGTH: 21
<212> TYPE: DNA
<213> ORGANISM: Homo sapiens

<400> SEQUENCE: 1145
gcagaaacag catgaatctc c 21

<210> SEQ ID NO 1146
<211> LENGTH: 21

<212> TYPE: DNA
<213> ORGANISM: Homo sapiens

<400> SEQUENCE: 1146
tgacttcaaa catcccatcc a 21

<210> SEQ ID NO 1147
<211> LENGTH: 21
<212> TYPE: DNA
<213> ORGANISM: Homo sapiens

<400> SEQUENCE: 1147
gtgggatgag ttctagagga a 21

<210> SEQ ID NO 1148
<211> LENGTH: 21
<212> TYPE: DNA
<213> ORGANISM: Homo sapiens

<400> SEQUENCE: 1148
agtcacacac atacacacag t 21

<210> SEQ ID NO 1149
<211> LENGTH: 21
<212> TYPE: DNA
<213> ORGANISM: Homo sapiens

<400> SEQUENCE: 1149
acgacttccc tgtgtaactt a 21

<210> SEQ ID NO 1150
<211> LENGTH: 21
<212> TYPE: DNA
<213> ORGANISM: Homo sapiens

<400> SEQUENCE: 1150
ccttctcttg tctctagtgc c 21

<210> SEQ ID NO 1151
<211> LENGTH: 21
<212> TYPE: DNA
<213> ORGANISM: Homo sapiens

<400> SEQUENCE: 1151
ctggaaatac acacacacct g 21

<210> SEQ ID NO 1152
<211> LENGTH: 21
<212> TYPE: DNA
<213> ORGANISM: Homo sapiens

<400> SEQUENCE: 1152
atttgtaaac cacccacttc g 21

<210> SEQ ID NO 1153
<211> LENGTH: 21
<212> TYPE: DNA
<213> ORGANISM: Homo sapiens

<400> SEQUENCE: 1153
tcactgtgct gacaaatcct a 21

<210> SEQ ID NO 1154

<211> LENGTH: 21
<212> TYPE: DNA
<213> ORGANISM: Homo sapiens

<400> SEQUENCE: 1154
cccatcatca tcccttcaga c 21

<210> SEQ ID NO 1155
<211> LENGTH: 21
<212> TYPE: DNA
<213> ORGANISM: Homo sapiens

<400> SEQUENCE: 1155
tcatcacttt atcctcccag t 21

<210> SEQ ID NO 1156
<211> LENGTH: 21
<212> TYPE: DNA
<213> ORGANISM: Homo sapiens

<400> SEQUENCE: 1156
atgggcacag gtaaagagtt t 21

<210> SEQ ID NO 1157
<211> LENGTH: 21
<212> TYPE: DNA
<213> ORGANISM: Homo sapiens

<400> SEQUENCE: 1157
tttgtaagct gagtgtgagg t 21

<210> SEQ ID NO 1158
<211> LENGTH: 21
<212> TYPE: DNA
<213> ORGANISM: Homo sapiens

<400> SEQUENCE: 1158
ttactgtttg aatgccagct c 21

<210> SEQ ID NO 1159
<211> LENGTH: 21
<212> TYPE: DNA
<213> ORGANISM: Homo sapiens

<400> SEQUENCE: 1159
tcccttctcc catcacaatt c 21

<210> SEQ ID NO 1160
<211> LENGTH: 21
<212> TYPE: DNA
<213> ORGANISM: Homo sapiens

<400> SEQUENCE: 1160
gaagactgca tgtgtgtcct a 21

<210> SEQ ID NO 1161
<211> LENGTH: 21
<212> TYPE: DNA
<213> ORGANISM: Homo sapiens

<400> SEQUENCE: 1161
ttctcactct caactgaacc a 21

<210> SEQ ID NO 1162
<211> LENGTH: 22
<212> TYPE: DNA
<213> ORGANISM: Homo sapiens

<400> SEQUENCE: 1162
tcagggagct tctaattaag ga 22

<210> SEQ ID NO 1163
<211> LENGTH: 21
<212> TYPE: DNA
<213> ORGANISM: Homo sapiens

<400> SEQUENCE: 1163
aagatgatcc caggcttaag g 21

<210> SEQ ID NO 1164
<211> LENGTH: 21
<212> TYPE: DNA
<213> ORGANISM: Homo sapiens

<400> SEQUENCE: 1164
gttgaggttt gctgatcttg g 21

<210> SEQ ID NO 1165
<211> LENGTH: 21
<212> TYPE: DNA
<213> ORGANISM: Homo sapiens

<400> SEQUENCE: 1165
caaagataga ttcgcacacc a 21

<210> SEQ ID NO 1166
<211> LENGTH: 21
<212> TYPE: DNA
<213> ORGANISM: Homo sapiens

<400> SEQUENCE: 1166
gagctggaca aattaaatgg c 21

<210> SEQ ID NO 1167
<211> LENGTH: 20
<212> TYPE: DNA
<213> ORGANISM: Homo sapiens

<400> SEQUENCE: 1167
ccagtgcatt tggtttgaca 20

<210> SEQ ID NO 1168
<211> LENGTH: 21
<212> TYPE: DNA
<213> ORGANISM: Homo sapiens

<400> SEQUENCE: 1168
tatgtgaatc ctctgtgtgg c 21

<210> SEQ ID NO 1169
<211> LENGTH: 21
<212> TYPE: DNA
<213> ORGANISM: Homo sapiens

<400> SEQUENCE: 1169
agcttctctc tcattctgct t 21

<210> SEQ ID NO 1170
<211> LENGTH: 21
<212> TYPE: DNA
<213> ORGANISM: Homo sapiens

<400> SEQUENCE: 1170
gactcccgat ttcatttgct g 21

<210> SEQ ID NO 1171
<211> LENGTH: 22
<212> TYPE: DNA
<213> ORGANISM: Homo sapiens

<400> SEQUENCE: 1171
tcccaatcgt tgtgaaacat ac 22

<210> SEQ ID NO 1172
<211> LENGTH: 21
<212> TYPE: DNA
<213> ORGANISM: Homo sapiens

<400> SEQUENCE: 1172
tctttacagg aagttgggac c 21

<210> SEQ ID NO 1173
<211> LENGTH: 21
<212> TYPE: DNA
<213> ORGANISM: Homo sapiens

<400> SEQUENCE: 1173
taagttcaga tcagggagca g 21

<210> SEQ ID NO 1174
<211> LENGTH: 22
<212> TYPE: DNA
<213> ORGANISM: Homo sapiens

<400> SEQUENCE: 1174
gttgaaagtc ttacagaacg ct 22

<210> SEQ ID NO 1175
<211> LENGTH: 21
<212> TYPE: DNA
<213> ORGANISM: Homo sapiens

<400> SEQUENCE: 1175
caacataggc acattgtcct c 21

<210> SEQ ID NO 1176
<211> LENGTH: 21
<212> TYPE: DNA
<213> ORGANISM: Homo sapiens

<400> SEQUENCE: 1176
gtcaggcctc ataactctct t 21

<210> SEQ ID NO 1177
<211> LENGTH: 21
<212> TYPE: DNA
<213> ORGANISM: Homo sapiens

<400> SEQUENCE: 1177
gttgtgtggc tttccttatc a 21

<210> SEQ ID NO 1178
<211> LENGTH: 21
<212> TYPE: DNA
<213> ORGANISM: Homo sapiens

<400> SEQUENCE: 1178
cctgcagctc tgtgtaaatt t 21

<210> SEQ ID NO 1179
<211> LENGTH: 21
<212> TYPE: DNA
<213> ORGANISM: Homo sapiens

<400> SEQUENCE: 1179
ctttggccag ttctttctct c 21

<210> SEQ ID NO 1180
<211> LENGTH: 20
<212> TYPE: DNA
<213> ORGANISM: Homo sapiens

<400> SEQUENCE: 1180
gtggcccagc attatttgtt 20

<210> SEQ ID NO 1181
<211> LENGTH: 21
<212> TYPE: DNA
<213> ORGANISM: Homo sapiens

<400> SEQUENCE: 1181
tcttggtgtg acttgctaac a 21

<210> SEQ ID NO 1182
<211> LENGTH: 21
<212> TYPE: DNA
<213> ORGANISM: Homo sapiens

<400> SEQUENCE: 1182
tttctggctg agataagacc c 21

<210> SEQ ID NO 1183
<211> LENGTH: 21
<212> TYPE: DNA
<213> ORGANISM: Homo sapiens

<400> SEQUENCE: 1183
acaattccgt ggtatacagc t 21

<210> SEQ ID NO 1184
<211> LENGTH: 21
<212> TYPE: DNA
<213> ORGANISM: Homo sapiens

<400> SEQUENCE: 1184
tgattgtgcc ctaaccaaac t 21

<210> SEQ ID NO 1185
<211> LENGTH: 21
<212> TYPE: DNA
<213> ORGANISM: Homo sapiens

<400> SEQUENCE: 1185
tgtcgtatcc tgctgtttag a 21

<210> SEQ ID NO 1186
<211> LENGTH: 21
<212> TYPE: DNA
<213> ORGANISM: Homo sapiens

<400> SEQUENCE: 1186
tcaggagtaa agtcaggacc t 21

<210> SEQ ID NO 1187
<211> LENGTH: 21
<212> TYPE: DNA
<213> ORGANISM: Homo sapiens

<400> SEQUENCE: 1187
tgagctgatt tactgtgaca c 21

<210> SEQ ID NO 1188
<211> LENGTH: 21
<212> TYPE: DNA
<213> ORGANISM: Homo sapiens

<400> SEQUENCE: 1188
tagcaccttg acttcaggat t 21

<210> SEQ ID NO 1189
<211> LENGTH: 21
<212> TYPE: DNA
<213> ORGANISM: Homo sapiens

<400> SEQUENCE: 1189
tgaggttgga aagggtcaat t 21

<210> SEQ ID NO 1190
<211> LENGTH: 21
<212> TYPE: DNA
<213> ORGANISM: Homo sapiens

<400> SEQUENCE: 1190
cagctttcct tcctcttctc t 21

<210> SEQ ID NO 1191
<211> LENGTH: 21
<212> TYPE: DNA
<213> ORGANISM: Homo sapiens

<400> SEQUENCE: 1191
acagtgagag gaaagaacag c 21

<210> SEQ ID NO 1192
<211> LENGTH: 21
<212> TYPE: DNA
<213> ORGANISM: Homo sapiens

<400> SEQUENCE: 1192
ggaaataaat tgtgagctgg c 21

<210> SEQ ID NO 1193
<211> LENGTH: 21
<212> TYPE: DNA
<213> ORGANISM: Homo sapiens

<400> SEQUENCE: 1193
agacagccct tcaatccata c 21

<210> SEQ ID NO 1194
<211> LENGTH: 21
<212> TYPE: DNA
<213> ORGANISM: Homo sapiens

<400> SEQUENCE: 1194
cctacatccc ttcctccttt c 21

<210> SEQ ID NO 1195
<211> LENGTH: 21
<212> TYPE: DNA
<213> ORGANISM: Homo sapiens

<400> SEQUENCE: 1195
tcacccatct tccaattagc t 21

<210> SEQ ID NO 1196
<211> LENGTH: 22
<212> TYPE: DNA
<213> ORGANISM: Homo sapiens

<400> SEQUENCE: 1196
tttctaagca caaactgaca cc 22

<210> SEQ ID NO 1197
<211> LENGTH: 21
<212> TYPE: DNA
<213> ORGANISM: Homo sapiens

<400> SEQUENCE: 1197
gatgtttgca ctggagggat a 21

<210> SEQ ID NO 1198
<211> LENGTH: 21
<212> TYPE: DNA
<213> ORGANISM: Homo sapiens

<400> SEQUENCE: 1198
gaagactaaa tgttggccga a 21

<210> SEQ ID NO 1199
<211> LENGTH: 21
<212> TYPE: DNA
<213> ORGANISM: Homo sapiens

<400> SEQUENCE: 1199
gtagagagag ggaggatcac a 21

<210> SEQ ID NO 1200
<211> LENGTH: 21
<212> TYPE: DNA
<213> ORGANISM: Homo sapiens

<400> SEQUENCE: 1200
cttgccatga agtttgacca g 21

<210> SEQ ID NO 1201
<211> LENGTH: 21
<212> TYPE: DNA
<213> ORGANISM: Homo sapiens

<400> SEQUENCE: 1201
aggatgagca tttgtaacct g 21

<210> SEQ ID NO 1202
<211> LENGTH: 21
<212> TYPE: DNA
<213> ORGANISM: Homo sapiens

<400> SEQUENCE: 1202
tgtcgctttc aaattaccca c 21

<210> SEQ ID NO 1203
<211> LENGTH: 21
<212> TYPE: DNA
<213> ORGANISM: Homo sapiens

<400> SEQUENCE: 1203
catacaagtg ctctgttagg c 21

<210> SEQ ID NO 1204
<211> LENGTH: 21
<212> TYPE: DNA
<213> ORGANISM: Homo sapiens

<400> SEQUENCE: 1204
aggacttgga accagaaaga c 21

<210> SEQ ID NO 1205
<211> LENGTH: 21
<212> TYPE: DNA
<213> ORGANISM: Homo sapiens

<400> SEQUENCE: 1205
aaagagggct gatatcgtct g 21

<210> SEQ ID NO 1206
<211> LENGTH: 21
<212> TYPE: DNA
<213> ORGANISM: Homo sapiens

<400> SEQUENCE: 1206
ctcactgcaa actatggaac c 21

<210> SEQ ID NO 1207
<211> LENGTH: 21
<212> TYPE: DNA
<213> ORGANISM: Homo sapiens

<400> SEQUENCE: 1207
tattctgccc atcttcttcc t 21

<210> SEQ ID NO 1208
<211> LENGTH: 20
<212> TYPE: DNA
<213> ORGANISM: Homo sapiens

<400> SEQUENCE: 1208
ggagacagcc caaacataga 20

<210> SEQ ID NO 1209
<211> LENGTH: 21
<212> TYPE: DNA
<213> ORGANISM: Homo sapiens

<400> SEQUENCE: 1209
agcaatggtg aagttctgga t 21

<210> SEQ ID NO 1210
<211> LENGTH: 21
<212> TYPE: DNA
<213> ORGANISM: Homo sapiens

<400> SEQUENCE: 1210
ctggtcagtg agagaaggga a 21

<210> SEQ ID NO 1211
<211> LENGTH: 20
<212> TYPE: DNA
<213> ORGANISM: Homo sapiens

<400> SEQUENCE: 1211
tttctccact ggcatgaact 20

<210> SEQ ID NO 1212
<211> LENGTH: 21
<212> TYPE: DNA
<213> ORGANISM: Homo sapiens

<400> SEQUENCE: 1212
catgatcaca attccaagcc a 21

<210> SEQ ID NO 1213
<211> LENGTH: 21
<212> TYPE: DNA
<213> ORGANISM: Homo sapiens

<400> SEQUENCE: 1213
acccagtcaa gttacagtct t 21

<210> SEQ ID NO 1214
<211> LENGTH: 22
<212> TYPE: DNA
<213> ORGANISM: Homo sapiens

<400> SEQUENCE: 1214
tgtaaagcat atcaagggaa cg 22

<210> SEQ ID NO 1215
<211> LENGTH: 21
<212> TYPE: DNA
<213> ORGANISM: Homo sapiens

<400> SEQUENCE: 1215
tgcagagata tgttcccgta t 21

<210> SEQ ID NO 1216
<211> LENGTH: 21
<212> TYPE: DNA
<213> ORGANISM: Homo sapiens

<400> SEQUENCE: 1216
agaagacagt acaaggaagg c 21

<210> SEQ ID NO 1217
<211> LENGTH: 21
<212> TYPE: DNA

<213> ORGANISM: Homo sapiens

<400> SEQUENCE: 1217
tgtttgccat ttgttctcct c 21

<210> SEQ ID NO 1218
<211> LENGTH: 21
<212> TYPE: DNA
<213> ORGANISM: Homo sapiens

<400> SEQUENCE: 1218
ttgaaggcaa gagaagtttg g 21

<210> SEQ ID NO 1219
<211> LENGTH: 21
<212> TYPE: DNA
<213> ORGANISM: Homo sapiens

<400> SEQUENCE: 1219
gccaaggaaa tgtagggaaa g 21

<210> SEQ ID NO 1220
<211> LENGTH: 21
<212> TYPE: DNA
<213> ORGANISM: Homo sapiens

<400> SEQUENCE: 1220
aaccttcaca cctagagaca g 21

<210> SEQ ID NO 1221
<211> LENGTH: 21
<212> TYPE: DNA
<213> ORGANISM: Homo sapiens

<400> SEQUENCE: 1221
gcataacagg gaaagtcacc t 21

<210> SEQ ID NO 1222
<211> LENGTH: 21
<212> TYPE: DNA
<213> ORGANISM: Homo sapiens

<400> SEQUENCE: 1222
aggatgttag tggtttgggt a 21

<210> SEQ ID NO 1223
<211> LENGTH: 20
<212> TYPE: DNA
<213> ORGANISM: Homo sapiens

<400> SEQUENCE: 1223
tctgacactg accttcaact 20

<210> SEQ ID NO 1224
<211> LENGTH: 20
<212> TYPE: DNA
<213> ORGANISM: Homo sapiens

<400> SEQUENCE: 1224
gaaacattgc tttccctcca 20

<210> SEQ ID NO 1225
<211> LENGTH: 20

<212> TYPE: DNA
<213> ORGANISM: Homo sapiens

<400> SEQUENCE: 1225
ttccacacat ctcttctccg 20

<210> SEQ ID NO 1226
<211> LENGTH: 20
<212> TYPE: DNA
<213> ORGANISM: Homo sapiens

<400> SEQUENCE: 1226
gggagccttg aaaacctgaa 20

<210> SEQ ID NO 1227
<211> LENGTH: 19
<212> TYPE: DNA
<213> ORGANISM: Homo sapiens

<400> SEQUENCE: 1227
attggtagcg ttgtcagca 19

<210> SEQ ID NO 1228
<211> LENGTH: 20
<212> TYPE: DNA
<213> ORGANISM: Homo sapiens

<400> SEQUENCE: 1228
ttcctgcatc ttgtagaccc 20

<210> SEQ ID NO 1229
<211> LENGTH: 20
<212> TYPE: DNA
<213> ORGANISM: Homo sapiens

<400> SEQUENCE: 1229
gggctaatgt tttgcttcca 20

<210> SEQ ID NO 1230
<211> LENGTH: 20
<212> TYPE: DNA
<213> ORGANISM: Homo sapiens

<400> SEQUENCE: 1230
tgttgattag agcttccccc 20

<210> SEQ ID NO 1231
<211> LENGTH: 19
<212> TYPE: DNA
<213> ORGANISM: Homo sapiens

<400> SEQUENCE: 1231
agaggttttc ttccccgtg 19

<210> SEQ ID NO 1232
<211> LENGTH: 20
<212> TYPE: DNA
<213> ORGANISM: Homo sapiens

<400> SEQUENCE: 1232
tagtgccctc tattgtgcct 20

<210> SEQ ID NO 1233

<211> LENGTH: 20
<212> TYPE: DNA
<213> ORGANISM: Homo sapiens

<400> SEQUENCE: 1233
actgctggac tttgaaatgc 20

<210> SEQ ID NO 1234
<211> LENGTH: 20
<212> TYPE: DNA
<213> ORGANISM: Homo sapiens

<400> SEQUENCE: 1234
caaacagtga gatgtggctg 20

<210> SEQ ID NO 1235
<211> LENGTH: 21
<212> TYPE: DNA
<213> ORGANISM: Homo sapiens

<400> SEQUENCE: 1235
ttgcttcctg aaaactggtt c 21

<210> SEQ ID NO 1236
<211> LENGTH: 20
<212> TYPE: DNA
<213> ORGANISM: Homo sapiens

<400> SEQUENCE: 1236
attccaatca cgtctctgca 20

<210> SEQ ID NO 1237
<211> LENGTH: 20
<212> TYPE: DNA
<213> ORGANISM: Homo sapiens

<400> SEQUENCE: 1237
acaatctcac agcctggaaa 20

<210> SEQ ID NO 1238
<211> LENGTH: 20
<212> TYPE: DNA
<213> ORGANISM: Homo sapiens

<400> SEQUENCE: 1238
tcagatgggt gaggttcttg 20

<210> SEQ ID NO 1239
<211> LENGTH: 20
<212> TYPE: DNA
<213> ORGANISM: Homo sapiens

<400> SEQUENCE: 1239
ctgctccttc cctccaatta 20

<210> SEQ ID NO 1240
<211> LENGTH: 20
<212> TYPE: DNA
<213> ORGANISM: Homo sapiens

<400> SEQUENCE: 1240
aaatgccagt cctgtaaagg 20

<210> SEQ ID NO 1241
<211> LENGTH: 20
<212> TYPE: DNA
<213> ORGANISM: Homo sapiens

<400> SEQUENCE: 1241
tgtcccattg cttaggaagt 20

<210> SEQ ID NO 1242
<211> LENGTH: 20
<212> TYPE: DNA
<213> ORGANISM: Homo sapiens

<400> SEQUENCE: 1242
tgtgtgatcc agagacccta 20

<210> SEQ ID NO 1243
<211> LENGTH: 20
<212> TYPE: DNA
<213> ORGANISM: Homo sapiens

<400> SEQUENCE: 1243
accaatgtag acttagcggg 20

<210> SEQ ID NO 1244
<211> LENGTH: 20
<212> TYPE: DNA
<213> ORGANISM: Homo sapiens

<400> SEQUENCE: 1244
actctcatat tgccccactt 20

<210> SEQ ID NO 1245
<211> LENGTH: 20
<212> TYPE: DNA
<213> ORGANISM: Homo sapiens

<400> SEQUENCE: 1245
ccagggattg atgtactggt 20

<210> SEQ ID NO 1246
<211> LENGTH: 20
<212> TYPE: DNA
<213> ORGANISM: Homo sapiens

<400> SEQUENCE: 1246
aattctggtc tatctggcgt 20

<210> SEQ ID NO 1247
<211> LENGTH: 20
<212> TYPE: DNA
<213> ORGANISM: Homo sapiens

<400> SEQUENCE: 1247
gccagccctt ttcacatatt 20

<210> SEQ ID NO 1248
<211> LENGTH: 20
<212> TYPE: DNA
<213> ORGANISM: Homo sapiens

<400> SEQUENCE: 1248
aactacacca tcccctgttt 20

<210> SEQ ID NO 1249
<211> LENGTH: 20
<212> TYPE: DNA
<213> ORGANISM: Homo sapiens

<400> SEQUENCE: 1249
ccatttcaaa catgctggtc 20

<210> SEQ ID NO 1250
<211> LENGTH: 22
<212> TYPE: DNA
<213> ORGANISM: Homo sapiens

<400> SEQUENCE: 1250
agattataag aaggcaggga ac 22

<210> SEQ ID NO 1251
<211> LENGTH: 22
<212> TYPE: DNA
<213> ORGANISM: Homo sapiens

<400> SEQUENCE: 1251
gtagagggct taaaacatgt cc 22

<210> SEQ ID NO 1252
<211> LENGTH: 21
<212> TYPE: DNA
<213> ORGANISM: Homo sapiens

<400> SEQUENCE: 1252
acaagaacac agtcgttaag c 21

<210> SEQ ID NO 1253
<211> LENGTH: 20
<212> TYPE: DNA
<213> ORGANISM: Homo sapiens

<400> SEQUENCE: 1253
tctctccttc actcccttca 20

<210> SEQ ID NO 1254
<211> LENGTH: 20
<212> TYPE: DNA
<213> ORGANISM: Homo sapiens

<400> SEQUENCE: 1254
tgtccacccc tctttgattg 20

<210> SEQ ID NO 1255
<211> LENGTH: 20
<212> TYPE: DNA
<213> ORGANISM: Homo sapiens

<400> SEQUENCE: 1255
tttagcttct cctgcctttg 20

<210> SEQ ID NO 1256
<211> LENGTH: 20
<212> TYPE: DNA
<213> ORGANISM: Homo sapiens

<400> SEQUENCE: 1256
agaagcaatt caccaggtca 20

<210> SEQ ID NO 1257
<211> LENGTH: 20
<212> TYPE: DNA
<213> ORGANISM: Homo sapiens

<400> SEQUENCE: 1257
tggagtcaga agtgtgtgtt 20

<210> SEQ ID NO 1258
<211> LENGTH: 20
<212> TYPE: DNA
<213> ORGANISM: Homo sapiens

<400> SEQUENCE: 1258
tctggtgtca aagcttaggg 20

<210> SEQ ID NO 1259
<211> LENGTH: 20
<212> TYPE: DNA
<213> ORGANISM: Homo sapiens

<400> SEQUENCE: 1259
tgccgatgat gtgtgttttg 20

<210> SEQ ID NO 1260
<211> LENGTH: 20
<212> TYPE: DNA
<213> ORGANISM: Homo sapiens

<400> SEQUENCE: 1260
tgtcccttcc taatcccaaa 20

<210> SEQ ID NO 1261
<211> LENGTH: 20
<212> TYPE: DNA
<213> ORGANISM: Homo sapiens

<400> SEQUENCE: 1261
aggatgttta agttgcagca 20

<210> SEQ ID NO 1262
<211> LENGTH: 20
<212> TYPE: DNA
<213> ORGANISM: Homo sapiens

<400> SEQUENCE: 1262
tatgcagttt tacccctcc 20

<210> SEQ ID NO 1263
<211> LENGTH: 20
<212> TYPE: DNA
<213> ORGANISM: Homo sapiens

<400> SEQUENCE: 1263
ttctgtgtgg tctcctcttg 20

<210> SEQ ID NO 1264
<211> LENGTH: 20
<212> TYPE: DNA
<213> ORGANISM: Homo sapiens

<400> SEQUENCE: 1264
atggagggac aagtgagaca 20

<210> SEQ ID NO 1265
<211> LENGTH: 20
<212> TYPE: DNA
<213> ORGANISM: Homo sapiens

<400> SEQUENCE: 1265
ggggaacatg gagctgtaaa 20

<210> SEQ ID NO 1266
<211> LENGTH: 20
<212> TYPE: DNA
<213> ORGANISM: Homo sapiens

<400> SEQUENCE: 1266
ggacccccta ccacatttac 20

<210> SEQ ID NO 1267
<211> LENGTH: 21
<212> TYPE: DNA
<213> ORGANISM: Homo sapiens

<400> SEQUENCE: 1267
agatggagaa atgtgcagag a 21

<210> SEQ ID NO 1268
<211> LENGTH: 19
<212> TYPE: DNA
<213> ORGANISM: Homo sapiens

<400> SEQUENCE: 1268
atgactgcat ccaagagca 19

<210> SEQ ID NO 1269
<211> LENGTH: 20
<212> TYPE: DNA
<213> ORGANISM: Homo sapiens

<400> SEQUENCE: 1269
cagaatttcc aggcagttgt 20

<210> SEQ ID NO 1270
<211> LENGTH: 21
<212> TYPE: DNA
<213> ORGANISM: Homo sapiens

<400> SEQUENCE: 1270
gaatccagaa gctcagtcct t 21

<210> SEQ ID NO 1271
<211> LENGTH: 20
<212> TYPE: DNA
<213> ORGANISM: Homo sapiens

<400> SEQUENCE: 1271
agccctggaa tcttgacatt 20

<210> SEQ ID NO 1272
<211> LENGTH: 19
<212> TYPE: DNA
<213> ORGANISM: Homo sapiens

<400> SEQUENCE: 1272
gtgcattata cggatggcc 19

<210> SEQ ID NO 1273
<211> LENGTH: 20
<212> TYPE: DNA
<213> ORGANISM: Homo sapiens

<400> SEQUENCE: 1273
ggtagagggt cctgtgattc 20

<210> SEQ ID NO 1274
<211> LENGTH: 20
<212> TYPE: DNA
<213> ORGANISM: Homo sapiens

<400> SEQUENCE: 1274
gtaactgcta gccactgagt 20

<210> SEQ ID NO 1275
<211> LENGTH: 20
<212> TYPE: DNA
<213> ORGANISM: Homo sapiens

<400> SEQUENCE: 1275
gcctttttgg gaatcctagt 20

<210> SEQ ID NO 1276
<211> LENGTH: 20
<212> TYPE: DNA
<213> ORGANISM: Homo sapiens

<400> SEQUENCE: 1276
aagggtggaa gcacattgac 20

<210> SEQ ID NO 1277
<211> LENGTH: 20
<212> TYPE: DNA
<213> ORGANISM: Homo sapiens

<400> SEQUENCE: 1277
atagaggaac aagctgcaca 20

<210> SEQ ID NO 1278
<211> LENGTH: 20
<212> TYPE: DNA
<213> ORGANISM: Homo sapiens

<400> SEQUENCE: 1278
ctcgtccctt gcacatctta 20

<210> SEQ ID NO 1279
<211> LENGTH: 20
<212> TYPE: DNA
<213> ORGANISM: Homo sapiens

<400> SEQUENCE: 1279
aggtggggaa gaacaaaaca 20

<210> SEQ ID NO 1280
<211> LENGTH: 20
<212> TYPE: DNA
<213> ORGANISM: Homo sapiens

<400> SEQUENCE: 1280
gagagtaggt gcagggaaac 20

<210> SEQ ID NO 1281
<211> LENGTH: 20
<212> TYPE: DNA
<213> ORGANISM: Homo sapiens

<400> SEQUENCE: 1281
atcccgcatt cttaaccaca 20

<210> SEQ ID NO 1282
<211> LENGTH: 21
<212> TYPE: DNA
<213> ORGANISM: Homo sapiens

<400> SEQUENCE: 1282
gactaagcaa aagcatctcc c 21

<210> SEQ ID NO 1283
<211> LENGTH: 20
<212> TYPE: DNA
<213> ORGANISM: Homo sapiens

<400> SEQUENCE: 1283
ttcttacagg ctcagggtat 20

<210> SEQ ID NO 1284
<211> LENGTH: 21
<212> TYPE: DNA
<213> ORGANISM: Homo sapiens

<400> SEQUENCE: 1284
cccatagctt aacccctaca a 21

<210> SEQ ID NO 1285
<211> LENGTH: 22
<212> TYPE: DNA
<213> ORGANISM: Homo sapiens

<400> SEQUENCE: 1285
tcttcatctt actgtctagc ac 22

<210> SEQ ID NO 1286
<211> LENGTH: 21
<212> TYPE: DNA
<213> ORGANISM: Homo sapiens

<400> SEQUENCE: 1286 tcataccta tccctgtgat c 21

<210> SEQ ID NO 1287
<211> LENGTH: 21
<212> TYPE: DNA
<213> ORGANISM: Homo sapiens

<400> SEQUENCE: 1287
tcttgccctt gatttgtttc c 21

<210> SEQ ID NO 1288
<211> LENGTH: 21
<212> TYPE: DNA
<213> ORGANISM: Homo sapiens

<400> SEQUENCE: 1288
gccttttatc catatgccac c 21

<210> SEQ ID NO 1289
<211> LENGTH: 20
<212> TYPE: DNA
<213> ORGANISM: Homo sapiens

<400> SEQUENCE: 1289
gccctcaact ttgcttttca 20

<210> SEQ ID NO 1290
<211> LENGTH: 20
<212> TYPE: DNA
<213> ORGANISM: Homo sapiens

<400> SEQUENCE: 1290
aaaaacctgc actgtgttcg 20

<210> SEQ ID NO 1291
<211> LENGTH: 22
<212> TYPE: DNA
<213> ORGANISM: Homo sapiens

<400> SEQUENCE: 1291
tttttacagc aatcttcact gc 22

<210> SEQ ID NO 1292
<211> LENGTH: 22
<212> TYPE: DNA
<213> ORGANISM: Homo sapiens

<400> SEQUENCE: 1292
taagccggaa tgatttgtaa gg 22

<210> SEQ ID NO 1293
<211> LENGTH: 20
<212> TYPE: DNA
<213> ORGANISM: Homo sapiens

<400> SEQUENCE: 1293
taccctttgg cttaacagct 20

<210> SEQ ID NO 1294
<211> LENGTH: 20
<212> TYPE: DNA
<213> ORGANISM: Homo sapiens

<400> SEQUENCE: 1294
agttgtcatg ttgggctcat 20

<210> SEQ ID NO 1295
<211> LENGTH: 22
<212> TYPE: DNA
<213> ORGANISM: Homo sapiens

<400> SEQUENCE: 1295
tgtcctaagt tacctgtctg ac 22

<210> SEQ ID NO 1296
<211> LENGTH: 21
<212> TYPE: DNA

<213> ORGANISM: Homo sapiens

<400> SEQUENCE: 1296
gccctggaaa gtactgtaac a 21

<210> SEQ ID NO 1297
<211> LENGTH: 20
<212> TYPE: DNA
<213> ORGANISM: Homo sapiens

<400> SEQUENCE: 1297
tgttacagcc aggctttcat 20

<210> SEQ ID NO 1298
<211> LENGTH: 20
<212> TYPE: DNA
<213> ORGANISM: Homo sapiens

<400> SEQUENCE: 1298
caacgaacac agggtttaca 20

<210> SEQ ID NO 1299
<211> LENGTH: 21
<212> TYPE: DNA
<213> ORGANISM: Homo sapiens

<400> SEQUENCE: 1299
ccaggactct ctcttttctt c 21

<210> SEQ ID NO 1300
<211> LENGTH: 22
<212> TYPE: DNA
<213> ORGANISM: Homo sapiens

<400> SEQUENCE: 1300
gacacataag accactttag gc 22

<210> SEQ ID NO 1301
<211> LENGTH: 21
<212> TYPE: DNA
<213> ORGANISM: Homo sapiens

<400> SEQUENCE: 1301
gatatgttct ggaggactgc t 21

<210> SEQ ID NO 1302
<211> LENGTH: 20
<212> TYPE: DNA
<213> ORGANISM: Homo sapiens

<400> SEQUENCE: 1302
tgattctcac aggctccttg 20

<210> SEQ ID NO 1303
<211> LENGTH: 22
<212> TYPE: DNA
<213> ORGANISM: Homo sapiens

<400> SEQUENCE: 1303
tgatggaagt ttctaggtca gt 22

<210> SEQ ID NO 1304
<211> LENGTH: 20

<212> TYPE: DNA
<213> ORGANISM: Homo sapiens

<400> SEQUENCE: 1304
aacactcttg ctccctatgt 20

<210> SEQ ID NO 1305
<211> LENGTH: 21
<212> TYPE: DNA
<213> ORGANISM: Homo sapiens

<400> SEQUENCE: 1305
tttctctccc agcttgatct t 21

<210> SEQ ID NO 1306
<211> LENGTH: 20
<212> TYPE: DNA
<213> ORGANISM: Homo sapiens

<400> SEQUENCE: 1306
ctgtgcagag acgaactaag 20

<210> SEQ ID NO 1307
<211> LENGTH: 19
<212> TYPE: DNA
<213> ORGANISM: Homo sapiens

<400> SEQUENCE: 1307
ctctcggagc aaagacctt 19

<210> SEQ ID NO 1308
<211> LENGTH: 20
<212> TYPE: DNA
<213> ORGANISM: Homo sapiens

<400> SEQUENCE: 1308
acctcataag tacgcccatc 20

<210> SEQ ID NO 1309
<211> LENGTH: 20
<212> TYPE: DNA
<213> ORGANISM: Homo sapiens

<400> SEQUENCE: 1309
tgatcttcct ttgctcctgt 20

<210> SEQ ID NO 1310
<211> LENGTH: 20
<212> TYPE: DNA
<213> ORGANISM: Homo sapiens

<400> SEQUENCE: 1310
atgacgacga tgttggagag 20

<210> SEQ ID NO 1311
<211> LENGTH: 20
<212> TYPE: DNA
<213> ORGANISM: Homo sapiens

<400> SEQUENCE: 1311
tccttcagca agcctctttt 20

<210> SEQ ID NO 1312

<211> LENGTH: 20
<212> TYPE: DNA
<213> ORGANISM: Homo sapiens

<400> SEQUENCE: 1312
tgagggtgat aacctgtgag 20

<210> SEQ ID NO 1313
<211> LENGTH: 20
<212> TYPE: DNA
<213> ORGANISM: Homo sapiens

<400> SEQUENCE: 1313
ggcttgaagt ttgtctgtga 20

<210> SEQ ID NO 1314
<211> LENGTH: 20
<212> TYPE: DNA
<213> ORGANISM: Homo sapiens

<400> SEQUENCE: 1314
ggattttcac attgctcagc 20

<210> SEQ ID NO 1315
<211> LENGTH: 21
<212> TYPE: DNA
<213> ORGANISM: Homo sapiens

<400> SEQUENCE: 1315
tagcatgaga gtgaactgag g 21

<210> SEQ ID NO 1316
<211> LENGTH: 20
<212> TYPE: DNA
<213> ORGANISM: Homo sapiens

<400> SEQUENCE: 1316
cagccacata gcccatatct 20

<210> SEQ ID NO 1317
<211> LENGTH: 20
<212> TYPE: DNA
<213> ORGANISM: Homo sapiens

<400> SEQUENCE: 1317
tgcccatgag tctacttgtg 20

<210> SEQ ID NO 1318
<211> LENGTH: 20
<212> TYPE: DNA
<213> ORGANISM: Homo sapiens

<400> SEQUENCE: 1318
aagtggactg agggacaatt 20

<210> SEQ ID NO 1319
<211> LENGTH: 22
<212> TYPE: DNA
<213> ORGANISM: Homo sapiens

<400> SEQUENCE: 1319
tcagactgag cattaaatca cc 22

<210> SEQ ID NO 1320
<211> LENGTH: 20
<212> TYPE: DNA
<213> ORGANISM: Homo sapiens

<400> SEQUENCE: 1320
taggtctgga agaatgccag 20

<210> SEQ ID NO 1321
<211> LENGTH: 20
<212> TYPE: DNA
<213> ORGANISM: Homo sapiens

<400> SEQUENCE: 1321
agtatcttgg gcttgtgaca 20

<210> SEQ ID NO 1322
<211> LENGTH: 20
<212> TYPE: DNA
<213> ORGANISM: Homo sapiens

<400> SEQUENCE: 1322
gctccacttc cagtctttct 20

<210> SEQ ID NO 1323
<211> LENGTH: 20
<212> TYPE: DNA
<213> ORGANISM: Homo sapiens

<400> SEQUENCE: 1323
ttggaatagt gagcctccct 20

<210> SEQ ID NO 1324
<211> LENGTH: 20
<212> TYPE: DNA
<213> ORGANISM: Homo sapiens

<400> SEQUENCE: 1324
tctggggctc tttgtctttg 20

<210> SEQ ID NO 1325
<211> LENGTH: 20
<212> TYPE: DNA
<213> ORGANISM: Homo sapiens

<400> SEQUENCE: 1325
atttttcctc ccctgtagct 20

<210> SEQ ID NO 1326
<211> LENGTH: 20
<212> TYPE: DNA
<213> ORGANISM: Homo sapiens

<400> SEQUENCE: 1326
ctgggcacac tgtattacca 20

<210> SEQ ID NO 1327
<211> LENGTH: 20
<212> TYPE: DNA
<213> ORGANISM: Homo sapiens

<400> SEQUENCE: 1327
caccacgttt ctaatgcaga 20

<210> SEQ ID NO 1328
<211> LENGTH: 20
<212> TYPE: DNA
<213> ORGANISM: Homo sapiens

<400> SEQUENCE: 1328
gagttgaaaa aggtccacgc 20

<210> SEQ ID NO 1329
<211> LENGTH: 20
<212> TYPE: DNA
<213> ORGANISM: Homo sapiens

<400> SEQUENCE: 1329
cagaggaaag acacagtgct 20

<210> SEQ ID NO 1330
<211> LENGTH: 20
<212> TYPE: DNA
<213> ORGANISM: Homo sapiens

<400> SEQUENCE: 1330
tcttggtttt gaggctgtca 20

<210> SEQ ID NO 1331
<211> LENGTH: 20
<212> TYPE: DNA
<213> ORGANISM: Homo sapiens

<400> SEQUENCE: 1331
atcagcctaa ttctccccac 20

<210> SEQ ID NO 1332
<211> LENGTH: 20
<212> TYPE: DNA
<213> ORGANISM: Homo sapiens

<400> SEQUENCE: 1332
atcccccatc atccatactc 20

<210> SEQ ID NO 1333
<211> LENGTH: 20
<212> TYPE: DNA
<213> ORGANISM: Homo sapiens

<400> SEQUENCE: 1333
catagctagg cctgtgagtg 20

<210> SEQ ID NO 1334
<211> LENGTH: 19
<212> TYPE: DNA
<213> ORGANISM: Homo sapiens

<400> SEQUENCE: 1334
tcagcttgct ccttctctg 19

<210> SEQ ID NO 1335
<211> LENGTH: 20
<212> TYPE: DNA
<213> ORGANISM: Homo sapiens

<400> SEQUENCE: 1335
ctaggtcctc agcagtgttt 20

<210> SEQ ID NO 1336
<211> LENGTH: 21
<212> TYPE: DNA
<213> ORGANISM: Homo sapiens

<400> SEQUENCE: 1336
tcccagagtt aacaataccc c 21

<210> SEQ ID NO 1337
<211> LENGTH: 20
<212> TYPE: DNA
<213> ORGANISM: Homo sapiens

<400> SEQUENCE: 1337
ccatttgcac tgccgatttc 20

<210> SEQ ID NO 1338
<211> LENGTH: 21
<212> TYPE: DNA
<213> ORGANISM: Homo sapiens

<400> SEQUENCE: 1338
actagtccca aaagcctaca c 21

<210> SEQ ID NO 1339
<211> LENGTH: 20
<212> TYPE: DNA
<213> ORGANISM: Homo sapiens

<400> SEQUENCE: 1339
aacagcagcg tcagaataac 20

<210> SEQ ID NO 1340
<211> LENGTH: 20
<212> TYPE: DNA
<213> ORGANISM: Homo sapiens

<400> SEQUENCE: 1340
aggtctttac gggaaggaaa 20

<210> SEQ ID NO 1341
<211> LENGTH: 20
<212> TYPE: DNA
<213> ORGANISM: Homo sapiens

<400> SEQUENCE: 1341
tgagggagaa gtttggtagg 20

<210> SEQ ID NO 1342
<211> LENGTH: 20
<212> TYPE: DNA
<213> ORGANISM: Homo sapiens

<400> SEQUENCE: 1342
ccctgtctaa agagccatgt 20

<210> SEQ ID NO 1343
<211> LENGTH: 20
<212> TYPE: DNA
<213> ORGANISM: Homo sapiens

<400> SEQUENCE: 1343
gtttggagtt tcgatgcctt 20

<210> SEQ ID NO 1344
<211> LENGTH: 20
<212> TYPE: DNA
<213> ORGANISM: Homo sapiens

<400> SEQUENCE: 1344
atgttttggt cctgggagaa 20

<210> SEQ ID NO 1345
<211> LENGTH: 20
<212> TYPE: DNA
<213> ORGANISM: Homo sapiens

<400> SEQUENCE: 1345
ggaagtggtt agggcagatt 20

<210> SEQ ID NO 1346
<211> LENGTH: 21
<212> TYPE: DNA
<213> ORGANISM: Homo sapiens

<400> SEQUENCE: 1346
agcccagtaa agataagagg c 21

<210> SEQ ID NO 1347
<211> LENGTH: 20
<212> TYPE: DNA
<213> ORGANISM: Homo sapiens

<400> SEQUENCE: 1347
cccttccctt tcatccaaga 20

<210> SEQ ID NO 1348
<211> LENGTH: 20
<212> TYPE: DNA
<213> ORGANISM: Homo sapiens

<400> SEQUENCE: 1348
ctgaaacctt ctccttagcc 20

<210> SEQ ID NO 1349
<211> LENGTH: 20
<212> TYPE: DNA
<213> ORGANISM: Homo sapiens

<400> SEQUENCE: 1349
attatccaac ctgacctgca 20

<210> SEQ ID NO 1350
<211> LENGTH: 19
<212> TYPE: DNA
<213> ORGANISM: Homo sapiens

<400> SEQUENCE: 1350
aggtgcaaag ctgttcatg 19

<210> SEQ ID NO 1351
<211> LENGTH: 20
<212> TYPE: DNA
<213> ORGANISM: Homo sapiens

<400> SEQUENCE: 1351
aatgccaaga ttgtccttca 20

<210> SEQ ID NO 1352
<211> LENGTH: 19
<212> TYPE: DNA
<213> ORGANISM: Homo sapiens

<400> SEQUENCE: 1352
tgcgaaacct cagtgatca 19

<210> SEQ ID NO 1353
<211> LENGTH: 20
<212> TYPE: DNA
<213> ORGANISM: Homo sapiens

<400> SEQUENCE: 1353
cacttccttc agcacacttt 20

<210> SEQ ID NO 1354
<211> LENGTH: 20
<212> TYPE: DNA
<213> ORGANISM: Homo sapiens

<400> SEQUENCE: 1354
ccggctctct atgaaagtga 20

<210> SEQ ID NO 1355
<211> LENGTH: 20
<212> TYPE: DNA
<213> ORGANISM: Homo sapiens

<400> SEQUENCE: 1355
acttgtctgt ctgcctgttt 20

<210> SEQ ID NO 1356
<211> LENGTH: 19
<212> TYPE: DNA
<213> ORGANISM: Homo sapiens

<400> SEQUENCE: 1356
ctgatgcgct gaaaaccaa 19

<210> SEQ ID NO 1357
<211> LENGTH: 20
<212> TYPE: DNA
<213> ORGANISM: Homo sapiens

<400> SEQUENCE: 1357
ttccatgtgt tcttcctccc 20

<210> SEQ ID NO 1358
<211> LENGTH: 20
<212> TYPE: DNA
<213> ORGANISM: Homo sapiens

<400> SEQUENCE: 1358
agcagtaggg ttaacaggag 20

<210> SEQ ID NO 1359
<211> LENGTH: 19
<212> TYPE: DNA
<213> ORGANISM: Homo sapiens

<400> SEQUENCE: 1359
gcagcaatgt ttcggtgta 19

<210> SEQ ID NO 1360
<211> LENGTH: 20
<212> TYPE: DNA
<213> ORGANISM: Homo sapiens

<400> SEQUENCE: 1360
tactaatggc tgggggtaac 20

<210> SEQ ID NO 1361
<211> LENGTH: 20
<212> TYPE: DNA
<213> ORGANISM: Homo sapiens

<400> SEQUENCE: 1361
ctgatgaggc taaaggacca 20

<210> SEQ ID NO 1362
<211> LENGTH: 20
<212> TYPE: DNA
<213> ORGANISM: Homo sapiens

<400> SEQUENCE: 1362
cagagttctc catcccagac 20

<210> SEQ ID NO 1363
<211> LENGTH: 20
<212> TYPE: DNA
<213> ORGANISM: Homo sapiens

<400> SEQUENCE: 1363
ctgagttcct ccttttgcct 20

<210> SEQ ID NO 1364
<211> LENGTH: 20
<212> TYPE: DNA
<213> ORGANISM: Homo sapiens

<400> SEQUENCE: 1364
gcaaaaggtg gtgttagctg 20

<210> SEQ ID NO 1365
<211> LENGTH: 20
<212> TYPE: DNA
<213> ORGANISM: Homo sapiens

<400> SEQUENCE: 1365
atccacatcc catgcctaag 20

<210> SEQ ID NO 1366
<211> LENGTH: 20
<212> TYPE: DNA
<213> ORGANISM: Homo sapiens

<400> SEQUENCE: 1366
tctattcctt tggcacctcc 20

<210> SEQ ID NO 1367
<211> LENGTH: 20
<212> TYPE: DNA
<213> ORGANISM: Homo sapiens

<400> SEQUENCE: 1367
aggaaaggag agctttgtcc 20

<210> SEQ ID NO 1368
<211> LENGTH: 20
<212> TYPE: DNA
<213> ORGANISM: Homo sapiens

<400> SEQUENCE: 1368
cctttcagct tccaagtcct 20

<210> SEQ ID NO 1369
<211> LENGTH: 21
<212> TYPE: DNA
<213> ORGANISM: Homo sapiens

<400> SEQUENCE: 1369
gctctcttcc tcccactaaa a 21

<210> SEQ ID NO 1370
<211> LENGTH: 20
<212> TYPE: DNA
<213> ORGANISM: Homo sapiens

<400> SEQUENCE: 1370
actgcctgtg ttttcttcct 20

<210> SEQ ID NO 1371
<211> LENGTH: 20
<212> TYPE: DNA
<213> ORGANISM: Homo sapiens

<400> SEQUENCE: 1371
aaagcaattt cttccccagc 20

<210> SEQ ID NO 1372
<211> LENGTH: 20
<212> TYPE: DNA
<213> ORGANISM: Homo sapiens

<400> SEQUENCE: 1372
tgtctgttgc cattccttct 20

<210> SEQ ID NO 1373
<211> LENGTH: 20
<212> TYPE: DNA
<213> ORGANISM: Homo sapiens

<400> SEQUENCE: 1373
tgactgtgac ttgtgctttc 20

<210> SEQ ID NO 1374
<211> LENGTH: 20
<212> TYPE: DNA
<213> ORGANISM: Homo sapiens

<400> SEQUENCE: 1374
gaattacatt tccctgggcg 20

<210> SEQ ID NO 1375
<211> LENGTH: 20
<212> TYPE: DNA

<213> ORGANISM: Homo sapiens

<400> SEQUENCE: 1375
tgaaaccgtc ttccttgtct 20

<210> SEQ ID NO 1376
<211> LENGTH: 20
<212> TYPE: DNA
<213> ORGANISM: Homo sapiens

<400> SEQUENCE: 1376
tttaaagcag agcaggacct 20

<210> SEQ ID NO 1377
<211> LENGTH: 20
<212> TYPE: DNA
<213> ORGANISM: Homo sapiens

<400> SEQUENCE: 1377
tttatgacac acagagcagc 20

<210> SEQ ID NO 1378
<211> LENGTH: 20
<212> TYPE: DNA
<213> ORGANISM: Homo sapiens

<400> SEQUENCE: 1378
atgtgtttga ccctttccct 20

<210> SEQ ID NO 1379
<211> LENGTH: 21
<212> TYPE: DNA
<213> ORGANISM: Homo sapiens

<400> SEQUENCE: 1379
atcctgaagt tgttccacat c 21

<210> SEQ ID NO 1380
<211> LENGTH: 21
<212> TYPE: DNA
<213> ORGANISM: Homo sapiens

<400> SEQUENCE: 1380
gaccctgctt tgttactagg a 21

<210> SEQ ID NO 1381
<211> LENGTH: 20
<212> TYPE: DNA
<213> ORGANISM: Homo sapiens

<400> SEQUENCE: 1381
tggacatgga catttcaacg 20

<210> SEQ ID NO 1382
<211> LENGTH: 20
<212> TYPE: DNA
<213> ORGANISM: Homo sapiens

<400> SEQUENCE: 1382
aaaaatgctt ccacttgcct 20

<210> SEQ ID NO 1383
<211> LENGTH: 20

<212> TYPE: DNA
<213> ORGANISM: Homo sapiens

<400> SEQUENCE: 1383
gcacctccaa caacattcaa 20

<210> SEQ ID NO 1384
<211> LENGTH: 18
<212> TYPE: DNA
<213> ORGANISM: Homo sapiens

<400> SEQUENCE: 1384
ttggaaatgg ggctggag 18

<210> SEQ ID NO 1385
<211> LENGTH: 21
<212> TYPE: DNA
<213> ORGANISM: Homo sapiens

<400> SEQUENCE: 1385
actggtctat tgggggaaaa t 21

<210> SEQ ID NO 1386
<211> LENGTH: 20
<212> TYPE: DNA
<213> ORGANISM: Homo sapiens

<400> SEQUENCE: 1386
agtgttagga aagcagagtg 20

<210> SEQ ID NO 1387
<211> LENGTH: 20
<212> TYPE: DNA
<213> ORGANISM: Homo sapiens

<400> SEQUENCE: 1387
tggacagggt ttcacaagat 20

<210> SEQ ID NO 1388
<211> LENGTH: 20
<212> TYPE: DNA
<213> ORGANISM: Homo sapiens

<400> SEQUENCE: 1388
ctcctctcca tctttccagg 20

<210> SEQ ID NO 1389
<211> LENGTH: 21
<212> TYPE: DNA
<213> ORGANISM: Homo sapiens

<400> SEQUENCE: 1389
ataggctgac ttccacatct c 21

<210> SEQ ID NO 1390
<211> LENGTH: 20
<212> TYPE: DNA
<213> ORGANISM: Homo sapiens

<400> SEQUENCE: 1390
tgtgggggtc aattctaacg 20

<210> SEQ ID NO 1391

<211> LENGTH: 20
<212> TYPE: DNA
<213> ORGANISM: Homo sapiens

<400> SEQUENCE: 1391
ccaacgggta gtggtagatt 20

<210> SEQ ID NO 1392
<211> LENGTH: 20
<212> TYPE: DNA
<213> ORGANISM: Homo sapiens

<400> SEQUENCE: 1392
cttaccccac ttcttcctga 20

<210> SEQ ID NO 1393
<211> LENGTH: 19
<212> TYPE: DNA
<213> ORGANISM: Homo sapiens

<400> SEQUENCE: 1393
cctgtcacaa ctgcctttg 19

<210> SEQ ID NO 1394
<211> LENGTH: 20
<212> TYPE: DNA
<213> ORGANISM: Homo sapiens

<400> SEQUENCE: 1394
tttgccattt tgtgatgcca 20

<210> SEQ ID NO 1395
<211> LENGTH: 20
<212> TYPE: DNA
<213> ORGANISM: Homo sapiens

<400> SEQUENCE: 1395
ggagtttcag gttggcagaa 20

<210> SEQ ID NO 1396
<211> LENGTH: 20
<212> TYPE: DNA
<213> ORGANISM: Homo sapiens

<400> SEQUENCE: 1396
acagcttgct tcaaactaca 20

<210> SEQ ID NO 1397
<211> LENGTH: 20
<212> TYPE: DNA
<213> ORGANISM: Homo sapiens

<400> SEQUENCE: 1397
ttgaaggggc aaaatacagc 20

<210> SEQ ID NO 1398
<211> LENGTH: 20
<212> TYPE: DNA
<213> ORGANISM: Homo sapiens

<400> SEQUENCE: 1398
gccccaaatt gtaacaaagc 20

<210> SEQ ID NO 1399
<211> LENGTH: 20
<212> TYPE: DNA
<213> ORGANISM: Homo sapiens

<400> SEQUENCE: 1399
tgacgaagac tccaacacaa 20

<210> SEQ ID NO 1400
<211> LENGTH: 20
<212> TYPE: DNA
<213> ORGANISM: Homo sapiens

<400> SEQUENCE: 1400
aagtcaggga aatgaagctg 20

<210> SEQ ID NO 1401
<211> LENGTH: 20
<212> TYPE: DNA
<213> ORGANISM: Homo sapiens

<400> SEQUENCE: 1401
gtaacacagt gctccttctc 20

<210> SEQ ID NO 1402
<211> LENGTH: 20
<212> TYPE: DNA
<213> ORGANISM: Homo sapiens

<400> SEQUENCE: 1402
ggccccaatt agctgatttc 20

<210> SEQ ID NO 1403
<211> LENGTH: 20
<212> TYPE: DNA
<213> ORGANISM: Homo sapiens

<400> SEQUENCE: 1403
ctgagcaggg aaaaatccag 20

<210> SEQ ID NO 1404
<211> LENGTH: 20
<212> TYPE: DNA
<213> ORGANISM: Homo sapiens

<400> SEQUENCE: 1404
acaaaggatt caggtgcagt 20

<210> SEQ ID NO 1405
<211> LENGTH: 20
<212> TYPE: DNA
<213> ORGANISM: Homo sapiens

<400> SEQUENCE: 1405
acaggttttg ctcttcagga 20

<210> SEQ ID NO 1406
<211> LENGTH: 21
<212> TYPE: DNA
<213> ORGANISM: Homo sapiens

<400> SEQUENCE: 1406
ggcaagtttg tctggttcat t 21

<210> SEQ ID NO 1407
<211> LENGTH: 20
<212> TYPE: DNA
<213> ORGANISM: Homo sapiens

<400> SEQUENCE: 1407
ccatctgcat ctgtctcctt 20

<210> SEQ ID NO 1408
<211> LENGTH: 19
<212> TYPE: DNA
<213> ORGANISM: Homo sapiens

<400> SEQUENCE: 1408
gctcctctcc ttctccctt 19

<210> SEQ ID NO 1409
<211> LENGTH: 20
<212> TYPE: DNA
<213> ORGANISM: Homo sapiens

<400> SEQUENCE: 1409
tgtataaggg caatcgtggt 20

<210> SEQ ID NO 1410
<211> LENGTH: 20
<212> TYPE: DNA
<213> ORGANISM: Homo sapiens

<400> SEQUENCE: 1410
aaggaaccag gtcagacaag 20

<210> SEQ ID NO 1411
<211> LENGTH: 21
<212> TYPE: DNA
<213> ORGANISM: Homo sapiens

<400> SEQUENCE: 1411
gttagaaggc aaacatcatg c 21

<210> SEQ ID NO 1412
<211> LENGTH: 20
<212> TYPE: DNA
<213> ORGANISM: Homo sapiens

<400> SEQUENCE: 1412
tgcagtcata ggaaaaggct 20

<210> SEQ ID NO 1413
<211> LENGTH: 19
<212> TYPE: DNA
<213> ORGANISM: Homo sapiens

<400> SEQUENCE: 1413
gcagtcagaa tggtttggc 19

<210> SEQ ID NO 1414
<211> LENGTH: 21
<212> TYPE: DNA
<213> ORGANISM: Homo sapiens

<400> SEQUENCE: 1414
agacattggt ttggttggtt c 21

<210> SEQ ID NO 1415
<211> LENGTH: 20
<212> TYPE: DNA
<213> ORGANISM: Homo sapiens

<400> SEQUENCE: 1415
acacaaatga aagcccgtac 20

<210> SEQ ID NO 1416
<211> LENGTH: 20
<212> TYPE: DNA
<213> ORGANISM: Homo sapiens

<400> SEQUENCE: 1416
ggtctgctgt ttctctttgc 20

<210> SEQ ID NO 1417
<211> LENGTH: 20
<212> TYPE: DNA
<213> ORGANISM: Homo sapiens

<400> SEQUENCE: 1417
agagccttac caagctgaag 20

<210> SEQ ID NO 1418
<211> LENGTH: 20
<212> TYPE: DNA
<213> ORGANISM: Homo sapiens

<400> SEQUENCE: 1418
gggatggtta cttagtgggg 20

<210> SEQ ID NO 1419
<211> LENGTH: 20
<212> TYPE: DNA
<213> ORGANISM: Homo sapiens

<400> SEQUENCE: 1419
ttacactcgc cttccaaaca 20

<210> SEQ ID NO 1420
<211> LENGTH: 20
<212> TYPE: DNA
<213> ORGANISM: Homo sapiens

<400> SEQUENCE: 1420
gagagaggag gagttggaag 20

<210> SEQ ID NO 1421
<211> LENGTH: 20
<212> TYPE: DNA
<213> ORGANISM: Homo sapiens

<400> SEQUENCE: 1421
atccacgaca tccaaaatca 20

<210> SEQ ID NO 1422
<211> LENGTH: 20
<212> TYPE: DNA
<213> ORGANISM: Homo sapiens

<400> SEQUENCE: 1422
ttgtgcaaga agaaacctgc 20

<210> SEQ ID NO 1423
<211> LENGTH: 20
<212> TYPE: DNA
<213> ORGANISM: Homo sapiens

<400> SEQUENCE: 1423
ggccttgcat aaaccacatt 20

<210> SEQ ID NO 1424
<211> LENGTH: 20
<212> TYPE: DNA
<213> ORGANISM: Homo sapiens

<400> SEQUENCE: 1424
tttgtaattg gtcctcgcct 20

<210> SEQ ID NO 1425
<211> LENGTH: 20
<212> TYPE: DNA
<213> ORGANISM: Homo sapiens

<400> SEQUENCE: 1425
caagtatttc atggcgctcc 20

<210> SEQ ID NO 1426
<211> LENGTH: 21
<212> TYPE: DNA
<213> ORGANISM: Homo sapiens

<400> SEQUENCE: 1426
gtcaacagta tcagcttcca a 21

<210> SEQ ID NO 1427
<211> LENGTH: 20
<212> TYPE: DNA
<213> ORGANISM: Homo sapiens

<400> SEQUENCE: 1427
tgggcttctt tttcattccg 20

<210> SEQ ID NO 1428
<211> LENGTH: 20
<212> TYPE: DNA
<213> ORGANISM: Homo sapiens

<400> SEQUENCE: 1428
tcaacaagct ctctgttcac 20

<210> SEQ ID NO 1429
<211> LENGTH: 20
<212> TYPE: DNA
<213> ORGANISM: Homo sapiens

<400> SEQUENCE: 1429
gtgcaaacag tgacctcaat 20

<210> SEQ ID NO 1430
<211> LENGTH: 20
<212> TYPE: DNA
<213> ORGANISM: Homo sapiens

<400> SEQUENCE: 1430
gctgggctgc tttaatttct 20

<210> SEQ ID NO 1431
<211> LENGTH: 20
<212> TYPE: DNA
<213> ORGANISM: Homo sapiens

<400> SEQUENCE: 1431
ggaattgtgg ggtcaaatgg 20

<210> SEQ ID NO 1432
<211> LENGTH: 21
<212> TYPE: DNA
<213> ORGANISM: Homo sapiens

<400> SEQUENCE: 1432
ctagtgcttc tacctccaga c 21

<210> SEQ ID NO 1433
<211> LENGTH: 20
<212> TYPE: DNA
<213> ORGANISM: Homo sapiens

<400> SEQUENCE: 1433
aaccacacac taacagggaa 20

<210> SEQ ID NO 1434
<211> LENGTH: 20
<212> TYPE: DNA
<213> ORGANISM: Homo sapiens

<400> SEQUENCE: 1434
tctagtttgc cctctttccc 20

<210> SEQ ID NO 1435
<211> LENGTH: 20
<212> TYPE: DNA
<213> ORGANISM: Homo sapiens

<400> SEQUENCE: 1435
cgaattgctt ccttgctctg 20

<210> SEQ ID NO 1436
<211> LENGTH: 22
<212> TYPE: DNA
<213> ORGANISM: Homo sapiens

<400> SEQUENCE: 1436
tctatcacag caggaaatca ct 22

<210> SEQ ID NO 1437
<211> LENGTH: 20
<212> TYPE: DNA
<213> ORGANISM: Homo sapiens

<400> SEQUENCE: 1437
tcttcgtgtt tctctagccc 20

<210> SEQ ID NO 1438
<211> LENGTH: 20
<212> TYPE: DNA
<213> ORGANISM: Homo sapiens

<400> SEQUENCE: 1438
ttgaagagct aaagggggag 20

<210> SEQ ID NO 1439
<211> LENGTH: 20
<212> TYPE: DNA
<213> ORGANISM: Homo sapiens

<400> SEQUENCE: 1439
tgtcaccgta ctacctaagc 20

<210> SEQ ID NO 1440
<211> LENGTH: 19
<212> TYPE: DNA
<213> ORGANISM: Homo sapiens

<400> SEQUENCE: 1440
agtacgctcc tttgcagag 19

<210> SEQ ID NO 1441
<211> LENGTH: 20
<212> TYPE: DNA
<213> ORGANISM: Homo sapiens

<400> SEQUENCE: 1441
ttacggggac acaaaatggt 20

<210> SEQ ID NO 1442
<211> LENGTH: 19
<212> TYPE: DNA
<213> ORGANISM: Homo sapiens

<400> SEQUENCE: 1442
ctgtgctttg cccttgaag 19

<210> SEQ ID NO 1443
<211> LENGTH: 20
<212> TYPE: DNA
<213> ORGANISM: Homo sapiens

<400> SEQUENCE: 1443
aagtcaaccc atatgccact 20

<210> SEQ ID NO 1444
<211> LENGTH: 20
<212> TYPE: DNA
<213> ORGANISM: Homo sapiens

<400> SEQUENCE: 1444
acattcaggc tgtcacacat 20

<210> SEQ ID NO 1445
<211> LENGTH: 23
<212> TYPE: DNA
<213> ORGANISM: Homo sapiens

<400> SEQUENCE: 1445
tcatgtcact agttttataa ggc 23

<210> SEQ ID NO 1446
<211> LENGTH: 20
<212> TYPE: DNA
<213> ORGANISM: Homo sapiens

<400> SEQUENCE: 1446
agtagtgagg ctccaaagtg 20

<210> SEQ ID NO 1447
<211> LENGTH: 20
<212> TYPE: DNA
<213> ORGANISM: Homo sapiens

<400> SEQUENCE: 1447
tgggaggagt ttgctgttta 20

<210> SEQ ID NO 1448
<211> LENGTH: 20
<212> TYPE: DNA
<213> ORGANISM: Homo sapiens

<400> SEQUENCE: 1448
ttctaagcct gtgactgaca 20

<210> SEQ ID NO 1449
<211> LENGTH: 20
<212> TYPE: DNA
<213> ORGANISM: Homo sapiens

<400> SEQUENCE: 1449
tgaacctgac tttccttggg 20

<210> SEQ ID NO 1450
<211> LENGTH: 20
<212> TYPE: DNA
<213> ORGANISM: Homo sapiens

<400> SEQUENCE: 1450
gccattctat catctcggga 20

<210> SEQ ID NO 1451
<211> LENGTH: 19
<212> TYPE: DNA
<213> ORGANISM: Homo sapiens

<400> SEQUENCE: 1451
agtctctccc tgaaaccca 19

<210> SEQ ID NO 1452
<211> LENGTH: 20
<212> TYPE: DNA
<213> ORGANISM: Homo sapiens

<400> SEQUENCE: 1452
aagagttggc ttggagttga 20

<210> SEQ ID NO 1453
<211> LENGTH: 21
<212> TYPE: DNA
<213> ORGANISM: Homo sapiens

<400> SEQUENCE: 1453
cccacaatta tgaaaggagg t 21

<210> SEQ ID NO 1454
<211> LENGTH: 20
<212> TYPE: DNA

<213> ORGANISM: Homo sapiens

<400> SEQUENCE: 1454
ttgaccagga caaatgagga 20

<210> SEQ ID NO 1455
<211> LENGTH: 20
<212> TYPE: DNA
<213> ORGANISM: Homo sapiens

<400> SEQUENCE: 1455
cactttgttg gtctgggtca 20

<210> SEQ ID NO 1456
<211> LENGTH: 20
<212> TYPE: DNA
<213> ORGANISM: Homo sapiens

<400> SEQUENCE: 1456
gggactctag gtggggttaa 20

<210> SEQ ID NO 1457
<211> LENGTH: 20
<212> TYPE: DNA
<213> ORGANISM: Homo sapiens

<400> SEQUENCE: 1457
gtttatgcct tgggattgcc 20

<210> SEQ ID NO 1458
<211> LENGTH: 20
<212> TYPE: DNA
<213> ORGANISM: Homo sapiens

<400> SEQUENCE: 1458
gtgtggtaag gatgctagga 20

<210> SEQ ID NO 1459
<211> LENGTH: 20
<212> TYPE: DNA
<213> ORGANISM: Homo sapiens

<400> SEQUENCE: 1459
gaaagtgact cctccctgac 20

<210> SEQ ID NO 1460
<211> LENGTH: 20
<212> TYPE: DNA
<213> ORGANISM: Homo sapiens

<400> SEQUENCE: 1460
ccaggttctg ttctctgtca 20

<210> SEQ ID NO 1461
<211> LENGTH: 20
<212> TYPE: DNA
<213> ORGANISM: Homo sapiens

<400> SEQUENCE: 1461
gtgagacatg gttgctgttc 20

<210> SEQ ID NO 1462
<211> LENGTH: 20

<212> TYPE: DNA
<213> ORGANISM: Homo sapiens

<400> SEQUENCE: 1462
ctttctcctg ctccacctat 20

<210> SEQ ID NO 1463
<211> LENGTH: 20
<212> TYPE: DNA
<213> ORGANISM: Homo sapiens

<400> SEQUENCE: 1463
ctatgtgtgt tccaacccga 20

<210> SEQ ID NO 1464
<211> LENGTH: 20
<212> TYPE: DNA
<213> ORGANISM: Homo sapiens

<400> SEQUENCE: 1464
gggaccttct aaccatgtgt 20

<210> SEQ ID NO 1465
<211> LENGTH: 20
<212> TYPE: DNA
<213> ORGANISM: Homo sapiens

<400> SEQUENCE: 1465
cgggattttg aaaaggcaga 20

<210> SEQ ID NO 1466
<211> LENGTH: 20
<212> TYPE: DNA
<213> ORGANISM: Homo sapiens

<400> SEQUENCE: 1466
gtgttgtctc tcagctcctc 20

<210> SEQ ID NO 1467
<211> LENGTH: 20
<212> TYPE: DNA
<213> ORGANISM: Homo sapiens

<400> SEQUENCE: 1467
gttctctggt taaggccctt 20

<210> SEQ ID NO 1468
<211> LENGTH: 20
<212> TYPE: DNA
<213> ORGANISM: Homo sapiens

<400> SEQUENCE: 1468
cctcttcacc tataagcccc 20

<210> SEQ ID NO 1469
<211> LENGTH: 20
<212> TYPE: DNA
<213> ORGANISM: Homo sapiens

<400> SEQUENCE: 1469
taggggacag taagccagat 20

<210> SEQ ID NO 1470

<211> LENGTH: 20
<212> TYPE: DNA
<213> ORGANISM: Homo sapiens

<400> SEQUENCE: 1470
acgatggacc tctgttgaac 20

<210> SEQ ID NO 1471
<211> LENGTH: 21
<212> TYPE: DNA
<213> ORGANISM: Homo sapiens

<400> SEQUENCE: 1471
attcccatcc atccatcact c 21

<210> SEQ ID NO 1472
<211> LENGTH: 20
<212> TYPE: DNA
<213> ORGANISM: Homo sapiens

<400> SEQUENCE: 1472
tcgtttttgg atggtggttg 20

<210> SEQ ID NO 1473
<211> LENGTH: 21
<212> TYPE: DNA
<213> ORGANISM: Homo sapiens

<400> SEQUENCE: 1473
gaagttcctc cagtagactc a 21

<210> SEQ ID NO 1474
<211> LENGTH: 20
<212> TYPE: DNA
<213> ORGANISM: Homo sapiens

<400> SEQUENCE: 1474
ttgtttgagt ctgggaggaa 20

<210> SEQ ID NO 1475
<211> LENGTH: 20
<212> TYPE: DNA
<213> ORGANISM: Homo sapiens

<400> SEQUENCE: 1475
aatactgtga gactgccacc 20

<210> SEQ ID NO 1476
<211> LENGTH: 20
<212> TYPE: DNA
<213> ORGANISM: Homo sapiens

<400> SEQUENCE: 1476
cagtcacgga aagtaccctc 20

<210> SEQ ID NO 1477
<211> LENGTH: 20
<212> TYPE: DNA
<213> ORGANISM: Homo sapiens

<400> SEQUENCE: 1477
accatgtttc cctctgtcac 20

<210> SEQ ID NO 1478
<211> LENGTH: 20
<212> TYPE: DNA
<213> ORGANISM: Homo sapiens

<400> SEQUENCE: 1478
ttaccaaggg acaggatgga 20

<210> SEQ ID NO 1479
<211> LENGTH: 20
<212> TYPE: DNA
<213> ORGANISM: Homo sapiens

<400> SEQUENCE: 1479
ccctagaggt caaggtatgg 20

<210> SEQ ID NO 1480
<211> LENGTH: 20
<212> TYPE: DNA
<213> ORGANISM: Homo sapiens

<400> SEQUENCE: 1480
ataggccctg tgtgttagtt 20

<210> SEQ ID NO 1481
<211> LENGTH: 20
<212> TYPE: DNA
<213> ORGANISM: Homo sapiens

<400> SEQUENCE: 1481
agaaagtccc ctccatttct 20

<210> SEQ ID NO 1482
<211> LENGTH: 20
<212> TYPE: DNA
<213> ORGANISM: Homo sapiens

<400> SEQUENCE: 1482
gccaatgcca aagtcagtta 20

<210> SEQ ID NO 1483
<211> LENGTH: 20
<212> TYPE: DNA
<213> ORGANISM: Homo sapiens

<400> SEQUENCE: 1483
gaggacgagt tgaacaaagc 20

<210> SEQ ID NO 1484
<211> LENGTH: 21
<212> TYPE: DNA
<213> ORGANISM: Homo sapiens

<400> SEQUENCE: 1484
atactggtct caaggtagca c 21

<210> SEQ ID NO 1485
<211> LENGTH: 22
<212> TYPE: DNA
<213> ORGANISM: Homo sapiens

<400> SEQUENCE: 1485
accaagtgaa gctgagttaa tg 22

<210> SEQ ID NO 1486
<211> LENGTH: 20
<212> TYPE: DNA
<213> ORGANISM: Homo sapiens

<400> SEQUENCE: 1486
cccagataca ctcctgcttc 20

<210> SEQ ID NO 1487
<211> LENGTH: 20
<212> TYPE: DNA
<213> ORGANISM: Homo sapiens

<400> SEQUENCE: 1487
caaacatgag agggggagaa 20

<210> SEQ ID NO 1488
<211> LENGTH: 20
<212> TYPE: DNA
<213> ORGANISM: Homo sapiens

<400> SEQUENCE: 1488
aaacacagca atgaggaagg 20

<210> SEQ ID NO 1489
<211> LENGTH: 20
<212> TYPE: DNA
<213> ORGANISM: Homo sapiens

<400> SEQUENCE: 1489
gatactcccc tgtgttgctt 20

<210> SEQ ID NO 1490
<211> LENGTH: 20
<212> TYPE: DNA
<213> ORGANISM: Homo sapiens

<400> SEQUENCE: 1490
gctcttacta ggatggcagg 20

<210> SEQ ID NO 1491
<211> LENGTH: 20
<212> TYPE: DNA
<213> ORGANISM: Homo sapiens

<400> SEQUENCE: 1491
gtttccagca gcaatccttt 20

<210> SEQ ID NO 1492
<211> LENGTH: 19
<212> TYPE: DNA
<213> ORGANISM: Homo sapiens

<400> SEQUENCE: 1492
ctgtgcagaa gggttagct 19

<210> SEQ ID NO 1493
<211> LENGTH: 20
<212> TYPE: DNA
<213> ORGANISM: Homo sapiens

<400> SEQUENCE: 1493
aaacccctgc tacccaaaat 20

<210> SEQ ID NO 1494
<211> LENGTH: 20
<212> TYPE: DNA
<213> ORGANISM: Homo sapiens

<400> SEQUENCE: 1494
aatgcccaga tgctgttttc 20

<210> SEQ ID NO 1495
<211> LENGTH: 21
<212> TYPE: DNA
<213> ORGANISM: Homo sapiens

<400> SEQUENCE: 1495
gagtggttgt tctctccaga t 21

<210> SEQ ID NO 1496
<211> LENGTH: 20
<212> TYPE: DNA
<213> ORGANISM: Homo sapiens

<400> SEQUENCE: 1496
cagtctagaa gctcacccag 20

<210> SEQ ID NO 1497
<211> LENGTH: 20
<212> TYPE: DNA
<213> ORGANISM: Homo sapiens

<400> SEQUENCE: 1497
tctcctctac ccctacactg 20

<210> SEQ ID NO 1498
<211> LENGTH: 20
<212> TYPE: DNA
<213> ORGANISM: Homo sapiens

<400> SEQUENCE: 1498
ggtgtaaatg tggcctctcc 20

<210> SEQ ID NO 1499
<211> LENGTH: 20
<212> TYPE: DNA
<213> ORGANISM: Homo sapiens

<400> SEQUENCE: 1499
acaaagctac aaactctggc 20

<210> SEQ ID NO 1500
<211> LENGTH: 20
<212> TYPE: DNA
<213> ORGANISM: Homo sapiens

<400> SEQUENCE: 1500
tttcactggg agactgatgc 20

<210> SEQ ID NO 1501
<211> LENGTH: 20
<212> TYPE: DNA
<213> ORGANISM: Homo sapiens

<400> SEQUENCE: 1501
ctgttctgtt cctgaggcta 20

<210> SEQ ID NO 1502
<211> LENGTH: 21
<212> TYPE: DNA
<213> ORGANISM: Homo sapiens

<400> SEQUENCE: 1502
tgtgtatcca ttgcctcatc t 21

<210> SEQ ID NO 1503
<211> LENGTH: 20
<212> TYPE: DNA
<213> ORGANISM: Homo sapiens

<400> SEQUENCE: 1503
gaagagggtg tgtgtaggac 20

<210> SEQ ID NO 1504
<211> LENGTH: 20
<212> TYPE: DNA
<213> ORGANISM: Homo sapiens

<400> SEQUENCE: 1504
tggttgctct tcctagttcc 20

<210> SEQ ID NO 1505
<211> LENGTH: 20
<212> TYPE: DNA
<213> ORGANISM: Homo sapiens

<400> SEQUENCE: 1505
caatgtggag gaagctcttg 20

<210> SEQ ID NO 1506
<211> LENGTH: 20
<212> TYPE: DNA
<213> ORGANISM: Homo sapiens

<400> SEQUENCE: 1506
ttgcacaccc aatatgctac 20

<210> SEQ ID NO 1507
<211> LENGTH: 20
<212> TYPE: DNA
<213> ORGANISM: Homo sapiens

<400> SEQUENCE: 1507
tccaaggttt ctctagcgac 20

<210> SEQ ID NO 1508
<211> LENGTH: 20
<212> TYPE: DNA
<213> ORGANISM: Homo sapiens

<400> SEQUENCE: 1508
tcgctattct ccttgccata 20

<210> SEQ ID NO 1509
<211> LENGTH: 20
<212> TYPE: DNA
<213> ORGANISM: Homo sapiens

<400> SEQUENCE: 1509
aacagcctct ttccttagca 20

<210> SEQ ID NO 1510
<211> LENGTH: 20
<212> TYPE: DNA
<213> ORGANISM: Homo sapiens

<400> SEQUENCE: 1510
tttttggctc agtgggatgt 20

<210> SEQ ID NO 1511
<211> LENGTH: 21
<212> TYPE: DNA
<213> ORGANISM: Homo sapiens

<400> SEQUENCE: 1511
ctgttcattc ttcttcaggg c 21

<210> SEQ ID NO 1512
<211> LENGTH: 20
<212> TYPE: DNA
<213> ORGANISM: Homo sapiens

<400> SEQUENCE: 1512
ttcccgagcc cataaactac 20

<210> SEQ ID NO 1513
<211> LENGTH: 20
<212> TYPE: DNA
<213> ORGANISM: Homo sapiens

<400> SEQUENCE: 1513
tgctcagatt tcagcttcct 20

<210> SEQ ID NO 1514
<211> LENGTH: 20
<212> TYPE: DNA
<213> ORGANISM: Homo sapiens

<400> SEQUENCE: 1514
gtcagcgatg tggatgtcta 20

<210> SEQ ID NO 1515
<211> LENGTH: 20
<212> TYPE: DNA
<213> ORGANISM: Homo sapiens

<400> SEQUENCE: 1515
aactgactcc atgacctgtg 20

<210> SEQ ID NO 1516
<211> LENGTH: 20
<212> TYPE: DNA
<213> ORGANISM: Homo sapiens

<400> SEQUENCE: 1516
gaagctgcta cttggtgaac 20

<210> SEQ ID NO 1517
<211> LENGTH: 20
<212> TYPE: DNA
<213> ORGANISM: Homo sapiens

<400> SEQUENCE: 1517
ttttcctcct gttctgttgc 20

<210> SEQ ID NO 1518
<211> LENGTH: 20
<212> TYPE: DNA
<213> ORGANISM: Homo sapiens

<400> SEQUENCE: 1518
ttctcaaatg caaccactcc 20

<210> SEQ ID NO 1519
<211> LENGTH: 20
<212> TYPE: DNA
<213> ORGANISM: Homo sapiens

<400> SEQUENCE: 1519
ctggcccttc aatttcatgc 20

<210> SEQ ID NO 1520
<211> LENGTH: 21
<212> TYPE: DNA
<213> ORGANISM: Homo sapiens

<400> SEQUENCE: 1520
ccagcagtac cgatatcaga g 21

<210> SEQ ID NO 1521
<211> LENGTH: 20
<212> TYPE: DNA
<213> ORGANISM: Homo sapiens

<400> SEQUENCE: 1521
cagaaggcag gagatggatt 20

<210> SEQ ID NO 1522
<211> LENGTH: 20
<212> TYPE: DNA
<213> ORGANISM: Homo sapiens

<400> SEQUENCE: 1522
aagcaaccat tttcctgagc 20

<210> SEQ ID NO 1523
<211> LENGTH: 20
<212> TYPE: DNA
<213> ORGANISM: Homo sapiens

<400> SEQUENCE: 1523
tcacccttca tctacccact 20

<210> SEQ ID NO 1524
<211> LENGTH: 20
<212> TYPE: DNA
<213> ORGANISM: Homo sapiens

<400> SEQUENCE: 1524
aagctggtga ccttctacag 20

<210> SEQ ID NO 1525
<211> LENGTH: 20
<212> TYPE: DNA
<213> ORGANISM: Homo sapiens

<400> SEQUENCE: 1525
aaaattctgg ttggggagga 20

<210> SEQ ID NO 1526
<211> LENGTH: 20
<212> TYPE: DNA
<213> ORGANISM: Homo sapiens

<400> SEQUENCE: 1526
ccatacctca tctgctctgt 20

<210> SEQ ID NO 1527
<211> LENGTH: 20
<212> TYPE: DNA
<213> ORGANISM: Homo sapiens

<400> SEQUENCE: 1527
ggctgtccct gaactacttt 20

<210> SEQ ID NO 1528
<211> LENGTH: 20
<212> TYPE: DNA
<213> ORGANISM: Homo sapiens

<400> SEQUENCE: 1528
cttggcttaa actctgctcc 20

<210> SEQ ID NO 1529
<211> LENGTH: 20
<212> TYPE: DNA
<213> ORGANISM: Homo sapiens

<400> SEQUENCE: 1529
gacttgaaca caccctcaga 20

<210> SEQ ID NO 1530
<211> LENGTH: 20
<212> TYPE: DNA
<213> ORGANISM: Homo sapiens

<400> SEQUENCE: 1530
aggagaagag accattgcag 20

<210> SEQ ID NO 1531
<211> LENGTH: 20
<212> TYPE: DNA
<213> ORGANISM: Homo sapiens

<400> SEQUENCE: 1531
ttagctaagt ctgtgcggag 20

<210> SEQ ID NO 1532
<211> LENGTH: 19
<212> TYPE: DNA
<213> ORGANISM: Homo sapiens

<400> SEQUENCE: 1532
gaagcaacac tgtacacgc 19

<210> SEQ ID NO 1533
<211> LENGTH: 20
<212> TYPE: DNA

<213> ORGANISM: Homo sapiens

<400> SEQUENCE: 1533
tctgataaag gctggctcat 20

<210> SEQ ID NO 1534
<211> LENGTH: 20
<212> TYPE: DNA
<213> ORGANISM: Homo sapiens

<400> SEQUENCE: 1534
taaaacagtg ccgctacttc 20

<210> SEQ ID NO 1535
<211> LENGTH: 20
<212> TYPE: DNA
<213> ORGANISM: Homo sapiens

<400> SEQUENCE: 1535
agtgctatga gtcttggtcc 20

<210> SEQ ID NO 1536
<211> LENGTH: 20
<212> TYPE: DNA
<213> ORGANISM: Homo sapiens

<400> SEQUENCE: 1536
ggaaaacatg cggtggtcta 20

<210> SEQ ID NO 1537
<211> LENGTH: 20
<212> TYPE: DNA
<213> ORGANISM: Homo sapiens

<400> SEQUENCE: 1537
gcagagaaat gggttaaggg 20

<210> SEQ ID NO 1538
<211> LENGTH: 20
<212> TYPE: DNA
<213> ORGANISM: Homo sapiens

<400> SEQUENCE: 1538
ggtagaggtg ggttatctgt 20

<210> SEQ ID NO 1539
<211> LENGTH: 19
<212> TYPE: DNA
<213> ORGANISM: Homo sapiens

<400> SEQUENCE: 1539
ctgtaaatct ccgggggtg 19

<210> SEQ ID NO 1540
<211> LENGTH: 20
<212> TYPE: DNA
<213> ORGANISM: Homo sapiens

<400> SEQUENCE: 1540
ggcgagaatg gagagagaaa 20

<210> SEQ ID NO 1541
<211> LENGTH: 20

<212> TYPE: DNA
<213> ORGANISM: Homo sapiens

<400> SEQUENCE: 1541
tcccaagcca ggattctttt 20

<210> SEQ ID NO 1542
<211> LENGTH: 20
<212> TYPE: DNA
<213> ORGANISM: Homo sapiens

<400> SEQUENCE: 1542
gaacaagtac aaccgtgcag 20

<210> SEQ ID NO 1543
<211> LENGTH: 20
<212> TYPE: DNA
<213> ORGANISM: Homo sapiens

<400> SEQUENCE: 1543
acaaatgccc catatcaacc 20

<210> SEQ ID NO 1544
<211> LENGTH: 20
<212> TYPE: DNA
<213> ORGANISM: Homo sapiens

<400> SEQUENCE: 1544
ggaaagaggc ctggagtaat 20

<210> SEQ ID NO 1545
<211> LENGTH: 20
<212> TYPE: DNA
<213> ORGANISM: Homo sapiens

<400> SEQUENCE: 1545
tttccactgg atgtcgtcat 20

<210> SEQ ID NO 1546
<211> LENGTH: 20
<212> TYPE: DNA
<213> ORGANISM: Homo sapiens

<400> SEQUENCE: 1546
aggacaaagt ttcagcctct 20

<210> SEQ ID NO 1547
<211> LENGTH: 21
<212> TYPE: DNA
<213> ORGANISM: Homo sapiens

<400> SEQUENCE: 1547
actcaggaca cgacttcata c 21

<210> SEQ ID NO 1548
<211> LENGTH: 20
<212> TYPE: DNA
<213> ORGANISM: Homo sapiens

<400> SEQUENCE: 1548
acatctttgg ctcactggtt 20

<210> SEQ ID NO 1549

<211> LENGTH: 20
<212> TYPE: DNA
<213> ORGANISM: Homo sapiens

<400> SEQUENCE: 1549
tcacagtggg cttcattcag 20

<210> SEQ ID NO 1550
<211> LENGTH: 22
<212> TYPE: DNA
<213> ORGANISM: Homo sapiens

<400> SEQUENCE: 1550
agctggaatc tatgtaggat gg 22

<210> SEQ ID NO 1551
<211> LENGTH: 20
<212> TYPE: DNA
<213> ORGANISM: Homo sapiens

<400> SEQUENCE: 1551
ctgcggaagg atctagtctt 20

<210> SEQ ID NO 1552
<211> LENGTH: 22
<212> TYPE: DNA
<213> ORGANISM: Homo sapiens

<400> SEQUENCE: 1552
tgagaagtat tcagcatttc cc 22

<210> SEQ ID NO 1553
<211> LENGTH: 19
<212> TYPE: DNA
<213> ORGANISM: Homo sapiens

<400> SEQUENCE: 1553
cactcacgga cttttaggc 19

<210> SEQ ID NO 1554
<211> LENGTH: 18
<212> TYPE: DNA
<213> ORGANISM: Homo sapiens

<400> SEQUENCE: 1554
aaaaaaaaaa aaaaaaaa 18

<210> SEQ ID NO 1555
<211> LENGTH: 20
<212> TYPE: DNA
<213> ORGANISM: Homo sapiens

<400> SEQUENCE: 1555
tcacacgcca ggttattaca 20

<210> SEQ ID NO 1556
<211> LENGTH: 20
<212> TYPE: DNA
<213> ORGANISM: Homo sapiens

<400> SEQUENCE: 1556
aagtgggttt gcagtttgga 20

<210> SEQ ID NO 1557
<211> LENGTH: 20
<212> TYPE: DNA
<213> ORGANISM: Homo sapiens

<400> SEQUENCE: 1557
atgtacgtgt gtgtccatgt 20

<210> SEQ ID NO 1558
<211> LENGTH: 20
<212> TYPE: DNA
<213> ORGANISM: Homo sapiens

<400> SEQUENCE: 1558
aggcgggttg gtcaataata 20

<210> SEQ ID NO 1559
<211> LENGTH: 20
<212> TYPE: DNA
<213> ORGANISM: Homo sapiens

<400> SEQUENCE: 1559
ccacaaatcc catcaacaca 20

<210> SEQ ID NO 1560
<211> LENGTH: 20
<212> TYPE: DNA
<213> ORGANISM: Homo sapiens

<400> SEQUENCE: 1560
tttcacagta acatcggcac 20

<210> SEQ ID NO 1561
<211> LENGTH: 20
<212> TYPE: DNA
<213> ORGANISM: Homo sapiens

<400> SEQUENCE: 1561
ctgacagcct gcatttgatt 20

<210> SEQ ID NO 1562
<211> LENGTH: 21
<212> TYPE: DNA
<213> ORGANISM: Homo sapiens

<400> SEQUENCE: 1562
tttcctggag taaagcgatc t 21

<210> SEQ ID NO 1563
<211> LENGTH: 20
<212> TYPE: DNA
<213> ORGANISM: Homo sapiens

<400> SEQUENCE: 1563
cccacaatca cccatctcta 20

<210> SEQ ID NO 1564
<211> LENGTH: 20
<212> TYPE: DNA
<213> ORGANISM: Homo sapiens

<400> SEQUENCE: 1564
tatctcactc cacagcttcc 20

<210> SEQ ID NO 1565
<211> LENGTH: 20
<212> TYPE: DNA
<213> ORGANISM: Homo sapiens

<400> SEQUENCE: 1565
acaggtagtt tggtggtgtc 20

<210> SEQ ID NO 1566
<211> LENGTH: 20
<212> TYPE: DNA
<213> ORGANISM: Homo sapiens

<400> SEQUENCE: 1566
gctgttgaat gccagaactt 20

<210> SEQ ID NO 1567
<211> LENGTH: 20
<212> TYPE: DNA
<213> ORGANISM: Homo sapiens

<400> SEQUENCE: 1567
atagggtcgg ttttggtctg 20

<210> SEQ ID NO 1568
<211> LENGTH: 20
<212> TYPE: DNA
<213> ORGANISM: Homo sapiens

<400> SEQUENCE: 1568
catcatccct gtcattccca 20

<210> SEQ ID NO 1569
<211> LENGTH: 20
<212> TYPE: DNA
<213> ORGANISM: Homo sapiens

<400> SEQUENCE: 1569
gtgggctaag aaaacacctc 20

<210> SEQ ID NO 1570
<211> LENGTH: 20
<212> TYPE: DNA
<213> ORGANISM: Homo sapiens

<400> SEQUENCE: 1570
attgtggttt gtggcatgtg 20

<210> SEQ ID NO 1571
<211> LENGTH: 20
<212> TYPE: DNA
<213> ORGANISM: Homo sapiens

<400> SEQUENCE: 1571
ccagattcag cctgtattcc 20

<210> SEQ ID NO 1572
<211> LENGTH: 20
<212> TYPE: DNA
<213> ORGANISM: Homo sapiens

<400> SEQUENCE: 1572
gcccatggaa gtaaacagtc 20

<210> SEQ ID NO 1573
<211> LENGTH: 22
<212> TYPE: DNA
<213> ORGANISM: Homo sapiens

<400> SEQUENCE: 1573
aggtttgaca taatagtgct gc 22

<210> SEQ ID NO 1574
<211> LENGTH: 20
<212> TYPE: DNA
<213> ORGANISM: Homo sapiens

<400> SEQUENCE: 1574
aatcctttcc ccactcactg 20

<210> SEQ ID NO 1575
<211> LENGTH: 20
<212> TYPE: DNA
<213> ORGANISM: Homo sapiens

<400> SEQUENCE: 1575
cacaaagcag ttccatgtcc 20

<210> SEQ ID NO 1576
<211> LENGTH: 20
<212> TYPE: DNA
<213> ORGANISM: Homo sapiens

<400> SEQUENCE: 1576
ggacaatttc tcacttgcca 20

<210> SEQ ID NO 1577
<211> LENGTH: 20
<212> TYPE: DNA
<213> ORGANISM: Homo sapiens

<400> SEQUENCE: 1577
aaggggtgtt gttagatgct 20

<210> SEQ ID NO 1578
<211> LENGTH: 20
<212> TYPE: DNA
<213> ORGANISM: Homo sapiens

<400> SEQUENCE: 1578
gcatcacaca cagcagatac 20

<210> SEQ ID NO 1579
<211> LENGTH: 20
<212> TYPE: DNA
<213> ORGANISM: Homo sapiens

<400> SEQUENCE: 1579
aaaatgtccg tcccagatga 20

<210> SEQ ID NO 1580
<211> LENGTH: 20
<212> TYPE: DNA
<213> ORGANISM: Homo sapiens

<400> SEQUENCE: 1580
gggggaaaat gtgttgtgtt 20

<210> SEQ ID NO 1581
<211> LENGTH: 20
<212> TYPE: DNA
<213> ORGANISM: Homo sapiens

<400> SEQUENCE: 1581
aactgttagc ttctccaccc 20

<210> SEQ ID NO 1582
<211> LENGTH: 20
<212> TYPE: DNA
<213> ORGANISM: Homo sapiens

<400> SEQUENCE: 1582
cgagtgtagg ttccggttta 20

<210> SEQ ID NO 1583
<211> LENGTH: 20
<212> TYPE: DNA
<213> ORGANISM: Homo sapiens

<400> SEQUENCE: 1583
agaatgccca tttcaggagt 20

<210> SEQ ID NO 1584
<211> LENGTH: 21
<212> TYPE: DNA
<213> ORGANISM: Homo sapiens

<400> SEQUENCE: 1584
atatgtggtt tgaggtcagc t 21

<210> SEQ ID NO 1585
<211> LENGTH: 19
<212> TYPE: DNA
<213> ORGANISM: Homo sapiens

<400> SEQUENCE: 1585
ggctttggtc acatggaga 19

<210> SEQ ID NO 1586
<211> LENGTH: 20
<212> TYPE: DNA
<213> ORGANISM: Homo sapiens

<400> SEQUENCE: 1586
tgaggcaaga ttcagtgact 20

<210> SEQ ID NO 1587
<211> LENGTH: 20
<212> TYPE: DNA
<213> ORGANISM: Homo sapiens

<400> SEQUENCE: 1587
acttcatctt gacagcagct 20

<210> SEQ ID NO 1588
<211> LENGTH: 22
<212> TYPE: DNA
<213> ORGANISM: Homo sapiens

<400> SEQUENCE: 1588
cacttcctca tgatgttttg ga 22

<210> SEQ ID NO 1589
<211> LENGTH: 20
<212> TYPE: DNA
<213> ORGANISM: Homo sapiens

<400> SEQUENCE: 1589
ggccagccca cttatttttg 20

<210> SEQ ID NO 1590
<211> LENGTH: 20
<212> TYPE: DNA
<213> ORGANISM: Homo sapiens

<400> SEQUENCE: 1590
ctcagggtgg agtttcaaac 20

<210> SEQ ID NO 1591
<211> LENGTH: 20
<212> TYPE: DNA
<213> ORGANISM: Homo sapiens

<400> SEQUENCE: 1591
gatctttctt cccctcctcc 20

<210> SEQ ID NO 1592
<211> LENGTH: 21
<212> TYPE: DNA
<213> ORGANISM: Homo sapiens

<400> SEQUENCE: 1592
tgtacatcca ccacttgttt g 21

<210> SEQ ID NO 1593
<211> LENGTH: 20
<212> TYPE: DNA
<213> ORGANISM: Homo sapiens

<400> SEQUENCE: 1593
agcggtagta agaaggcaaa 20

<210> SEQ ID NO 1594
<211> LENGTH: 20
<212> TYPE: DNA
<213> ORGANISM: Homo sapiens

<400> SEQUENCE: 1594
agacaggtga ccattttccc 20

<210> SEQ ID NO 1595
<211> LENGTH: 20
<212> TYPE: DNA
<213> ORGANISM: Homo sapiens

<400> SEQUENCE: 1595
tgtggaactt ttgagccaga 20

<210> SEQ ID NO 1596
<211> LENGTH: 21
<212> TYPE: DNA
<213> ORGANISM: Homo sapiens

<400> SEQUENCE: 1596
cataacgaaa tagggccttc c 21

<210> SEQ ID NO 1597
<211> LENGTH: 21
<212> TYPE: DNA
<213> ORGANISM: Homo sapiens

<400> SEQUENCE: 1597
atttctgcct cttctcttcc c 21

<210> SEQ ID NO 1598
<211> LENGTH: 20
<212> TYPE: DNA
<213> ORGANISM: Homo sapiens

<400> SEQUENCE: 1598
tcatcaagtc acctctccac 20

<210> SEQ ID NO 1599
<211> LENGTH: 20
<212> TYPE: DNA
<213> ORGANISM: Homo sapiens

<400> SEQUENCE: 1599
tggaaaacta gacagcagcc 20

<210> SEQ ID NO 1600
<211> LENGTH: 20
<212> TYPE: DNA
<213> ORGANISM: Homo sapiens

<400> SEQUENCE: 1600
ggaaagggga aaaggtgaca 20

<210> SEQ ID NO 1601
<211> LENGTH: 20
<212> TYPE: DNA
<213> ORGANISM: Homo sapiens

<400> SEQUENCE: 1601
ctgtcctctg tcccacataa 20

<210> SEQ ID NO 1602
<211> LENGTH: 20
<212> TYPE: DNA
<213> ORGANISM: Homo sapiens

<400> SEQUENCE: 1602
tttctgagtc cattccccat 20

<210> SEQ ID NO 1603
<211> LENGTH: 20
<212> TYPE: DNA
<213> ORGANISM: Homo sapiens

<400> SEQUENCE: 1603
ggccatcctg atatcttcca 20

<210> SEQ ID NO 1604
<211> LENGTH: 20
<212> TYPE: DNA
<213> ORGANISM: Homo sapiens

<400> SEQUENCE: 1604
cagagagatg cagaggttca 20

<210> SEQ ID NO 1605
<211> LENGTH: 20
<212> TYPE: DNA
<213> ORGANISM: Homo sapiens

<400> SEQUENCE: 1605
tgtgtgtgag ctagctgaat 20

<210> SEQ ID NO 1606
<211> LENGTH: 20
<212> TYPE: DNA
<213> ORGANISM: Homo sapiens

<400> SEQUENCE: 1606
ggtttcccat cctaccacat 20

<210> SEQ ID NO 1607
<211> LENGTH: 20
<212> TYPE: DNA
<213> ORGANISM: Homo sapiens

<400> SEQUENCE: 1607
ggtgcttttg ttgccttact 20

<210> SEQ ID NO 1608
<211> LENGTH: 20
<212> TYPE: DNA
<213> ORGANISM: Homo sapiens

<400> SEQUENCE: 1608
actagaaagc agggtacagt 20

<210> SEQ ID NO 1609
<211> LENGTH: 20
<212> TYPE: DNA
<213> ORGANISM: Homo sapiens

<400> SEQUENCE: 1609
gctttttcca acttctgctg 20

<210> SEQ ID NO 1610
<211> LENGTH: 20
<212> TYPE: DNA
<213> ORGANISM: Homo sapiens

<400> SEQUENCE: 1610
caacagacaa gtcacctcct 20

<210> SEQ ID NO 1611
<211> LENGTH: 20
<212> TYPE: DNA
<213> ORGANISM: Homo sapiens

<400> SEQUENCE: 1611
ggttcttcct ggacttcaaa 20

<210> SEQ ID NO 1612
<211> LENGTH: 21
<212> TYPE: DNA

<213> ORGANISM: Homo sapiens

<400> SEQUENCE: 1612
gaaagcagta gtttcaggtg t 21

<210> SEQ ID NO 1613
<211> LENGTH: 20
<212> TYPE: DNA
<213> ORGANISM: Homo sapiens

<400> SEQUENCE: 1613
tgaaagactc tgttgccatg 20

<210> SEQ ID NO 1614
<211> LENGTH: 20
<212> TYPE: DNA
<213> ORGANISM: Homo sapiens

<400> SEQUENCE: 1614
cactacacgc tcagaacaaa 20

<210> SEQ ID NO 1615
<211> LENGTH: 20
<212> TYPE: DNA
<213> ORGANISM: Homo sapiens

<400> SEQUENCE: 1615
aaggcaagca ataatgaggc 20

<210> SEQ ID NO 1616
<211> LENGTH: 21
<212> TYPE: DNA
<213> ORGANISM: Homo sapiens

<400> SEQUENCE: 1616
ggacagtctg tgaaaattgc t 21

<210> SEQ ID NO 1617
<211> LENGTH: 20
<212> TYPE: DNA
<213> ORGANISM: Homo sapiens

<400> SEQUENCE: 1617
acaaacaacc cttaatgccc 20

<210> SEQ ID NO 1618
<211> LENGTH: 20
<212> TYPE: DNA
<213> ORGANISM: Homo sapiens

<400> SEQUENCE: 1618
tgaaacagtg aatccgcaat 20

<210> SEQ ID NO 1619
<211> LENGTH: 21
<212> TYPE: DNA
<213> ORGANISM: Homo sapiens

<400> SEQUENCE: 1619
aagggaaatg tggatgcagt a 21

<210> SEQ ID NO 1620
<211> LENGTH: 19

<212> TYPE: DNA
<213> ORGANISM: Homo sapiens

<400> SEQUENCE: 1620
ttgaagggaa gcggaaagt 19

<210> SEQ ID NO 1621
<211> LENGTH: 21
<212> TYPE: DNA
<213> ORGANISM: Homo sapiens

<400> SEQUENCE: 1621
atttccagct aatgatgctc c 21

<210> SEQ ID NO 1622
<211> LENGTH: 20
<212> TYPE: DNA
<213> ORGANISM: Homo sapiens

<400> SEQUENCE: 1622
gctcacttac gcattaacca 20

<210> SEQ ID NO 1623
<211> LENGTH: 20
<212> TYPE: DNA
<213> ORGANISM: Homo sapiens

<400> SEQUENCE: 1623
acaggcaaaa ttcagttgga 20

<210> SEQ ID NO 1624
<211> LENGTH: 20
<212> TYPE: DNA
<213> ORGANISM: Homo sapiens

<400> SEQUENCE: 1624
aggctgaatc acgtcaaaac 20

<210> SEQ ID NO 1625
<211> LENGTH: 19
<212> TYPE: DNA
<213> ORGANISM: Homo sapiens

<400> SEQUENCE: 1625
cctcgttcac atttgacgc 19

<210> SEQ ID NO 1626
<211> LENGTH: 20
<212> TYPE: DNA
<213> ORGANISM: Homo sapiens

<400> SEQUENCE: 1626
tgtctgggtt caactgtttg 20

<210> SEQ ID NO 1627
<211> LENGTH: 20
<212> TYPE: DNA
<213> ORGANISM: Homo sapiens

<400> SEQUENCE: 1627
attttgcatg cctgttgaga 20

<210> SEQ ID NO 1628

<211> LENGTH: 20
<212> TYPE: DNA
<213> ORGANISM: Homo sapiens

<400> SEQUENCE: 1628
gctctcctca aaacccaagt 20

<210> SEQ ID NO 1629
<211> LENGTH: 20
<212> TYPE: DNA
<213> ORGANISM: Homo sapiens

<400> SEQUENCE: 1629
cttaatgagg gggcacaaag 20

<210> SEQ ID NO 1630
<211> LENGTH: 20
<212> TYPE: DNA
<213> ORGANISM: Homo sapiens

<400> SEQUENCE: 1630
ttttcgtcca gtcttccacc 20

<210> SEQ ID NO 1631
<211> LENGTH: 20
<212> TYPE: DNA
<213> ORGANISM: Homo sapiens

<400> SEQUENCE: 1631
tacaggaccg tcagtgagag 20

<210> SEQ ID NO 1632
<211> LENGTH: 20
<212> TYPE: DNA
<213> ORGANISM: Homo sapiens

<400> SEQUENCE: 1632
ttagctactg acgcttcacc 20

<210> SEQ ID NO 1633
<211> LENGTH: 20
<212> TYPE: DNA
<213> ORGANISM: Homo sapiens

<400> SEQUENCE: 1633
gcacagacaa catgctagtt 20

<210> SEQ ID NO 1634
<211> LENGTH: 20
<212> TYPE: DNA
<213> ORGANISM: Homo sapiens

<400> SEQUENCE: 1634
ttagtctgtt cactggcaca 20

<210> SEQ ID NO 1635
<211> LENGTH: 19
<212> TYPE: DNA
<213> ORGANISM: Homo sapiens

<400> SEQUENCE: 1635
cttatcagca gggcacagt 19

<210> SEQ ID NO 1636
<211> LENGTH: 20
<212> TYPE: DNA
<213> ORGANISM: Homo sapiens

<400> SEQUENCE: 1636
ttgcatcaaa caaagccaca 20

<210> SEQ ID NO 1637
<211> LENGTH: 20
<212> TYPE: DNA
<213> ORGANISM: Homo sapiens

<400> SEQUENCE: 1637
gagagacaag tcaccccttc 20

<210> SEQ ID NO 1638
<211> LENGTH: 20
<212> TYPE: DNA
<213> ORGANISM: Homo sapiens

<400> SEQUENCE: 1638
agtcaactac aaatggggga 20

<210> SEQ ID NO 1639
<211> LENGTH: 20
<212> TYPE: DNA
<213> ORGANISM: Homo sapiens

<400> SEQUENCE: 1639
gtgccaaaat caacgaaagc 20

<210> SEQ ID NO 1640
<211> LENGTH: 21
<212> TYPE: DNA
<213> ORGANISM: Homo sapiens

<400> SEQUENCE: 1640
aaggagggag tacaaagtga g 21

<210> SEQ ID NO 1641
<211> LENGTH: 20
<212> TYPE: DNA
<213> ORGANISM: Homo sapiens

<400> SEQUENCE: 1641
atcacatttt cagcacgagg 20

<210> SEQ ID NO 1642
<211> LENGTH: 20
<212> TYPE: DNA
<213> ORGANISM: Homo sapiens

<400> SEQUENCE: 1642
cagggaggga tgatttggaa 20

<210> SEQ ID NO 1643
<211> LENGTH: 20
<212> TYPE: DNA
<213> ORGANISM: Homo sapiens

<400> SEQUENCE: 1643
agaactgaga ggggagcata 20

<210> SEQ ID NO 1644
<211> LENGTH: 20
<212> TYPE: DNA
<213> ORGANISM: Homo sapiens

<400> SEQUENCE: 1644
cagtcaccaa caaaggcttt 20

<210> SEQ ID NO 1645
<211> LENGTH: 20
<212> TYPE: DNA
<213> ORGANISM: Homo sapiens

<400> SEQUENCE: 1645
tccccatctc cctaactcat 20

<210> SEQ ID NO 1646
<211> LENGTH: 20
<212> TYPE: DNA
<213> ORGANISM: Homo sapiens

<400> SEQUENCE: 1646
tttttctgct gcatccaagg 20

<210> SEQ ID NO 1647
<211> LENGTH: 20
<212> TYPE: DNA
<213> ORGANISM: Homo sapiens

<400> SEQUENCE: 1647
actgtacgcc atgaaaaaca 20

<210> SEQ ID NO 1648
<211> LENGTH: 20
<212> TYPE: DNA
<213> ORGANISM: Homo sapiens

<400> SEQUENCE: 1648
ggcaaatcaa gtgagctgac 20

<210> SEQ ID NO 1649
<211> LENGTH: 20
<212> TYPE: DNA
<213> ORGANISM: Homo sapiens

<400> SEQUENCE: 1649
cgtgggtgga gaatttcaca 20

<210> SEQ ID NO 1650
<211> LENGTH: 20
<212> TYPE: DNA
<213> ORGANISM: Homo sapiens

<400> SEQUENCE: 1650
acttaggtca gttgcttggt 20

<210> SEQ ID NO 1651
<211> LENGTH: 20
<212> TYPE: DNA
<213> ORGANISM: Homo sapiens

<400> SEQUENCE: 1651
gacttcatca gcacgtactt 20

<210> SEQ ID NO 1652
<211> LENGTH: 20
<212> TYPE: DNA
<213> ORGANISM: Homo sapiens

<400> SEQUENCE: 1652
tgcaggcaaa attagcatgg 20

<210> SEQ ID NO 1653
<211> LENGTH: 20
<212> TYPE: DNA
<213> ORGANISM: Homo sapiens

<400> SEQUENCE: 1653
gacttatctg ctttcacccc 20

<210> SEQ ID NO 1654
<211> LENGTH: 20
<212> TYPE: DNA
<213> ORGANISM: Homo sapiens

<400> SEQUENCE: 1654
ccccatgaac ctaagaccat 20

<210> SEQ ID NO 1655
<211> LENGTH: 20
<212> TYPE: DNA
<213> ORGANISM: Homo sapiens

<400> SEQUENCE: 1655
tctggacatg tctttgcgta 20

<210> SEQ ID NO 1656
<211> LENGTH: 20
<212> TYPE: DNA
<213> ORGANISM: Homo sapiens

<400> SEQUENCE: 1656
ctccaggaca tctcagcaat 20

<210> SEQ ID NO 1657
<211> LENGTH: 20
<212> TYPE: DNA
<213> ORGANISM: Homo sapiens

<400> SEQUENCE: 1657
cctctcgtgt gggaaatgta 20

<210> SEQ ID NO 1658
<211> LENGTH: 20
<212> TYPE: DNA
<213> ORGANISM: Homo sapiens

<400> SEQUENCE: 1658
tatctctggc tacctcctgt 20

<210> SEQ ID NO 1659
<211> LENGTH: 19
<212> TYPE: DNA
<213> ORGANISM: Homo sapiens

<400> SEQUENCE: 1659
ccccatccct gtaccaaag 19

<210> SEQ ID NO 1660
<211> LENGTH: 20
<212> TYPE: DNA
<213> ORGANISM: Homo sapiens

<400> SEQUENCE: 1660
ctgcagagat attccatggc 20

<210> SEQ ID NO 1661
<211> LENGTH: 20
<212> TYPE: DNA
<213> ORGANISM: Homo sapiens

<400> SEQUENCE: 1661
aaagctgggt tcttaggctt 20

<210> SEQ ID NO 1662
<211> LENGTH: 20
<212> TYPE: DNA
<213> ORGANISM: Homo sapiens

<400> SEQUENCE: 1662
gctgttttag gggcacattt 20

<210> SEQ ID NO 1663
<211> LENGTH: 20
<212> TYPE: DNA
<213> ORGANISM: Homo sapiens

<400> SEQUENCE: 1663
aagaggcaat gtggaggtta 20

<210> SEQ ID NO 1664
<211> LENGTH: 21
<212> TYPE: DNA
<213> ORGANISM: Homo sapiens

<400> SEQUENCE: 1664
gcccaaacaa tctgcctttt a 21

<210> SEQ ID NO 1665
<211> LENGTH: 20
<212> TYPE: DNA
<213> ORGANISM: Homo sapiens

<400> SEQUENCE: 1665
tggcttcaaa taactgggct 20

<210> SEQ ID NO 1666
<211> LENGTH: 20
<212> TYPE: DNA
<213> ORGANISM: Homo sapiens

<400> SEQUENCE: 1666
agagcacaca gaacagaact 20

<210> SEQ ID NO 1667
<211> LENGTH: 20
<212> TYPE: DNA
<213> ORGANISM: Homo sapiens

<400> SEQUENCE: 1667
ctggtggatt tctcgtcaga 20

<210> SEQ ID NO 1668
<211> LENGTH: 20
<212> TYPE: DNA
<213> ORGANISM: Homo sapiens

<400> SEQUENCE: 1668
taggtgtttg tgtgaggctt 20

<210> SEQ ID NO 1669
<211> LENGTH: 20
<212> TYPE: DNA
<213> ORGANISM: Homo sapiens

<400> SEQUENCE: 1669
gcctcactgc tcctatcttt 20

<210> SEQ ID NO 1670
<211> LENGTH: 19
<212> TYPE: DNA
<213> ORGANISM: Homo sapiens

<400> SEQUENCE: 1670
ctctagcagc tgttcctcc 19

<210> SEQ ID NO 1671
<211> LENGTH: 20
<212> TYPE: DNA
<213> ORGANISM: Homo sapiens

<400> SEQUENCE: 1671
cgtcgtatct ctggctttgt 20

<210> SEQ ID NO 1672
<211> LENGTH: 20
<212> TYPE: DNA
<213> ORGANISM: Homo sapiens

<400> SEQUENCE: 1672
gtccccaacc tcatctttca 20

<210> SEQ ID NO 1673
<211> LENGTH: 20
<212> TYPE: DNA
<213> ORGANISM: Homo sapiens

<400> SEQUENCE: 1673
tcttcaaaga tggctgcaaa 20

<210> SEQ ID NO 1674
<211> LENGTH: 21
<212> TYPE: DNA
<213> ORGANISM: Homo sapiens

<400> SEQUENCE: 1674
agtataacca gatagccgtg c 21

<210> SEQ ID NO 1675
<211> LENGTH: 20
<212> TYPE: DNA
<213> ORGANISM: Homo sapiens

<400> SEQUENCE: 1675
tgtcctcagg gcaataaagt 20

<210> SEQ ID NO 1676
<211> LENGTH: 20
<212> TYPE: DNA
<213> ORGANISM: Homo sapiens

<400> SEQUENCE: 1676
tttgctgctt gaagtggaac 20

<210> SEQ ID NO 1677
<211> LENGTH: 20
<212> TYPE: DNA
<213> ORGANISM: Homo sapiens

<400> SEQUENCE: 1677
gctgcaatga cctgatttct 20

<210> SEQ ID NO 1678
<211> LENGTH: 20
<212> TYPE: DNA
<213> ORGANISM: Homo sapiens

<400> SEQUENCE: 1678
tccctctctc ctccaaatga 20

<210> SEQ ID NO 1679
<211> LENGTH: 21
<212> TYPE: DNA
<213> ORGANISM: Homo sapiens

<400> SEQUENCE: 1679
tgccacagta ggtataggtt g 21

<210> SEQ ID NO 1680
<211> LENGTH: 20
<212> TYPE: DNA
<213> ORGANISM: Homo sapiens

<400> SEQUENCE: 1680
ccctcgccct aaagaaacta 20

<210> SEQ ID NO 1681
<211> LENGTH: 20
<212> TYPE: DNA
<213> ORGANISM: Homo sapiens

<400> SEQUENCE: 1681
cccctgaatc cctacctcat 20

<210> SEQ ID NO 1682
<211> LENGTH: 21
<212> TYPE: DNA
<213> ORGANISM: Homo sapiens

<400> SEQUENCE: 1682
tgttgtacaa gtgagccatt c 21

<210> SEQ ID NO 1683
<211> LENGTH: 21
<212> TYPE: DNA
<213> ORGANISM: Homo sapiens

<400> SEQUENCE: 1683
accaagcaat caactcactc t 21

<210> SEQ ID NO 1684
<211> LENGTH: 21
<212> TYPE: DNA
<213> ORGANISM: Homo sapiens

<400> SEQUENCE: 1684
gcccaatttg tctagccaat a 21

<210> SEQ ID NO 1685
<211> LENGTH: 21
<212> TYPE: DNA
<213> ORGANISM: Homo sapiens

<400> SEQUENCE: 1685
ctactgatcc caaagaaggc a 21

<210> SEQ ID NO 1686
<211> LENGTH: 21
<212> TYPE: DNA
<213> ORGANISM: Homo sapiens

<400> SEQUENCE: 1686
gtgaaaggtt ctatctgcca a 21

<210> SEQ ID NO 1687
<211> LENGTH: 21
<212> TYPE: DNA
<213> ORGANISM: Homo sapiens

<400> SEQUENCE: 1687
ggcataccga gcatacatag a 21

<210> SEQ ID NO 1688
<211> LENGTH: 21
<212> TYPE: DNA
<213> ORGANISM: Homo sapiens

<400> SEQUENCE: 1688
cacctgtttc accaaatcac t 21

<210> SEQ ID NO 1689
<211> LENGTH: 21
<212> TYPE: DNA
<213> ORGANISM: Homo sapiens

<400> SEQUENCE: 1689
tctcatgctc tgacagacaa g 21

<210> SEQ ID NO 1690
<211> LENGTH: 21
<212> TYPE: DNA
<213> ORGANISM: Homo sapiens

<400> SEQUENCE: 1690
ttgtcctgtt tctcttgtga c 21

<210> SEQ ID NO 1691
<211> LENGTH: 21
<212> TYPE: DNA

<213> ORGANISM: Homo sapiens

<400> SEQUENCE: 1691
cacaggactg catgcctatt a 21

<210> SEQ ID NO 1692
<211> LENGTH: 21
<212> TYPE: DNA
<213> ORGANISM: Homo sapiens

<400> SEQUENCE: 1692
gactctctca gcatcgagtt t 21

<210> SEQ ID NO 1693
<211> LENGTH: 21
<212> TYPE: DNA
<213> ORGANISM: Homo sapiens

<400> SEQUENCE: 1693
ctgatggaag ggcattatcc a 21

<210> SEQ ID NO 1694
<211> LENGTH: 22
<212> TYPE: DNA
<213> ORGANISM: Homo sapiens

<400> SEQUENCE: 1694
ttctggttcc ataaatccat gc 22

<210> SEQ ID NO 1695
<211> LENGTH: 22
<212> TYPE: DNA
<213> ORGANISM: Homo sapiens

<400> SEQUENCE: 1695
gggattattg ttggctactg ag 22

<210> SEQ ID NO 1696
<211> LENGTH: 21
<212> TYPE: DNA
<213> ORGANISM: Homo sapiens

<400> SEQUENCE: 1696
aattggtgac ctagggatca g 21

<210> SEQ ID NO 1697
<211> LENGTH: 21
<212> TYPE: DNA
<213> ORGANISM: Homo sapiens

<400> SEQUENCE: 1697
gggtttggta agggagaatg a 21

<210> SEQ ID NO 1698
<211> LENGTH: 23
<212> TYPE: DNA
<213> ORGANISM: Homo sapiens

<400> SEQUENCE: 1698
aagacatccc agttatgcat tgt 23

<210> SEQ ID NO 1699
<211> LENGTH: 21

<212> TYPE: DNA
<213> ORGANISM: Homo sapiens

<400> SEQUENCE: 1699
agatgggagg gagattagac a 21

<210> SEQ ID NO 1700
<211> LENGTH: 21
<212> TYPE: DNA
<213> ORGANISM: Homo sapiens

<400> SEQUENCE: 1700
gagtagcaac aacacatgga g 21

<210> SEQ ID NO 1701
<211> LENGTH: 21
<212> TYPE: DNA
<213> ORGANISM: Homo sapiens

<400> SEQUENCE: 1701
ttctccttca ttagccacac a 21

<210> SEQ ID NO 1702
<211> LENGTH: 21
<212> TYPE: DNA
<213> ORGANISM: Homo sapiens

<400> SEQUENCE: 1702
agtctgcact gtactcttct g 21

<210> SEQ ID NO 1703
<211> LENGTH: 21
<212> TYPE: DNA
<213> ORGANISM: Homo sapiens

<400> SEQUENCE: 1703
acaaatggtt catgatggtg g 21

<210> SEQ ID NO 1704
<211> LENGTH: 21
<212> TYPE: DNA
<213> ORGANISM: Homo sapiens

<400> SEQUENCE: 1704
ggtactcacg tttcagtttc c 21

<210> SEQ ID NO 1705
<211> LENGTH: 21
<212> TYPE: DNA
<213> ORGANISM: Homo sapiens

<400> SEQUENCE: 1705
gttcatttct acagtccagg c 21

<210> SEQ ID NO 1706
<211> LENGTH: 21
<212> TYPE: DNA
<213> ORGANISM: Homo sapiens

<400> SEQUENCE: 1706
ctctcactgt gctgcttaaa g 21

<210> SEQ ID NO 1707

<211> LENGTH: 22
<212> TYPE: DNA
<213> ORGANISM: Homo sapiens

<400> SEQUENCE: 1707
caaagaattc cacagagatg gg 22

<210> SEQ ID NO 1708
<211> LENGTH: 21
<212> TYPE: DNA
<213> ORGANISM: Homo sapiens

<400> SEQUENCE: 1708
tgagctacag acaagattgc a 21

<210> SEQ ID NO 1709
<211> LENGTH: 21
<212> TYPE: DNA
<213> ORGANISM: Homo sapiens

<400> SEQUENCE: 1709
tcacatggga tcgacatatg c 21

<210> SEQ ID NO 1710
<211> LENGTH: 21
<212> TYPE: DNA
<213> ORGANISM: Homo sapiens

<400> SEQUENCE: 1710
ccacacaatt tcctggctat g 21

<210> SEQ ID NO 1711
<211> LENGTH: 21
<212> TYPE: DNA
<213> ORGANISM: Homo sapiens

<400> SEQUENCE: 1711
tcttgcttct ggagagttct t 21

<210> SEQ ID NO 1712
<211> LENGTH: 21
<212> TYPE: DNA
<213> ORGANISM: Homo sapiens

<400> SEQUENCE: 1712
aggttatgca gacttcagga a 21

<210> SEQ ID NO 1713
<211> LENGTH: 21
<212> TYPE: DNA
<213> ORGANISM: Homo sapiens

<400> SEQUENCE: 1713
aagccaattc tgcctctcta g 21

<210> SEQ ID NO 1714
<211> LENGTH: 21
<212> TYPE: DNA
<213> ORGANISM: Homo sapiens

<400> SEQUENCE: 1714
tcccttcctt attctggcaa c 21

<210> SEQ ID NO 1715
<211> LENGTH: 21
<212> TYPE: DNA
<213> ORGANISM: Homo sapiens

<400> SEQUENCE: 1715
gcttcaaaca ctctaaaggg c 21

<210> SEQ ID NO 1716
<211> LENGTH: 21
<212> TYPE: DNA
<213> ORGANISM: Homo sapiens

<400> SEQUENCE: 1716
tgccattaat gagaagtgct g 21

<210> SEQ ID NO 1717
<211> LENGTH: 22
<212> TYPE: DNA
<213> ORGANISM: Homo sapiens

<400> SEQUENCE: 1717
tggcaatcct gttaaacaac tc 22

<210> SEQ ID NO 1718
<211> LENGTH: 22
<212> TYPE: DNA
<213> ORGANISM: Homo sapiens

<400> SEQUENCE: 1718
cccgaacatt gataacagaa ga 22

<210> SEQ ID NO 1719
<211> LENGTH: 22
<212> TYPE: DNA
<213> ORGANISM: Homo sapiens

<400> SEQUENCE: 1719
gcaactcagg aaagactaca tc 22

<210> SEQ ID NO 1720
<211> LENGTH: 22
<212> TYPE: DNA
<213> ORGANISM: Homo sapiens

<400> SEQUENCE: 1720
ttaagaaagt acccatcctc cc 22

<210> SEQ ID NO 1721
<211> LENGTH: 21
<212> TYPE: DNA
<213> ORGANISM: Homo sapiens

<400> SEQUENCE: 1721
gtcatgcctt acaacttagc a 21

<210> SEQ ID NO 1722
<211> LENGTH: 21
<212> TYPE: DNA
<213> ORGANISM: Homo sapiens

<400> SEQUENCE: 1722
aatctttgcc aaggtatgag c 21

<210> SEQ ID NO 1723
<211> LENGTH: 21
<212> TYPE: DNA
<213> ORGANISM: Homo sapiens

<400> SEQUENCE: 1723
gccacttata cctccagaca t 21

<210> SEQ ID NO 1724
<211> LENGTH: 20
<212> TYPE: DNA
<213> ORGANISM: Homo sapiens

<400> SEQUENCE: 1724
ccacaatcct gaatgccatg 20

<210> SEQ ID NO 1725
<211> LENGTH: 21
<212> TYPE: DNA
<213> ORGANISM: Homo sapiens

<400> SEQUENCE: 1725
ctgcaaggta caacacaagt c 21

<210> SEQ ID NO 1726
<211> LENGTH: 21
<212> TYPE: DNA
<213> ORGANISM: Homo sapiens

<400> SEQUENCE: 1726
atctctgtgc cagcaagtat t 21

<210> SEQ ID NO 1727
<211> LENGTH: 21
<212> TYPE: DNA
<213> ORGANISM: Homo sapiens

<400> SEQUENCE: 1727
attgggaaac tgtcactgat g 21

<210> SEQ ID NO 1728
<211> LENGTH: 21
<212> TYPE: DNA
<213> ORGANISM: Homo sapiens

<400> SEQUENCE: 1728
gccctaatag agaagcaaag c 21

<210> SEQ ID NO 1729
<211> LENGTH: 21
<212> TYPE: DNA
<213> ORGANISM: Homo sapiens

<400> SEQUENCE: 1729
gggagccaat cagatagaag t 21

<210> SEQ ID NO 1730
<211> LENGTH: 22
<212> TYPE: DNA
<213> ORGANISM: Homo sapiens

<400> SEQUENCE: 1730
gggaagttgg gctatttaat gc 22

<210> SEQ ID NO 1731
<211> LENGTH: 21
<212> TYPE: DNA
<213> ORGANISM: Homo sapiens

<400> SEQUENCE: 1731
aactgtgtag agcgaccaaa t 21

<210> SEQ ID NO 1732
<211> LENGTH: 21
<212> TYPE: DNA
<213> ORGANISM: Homo sapiens

<400> SEQUENCE: 1732
cagtaaggcc atggtctaga t 21

<210> SEQ ID NO 1733
<211> LENGTH: 21
<212> TYPE: DNA
<213> ORGANISM: Homo sapiens

<400> SEQUENCE: 1733
ctcagaacat ttgcaccttc t 21

<210> SEQ ID NO 1734
<211> LENGTH: 21
<212> TYPE: DNA
<213> ORGANISM: Homo sapiens

<400> SEQUENCE: 1734
acctgataca atggagcatg t 21

<210> SEQ ID NO 1735
<211> LENGTH: 21
<212> TYPE: DNA
<213> ORGANISM: Homo sapiens

<400> SEQUENCE: 1735
gggacctaaa ctcctttgga a 21

<210> SEQ ID NO 1736
<211> LENGTH: 21
<212> TYPE: DNA
<213> ORGANISM: Homo sapiens

<400> SEQUENCE: 1736
tctgcagtgg tgttatctag t 21

<210> SEQ ID NO 1737
<211> LENGTH: 20
<212> TYPE: DNA
<213> ORGANISM: Homo sapiens

<400> SEQUENCE: 1737
cacttaagtt tccacgccag 20

<210> SEQ ID NO 1738
<211> LENGTH: 21
<212> TYPE: DNA
<213> ORGANISM: Homo sapiens

<400> SEQUENCE: 1738
gtaatggcga gaggttaaag c 21

<210> SEQ ID NO 1739
<211> LENGTH: 22
<212> TYPE: DNA
<213> ORGANISM: Homo sapiens

<400> SEQUENCE: 1739
tttaggtatc gaagttgggt ca 22

<210> SEQ ID NO 1740
<211> LENGTH: 22
<212> TYPE: DNA
<213> ORGANISM: Homo sapiens

<400> SEQUENCE: 1740
gataagtttg gaagctgcat ca 22

<210> SEQ ID NO 1741
<211> LENGTH: 21
<212> TYPE: DNA
<213> ORGANISM: Homo sapiens

<400> SEQUENCE: 1741
aagctctgcc attgacttta c 21

<210> SEQ ID NO 1742
<211> LENGTH: 20
<212> TYPE: DNA
<213> ORGANISM: Homo sapiens

<400> SEQUENCE: 1742
ccctacagaa ccgaggaatc 20

<210> SEQ ID NO 1743
<211> LENGTH: 21
<212> TYPE: DNA
<213> ORGANISM: Homo sapiens

<400> SEQUENCE: 1743
tcaatctttg catacacagc c 21

<210> SEQ ID NO 1744
<211> LENGTH: 22
<212> TYPE: DNA
<213> ORGANISM: Homo sapiens

<400> SEQUENCE: 1744
gtaggtttac atggacagat gc 22

<210> SEQ ID NO 1745
<211> LENGTH: 21
<212> TYPE: DNA
<213> ORGANISM: Homo sapiens

<400> SEQUENCE: 1745
tcttctgttt agtgctgtgg t 21

<210> SEQ ID NO 1746
<211> LENGTH: 21
<212> TYPE: DNA
<213> ORGANISM: Homo sapiens

<400> SEQUENCE: 1746
caagttcatt tcttccctgc a 21

<210> SEQ ID NO 1747
<211> LENGTH: 21
<212> TYPE: DNA
<213> ORGANISM: Homo sapiens

<400> SEQUENCE: 1747
tgcaggaata catggtagac a 21

<210> SEQ ID NO 1748
<211> LENGTH: 21
<212> TYPE: DNA
<213> ORGANISM: Homo sapiens

<400> SEQUENCE: 1748
cataggcctt catgtctctc a 21

<210> SEQ ID NO 1749
<211> LENGTH: 21
<212> TYPE: DNA
<213> ORGANISM: Homo sapiens

<400> SEQUENCE: 1749
tatgagggtg cactaacaga t 21

<210> SEQ ID NO 1750
<211> LENGTH: 21
<212> TYPE: DNA
<213> ORGANISM: Homo sapiens

<400> SEQUENCE: 1750
ggtgctacta ctggtgtatg t 21

<210> SEQ ID NO 1751
<211> LENGTH: 21
<212> TYPE: DNA
<213> ORGANISM: Homo sapiens

<400> SEQUENCE: 1751
gccatgcaat atcaaatccc a 21

<210> SEQ ID NO 1752
<211> LENGTH: 21
<212> TYPE: DNA
<213> ORGANISM: Homo sapiens

<400> SEQUENCE: 1752
gaaaccaaag actagtgcag c 21

<210> SEQ ID NO 1753
<211> LENGTH: 21
<212> TYPE: DNA
<213> ORGANISM: Homo sapiens

<400> SEQUENCE: 1753
atgactaaca ctctgccaag t 21

<210> SEQ ID NO 1754
<211> LENGTH: 21
<212> TYPE: DNA
<213> ORGANISM: Homo sapiens

<400> SEQUENCE: 1754
aacaaatgca tcccagacag a 21

<210> SEQ ID NO 1755
<211> LENGTH: 21
<212> TYPE: DNA
<213> ORGANISM: Homo sapiens

<400> SEQUENCE: 1755
gcagagagga gtatgtggta t 21

<210> SEQ ID NO 1756
<211> LENGTH: 21
<212> TYPE: DNA
<213> ORGANISM: Homo sapiens

<400> SEQUENCE: 1756
atgggtcatt ctacgaagca a 21

<210> SEQ ID NO 1757
<211> LENGTH: 22
<212> TYPE: DNA
<213> ORGANISM: Homo sapiens

<400> SEQUENCE: 1757
tggtgtgtgt ggtgataatt ag 22

<210> SEQ ID NO 1758
<211> LENGTH: 21
<212> TYPE: DNA
<213> ORGANISM: Homo sapiens

<400> SEQUENCE: 1758
agtgaccctc tgaataacct g 21

<210> SEQ ID NO 1759
<211> LENGTH: 21
<212> TYPE: DNA
<213> ORGANISM: Homo sapiens

<400> SEQUENCE: 1759
tcagcaagta aacctgagac c 21

<210> SEQ ID NO 1760
<211> LENGTH: 20
<212> TYPE: DNA
<213> ORGANISM: Homo sapiens

<400> SEQUENCE: 1760
gtaccttcac cctccagatc 20

<210> SEQ ID NO 1761
<211> LENGTH: 21
<212> TYPE: DNA
<213> ORGANISM: Homo sapiens

<400> SEQUENCE: 1761
tcatcaaatt gcccactcct a 21

<210> SEQ ID NO 1762
<211> LENGTH: 21
<212> TYPE: DNA
<213> ORGANISM: Homo sapiens

<400> SEQUENCE: 1762
catcagactg tcttgccttt c 21

<210> SEQ ID NO 1763
<211> LENGTH: 21
<212> TYPE: DNA
<213> ORGANISM: Homo sapiens

<400> SEQUENCE: 1763
cattcttgct gacatttccc a 21

<210> SEQ ID NO 1764
<211> LENGTH: 22
<212> TYPE: DNA
<213> ORGANISM: Homo sapiens

<400> SEQUENCE: 1764
gaagatcagg gtattgctga aa 22

<210> SEQ ID NO 1765
<211> LENGTH: 21
<212> TYPE: DNA
<213> ORGANISM: Homo sapiens

<400> SEQUENCE: 1765
tttgtaggtc attcagcctc c 21

<210> SEQ ID NO 1766
<211> LENGTH: 22
<212> TYPE: DNA
<213> ORGANISM: Homo sapiens

<400> SEQUENCE: 1766
tggctaggat tcacttagga aa 22

<210> SEQ ID NO 1767
<211> LENGTH: 21
<212> TYPE: DNA
<213> ORGANISM: Homo sapiens

<400> SEQUENCE: 1767
gcaaacaggg tgaattatgc t 21

<210> SEQ ID NO 1768
<211> LENGTH: 21
<212> TYPE: DNA
<213> ORGANISM: Homo sapiens

<400> SEQUENCE: 1768
agaagtctgg gaaacgaaga g 21

<210> SEQ ID NO 1769
<211> LENGTH: 21
<212> TYPE: DNA
<213> ORGANISM: Homo sapiens

<400> SEQUENCE: 1769
cagatgctcc attactaggt g 21

<210> SEQ ID NO 1770
<211> LENGTH: 21
<212> TYPE: DNA

<213> ORGANISM: Homo sapiens

<400> SEQUENCE: 1770
cacatggaga aaggtgaatc a 21

<210> SEQ ID NO 1771
<211> LENGTH: 20
<212> TYPE: DNA
<213> ORGANISM: Homo sapiens

<400> SEQUENCE: 1771
tcccatccaa tactgccttc 20

<210> SEQ ID NO 1772
<211> LENGTH: 21
<212> TYPE: DNA
<213> ORGANISM: Homo sapiens

<400> SEQUENCE: 1772
tctggctcaa aggatcacat g 21

<210> SEQ ID NO 1773
<211> LENGTH: 21
<212> TYPE: DNA
<213> ORGANISM: Homo sapiens

<400> SEQUENCE: 1773
aagatcccat tgaccctgaa t 21

<210> SEQ ID NO 1774
<211> LENGTH: 21
<212> TYPE: DNA
<213> ORGANISM: Homo sapiens

<400> SEQUENCE: 1774
ccacaggctc tctagaacta a 21

<210> SEQ ID NO 1775
<211> LENGTH: 21
<212> TYPE: DNA
<213> ORGANISM: Homo sapiens

<400> SEQUENCE: 1775
ttgagagggt ttacaaggtc c 21

<210> SEQ ID NO 1776
<211> LENGTH: 22
<212> TYPE: DNA
<213> ORGANISM: Homo sapiens

<400> SEQUENCE: 1776
cttctcctac tctgcattct ca 22

<210> SEQ ID NO 1777
<211> LENGTH: 21
<212> TYPE: DNA
<213> ORGANISM: Homo sapiens

<400> SEQUENCE: 1777
gacattagtg gattcaggcc a 21

<210> SEQ ID NO 1778
<211> LENGTH: 21

<212> TYPE: DNA
<213> ORGANISM: Homo sapiens

<400> SEQUENCE: 1778
gctgaagtgg aggcaattaa c 21

<210> SEQ ID NO 1779
<211> LENGTH: 21
<212> TYPE: DNA
<213> ORGANISM: Homo sapiens

<400> SEQUENCE: 1779
tataactgtt gagtctgccc a 21

<210> SEQ ID NO 1780
<211> LENGTH: 21
<212> TYPE: DNA
<213> ORGANISM: Homo sapiens

<400> SEQUENCE: 1780
actgagctta cattcatgca c 21

<210> SEQ ID NO 1781
<211> LENGTH: 21
<212> TYPE: DNA
<213> ORGANISM: Homo sapiens

<400> SEQUENCE: 1781
gccactttct ctgcaaagaa t 21

<210> SEQ ID NO 1782
<211> LENGTH: 21
<212> TYPE: DNA
<213> ORGANISM: Homo sapiens

<400> SEQUENCE: 1782
acttcctacg gactcaaatc t 21

<210> SEQ ID NO 1783
<211> LENGTH: 21
<212> TYPE: DNA
<213> ORGANISM: Homo sapiens

<400> SEQUENCE: 1783
ggctctcatt acaattggct g 21

<210> SEQ ID NO 1784
<211> LENGTH: 21
<212> TYPE: DNA
<213> ORGANISM: Homo sapiens

<400> SEQUENCE: 1784
attgctttca gtggtggatt g 21

<210> SEQ ID NO 1785
<211> LENGTH: 21
<212> TYPE: DNA
<213> ORGANISM: Homo sapiens

<400> SEQUENCE: 1785
ggaatgaaac agaggagtcc c 21

<210> SEQ ID NO 1786

<211> LENGTH: 21
<212> TYPE: DNA
<213> ORGANISM: Homo sapiens

<400> SEQUENCE: 1786
aagatgctag aaacccacaa g 21

<210> SEQ ID NO 1787
<211> LENGTH: 20
<212> TYPE: DNA
<213> ORGANISM: Homo sapiens

<400> SEQUENCE: 1787
aatgggtggg ttacagagag 20

<210> SEQ ID NO 1788
<211> LENGTH: 20
<212> TYPE: DNA
<213> ORGANISM: Homo sapiens

<400> SEQUENCE: 1788
gcatttggac atgaacaagc 20

<210> SEQ ID NO 1789
<211> LENGTH: 20
<212> TYPE: DNA
<213> ORGANISM: Homo sapiens

<400> SEQUENCE: 1789
cattggtggg tggatagctg 20

<210> SEQ ID NO 1790
<211> LENGTH: 20
<212> TYPE: DNA
<213> ORGANISM: Homo sapiens

<400> SEQUENCE: 1790
accaggagga gaaaagcaaa 20

<210> SEQ ID NO 1791
<211> LENGTH: 20
<212> TYPE: DNA
<213> ORGANISM: Homo sapiens

<400> SEQUENCE: 1791
cggaaaacaa accctgaagt 20

<210> SEQ ID NO 1792
<211> LENGTH: 20
<212> TYPE: DNA
<213> ORGANISM: Homo sapiens

<400> SEQUENCE: 1792
acctgcatat tgagccatac 20

<210> SEQ ID NO 1793
<211> LENGTH: 21
<212> TYPE: DNA
<213> ORGANISM: Homo sapiens

<400> SEQUENCE: 1793
tgttctttca cttttagccc c 21

<210> SEQ ID NO 1794
<211> LENGTH: 21
<212> TYPE: DNA
<213> ORGANISM: Homo sapiens

<400> SEQUENCE: 1794
tttctagaac cctcagcaac t 21

<210> SEQ ID NO 1795
<211> LENGTH: 21
<212> TYPE: DNA
<213> ORGANISM: Homo sapiens

<400> SEQUENCE: 1795
cccccaacag tttttagtgg t 21

<210> SEQ ID NO 1796
<211> LENGTH: 20
<212> TYPE: DNA
<213> ORGANISM: Homo sapiens

<400> SEQUENCE: 1796
aaggcaaaac actccctttt 20

<210> SEQ ID NO 1797
<211> LENGTH: 22
<212> TYPE: DNA
<213> ORGANISM: Homo sapiens

<400> SEQUENCE: 1797
cagtgattgc ctctagaaaa gg 22

<210> SEQ ID NO 1798
<211> LENGTH: 20
<212> TYPE: DNA
<213> ORGANISM: Homo sapiens

<400> SEQUENCE: 1798
ctaagcagat tgaagcagct 20

<210> SEQ ID NO 1799
<211> LENGTH: 20
<212> TYPE: DNA
<213> ORGANISM: Homo sapiens

<400> SEQUENCE: 1799
tgtccccagg cttaagaatc 20

<210> SEQ ID NO 1800
<211> LENGTH: 20
<212> TYPE: DNA
<213> ORGANISM: Homo sapiens

<400> SEQUENCE: 1800
agccagaata agcaactgtc 20

<210> SEQ ID NO 1801
<211> LENGTH: 20
<212> TYPE: DNA
<213> ORGANISM: Homo sapiens

<400> SEQUENCE: 1801
tttctcctat cccagcttgc 20

<210> SEQ ID NO 1802
<211> LENGTH: 21
<212> TYPE: DNA
<213> ORGANISM: Homo sapiens

<400> SEQUENCE: 1802
agtacagagg ataacaaggg t 21

<210> SEQ ID NO 1803
<211> LENGTH: 20
<212> TYPE: DNA
<213> ORGANISM: Homo sapiens

<400> SEQUENCE: 1803
ctcccatcag taccctctct 20

<210> SEQ ID NO 1804
<211> LENGTH: 21
<212> TYPE: DNA
<213> ORGANISM: Homo sapiens

<400> SEQUENCE: 1804
ggaatgccta aaccatactg t 21

<210> SEQ ID NO 1805
<211> LENGTH: 22
<212> TYPE: DNA
<213> ORGANISM: Homo sapiens

<400> SEQUENCE: 1805
agtggtattt caatgctcta cc 22

<210> SEQ ID NO 1806
<211> LENGTH: 19
<212> TYPE: DNA
<213> ORGANISM: Homo sapiens

<400> SEQUENCE: 1806
gcagtacatc gtcctggaa 19

<210> SEQ ID NO 1807
<211> LENGTH: 21
<212> TYPE: DNA
<213> ORGANISM: Homo sapiens

<400> SEQUENCE: 1807
cctgagcgag aagaaatttg t 21

<210> SEQ ID NO 1808
<211> LENGTH: 21
<212> TYPE: DNA
<213> ORGANISM: Homo sapiens

<400> SEQUENCE: 1808
ggaactgaac aagaagtgga g 21

<210> SEQ ID NO 1809
<211> LENGTH: 20
<212> TYPE: DNA
<213> ORGANISM: Homo sapiens

<400> SEQUENCE: 1809
acctactctt attccgcact 20

<210> SEQ ID NO 1810
<211> LENGTH: 20
<212> TYPE: DNA
<213> ORGANISM: Homo sapiens

<400> SEQUENCE: 1810
tgacagcctc tctcttcaat 20

<210> SEQ ID NO 1811
<211> LENGTH: 18
<212> TYPE: DNA
<213> ORGANISM: Homo sapiens

<400> SEQUENCE: 1811
aaaaaaaaaa aaaaaaaa 18

<210> SEQ ID NO 1812
<211> LENGTH: 20
<212> TYPE: DNA
<213> ORGANISM: Homo sapiens

<400> SEQUENCE: 1812
gctgtttttc tgtgtgcttc 20

<210> SEQ ID NO 1813
<211> LENGTH: 20
<212> TYPE: DNA
<213> ORGANISM: Homo sapiens

<400> SEQUENCE: 1813
atgtatttcc tttagcgccc 20

<210> SEQ ID NO 1814
<211> LENGTH: 20
<212> TYPE: DNA
<213> ORGANISM: Homo sapiens

<400> SEQUENCE: 1814
aattttgcaa gacttccggt 20

<210> SEQ ID NO 1815
<211> LENGTH: 20
<212> TYPE: DNA
<213> ORGANISM: Homo sapiens

<400> SEQUENCE: 1815
tcccagttgt gaacatttgc 20

<210> SEQ ID NO 1816
<211> LENGTH: 21
<212> TYPE: DNA
<213> ORGANISM: Homo sapiens

<400> SEQUENCE: 1816
atgggttttt gcacagatga c 21

<210> SEQ ID NO 1817
<211> LENGTH: 19
<212> TYPE: DNA
<213> ORGANISM: Homo sapiens

<400> SEQUENCE: 1817
gggagtcaga aggaggtca 19

<210> SEQ ID NO 1818
<211> LENGTH: 21
<212> TYPE: DNA
<213> ORGANISM: Homo sapiens

<400> SEQUENCE: 1818
cctctttttg catgaacctg a 21

<210> SEQ ID NO 1819
<211> LENGTH: 20
<212> TYPE: DNA
<213> ORGANISM: Homo sapiens

<400> SEQUENCE: 1819
ccttaccctt tccactcaga 20

<210> SEQ ID NO 1820
<211> LENGTH: 21
<212> TYPE: DNA
<213> ORGANISM: Homo sapiens

<400> SEQUENCE: 1820
gactggtata atcttgccgt g 21

<210> SEQ ID NO 1821
<211> LENGTH: 21
<212> TYPE: DNA
<213> ORGANISM: Homo sapiens

<400> SEQUENCE: 1821
tgtctgcatc ttgatctctg g 21

<210> SEQ ID NO 1822
<211> LENGTH: 19
<212> TYPE: DNA
<213> ORGANISM: Homo sapiens

<400> SEQUENCE: 1822
ggttccacag catttgagc 19

<210> SEQ ID NO 1823
<211> LENGTH: 20
<212> TYPE: DNA
<213> ORGANISM: Homo sapiens

<400> SEQUENCE: 1823
aggagccctt aactatggtg 20

<210> SEQ ID NO 1824
<211> LENGTH: 20
<212> TYPE: DNA
<213> ORGANISM: Homo sapiens

<400> SEQUENCE: 1824
tggcttgggt attgcagata 20

<210> SEQ ID NO 1825
<211> LENGTH: 20
<212> TYPE: DNA
<213> ORGANISM: Homo sapiens

<400> SEQUENCE: 1825
ggggacagta gaagatgagt 20

<210> SEQ ID NO 1826
<211> LENGTH: 20
<212> TYPE: DNA
<213> ORGANISM: Homo sapiens

<400> SEQUENCE: 1826
agttgtttct ggacggactt 20

<210> SEQ ID NO 1827
<211> LENGTH: 21
<212> TYPE: DNA
<213> ORGANISM: Homo sapiens

<400> SEQUENCE: 1827
agaatttccc tgtccatacc a 21

<210> SEQ ID NO 1828
<211> LENGTH: 20
<212> TYPE: DNA
<213> ORGANISM: Homo sapiens

<400> SEQUENCE: 1828
agtgagtgaa cttgccatca 20

<210> SEQ ID NO 1829
<211> LENGTH: 20
<212> TYPE: DNA
<213> ORGANISM: Homo sapiens

<400> SEQUENCE: 1829
ggcttttctc tgcactgatt 20

<210> SEQ ID NO 1830
<211> LENGTH: 21
<212> TYPE: DNA
<213> ORGANISM: Homo sapiens

<400> SEQUENCE: 1830
gcaaaggaaa caggctaact a 21

<210> SEQ ID NO 1831
<211> LENGTH: 21
<212> TYPE: DNA
<213> ORGANISM: Homo sapiens

<400> SEQUENCE: 1831
atggcagctg aatcgatatc t 21

<210> SEQ ID NO 1832
<211> LENGTH: 21
<212> TYPE: DNA
<213> ORGANISM: Homo sapiens

<400> SEQUENCE: 1832
taggtgatgg gcaaattctc a 21

<210> SEQ ID NO 1833
<211> LENGTH: 22
<212> TYPE: DNA
<213> ORGANISM: Homo sapiens

<400> SEQUENCE: 1833
gaaatgcctt cccacttaca at 22

<210> SEQ ID NO 1834
<211> LENGTH: 21
<212> TYPE: DNA
<213> ORGANISM: Homo sapiens

<400> SEQUENCE: 1834
attggcaaat gtacctgaag c 21

<210> SEQ ID NO 1835
<211> LENGTH: 21
<212> TYPE: DNA
<213> ORGANISM: Homo sapiens

<400> SEQUENCE: 1835
caatgattgc tcttgtgcca a 21

<210> SEQ ID NO 1836
<211> LENGTH: 21
<212> TYPE: DNA
<213> ORGANISM: Homo sapiens

<400> SEQUENCE: 1836
agctgtcctc ctctccatat a 21

<210> SEQ ID NO 1837
<211> LENGTH: 21
<212> TYPE: DNA
<213> ORGANISM: Homo sapiens

<400> SEQUENCE: 1837
ggcgttcaag ttactcgatt g 21

<210> SEQ ID NO 1838
<211> LENGTH: 21
<212> TYPE: DNA
<213> ORGANISM: Homo sapiens

<400> SEQUENCE: 1838
tagtgactag ctttggagag t 21

<210> SEQ ID NO 1839
<211> LENGTH: 22
<212> TYPE: DNA
<213> ORGANISM: Homo sapiens

<400> SEQUENCE: 1839
agccaatgat cccttatgac tt 22

<210> SEQ ID NO 1840
<211> LENGTH: 21
<212> TYPE: DNA
<213> ORGANISM: Homo sapiens

<400> SEQUENCE: 1840
aactaaactg gtaggcaatc g 21

<210> SEQ ID NO 1841
<211> LENGTH: 21
<212> TYPE: DNA
<213> ORGANISM: Homo sapiens

<400> SEQUENCE: 1841
caatcagacc acaggaagga a 21

<210> SEQ ID NO 1842
<211> LENGTH: 21
<212> TYPE: DNA
<213> ORGANISM: Homo sapiens

<400> SEQUENCE: 1842
gatgtgttta ttgcctgtgg t 21

<210> SEQ ID NO 1843
<211> LENGTH: 21
<212> TYPE: DNA
<213> ORGANISM: Homo sapiens

<400> SEQUENCE: 1843
gctcctttca tagtttcagg g 21

<210> SEQ ID NO 1844
<211> LENGTH: 22
<212> TYPE: DNA
<213> ORGANISM: Homo sapiens

<400> SEQUENCE: 1844
acacactgca gttctcacta ta 22

<210> SEQ ID NO 1845
<211> LENGTH: 21
<212> TYPE: DNA
<213> ORGANISM: Homo sapiens

<400> SEQUENCE: 1845
tgaatcaagt gacatgacag c 21

<210> SEQ ID NO 1846
<211> LENGTH: 21
<212> TYPE: DNA
<213> ORGANISM: Homo sapiens

<400> SEQUENCE: 1846
ttcttacagt cctcagcact t 21

<210> SEQ ID NO 1847
<211> LENGTH: 21
<212> TYPE: DNA
<213> ORGANISM: Homo sapiens

<400> SEQUENCE: 1847
ccactaggct gcactaatgt a 21

<210> SEQ ID NO 1848
<211> LENGTH: 22
<212> TYPE: DNA
<213> ORGANISM: Homo sapiens

<400> SEQUENCE: 1848
cactagcttc tgtaactgtg tg 22

<210> SEQ ID NO 1849
<211> LENGTH: 21
<212> TYPE: DNA

<213> ORGANISM: Homo sapiens

<400> SEQUENCE: 1849
gtctcacact gctcatttcc a 21

<210> SEQ ID NO 1850
<211> LENGTH: 21
<212> TYPE: DNA
<213> ORGANISM: Homo sapiens

<400> SEQUENCE: 1850
cactagggtt catcagctgt t 21

<210> SEQ ID NO 1851
<211> LENGTH: 21
<212> TYPE: DNA
<213> ORGANISM: Homo sapiens

<400> SEQUENCE: 1851
caaccaacat tagagtgacc c 21

<210> SEQ ID NO 1852
<211> LENGTH: 21
<212> TYPE: DNA
<213> ORGANISM: Homo sapiens

<400> SEQUENCE: 1852
gctggttgag agagagagag a 21

<210> SEQ ID NO 1853
<211> LENGTH: 21
<212> TYPE: DNA
<213> ORGANISM: Homo sapiens

<400> SEQUENCE: 1853
acaccagccg aatacagatt t 21

<210> SEQ ID NO 1854
<211> LENGTH: 21
<212> TYPE: DNA
<213> ORGANISM: Homo sapiens

<400> SEQUENCE: 1854
tgcttcatac ctttctgctt c 21

<210> SEQ ID NO 1855
<211> LENGTH: 21
<212> TYPE: DNA
<213> ORGANISM: Homo sapiens

<400> SEQUENCE: 1855
atttcccatg cctttcaact c 21

<210> SEQ ID NO 1856
<211> LENGTH: 21
<212> TYPE: DNA
<213> ORGANISM: Homo sapiens

<400> SEQUENCE: 1856
tctctcagta ggcgtcttta a 21

<210> SEQ ID NO 1857
<211> LENGTH: 20

<212> TYPE: DNA
<213> ORGANISM: Homo sapiens

<400> SEQUENCE: 1857
tgactgctac gctagacttg 20

<210> SEQ ID NO 1858
<211> LENGTH: 20
<212> TYPE: DNA
<213> ORGANISM: Homo sapiens

<400> SEQUENCE: 1858
ggatagagga aacccaggtg 20

<210> SEQ ID NO 1859
<211> LENGTH: 21
<212> TYPE: DNA
<213> ORGANISM: Homo sapiens

<400> SEQUENCE: 1859
ggctctttca aagtatccag g 21

<210> SEQ ID NO 1860
<211> LENGTH: 22
<212> TYPE: DNA
<213> ORGANISM: Homo sapiens

<400> SEQUENCE: 1860
agactttctt tgttgccttc ag 22

<210> SEQ ID NO 1861
<211> LENGTH: 20
<212> TYPE: DNA
<213> ORGANISM: Homo sapiens

<400> SEQUENCE: 1861
gcctcaacaa ttcagtccac 20

<210> SEQ ID NO 1862
<211> LENGTH: 22
<212> TYPE: DNA
<213> ORGANISM: Homo sapiens

<400> SEQUENCE: 1862
cataagttgc tggaagagaa ca 22

<210> SEQ ID NO 1863
<211> LENGTH: 21
<212> TYPE: DNA
<213> ORGANISM: Homo sapiens

<400> SEQUENCE: 1863
tcgactgctt taagtgaagg a 21

<210> SEQ ID NO 1864
<211> LENGTH: 22
<212> TYPE: DNA
<213> ORGANISM: Homo sapiens

<400> SEQUENCE: 1864
accagtgatt agtgtttctc ct 22

<210> SEQ ID NO 1865

<211> LENGTH: 21
<212> TYPE: DNA
<213> ORGANISM: Homo sapiens

<400> SEQUENCE: 1865
caagacacac acaaacacac a 21

<210> SEQ ID NO 1866
<211> LENGTH: 21
<212> TYPE: DNA
<213> ORGANISM: Homo sapiens

<400> SEQUENCE: 1866
ggtaagagtt gccctaatgt c 21

<210> SEQ ID NO 1867
<211> LENGTH: 20
<212> TYPE: DNA
<213> ORGANISM: Homo sapiens

<400> SEQUENCE: 1867
gcttggcttc tcacaaatgt 20

<210> SEQ ID NO 1868
<211> LENGTH: 20
<212> TYPE: DNA
<213> ORGANISM: Homo sapiens

<400> SEQUENCE: 1868
gtttgccagt agaaatggga 20

<210> SEQ ID NO 1869
<211> LENGTH: 20
<212> TYPE: DNA
<213> ORGANISM: Homo sapiens

<400> SEQUENCE: 1869
gtaaagtgtt cagaggacgg 20

<210> SEQ ID NO 1870
<211> LENGTH: 21
<212> TYPE: DNA
<213> ORGANISM: Homo sapiens

<400> SEQUENCE: 1870
actagggaga agaattggca g 21

<210> SEQ ID NO 1871
<211> LENGTH: 20
<212> TYPE: DNA
<213> ORGANISM: Homo sapiens

<400> SEQUENCE: 1871
ccagttcatt ccagcttcca 20

<210> SEQ ID NO 1872
<211> LENGTH: 22
<212> TYPE: DNA
<213> ORGANISM: Homo sapiens

<400> SEQUENCE: 1872
gatcgccaac ctgttttata ag 22

<210> SEQ ID NO 1873
<211> LENGTH: 21
<212> TYPE: DNA
<213> ORGANISM: Homo sapiens

<400> SEQUENCE: 1873
gctgtcaaag tggagataac c 21

<210> SEQ ID NO 1874
<211> LENGTH: 21
<212> TYPE: DNA
<213> ORGANISM: Homo sapiens

<400> SEQUENCE: 1874
aacgcttcca tccacctaat t 21

<210> SEQ ID NO 1875
<211> LENGTH: 21
<212> TYPE: DNA
<213> ORGANISM: Homo sapiens

<400> SEQUENCE: 1875
acctgcctgt cttaccatta a 21

<210> SEQ ID NO 1876
<211> LENGTH: 23
<212> TYPE: DNA
<213> ORGANISM: Homo sapiens

<400> SEQUENCE: 1876
gatactttcc tttctccaga tct 23

<210> SEQ ID NO 1877
<211> LENGTH: 20
<212> TYPE: DNA
<213> ORGANISM: Homo sapiens

<400> SEQUENCE: 1877
ggccgcagtt tttgatttag 20

<210> SEQ ID NO 1878
<211> LENGTH: 19
<212> TYPE: DNA
<213> ORGANISM: Homo sapiens

<400> SEQUENCE: 1878
tgggaaggac ggtttgtta 19

<210> SEQ ID NO 1879
<211> LENGTH: 20
<212> TYPE: DNA
<213> ORGANISM: Homo sapiens

<400> SEQUENCE: 1879
tgaatcatgc tgtggagaac 20

<210> SEQ ID NO 1880
<211> LENGTH: 20
<212> TYPE: DNA
<213> ORGANISM: Homo sapiens

<400> SEQUENCE: 1880
atagaagagg tacccagcaa 20

<210> SEQ ID NO 1881
<211> LENGTH: 20
<212> TYPE: DNA
<213> ORGANISM: Homo sapiens

<400> SEQUENCE: 1881
ccctgactat gctaagttgc 20

<210> SEQ ID NO 1882
<211> LENGTH: 20
<212> TYPE: DNA
<213> ORGANISM: Homo sapiens

<400> SEQUENCE: 1882
tgcaagcaaa atgaaaccag 20

<210> SEQ ID NO 1883
<211> LENGTH: 18
<212> TYPE: DNA
<213> ORGANISM: Homo sapiens

<400> SEQUENCE: 1883
aaaaaaaaaa aaaaaaaa 18

<210> SEQ ID NO 1884
<211> LENGTH: 19
<212> TYPE: DNA
<213> ORGANISM: Homo sapiens

<400> SEQUENCE: 1884
cagctgctcc ttctttagc 19

<210> SEQ ID NO 1885
<211> LENGTH: 20
<212> TYPE: DNA
<213> ORGANISM: Homo sapiens

<400> SEQUENCE: 1885
tatactgcca aaggtgacct 20

<210> SEQ ID NO 1886
<211> LENGTH: 21
<212> TYPE: DNA
<213> ORGANISM: Homo sapiens

<400> SEQUENCE: 1886
gaagcataat gagaacctcc a 21

<210> SEQ ID NO 1887
<211> LENGTH: 20
<212> TYPE: DNA
<213> ORGANISM: Homo sapiens

<400> SEQUENCE: 1887
aacccaactt gcagacaatc 20

<210> SEQ ID NO 1888
<211> LENGTH: 20
<212> TYPE: DNA
<213> ORGANISM: Homo sapiens

<400> SEQUENCE: 1888
atctgtttgc tgtgtcagaa 20

<210> SEQ ID NO 1889
<211> LENGTH: 23
<212> TYPE: DNA
<213> ORGANISM: Homo sapiens

<400> SEQUENCE: 1889
tccagatata ttcaaaaggg aga 23

<210> SEQ ID NO 1890
<211> LENGTH: 20
<212> TYPE: DNA
<213> ORGANISM: Homo sapiens

<400> SEQUENCE: 1890
aggtttttat caaagcccca 20

<210> SEQ ID NO 1891
<211> LENGTH: 21
<212> TYPE: DNA
<213> ORGANISM: Homo sapiens

<400> SEQUENCE: 1891
gggacttgat gttctaagca a 21

<210> SEQ ID NO 1892
<211> LENGTH: 20
<212> TYPE: DNA
<213> ORGANISM: Homo sapiens

<400> SEQUENCE: 1892
cctacatgat acgcacagtc 20

<210> SEQ ID NO 1893
<211> LENGTH: 18
<212> TYPE: DNA
<213> ORGANISM: Homo sapiens

<400> SEQUENCE: 1893
aaaaaaaaaa aaaaaaaa 18

<210> SEQ ID NO 1894
<211> LENGTH: 20
<212> TYPE: DNA
<213> ORGANISM: Homo sapiens

<400> SEQUENCE: 1894
gtttttctct acccagcaca 20

<210> SEQ ID NO 1895
<211> LENGTH: 21
<212> TYPE: DNA
<213> ORGANISM: Homo sapiens

<400> SEQUENCE: 1895
ctctaatttg ccaccctctt t 21

<210> SEQ ID NO 1896
<211> LENGTH: 20
<212> TYPE: DNA
<213> ORGANISM: Homo sapiens

<400> SEQUENCE: 1896
gaacgctaaa gcttttccca 20

<210> SEQ ID NO 1897
<211> LENGTH: 20
<212> TYPE: DNA
<213> ORGANISM: Homo sapiens

<400> SEQUENCE: 1897
tctttctcct gccaagtaga 20

<210> SEQ ID NO 1898
<211> LENGTH: 20
<212> TYPE: DNA
<213> ORGANISM: Homo sapiens

<400> SEQUENCE: 1898
ataacactgt ccttctgggc 20

<210> SEQ ID NO 1899
<211> LENGTH: 20
<212> TYPE: DNA
<213> ORGANISM: Homo sapiens

<400> SEQUENCE: 1899
gagcctactc tctgatacga 20

<210> SEQ ID NO 1900
<211> LENGTH: 21
<212> TYPE: DNA
<213> ORGANISM: Homo sapiens

<400> SEQUENCE: 1900
ccagttgttc acttctctga t 21

<210> SEQ ID NO 1901
<211> LENGTH: 20
<212> TYPE: DNA
<213> ORGANISM: Homo sapiens

<400> SEQUENCE: 1901
gccttaaaac caaactgtgt 20

<210> SEQ ID NO 1902
<211> LENGTH: 20
<212> TYPE: DNA
<213> ORGANISM: Homo sapiens

<400> SEQUENCE: 1902
ctggacttca atcacccaag 20

<210> SEQ ID NO 1903
<211> LENGTH: 20
<212> TYPE: DNA
<213> ORGANISM: Homo sapiens

<400> SEQUENCE: 1903
tgaacaaatt gctgtgctga 20

<210> SEQ ID NO 1904
<211> LENGTH: 20
<212> TYPE: DNA
<213> ORGANISM: Homo sapiens

<400> SEQUENCE: 1904
ccccctaaat gaaagtggtc 20

<210> SEQ ID NO 1905
<211> LENGTH: 18
<212> TYPE: DNA
<213> ORGANISM: Homo sapiens

<400> SEQUENCE: 1905
aaaaaaaaaa aaaaaaaa 18

<210> SEQ ID NO 1906
<211> LENGTH: 20
<212> TYPE: DNA
<213> ORGANISM: Homo sapiens

<400> SEQUENCE: 1906
tgagtgcttg gaattttgca 20

<210> SEQ ID NO 1907
<211> LENGTH: 20
<212> TYPE: DNA
<213> ORGANISM: Homo sapiens

<400> SEQUENCE: 1907
ggttggctac ttcatggtac 20

<210> SEQ ID NO 1908
<211> LENGTH: 20
<212> TYPE: DNA
<213> ORGANISM: Homo sapiens

<400> SEQUENCE: 1908
tcactgcatt cctagaacct 20

<210> SEQ ID NO 1909
<211> LENGTH: 20
<212> TYPE: DNA
<213> ORGANISM: Homo sapiens

<400> SEQUENCE: 1909
ataactcagg caaaatgggg 20

<210> SEQ ID NO 1910
<211> LENGTH: 20
<212> TYPE: DNA
<213> ORGANISM: Homo sapiens

<400> SEQUENCE: 1910
ccttctgctc tcactttacg 20

<210> SEQ ID NO 1911
<211> LENGTH: 20
<212> TYPE: DNA
<213> ORGANISM: Homo sapiens

<400> SEQUENCE: 1911
ggatactagc agaggtggag 20

<210> SEQ ID NO 1912
<211> LENGTH: 21
<212> TYPE: DNA
<213> ORGANISM: Homo sapiens

<400> SEQUENCE: 1912
tgtacacaat atgccaggaa c 21

<210> SEQ ID NO 1913
<211> LENGTH: 20
<212> TYPE: DNA
<213> ORGANISM: Homo sapiens

<400> SEQUENCE: 1913
gcacttgagt tatgggactt 20

<210> SEQ ID NO 1914
<211> LENGTH: 23
<212> TYPE: DNA
<213> ORGANISM: Homo sapiens

<400> SEQUENCE: 1914
tgtgatatgt agtgtgtatc agt 23

<210> SEQ ID NO 1915
<211> LENGTH: 20
<212> TYPE: DNA
<213> ORGANISM: Homo sapiens

<400> SEQUENCE: 1915
gaatgtgttc aaaggagggt 20

<210> SEQ ID NO 1916
<211> LENGTH: 20
<212> TYPE: DNA
<213> ORGANISM: Homo sapiens

<400> SEQUENCE: 1916
gatgaagggg attacgggaa 20

<210> SEQ ID NO 1917
<211> LENGTH: 20
<212> TYPE: DNA
<213> ORGANISM: Homo sapiens

<400> SEQUENCE: 1917
tttaggaagc agcacaagaa 20

<210> SEQ ID NO 1918
<211> LENGTH: 18
<212> TYPE: DNA
<213> ORGANISM: Homo sapiens

<400> SEQUENCE: 1918
gagggtgctg gggttatc 18

<210> SEQ ID NO 1919
<211> LENGTH: 20
<212> TYPE: DNA
<213> ORGANISM: Homo sapiens

<400> SEQUENCE: 1919
cccgaaagca cttacctttt 20

<210> SEQ ID NO 1920
<211> LENGTH: 20
<212> TYPE: DNA
<213> ORGANISM: Homo sapiens

<400> SEQUENCE: 1920
ttcatgagct gcaatgtgtt 20

<210> SEQ ID NO 1921
<211> LENGTH: 20
<212> TYPE: DNA
<213> ORGANISM: Homo sapiens

<400> SEQUENCE: 1921
tgctatgaaa agagggacca 20

<210> SEQ ID NO 1922
<211> LENGTH: 20
<212> TYPE: DNA
<213> ORGANISM: Homo sapiens

<400> SEQUENCE: 1922
gtcctggatc tacacgtgaa 20

<210> SEQ ID NO 1923
<211> LENGTH: 20
<212> TYPE: DNA
<213> ORGANISM: Homo sapiens

<400> SEQUENCE: 1923
gtaaatctgt gtgccagcaa 20

<210> SEQ ID NO 1924
<211> LENGTH: 20
<212> TYPE: DNA
<213> ORGANISM: Homo sapiens

<400> SEQUENCE: 1924
taaaagaggc gtgtggaaaa 20

<210> SEQ ID NO 1925
<211> LENGTH: 20
<212> TYPE: DNA
<213> ORGANISM: Homo sapiens

<400> SEQUENCE: 1925
ccagtagctt gtgatgtgta 20

<210> SEQ ID NO 1926
<211> LENGTH: 20
<212> TYPE: DNA
<213> ORGANISM: Homo sapiens

<400> SEQUENCE: 1926
tacaggcctc tgaaagatga 20

<210> SEQ ID NO 1927
<211> LENGTH: 20
<212> TYPE: DNA
<213> ORGANISM: Homo sapiens

<400> SEQUENCE: 1927
agagcatgct agacgtcttt 20

<210> SEQ ID NO 1928
<211> LENGTH: 20
<212> TYPE: DNA

<213> ORGANISM: Homo sapiens

<400> SEQUENCE: 1928
ctgggctgta attaaggctc 20

<210> SEQ ID NO 1929
<211> LENGTH: 20
<212> TYPE: DNA
<213> ORGANISM: Homo sapiens

<400> SEQUENCE: 1929
aacacctgca cactttgaaa 20

<210> SEQ ID NO 1930
<211> LENGTH: 20
<212> TYPE: DNA
<213> ORGANISM: Homo sapiens

<400> SEQUENCE: 1930
aatgaacttt gtgggctgaa 20

<210> SEQ ID NO 1931
<211> LENGTH: 20
<212> TYPE: DNA
<213> ORGANISM: Homo sapiens

<400> SEQUENCE: 1931
ccacactctc actggttcta 20

<210> SEQ ID NO 1932
<211> LENGTH: 20
<212> TYPE: DNA
<213> ORGANISM: Homo sapiens

<400> SEQUENCE: 1932
cacagtggat acctcaggaa 20

<210> SEQ ID NO 1933
<211> LENGTH: 20
<212> TYPE: DNA
<213> ORGANISM: Homo sapiens

<400> SEQUENCE: 1933
ccaacacagg aggaactttt 20

<210> SEQ ID NO 1934
<211> LENGTH: 22
<212> TYPE: DNA
<213> ORGANISM: Homo sapiens

<400> SEQUENCE: 1934
gagaaaagcc aacaaaaatg tg 22

<210> SEQ ID NO 1935
<211> LENGTH: 22
<212> TYPE: DNA
<213> ORGANISM: Homo sapiens

<400> SEQUENCE: 1935
tgtcattact agaagcacct tt 22

<210> SEQ ID NO 1936
<211> LENGTH: 23

<212> TYPE: DNA
<213> ORGANISM: Homo sapiens

<400> SEQUENCE: 1936
tggtgtgagt tcaggagggt tta 23

<210> SEQ ID NO 1937
<211> LENGTH: 20
<212> TYPE: DNA
<213> ORGANISM: Homo sapiens

<400> SEQUENCE: 1937
accatttctg acagaacaga 20

<210> SEQ ID NO 1938
<211> LENGTH: 20
<212> TYPE: DNA
<213> ORGANISM: Homo sapiens

<400> SEQUENCE: 1938
tgatgcttaa acacatgcct 20

<210> SEQ ID NO 1939
<211> LENGTH: 20
<212> TYPE: DNA
<213> ORGANISM: Homo sapiens

<400> SEQUENCE: 1939
aagggatatg cagcttgttc 20

<210> SEQ ID NO 1940
<211> LENGTH: 18
<212> TYPE: DNA
<213> ORGANISM: Homo sapiens

<400> SEQUENCE: 1940
aaaaaaaaaa aaaaaaaa 18

<210> SEQ ID NO 1941
<211> LENGTH: 22
<212> TYPE: DNA
<213> ORGANISM: Homo sapiens

<400> SEQUENCE: 1941
gttgtcattc aaatgtcacc ac 22

<210> SEQ ID NO 1942
<211> LENGTH: 19
<212> TYPE: DNA
<213> ORGANISM: Homo sapiens

<400> SEQUENCE: 1942
ctcagattcc agagccctc 19

<210> SEQ ID NO 1943
<211> LENGTH: 20
<212> TYPE: DNA
<213> ORGANISM: Homo sapiens

<400> SEQUENCE: 1943
acattgctag cagcttttgt 20

<210> SEQ ID NO 1944

<211> LENGTH: 21
<212> TYPE: DNA
<213> ORGANISM: Homo sapiens

<400> SEQUENCE: 1944
acttgccaag aacagtatct g 21

<210> SEQ ID NO 1945
<211> LENGTH: 20
<212> TYPE: DNA
<213> ORGANISM: Homo sapiens

<400> SEQUENCE: 1945
ttccttcttc caggtgaaca 20

<210> SEQ ID NO 1946
<211> LENGTH: 20
<212> TYPE: DNA
<213> ORGANISM: Homo sapiens

<400> SEQUENCE: 1946
tgtttctcct tcatctggtc 20

<210> SEQ ID NO 1947
<211> LENGTH: 20
<212> TYPE: DNA
<213> ORGANISM: Homo sapiens

<400> SEQUENCE: 1947
tgtcaccttg cagatacagg 20

<210> SEQ ID NO 1948
<211> LENGTH: 20
<212> TYPE: DNA
<213> ORGANISM: Homo sapiens

<400> SEQUENCE: 1948
attgttcaca gggtcaagtc 20

<210> SEQ ID NO 1949
<211> LENGTH: 20
<212> TYPE: DNA
<213> ORGANISM: Homo sapiens

<400> SEQUENCE: 1949
atgagccagg agaatcatca 20

<210> SEQ ID NO 1950
<211> LENGTH: 20
<212> TYPE: DNA
<213> ORGANISM: Homo sapiens

<400> SEQUENCE: 1950
catcatttca aaggggctca 20

<210> SEQ ID NO 1951
<211> LENGTH: 20
<212> TYPE: DNA
<213> ORGANISM: Homo sapiens

<400> SEQUENCE: 1951
tcttctctaa cacccactcc 20

<210> SEQ ID NO 1952
<211> LENGTH: 20
<212> TYPE: DNA
<213> ORGANISM: Homo sapiens

<400> SEQUENCE: 1952
acccttacca aagtagcatc 20

<210> SEQ ID NO 1953
<211> LENGTH: 20
<212> TYPE: DNA
<213> ORGANISM: Homo sapiens

<400> SEQUENCE: 1953
atcacgacgc cttgtttatt 20

<210> SEQ ID NO 1954
<211> LENGTH: 20
<212> TYPE: DNA
<213> ORGANISM: Homo sapiens

<400> SEQUENCE: 1954
actttcctgc caacaatctc 20

<210> SEQ ID NO 1955
<211> LENGTH: 20
<212> TYPE: DNA
<213> ORGANISM: Homo sapiens

<400> SEQUENCE: 1955
ttgatagttg catctgggga 20

<210> SEQ ID NO 1956
<211> LENGTH: 22
<212> TYPE: DNA
<213> ORGANISM: Homo sapiens

<400> SEQUENCE: 1956
tttgttaact aacgtgattc ca 22

<210> SEQ ID NO 1957
<211> LENGTH: 20
<212> TYPE: DNA
<213> ORGANISM: Homo sapiens

<400> SEQUENCE: 1957
cccactctcc atgtgttctt 20

<210> SEQ ID NO 1958
<211> LENGTH: 20
<212> TYPE: DNA
<213> ORGANISM: Homo sapiens

<400> SEQUENCE: 1958
tcctgcttca actcaatacg 20

<210> SEQ ID NO 1959
<211> LENGTH: 20
<212> TYPE: DNA
<213> ORGANISM: Homo sapiens

<400> SEQUENCE: 1959
acccctcatt ttcgtatgtc 20

<210> SEQ ID NO 1960
<211> LENGTH: 20
<212> TYPE: DNA
<213> ORGANISM: Homo sapiens

<400> SEQUENCE: 1960
acagttatgg aggaattgcg 20

<210> SEQ ID NO 1961
<211> LENGTH: 22
<212> TYPE: DNA
<213> ORGANISM: Homo sapiens

<400> SEQUENCE: 1961
tcaaacctct tttatctgtc cc 22

<210> SEQ ID NO 1962
<211> LENGTH: 20
<212> TYPE: DNA
<213> ORGANISM: Homo sapiens

<400> SEQUENCE: 1962
atttcacgta acactctggt 20

<210> SEQ ID NO 1963
<211> LENGTH: 21
<212> TYPE: DNA
<213> ORGANISM: Homo sapiens

<400> SEQUENCE: 1963
ctctggcaaa actttctgga t 21

<210> SEQ ID NO 1964
<211> LENGTH: 19
<212> TYPE: DNA
<213> ORGANISM: Homo sapiens

<400> SEQUENCE: 1964
gcttctcatg ctcacactg 19

<210> SEQ ID NO 1965
<211> LENGTH: 21
<212> TYPE: DNA
<213> ORGANISM: Homo sapiens

<400> SEQUENCE: 1965
aatatgactt gcccttttga a 21

<210> SEQ ID NO 1966
<211> LENGTH: 19
<212> TYPE: DNA
<213> ORGANISM: Homo sapiens

<400> SEQUENCE: 1966
tcacagccag ttacacaga 19

<210> SEQ ID NO 1967
<211> LENGTH: 20
<212> TYPE: DNA
<213> ORGANISM: Homo sapiens

<400> SEQUENCE: 1967
ctacagtgca gaagagtccc 20

<210> SEQ ID NO 1968
<211> LENGTH: 20
<212> TYPE: DNA
<213> ORGANISM: Homo sapiens

<400> SEQUENCE: 1968
ttggtttcat gtggctttga 20

<210> SEQ ID NO 1969
<211> LENGTH: 20
<212> TYPE: DNA
<213> ORGANISM: Homo sapiens

<400> SEQUENCE: 1969
tccttctccc caactttctt 20

<210> SEQ ID NO 1970
<211> LENGTH: 21
<212> TYPE: DNA
<213> ORGANISM: Homo sapiens

<400> SEQUENCE: 1970
ctttagattc cagggctctt g 21

<210> SEQ ID NO 1971
<211> LENGTH: 20
<212> TYPE: DNA
<213> ORGANISM: Homo sapiens

<400> SEQUENCE: 1971
tgaaagcgtg aaaatcagct 20

<210> SEQ ID NO 1972
<211> LENGTH: 20
<212> TYPE: DNA
<213> ORGANISM: Homo sapiens

<400> SEQUENCE: 1972
actcgatccc taggtaatgt 20

<210> SEQ ID NO 1973
<211> LENGTH: 20
<212> TYPE: DNA
<213> ORGANISM: Homo sapiens

<400> SEQUENCE: 1973
acaagtgggt agggatgttc 20

<210> SEQ ID NO 1974
<211> LENGTH: 20
<212> TYPE: DNA
<213> ORGANISM: Homo sapiens

<400> SEQUENCE: 1974
gcacaagttt tcagggaatg 20

<210> SEQ ID NO 1975
<211> LENGTH: 20
<212> TYPE: DNA
<213> ORGANISM: Homo sapiens

<400> SEQUENCE: 1975
gtggaaagtc tcgtcagaat 20

<210> SEQ ID NO 1976
<211> LENGTH: 20
<212> TYPE: DNA
<213> ORGANISM: Homo sapiens

<400> SEQUENCE: 1976
tccacctctg agcataacat 20

<210> SEQ ID NO 1977
<211> LENGTH: 18
<212> TYPE: DNA
<213> ORGANISM: Homo sapiens

<400> SEQUENCE: 1977
aaaaaaaaaa aaaaaaaa 18

<210> SEQ ID NO 1978
<211> LENGTH: 18
<212> TYPE: DNA
<213> ORGANISM: Homo sapiens

<400> SEQUENCE: 1978
aaaaaaaaaa aaaaaaaa 18

<210> SEQ ID NO 1979
<211> LENGTH: 20
<212> TYPE: DNA
<213> ORGANISM: Homo sapiens

<400> SEQUENCE: 1979
ccatcccact tctccagata 20

<210> SEQ ID NO 1980
<211> LENGTH: 20
<212> TYPE: DNA
<213> ORGANISM: Homo sapiens

<400> SEQUENCE: 1980
ccaccttcct gcttaaagaa 20

<210> SEQ ID NO 1981
<211> LENGTH: 20
<212> TYPE: DNA
<213> ORGANISM: Homo sapiens

<400> SEQUENCE: 1981
ctccttactt gcactgagtt 20

<210> SEQ ID NO 1982
<211> LENGTH: 20
<212> TYPE: DNA
<213> ORGANISM: Homo sapiens

<400> SEQUENCE: 1982
gggaaaactt acgggaactt 20

<210> SEQ ID NO 1983
<211> LENGTH: 22
<212> TYPE: DNA
<213> ORGANISM: Homo sapiens

<400> SEQUENCE: 1983
tagaaatgtt tagggtgcat ga 22

<210> SEQ ID NO 1984
<211> LENGTH: 20
<212> TYPE: DNA
<213> ORGANISM: Homo sapiens

<400> SEQUENCE: 1984 taccccctctt ttccatctgc 20

<210> SEQ ID NO 1985
<211> LENGTH: 20
<212> TYPE: DNA
<213> ORGANISM: Homo sapiens

<400> SEQUENCE: 1985
gcattttgac aggaaagtgg 20

<210> SEQ ID NO 1986
<211> LENGTH: 20
<212> TYPE: DNA
<213> ORGANISM: Homo sapiens

<400> SEQUENCE: 1986
tagggccaca gtttctcaat 20

<210> SEQ ID NO 1987
<211> LENGTH: 20
<212> TYPE: DNA
<213> ORGANISM: Homo sapiens

<400> SEQUENCE: 1987
gaatgagaaa tctggcagga 20

<210> SEQ ID NO 1988
<211> LENGTH: 20
<212> TYPE: DNA
<213> ORGANISM: Homo sapiens

<400> SEQUENCE: 1988
tcagatgcct gatgaccata 20

<210> SEQ ID NO 1989
<211> LENGTH: 20
<212> TYPE: DNA
<213> ORGANISM: Homo sapiens

<400> SEQUENCE: 1989
aatatgcagt gggtaggagc 20

<210> SEQ ID NO 1990
<211> LENGTH: 20
<212> TYPE: DNA
<213> ORGANISM: Homo sapiens

<400> SEQUENCE: 1990
gacaacagct gacttccatt 20

<210> SEQ ID NO 1991
<211> LENGTH: 20
<212> TYPE: DNA
<213> ORGANISM: Homo sapiens

<400> SEQUENCE: 1991
cactctctgg aacaaacaca 20

<210> SEQ ID NO 1992
<211> LENGTH: 20
<212> TYPE: DNA
<213> ORGANISM: Homo sapiens

<400> SEQUENCE: 1992
gttttgaggc ggtttcatga 20

<210> SEQ ID NO 1993
<211> LENGTH: 18
<212> TYPE: DNA
<213> ORGANISM: Homo sapiens

<400> SEQUENCE: 1993
aaaaaaaaaa aaaaaaaa 18

<210> SEQ ID NO 1994
<211> LENGTH: 20
<212> TYPE: DNA
<213> ORGANISM: Homo sapiens

<400> SEQUENCE: 1994
gaacacctca aagttgctca 20

<210> SEQ ID NO 1995
<211> LENGTH: 20
<212> TYPE: DNA
<213> ORGANISM: Homo sapiens

<400> SEQUENCE: 1995
aagaagcaag gacaaggatg 20

<210> SEQ ID NO 1996
<211> LENGTH: 20
<212> TYPE: DNA
<213> ORGANISM: Homo sapiens

<400> SEQUENCE: 1996
gaaacaacca ccacaacaaa 20

<210> SEQ ID NO 1997
<211> LENGTH: 20
<212> TYPE: DNA
<213> ORGANISM: Homo sapiens

<400> SEQUENCE: 1997
ccaccatgtt tacaccgttt 20

<210> SEQ ID NO 1998
<211> LENGTH: 20
<212> TYPE: DNA
<213> ORGANISM: Homo sapiens

<400> SEQUENCE: 1998
tttacccatg aattgctgca 20

<210> SEQ ID NO 1999
<211> LENGTH: 20
<212> TYPE: DNA
<213> ORGANISM: Homo sapiens

<400> SEQUENCE: 1999
agtttgcatt tgttcaggga 20

<210> SEQ ID NO 2000
<211> LENGTH: 20
<212> TYPE: DNA
<213> ORGANISM: Homo sapiens

<400> SEQUENCE: 2000
ttcggatggc tttgattgtc 20

<210> SEQ ID NO 2001
<211> LENGTH: 21
<212> TYPE: DNA
<213> ORGANISM: Homo sapiens

<400> SEQUENCE: 2001
cattgtaaat taaacggcct c 21

<210> SEQ ID NO 2002
<211> LENGTH: 20
<212> TYPE: DNA
<213> ORGANISM: Homo sapiens

<400> SEQUENCE: 2002
ctaatgcaag ctgcttctct 20

<210> SEQ ID NO 2003
<211> LENGTH: 20
<212> TYPE: DNA
<213> ORGANISM: Homo sapiens

<400> SEQUENCE: 2003
tgtctagtgg taatctgggg 20

<210> SEQ ID NO 2004
<211> LENGTH: 20
<212> TYPE: DNA
<213> ORGANISM: Homo sapiens

<400> SEQUENCE: 2004
tctggacagt ggagttgaaa 20

<210> SEQ ID NO 2005
<211> LENGTH: 18
<212> TYPE: DNA
<213> ORGANISM: Homo sapiens

<400> SEQUENCE: 2005
aaaaaaaaaa aaaaaaaa 18

<210> SEQ ID NO 2006
<211> LENGTH: 20
<212> TYPE: DNA
<213> ORGANISM: Homo sapiens

<400> SEQUENCE: 2006
aggagagaca taactggtct 20

<210> SEQ ID NO 2007
<211> LENGTH: 20
<212> TYPE: DNA

<213> ORGANISM: Homo sapiens

<400> SEQUENCE: 2007
attgcaatgt ctgtggatgt 20

<210> SEQ ID NO 2008
<211> LENGTH: 19
<212> TYPE: DNA
<213> ORGANISM: Homo sapiens

<400> SEQUENCE: 2008
aagaagttga ggtagcacg 19

<210> SEQ ID NO 2009
<211> LENGTH: 20
<212> TYPE: DNA
<213> ORGANISM: Homo sapiens

<400> SEQUENCE: 2009
agtgtccttt cctccagttc 20

<210> SEQ ID NO 2010
<211> LENGTH: 21
<212> TYPE: DNA
<213> ORGANISM: Homo sapiens

<400> SEQUENCE: 2010
ttgaacctga aaggaactgt g 21

<210> SEQ ID NO 2011
<211> LENGTH: 20
<212> TYPE: DNA
<213> ORGANISM: Homo sapiens

<400> SEQUENCE: 2011
gctcaatcac ctgttccctt 20

<210> SEQ ID NO 2012
<211> LENGTH: 21
<212> TYPE: DNA
<213> ORGANISM: Homo sapiens

<400> SEQUENCE: 2012
cattgaagct cactctaagg g 21

<210> SEQ ID NO 2013
<211> LENGTH: 20
<212> TYPE: DNA
<213> ORGANISM: Homo sapiens

<400> SEQUENCE: 2013
ctaaagtttg ggttaggggt 20

<210> SEQ ID NO 2014
<211> LENGTH: 20
<212> TYPE: DNA
<213> ORGANISM: Homo sapiens

<400> SEQUENCE: 2014
tgccttacat tttctgtggg 20

<210> SEQ ID NO 2015
<211> LENGTH: 20

<212> TYPE: DNA
<213> ORGANISM: Homo sapiens

<400> SEQUENCE: 2015
gccataagat ttccccactc 20

<210> SEQ ID NO 2016
<211> LENGTH: 21
<212> TYPE: DNA
<213> ORGANISM: Homo sapiens

<400> SEQUENCE: 2016
acaaagcaag aggatgaaac a 21

<210> SEQ ID NO 2017
<211> LENGTH: 20
<212> TYPE: DNA
<213> ORGANISM: Homo sapiens

<400> SEQUENCE: 2017
caaagcacca tcaacactta 20

<210> SEQ ID NO 2018
<211> LENGTH: 20
<212> TYPE: DNA
<213> ORGANISM: Homo sapiens

<400> SEQUENCE: 2018
cactgcaact cctagaatga 20

<210> SEQ ID NO 2019
<211> LENGTH: 20
<212> TYPE: DNA
<213> ORGANISM: Homo sapiens

<400> SEQUENCE: 2019
tgtggggaaa ttgctgttta 20

<210> SEQ ID NO 2020
<211> LENGTH: 20
<212> TYPE: DNA
<213> ORGANISM: Homo sapiens

<400> SEQUENCE: 2020
gtatgggcag ctgtaacttg 20

<210> SEQ ID NO 2021
<211> LENGTH: 20
<212> TYPE: DNA
<213> ORGANISM: Homo sapiens

<400> SEQUENCE: 2021
tcacaagcca ctgaaaatgt 20

<210> SEQ ID NO 2022
<211> LENGTH: 21
<212> TYPE: DNA
<213> ORGANISM: Homo sapiens

<400> SEQUENCE: 2022
tgtatgttaa gctagccaac a 21

<210> SEQ ID NO 2023

<211> LENGTH: 20
<212> TYPE: DNA
<213> ORGANISM: Homo sapiens

<400> SEQUENCE: 2023
tgtgttattg aactttgcca 20

<210> SEQ ID NO 2024
<211> LENGTH: 20
<212> TYPE: DNA
<213> ORGANISM: Homo sapiens

<400> SEQUENCE: 2024
ttcatcccta cctcatcacc 20

<210> SEQ ID NO 2025
<211> LENGTH: 21
<212> TYPE: DNA
<213> ORGANISM: Homo sapiens

<400> SEQUENCE: 2025
agatcacttt tggctgtaac c 21

<210> SEQ ID NO 2026
<211> LENGTH: 20
<212> TYPE: DNA
<213> ORGANISM: Homo sapiens

<400> SEQUENCE: 2026
caagtgacaa tctcagccaa 20

<210> SEQ ID NO 2027
<211> LENGTH: 20
<212> TYPE: DNA
<213> ORGANISM: Homo sapiens

<400> SEQUENCE: 2027
gcattttcag atggttccct 20

<210> SEQ ID NO 2028
<211> LENGTH: 20
<212> TYPE: DNA
<213> ORGANISM: Homo sapiens

<400> SEQUENCE: 2028
atggagagtt tgagtggagt 20

<210> SEQ ID NO 2029
<211> LENGTH: 22
<212> TYPE: DNA
<213> ORGANISM: Homo sapiens

<400> SEQUENCE: 2029
ctgccactgg gtttatagaa aa 22

<210> SEQ ID NO 2030
<211> LENGTH: 20
<212> TYPE: DNA
<213> ORGANISM: Homo sapiens

<400> SEQUENCE: 2030
acacctttac tcctgtggat 20

<210> SEQ ID NO 2031
<211> LENGTH: 20
<212> TYPE: DNA
<213> ORGANISM: Homo sapiens

<400> SEQUENCE: 2031
gatgtagggc cttatccaca 20

<210> SEQ ID NO 2032
<211> LENGTH: 20
<212> TYPE: DNA
<213> ORGANISM: Homo sapiens

<400> SEQUENCE: 2032
agcttggtga tcttcaaaca 20

<210> SEQ ID NO 2033
<211> LENGTH: 20
<212> TYPE: DNA
<213> ORGANISM: Homo sapiens

<400> SEQUENCE: 2033
tgaaatggtg ggtaatgctc 20

<210> SEQ ID NO 2034
<211> LENGTH: 20
<212> TYPE: DNA
<213> ORGANISM: Homo sapiens

<400> SEQUENCE: 2034
catgcaagtt cacgaggtta 20

<210> SEQ ID NO 2035
<211> LENGTH: 20
<212> TYPE: DNA
<213> ORGANISM: Homo sapiens

<400> SEQUENCE: 2035
agtctgagga agaagcaact 20

<210> SEQ ID NO 2036
<211> LENGTH: 20
<212> TYPE: DNA
<213> ORGANISM: Homo sapiens

<400> SEQUENCE: 2036
gagtccaatc ttttcccaca 20

<210> SEQ ID NO 2037
<211> LENGTH: 20
<212> TYPE: DNA
<213> ORGANISM: Homo sapiens

<400> SEQUENCE: 2037
tccactgcgt tcttatcctt 20

<210> SEQ ID NO 2038
<211> LENGTH: 20
<212> TYPE: DNA
<213> ORGANISM: Homo sapiens

<400> SEQUENCE: 2038
ggacagaaca gctacaaagg 20

<210> SEQ ID NO 2039
<211> LENGTH: 20
<212> TYPE: DNA
<213> ORGANISM: Homo sapiens

<400> SEQUENCE: 2039
ctggcttgtg aattagaggg 20

<210> SEQ ID NO 2040
<211> LENGTH: 19
<212> TYPE: DNA
<213> ORGANISM: Homo sapiens

<400> SEQUENCE: 2040
gtaagatggt gggcaggat 19

<210> SEQ ID NO 2041
<211> LENGTH: 20
<212> TYPE: DNA
<213> ORGANISM: Homo sapiens

<400> SEQUENCE: 2041
agaagggctc aaaacacatc 20

<210> SEQ ID NO 2042
<211> LENGTH: 21
<212> TYPE: DNA
<213> ORGANISM: Homo sapiens

<400> SEQUENCE: 2042
tcatgtaggc tttctgattt t 21

<210> SEQ ID NO 2043
<211> LENGTH: 20
<212> TYPE: DNA
<213> ORGANISM: Homo sapiens

<400> SEQUENCE: 2043
tgtagctctt gacctagcaa 20

<210> SEQ ID NO 2044
<211> LENGTH: 21
<212> TYPE: DNA
<213> ORGANISM: Homo sapiens

<400> SEQUENCE: 2044
taagttcacg gtgaagtcaa c 21

<210> SEQ ID NO 2045
<211> LENGTH: 20
<212> TYPE: DNA
<213> ORGANISM: Homo sapiens

<400> SEQUENCE: 2045
gtggcttcaa ctaactggac 20

<210> SEQ ID NO 2046
<211> LENGTH: 20
<212> TYPE: DNA
<213> ORGANISM: Homo sapiens

<400> SEQUENCE: 2046
acccgtaagt gtttgagtga 20

<210> SEQ ID NO 2047
<211> LENGTH: 20
<212> TYPE: DNA
<213> ORGANISM: Homo sapiens

<400> SEQUENCE: 2047
tgtagaagta gggtttgcgt 20

<210> SEQ ID NO 2048
<211> LENGTH: 20
<212> TYPE: DNA
<213> ORGANISM: Homo sapiens

<400> SEQUENCE: 2048
caggggacat ttgaagatgg 20

<210> SEQ ID NO 2049
<211> LENGTH: 20
<212> TYPE: DNA
<213> ORGANISM: Homo sapiens

<400> SEQUENCE: 2049
gaaattgtgc agtgaaagca 20

<210> SEQ ID NO 2050
<211> LENGTH: 21
<212> TYPE: DNA
<213> ORGANISM: Homo sapiens

<400> SEQUENCE: 2050
atgtaagaag tgcgttgctt a 21

<210> SEQ ID NO 2051
<211> LENGTH: 21
<212> TYPE: DNA
<213> ORGANISM: Homo sapiens

<400> SEQUENCE: 2051
agatctggaa tctgagactc c 21

<210> SEQ ID NO 2052
<211> LENGTH: 22
<212> TYPE: DNA
<213> ORGANISM: Homo sapiens

<400> SEQUENCE: 2052
tataggataa ggtcaagcag gt 22

<210> SEQ ID NO 2053
<211> LENGTH: 18
<212> TYPE: DNA
<213> ORGANISM: Homo sapiens

<400> SEQUENCE: 2053
aaaaaaaaaa aaaaaaaa 18

<210> SEQ ID NO 2054
<211> LENGTH: 21
<212> TYPE: DNA
<213> ORGANISM: Homo sapiens

<400> SEQUENCE: 2054
tcagtgaatg aggaatcatg c 21

<210> SEQ ID NO 2055
<211> LENGTH: 20
<212> TYPE: DNA
<213> ORGANISM: Homo sapiens

<400> SEQUENCE: 2055
ttctcaggag taccacaagc 20

<210> SEQ ID NO 2056
<211> LENGTH: 20
<212> TYPE: DNA
<213> ORGANISM: Homo sapiens

<400> SEQUENCE: 2056
ggatgaaaca cagaaccatg 20

<210> SEQ ID NO 2057
<211> LENGTH: 20
<212> TYPE: DNA
<213> ORGANISM: Homo sapiens

<400> SEQUENCE: 2057
cagatccctt tcattttgca 20

<210> SEQ ID NO 2058
<211> LENGTH: 20
<212> TYPE: DNA
<213> ORGANISM: Homo sapiens

<400> SEQUENCE: 2058
ggaaaagtgc tcaattaggc 20

<210> SEQ ID NO 2059
<211> LENGTH: 20
<212> TYPE: DNA
<213> ORGANISM: Homo sapiens

<400> SEQUENCE: 2059
ctggcagtta tagtcaccaa 20

<210> SEQ ID NO 2060
<211> LENGTH: 20
<212> TYPE: DNA
<213> ORGANISM: Homo sapiens

<400> SEQUENCE: 2060
aggaagtcct tatgatgcca 20

<210> SEQ ID NO 2061
<211> LENGTH: 20
<212> TYPE: DNA
<213> ORGANISM: Homo sapiens

<400> SEQUENCE: 2061
gctggtgaag ttggagtttt 20

<210> SEQ ID NO 2062
<211> LENGTH: 20
<212> TYPE: DNA
<213> ORGANISM: Homo sapiens

<400> SEQUENCE: 2062
gctgggttta agccacatat 20

<210> SEQ ID NO 2063
<211> LENGTH: 20
<212> TYPE: DNA
<213> ORGANISM: Homo sapiens

<400> SEQUENCE: 2063
tgtagcctaa atagcagcct 20

<210> SEQ ID NO 2064
<211> LENGTH: 23
<212> TYPE: DNA
<213> ORGANISM: Homo sapiens

<400> SEQUENCE: 2064
aggaattgct tttattttaa cca 23

<210> SEQ ID NO 2065
<211> LENGTH: 20
<212> TYPE: DNA
<213> ORGANISM: Homo sapiens

<400> SEQUENCE: 2065
gctgctttca ggtttttgtg 20

<210> SEQ ID NO 2066
<211> LENGTH: 20
<212> TYPE: DNA
<213> ORGANISM: Homo sapiens

<400> SEQUENCE: 2066
atggtgcaga aaagagcaat 20

<210> SEQ ID NO 2067
<211> LENGTH: 20
<212> TYPE: DNA
<213> ORGANISM: Homo sapiens

<400> SEQUENCE: 2067
gtgtggtgcc attttctttc 20

<210> SEQ ID NO 2068
<211> LENGTH: 20
<212> TYPE: DNA
<213> ORGANISM: Homo sapiens

<400> SEQUENCE: 2068
gaacaatact ttctccccgg 20

<210> SEQ ID NO 2069
<211> LENGTH: 20
<212> TYPE: DNA
<213> ORGANISM: Homo sapiens

<400> SEQUENCE: 2069
gaaatggcca tgctaggaat 20

<210> SEQ ID NO 2070
<211> LENGTH: 20
<212> TYPE: DNA
<213> ORGANISM: Homo sapiens

<400> SEQUENCE: 2070
acttccagta acatggatgc 20

<210> SEQ ID NO 2071
<211> LENGTH: 20
<212> TYPE: DNA
<213> ORGANISM: Homo sapiens

<400> SEQUENCE: 2071
gaaacaccca gacttgtagc 20

<210> SEQ ID NO 2072
<211> LENGTH: 20
<212> TYPE: DNA
<213> ORGANISM: Homo sapiens

<400> SEQUENCE: 2072
ttaaatcttt gtgtgcgtgt 20

<210> SEQ ID NO 2073
<211> LENGTH: 20
<212> TYPE: DNA
<213> ORGANISM: Homo sapiens

<400> SEQUENCE: 2073
cctccaggaa ctttgttcag 20

<210> SEQ ID NO 2074
<211> LENGTH: 20
<212> TYPE: DNA
<213> ORGANISM: Homo sapiens

<400> SEQUENCE: 2074
aaaaaccttc acaaacccca 20

<210> SEQ ID NO 2075
<211> LENGTH: 20
<212> TYPE: DNA
<213> ORGANISM: Homo sapiens

<400> SEQUENCE: 2075
gagtggatat tgtctcgctg 20

<210> SEQ ID NO 2076
<211> LENGTH: 20
<212> TYPE: DNA
<213> ORGANISM: Homo sapiens

<400> SEQUENCE: 2076
actagcccac taatgttgct 20

<210> SEQ ID NO 2077
<211> LENGTH: 22
<212> TYPE: DNA
<213> ORGANISM: Homo sapiens

<400> SEQUENCE: 2077
cgattatcag aacagatgag gt 22

<210> SEQ ID NO 2078
<211> LENGTH: 20
<212> TYPE: DNA
<213> ORGANISM: Homo sapiens

<400> SEQUENCE: 2078
attgcacagc tgaaaatcct 20

<210> SEQ ID NO 2079
<211> LENGTH: 20
<212> TYPE: DNA
<213> ORGANISM: Homo sapiens

<400> SEQUENCE: 2079
ggcacactga ccgtatttat 20

<210> SEQ ID NO 2080
<211> LENGTH: 20
<212> TYPE: DNA
<213> ORGANISM: Homo sapiens

<400> SEQUENCE: 2080
tggtagtggg tcaggaattt 20

<210> SEQ ID NO 2081
<211> LENGTH: 20
<212> TYPE: DNA
<213> ORGANISM: Homo sapiens

<400> SEQUENCE: 2081
tctcttgaaa agaaaggcgg 20

<210> SEQ ID NO 2082
<211> LENGTH: 20
<212> TYPE: DNA
<213> ORGANISM: Homo sapiens

<400> SEQUENCE: 2082
tgaattacac agcaaagccc 20

<210> SEQ ID NO 2083
<211> LENGTH: 20
<212> TYPE: DNA
<213> ORGANISM: Homo sapiens

<400> SEQUENCE: 2083
ctgccaatgg gatcgaattt 20

<210> SEQ ID NO 2084
<211> LENGTH: 20
<212> TYPE: DNA
<213> ORGANISM: Homo sapiens

<400> SEQUENCE: 2084
gagtgacgct gttcattctt 20

<210> SEQ ID NO 2085
<211> LENGTH: 20
<212> TYPE: DNA
<213> ORGANISM: Homo sapiens

<400> SEQUENCE: 2085
gatagtaacc gggtgtagca 20

<210> SEQ ID NO 2086
<211> LENGTH: 18
<212> TYPE: DNA

<213> ORGANISM: Homo sapiens

<400> SEQUENCE: 2086
aaaaaaaaaa aaaaaaaa 18

<210> SEQ ID NO 2087
<211> LENGTH: 23
<212> TYPE: DNA
<213> ORGANISM: Homo sapiens

<400> SEQUENCE: 2087
tctaataagg gattgatgga gtt 23

<210> SEQ ID NO 2088
<211> LENGTH: 20
<212> TYPE: DNA
<213> ORGANISM: Homo sapiens

<400> SEQUENCE: 2088
gggagatttc ctgcttgtag 20

<210> SEQ ID NO 2089
<211> LENGTH: 20
<212> TYPE: DNA
<213> ORGANISM: Homo sapiens

<400> SEQUENCE: 2089
aatccatgca gcttctctct 20

<210> SEQ ID NO 2090
<211> LENGTH: 20
<212> TYPE: DNA
<213> ORGANISM: Homo sapiens

<400> SEQUENCE: 2090
tgcattgtct ctggtttgaa 20

<210> SEQ ID NO 2091
<211> LENGTH: 20
<212> TYPE: DNA
<213> ORGANISM: Homo sapiens

<400> SEQUENCE: 2091
tcctgaatgc atccttaacc 20

<210> SEQ ID NO 2092
<211> LENGTH: 20
<212> TYPE: DNA
<213> ORGANISM: Homo sapiens

<400> SEQUENCE: 2092
tgggaaaggt gagaaggatt 20

<210> SEQ ID NO 2093
<211> LENGTH: 20
<212> TYPE: DNA
<213> ORGANISM: Homo sapiens

<400> SEQUENCE: 2093
ttcgggaccc atacctaaaa 20

<210> SEQ ID NO 2094
<211> LENGTH: 20

<212> TYPE: DNA
<213> ORGANISM: Homo sapiens

<400> SEQUENCE: 2094
tcttttctgg acccacatga 20

<210> SEQ ID NO 2095
<211> LENGTH: 22
<212> TYPE: DNA
<213> ORGANISM: Homo sapiens

<400> SEQUENCE: 2095
gacctctaca tctgtatctt cc 22

<210> SEQ ID NO 2096
<211> LENGTH: 20
<212> TYPE: DNA
<213> ORGANISM: Homo sapiens

<400> SEQUENCE: 2096
cccttcattt tctgtcccat 20

<210> SEQ ID NO 2097
<211> LENGTH: 21
<212> TYPE: DNA
<213> ORGANISM: Homo sapiens

<400> SEQUENCE: 2097
tcagccttga gtattagcct a 21

<210> SEQ ID NO 2098
<211> LENGTH: 20
<212> TYPE: DNA
<213> ORGANISM: Homo sapiens

<400> SEQUENCE: 2098
aagtttgcca tgaaggtcat 20

<210> SEQ ID NO 2099
<211> LENGTH: 20
<212> TYPE: DNA
<213> ORGANISM: Homo sapiens

<400> SEQUENCE: 2099
gacttctggt tgtttcctca 20

<210> SEQ ID NO 2100
<211> LENGTH: 20
<212> TYPE: DNA
<213> ORGANISM: Homo sapiens

<400> SEQUENCE: 2100
atgtgtctat tgccctacct 20

<210> SEQ ID NO 2101
<211> LENGTH: 19
<212> TYPE: DNA
<213> ORGANISM: Homo sapiens

<400> SEQUENCE: 2101
tgcgggaagt tcacatgaa 19

<210> SEQ ID NO 2102

<211> LENGTH: 19
<212> TYPE: DNA
<213> ORGANISM: Homo sapiens

<400> SEQUENCE: 2102
gtgaacttca ggctgctta 19

<210> SEQ ID NO 2103
<211> LENGTH: 20
<212> TYPE: DNA
<213> ORGANISM: Homo sapiens

<400> SEQUENCE: 2103
tggtttcgtc ccgtaaatag 20

<210> SEQ ID NO 2104
<211> LENGTH: 20
<212> TYPE: DNA
<213> ORGANISM: Homo sapiens

<400> SEQUENCE: 2104
aattcctttc aatgctggct 20

<210> SEQ ID NO 2105
<211> LENGTH: 21
<212> TYPE: DNA
<213> ORGANISM: Homo sapiens

<400> SEQUENCE: 2105
agaaagacac atatgccatg g 21

<210> SEQ ID NO 2106
<211> LENGTH: 20
<212> TYPE: DNA
<213> ORGANISM: Homo sapiens

<400> SEQUENCE: 2106
ttgttggtgt cagttctgaa 20

<210> SEQ ID NO 2107
<211> LENGTH: 20
<212> TYPE: DNA
<213> ORGANISM: Homo sapiens

<400> SEQUENCE: 2107
tgtaggaaca gattagggca 20

<210> SEQ ID NO 2108
<211> LENGTH: 20
<212> TYPE: DNA
<213> ORGANISM: Homo sapiens

<400> SEQUENCE: 2108
ctccaagctg atatgccatc 20

<210> SEQ ID NO 2109
<211> LENGTH: 20
<212> TYPE: DNA
<213> ORGANISM: Homo sapiens

<400> SEQUENCE: 2109
ccacccctca tttcttcctt 20

<210> SEQ ID NO 2110
<211> LENGTH: 20
<212> TYPE: DNA
<213> ORGANISM: Homo sapiens

<400> SEQUENCE: 2110
gggtccttcg ttttctgttt 20

<210> SEQ ID NO 2111
<211> LENGTH: 21
<212> TYPE: DNA
<213> ORGANISM: Homo sapiens

<400> SEQUENCE: 2111
taggaaacag gctaaaaggg a 21

<210> SEQ ID NO 2112
<211> LENGTH: 20
<212> TYPE: DNA
<213> ORGANISM: Homo sapiens

<400> SEQUENCE: 2112
tactgtgtag aaggcagtgt 20

<210> SEQ ID NO 2113
<211> LENGTH: 20
<212> TYPE: DNA
<213> ORGANISM: Homo sapiens

<400> SEQUENCE: 2113
gctaaggaca aagaaccact 20

<210> SEQ ID NO 2114
<211> LENGTH: 18
<212> TYPE: DNA
<213> ORGANISM: Homo sapiens

<400> SEQUENCE: 2114
aaaaaaaaaa aaaaaaaa 18

<210> SEQ ID NO 2115
<211> LENGTH: 20
<212> TYPE: DNA
<213> ORGANISM: Homo sapiens

<400> SEQUENCE: 2115
tggctaagac caggattgtt 20

<210> SEQ ID NO 2116
<211> LENGTH: 18
<212> TYPE: DNA
<213> ORGANISM: Homo sapiens

<400> SEQUENCE: 2116
aaaaaaaaaa aaaaaaaa 18

<210> SEQ ID NO 2117
<211> LENGTH: 20
<212> TYPE: DNA
<213> ORGANISM: Homo sapiens

<400> SEQUENCE: 2117
tgataggcag atcattcccc 20

<210> SEQ ID NO 2118
<211> LENGTH: 20
<212> TYPE: DNA
<213> ORGANISM: Homo sapiens

<400> SEQUENCE: 2118
gcaaatggca aagggaaaac 20

<210> SEQ ID NO 2119
<211> LENGTH: 19
<212> TYPE: DNA
<213> ORGANISM: Homo sapiens

<400> SEQUENCE: 2119
cacggctagt gctcatttt 19

<210> SEQ ID NO 2120
<211> LENGTH: 21
<212> TYPE: DNA
<213> ORGANISM: Homo sapiens

<400> SEQUENCE: 2120
ccgtaatacc caagtcatct g 21

<210> SEQ ID NO 2121
<211> LENGTH: 22
<212> TYPE: DNA
<213> ORGANISM: Homo sapiens

<400> SEQUENCE: 2121
agcaaactaa aacagcaact tc 22

<210> SEQ ID NO 2122
<211> LENGTH: 19
<212> TYPE: DNA
<213> ORGANISM: Homo sapiens

<400> SEQUENCE: 2122
agcctgctat cttcactgg 19

<210> SEQ ID NO 2123
<211> LENGTH: 23
<212> TYPE: DNA
<213> ORGANISM: Homo sapiens

<400> SEQUENCE: 2123
accacatata tagagacttt gaa 23

<210> SEQ ID NO 2124
<211> LENGTH: 19
<212> TYPE: DNA
<213> ORGANISM: Homo sapiens

<400> SEQUENCE: 2124
ctccagactc tgcaaggat 19

<210> SEQ ID NO 2125
<211> LENGTH: 20
<212> TYPE: DNA
<213> ORGANISM: Homo sapiens

<400> SEQUENCE: 2125
tttcctgttg ctcttgatca 20

<210> SEQ ID NO 2126
<211> LENGTH: 20
<212> TYPE: DNA
<213> ORGANISM: Homo sapiens

<400> SEQUENCE: 2126
ccacaaagat gaaggccaag 20

<210> SEQ ID NO 2127
<211> LENGTH: 21
<212> TYPE: DNA
<213> ORGANISM: Homo sapiens

<400> SEQUENCE: 2127
ccatacctta gttctcaggg t 21

<210> SEQ ID NO 2128
<211> LENGTH: 20
<212> TYPE: DNA
<213> ORGANISM: Homo sapiens

<400> SEQUENCE: 2128
gtaagagaga gctgggacaa 20

<210> SEQ ID NO 2129
<211> LENGTH: 20
<212> TYPE: DNA
<213> ORGANISM: Homo sapiens

<400> SEQUENCE: 2129
tgtgaccatc ctatccacaa 20

<210> SEQ ID NO 2130
<211> LENGTH: 20
<212> TYPE: DNA
<213> ORGANISM: Homo sapiens

<400> SEQUENCE: 2130
agaaccagtt gtacgagttc 20

<210> SEQ ID NO 2131
<211> LENGTH: 20
<212> TYPE: DNA
<213> ORGANISM: Homo sapiens

<400> SEQUENCE: 2131
agtcttctcc cttccttgtc 20

<210> SEQ ID NO 2132
<211> LENGTH: 20
<212> TYPE: DNA
<213> ORGANISM: Homo sapiens

<400> SEQUENCE: 2132
gcccttttct ctctttgacc 20

<210> SEQ ID NO 2133
<211> LENGTH: 21
<212> TYPE: DNA
<213> ORGANISM: Homo sapiens

<400> SEQUENCE: 2133
tcttgttcca agtattcctg g 21

<210> SEQ ID NO 2134
<211> LENGTH: 20
<212> TYPE: DNA
<213> ORGANISM: Homo sapiens

<400> SEQUENCE: 2134
accactttag cccatctctt 20

<210> SEQ ID NO 2135
<211> LENGTH: 20
<212> TYPE: DNA
<213> ORGANISM: Homo sapiens

<400> SEQUENCE: 2135
gtggtggatt attgagctgg 20

<210> SEQ ID NO 2136
<211> LENGTH: 21
<212> TYPE: DNA
<213> ORGANISM: Homo sapiens

<400> SEQUENCE: 2136
tgcttaatgg gatcattgac c 21

<210> SEQ ID NO 2137
<211> LENGTH: 20
<212> TYPE: DNA
<213> ORGANISM: Homo sapiens

<400> SEQUENCE: 2137
cccacatagt gcaaaagaca 20

<210> SEQ ID NO 2138
<211> LENGTH: 20
<212> TYPE: DNA
<213> ORGANISM: Homo sapiens

<400> SEQUENCE: 2138
gtatgtgtga agtagccgag 20

<210> SEQ ID NO 2139
<211> LENGTH: 20
<212> TYPE: DNA
<213> ORGANISM: Homo sapiens

<400> SEQUENCE: 2139
tggtcctaac tcagaccttt 20

<210> SEQ ID NO 2140
<211> LENGTH: 20
<212> TYPE: DNA
<213> ORGANISM: Homo sapiens

<400> SEQUENCE: 2140
aacatgaagg gaaggttgtg 20

<210> SEQ ID NO 2141
<211> LENGTH: 21
<212> TYPE: DNA
<213> ORGANISM: Homo sapiens

<400> SEQUENCE: 2141
tatacttcaa cttgcaggca g 21

<210> SEQ ID NO 2142
<211> LENGTH: 21
<212> TYPE: DNA
<213> ORGANISM: Homo sapiens

<400> SEQUENCE: 2142
gccaaagaca atgagagagt c 21

<210> SEQ ID NO 2143
<211> LENGTH: 21
<212> TYPE: DNA
<213> ORGANISM: Homo sapiens

<400> SEQUENCE: 2143
atttagcagc catgaccagt a 21

<210> SEQ ID NO 2144
<211> LENGTH: 21
<212> TYPE: DNA
<213> ORGANISM: Homo sapiens

<400> SEQUENCE: 2144
tgggccaatt cctaatccat t 21

<210> SEQ ID NO 2145
<211> LENGTH: 23
<212> TYPE: DNA
<213> ORGANISM: Homo sapiens

<400> SEQUENCE: 2145
cgatctcatg aataagtctg acc 23

<210> SEQ ID NO 2146
<211> LENGTH: 21
<212> TYPE: DNA
<213> ORGANISM: Homo sapiens

<400> SEQUENCE: 2146
tggaaagcag actaacagtg a 21

<210> SEQ ID NO 2147
<211> LENGTH: 21
<212> TYPE: DNA
<213> ORGANISM: Homo sapiens

<400> SEQUENCE: 2147
gggaccctat gtagagattg t 21

<210> SEQ ID NO 2148
<211> LENGTH: 21
<212> TYPE: DNA
<213> ORGANISM: Homo sapiens

<400> SEQUENCE: 2148
ggagcccaag gatgtattag a 21

<210> SEQ ID NO 2149
<211> LENGTH: 21
<212> TYPE: DNA
<213> ORGANISM: Homo sapiens

<400> SEQUENCE: 2149
ctaatagctg gttctgcaca c 21

<210> SEQ ID NO 2150
<211> LENGTH: 22
<212> TYPE: DNA
<213> ORGANISM: Homo sapiens

<400> SEQUENCE: 2150
gatgaaatga atgctgactc tc 22

<210> SEQ ID NO 2151
<211> LENGTH: 21
<212> TYPE: DNA
<213> ORGANISM: Homo sapiens

<400> SEQUENCE: 2151
aaactgaagc ttcgagaacc c 21

<210> SEQ ID NO 2152
<211> LENGTH: 21
<212> TYPE: DNA
<213> ORGANISM: Homo sapiens

<400> SEQUENCE: 2152
tgccgacaac tactttaggt a 21

<210> SEQ ID NO 2153
<211> LENGTH: 21
<212> TYPE: DNA
<213> ORGANISM: Homo sapiens

<400> SEQUENCE: 2153
tgtatccaat cacctgtcag a 21

<210> SEQ ID NO 2154
<211> LENGTH: 21
<212> TYPE: DNA
<213> ORGANISM: Homo sapiens

<400> SEQUENCE: 2154
cagcacctta agcagaaatc a 21

<210> SEQ ID NO 2155
<211> LENGTH: 21
<212> TYPE: DNA
<213> ORGANISM: Homo sapiens

<400> SEQUENCE: 2155
aagcccttca tccatttctc t 21

<210> SEQ ID NO 2156
<211> LENGTH: 21
<212> TYPE: DNA
<213> ORGANISM: Homo sapiens

<400> SEQUENCE: 2156
atcttggtgc catcttaagg t 21

<210> SEQ ID NO 2157
<211> LENGTH: 21
<212> TYPE: DNA
<213> ORGANISM: Homo sapiens

<400> SEQUENCE: 2157
agcaaaccaa tcgcaaacta g 21

<210> SEQ ID NO 2158
<211> LENGTH: 22
<212> TYPE: DNA
<213> ORGANISM: Homo sapiens

<400> SEQUENCE: 2158
aatcatcatc ttcatcagct cg 22

<210> SEQ ID NO 2159
<211> LENGTH: 21
<212> TYPE: DNA
<213> ORGANISM: Homo sapiens

<400> SEQUENCE: 2159
cctttcgcct tgcttatatg g 21

<210> SEQ ID NO 2160
<211> LENGTH: 21
<212> TYPE: DNA
<213> ORGANISM: Homo sapiens

<400> SEQUENCE: 2160
actactcaac agcctaccaa a 21

<210> SEQ ID NO 2161
<211> LENGTH: 21
<212> TYPE: DNA
<213> ORGANISM: Homo sapiens

<400> SEQUENCE: 2161
tggagctggg aactttaatg t 21

<210> SEQ ID NO 2162
<211> LENGTH: 21
<212> TYPE: DNA
<213> ORGANISM: Homo sapiens

<400> SEQUENCE: 2162
gaagagagag agaatgcgtg t 21

<210> SEQ ID NO 2163
<211> LENGTH: 21
<212> TYPE: DNA
<213> ORGANISM: Homo sapiens

<400> SEQUENCE: 2163
gacatggata ttctggtgcc a 21

<210> SEQ ID NO 2164
<211> LENGTH: 21
<212> TYPE: DNA
<213> ORGANISM: Homo sapiens

<400> SEQUENCE: 2164
ctgttgcaag atgacccaaa t 21

<210> SEQ ID NO 2165
<211> LENGTH: 22
<212> TYPE: DNA

<213> ORGANISM: Homo sapiens

<400> SEQUENCE: 2165
agatacacac acgttcacaa ac 22

<210> SEQ ID NO 2166
<211> LENGTH: 21
<212> TYPE: DNA
<213> ORGANISM: Homo sapiens

<400> SEQUENCE: 2166
gatggcaatg cttgataacg a 21

<210> SEQ ID NO 2167
<211> LENGTH: 22
<212> TYPE: DNA
<213> ORGANISM: Homo sapiens

<400> SEQUENCE: 2167
ttccatgaag ttcctcaaga ct 22

<210> SEQ ID NO 2168
<211> LENGTH: 21
<212> TYPE: DNA
<213> ORGANISM: Homo sapiens

<400> SEQUENCE: 2168
ccacccacat accctgaaat t 21

<210> SEQ ID NO 2169
<211> LENGTH: 20
<212> TYPE: DNA
<213> ORGANISM: Homo sapiens

<400> SEQUENCE: 2169
gtaacacacg gatgctgaag 20

<210> SEQ ID NO 2170
<211> LENGTH: 21
<212> TYPE: DNA
<213> ORGANISM: Homo sapiens

<400> SEQUENCE: 2170
tggacacgag gctatttgta g 21

<210> SEQ ID NO 2171
<211> LENGTH: 21
<212> TYPE: DNA
<213> ORGANISM: Homo sapiens

<400> SEQUENCE: 2171
ggcttaagaa ggagagtggt t 21

<210> SEQ ID NO 2172
<211> LENGTH: 21
<212> TYPE: DNA
<213> ORGANISM: Homo sapiens

<400> SEQUENCE: 2172
tagtttcctt tggccttctc c 21

<210> SEQ ID NO 2173
<211> LENGTH: 21

<212> TYPE: DNA
<213> ORGANISM: Homo sapiens

<400> SEQUENCE: 2173
ctagggttcc cagttcacaa a 21

<210> SEQ ID NO 2174
<211> LENGTH: 21
<212> TYPE: DNA
<213> ORGANISM: Homo sapiens

<400> SEQUENCE: 2174
gaaacaacat tgagggcatt g 21

<210> SEQ ID NO 2175
<211> LENGTH: 21
<212> TYPE: DNA
<213> ORGANISM: Homo sapiens

<400> SEQUENCE: 2175
gagctctttg aagtagaagc a 21

<210> SEQ ID NO 2176
<211> LENGTH: 20
<212> TYPE: DNA
<213> ORGANISM: Homo sapiens

<400> SEQUENCE: 2176
ccattccaac aaagcttccg 20

<210> SEQ ID NO 2177
<211> LENGTH: 21
<212> TYPE: DNA
<213> ORGANISM: Homo sapiens

<400> SEQUENCE: 2177
ctacttgccc tattgtgtcg a 21

<210> SEQ ID NO 2178
<211> LENGTH: 21
<212> TYPE: DNA
<213> ORGANISM: Homo sapiens

<400> SEQUENCE: 2178
ccagggtgtt tgaaggtaga a 21

<210> SEQ ID NO 2179
<211> LENGTH: 21
<212> TYPE: DNA
<213> ORGANISM: Homo sapiens

<400> SEQUENCE: 2179
ctggaggtaa gaaggaatgc a 21

<210> SEQ ID NO 2180
<211> LENGTH: 20
<212> TYPE: DNA
<213> ORGANISM: Homo sapiens

<400> SEQUENCE: 2180
atgtgggact ctttgctctc 20

<210> SEQ ID NO 2181

<211> LENGTH: 21
<212> TYPE: DNA
<213> ORGANISM: Homo sapiens

<400> SEQUENCE: 2181
atgaatacag ctttgcatgg c 21

<210> SEQ ID NO 2182
<211> LENGTH: 21
<212> TYPE: DNA
<213> ORGANISM: Homo sapiens

<400> SEQUENCE: 2182
gttaaagcat tcacagccct c 21

<210> SEQ ID NO 2183
<211> LENGTH: 21
<212> TYPE: DNA
<213> ORGANISM: Homo sapiens

<400> SEQUENCE: 2183
ctgggacttg tctatcctcc t 21

<210> SEQ ID NO 2184
<211> LENGTH: 21
<212> TYPE: DNA
<213> ORGANISM: Homo sapiens

<400> SEQUENCE: 2184
atgtctgtcc aagtgaacag t 21

<210> SEQ ID NO 2185
<211> LENGTH: 21
<212> TYPE: DNA
<213> ORGANISM: Homo sapiens

<400> SEQUENCE: 2185
aaagtatcca gacccagaac c 21

<210> SEQ ID NO 2186
<211> LENGTH: 21
<212> TYPE: DNA
<213> ORGANISM: Homo sapiens

<400> SEQUENCE: 2186
ataggccagc actccaaata a 21

<210> SEQ ID NO 2187
<211> LENGTH: 21
<212> TYPE: DNA
<213> ORGANISM: Homo sapiens

<400> SEQUENCE: 2187
caaatcaagt cccatggtag g 21

<210> SEQ ID NO 2188
<211> LENGTH: 21
<212> TYPE: DNA
<213> ORGANISM: Homo sapiens

<400> SEQUENCE: 2188
ctttccgtct ttataggcag c 21

<210> SEQ ID NO 2189
<211> LENGTH: 21
<212> TYPE: DNA
<213> ORGANISM: Homo sapiens

<400> SEQUENCE: 2189
agaaatcgtg ttcacagcct a 21

<210> SEQ ID NO 2190
<211> LENGTH: 21
<212> TYPE: DNA
<213> ORGANISM: Homo sapiens

<400> SEQUENCE: 2190
ccgtaaatga agtggcttga a 21

<210> SEQ ID NO 2191
<211> LENGTH: 21
<212> TYPE: DNA
<213> ORGANISM: Homo sapiens

<400> SEQUENCE: 2191
cctttcttgc aaccttgaga t 21

<210> SEQ ID NO 2192
<211> LENGTH: 21
<212> TYPE: DNA
<213> ORGANISM: Homo sapiens

<400> SEQUENCE: 2192
ctctagatgc tcaacctcag g 21

<210> SEQ ID NO 2193
<211> LENGTH: 21
<212> TYPE: DNA
<213> ORGANISM: Homo sapiens

<400> SEQUENCE: 2193
aataacagtc caccagaacc a 21

<210> SEQ ID NO 2194
<211> LENGTH: 21
<212> TYPE: DNA
<213> ORGANISM: Homo sapiens

<400> SEQUENCE: 2194
tccaaggacc tgcaaatgtt a 21

<210> SEQ ID NO 2195
<211> LENGTH: 21
<212> TYPE: DNA
<213> ORGANISM: Homo sapiens

<400> SEQUENCE: 2195
aggttacatc attcacccac a 21

<210> SEQ ID NO 2196
<211> LENGTH: 21
<212> TYPE: DNA
<213> ORGANISM: Homo sapiens

<400> SEQUENCE: 2196
atgaagacaa tgacatctgc g 21

<210> SEQ ID NO 2197
<211> LENGTH: 21
<212> TYPE: DNA
<213> ORGANISM: Homo sapiens

<400> SEQUENCE: 2197
cacttgtcat ggtttaggga c 21

<210> SEQ ID NO 2198
<211> LENGTH: 21
<212> TYPE: DNA
<213> ORGANISM: Homo sapiens

<400> SEQUENCE: 2198
acctccacct tattgcttca a 21

<210> SEQ ID NO 2199
<211> LENGTH: 21
<212> TYPE: DNA
<213> ORGANISM: Homo sapiens

<400> SEQUENCE: 2199
gaattgcaaa ggatgggtag g 21

<210> SEQ ID NO 2200
<211> LENGTH: 21
<212> TYPE: DNA
<213> ORGANISM: Homo sapiens

<400> SEQUENCE: 2200
ctgcattgtg agtccatgta a 21

<210> SEQ ID NO 2201
<211> LENGTH: 21
<212> TYPE: DNA
<213> ORGANISM: Homo sapiens

<400> SEQUENCE: 2201
tcctatcttc atccctcttc c 21

<210> SEQ ID NO 2202
<211> LENGTH: 21
<212> TYPE: DNA
<213> ORGANISM: Homo sapiens

<400> SEQUENCE: 2202
ttccatttag cctcccatct g 21

<210> SEQ ID NO 2203
<211> LENGTH: 21
<212> TYPE: DNA
<213> ORGANISM: Homo sapiens

<400> SEQUENCE: 2203
tagctttatg ggccttgttc t 21

<210> SEQ ID NO 2204
<211> LENGTH: 21
<212> TYPE: DNA
<213> ORGANISM: Homo sapiens

<400> SEQUENCE: 2204
ccacctctca aacccagatt t 21

<210> SEQ ID NO 2205
<211> LENGTH: 22
<212> TYPE: DNA
<213> ORGANISM: Homo sapiens

<400> SEQUENCE: 2205
gtcagcgtat ttgggattga at 22

<210> SEQ ID NO 2206
<211> LENGTH: 21
<212> TYPE: DNA
<213> ORGANISM: Homo sapiens

<400> SEQUENCE: 2206
aaatctgcca cccatttctt c 21

<210> SEQ ID NO 2207
<211> LENGTH: 21
<212> TYPE: DNA
<213> ORGANISM: Homo sapiens

<400> SEQUENCE: 2207
tattctgagt tctacccagg t 21

<210> SEQ ID NO 2208
<211> LENGTH: 21
<212> TYPE: DNA
<213> ORGANISM: Homo sapiens

<400> SEQUENCE: 2208
tacatgagac ccagaaacag a 21

<210> SEQ ID NO 2209
<211> LENGTH: 21
<212> TYPE: DNA
<213> ORGANISM: Homo sapiens

<400> SEQUENCE: 2209
cttcttggca gactatcagg a 21

<210> SEQ ID NO 2210
<211> LENGTH: 21
<212> TYPE: DNA
<213> ORGANISM: Homo sapiens

<400> SEQUENCE: 2210
aagctgctaa atctgtaggg a 21

<210> SEQ ID NO 2211
<211> LENGTH: 21
<212> TYPE: DNA
<213> ORGANISM: Homo sapiens

<400> SEQUENCE: 2211
ctgaccagac ctgttgacta a 21

<210> SEQ ID NO 2212
<211> LENGTH: 22
<212> TYPE: DNA
<213> ORGANISM: Homo sapiens

<400> SEQUENCE: 2212
tgatatgttc agtttgccta cc 22

<210> SEQ ID NO 2213
<211> LENGTH: 20
<212> TYPE: DNA
<213> ORGANISM: Homo sapiens

<400> SEQUENCE: 2213
agcttgagtt tcttgctggg 20

<210> SEQ ID NO 2214
<211> LENGTH: 21
<212> TYPE: DNA
<213> ORGANISM: Homo sapiens

<400> SEQUENCE: 2214
ttcccgcaaa gtagaagcta t 21

<210> SEQ ID NO 2215
<211> LENGTH: 21
<212> TYPE: DNA
<213> ORGANISM: Homo sapiens

<400> SEQUENCE: 2215
aaacgcatac aaacaggaga c 21

<210> SEQ ID NO 2216
<211> LENGTH: 21
<212> TYPE: DNA
<213> ORGANISM: Homo sapiens

<400> SEQUENCE: 2216
cttctaaacc catcacctgc t 21

<210> SEQ ID NO 2217
<211> LENGTH: 21
<212> TYPE: DNA
<213> ORGANISM: Homo sapiens

<400> SEQUENCE: 2217
cacccaaact cacaggtaca a 21

<210> SEQ ID NO 2218
<211> LENGTH: 21
<212> TYPE: DNA
<213> ORGANISM: Homo sapiens

<400> SEQUENCE: 2218
tgaattctga gatcgagagc c 21

<210> SEQ ID NO 2219
<211> LENGTH: 21
<212> TYPE: DNA
<213> ORGANISM: Homo sapiens

<400> SEQUENCE: 2219
agattaactg ttgcctcact g 21

<210> SEQ ID NO 2220
<211> LENGTH: 20
<212> TYPE: DNA
<213> ORGANISM: Homo sapiens

<400> SEQUENCE: 2220
caagacagtg cattccatgg 20

<210> SEQ ID NO 2221
<211> LENGTH: 21
<212> TYPE: DNA
<213> ORGANISM: Homo sapiens

<400> SEQUENCE: 2221
ccaaggaaag agttgagaag g 21

<210> SEQ ID NO 2222
<211> LENGTH: 21
<212> TYPE: DNA
<213> ORGANISM: Homo sapiens

<400> SEQUENCE: 2222
tgagtgcagt cgataaggaa g 21

<210> SEQ ID NO 2223
<211> LENGTH: 21
<212> TYPE: DNA
<213> ORGANISM: Homo sapiens

<400> SEQUENCE: 2223
aacaccgaga aagagagaga g 21

<210> SEQ ID NO 2224
<211> LENGTH: 21
<212> TYPE: DNA
<213> ORGANISM: Homo sapiens

<400> SEQUENCE: 2224
tgtactgctt tcgtcttatg c 21

<210> SEQ ID NO 2225
<211> LENGTH: 21
<212> TYPE: DNA
<213> ORGANISM: Homo sapiens

<400> SEQUENCE: 2225
catattcgca ctgtatagcc g 21

<210> SEQ ID NO 2226
<211> LENGTH: 21
<212> TYPE: DNA
<213> ORGANISM: Homo sapiens

<400> SEQUENCE: 2226
ctgatggatt ctctggtgtg a 21

<210> SEQ ID NO 2227
<211> LENGTH: 21
<212> TYPE: DNA
<213> ORGANISM: Homo sapiens

<400> SEQUENCE: 2227
tcaaggagaa gagagagggt a 21

<210> SEQ ID NO 2228
<211> LENGTH: 21
<212> TYPE: DNA
<213> ORGANISM: Homo sapiens

<400> SEQUENCE: 2228
tctcccaaag cagacaaaga c 21

<210> SEQ ID NO 2229
<211> LENGTH: 21
<212> TYPE: DNA
<213> ORGANISM: Homo sapiens

<400> SEQUENCE: 2229
agtcagttgt tacgtgcaaa g 21

<210> SEQ ID NO 2230
<211> LENGTH: 21
<212> TYPE: DNA
<213> ORGANISM: Homo sapiens

<400> SEQUENCE: 2230
aaaggtttgt tcatcctccc t 21

<210> SEQ ID NO 2231
<211> LENGTH: 21
<212> TYPE: DNA
<213> ORGANISM: Homo sapiens

<400> SEQUENCE: 2231
acagagcacg caatatagga a 21

<210> SEQ ID NO 2232
<211> LENGTH: 21
<212> TYPE: DNA
<213> ORGANISM: Homo sapiens

<400> SEQUENCE: 2232
ctgcattcac ccatgtactt t 21

<210> SEQ ID NO 2233
<211> LENGTH: 21
<212> TYPE: DNA
<213> ORGANISM: Homo sapiens

<400> SEQUENCE: 2233
tccagccata ccatgtctat c 21

<210> SEQ ID NO 2234
<211> LENGTH: 21
<212> TYPE: DNA
<213> ORGANISM: Homo sapiens

<400> SEQUENCE: 2234
ctcactaggg aagaacagca g 21

<210> SEQ ID NO 2235
<211> LENGTH: 22
<212> TYPE: DNA
<213> ORGANISM: Homo sapiens

<400> SEQUENCE: 2235
tgctgggtct gagtgttata aa 22

<210> SEQ ID NO 2236
<211> LENGTH: 21
<212> TYPE: DNA
<213> ORGANISM: Homo sapiens

<400> SEQUENCE: 2236
gttgtgtgaa tggtgctgtt a 21

<210> SEQ ID NO 2237
<211> LENGTH: 21
<212> TYPE: DNA
<213> ORGANISM: Homo sapiens

<400> SEQUENCE: 2237
ggcccagaag actcttgtaa t 21

<210> SEQ ID NO 2238
<211> LENGTH: 21
<212> TYPE: DNA
<213> ORGANISM: Homo sapiens

<400> SEQUENCE: 2238
cgacctacat cagctaatgg t 21

<210> SEQ ID NO 2239
<211> LENGTH: 22
<212> TYPE: DNA
<213> ORGANISM: Homo sapiens

<400> SEQUENCE: 2239
aagggaagaa taacaatggt gc 22

<210> SEQ ID NO 2240
<211> LENGTH: 21
<212> TYPE: DNA
<213> ORGANISM: Homo sapiens

<400> SEQUENCE: 2240
atgggagtat gggagtagga a 21

<210> SEQ ID NO 2241
<211> LENGTH: 20
<212> TYPE: DNA
<213> ORGANISM: Homo sapiens

<400> SEQUENCE: 2241
ttggtggctt gcagagattt 20

<210> SEQ ID NO 2242
<211> LENGTH: 22
<212> TYPE: DNA
<213> ORGANISM: Homo sapiens

<400> SEQUENCE: 2242
tcacacgatc atcatactca ca 22

<210> SEQ ID NO 2243
<211> LENGTH: 21
<212> TYPE: DNA
<213> ORGANISM: Homo sapiens

<400> SEQUENCE: 2243
ggtagcagat gactagacga t 21

<210> SEQ ID NO 2244
<211> LENGTH: 21
<212> TYPE: DNA

<213> ORGANISM: Homo sapiens

<400> SEQUENCE: 2244
acgcctctgt catttcctaa c 21

<210> SEQ ID NO 2245
<211> LENGTH: 21
<212> TYPE: DNA
<213> ORGANISM: Homo sapiens

<400> SEQUENCE: 2245
cagttgactc aatggtgcaa t 21

<210> SEQ ID NO 2246
<211> LENGTH: 21
<212> TYPE: DNA
<213> ORGANISM: Homo sapiens

<400> SEQUENCE: 2246
ataggttaca gattgccacg t 21

<210> SEQ ID NO 2247
<211> LENGTH: 21
<212> TYPE: DNA
<213> ORGANISM: Homo sapiens

<400> SEQUENCE: 2247
gatgctgcta tcaaaggaac a 21

<210> SEQ ID NO 2248
<211> LENGTH: 21
<212> TYPE: DNA
<213> ORGANISM: Homo sapiens

<400> SEQUENCE: 2248
aagacaaaga gatggaaggc a 21

<210> SEQ ID NO 2249
<211> LENGTH: 21
<212> TYPE: DNA
<213> ORGANISM: Homo sapiens

<400> SEQUENCE: 2249
aataccctct tcccttcctc a 21

<210> SEQ ID NO 2250
<211> LENGTH: 22
<212> TYPE: DNA
<213> ORGANISM: Homo sapiens

<400> SEQUENCE: 2250
ccaccgtcaa tatttatcag ct 22

<210> SEQ ID NO 2251
<211> LENGTH: 21
<212> TYPE: DNA
<213> ORGANISM: Homo sapiens

<400> SEQUENCE: 2251
gcctcagtcc aaatcttaga t 21

<210> SEQ ID NO 2252
<211> LENGTH: 22

<212> TYPE: DNA
<213> ORGANISM: Homo sapiens

<400> SEQUENCE: 2252
ccttaggatt ctcaaagagt gt 22

<210> SEQ ID NO 2253
<211> LENGTH: 22
<212> TYPE: DNA
<213> ORGANISM: Homo sapiens

<400> SEQUENCE: 2253
gcagtacaga ttcttgaaca gt 22

<210> SEQ ID NO 2254
<211> LENGTH: 22
<212> TYPE: DNA
<213> ORGANISM: Homo sapiens

<400> SEQUENCE: 2254
agaggattag atgtcttgct gt 22

<210> SEQ ID NO 2255
<211> LENGTH: 21
<212> TYPE: DNA
<213> ORGANISM: Homo sapiens

<400> SEQUENCE: 2255
tactgcaggc aattcaggta a 21

<210> SEQ ID NO 2256
<211> LENGTH: 21
<212> TYPE: DNA
<213> ORGANISM: Homo sapiens

<400> SEQUENCE: 2256
gaagaggtcc agtaagtgag g 21

<210> SEQ ID NO 2257
<211> LENGTH: 21
<212> TYPE: DNA
<213> ORGANISM: Homo sapiens

<400> SEQUENCE: 2257
ttgtgagtcc ttgtctcctt g 21

<210> SEQ ID NO 2258
<211> LENGTH: 21
<212> TYPE: DNA
<213> ORGANISM: Homo sapiens

<400> SEQUENCE: 2258
gacgactaag acattgcatc a 21

<210> SEQ ID NO 2259
<211> LENGTH: 21
<212> TYPE: DNA
<213> ORGANISM: Homo sapiens

<400> SEQUENCE: 2259
agaagtctct ctccgttgtt t 21

<210> SEQ ID NO 2260

<211> LENGTH: 21
<212> TYPE: DNA
<213> ORGANISM: Homo sapiens

<400> SEQUENCE: 2260
cttatgtgca tcaactgtgc t 21

<210> SEQ ID NO 2261
<211> LENGTH: 21
<212> TYPE: DNA
<213> ORGANISM: Homo sapiens

<400> SEQUENCE: 2261
agtgtctctc agaatcagga c 21

<210> SEQ ID NO 2262
<211> LENGTH: 21
<212> TYPE: DNA
<213> ORGANISM: Homo sapiens

<400> SEQUENCE: 2262
tttatttccc tacgcaaagc c 21

<210> SEQ ID NO 2263
<211> LENGTH: 21
<212> TYPE: DNA
<213> ORGANISM: Homo sapiens

<400> SEQUENCE: 2263
agcctttgat gactgagttg a 21

<210> SEQ ID NO 2264
<211> LENGTH: 21
<212> TYPE: DNA
<213> ORGANISM: Homo sapiens

<400> SEQUENCE: 2264
ttggtttcta ttctgcactg c 21

<210> SEQ ID NO 2265
<211> LENGTH: 21
<212> TYPE: DNA
<213> ORGANISM: Homo sapiens

<400> SEQUENCE: 2265
ttagagcttg ctagtatcgg g 21

<210> SEQ ID NO 2266
<211> LENGTH: 21
<212> TYPE: DNA
<213> ORGANISM: Homo sapiens

<400> SEQUENCE: 2266
gaaatcccaa actgcctgaa a 21

<210> SEQ ID NO 2267
<211> LENGTH: 21
<212> TYPE: DNA
<213> ORGANISM: Homo sapiens

<400> SEQUENCE: 2267
atccttcttg tgaaccttcc t 21

<210> SEQ ID NO 2268
<211> LENGTH: 22
<212> TYPE: DNA
<213> ORGANISM: Homo sapiens

<400> SEQUENCE: 2268
accagatgca tgtgattaaa gg 22

<210> SEQ ID NO 2269
<211> LENGTH: 21
<212> TYPE: DNA
<213> ORGANISM: Homo sapiens

<400> SEQUENCE: 2269
gtgtactcta ggctactgtc a 21

<210> SEQ ID NO 2270
<211> LENGTH: 21
<212> TYPE: DNA
<213> ORGANISM: Homo sapiens

<400> SEQUENCE: 2270
gtcagcagca agtaaaggtt c 21

<210> SEQ ID NO 2271
<211> LENGTH: 21
<212> TYPE: DNA
<213> ORGANISM: Homo sapiens

<400> SEQUENCE: 2271
catctagtca agggttccac a 21

<210> SEQ ID NO 2272
<211> LENGTH: 21
<212> TYPE: DNA
<213> ORGANISM: Homo sapiens

<400> SEQUENCE: 2272
caagtcatgc tccaaactgt t 21

<210> SEQ ID NO 2273
<211> LENGTH: 21
<212> TYPE: DNA
<213> ORGANISM: Homo sapiens

<400> SEQUENCE: 2273
aggacttagg acaacagaga a 21

<210> SEQ ID NO 2274
<211> LENGTH: 21
<212> TYPE: DNA
<213> ORGANISM: Homo sapiens

<400> SEQUENCE: 2274
tgcccaacac catctctaat a 21

<210> SEQ ID NO 2275
<211> LENGTH: 21
<212> TYPE: DNA
<213> ORGANISM: Homo sapiens

<400> SEQUENCE: 2275
gccttcatca ctcagaactt c 21

<210> SEQ ID NO 2276
<211> LENGTH: 21
<212> TYPE: DNA
<213> ORGANISM: Homo sapiens

<400> SEQUENCE: 2276
agggtatcta ttctccggac a 21

<210> SEQ ID NO 2277
<211> LENGTH: 21
<212> TYPE: DNA
<213> ORGANISM: Homo sapiens

<400> SEQUENCE: 2277
atttgcccaa gtaagttcca c 21

<210> SEQ ID NO 2278
<211> LENGTH: 21
<212> TYPE: DNA
<213> ORGANISM: Homo sapiens

<400> SEQUENCE: 2278
tggaagtaca tgggatgcat t 21

<210> SEQ ID NO 2279
<211> LENGTH: 21
<212> TYPE: DNA
<213> ORGANISM: Homo sapiens

<400> SEQUENCE: 2279
cttgaagagt tccaatgcca a 21

<210> SEQ ID NO 2280
<211> LENGTH: 21
<212> TYPE: DNA
<213> ORGANISM: Homo sapiens

<400> SEQUENCE: 2280
cgctgctgtt taaatcgatc a 21

<210> SEQ ID NO 2281
<211> LENGTH: 21
<212> TYPE: DNA
<213> ORGANISM: Homo sapiens

<400> SEQUENCE: 2281
gctctgcttt gctcaaattc t 21

<210> SEQ ID NO 2282
<211> LENGTH: 22
<212> TYPE: DNA
<213> ORGANISM: Homo sapiens

<400> SEQUENCE: 2282
tgagctccag aattagatgt gt 22

<210> SEQ ID NO 2283
<211> LENGTH: 22
<212> TYPE: DNA
<213> ORGANISM: Homo sapiens

<400> SEQUENCE: 2283
aacacctcct ttctcactac ag 22

<210> SEQ ID NO 2284
<211> LENGTH: 20
<212> TYPE: DNA
<213> ORGANISM: Homo sapiens

<400> SEQUENCE: 2284
acaaacttca ttcaccgcag 20

<210> SEQ ID NO 2285
<211> LENGTH: 20
<212> TYPE: DNA
<213> ORGANISM: Homo sapiens

<400> SEQUENCE: 2285
aactacgcca cccaactaaa 20

<210> SEQ ID NO 2286
<211> LENGTH: 21
<212> TYPE: DNA
<213> ORGANISM: Homo sapiens

<400> SEQUENCE: 2286
gcttcagtgt aaccatgact c 21

<210> SEQ ID NO 2287
<211> LENGTH: 22
<212> TYPE: DNA
<213> ORGANISM: Homo sapiens

<400> SEQUENCE: 2287
tgcacaatta agctacttct cc 22

<210> SEQ ID NO 2288
<211> LENGTH: 21
<212> TYPE: DNA
<213> ORGANISM: Homo sapiens

<400> SEQUENCE: 2288
caacaccaaa cttgcctgaa t 21

<210> SEQ ID NO 2289
<211> LENGTH: 21
<212> TYPE: DNA
<213> ORGANISM: Homo sapiens

<400> SEQUENCE: 2289
tccacaattt ctacagcaac c 21

<210> SEQ ID NO 2290
<211> LENGTH: 21
<212> TYPE: DNA
<213> ORGANISM: Homo sapiens

<400> SEQUENCE: 2290
gtgtcatttg attggtgctc t 21

<210> SEQ ID NO 2291
<211> LENGTH: 22
<212> TYPE: DNA
<213> ORGANISM: Homo sapiens

<400> SEQUENCE: 2291
gggtgtttca gtaggttagg at 22

<210> SEQ ID NO 2292
<211> LENGTH: 21
<212> TYPE: DNA
<213> ORGANISM: Homo sapiens

<400> SEQUENCE: 2292
tgggattcta atgtctggtg c 21

<210> SEQ ID NO 2293
<211> LENGTH: 18
<212> TYPE: DNA
<213> ORGANISM: Homo sapiens

<400> SEQUENCE: 2293
agaggtggtt ggttggtt 18

<210> SEQ ID NO 2294
<211> LENGTH: 21
<212> TYPE: DNA
<213> ORGANISM: Homo sapiens

<400> SEQUENCE: 2294
gggcatcctg tctgaaatat g 21

<210> SEQ ID NO 2295
<211> LENGTH: 21
<212> TYPE: DNA
<213> ORGANISM: Homo sapiens

<400> SEQUENCE: 2295
aagaagcgca gatacagtac a 21

<210> SEQ ID NO 2296
<211> LENGTH: 21
<212> TYPE: DNA
<213> ORGANISM: Homo sapiens

<400> SEQUENCE: 2296
cacagcaagt ttgaacctag t 21

<210> SEQ ID NO 2297
<211> LENGTH: 21
<212> TYPE: DNA
<213> ORGANISM: Homo sapiens

<400> SEQUENCE: 2297
agtgcaaatg atgacctgtt g 21

<210> SEQ ID NO 2298
<211> LENGTH: 21
<212> TYPE: DNA
<213> ORGANISM: Homo sapiens

<400> SEQUENCE: 2298
gaactgttgc atgagaggta c 21

<210> SEQ ID NO 2299
<211> LENGTH: 21
<212> TYPE: DNA
<213> ORGANISM: Homo sapiens

<400> SEQUENCE: 2299
ctttgtcctt ctctgttgtg t 21

<210> SEQ ID NO 2300
<211> LENGTH: 22
<212> TYPE: DNA
<213> ORGANISM: Homo sapiens

<400> SEQUENCE: 2300
tttcttctag agtccagagg tg 22

<210> SEQ ID NO 2301
<211> LENGTH: 21
<212> TYPE: DNA
<213> ORGANISM: Homo sapiens

<400> SEQUENCE: 2301
attctcttct ctcttccagc c 21

<210> SEQ ID NO 2302
<211> LENGTH: 21
<212> TYPE: DNA
<213> ORGANISM: Homo sapiens

<400> SEQUENCE: 2302
tatggctttg ctaccttgtc a 21

<210> SEQ ID NO 2303
<211> LENGTH: 21
<212> TYPE: DNA
<213> ORGANISM: Homo sapiens

<400> SEQUENCE: 2303
ctatttctct ggctcttgac c 21

<210> SEQ ID NO 2304
<211> LENGTH: 21
<212> TYPE: DNA
<213> ORGANISM: Homo sapiens

<400> SEQUENCE: 2304
ttcttaaacc tctgtgtggc t 21

<210> SEQ ID NO 2305
<211> LENGTH: 21
<212> TYPE: DNA
<213> ORGANISM: Homo sapiens

<400> SEQUENCE: 2305
tggacaaaca agaactgggt a 21

<210> SEQ ID NO 2306
<211> LENGTH: 21
<212> TYPE: DNA
<213> ORGANISM: Homo sapiens

<400> SEQUENCE: 2306
ccatgatcac tgaaaccaac a 21

<210> SEQ ID NO 2307
<211> LENGTH: 21
<212> TYPE: DNA
<213> ORGANISM: Homo sapiens

<400> SEQUENCE: 2307
ccatatgccc tgctctttaa g 21

<210> SEQ ID NO 2308
<211> LENGTH: 21
<212> TYPE: DNA
<213> ORGANISM: Homo sapiens

<400> SEQUENCE: 2308
gggtggacaa agcaattcaa a 21

<210> SEQ ID NO 2309
<211> LENGTH: 22
<212> TYPE: DNA
<213> ORGANISM: Homo sapiens

<400> SEQUENCE: 2309
cagcattcaa ttcatccttg tg 22

<210> SEQ ID NO 2310
<211> LENGTH: 21
<212> TYPE: DNA
<213> ORGANISM: Homo sapiens

<400> SEQUENCE: 2310
aagtagaagc aagccctgaa t 21

<210> SEQ ID NO 2311
<211> LENGTH: 22
<212> TYPE: DNA
<213> ORGANISM: Homo sapiens

<400> SEQUENCE: 2311
gtgtggtagg gatgagaatt at 22

<210> SEQ ID NO 2312
<211> LENGTH: 20
<212> TYPE: DNA
<213> ORGANISM: Homo sapiens

<400> SEQUENCE: 2312
tcaggtaagc ttccctccac 20

<210> SEQ ID NO 2313
<211> LENGTH: 21
<212> TYPE: DNA
<213> ORGANISM: Homo sapiens

<400> SEQUENCE: 2313
actggttgta gaaaggacct c 21

<210> SEQ ID NO 2314
<211> LENGTH: 21
<212> TYPE: DNA
<213> ORGANISM: Homo sapiens

<400> SEQUENCE: 2314
agtaagaggc cagaagtcag a 21

<210> SEQ ID NO 2315
<211> LENGTH: 21
<212> TYPE: DNA
<213> ORGANISM: Homo sapiens

<400> SEQUENCE: 2315
gcagtgcagg cctatatata g 21

<210> SEQ ID NO 2316
<211> LENGTH: 21
<212> TYPE: DNA
<213> ORGANISM: Homo sapiens

<400> SEQUENCE: 2316
aaatctctga gtcggccata a 21

<210> SEQ ID NO 2317
<211> LENGTH: 20
<212> TYPE: DNA
<213> ORGANISM: Homo sapiens

<400> SEQUENCE: 2317
aggcatggca aacttacttg 20

<210> SEQ ID NO 2318
<211> LENGTH: 21
<212> TYPE: DNA
<213> ORGANISM: Homo sapiens

<400> SEQUENCE: 2318
catttcactt tcgaggatgg t 21

<210> SEQ ID NO 2319
<211> LENGTH: 21
<212> TYPE: DNA
<213> ORGANISM: Homo sapiens

<400> SEQUENCE: 2319
gtcagactaa agtgaggacc a 21

<210> SEQ ID NO 2320
<211> LENGTH: 21
<212> TYPE: DNA
<213> ORGANISM: Homo sapiens

<400> SEQUENCE: 2320
ccagccctac ctaaagtgaa t 21

<210> SEQ ID NO 2321
<211> LENGTH: 21
<212> TYPE: DNA
<213> ORGANISM: Homo sapiens

<400> SEQUENCE: 2321
ccctttcaca agactcttct c 21

<210> SEQ ID NO 2322
<211> LENGTH: 18
<212> TYPE: DNA
<213> ORGANISM: Homo sapiens

<400> SEQUENCE: 2322
aaaaaaaaaa aaaaaaaa 18

<210> SEQ ID NO 2323
<211> LENGTH: 22
<212> TYPE: DNA

<213> ORGANISM: Homo sapiens

<400> SEQUENCE: 2323
ccaaatgtag aacaggatca gc 22

<210> SEQ ID NO 2324
<211> LENGTH: 20
<212> TYPE: DNA
<213> ORGANISM: Homo sapiens

<400> SEQUENCE: 2324
tagcagtagg tgtggctttc 20

<210> SEQ ID NO 2325
<211> LENGTH: 21
<212> TYPE: DNA
<213> ORGANISM: Homo sapiens

<400> SEQUENCE: 2325
ttggattctc ttggttgtga g 21

<210> SEQ ID NO 2326
<211> LENGTH: 22
<212> TYPE: DNA
<213> ORGANISM: Homo sapiens

<400> SEQUENCE: 2326
caacgctttg gtatagtttg tg 22

<210> SEQ ID NO 2327
<211> LENGTH: 21
<212> TYPE: DNA
<213> ORGANISM: Homo sapiens

<400> SEQUENCE: 2327
ccaggtgcca tcgttaaaga a 21

<210> SEQ ID NO 2328
<211> LENGTH: 18
<212> TYPE: DNA
<213> ORGANISM: Homo sapiens

<400> SEQUENCE: 2328
aaaaaaaaaa aaaaaaaa 18

<210> SEQ ID NO 2329
<211> LENGTH: 22
<212> TYPE: DNA
<213> ORGANISM: Homo sapiens

<400> SEQUENCE: 2329
ggataagtca actaccatgg tt 22

<210> SEQ ID NO 2330
<211> LENGTH: 21
<212> TYPE: DNA
<213> ORGANISM: Homo sapiens

<400> SEQUENCE: 2330
aatggaatta ctcagctgtg g 21

<210> SEQ ID NO 2331
<211> LENGTH: 21

<212> TYPE: DNA
<213> ORGANISM: Homo sapiens

<400> SEQUENCE: 2331
ggcagaaact gatagagact g 21

<210> SEQ ID NO 2332
<211> LENGTH: 21
<212> TYPE: DNA
<213> ORGANISM: Homo sapiens

<400> SEQUENCE: 2332
accatgttct gagtacctct t 21

<210> SEQ ID NO 2333
<211> LENGTH: 23
<212> TYPE: DNA
<213> ORGANISM: Homo sapiens

<400> SEQUENCE: 2333
agtcctgaat caatgtctaa cac 23

<210> SEQ ID NO 2334
<211> LENGTH: 20
<212> TYPE: DNA
<213> ORGANISM: Homo sapiens

<400> SEQUENCE: 2334
tggtccctgt gctttgatat 20

<210> SEQ ID NO 2335
<211> LENGTH: 20
<212> TYPE: DNA
<213> ORGANISM: Homo sapiens

<400> SEQUENCE: 2335
tggcttttct ttcctcggta 20

<210> SEQ ID NO 2336
<211> LENGTH: 20
<212> TYPE: DNA
<213> ORGANISM: Homo sapiens

<400> SEQUENCE: 2336
ccaaggctgc tttaattcca 20

<210> SEQ ID NO 2337
<211> LENGTH: 20
<212> TYPE: DNA
<213> ORGANISM: Homo sapiens

<400> SEQUENCE: 2337
caaactatcg ctgaggacct 20

<210> SEQ ID NO 2338
<211> LENGTH: 20
<212> TYPE: DNA
<213> ORGANISM: Homo sapiens

<400> SEQUENCE: 2338
gtctgctgcc attgagttat 20

<210> SEQ ID NO 2339

<211> LENGTH: 20
<212> TYPE: DNA
<213> ORGANISM: Homo sapiens

<400> SEQUENCE: 2339
gctcaccctc tcttctctct 20

<210> SEQ ID NO 2340
<211> LENGTH: 20
<212> TYPE: DNA
<213> ORGANISM: Homo sapiens

<400> SEQUENCE: 2340
acctgtttct cccagttaca 20

<210> SEQ ID NO 2341
<211> LENGTH: 20
<212> TYPE: DNA
<213> ORGANISM: Homo sapiens

<400> SEQUENCE: 2341
gcccatgaaa gagaaaccag 20

<210> SEQ ID NO 2342
<211> LENGTH: 20
<212> TYPE: DNA
<213> ORGANISM: Homo sapiens

<400> SEQUENCE: 2342
ctccatcagt gcagaagtcc 20

<210> SEQ ID NO 2343
<211> LENGTH: 20
<212> TYPE: DNA
<213> ORGANISM: Homo sapiens

<400> SEQUENCE: 2343
acagtcagca gccctaaaat 20

<210> SEQ ID NO 2344
<211> LENGTH: 20
<212> TYPE: DNA
<213> ORGANISM: Homo sapiens

<400> SEQUENCE: 2344
gcctccttca cataatgcag 20

<210> SEQ ID NO 2345
<211> LENGTH: 20
<212> TYPE: DNA
<213> ORGANISM: Homo sapiens

<400> SEQUENCE: 2345
ttgtcaacag agagtcagct 20

<210> SEQ ID NO 2346
<211> LENGTH: 20
<212> TYPE: DNA
<213> ORGANISM: Homo sapiens

<400> SEQUENCE: 2346
ctgaaatggt ctgggagtct 20

<210> SEQ ID NO 2347
<211> LENGTH: 20
<212> TYPE: DNA
<213> ORGANISM: Homo sapiens

<400> SEQUENCE: 2347
tcaaagacag agtgagtgga 20

<210> SEQ ID NO 2348
<211> LENGTH: 21
<212> TYPE: DNA
<213> ORGANISM: Homo sapiens

<400> SEQUENCE: 2348
tttgggggtt acacttcata g 21

<210> SEQ ID NO 2349
<211> LENGTH: 21
<212> TYPE: DNA
<213> ORGANISM: Homo sapiens

<400> SEQUENCE: 2349
agccagcaga ataataccag g 21

<210> SEQ ID NO 2350
<211> LENGTH: 20
<212> TYPE: DNA
<213> ORGANISM: Homo sapiens

<400> SEQUENCE: 2350
acctcatctt ttgtcagcct 20

<210> SEQ ID NO 2351
<211> LENGTH: 20
<212> TYPE: DNA
<213> ORGANISM: Homo sapiens

<400> SEQUENCE: 2351
acagttccat aggcaggttt 20

<210> SEQ ID NO 2352
<211> LENGTH: 21
<212> TYPE: DNA
<213> ORGANISM: Homo sapiens

<400> SEQUENCE: 2352
gcagttccag atccaatatg c 21

<210> SEQ ID NO 2353
<211> LENGTH: 20
<212> TYPE: DNA
<213> ORGANISM: Homo sapiens

<400> SEQUENCE: 2353
tttgggaaag atgggagagc 20

<210> SEQ ID NO 2354
<211> LENGTH: 21
<212> TYPE: DNA
<213> ORGANISM: Homo sapiens

<400> SEQUENCE: 2354
ttgcaggtaa ggtacagaag a 21

<210> SEQ ID NO 2355
<211> LENGTH: 19
<212> TYPE: DNA
<213> ORGANISM: Homo sapiens

<400> SEQUENCE: 2355
cttcagctgc atcttgagc 19

<210> SEQ ID NO 2356
<211> LENGTH: 20
<212> TYPE: DNA
<213> ORGANISM: Homo sapiens

<400> SEQUENCE: 2356
ggcacttcaa aaacaaaccc 20

<210> SEQ ID NO 2357
<211> LENGTH: 20
<212> TYPE: DNA
<213> ORGANISM: Homo sapiens

<400> SEQUENCE: 2357
agggttttat ggtctcctgg 20

<210> SEQ ID NO 2358
<211> LENGTH: 21
<212> TYPE: DNA
<213> ORGANISM: Homo sapiens

<400> SEQUENCE: 2358
tcaacacgga gaactgaaaa c 21

<210> SEQ ID NO 2359
<211> LENGTH: 22
<212> TYPE: DNA
<213> ORGANISM: Homo sapiens

<400> SEQUENCE: 2359
tccgtgtaaa tgaacaaagc ac 22

<210> SEQ ID NO 2360
<211> LENGTH: 20
<212> TYPE: DNA
<213> ORGANISM: Homo sapiens

<400> SEQUENCE: 2360
ttcagggaat ggtttgcatt 20

<210> SEQ ID NO 2361
<211> LENGTH: 20
<212> TYPE: DNA
<213> ORGANISM: Homo sapiens

<400> SEQUENCE: 2361
gagatgccat tcccaaaagg 20

<210> SEQ ID NO 2362
<211> LENGTH: 20
<212> TYPE: DNA
<213> ORGANISM: Homo sapiens

<400> SEQUENCE: 2362
ccctaccata gtgccagatg 20

<210> SEQ ID NO 2363
<211> LENGTH: 20
<212> TYPE: DNA
<213> ORGANISM: Homo sapiens

<400> SEQUENCE: 2363
cagctttcag tgacagagga 20

<210> SEQ ID NO 2364
<211> LENGTH: 20
<212> TYPE: DNA
<213> ORGANISM: Homo sapiens

<400> SEQUENCE: 2364
ccaaaggcag atgagtgttt 20

<210> SEQ ID NO 2365
<211> LENGTH: 20
<212> TYPE: DNA
<213> ORGANISM: Homo sapiens

<400> SEQUENCE: 2365
gcctgggata gaaatgggaa 20

<210> SEQ ID NO 2366
<211> LENGTH: 20
<212> TYPE: DNA
<213> ORGANISM: Homo sapiens

<400> SEQUENCE: 2366
ggaaaggaaa ggaagctgtg 20

<210> SEQ ID NO 2367
<211> LENGTH: 20
<212> TYPE: DNA
<213> ORGANISM: Homo sapiens

<400> SEQUENCE: 2367
tcagagaggt cttgctgaag 20

<210> SEQ ID NO 2368
<211> LENGTH: 21
<212> TYPE: DNA
<213> ORGANISM: Homo sapiens

<400> SEQUENCE: 2368
tctctctgtt gcttgtttcc t 21

<210> SEQ ID NO 2369
<211> LENGTH: 20
<212> TYPE: DNA
<213> ORGANISM: Homo sapiens

<400> SEQUENCE: 2369
cgcatgtggt agatcatcag 20

<210> SEQ ID NO 2370
<211> LENGTH: 20
<212> TYPE: DNA
<213> ORGANISM: Homo sapiens

<400> SEQUENCE: 2370
tataacaccc tcacctccca 20

<210> SEQ ID NO 2371
<211> LENGTH: 21
<212> TYPE: DNA
<213> ORGANISM: Homo sapiens

<400> SEQUENCE: 2371
cacccaaatc accttgctat g 21

<210> SEQ ID NO 2372
<211> LENGTH: 20
<212> TYPE: DNA
<213> ORGANISM: Homo sapiens

<400> SEQUENCE: 2372
caactaccgt ggattccgtt 20

<210> SEQ ID NO 2373
<211> LENGTH: 20
<212> TYPE: DNA
<213> ORGANISM: Homo sapiens

<400> SEQUENCE: 2373
tctatcatga gtcgcttcca 20

<210> SEQ ID NO 2374
<211> LENGTH: 20
<212> TYPE: DNA
<213> ORGANISM: Homo sapiens

<400> SEQUENCE: 2374
tttctgtcac tttctgggct 20

<210> SEQ ID NO 2375
<211> LENGTH: 21
<212> TYPE: DNA
<213> ORGANISM: Homo sapiens

<400> SEQUENCE: 2375
cgtgtgtttc tagtgcattg t 21

<210> SEQ ID NO 2376
<211> LENGTH: 20
<212> TYPE: DNA
<213> ORGANISM: Homo sapiens

<400> SEQUENCE: 2376
gggctcagag ggaatatcag 20

<210> SEQ ID NO 2377
<211> LENGTH: 20
<212> TYPE: DNA
<213> ORGANISM: Homo sapiens

<400> SEQUENCE: 2377
ccgacgaatg gatgaaagac 20

<210> SEQ ID NO 2378
<211> LENGTH: 20
<212> TYPE: DNA
<213> ORGANISM: Homo sapiens

<400> SEQUENCE: 2378
acccaaattc catgcctact 20

<210> SEQ ID NO 2379
<211> LENGTH: 20
<212> TYPE: DNA
<213> ORGANISM: Homo sapiens

<400> SEQUENCE: 2379
tgtacagcag tctccagaaa 20

<210> SEQ ID NO 2380
<211> LENGTH: 20
<212> TYPE: DNA
<213> ORGANISM: Homo sapiens

<400> SEQUENCE: 2380
gccctcttac cctttctcat 20

<210> SEQ ID NO 2381
<211> LENGTH: 21
<212> TYPE: DNA
<213> ORGANISM: Homo sapiens

<400> SEQUENCE: 2381
cattcaaaga tccagaccag g 21

<210> SEQ ID NO 2382
<211> LENGTH: 19
<212> TYPE: DNA
<213> ORGANISM: Homo sapiens

<400> SEQUENCE: 2382
atctgtgatt gctgccctc 19

<210> SEQ ID NO 2383
<211> LENGTH: 20
<212> TYPE: DNA
<213> ORGANISM: Homo sapiens

<400> SEQUENCE: 2383
ctagaaactc ccaggacaga 20

<210> SEQ ID NO 2384
<211> LENGTH: 20
<212> TYPE: DNA
<213> ORGANISM: Homo sapiens

<400> SEQUENCE: 2384
catgtgtgga aaggattggt 20

<210> SEQ ID NO 2385
<211> LENGTH: 20
<212> TYPE: DNA
<213> ORGANISM: Homo sapiens

<400> SEQUENCE: 2385
tatgaatgaa ccgtggctca 20

<210> SEQ ID NO 2386
<211> LENGTH: 20
<212> TYPE: DNA
<213> ORGANISM: Homo sapiens

<400> SEQUENCE: 2386
aagttgagtc gtttgtccca 20

<210> SEQ ID NO 2387
<211> LENGTH: 20
<212> TYPE: DNA
<213> ORGANISM: Homo sapiens

<400> SEQUENCE: 2387
tagtgtttca ggagcgtgtt 20

<210> SEQ ID NO 2388
<211> LENGTH: 20
<212> TYPE: DNA
<213> ORGANISM: Homo sapiens

<400> SEQUENCE: 2388
ccaggacaag cagacatttt 20

<210> SEQ ID NO 2389
<211> LENGTH: 21
<212> TYPE: DNA
<213> ORGANISM: Homo sapiens

<400> SEQUENCE: 2389
gctgctggtg atttttgaag a 21

<210> SEQ ID NO 2390
<211> LENGTH: 20
<212> TYPE: DNA
<213> ORGANISM: Homo sapiens

<400> SEQUENCE: 2390
ctctgggcaa acaagaaacc 20

<210> SEQ ID NO 2391
<211> LENGTH: 20
<212> TYPE: DNA
<213> ORGANISM: Homo sapiens

<400> SEQUENCE: 2391
gtgtgtgttt gtggaagtgt 20

<210> SEQ ID NO 2392
<211> LENGTH: 21
<212> TYPE: DNA
<213> ORGANISM: Homo sapiens

<400> SEQUENCE: 2392
aaagcccaat ctctctggtt a 21

<210> SEQ ID NO 2393
<211> LENGTH: 20
<212> TYPE: DNA
<213> ORGANISM: Homo sapiens

<400> SEQUENCE: 2393
taggcgggct tattgtgttt 20

<210> SEQ ID NO 2394
<211> LENGTH: 20
<212> TYPE: DNA
<213> ORGANISM: Homo sapiens

<400> SEQUENCE: 2394
tcaatgtaaa ctgcccggag 20

<210> SEQ ID NO 2395
<211> LENGTH: 21
<212> TYPE: DNA
<213> ORGANISM: Homo sapiens

<400> SEQUENCE: 2395
atgggagtcg aatggtgtaa a 21

<210> SEQ ID NO 2396
<211> LENGTH: 20
<212> TYPE: DNA
<213> ORGANISM: Homo sapiens

<400> SEQUENCE: 2396
taacatttga gggcatggga 20

<210> SEQ ID NO 2397
<211> LENGTH: 20
<212> TYPE: DNA
<213> ORGANISM: Homo sapiens

<400> SEQUENCE: 2397
cagaataccc tcactgtgct 20

<210> SEQ ID NO 2398
<211> LENGTH: 20
<212> TYPE: DNA
<213> ORGANISM: Homo sapiens

<400> SEQUENCE: 2398
ggagataaca gcagaggtcc 20

<210> SEQ ID NO 2399
<211> LENGTH: 20
<212> TYPE: DNA
<213> ORGANISM: Homo sapiens

<400> SEQUENCE: 2399
tgtgggtgat atctgtgtct 20

<210> SEQ ID NO 2400
<211> LENGTH: 20
<212> TYPE: DNA
<213> ORGANISM: Homo sapiens

<400> SEQUENCE: 2400
gccatcctgt aactgaatgc 20

<210> SEQ ID NO 2401
<211> LENGTH: 20
<212> TYPE: DNA
<213> ORGANISM: Homo sapiens

<400> SEQUENCE: 2401
gtattttccc tttgccgcag 20

<210> SEQ ID NO 2402
<211> LENGTH: 20
<212> TYPE: DNA

<213> ORGANISM: Homo sapiens

<400> SEQUENCE: 2402
attacagcaa agaacgtggc 20

<210> SEQ ID NO 2403
<211> LENGTH: 20
<212> TYPE: DNA
<213> ORGANISM: Homo sapiens

<400> SEQUENCE: 2403
tctgtgtgtt ttgcattggt 20

<210> SEQ ID NO 2404
<211> LENGTH: 20
<212> TYPE: DNA
<213> ORGANISM: Homo sapiens

<400> SEQUENCE: 2404
gtgacagttt tccaaggcat 20

<210> SEQ ID NO 2405
<211> LENGTH: 20
<212> TYPE: DNA
<213> ORGANISM: Homo sapiens

<400> SEQUENCE: 2405
gcattacttt ttcgcacact 20

<210> SEQ ID NO 2406
<211> LENGTH: 20
<212> TYPE: DNA
<213> ORGANISM: Homo sapiens

<400> SEQUENCE: 2406
ggggattgtt ttaagcaggc 20

<210> SEQ ID NO 2407
<211> LENGTH: 20
<212> TYPE: DNA
<213> ORGANISM: Homo sapiens

<400> SEQUENCE: 2407
ccattgttct caccaactct 20

<210> SEQ ID NO 2408
<211> LENGTH: 19
<212> TYPE: DNA
<213> ORGANISM: Homo sapiens

<400> SEQUENCE: 2408
cctgaaacac aagcagcag 19

<210> SEQ ID NO 2409
<211> LENGTH: 20
<212> TYPE: DNA
<213> ORGANISM: Homo sapiens

<400> SEQUENCE: 2409
agctgcctat ttgattggtg 20

<210> SEQ ID NO 2410
<211> LENGTH: 20

<212> TYPE: DNA
<213> ORGANISM: Homo sapiens

<400> SEQUENCE: 2410
cagtacagtc agccttcctt 20

<210> SEQ ID NO 2411
<211> LENGTH: 20
<212> TYPE: DNA
<213> ORGANISM: Homo sapiens

<400> SEQUENCE: 2411
tgcattcaaa ctaccccaag 20

<210> SEQ ID NO 2412
<211> LENGTH: 20
<212> TYPE: DNA
<213> ORGANISM: Homo sapiens

<400> SEQUENCE: 2412
ccgaaaagag gcaagcaatt 20

<210> SEQ ID NO 2413
<211> LENGTH: 20
<212> TYPE: DNA
<213> ORGANISM: Homo sapiens

<400> SEQUENCE: 2413
gtcacctcaa cctaactcca 20

<210> SEQ ID NO 2414
<211> LENGTH: 20
<212> TYPE: DNA
<213> ORGANISM: Homo sapiens

<400> SEQUENCE: 2414
gcaacagtct acccgtctag 20

<210> SEQ ID NO 2415
<211> LENGTH: 20
<212> TYPE: DNA
<213> ORGANISM: Homo sapiens

<400> SEQUENCE: 2415
atcaatgctc tgacctcctg 20

<210> SEQ ID NO 2416
<211> LENGTH: 21
<212> TYPE: DNA
<213> ORGANISM: Homo sapiens

<400> SEQUENCE: 2416
atacatcagg cctccagaat t 21

<210> SEQ ID NO 2417
<211> LENGTH: 22
<212> TYPE: DNA
<213> ORGANISM: Homo sapiens

<400> SEQUENCE: 2417
cacatcttta gagctcaggt ga 22

<210> SEQ ID NO 2418

<211> LENGTH: 21
<212> TYPE: DNA
<213> ORGANISM: Homo sapiens

<400> SEQUENCE: 2418
ccatcacttc acaatccaca c 21

<210> SEQ ID NO 2419
<211> LENGTH: 20
<212> TYPE: DNA
<213> ORGANISM: Homo sapiens

<400> SEQUENCE: 2419
aatcctgcag tcatcttccc 20

<210> SEQ ID NO 2420
<211> LENGTH: 21
<212> TYPE: DNA
<213> ORGANISM: Homo sapiens

<400> SEQUENCE: 2420
caagtctggt ttgtgagaag c 21

<210> SEQ ID NO 2421
<211> LENGTH: 21
<212> TYPE: DNA
<213> ORGANISM: Homo sapiens

<400> SEQUENCE: 2421
gggagcttct gtagtctttg a 21

<210> SEQ ID NO 2422
<211> LENGTH: 21
<212> TYPE: DNA
<213> ORGANISM: Homo sapiens

<400> SEQUENCE: 2422
taaggagagc aggacttaca g 21

<210> SEQ ID NO 2423
<211> LENGTH: 21
<212> TYPE: DNA
<213> ORGANISM: Homo sapiens

<400> SEQUENCE: 2423
ccaacggttc atttgtcgta t 21

<210> SEQ ID NO 2424
<211> LENGTH: 21
<212> TYPE: DNA
<213> ORGANISM: Homo sapiens

<400> SEQUENCE: 2424
ccttgctctg ttaatgggtt t 21

<210> SEQ ID NO 2425
<211> LENGTH: 21
<212> TYPE: DNA
<213> ORGANISM: Homo sapiens

<400> SEQUENCE: 2425
aacaatgctt aacgggaatc c 21

<210> SEQ ID NO 2426
<211> LENGTH: 21
<212> TYPE: DNA
<213> ORGANISM: Homo sapiens

<400> SEQUENCE: 2426
gcagagttca tagaagggtc a 21

<210> SEQ ID NO 2427
<211> LENGTH: 21
<212> TYPE: DNA
<213> ORGANISM: Homo sapiens

<400> SEQUENCE: 2427
aaaccgagac gaccacctaa t 21

<210> SEQ ID NO 2428
<211> LENGTH: 21
<212> TYPE: DNA
<213> ORGANISM: Homo sapiens

<400> SEQUENCE: 2428
gagtgatgat gagccatgat g 21

<210> SEQ ID NO 2429
<211> LENGTH: 21
<212> TYPE: DNA
<213> ORGANISM: Homo sapiens

<400> SEQUENCE: 2429
ggatattgga gatagcaggc a 21

<210> SEQ ID NO 2430
<211> LENGTH: 21
<212> TYPE: DNA
<213> ORGANISM: Homo sapiens

<400> SEQUENCE: 2430
gtttggcact gcaactagat a 21

<210> SEQ ID NO 2431
<211> LENGTH: 21
<212> TYPE: DNA
<213> ORGANISM: Homo sapiens

<400> SEQUENCE: 2431
tgaaataagg gaagccacac a 21

<210> SEQ ID NO 2432
<211> LENGTH: 21
<212> TYPE: DNA
<213> ORGANISM: Homo sapiens

<400> SEQUENCE: 2432
tccttagtgt gccaattagc c 21

<210> SEQ ID NO 2433
<211> LENGTH: 20
<212> TYPE: DNA
<213> ORGANISM: Homo sapiens

<400> SEQUENCE: 2433
ttaatgtgga gagacaggcc 20

<210> SEQ ID NO 2434
<211> LENGTH: 21
<212> TYPE: DNA
<213> ORGANISM: Homo sapiens

<400> SEQUENCE: 2434
caatgcatct tactcaccct t 21

<210> SEQ ID NO 2435
<211> LENGTH: 21
<212> TYPE: DNA
<213> ORGANISM: Homo sapiens

<400> SEQUENCE: 2435
agtatggaag tgggaattgg a 21

<210> SEQ ID NO 2436
<211> LENGTH: 21
<212> TYPE: DNA
<213> ORGANISM: Homo sapiens

<400> SEQUENCE: 2436
ttgcttccac agaaactctt c 21

<210> SEQ ID NO 2437
<211> LENGTH: 21
<212> TYPE: DNA
<213> ORGANISM: Homo sapiens

<400> SEQUENCE: 2437
aaccgaccta ttccaaagtc t 21

<210> SEQ ID NO 2438
<211> LENGTH: 21
<212> TYPE: DNA
<213> ORGANISM: Homo sapiens

<400> SEQUENCE: 2438
tgtgaagcga atacagctca a 21

<210> SEQ ID NO 2439
<211> LENGTH: 21
<212> TYPE: DNA
<213> ORGANISM: Homo sapiens

<400> SEQUENCE: 2439
gttctaacta caccaggctc t 21

<210> SEQ ID NO 2440
<211> LENGTH: 21
<212> TYPE: DNA
<213> ORGANISM: Homo sapiens

<400> SEQUENCE: 2440
gtatgagtgt aggtgtggag g 21

<210> SEQ ID NO 2441
<211> LENGTH: 21
<212> TYPE: DNA
<213> ORGANISM: Homo sapiens

<400> SEQUENCE: 2441
aatctggatc tagcgaagga c 21

<210> SEQ ID NO 2442
<211> LENGTH: 21
<212> TYPE: DNA
<213> ORGANISM: Homo sapiens

<400> SEQUENCE: 2442
taatgagaag gcaggatgag g 21

<210> SEQ ID NO 2443
<211> LENGTH: 21
<212> TYPE: DNA
<213> ORGANISM: Homo sapiens

<400> SEQUENCE: 2443
aagacaactc tctaggcctc a 21

<210> SEQ ID NO 2444
<211> LENGTH: 21
<212> TYPE: DNA
<213> ORGANISM: Homo sapiens

<400> SEQUENCE: 2444
gtttatggtt gtccctggag a 21

<210> SEQ ID NO 2445
<211> LENGTH: 21
<212> TYPE: DNA
<213> ORGANISM: Homo sapiens

<400> SEQUENCE: 2445
tccaccttct gatcacacaa t 21

<210> SEQ ID NO 2446
<211> LENGTH: 21
<212> TYPE: DNA
<213> ORGANISM: Homo sapiens

<400> SEQUENCE: 2446
aagatcaggt accaaggcat t 21

<210> SEQ ID NO 2447
<211> LENGTH: 21
<212> TYPE: DNA
<213> ORGANISM: Homo sapiens

<400> SEQUENCE: 2447
atgatgtgaa gtccatggtg a 21

<210> SEQ ID NO 2448
<211> LENGTH: 21
<212> TYPE: DNA
<213> ORGANISM: Homo sapiens

<400> SEQUENCE: 2448
tccaaattga cttccatgag c 21

<210> SEQ ID NO 2449
<211> LENGTH: 21
<212> TYPE: DNA
<213> ORGANISM: Homo sapiens

<400> SEQUENCE: 2449
gtggtttcag gaatttggag g 21

<210> SEQ ID NO 2450
<211> LENGTH: 22
<212> TYPE: DNA
<213> ORGANISM: Homo sapiens

<400> SEQUENCE: 2450
tatttgctgc ttcattcttc cc 22

<210> SEQ ID NO 2451
<211> LENGTH: 21
<212> TYPE: DNA
<213> ORGANISM: Homo sapiens

<400> SEQUENCE: 2451
aagtcattac gtcccacact g 21

<210> SEQ ID NO 2452
<211> LENGTH: 21
<212> TYPE: DNA
<213> ORGANISM: Homo sapiens

<400> SEQUENCE: 2452
aaagtcatca gaagggtagc a 21

<210> SEQ ID NO 2453
<211> LENGTH: 21
<212> TYPE: DNA
<213> ORGANISM: Homo sapiens

<400> SEQUENCE: 2453
aatgatgccg aacagtgagt a 21

<210> SEQ ID NO 2454
<211> LENGTH: 21
<212> TYPE: DNA
<213> ORGANISM: Homo sapiens

<400> SEQUENCE: 2454
aatgtaagac agggacagag a 21

<210> SEQ ID NO 2455
<211> LENGTH: 21
<212> TYPE: DNA
<213> ORGANISM: Homo sapiens

<400> SEQUENCE: 2455
tgaattccac agtccagtca a 21

<210> SEQ ID NO 2456
<211> LENGTH: 21
<212> TYPE: DNA
<213> ORGANISM: Homo sapiens

<400> SEQUENCE: 2456
aatgccttca aagacagtga c 21

<210> SEQ ID NO 2457
<211> LENGTH: 21
<212> TYPE: DNA
<213> ORGANISM: Homo sapiens

<400> SEQUENCE: 2457
cacacctgca attgagatga a 21

<210> SEQ ID NO 2458
<211> LENGTH: 21
<212> TYPE: DNA
<213> ORGANISM: Homo sapiens

<400> SEQUENCE: 2458
gtcatgatga tgcaacagct a 21

<210> SEQ ID NO 2459
<211> LENGTH: 21
<212> TYPE: DNA
<213> ORGANISM: Homo sapiens

<400> SEQUENCE: 2459
tttcacggta agaggagcaa a 21

<210> SEQ ID NO 2460
<211> LENGTH: 21
<212> TYPE: DNA
<213> ORGANISM: Homo sapiens

<400> SEQUENCE: 2460
ttctctctag gcaggtgaac t 21

<210> SEQ ID NO 2461
<211> LENGTH: 21
<212> TYPE: DNA
<213> ORGANISM: Homo sapiens

<400> SEQUENCE: 2461
accctttgaa agaaccagga a 21

<210> SEQ ID NO 2462
<211> LENGTH: 21
<212> TYPE: DNA
<213> ORGANISM: Homo sapiens

<400> SEQUENCE: 2462
aatgagccac tgttctctag g 21

<210> SEQ ID NO 2463
<211> LENGTH: 21
<212> TYPE: DNA
<213> ORGANISM: Homo sapiens

<400> SEQUENCE: 2463
atttgcacat tagggcctca a 21

<210> SEQ ID NO 2464
<211> LENGTH: 20
<212> TYPE: DNA
<213> ORGANISM: Homo sapiens

<400> SEQUENCE: 2464
gaacttccct gcttccttct 20

<210> SEQ ID NO 2465
<211> LENGTH: 21
<212> TYPE: DNA
<213> ORGANISM: Homo sapiens

<400> SEQUENCE: 2465
aaatacttgg ctgtgaccat g 21

<210> SEQ ID NO 2466
<211> LENGTH: 21
<212> TYPE: DNA
<213> ORGANISM: Homo sapiens

<400> SEQUENCE: 2466
aagacccttg agaacttcca a 21

<210> SEQ ID NO 2467
<211> LENGTH: 21
<212> TYPE: DNA
<213> ORGANISM: Homo sapiens

<400> SEQUENCE: 2467
atgtgtaaag acgtcctgga a 21

<210> SEQ ID NO 2468
<211> LENGTH: 21
<212> TYPE: DNA
<213> ORGANISM: Homo sapiens

<400> SEQUENCE: 2468
tctatgtgga gggatttgac a 21

<210> SEQ ID NO 2469
<211> LENGTH: 22
<212> TYPE: DNA
<213> ORGANISM: Homo sapiens

<400> SEQUENCE: 2469
ttcctgaagt ttatggtgca ac 22

<210> SEQ ID NO 2470
<211> LENGTH: 21
<212> TYPE: DNA
<213> ORGANISM: Homo sapiens

<400> SEQUENCE: 2470
aaggttgaat gaggatcaag c 21

<210> SEQ ID NO 2471
<211> LENGTH: 21
<212> TYPE: DNA
<213> ORGANISM: Homo sapiens

<400> SEQUENCE: 2471
gagggaagaa cacaacacat g 21

<210> SEQ ID NO 2472
<211> LENGTH: 21
<212> TYPE: DNA
<213> ORGANISM: Homo sapiens

<400> SEQUENCE: 2472
cagactagcc tacaatcctc c 21

<210> SEQ ID NO 2473
<211> LENGTH: 21
<212> TYPE: DNA
<213> ORGANISM: Homo sapiens

<400> SEQUENCE: 2473
cattcaggtt cttaagggct g 21

<210> SEQ ID NO 2474
<211> LENGTH: 21
<212> TYPE: DNA
<213> ORGANISM: Homo sapiens

<400> SEQUENCE: 2474
gaaaggcaga cgatgaaaga g 21

<210> SEQ ID NO 2475
<211> LENGTH: 21
<212> TYPE: DNA
<213> ORGANISM: Homo sapiens

<400> SEQUENCE: 2475
atctccatca gcacaggaat t 21

<210> SEQ ID NO 2476
<211> LENGTH: 21
<212> TYPE: DNA
<213> ORGANISM: Homo sapiens

<400> SEQUENCE: 2476
gcagtgtgac atctgtgaat g 21

<210> SEQ ID NO 2477
<211> LENGTH: 21
<212> TYPE: DNA
<213> ORGANISM: Homo sapiens

<400> SEQUENCE: 2477
agactttcct gttcctcttc a 21

<210> SEQ ID NO 2478
<211> LENGTH: 21
<212> TYPE: DNA
<213> ORGANISM: Homo sapiens

<400> SEQUENCE: 2478
tttacaatga actagccagg c 21

<210> SEQ ID NO 2479
<211> LENGTH: 21
<212> TYPE: DNA
<213> ORGANISM: Homo sapiens

<400> SEQUENCE: 2479
taacatctgc ctgaaagctt c 21

<210> SEQ ID NO 2480
<211> LENGTH: 21
<212> TYPE: DNA
<213> ORGANISM: Homo sapiens

<400> SEQUENCE: 2480
ctcgtgtgtg caatttggaa t 21

<210> SEQ ID NO 2481
<211> LENGTH: 21
<212> TYPE: DNA

<213> ORGANISM: Homo sapiens

<400> SEQUENCE: 2481
ggagagatgg agaagacctt t 21

<210> SEQ ID NO 2482
<211> LENGTH: 21
<212> TYPE: DNA
<213> ORGANISM: Homo sapiens

<400> SEQUENCE: 2482
aatgtattac tgtgctcccg t 21

<210> SEQ ID NO 2483
<211> LENGTH: 21
<212> TYPE: DNA
<213> ORGANISM: Homo sapiens

<400> SEQUENCE: 2483
accacctgcc actgtataaa t 21

<210> SEQ ID NO 2484
<211> LENGTH: 21
<212> TYPE: DNA
<213> ORGANISM: Homo sapiens

<400> SEQUENCE: 2484
aattcttctt ctggtgcaag g 21

<210> SEQ ID NO 2485
<211> LENGTH: 21
<212> TYPE: DNA
<213> ORGANISM: Homo sapiens

<400> SEQUENCE: 2485
ttgccctttg aactgttgat c 21

<210> SEQ ID NO 2486
<211> LENGTH: 21
<212> TYPE: DNA
<213> ORGANISM: Homo sapiens

<400> SEQUENCE: 2486
aagcacacta aggcctgata a 21

<210> SEQ ID NO 2487
<211> LENGTH: 21
<212> TYPE: DNA
<213> ORGANISM: Homo sapiens

<400> SEQUENCE: 2487
tcagtatcca ttcagcatcc a 21

<210> SEQ ID NO 2488
<211> LENGTH: 20
<212> TYPE: DNA
<213> ORGANISM: Homo sapiens

<400> SEQUENCE: 2488
taaccgaagc ccatactctg 20

<210> SEQ ID NO 2489
<211> LENGTH: 21

<212> TYPE: DNA
<213> ORGANISM: Homo sapiens

<400> SEQUENCE: 2489
tccttactcc agatacccga t 21

<210> SEQ ID NO 2490
<211> LENGTH: 21
<212> TYPE: DNA
<213> ORGANISM: Homo sapiens

<400> SEQUENCE: 2490
tctggcttct ttcttggaga g 21

<210> SEQ ID NO 2491
<211> LENGTH: 21
<212> TYPE: DNA
<213> ORGANISM: Homo sapiens

<400> SEQUENCE: 2491
gcaacattca tttcatcctg c 21

<210> SEQ ID NO 2492
<211> LENGTH: 21
<212> TYPE: DNA
<213> ORGANISM: Homo sapiens

<400> SEQUENCE: 2492
catcacgaca tccatttcca c 21

<210> SEQ ID NO 2493
<211> LENGTH: 21
<212> TYPE: DNA
<213> ORGANISM: Homo sapiens

<400> SEQUENCE: 2493
gtggttatta tcggtgggtg a 21

<210> SEQ ID NO 2494
<211> LENGTH: 20
<212> TYPE: DNA
<213> ORGANISM: Homo sapiens

<400> SEQUENCE: 2494
ctgccattcc ttgtttccaa 20

<210> SEQ ID NO 2495
<211> LENGTH: 20
<212> TYPE: DNA
<213> ORGANISM: Homo sapiens

<400> SEQUENCE: 2495
atttggactt gaagcagcct 20

<210> SEQ ID NO 2496
<211> LENGTH: 21
<212> TYPE: DNA
<213> ORGANISM: Homo sapiens

<400> SEQUENCE: 2496
ctgtattctt tgtccaccac c 21

<210> SEQ ID NO 2497

<211> LENGTH: 21
<212> TYPE: DNA
<213> ORGANISM: Homo sapiens

<400> SEQUENCE: 2497
gacaggacac cttggattga t 21

<210> SEQ ID NO 2498
<211> LENGTH: 20
<212> TYPE: DNA
<213> ORGANISM: Homo sapiens

<400> SEQUENCE: 2498
gagtaattcc cccgatgcag 20

<210> SEQ ID NO 2499
<211> LENGTH: 21
<212> TYPE: DNA
<213> ORGANISM: Homo sapiens

<400> SEQUENCE: 2499
tgagaatcat tgagccaaac c 21

<210> SEQ ID NO 2500
<211> LENGTH: 20
<212> TYPE: DNA
<213> ORGANISM: Homo sapiens

<400> SEQUENCE: 2500
aattgtgagc gttagagtgc 20

<210> SEQ ID NO 2501
<211> LENGTH: 21
<212> TYPE: DNA
<213> ORGANISM: Homo sapiens

<400> SEQUENCE: 2501
ccagtgggtc ttaacattga g 21

<210> SEQ ID NO 2502
<211> LENGTH: 20
<212> TYPE: DNA
<213> ORGANISM: Homo sapiens

<400> SEQUENCE: 2502
aaaaggctag tagagggtgc 20

<210> SEQ ID NO 2503
<211> LENGTH: 20
<212> TYPE: DNA
<213> ORGANISM: Homo sapiens

<400> SEQUENCE: 2503
tcgctgaaga actgagacac 20

<210> SEQ ID NO 2504
<211> LENGTH: 20
<212> TYPE: DNA
<213> ORGANISM: Homo sapiens

<400> SEQUENCE: 2504
gggaagtgat tggagagagg 20

<210> SEQ ID NO 2505
<211> LENGTH: 20
<212> TYPE: DNA
<213> ORGANISM: Homo sapiens

<400> SEQUENCE: 2505
ccgcttggta tagagtgctg 20

<210> SEQ ID NO 2506
<211> LENGTH: 20
<212> TYPE: DNA
<213> ORGANISM: Homo sapiens

<400> SEQUENCE: 2506
ttgaggttgt caggaaagct 20

<210> SEQ ID NO 2507
<211> LENGTH: 20
<212> TYPE: DNA
<213> ORGANISM: Homo sapiens

<400> SEQUENCE: 2507
tcttgggaaa gggtcattct 20

<210> SEQ ID NO 2508
<211> LENGTH: 19
<212> TYPE: DNA
<213> ORGANISM: Homo sapiens

<400> SEQUENCE: 2508
tctcttccat gcactccac 19

<210> SEQ ID NO 2509
<211> LENGTH: 19
<212> TYPE: DNA
<213> ORGANISM: Homo sapiens

<400> SEQUENCE: 2509
gatctgaccc tctgctcac 19

<210> SEQ ID NO 2510
<211> LENGTH: 20
<212> TYPE: DNA
<213> ORGANISM: Homo sapiens

<400> SEQUENCE: 2510
cctgaaagat gcatggttgg 20

<210> SEQ ID NO 2511
<211> LENGTH: 20
<212> TYPE: DNA
<213> ORGANISM: Homo sapiens

<400> SEQUENCE: 2511
gccacagaac aaccagattc 20

<210> SEQ ID NO 2512
<211> LENGTH: 20
<212> TYPE: DNA
<213> ORGANISM: Homo sapiens

<400> SEQUENCE: 2512
tggggttaag agctcaagag 20

<210> SEQ ID NO 2513
<211> LENGTH: 20
<212> TYPE: DNA
<213> ORGANISM: Homo sapiens

<400> SEQUENCE: 2513
agtgtggatg acttctgcaa 20

<210> SEQ ID NO 2514
<211> LENGTH: 20
<212> TYPE: DNA
<213> ORGANISM: Homo sapiens

<400> SEQUENCE: 2514
gccccattat cctcctttgt 20

<210> SEQ ID NO 2515
<211> LENGTH: 21
<212> TYPE: DNA
<213> ORGANISM: Homo sapiens

<400> SEQUENCE: 2515
caaatcagac ccactaagca c 21

<210> SEQ ID NO 2516
<211> LENGTH: 20
<212> TYPE: DNA
<213> ORGANISM: Homo sapiens

<400> SEQUENCE: 2516
tgttttggac tgcttcactc 20

<210> SEQ ID NO 2517
<211> LENGTH: 21
<212> TYPE: DNA
<213> ORGANISM: Homo sapiens

<400> SEQUENCE: 2517
attatcatgc tcactcctcc a 21

<210> SEQ ID NO 2518
<211> LENGTH: 19
<212> TYPE: DNA
<213> ORGANISM: Homo sapiens

<400> SEQUENCE: 2518
gacatagcac gggagagta 19

<210> SEQ ID NO 2519
<211> LENGTH: 20
<212> TYPE: DNA
<213> ORGANISM: Homo sapiens

<400> SEQUENCE: 2519
gctagtggcg ttttaggaaa 20

<210> SEQ ID NO 2520
<211> LENGTH: 19
<212> TYPE: DNA
<213> ORGANISM: Homo sapiens

<400> SEQUENCE: 2520
tcgcttggaa gtcatagcc 19

<210> SEQ ID NO 2521
<211> LENGTH: 23
<212> TYPE: DNA
<213> ORGANISM: Homo sapiens

<400> SEQUENCE: 2521
cagagctgct ttgaagataa tcc 23

<210> SEQ ID NO 2522
<211> LENGTH: 20
<212> TYPE: DNA
<213> ORGANISM: Homo sapiens

<400> SEQUENCE: 2522
gaagcctgat agatgtgcct 20

<210> SEQ ID NO 2523
<211> LENGTH: 20
<212> TYPE: DNA
<213> ORGANISM: Homo sapiens

<400> SEQUENCE: 2523
tacctctgcc tccaattgtc 20

<210> SEQ ID NO 2524
<211> LENGTH: 20
<212> TYPE: DNA
<213> ORGANISM: Homo sapiens

<400> SEQUENCE: 2524
cccatgtaga caaagtgctt 20

<210> SEQ ID NO 2525
<211> LENGTH: 20
<212> TYPE: DNA
<213> ORGANISM: Homo sapiens

<400> SEQUENCE: 2525
ggcaggtttg tcttacagtt 20

<210> SEQ ID NO 2526
<211> LENGTH: 20
<212> TYPE: DNA
<213> ORGANISM: Homo sapiens

<400> SEQUENCE: 2526
tgtgagattg cattcccctt 20

<210> SEQ ID NO 2527
<211> LENGTH: 20
<212> TYPE: DNA
<213> ORGANISM: Homo sapiens

<400> SEQUENCE: 2527
cgggtcagag aaagatcagg 20

<210> SEQ ID NO 2528
<211> LENGTH: 22
<212> TYPE: DNA
<213> ORGANISM: Homo sapiens

<400> SEQUENCE: 2528
aaacatttgt aaccactccc tg 22

<210> SEQ ID NO 2529
<211> LENGTH: 21
<212> TYPE: DNA
<213> ORGANISM: Homo sapiens

<400> SEQUENCE: 2529
cctgtaatat gggactcctg g 21

<210> SEQ ID NO 2530
<211> LENGTH: 20
<212> TYPE: DNA
<213> ORGANISM: Homo sapiens

<400> SEQUENCE: 2530
ccaaaccaca cacacaaact 20

<210> SEQ ID NO 2531
<211> LENGTH: 21
<212> TYPE: DNA
<213> ORGANISM: Homo sapiens

<400> SEQUENCE: 2531
aggagaagga catttcacag g 21

<210> SEQ ID NO 2532
<211> LENGTH: 20
<212> TYPE: DNA
<213> ORGANISM: Homo sapiens

<400> SEQUENCE: 2532
aggccgataa gacaaggttc 20

<210> SEQ ID NO 2533
<211> LENGTH: 19
<212> TYPE: DNA
<213> ORGANISM: Homo sapiens

<400> SEQUENCE: 2533
gtttcccata gagccctgg 19

<210> SEQ ID NO 2534
<211> LENGTH: 20
<212> TYPE: DNA
<213> ORGANISM: Homo sapiens

<400> SEQUENCE: 2534
ctccactctc tccaaccaac 20

<210> SEQ ID NO 2535
<211> LENGTH: 20
<212> TYPE: DNA
<213> ORGANISM: Homo sapiens

<400> SEQUENCE: 2535
aaactgtgaa aggacgagga 20

<210> SEQ ID NO 2536
<211> LENGTH: 20
<212> TYPE: DNA
<213> ORGANISM: Homo sapiens

<400> SEQUENCE: 2536
tcccttgctt ttgtaccagg 20

<210> SEQ ID NO 2537
<211> LENGTH: 20
<212> TYPE: DNA
<213> ORGANISM: Homo sapiens

<400> SEQUENCE: 2537
catgtgtgta ctgtgcctca 20

<210> SEQ ID NO 2538
<211> LENGTH: 21
<212> TYPE: DNA
<213> ORGANISM: Homo sapiens

<400> SEQUENCE: 2538
tctttcactg tcactatggg g 21

<210> SEQ ID NO 2539
<211> LENGTH: 20
<212> TYPE: DNA
<213> ORGANISM: Homo sapiens

<400> SEQUENCE: 2539
aaatgcagct tcccaacatc 20

<210> SEQ ID NO 2540
<211> LENGTH: 20
<212> TYPE: DNA
<213> ORGANISM: Homo sapiens

<400> SEQUENCE: 2540
gagactttct ggaggacgaa 20

<210> SEQ ID NO 2541
<211> LENGTH: 22
<212> TYPE: DNA
<213> ORGANISM: Homo sapiens

<400> SEQUENCE: 2541
gaaacgtaat ttagtgactg gc 22

<210> SEQ ID NO 2542
<211> LENGTH: 22
<212> TYPE: DNA
<213> ORGANISM: Homo sapiens

<400> SEQUENCE: 2542
atgtgtctat tgctacctgt ga 22

<210> SEQ ID NO 2543
<211> LENGTH: 20
<212> TYPE: DNA
<213> ORGANISM: Homo sapiens

<400> SEQUENCE: 2543
ctccttcatt ttgctggtgg 20

<210> SEQ ID NO 2544
<211> LENGTH: 20
<212> TYPE: DNA
<213> ORGANISM: Homo sapiens

```
<400> SEQUENCE: 2544

ggtgatcatt tgtctgcaca                                                20


<210> SEQ ID NO 2545
<211> LENGTH: 20
<212> TYPE: DNA
<213> ORGANISM: Homo sapiens

<400> SEQUENCE: 2545

tgaagggatg aaggcagaag                                                20


<210> SEQ ID NO 2546
<211> LENGTH: 20
<212> TYPE: DNA
<213> ORGANISM: Homo sapiens

<400> SEQUENCE: 2546

attgtgttgt ccttccgttt                                                20


<210> SEQ ID NO 2547
<211> LENGTH: 20
<212> TYPE: DNA
<213> ORGANISM: Homo sapiens

<400> SEQUENCE: 2547

ctgaagcatc actggcattg                                                20


<210> SEQ ID NO 2548
<211> LENGTH: 20
<212> TYPE: DNA
<213> ORGANISM: Homo sapiens

<400> SEQUENCE: 2548

aagcttgtag tctgggtagc                                                20


<210> SEQ ID NO 2549
<211> LENGTH: 22
<212> TYPE: DNA
<213> ORGANISM: Homo sapiens

<400> SEQUENCE: 2549

tccctctgta ctatgtagca tg                                             22


<210> SEQ ID NO 2550
<211> LENGTH: 20
<212> TYPE: DNA
<213> ORGANISM: Homo sapiens

<400> SEQUENCE: 2550

ttcatttccc tttgttgccc                                                20
```

TARGET-ENRICHED MULTIPLEXED PARALLEL ANALYSIS FOR ASSESSMENT OF TUMOR BIOMARKERS

CROSS REFERENCE TO RELATED PATENT APPLICATIONS

This application is a U.S. national phase application of International Application No. PCT/EP2018/068441, which was filed on Jul. 6, 2018, and claims priority to U.S. Provisional Application No. 62/529,779, which was filed on Jul. 7, 2017. The content of these earlier filed applications is hereby incorporated by reference herein in its entirety.

INCORPORATION OF THE SEQUENCE LISTING

The present application contains a sequence listing that was submitted herewith in ASCII format via EFS-Web, containing the file name "37578_0073U1_SL" which is 385,738 bytes in size, created on Dec. 18, 2019, and is herein incorporated by reference in its entirety pursuant to 37 C.F.R. § 1.52(e)(5).

FIELD OF THE INVENTION

The invention is in the field of biology, medicine and chemistry, more in particular in the field of molecular biology and more in particular in the field of molecular diagnostics.

BACKGROUND OF THE INVENTION

The identification of tumor biomarkers has been an important advance in the detection, diagnosis and treatment of a wide variety of cancers. Various methods of detecting tumor biomarkers are known in the art; however, additional methods are still needed, in particular methods that allow for detection of tumor biomarkers non-invasively, such as in a plasma sample (liquid biopsy). The identification of hereditary (germline) mutations in patients with cancer or high risk individuals suspected of cancer-predisposing syndrome is a useful clinical tool that enables early medical intervention, prophylactic surgery and close monitoring. These germline mutations can be identified in an individual's healthy tissue (such as buccal swab or lymphocytes).

Next generation sequencing (NGS) technologies have been implemented in the development of non-invasive prenatal testing (NIPT). In 2008, two independent groups demonstrated that NIPT of trisomy 21 could be achieved using next generation massively parallel shotgun sequencing (MPSS) (Chiu, R. W. et al. (2008) *Proc. Natl. Acad. Sci. USA* 105:20458-20463; Fan, H. C. et al. (2008) *Proc. Natl. Acad. Sci. USA* 105:16266-162710). Large-scale clinical studies using NGS for NIPT have been described . . . (Palomaki, G. E. et al. (2011) *Genet. Med.* 13:913-920; Ehrich, M. et al. (2011) *Am. J. Obstet. Gynecol.* 204: 205e1-11; Chen, E. Z. et al. (2011) *PLOS One* 6: e21791; Sehnert, A. J. et al. (2011) *Clin. Chem.* 57:1042-1049; Palomaki, G. E. et al. (2012); *Genet. Med.* 14:296-305; Bianchi, D. W. et al. (2012) *Obstet. Gynecol.* 119:890-901; Zimmerman, B. et al. (2012) *Prenat. Diag.* 32:1233-1241; Nicolaides, K. H. et al. (2013) *Prenat. Diagn.* 33:575-579; Sparks, A. B. et al. (2012) *Prenat. Diagn.* 32:3-9).

Initial NIPT approaches used massively parallel shotgun sequencing (MPSS) NGS methodologies (see e.g., U.S. Pat. Nos. 7,888,017; 8,008,018; 8,195,415; 8,296,076; 8,682,594; US Patent Publication 20110201507; US Patent Publication 20120270739). Thus, these approaches are whole genome-based. More recently, targeted-based NGS approaches for NIPT, in which only specific sequences of interest are sequenced, have been developed. For example, a targeted NIPT approach using TArget Capture Sequences (TACS) for identifying fetal chromosomal abnormalities using a maternal blood sample has been described (PCT Publication WO 2016/189388; US Patent Publication 2016/0340733; Koumbaris, G. et al. (2016) *Clinical chemistry,* 62 (6), pp. 848-855.). Such targeted approaches require significantly less sequencing than the MPSS approaches, since sequencing is only performed on specific loci on the target sequence of interest rather than across the whole genome.

Additional methodologies for NGS-based approaches are still needed, in particular approaches that can target specific sequences of interest, such as for example tumor biomarkers, thereby greatly reducing the amount of sequencing needed as compared to whole genome-based approaches, as well as increasing the read-depth of regions of interest, thus enabling detection of low signal to noise ratio regions. In particular, additional methodologies are still needed that allow for genetic aberrations present in diminutive amounts in a sample to be reliably detected, such as for example in the early detection of cancer.

SUMMARY OF THE INVENTION

This invention provides improved methods for enriching targeted genomic regions of interest to be analyzed by multiplexed parallel sequencing, wherein the enriched sequences are tumor biomarker sequences and the DNA sample used in the method is from a subject having or suspected of having a tumor. Accordingly, the methods allow for detection of tumor biomarkers in a variety of biological samples, including liquid samples, such as plasma samples (liquid biopsy), thereby providing non-invasive means for tumor detection and monitoring. The methods of the invention utilize a pool of TArget Capture Sequences (TACS) designed such that the sequences within the pool have features that optimize the efficiency, specificity and accuracy of genetic assessment of tumor biomarkers. The methods of the invention can be used, for example, in cancer diagnosis, cancer screening, cancer treatment regimen selection and/or cancer therapy monitoring.

Accordingly, in one aspect, the invention pertains to a method of detecting one or more tumor biomarkers in a DNA sample from a subject having or suspected of having a tumor, the method comprising:

(a) preparing a sequencing library from the DNA sample;

(b) hybridizing the sequencing library to a pool of double-stranded TArget Capture Sequences (TACS) that bind to one or more tumor biomarker sequences of interest, wherein:

(i) each member sequence within the pool of TACS is between 100-500 base pairs in length, each member sequence having a 5' end and a 3' end;

(ii) preferably each member sequence binds to the tumor biomarker sequence of interest at least 50 base pairs away, on both the 5' end and the 3' end, from regions harboring Copy Number Variations (CNVs), Segmental duplications or repetitive DNA elements; and (iii) the GC content of the pool of TACS is between 19% and 80%, as determined by calculating the GC content of each member within the pool of TACS;

(c) isolating members of the sequencing library that bind to the pool of TACS to obtain an enriched library;
(d) amplifying and sequencing the enriched library; and
(e) performing statistical analysis on the enriched library sequences, optionally utilizing only fragments of a specific size range, to thereby detect the tumor biomarker(s) in the DNA sample.

In one embodiment, the pool of TACS comprises a plurality of TACS families, wherein each member of a TACS family binds to the same tumor biomarker sequence of interest but with different start and/or stop positions on the sequence with respect to a reference coordinate system (i.e., binding of TACS family members to the target sequence is staggered) to thereby enrich for target sequences of interest, followed by massive parallel sequencing and statistical analysis of the enriched population. The use of families of TACS with the TACS pool that bind to each target sequence of interest, as compared to use of a single TACS within the TACS pool that binds to each target sequence of interest, significantly increases enrichment for the target sequences of interest, as evidenced by a greater than 50% average increase in read-depth for the family of TACS versus a single TACS. Herein, the mutations detected or biomarkers detected may be due to somatic mutation or may be hereditary, i.e already present in the germ line.

Accordingly, in one embodiment, the pool of TACS comprises a plurality of TACS families directed to different tumor biomarker sequences of interest, wherein each TACS family comprises a plurality of member sequences, wherein each member sequence binds to the same tumor biomarker sequence of interest but has different start and/or stop positions with respect to a reference coordinate system for the genomic sequence of interest.

In certain embodiments, each TACS family comprises at least 3 member sequences or at least 5 member sequences. Alternative numbers of member sequences in each TACS family are described herein. In one embodiment, the pool of TACS comprises at least 50 different TACS families. Alternative numbers of different TACS families within the pool of TACS are described herein. In certain embodiments, the start and/or stop positions for the member sequences within a TACS family, with respect to a reference coordinate system for the genomic sequence of interest, are staggered by at least 3 base pairs or at least 5 base pairs or by at least 10 base pairs. Alternative lengths (sizes) for the number of base pairs within the stagger are described herein.

In one embodiment, each member sequence within the pool of TACS is at least 160 base pairs in length. In certain embodiments, the GC content of the pool of TACS is between 19% and 80% or is between 19% and 46%. Alternative % ranges for the GC content of the pool of TACS are described herein.

In one embodiment, the pool of TACS is fixed to a solid support. For example, in one embodiment, the TACS are biotinylated and are bound to streptavidin-coated magnetic beads.

In one embodiment, amplification of the enriched library is performed in the presence of blocking sequences that inhibit amplification of wild-type sequences.

In one embodiment, members of the sequencing library that bind to the pool of TACS are partially complementary to the TACS.

In one embodiment, the statistical analysis comprises a segmentation algorithm, for example, likelihood-based segmentation, segmentation using small overlapping windows, segmentation using parallel pairwise testing, and combinations thereof. In one embodiment, the statistical analysis comprises a score-based classification system. In one embodiment, sequencing of the enriched library provides a read-depth for the genomic sequences of interest and read-depths for reference loci and the statistical analysis comprises applying an algorithm that tests sequentially the read-depth of the loci of from the genomic sequences of interest against the read-depth of the reference loci, the algorithm comprising steps for: (a) removal of inadequately sequenced loci; (b) GC-content bias alleviation; and (c) genetic status determination. In one embodiment, GC-content bias is alleviated by grouping together loci of matching GC content. In one embodiment, sequencing of the enriched library . . . provides the number and size of sequenced fragments for TACS-specific coordinates and the statistical analysis comprises applying an algorithm that tests sequentially the fragment-size proportion for the genomic sequence of interest against the fragment-size proportion of the reference loci, the algorithm comprising steps for: (a) removal of fragment-size outliers; (b) fragment-size proportion calculation; and (c) genetic status determination.

In one embodiment, the DNA sample comprises cell free tumor DNA (cftDNA). In various embodiments, the DNA sample is selected from a group comprising of a plasma sample, a urine sample, a sputum sample, a cerebrospinal fluid sample, an ascites sample and a pleural effusion sample from subject having or suspected of having a tumor. In one embodiment, the DNA sample is from a tissue sample from a subject having or suspected of having a tumor.

In one embodiment, the pool of TACS binds to a plurality of tumor biomarker sequences of interest selected from a group comprising ABL, AKT, AKT1, ALK, APC, AR, ARAF, ATM, BAP1, BARD1, BCL, BMPR1A, BRAF, BRCA, BRCA1, BRCA2, BRIP1, CDH1, CDKN, CHEK2, CTNNB1, DDB2, DDR2, DICER1, EGFR, EPCAM, ErbB, ErcC, ESR1, FANCA, FANCB, FANCC, FANCD2, FANCE, FANCF, FANCG, FANCI, FANCL, FANCM, FBXW7, FGFR, FLT, FLT3, FOXA1, FOXL2, GATA3, GNA11, GNAQ, GNAS, GREM1, HOX, HOXB13, HRAS, IDH1, JAK, JAK2, KEAP1, KIT, KRAS, MAP2Ks, MAP3Ks, MET, MLH1, MPL, MRE11A, MSH2, MSH6, MTOR, MUTYH, NBN, NPM1, NRAS, NTRK1, PALB2, PDGFRs, PI3KCs, PMS2, POLD1, POLE, POLH, PTEN, RAD50, RAD51C, RAD51D, RAF1, RB1, RET, RUNX1, SLX4, SMAD, SMAD4, SMARCA4, SPOP, STAT, STK11, TP53, VHL, XPA and XPC, and combinations thereof.

In another embodiment, the pool of TACS binds to a plurality of tumor biomarker sequences of interest selected from a group comprising, AKT1, ALK, APC, AR, ARAF, ATM, BAP1, BARD1, BMPR1A, BRAF, BRCA1, BRCA2, BRIP1, CDH1, CDK4, CDKN2A (p14ARF), CDKN2A (p16INK4a), CHEK2, CTNNB1, DDB2, DDR2, DICER1, EGFR, EPCAM, ERBB2, ERBB3, ERBB4, ERCC1, ERCC2, ERCC3, ERCC4, ERCC5, ESR1, FANCA, FANCB, FANCC, FANCD2, FANCE, FANCF, FANCG, FANCI, FANCL, FANCM, FBXW7, FGFR1, FGFR2, FLT3, FOXA1, FOXL2, GATA3, GNA11, GNAQ, GNAS, GREM1, HOXB13, IDH1, IDH2, JAK2, KEAP1, KIT, KRAS, MAP2K1, MAP3K1, MEN1, MET, MLH1, MPL, MRE11A, MSH2, MSH6, MTOR, MUTYH, MYC, MYCN, NBN, NPM1, NRAS, NTRK1, PALB2, PDGFRA, PIK3CA, PIK3CB, PMS2, POLD1, POLE, POLH, PTEN, RAD50, RAD51C, RAD51D, RAF1, RB1, RET, ROS1, RUNX1, SDHA, SDHAF2, SDHB, SDHC, SDHD, SLX4, SMAD4, SMARCA4, SPOP, STAT, STK11, TMPRSS2, TP53, VHL, XPA, XPC and combinations thereof.

In one embodiment, the pool of TACS binds to a plurality of tumor biomarker sequences of interest selected from a group comprising EGFR_6240, KRAS_521, EGFR_6225, NRAS_578, NRAS_580, PIK3CA_763, EGFR_13553, EGFR_18430, BRAF_476, KIT_1314, NRAS_584, EGFR_12378, and combinations thereof.

In another embodiment, the pool of TACS binds to a plurality of tumor biomarker sequences of interest selected from a group comprising COSM6240 (EGFR_6240), COSM521 (KRAS_521), COSM6225 (EGFR_6225), COSM578 (NRAS_578), COSM580 (NRAS_580), COSM763 (PIK3CA_763), COSM13553 (EGFR_13553), COSM18430 (EGFR_18430), COSM476 (BRAF_476), COSM1314 (KIT_1314), COSM584 (NRAS_584), COSM12378 (EGFR_12378), and combinations thereof, wherein the identifiers refer to the COSMIC database ID number of the biomarker.

In one embodiment, the method further comprises making a diagnosis of the subject based on detection of at least one tumor biomarker sequence. In another embodiment, the method further comprises selecting a therapeutic regimen for the subject based on detection of at least one tumor biomarker sequence. In yet another embodiment, the method further comprises monitoring treatment efficacy of a therapeutic regimen in the subject based on detection of at least one tumor biomarker sequence.

In another aspect, kits for performing the methods of the invention are also encompassed.

BRIEF DESCRIPTION OF THE FIGURES

FIGS. 2A-2CB are a listing of exemplary chromosomal regions for amplifying TACS that bind to for example chromosomes 13, 18, 21 or X. A more extensive list is shown in Table 1 below.

FIG. 4A shows loci enriched using a family of TACS (red dots) as compared to loci enriched using a single TACS (blue dots), with different target sequences shown on the x-axis and the fold change in read-depth shown on the y-axis. FIG. 4B is a bar graph illustrating the average fold-increase in read-depth (54.7%) using a family of TACS (right) versus a single TACS (left).

FIG. 10 is a listing of exemplary chromosomal regions for amplifying TACS that bind to exemplary, non-limiting tumor biomarker genes.

Figure 1:
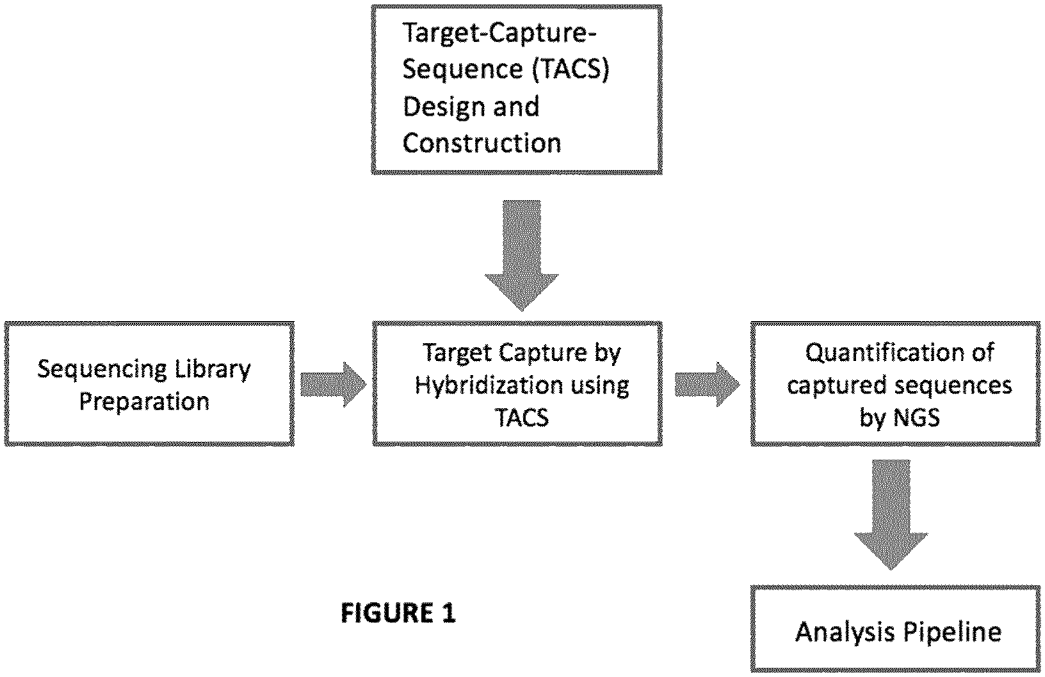
FIG. 1 is a schematic diagram of multiplexed parallel analysis of targeted genomic regions for non-invasive prenatal testing using TArget Capture Sequences (TACS).

Table 1 shows exemplary and preferred TACS positions.

| Chr. | Start | Stop | GC | Gene |
|---|---|---|---|---|
| chr1 | 11169250 | 11169491 | 0.434 | MTOR |
| chr1 | 11169262 | 11169509 | 0.419 | MTOR |
| chr1 | 11169280 | 11169519 | 0.400 | MTOR |
| chr1 | 11169299 | 11169548 | 0.392 | MTOR |
| chr1 | 11174376 | 11174632 | 0.541 | MTOR |
| chr1 | 11174392 | 11174632 | 0.535 | MTOR |
| chr1 | 11174392 | 11174691 | 0.527 | MTOR |
| chr1 | 11174468 | 11174698 | 0.515 | MTOR |
| chr1 | 11184541 | 11184796 | 0.504 | MTOR |
| chr1 | 11184563 | 11184812 | 0.504 | MTOR |
| chr1 | 11184564 | 11184816 | 0.502 | MTOR |
| chr1 | 11187992 | 11188236 | 0.535 | MTOR |
| chr1 | 11188010 | 11188249 | 0.521 | MTOR |
| chr1 | 11188018 | 11188257 | 0.513 | MTOR |
| chr1 | 11188029 | 11188274 | 0.492 | MTOR |
| chr1 | 17345194 | 17345459 | 0.316 | SDHB |
| chr1 | 17349096 | 17349342 | 0.543 | SDHB |
| chr1 | 17350413 | 17350563 | 0.497 | SDHB |
| chr1 | 17350566 | 17350779 | 0.430 | SDHB |
| chr1 | 17354089 | 17354304 | 0.463 | SDHB |
| chr1 | 17355058 | 17355208 | 0.417 | SDHB |
| chr1 | 17359477 | 17359689 | 0.427 | SDHB |
| chr1 | 17371214 | 17371394 | 0.470 | SDHB |
| chr1 | 17380408 | 17380619 | 0.670 | SDHB |
| chr1 | 43814917 | 43815186 | 0.633 | MPL |
| chr1 | 45795001 | 45795250 | 0.536 | MUTYH |
| chr1 | 45796024 | 45796223 | 0.530 | MUTYH |
| chr1 | 45796871 | 45797092 | 0.536 | MUTYH |
| chr1 | 45797060 | 45797289 | 0.648 | MUTYH |
| chr1 | 45797289 | 45797529 | 0.635 | MUTYH |
| chr1 | 45797602 | 45797802 | 0.577 | MUTYH |
| chr1 | 45797819 | 45798019 | 0.622 | MUTYH |
| chr1 | 45797986 | 45798270 | 0.593 | MUTYH |
| chr1 | 45798204 | 45798404 | 0.602 | MUTYH |
| chr1 | 45798364 | 45798564 | 0.547 | MUTYH |
| chr1 | 45798532 | 45798732 | 0.557 | MUTYH |
| chr1 | 45798672 | 45798872 | 0.567 | MUTYH |
| chr1 | 45798867 | 45799097 | 0.628 | MUTYH |
| chr1 | 45799150 | 45799357 | 0.582 | MUTYH |
| chr1 | 45800062 | 45800304 | 0.539 | MUTYH |
| chr1 | 115252133 | 115252352 | 0.445 | NRAS |
| chr1 | 115252133 | 115252354 | 0.441 | NRAS |
| chr1 | 115252138 | 115252350 | 0.446 | NRAS |

-continued

| Chr. | Start | Stop | GC | Gene |
|---|---|---|---|---|
| chr1 | 115252142 | 115252350 | 0.450 | NRAS |
| chr1 | 115256347 | 115256588 | 0.409 | NRAS |
| chr1 | 115256398 | 115256647 | 0.448 | NRAS |
| chr1 | 115256410 | 115256649 | 0.458 | NRAS |
| chr1 | 115256442 | 115256691 | 0.440 | NRAS |
| chr1 | 115256467 | 115256726 | 0.442 | NRAS |
| chr1 | 115256470 | 115256715 | 0.451 | NRAS |
| chr1 | 115258538 | 115258778 | 0.440 | NRAS |
| chr1 | 115258570 | 115258813 | 0.463 | NRAS |
| chr1 | 115258607 | 115258846 | 0.492 | NRAS |
| chr1 | 115258659 | 115258901 | 0.444 | NRAS |
| chr1 | 156268500 | 156268651 | 0.454 | VHLL |
| chr1 | 156269007 | 156269221 | 0.493 | VHLL |
| chr1 | 156846129 | 156846362 | 0.641 | NTRK1 |
| chr1 | 156846129 | 156846377 | 0.643 | NTRK1 |
| chr1 | 156846130 | 156846362 | 0.639 | NTRK1 |
| chr1 | 156848889 | 156849132 | 0.611 | NTRK1 |
| chr1 | 156848911 | 156849153 | 0.617 | NTRK1 |
| chr1 | 156848921 | 156849168 | 0.613 | NTRK1 |
| chr1 | 156848925 | 156849168 | 0.611 | NTRK1 |
| chr1 | 161284168 | 161284376 | 0.598 | SDHC |
| chr1 | 161293229 | 161293429 | 0.343 | SDHC |
| chr1 | 161298181 | 161298414 | 0.436 | SDHC |
| chr1 | 161333007 | 161333261 | 0.447 | SDHC |
| chr1 | 161333275 | 161333550 | 0.391 | SDHC |
| chr1 | 161333589 | 161333868 | 0.439 | SDHC |
| chr1 | 161333890 | 161334157 | 0.392 | SDHC |
| chr1 | 161334206 | 161334492 | 0.394 | SDHC |
| chr1 | 162748235 | 162748450 | 0.440 | DDR2 |
| chr1 | 162748273 | 162748512 | 0.442 | DDR2 |
| chr1 | 162748316 | 162748557 | 0.450 | DDR2 |
| chr1 | 162748370 | 162748580 | 0.483 | DDR2 |
| chr10 | 8111358 | 8111588 | 0.506 | GATA3 |
| chr10 | 8111468 | 8111707 | 0.529 | GATA3 |
| chr10 | 8115737 | 8115986 | 0.572 | GATA3 |
| chr10 | 8115741 | 8115988 | 0.569 | GATA3 |
| chr10 | 8115783 | 8115988 | 0.612 | GATA3 |
| chr10 | 8115789 | 8115988 | 0.620 | GATA3 |
| chr10 | 43595933 | 43596179 | 0.623 | RET |
| chr10 | 43597765 | 43598054 | 0.614 | RET |
| chr10 | 43600476 | 43600682 | 0.686 | RET |
| chr10 | 43601846 | 43602088 | 0.638 | RET |
| chr10 | 43604444 | 43604706 | 0.620 | RET |
| chr10 | 43606653 | 43606911 | 0.595 | RET |
| chr10 | 43607465 | 43607728 | 0.659 | RET |
| chr10 | 43608226 | 43608455 | 0.596 | RET |
| chr10 | 43608980 | 43609217 | 0.626 | RET |
| chr10 | 43609917 | 43610183 | 0.625 | RET |
| chr10 | 43611943 | 43612187 | 0.522 | RET |
| chr10 | 43613689 | 43613933 | 0.555 | RET |
| chr10 | 43614921 | 43615150 | 0.687 | RET |
| chr10 | 43615517 | 43615759 | 0.568 | RET |
| chr10 | 43617287 | 43617531 | 0.457 | RET |
| chr10 | 43619092 | 43619322 | 0.584 | RET |
| chr10 | 43620303 | 43620509 | 0.551 | RET |
| chr10 | 43623746 | 43624029 | 0.493 | RET |
| chr10 | 43624152 | 43624439 | 0.490 | RET |
| chr10 | 43624946 | 43625222 | 0.433 | RET |
| chr10 | 50686414 | 50686655 | 0.368 | ERCC6 |
| chr10 | 88635669 | 88635923 | 0.333 | BMPR1A |
| chr10 | 88649829 | 88650073 | 0.384 | BMPR1A |
| chr10 | 88659444 | 88659644 | 0.368 | BMPR1A |
| chr10 | 88677042 | 88677242 | 0.388 | BMPR1A |
| chr10 | 89622844 | 89623045 | 0.594 | KLLN |
| chr10 | 89624131 | 89624370 | 0.492 | PTEN |
| chr10 | 89624178 | 89624422 | 0.465 | PTEN |
| chr10 | 89624198 | 89624444 | 0.445 | PTEN |
| chr10 | 89624214 | 89624463 | 0.436 | PTEN |
| chr10 | 89685273 | 89685522 | 0.304 | PTEN |
| chr10 | 89692746 | 89692946 | 0.398 | PTEN |
| chr10 | 89692746 | 89692977 | 0.392 | PTEN |
| chr10 | 89692746 | 89692999 | 0.402 | PTEN |
| chr10 | 89692763 | 89693015 | 0.403 | PTEN |
| chr10 | 89692787 | 89692999 | 0.413 | PTEN |
| chr10 | 89711788 | 89712024 | 0.380 | PTEN |
| chr10 | 89711798 | 89712045 | 0.367 | PTEN |
| chr10 | 89711867 | 89712069 | 0.399 | PTEN |
| chr10 | 89711880 | 89712129 | 0.348 | PTEN |
| chr10 | 89717531 | 89717770 | 0.404 | PTEN |
| chr10 | 89717558 | 89717802 | 0.408 | PTEN |
| chr10 | 89717558 | 89717831 | 0.394 | PTEN |
| chr10 | 89717571 | 89717820 | 0.400 | PTEN |
| chr10 | 89717602 | 89717831 | 0.413 | PTEN |
| chr10 | 89717603 | 89717769 | 0.455 | PTEN |
| chr10 | 89717627 | 89717872 | 0.362 | PTEN |
| chr10 | 89720757 | 89720967 | 0.336 | PTEN |
| chr10 | 89720757 | 89721005 | 0.329 | PTEN |
| chr10 | 89720767 | 89720968 | 0.337 | PTEN |
| chr10 | 89720775 | 89721018 | 0.324 | PTEN |
| chr10 | 89726371 | 89726571 | 0.289 | PTEN |
| chr10 | 89726794 | 89727038 | 0.310 | PTEN |
| chr10 | 89727021 | 89727240 | 0.282 | PTEN |
| chr10 | 89727261 | 89727519 | 0.317 | PTEN |
| chr10 | 89727756 | 89727916 | 0.404 | PTEN |
| chr10 | 89727978 | 89728203 | 0.389 | PTEN |
| chr10 | 89728310 | 89728512 | 0.389 | PTEN |
| chr10 | 89729027 | 89729257 | 0.251 | PTEN |
| chr10 | 89729816 | 89729967 | 0.336 | PTEN |
| chr10 | 89730284 | 89730433 | 0.307 | PTEN |
| chr10 | 89731453 | 89731610 | 0.329 | PTEN |
| chr11 | 22644366 | 22644570 | 0.273 | FANCF |
| chr11 | 22644511 | 22644731 | 0.344 | FANCF |
| chr11 | 22644738 | 22644938 | 0.318 | FANCF |
| chr11 | 22645645 | 22645808 | 0.348 | FANCF |
| chr11 | 22645808 | 22646060 | 0.352 | FANCF |
| chr11 | 22646058 | 22646268 | 0.322 | FANCF |
| chr11 | 22646388 | 22646588 | 0.532 | FANCF |
| chr11 | 22646657 | 22646927 | 0.598 | FANCF |
| chr11 | 22646959 | 22647229 | 0.657 | FANCF |
| chr11 | 22647378 | 22647578 | 0.478 | FANCF |
| chr11 | 47236728 | 47236949 | 0.635 | DDB2 |
| chr11 | 47237804 | 47238058 | 0.537 | DDB2 |
| chr11 | 47238291 | 47238491 | 0.483 | DDB2 |
| chr11 | 47254333 | 47254547 | 0.470 | DDB2 |
| chr11 | 47256241 | 47256494 | 0.547 | DDB2 |
| chr11 | 47256782 | 47257010 | 0.594 | DDB2 |
| chr11 | 47259397 | 47259552 | 0.468 | DDB2 |
| chr11 | 47259555 | 47259796 | 0.492 | DDB2 |
| chr11 | 47260567 | 47260808 | 0.483 | DDB2 |
| chr11 | 61197603 | 61197830 | 0.588 | SDHAF2 |
| chr11 | 61205114 | 61205296 | 0.481 | SDHAF2 |
| chr11 | 61205433 | 61205588 | 0.404 | SDHAF2 |
| chr11 | 61213390 | 61213639 | 0.488 | SDHAF2 |
| chr11 | 61213676 | 61213931 | 0.508 | SDHAF2 |
| chr11 | 61213967 | 61214232 | 0.462 | SDHAF2 |
| chr11 | 64570946 | 64571196 | 0.478 | MEN1 |
| chr11 | 64571178 | 64571436 | 0.544 | MEN1 |
| chr11 | 64571465 | 64571704 | 0.546 | MEN1 |
| chr11 | 64571732 | 64571978 | 0.567 | MEN1 |
| chr11 | 64572483 | 64572713 | 0.619 | MEN1 |
| chr11 | 64573013 | 64573278 | 0.602 | MEN1 |
| chr11 | 64573641 | 64573871 | 0.593 | MEN1 |
| chr11 | 64574483 | 64574728 | 0.602 | MEN1 |
| chr11 | 64575094 | 64575345 | 0.544 | MEN1 |
| chr11 | 64575352 | 64575623 | 0.614 | MEN1 |
| chr11 | 64577138 | 64577410 | 0.634 | MEN1 |
| chr11 | 64577437 | 64577683 | 0.700 | MEN1 |
| chr11 | 64577902 | 64578171 | 0.681 | MEN1 |
| chr11 | 94150558 | 94150800 | 0.362 | MRE11A |
| chr11 | 94151042 | 94151242 | 0.373 | MRE11A |
| chr11 | 94151616 | 94151816 | 0.537 | MRE11A |
| chr11 | 94151903 | 94152103 | 0.343 | MRE11A |
| chr11 | 94152190 | 94152390 | 0.333 | MRE11A |
| chr11 | 94153182 | 94153395 | 0.308 | MRE11A |
| chr11 | 94168979 | 94169178 | 0.335 | MRE11A |
| chr11 | 94170337 | 94170576 | 0.300 | MRE11A |
| chr11 | 94178876 | 94179116 | 0.386 | MRE11A |
| chr11 | 94180384 | 94180615 | 0.500 | MRE11A |
| chr11 | 94189360 | 94189588 | 0.323 | MRE11A |
| chr11 | 94192639 | 94192838 | 0.370 | MRE11A |
| chr11 | 94193992 | 94194257 | 0.301 | MRE11A |
| chr11 | 94197223 | 94197451 | 0.349 | MRE11A |
| chr11 | 94200864 | 94201064 | 0.363 | MRE11A |
| chr11 | 94203635 | 94203874 | 0.404 | MRE11A |

-continued

| Chr. | Start | Stop | GC | Gene |
|---|---|---|---|---|
| chr11 | 94204708 | 94204908 | 0.368 | MRE11A |
| chr11 | 94209357 | 94209557 | 0.348 | MRE11A |
| chr11 | 94211862 | 94212106 | 0.359 | MRE11A |
| chr11 | 94212728 | 94212928 | 0.378 | MRE11A |
| chr11 | 94219015 | 94219215 | 0.348 | MRE11A |
| chr11 | 94219225 | 94219425 | 0.264 | MRE11A |
| chr11 | 94223880 | 94224120 | 0.344 | MRE11A |
| chr11 | 94223898 | 94224142 | 0.327 | MRE11A |
| chr11 | 94225885 | 94226125 | 0.394 | MRE11A |
| chr11 | 108093593 | 108093813 | 0.615 | ATM |
| chr11 | 108093873 | 108094073 | 0.617 | ATM |
| chr11 | 108098331 | 108098581 | 0.335 | ATM |
| chr11 | 108098372 | 108098572 | 0.333 | ATM |
| chr11 | 108098382 | 108098631 | 0.316 | ATM |
| chr11 | 108098397 | 108098626 | 0.309 | ATM |
| chr11 | 108098399 | 108098628 | 0.304 | ATM |
| chr11 | 108099818 | 108100062 | 0.327 | ATM |
| chr11 | 108106395 | 108106596 | 0.356 | ATM |
| chr11 | 108114723 | 108115004 | 0.333 | ATM |
| chr11 | 108114777 | 108115004 | 0.329 | ATM |
| chr11 | 108115492 | 108115736 | 0.351 | ATM |
| chr11 | 108117690 | 108117930 | 0.324 | ATM |
| chr11 | 108119692 | 108119907 | 0.343 | ATM |
| chr11 | 108119737 | 108119952 | 0.361 | ATM |
| chr11 | 108121367 | 108121602 | 0.377 | ATM |
| chr11 | 108121609 | 108121764 | 0.359 | ATM |
| chr11 | 108122506 | 108122706 | 0.363 | ATM |
| chr11 | 108122716 | 108122936 | 0.317 | ATM |
| chr11 | 108123498 | 108123718 | 0.321 | ATM |
| chr11 | 108124529 | 108124729 | 0.393 | ATM |
| chr11 | 108126954 | 108127154 | 0.363 | ATM |
| chr11 | 108128041 | 108128241 | 0.294 | ATM |
| chr11 | 108129523 | 108129756 | 0.316 | ATM |
| chr11 | 108137908 | 108138102 | 0.374 | ATM |
| chr11 | 108139112 | 108139322 | 0.374 | ATM |
| chr11 | 108139329 | 108139529 | 0.338 | ATM |
| chr11 | 108141794 | 108142040 | 0.324 | ATM |
| chr11 | 108142019 | 108142263 | 0.359 | ATM |
| chr11 | 108143141 | 108143341 | 0.323 | ATM |
| chr11 | 108143328 | 108143577 | 0.336 | ATM |
| chr11 | 108150264 | 108150498 | 0.328 | ATM |
| chr11 | 108151721 | 108151951 | 0.364 | ATM |
| chr11 | 108153427 | 108153675 | 0.285 | ATM |
| chr11 | 108153471 | 108153632 | 0.284 | ATM |
| chr11 | 108153471 | 108153677 | 0.275 | ATM |
| chr11 | 108153505 | 108153680 | 0.267 | ATM |
| chr11 | 108153510 | 108153680 | 0.269 | ATM |
| chr11 | 108154843 | 108155094 | 0.282 | ATM |
| chr11 | 108154858 | 108155070 | 0.291 | ATM |
| chr11 | 108154954 | 108155155 | 0.396 | ATM |
| chr11 | 108154962 | 108155211 | 0.388 | ATM |
| chr11 | 108157899 | 108158161 | 0.354 | ATM |
| chr11 | 108158376 | 108158580 | 0.337 | ATM |
| chr11 | 108159642 | 108159842 | 0.343 | ATM |
| chr11 | 108160273 | 108160473 | 0.299 | ATM |
| chr11 | 108163344 | 108163589 | 0.378 | ATM |
| chr11 | 108164044 | 108164225 | 0.324 | ATM |
| chr11 | 108164078 | 108164281 | 0.314 | ATM |
| chr11 | 108165595 | 108165795 | 0.358 | ATM |
| chr11 | 108167798 | 108168039 | 0.269 | ATM |
| chr11 | 108167811 | 108168065 | 0.267 | ATM |
| chr11 | 108170423 | 108170622 | 0.380 | ATM |
| chr11 | 108172321 | 108172561 | 0.340 | ATM |
| chr11 | 108173513 | 108173723 | 0.351 | ATM |
| chr11 | 108173723 | 108173923 | 0.313 | ATM |
| chr11 | 108175366 | 108175566 | 0.398 | ATM |
| chr11 | 108178629 | 108178814 | 0.360 | ATM |
| chr11 | 108179595 | 108179834 | 0.375 | ATM |
| chr11 | 108180801 | 108181050 | 0.320 | ATM |
| chr11 | 108180821 | 108181050 | 0.322 | ATM |
| chr11 | 108180821 | 108181066 | 0.313 | ATM |
| chr11 | 108180871 | 108181071 | 0.333 | ATM |
| chr11 | 108183026 | 108183226 | 0.333 | ATM |
| chr11 | 108186520 | 108186768 | 0.357 | ATM |
| chr11 | 108186672 | 108186911 | 0.404 | ATM |
| chr11 | 108188080 | 108188262 | 0.399 | ATM |
| chr11 | 108190668 | 108190878 | 0.313 | ATM |

-continued

| Chr. | Start | Stop | GC | Gene |
|---|---|---|---|---|
| chr11 | 108191937 | 108192186 | 0.392 | ATM |
| chr11 | 108195999 | 108196199 | 0.413 | ATM |
| chr11 | 108196116 | 108196316 | 0.388 | ATM |
| chr11 | 108196772 | 108196944 | 0.422 | ATM |
| chr11 | 108198304 | 108198504 | 0.398 | ATM |
| chr11 | 108199732 | 108199932 | 0.373 | ATM |
| chr11 | 108200863 | 108201105 | 0.374 | ATM |
| chr11 | 108201993 | 108202237 | 0.318 | ATM |
| chr11 | 108202461 | 108202678 | 0.330 | ATM |
| chr11 | 108202483 | 108202676 | 0.309 | ATM |
| chr11 | 108202496 | 108202676 | 0.298 | ATM |
| chr11 | 108202530 | 108202730 | 0.308 | ATM |
| chr11 | 108203403 | 108203613 | 0.336 | ATM |
| chr11 | 108203427 | 108203679 | 0.344 | ATM |
| chr11 | 108203480 | 108203724 | 0.339 | ATM |
| chr11 | 108203524 | 108203768 | 0.339 | ATM |
| chr11 | 108203540 | 108203784 | 0.347 | ATM |
| chr11 | 108204436 | 108204676 | 0.407 | ATM |
| chr11 | 108205641 | 108205841 | 0.368 | ATM |
| chr11 | 108206452 | 108206651 | 0.400 | ATM |
| chr11 | 108213868 | 108214068 | 0.393 | ATM |
| chr11 | 108216481 | 108216700 | 0.355 | ATM |
| chr11 | 108217894 | 108218094 | 0.328 | ATM |
| chr11 | 108224395 | 108224595 | 0.403 | ATM |
| chr11 | 108225445 | 108225655 | 0.346 | ATM |
| chr11 | 108235722 | 108235932 | 0.365 | ATM |
| chr11 | 108235932 | 108236132 | 0.383 | ATM |
| chr11 | 108235986 | 108236232 | 0.433 | ATM |
| chr11 | 108236004 | 108236249 | 0.431 | ATM |
| chr11 | 108236050 | 108236290 | 0.415 | ATM |
| chr11 | 108236051 | 108236251 | 0.438 | ATM |
| chr11 | 108236071 | 108236273 | 0.438 | ATM |
| chr11 | 108238313 | 108238513 | 0.373 | ATM |
| chr11 | 111957513 | 111957759 | 0.591 | SDHD |
| chr11 | 111959529 | 111959746 | 0.486 | SDHD |
| chr11 | 111965449 | 111965740 | 0.414 | SDHD |
| chr11 | 111965464 | 111965754 | 0.416 | SDHD |
| chr12 | 25378488 | 25378688 | 0.353 | KRAS |
| chr12 | 25378503 | 25378751 | 0.341 | KRAS |
| chr12 | 25378546 | 25378778 | 0.352 | KRAS |
| chr12 | 25378554 | 25378783 | 0.348 | KRAS |
| chr12 | 25380153 | 25380359 | 0.411 | KRAS |
| chr12 | 25380166 | 25380337 | 0.407 | KRAS |
| chr12 | 25380167 | 25380326 | 0.406 | KRAS |
| chr12 | 25380167 | 25380359 | 0.420 | KRAS |
| chr12 | 25398080 | 25398329 | 0.360 | KRAS |
| chr12 | 25398145 | 25398394 | 0.348 | KRAS |
| chr12 | 25398153 | 25398397 | 0.351 | KRAS |
| chr12 | 25398159 | 25398408 | 0.356 | KRAS |
| chr12 | 25398186 | 25398433 | 0.347 | KRAS |
| chr12 | 56478765 | 56478994 | 0.552 | ERBB3 |
| chr12 | 56478781 | 56479029 | 0.558 | ERBB3 |
| chr12 | 56478784 | 56479029 | 0.561 | ERBB3 |
| chr12 | 56478807 | 56479047 | 0.560 | ERBB3 |
| chr12 | 56481533 | 56481774 | 0.541 | ERBB3 |
| chr12 | 56481559 | 56481798 | 0.521 | ERBB3 |
| chr12 | 56481594 | 56481833 | 0.546 | ERBB3 |
| chr12 | 56481628 | 56481942 | 0.530 | ERBB3 |
| chr12 | 56481740 | 56481979 | 0.517 | ERBB3 |
| chr12 | 56481773 | 56482020 | 0.476 | ERBB3 |
| chr12 | 56481807 | 56482048 | 0.467 | ERBB3 |
| chr12 | 56482218 | 56482457 | 0.513 | ERBB3 |
| chr12 | 56482252 | 56482491 | 0.496 | ERBB3 |
| chr12 | 56482278 | 56482521 | 0.504 | ERBB3 |
| chr12 | 56482331 | 56482580 | 0.528 | ERBB3 |
| chr12 | 56486559 | 56486791 | 0.502 | ERBB3 |
| chr12 | 56486561 | 56486791 | 0.502 | ERBB3 |
| chr12 | 56486566 | 56486813 | 0.508 | ERBB3 |
| chr12 | 56486569 | 56486818 | 0.508 | ERBB3 |
| chr12 | 56490766 | 56491006 | 0.523 | ERBB3 |
| chr12 | 56490766 | 56491013 | 0.520 | ERBB3 |
| chr12 | 56490773 | 56491013 | 0.519 | ERBB3 |
| chr12 | 56490777 | 56491011 | 0.523 | ERBB3 |
| chr12 | 56491580 | 56491801 | 0.554 | ERBB3 |
| chr12 | 56491592 | 56491801 | 0.557 | ERBB3 |
| chr12 | 56491596 | 56491799 | 0.559 | ERBB3 |
| chr12 | 56491596 | 56491801 | 0.558 | ERBB3 |

-continued

| Chr. | Start | Stop | GC | Gene |
|---|---|---|---|---|
| chr12 | 58141882 | 58142151 | 0.396 | CDK4 |
| chr12 | 58142160 | 58142391 | 0.474 | CDK4 |
| chr12 | 58142983 | 58143287 | 0.570 | CDK4 |
| chr12 | 58142985 | 58143287 | 0.568 | CDK4 |
| chr12 | 58144413 | 58144686 | 0.478 | CDK4 |
| chr12 | 58144452 | 58144687 | 0.479 | CDK4 |
| chr12 | 58144692 | 58144932 | 0.490 | CDK4 |
| chr12 | 58144696 | 58144939 | 0.492 | CDK4 |
| chr12 | 58144957 | 58145214 | 0.523 | CDK4 |
| chr12 | 58145023 | 58145294 | 0.515 | CDK4 |
| chr12 | 58145309 | 58145580 | 0.544 | CDK4 |
| chr12 | 58145326 | 58145580 | 0.541 | CDK4 |
| chr12 | 58145924 | 58146140 | 0.673 | CDK4 |
| chr12 | 133200375 | 133200607 | 0.541 | POLE |
| chr12 | 133200794 | 133201005 | 0.604 | POLE |
| chr12 | 133200978 | 133201217 | 0.608 | POLE |
| chr12 | 133201185 | 133201425 | 0.610 | POLE |
| chr12 | 133201428 | 133201670 | 0.654 | POLE |
| chr12 | 133202187 | 133202429 | 0.621 | POLE |
| chr12 | 133202217 | 133202436 | 0.605 | POLE |
| chr12 | 133202217 | 133202437 | 0.606 | POLE |
| chr12 | 133202218 | 133202437 | 0.605 | POLE |
| chr12 | 133202355 | 133202555 | 0.622 | POLE |
| chr12 | 133202648 | 133202868 | 0.606 | POLE |
| chr12 | 133208842 | 133209042 | 0.517 | POLE |
| chr12 | 133209059 | 133209259 | 0.577 | POLE |
| chr12 | 133209191 | 133209391 | 0.647 | POLE |
| chr12 | 133210529 | 133210806 | 0.590 | POLE |
| chr12 | 133212413 | 133212654 | 0.488 | POLE |
| chr12 | 133214538 | 133214738 | 0.557 | POLE |
| chr12 | 133215637 | 133215885 | 0.582 | POLE |
| chr12 | 133218204 | 133218451 | 0.597 | POLE |
| chr12 | 133218707 | 133218953 | 0.579 | POLE |
| chr12 | 133219069 | 133219298 | 0.574 | POLE |
| chr12 | 133219399 | 133219599 | 0.617 | POLE |
| chr12 | 133219778 | 133220012 | 0.591 | POLE |
| chr12 | 133219996 | 133220226 | 0.606 | POLE |
| chr12 | 133220308 | 133220545 | 0.571 | POLE |
| chr12 | 133225529 | 133225773 | 0.612 | POLE |
| chr12 | 133225887 | 133226117 | 0.645 | POLE |
| chr12 | 133226161 | 133226408 | 0.613 | POLE |
| chr12 | 133233672 | 133233909 | 0.550 | POLE |
| chr12 | 133233774 | 133234003 | 0.557 | POLE |
| chr12 | 133234350 | 133234550 | 0.458 | POLE |
| chr12 | 133235953 | 133236173 | 0.534 | POLE |
| chr12 | 133237539 | 133237827 | 0.543 | POLE |
| chr12 | 133237547 | 133237781 | 0.519 | POLE |
| chr12 | 133238036 | 133238236 | 0.468 | POLE |
| chr12 | 133240495 | 133240681 | 0.545 | POLE |
| chr12 | 133241011 | 133241211 | 0.587 | POLE |
| chr12 | 133241805 | 133242034 | 0.600 | POLE |
| chr12 | 133244016 | 133244246 | 0.563 | POLE |
| chr12 | 133244860 | 133245070 | 0.578 | POLE |
| chr12 | 133245148 | 133245397 | 0.616 | POLE |
| chr12 | 133245378 | 133245623 | 0.537 | POLE |
| chr12 | 133248734 | 133248981 | 0.556 | POLE |
| chr12 | 133249169 | 133249404 | 0.568 | POLE |
| chr12 | 133249662 | 133249902 | 0.539 | POLE |
| chr12 | 133250240 | 133250445 | 0.549 | POLE |
| chr12 | 133250282 | 133250482 | 0.517 | POLE |
| chr12 | 133251897 | 133252126 | 0.600 | POLE |
| chr12 | 133252231 | 133252480 | 0.512 | POLE |
| chr12 | 133252591 | 133252826 | 0.470 | POLE |
| chr12 | 133253058 | 133253290 | 0.502 | POLE |
| chr12 | 133253869 | 133254099 | 0.429 | POLE |
| chr12 | 133254080 | 133254312 | 0.502 | POLE |
| chr12 | 133256057 | 133256299 | 0.494 | POLE |
| chr12 | 133256546 | 133256806 | 0.441 | POLE |
| chr12 | 133256751 | 133257006 | 0.469 | POLE |
| chr12 | 133257134 | 133257364 | 0.429 | POLE |
| chr12 | 133257609 | 133257851 | 0.523 | POLE |
| chr13 | 28592527 | 28592791 | 0.434 | FLT3 |
| chr13 | 32889625 | 32889857 | 0.631 | BRCA2 |
| chr13 | 32889901 | 32890111 | 0.583 | BRCA2 |
| chr13 | 32890514 | 32890741 | 0.346 | BRCA2 |
| chr13 | 32893139 | 32893383 | 0.339 | BRCA2 |
| chr13 | 32900135 | 32900368 | 0.252 | BRCA2 |

-continued

| Chr. | Start | Stop | GC | Gene |
|---|---|---|---|---|
| chr13 | 32900239 | 32900484 | 0.305 | BRCA2 |
| chr13 | 32900514 | 32900762 | 0.373 | BRCA2 |
| chr13 | 32903445 | 32903674 | 0.278 | BRCA2 |
| chr13 | 32904938 | 32905182 | 0.343 | BRCA2 |
| chr13 | 32905002 | 32905201 | 0.315 | BRCA2 |
| chr13 | 32905048 | 32905165 | 0.339 | BRCA2 |
| chr13 | 32905048 | 32905168 | 0.347 | BRCA2 |
| chr13 | 32905048 | 32905170 | 0.341 | BRCA2 |
| chr13 | 32905049 | 32905165 | 0.342 | BRCA2 |
| chr13 | 32906224 | 32906468 | 0.302 | BRCA2 |
| chr13 | 32906406 | 32906650 | 0.310 | BRCA2 |
| chr13 | 32906408 | 32906628 | 0.317 | BRCA2 |
| chr13 | 32906426 | 32906673 | 0.306 | BRCA2 |
| chr13 | 32906464 | 32906663 | 0.305 | BRCA2 |
| chr13 | 32906520 | 32906768 | 0.317 | BRCA2 |
| chr13 | 32906575 | 32906818 | 0.361 | BRCA2 |
| chr13 | 32906606 | 32906846 | 0.378 | BRCA2 |
| chr13 | 32906668 | 32906912 | 0.388 | BRCA2 |
| chr13 | 32906748 | 32906987 | 0.388 | BRCA2 |
| chr13 | 32906815 | 32907062 | 0.363 | BRCA2 |
| chr13 | 32906856 | 32907103 | 0.367 | BRCA2 |
| chr13 | 32906893 | 32907106 | 0.383 | BRCA2 |
| chr13 | 32906938 | 32907183 | 0.378 | BRCA2 |
| chr13 | 32907059 | 32907264 | 0.374 | BRCA2 |
| chr13 | 32907059 | 32907307 | 0.378 | BRCA2 |
| chr13 | 32907288 | 32907533 | 0.350 | BRCA2 |
| chr13 | 32910416 | 32910655 | 0.354 | BRCA2 |
| chr13 | 32910596 | 32910835 | 0.388 | BRCA2 |
| chr13 | 32910778 | 32911027 | 0.340 | BRCA2 |
| chr13 | 32910967 | 32911215 | 0.317 | BRCA2 |
| chr13 | 32910988 | 32911187 | 0.335 | BRCA2 |
| chr13 | 32911008 | 32911252 | 0.331 | BRCA2 |
| chr13 | 32911035 | 32911252 | 0.321 | BRCA2 |
| chr13 | 32911045 | 32911295 | 0.331 | BRCA2 |
| chr13 | 32911167 | 32911415 | 0.341 | BRCA2 |
| chr13 | 32911340 | 32911588 | 0.333 | BRCA2 |
| chr13 | 32911594 | 32911838 | 0.322 | BRCA2 |
| chr13 | 32911841 | 32912085 | 0.384 | BRCA2 |
| chr13 | 32912080 | 32912319 | 0.342 | BRCA2 |
| chr13 | 32912267 | 32912511 | 0.265 | BRCA2 |
| chr13 | 32912502 | 32912746 | 0.331 | BRCA2 |
| chr13 | 32912749 | 32912986 | 0.307 | BRCA2 |
| chr13 | 32912979 | 32913218 | 0.404 | BRCA2 |
| chr13 | 32913217 | 32913460 | 0.336 | BRCA2 |
| chr13 | 32913444 | 32913691 | 0.323 | BRCA2 |
| chr13 | 32913682 | 32913927 | 0.321 | BRCA2 |
| chr13 | 32913944 | 32914192 | 0.329 | BRCA2 |
| chr13 | 32914208 | 32914455 | 0.347 | BRCA2 |
| chr13 | 32914462 | 32914709 | 0.343 | BRCA2 |
| chr13 | 32914691 | 32914936 | 0.329 | BRCA2 |
| chr13 | 32914776 | 32915021 | 0.333 | BRCA2 |
| chr13 | 32914895 | 32915115 | 0.326 | BRCA2 |
| chr13 | 32914896 | 32915115 | 0.327 | BRCA2 |
| chr13 | 32914906 | 32915155 | 0.328 | BRCA2 |
| chr13 | 32915087 | 32915334 | 0.355 | BRCA2 |
| chr13 | 32915144 | 32915384 | 0.357 | BRCA2 |
| chr13 | 32918540 | 32918787 | 0.258 | BRCA2 |
| chr13 | 32920834 | 32921033 | 0.295 | BRCA2 |
| chr13 | 32928970 | 32929189 | 0.345 | BRCA2 |
| chr13 | 32928972 | 32929201 | 0.357 | BRCA2 |
| chr13 | 32928992 | 32929236 | 0.351 | BRCA2 |
| chr13 | 32928996 | 32929196 | 0.358 | BRCA2 |
| chr13 | 32928996 | 32929208 | 0.357 | BRCA2 |
| chr13 | 32929176 | 32929423 | 0.339 | BRCA2 |
| chr13 | 32929177 | 32929426 | 0.344 | BRCA2 |
| chr13 | 32929220 | 32929467 | 0.323 | BRCA2 |
| chr13 | 32929274 | 32929479 | 0.335 | BRCA2 |
| chr13 | 32929297 | 32929498 | 0.322 | BRCA2 |
| chr13 | 32930589 | 32930789 | 0.448 | BRCA2 |
| chr13 | 32931650 | 32931879 | 0.257 | BRCA2 |
| chr13 | 32931817 | 32932017 | 0.318 | BRCA2 |
| chr13 | 32932034 | 32932234 | 0.313 | BRCA2 |
| chr13 | 32936641 | 32936885 | 0.384 | BRCA2 |
| chr13 | 32937319 | 32937563 | 0.384 | BRCA2 |
| chr13 | 32937529 | 32937773 | 0.376 | BRCA2 |
| chr13 | 32944444 | 32944688 | 0.359 | BRCA2 |
| chr13 | 32945080 | 32945249 | 0.359 | BRCA2 |

-continued

| Chr. | Start | Stop | GC | Gene |
|---|---|---|---|---|
| chr13 | 32950820 | 32951019 | 0.440 | BRCA2 |
| chr13 | 32953333 | 32953533 | 0.348 | BRCA2 |
| chr13 | 32953442 | 32953686 | 0.363 | BRCA2 |
| chr13 | 32953840 | 32954084 | 0.327 | BRCA2 |
| chr13 | 32954054 | 32954299 | 0.346 | BRCA2 |
| chr13 | 32954054 | 32954300 | 0.344 | BRCA2 |
| chr13 | 32968741 | 32968971 | 0.359 | BRCA2 |
| chr13 | 32968820 | 32969069 | 0.384 | BRCA2 |
| chr13 | 32970989 | 32971236 | 0.379 | BRCA2 |
| chr13 | 32971106 | 32971335 | 0.348 | BRCA2 |
| chr13 | 32972257 | 32972489 | 0.373 | BRCA2 |
| chr13 | 32972463 | 32972703 | 0.390 | BRCA2 |
| chr13 | 32972600 | 32972845 | 0.378 | BRCA2 |
| chr13 | 32972664 | 32972864 | 0.418 | BRCA2 |
| chr13 | 32972671 | 32972922 | 0.397 | BRCA2 |
| chr13 | 32972708 | 32972954 | 0.389 | BRCA2 |
| chr13 | 32973392 | 32973641 | 0.336 | BRCA2 |
| chr13 | 32973613 | 32973807 | 0.267 | BRCA2 |
| chr13 | 48916668 | 48916868 | 0.318 | RB1 |
| chr13 | 48919151 | 48919351 | 0.284 | RB1 |
| chr13 | 48921945 | 48922145 | 0.308 | RB1 |
| chr13 | 48923001 | 48923221 | 0.258 | RB1 |
| chr13 | 48936897 | 48937117 | 0.330 | RB1 |
| chr13 | 48939068 | 48939268 | 0.318 | RB1 |
| chr13 | 48941560 | 48941760 | 0.318 | RB1 |
| chr13 | 48947429 | 48947629 | 0.323 | RB1 |
| chr13 | 48951017 | 48951237 | 0.348 | RB1 |
| chr13 | 48954364 | 48954564 | 0.328 | RB1 |
| chr13 | 48955326 | 48955526 | 0.303 | RB1 |
| chr13 | 48955536 | 48955736 | 0.338 | RB1 |
| chr13 | 49027033 | 49027233 | 0.333 | RB1 |
| chr13 | 49030212 | 49030472 | 0.364 | RB1 |
| chr13 | 49033792 | 49033992 | 0.428 | RB1 |
| chr13 | 49037854 | 49038084 | 0.299 | RB1 |
| chr13 | 49039190 | 49039390 | 0.378 | RB1 |
| chr13 | 49039267 | 49039467 | 0.383 | RB1 |
| chr13 | 49047356 | 49047616 | 0.287 | RB1 |
| chr13 | 49050783 | 49050983 | 0.373 | RB1 |
| chr13 | 49051484 | 49051724 | 0.299 | RB1 |
| chr13 | 49054133 | 49054333 | 0.413 | RB1 |
| chr13 | 49054700 | 49054910 | 0.251 | RB1 |
| chr13 | 49055078 | 49055278 | 0.323 | RB1 |
| chr13 | 49055456 | 49055656 | 0.343 | RB1 |
| chr13 | 49055834 | 49056034 | 0.254 | RB1 |
| chr13 | 103498123 | 103498440 | 0.629 | ERCC5 |
| chr13 | 103498155 | 103498432 | 0.640 | ERCC5 |
| chr13 | 103498190 | 103498390 | 0.642 | ERCC5 |
| chr13 | 103498192 | 103498440 | 0.631 | ERCC5 |
| chr13 | 103498192 | 103498453 | 0.626 | ERCC5 |
| chr13 | 103498470 | 103498701 | 0.608 | ERCC5 |
| chr13 | 103498494 | 103498713 | 0.618 | ERCC5 |
| chr13 | 103498494 | 103498717 | 0.621 | ERCC5 |
| chr13 | 103498574 | 103498757 | 0.641 | ERCC5 |
| chr13 | 103504312 | 103504529 | 0.349 | ERCC5 |
| chr13 | 103504364 | 103504578 | 0.372 | ERCC5 |
| chr13 | 103506028 | 103506230 | 0.409 | ERCC5 |
| chr13 | 103506526 | 103506726 | 0.463 | ERCC5 |
| chr13 | 103508374 | 103508544 | 0.275 | ERCC5 |
| chr13 | 103510603 | 103510803 | 0.393 | ERCC5 |
| chr13 | 103513836 | 103514056 | 0.407 | ERCC5 |
| chr13 | 103514321 | 103514572 | 0.433 | ERCC5 |
| chr13 | 103514574 | 103514792 | 0.534 | ERCC5 |
| chr13 | 103514801 | 103515020 | 0.482 | ERCC5 |
| chr13 | 103515021 | 103515221 | 0.428 | ERCC5 |
| chr13 | 103515235 | 103515435 | 0.433 | ERCC5 |
| chr13 | 103517984 | 103518184 | 0.478 | ERCC5 |
| chr13 | 103518194 | 103518404 | 0.412 | ERCC5 |
| chr13 | 103518516 | 103518726 | 0.370 | ERCC5 |
| chr13 | 103519057 | 103519257 | 0.368 | ERCC5 |
| chr13 | 103520541 | 103520748 | 0.370 | ERCC5 |
| chr13 | 103524493 | 103524693 | 0.413 | ERCC5 |
| chr13 | 103524585 | 103524802 | 0.445 | ERCC5 |
| chr13 | 103525496 | 103525696 | 0.368 | ERCC5 |
| chr13 | 103527656 | 103527856 | 0.408 | ERCC5 |
| chr13 | 103527863 | 103528063 | 0.408 | ERCC5 |
| chr13 | 103528070 | 103528300 | 0.437 | ERCC5 |
| chr14 | 38060515 | 38060750 | 0.589 | FOXA1 |

-continued

| Chr. | Start | Stop | GC | Gene |
|---|---|---|---|---|
| chr14 | 38060564 | 38060810 | 0.591 | FOXA1 |
| chr14 | 38060574 | 38060818 | 0.592 | FOXA1 |
| chr14 | 38060586 | 38060833 | 0.601 | FOXA1 |
| chr14 | 45605103 | 45605333 | 0.558 | FANCM |
| chr14 | 45605305 | 45605553 | 0.610 | FANCM |
| chr14 | 45605573 | 45605799 | 0.511 | FANCM |
| chr14 | 45606233 | 45606433 | 0.398 | FANCM |
| chr14 | 45618024 | 45618224 | 0.363 | FANCM |
| chr14 | 45620541 | 45620741 | 0.333 | FANCM |
| chr14 | 45623034 | 45623234 | 0.348 | FANCM |
| chr14 | 45628297 | 45628497 | 0.408 | FANCM |
| chr14 | 45633510 | 45633710 | 0.373 | FANCM |
| chr14 | 45633720 | 45633920 | 0.383 | FANCM |
| chr14 | 45636166 | 45636386 | 0.376 | FANCM |
| chr14 | 45639788 | 45640013 | 0.341 | FANCM |
| chr14 | 45642242 | 45642442 | 0.403 | FANCM |
| chr14 | 45644281 | 45644486 | 0.340 | FANCM |
| chr14 | 45644653 | 45644863 | 0.313 | FANCM |
| chr14 | 45644862 | 45645099 | 0.382 | FANCM |
| chr14 | 45645143 | 45645342 | 0.350 | FANCM |
| chr14 | 45645413 | 45645613 | 0.378 | FANCM |
| chr14 | 45645666 | 45645955 | 0.331 | FANCM |
| chr14 | 45645983 | 45646183 | 0.303 | FANCM |
| chr14 | 45650718 | 45650970 | 0.332 | FANCM |
| chr14 | 45650772 | 45650971 | 0.320 | FANCM |
| chr14 | 45652886 | 45653086 | 0.338 | FANCM |
| chr14 | 45654389 | 45654589 | 0.303 | FANCM |
| chr14 | 45656912 | 45657134 | 0.269 | FANCM |
| chr14 | 45658004 | 45658204 | 0.333 | FANCM |
| chr14 | 45658183 | 45658427 | 0.371 | FANCM |
| chr14 | 45658417 | 45658644 | 0.368 | FANCM |
| chr14 | 45665608 | 45665811 | 0.348 | FANCM |
| chr14 | 45667934 | 45668145 | 0.358 | FANCM |
| chr14 | 45668983 | 45669204 | 0.320 | FANCM |
| chr14 | 45669474 | 45669678 | 0.346 | FANCM |
| chr14 | 95557315 | 95557515 | 0.313 | DICER1 |
| chr14 | 95557526 | 95557726 | 0.463 | DICER1 |
| chr14 | 95559982 | 95560182 | 0.542 | DICER1 |
| chr14 | 95560204 | 95560434 | 0.494 | DICER1 |
| chr14 | 95560444 | 95560644 | 0.398 | DICER1 |
| chr14 | 95562161 | 95562361 | 0.368 | DICER1 |
| chr14 | 95562361 | 95562592 | 0.530 | DICER1 |
| chr14 | 95562601 | 95562801 | 0.438 | DICER1 |
| chr14 | 95562666 | 95562891 | 0.398 | DICER1 |
| chr14 | 95566129 | 95566335 | 0.406 | DICER1 |
| chr14 | 95569682 | 95569882 | 0.468 | DICER1 |
| chr14 | 95569994 | 95570194 | 0.403 | DICER1 |
| chr14 | 95570228 | 95570428 | 0.418 | DICER1 |
| chr14 | 95571340 | 95571540 | 0.488 | DICER1 |
| chr14 | 95571974 | 95572174 | 0.348 | DICER1 |
| chr14 | 95572314 | 95572514 | 0.428 | DICER1 |
| chr14 | 95572524 | 95572764 | 0.249 | DICER1 |
| chr14 | 95573959 | 95574159 | 0.338 | DICER1 |
| chr14 | 95574168 | 95574368 | 0.348 | DICER1 |
| chr14 | 95574657 | 95574857 | 0.443 | DICER1 |
| chr14 | 95577599 | 95577799 | 0.433 | DICER1 |
| chr14 | 95578391 | 95578591 | 0.358 | DICER1 |
| chr14 | 95579340 | 95579540 | 0.358 | DICER1 |
| chr14 | 95581926 | 95582126 | 0.433 | DICER1 |
| chr14 | 95582756 | 95582956 | 0.358 | DICER1 |
| chr14 | 95582966 | 95583166 | 0.348 | DICER1 |
| chr14 | 95583900 | 95584100 | 0.378 | DICER1 |
| chr14 | 95590532 | 95590732 | 0.358 | DICER1 |
| chr14 | 95590767 | 95590967 | 0.393 | DICER1 |
| chr14 | 95592822 | 95593064 | 0.305 | DICER1 |
| chr14 | 95595734 | 95595934 | 0.358 | DICER1 |
| chr14 | 95596337 | 95596537 | 0.343 | DICER1 |
| chr14 | 95598778 | 95598978 | 0.383 | DICER1 |
| chr14 | 95598988 | 95599188 | 0.308 | DICER1 |
| chr14 | 95599591 | 95599801 | 0.436 | DICER1 |
| chr14 | 95623722 | 95623973 | 0.750 | DICER1 |
| chr14 | 105246388 | 105246637 | 0.596 | AKT1 |
| chr14 | 105246483 | 105246730 | 0.617 | AKT1 |
| chr14 | 105246501 | 105246707 | 0.633 | AKT1 |
| chr14 | 105246501 | 105246745 | 0.633 | AKT1 |
| chr15 | 32968921 | 32969121 | 0.303 | GREM1 |
| chr15 | 32976883 | 32977083 | 0.393 | GREM1 |

-continued

| Chr. | Start | Stop | GC | Gene |
|---|---|---|---|---|
| chr15 | 32984845 | 32985055 | 0.469 | GREM1 |
| chr15 | 32988826 | 32989036 | 0.370 | SCG5 |
| chr15 | 33000769 | 33000969 | 0.512 | GREM1 |
| chr15 | 33022952 | 33023162 | 0.654 | GREM1 |
| chr15 | 33022952 | 33023205 | 0.638 | GREM1 |
| chr15 | 33023018 | 33023279 | 0.626 | GREM1 |
| chr15 | 33023148 | 33023435 | 0.521 | GREM1 |
| chr15 | 33023151 | 33023435 | 0.519 | GREM1 |
| chr15 | 33023205 | 33023450 | 0.504 | GREM1 |
| chr15 | 33023686 | 33023886 | 0.517 | GREM1 |
| chr15 | 33024084 | 33024294 | 0.464 | GREM1 |
| chr15 | 33024482 | 33024682 | 0.398 | GREM1 |
| chr15 | 33026472 | 33026672 | 0.299 | GREM1 |
| chr15 | 66727327 | 66727566 | 0.546 | MAP2K1 |
| chr15 | 66727339 | 66727587 | 0.550 | MAP2K1 |
| chr15 | 66727339 | 66727588 | 0.548 | MAP2K1 |
| chr15 | 66727359 | 66727598 | 0.542 | MAP2K1 |
| chr15 | 66729024 | 66729277 | 0.496 | MAP2K1 |
| chr15 | 66729065 | 66729264 | 0.515 | MAP2K1 |
| chr15 | 66774016 | 66774220 | 0.527 | MAP2K1 |
| chr15 | 66774016 | 66774260 | 0.510 | MAP2K1 |
| chr15 | 66774048 | 66774260 | 0.516 | MAP2K1 |
| chr15 | 66774052 | 66774260 | 0.517 | MAP2K1 |
| chr15 | 66777305 | 66777541 | 0.591 | MAP2K1 |
| chr15 | 66777336 | 66777568 | 0.597 | MAP2K1 |
| chr15 | 66777336 | 66777570 | 0.600 | MAP2K1 |
| chr15 | 66777338 | 66777568 | 0.597 | MAP2K1 |
| chr15 | 89787224 | 89787484 | 0.651 | FANCI |
| chr15 | 89790756 | 89790956 | 0.368 | FANCI |
| chr15 | 89801818 | 89802048 | 0.403 | FANCI |
| chr15 | 89803854 | 89804054 | 0.403 | FANCI |
| chr15 | 89804662 | 89804884 | 0.372 | FANCI |
| chr15 | 89804949 | 89805159 | 0.365 | FANCI |
| chr15 | 89806635 | 89806874 | 0.371 | FANCI |
| chr15 | 89807040 | 89807240 | 0.403 | FANCI |
| chr15 | 89807671 | 89807891 | 0.344 | FANCI |
| chr15 | 89811673 | 89811922 | 0.364 | FANCI |
| chr15 | 89817473 | 89817702 | 0.370 | FANCI |
| chr15 | 89819937 | 89820137 | 0.418 | FANCI |
| chr15 | 89821824 | 89822080 | 0.358 | FANCI |
| chr15 | 89824311 | 89824511 | 0.333 | FANCI |
| chr15 | 89824830 | 89825066 | 0.359 | FANCI |
| chr15 | 89828191 | 89828429 | 0.439 | FANCI |
| chr15 | 89833373 | 89833592 | 0.368 | FANCI |
| chr15 | 89834739 | 89834949 | 0.365 | FANCI |
| chr15 | 89835684 | 89835936 | 0.336 | FANCI |
| chr15 | 89836099 | 89836321 | 0.327 | FANCI |
| chr15 | 89837021 | 89837221 | 0.358 | FANCI |
| chr15 | 89838207 | 89838356 | 0.480 | FANCI |
| chr15 | 89843116 | 89843345 | 0.417 | FANCI |
| chr15 | 89843449 | 89843649 | 0.403 | FANCI |
| chr15 | 89844490 | 89844700 | 0.455 | FANCI |
| chr15 | 89846965 | 89847165 | 0.388 | FANCI |
| chr15 | 89848390 | 89848629 | 0.479 | FANCI |
| chr15 | 89848727 | 89848927 | 0.478 | FANCI |
| chr15 | 89849176 | 89849396 | 0.439 | FANCI |
| chr15 | 89850578 | 89850778 | 0.403 | FANCI |
| chr15 | 89850795 | 89850995 | 0.438 | FANCI |
| chr15 | 89857735 | 89857935 | 0.398 | FANCI |
| chr15 | 89858460 | 89858694 | 0.498 | FANCI |
| chr15 | 89859420 | 89859663 | 0.430 | FANCI |
| chr15 | 89859773 | 89859973 | 0.517 | FANCI |
| chr15 | 89859992 | 89860192 | 0.443 | FANCI |
| chr15 | 89860258 | 89860477 | 0.359 | FANCI |
| chr15 | 90631785 | 90632007 | 0.570 | IDH2 |
| chr15 | 90631814 | 90632043 | 0.548 | IDH2 |
| chr15 | 90631843 | 90632054 | 0.519 | IDH2 |
| chr16 | 3631168 | 3631388 | 0.443 | SLX4 |
| chr16 | 3632424 | 3632665 | 0.645 | SLX4 |
| chr16 | 3632693 | 3632893 | 0.597 | SLX4 |
| chr16 | 3633083 | 3633283 | 0.582 | SLX4 |
| chr16 | 3633339 | 3633565 | 0.590 | SLX4 |
| chr16 | 3634696 | 3634896 | 0.502 | SLX4 |
| chr16 | 3639002 | 3639202 | 0.617 | SLX4 |
| chr16 | 3639197 | 3639423 | 0.652 | SLX4 |
| chr16 | 3639505 | 3639754 | 0.632 | SLX4 |
| chr16 | 3639692 | 3639932 | 0.639 | SLX4 |

-continued

| Chr. | Start | Stop | GC | Gene |
|---|---|---|---|---|
| chr16 | 3639911 | 3640159 | 0.530 | SLX4 |
| chr16 | 3640185 | 3640409 | 0.498 | SLX4 |
| chr16 | 3640478 | 3640721 | 0.607 | SLX4 |
| chr16 | 3640760 | 3641047 | 0.660 | SLX4 |
| chr16 | 3641072 | 3641272 | 0.468 | SLX4 |
| chr16 | 3642628 | 3642858 | 0.597 | SLX4 |
| chr16 | 3644537 | 3644773 | 0.608 | SLX4 |
| chr16 | 3645495 | 3645705 | 0.673 | SLX4 |
| chr16 | 3646003 | 3646244 | 0.698 | SLX4 |
| chr16 | 3646031 | 3646244 | 0.720 | SLX4 |
| chr16 | 3646124 | 3646405 | 0.699 | SLX4 |
| chr16 | 3646149 | 3646391 | 0.712 | SLX4 |
| chr16 | 3646157 | 3646403 | 0.704 | SLX4 |
| chr16 | 3647312 | 3647583 | 0.610 | SLX4 |
| chr16 | 3647601 | 3647800 | 0.540 | SLX4 |
| chr16 | 3647864 | 3648074 | 0.578 | SLX4 |
| chr16 | 3650971 | 3651251 | 0.530 | SLX4 |
| chr16 | 3652058 | 3652258 | 0.557 | SLX4 |
| chr16 | 3656390 | 3656622 | 0.506 | SLX4 |
| chr16 | 3656642 | 3656842 | 0.443 | SLX4 |
| chr16 | 3658480 | 3658725 | 0.528 | SLX4 |
| chr16 | 3658510 | 3658671 | 0.562 | SLX4 |
| chr16 | 3658784 | 3659014 | 0.455 | SLX4 |
| chr16 | 3659560 | 3659760 | 0.438 | SLX4 |
| chr16 | 14013935 | 14014175 | 0.651 | ERCC4 |
| chr16 | 14013966 | 14014166 | 0.662 | ERCC4 |
| chr16 | 14013970 | 14014170 | 0.662 | ERCC4 |
| chr16 | 14013971 | 14014170 | 0.665 | ERCC4 |
| chr16 | 14015823 | 14016023 | 0.373 | ERCC4 |
| chr16 | 14016033 | 14016243 | 0.355 | ERCC4 |
| chr16 | 14020466 | 14020710 | 0.351 | ERCC4 |
| chr16 | 14021912 | 14022151 | 0.338 | ERCC4 |
| chr16 | 14024532 | 14024732 | 0.373 | ERCC4 |
| chr16 | 14025949 | 14026157 | 0.344 | ERCC4 |
| chr16 | 14027949 | 14028149 | 0.348 | ERCC4 |
| chr16 | 14028984 | 14029224 | 0.415 | ERCC4 |
| chr16 | 14029445 | 14029685 | 0.452 | ERCC4 |
| chr16 | 14031514 | 14031714 | 0.373 | ERCC4 |
| chr16 | 14038575 | 14038734 | 0.494 | ERCC4 |
| chr16 | 14041470 | 14041670 | 0.468 | ERCC4 |
| chr16 | 14041655 | 14041919 | 0.509 | ERCC4 |
| chr16 | 14041900 | 14042126 | 0.498 | ERCC4 |
| chr16 | 14042120 | 14042369 | 0.404 | ERCC4 |
| chr16 | 14042584 | 14042854 | 0.424 | ERCC4 |
| chr16 | 14042844 | 14043078 | 0.336 | ERCC4 |
| chr16 | 14042902 | 14043146 | 0.347 | ERCC4 |
| chr16 | 14043430 | 14043679 | 0.284 | ERCC4 |
| chr16 | 14044214 | 14044436 | 0.332 | ERCC4 |
| chr16 | 14045149 | 14045380 | 0.276 | ERCC4 |
| chr16 | 14045389 | 14045634 | 0.427 | ERCC4 |
| chr16 | 14045727 | 14045927 | 0.328 | ERCC4 |
| chr16 | 14046154 | 14046384 | 0.303 | ERCC4 |
| chr16 | 23614570 | 23614827 | 0.310 | PALB2 |
| chr16 | 23614836 | 23615076 | 0.407 | PALB2 |
| chr16 | 23619110 | 23619349 | 0.479 | PALB2 |
| chr16 | 23625213 | 23625413 | 0.398 | PALB2 |
| chr16 | 23632741 | 23632891 | 0.391 | PALB2 |
| chr16 | 23634215 | 23634415 | 0.393 | PALB2 |
| chr16 | 23635260 | 23635465 | 0.374 | PALB2 |
| chr16 | 23637513 | 23637713 | 0.458 | PALB2 |
| chr16 | 23640440 | 23640682 | 0.370 | PALB2 |
| chr16 | 23640927 | 23641175 | 0.470 | PALB2 |
| chr16 | 23641292 | 23641502 | 0.431 | PALB2 |
| chr16 | 23641570 | 23641813 | 0.385 | PALB2 |
| chr16 | 23646217 | 23646416 | 0.470 | PALB2 |
| chr16 | 23646250 | 23646449 | 0.460 | PALB2 |
| chr16 | 23646427 | 23646636 | 0.390 | PALB2 |
| chr16 | 23646623 | 23646823 | 0.403 | PALB2 |
| chr16 | 23646780 | 23647008 | 0.345 | PALB2 |
| chr16 | 23646984 | 23647228 | 0.400 | PALB2 |
| chr16 | 23647144 | 23647434 | 0.385 | PALB2 |
| chr16 | 23647358 | 23647558 | 0.483 | PALB2 |
| chr16 | 23647369 | 23647610 | 0.467 | PALB2 |
| chr16 | 23649127 | 23649357 | 0.355 | PALB2 |
| chr16 | 23649265 | 23649465 | 0.358 | PALB2 |
| chr16 | 23652430 | 23652650 | 0.692 | PALB2 |
| chr16 | 23652647 | 23652887 | 0.647 | PALB2 |

-continued

| Chr. | Start | Stop | GC | Gene |
|---|---|---|---|---|
| chr16 | 68772169 | 68772389 | 0.679 | CDH1 |
| chr16 | 68835529 | 68835729 | 0.463 | CDH1 |
| chr16 | 68835564 | 68835767 | 0.485 | CDH1 |
| chr16 | 68842243 | 68842453 | 0.469 | CDH1 |
| chr16 | 68842518 | 68842718 | 0.423 | CDH1 |
| chr16 | 68844017 | 68844227 | 0.512 | CDH1 |
| chr16 | 68845519 | 68845719 | 0.483 | CDH1 |
| chr16 | 68845706 | 68845945 | 0.517 | CDH1 |
| chr16 | 68845947 | 68846147 | 0.502 | CDH1 |
| chr16 | 68846157 | 68846377 | 0.416 | CDH1 |
| chr16 | 68847216 | 68847450 | 0.477 | CDH1 |
| chr16 | 68849385 | 68849585 | 0.488 | CDH1 |
| chr16 | 68849423 | 68849649 | 0.529 | CDH1 |
| chr16 | 68853169 | 68853348 | 0.522 | CDH1 |
| chr16 | 68855861 | 68856061 | 0.453 | CDH1 |
| chr16 | 68856071 | 68856271 | 0.488 | CDH1 |
| chr16 | 68856802 | 68857067 | 0.560 | CDH1 |
| chr16 | 68857287 | 68857494 | 0.481 | CDH1 |
| chr16 | 68862023 | 68862255 | 0.511 | CDH1 |
| chr16 | 68863473 | 68863683 | 0.488 | CDH1 |
| chr16 | 68867121 | 68867366 | 0.488 | CDH1 |
| chr16 | 68867369 | 68867599 | 0.476 | CDH1 |
| chr16 | 89804046 | 89804215 | 0.553 | FANCA |
| chr16 | 89804303 | 89804513 | 0.592 | FANCA |
| chr16 | 89804648 | 89804858 | 0.635 | FANCA |
| chr16 | 89804928 | 89805172 | 0.596 | FANCA |
| chr16 | 89805241 | 89805441 | 0.498 | FANCA |
| chr16 | 89805462 | 89805662 | 0.612 | FANCA |
| chr16 | 89805672 | 89805892 | 0.548 | FANCA |
| chr16 | 89806299 | 89806509 | 0.502 | FANCA |
| chr16 | 89807188 | 89807437 | 0.364 | FANCA |
| chr16 | 89809197 | 89809432 | 0.542 | FANCA |
| chr16 | 89811314 | 89811494 | 0.646 | FANCA |
| chr16 | 89812889 | 89813109 | 0.557 | FANCA |
| chr16 | 89813161 | 89813385 | 0.551 | FANCA |
| chr16 | 89814966 | 89815166 | 0.587 | FANCA |
| chr16 | 89816227 | 89816392 | 0.608 | FANCA |
| chr16 | 89818546 | 89818699 | 0.416 | FANCA |
| chr16 | 89825033 | 89825256 | 0.563 | FANCA |
| chr16 | 89825068 | 89825276 | 0.545 | FANCA |
| chr16 | 89828413 | 89828604 | 0.396 | FANCA |
| chr16 | 89831297 | 89831493 | 0.533 | FANCA |
| chr16 | 89833531 | 89833695 | 0.358 | FANCA |
| chr16 | 89836321 | 89836521 | 0.617 | FANCA |
| chr16 | 89836550 | 89836790 | 0.598 | FANCA |
| chr16 | 89836823 | 89837062 | 0.604 | FANCA |
| chr16 | 89836842 | 89837075 | 0.615 | FANCA |
| chr16 | 89836876 | 89837138 | 0.635 | FANCA |
| chr16 | 89836882 | 89837082 | 0.627 | FANCA |
| chr16 | 89836894 | 89837156 | 0.627 | FANCA |
| chr16 | 89838040 | 89838261 | 0.514 | FANCA |
| chr16 | 89839593 | 89839838 | 0.573 | FANCA |
| chr16 | 89842062 | 89842262 | 0.498 | FANCA |
| chr16 | 89845140 | 89845350 | 0.483 | FANCA |
| chr16 | 89845256 | 89845456 | 0.527 | FANCA |
| chr16 | 89846317 | 89846557 | 0.498 | FANCA |
| chr16 | 89849141 | 89849341 | 0.502 | FANCA |
| chr16 | 89849323 | 89849591 | 0.554 | FANCA |
| chr16 | 89857774 | 89858016 | 0.560 | FANCA |
| chr16 | 89858250 | 89858450 | 0.567 | FANCA |
| chr16 | 89858752 | 89858951 | 0.555 | FANCA |
| chr16 | 89862215 | 89862425 | 0.512 | FANCA |
| chr16 | 89865452 | 89865652 | 0.532 | FANCA |
| chr16 | 89865648 | 89865886 | 0.498 | FANCA |
| chr16 | 89865874 | 89866074 | 0.408 | FANCA |
| chr16 | 89869678 | 89869909 | 0.461 | FANCA |
| chr16 | 89871619 | 89871819 | 0.522 | FANCA |
| chr16 | 89874567 | 89874718 | 0.375 | FANCA |
| chr16 | 89877021 | 89877274 | 0.382 | FANCA |
| chr16 | 89877278 | 89877525 | 0.520 | FANCA |
| chr16 | 89880876 | 89881036 | 0.342 | FANCA |
| chr16 | 89882268 | 89882508 | 0.564 | FANCA |
| chr17 | 7572710 | 7572941 | 0.547 | TP53 |
| chr17 | 7572841 | 7573094 | 0.524 | TP53 |
| chr17 | 7573785 | 7574015 | 0.571 | TP53 |
| chr17 | 7573785 | 7574050 | 0.583 | TP53 |
| chr17 | 7573803 | 7574050 | 0.593 | TP53 |

-continued

| Chr. | Start | Stop | GC | Gene |
|---|---|---|---|---|
| chr17 | 7573811 | 7574017 | 0.580 | TP53 |
| chr17 | 7576734 | 7576934 | 0.468 | TP53 |
| chr17 | 7576933 | 7577155 | 0.552 | TP53 |
| chr17 | 7576951 | 7577151 | 0.557 | TP53 |
| chr17 | 7576970 | 7577197 | 0.548 | TP53 |
| chr17 | 7576998 | 7577191 | 0.552 | TP53 |
| chr17 | 7576998 | 7577241 | 0.529 | TP53 |
| chr17 | 7576998 | 7577242 | 0.531 | TP53 |
| chr17 | 7577014 | 7577263 | 0.532 | TP53 |
| chr17 | 7577304 | 7577572 | 0.565 | TP53 |
| chr17 | 7577329 | 7577570 | 0.574 | TP53 |
| chr17 | 7577329 | 7577576 | 0.569 | TP53 |
| chr17 | 7577346 | 7577570 | 0.596 | TP53 |
| chr17 | 7577346 | 7577576 | 0.589 | TP53 |
| chr17 | 7577371 | 7577620 | 0.564 | TP53 |
| chr17 | 7577398 | 7577598 | 0.572 | TP53 |
| chr17 | 7578196 | 7578426 | 0.563 | TP53 |
| chr17 | 7578263 | 7578502 | 0.629 | TP53 |
| chr17 | 7578283 | 7578494 | 0.637 | TP53 |
| chr17 | 7578298 | 7578566 | 0.617 | TP53 |
| chr17 | 7578299 | 7578502 | 0.642 | TP53 |
| chr17 | 7578363 | 7578562 | 0.615 | TP53 |
| chr17 | 7578363 | 7578598 | 0.597 | TP53 |
| chr17 | 7579266 | 7579515 | 0.624 | TP53 |
| chr17 | 7579311 | 7579460 | 0.620 | TP53 |
| chr17 | 7579326 | 7579526 | 0.627 | TP53 |
| chr17 | 7579332 | 7579550 | 0.616 | TP53 |
| chr17 | 7579817 | 7579987 | 0.556 | TP53 |
| chr17 | 7590681 | 7590919 | 0.573 | TP53 |
| chr17 | 33426833 | 33427064 | 0.474 | RAD51D |
| chr17 | 33427044 | 33427283 | 0.500 | RAD51D |
| chr17 | 33427269 | 33427513 | 0.437 | RAD51D |
| chr17 | 33427477 | 33427725 | 0.518 | RAD51D |
| chr17 | 33427706 | 33427935 | 0.504 | RAD51D |
| chr17 | 33427916 | 33428162 | 0.498 | RAD51D |
| chr17 | 33428100 | 33428345 | 0.577 | RAD51D |
| chr17 | 33430196 | 33430419 | 0.567 | RAD51D |
| chr17 | 33430401 | 33430620 | 0.573 | RAD51D |
| chr17 | 33433344 | 33433506 | 0.564 | RAD51D |
| chr17 | 33433897 | 33434133 | 0.489 | RAD51D |
| chr17 | 33434295 | 33434532 | 0.500 | RAD51D |
| chr17 | 33445499 | 33445672 | 0.586 | RAD51D |
| chr17 | 33446550 | 33446780 | 0.662 | RAD51D |
| chr17 | 37868175 | 37868423 | 0.606 | ERBB2 |
| chr17 | 37868177 | 37868424 | 0.605 | ERBB2 |
| chr17 | 37868184 | 37868432 | 0.614 | ERBB2 |
| chr17 | 37868192 | 37868432 | 0.622 | ERBB2 |
| chr17 | 41226314 | 41226567 | 0.433 | BRCA1 |
| chr17 | 41228463 | 41228682 | 0.368 | BRCA1 |
| chr17 | 41231290 | 41231560 | 0.432 | BRCA1 |
| chr17 | 41234185 | 41234455 | 0.435 | BRCA1 |
| chr17 | 41234392 | 41234631 | 0.438 | BRCA1 |
| chr17 | 41242906 | 41243146 | 0.444 | BRCA1 |
| chr17 | 41243450 | 41243690 | 0.411 | BRCA1 |
| chr17 | 41243675 | 41243921 | 0.397 | BRCA1 |
| chr17 | 41243914 | 41244153 | 0.433 | BRCA1 |
| chr17 | 41244048 | 41244300 | 0.368 | BRCA1 |
| chr17 | 41244075 | 41244265 | 0.366 | BRCA1 |
| chr17 | 41244473 | 41244712 | 0.371 | BRCA1 |
| chr17 | 41244534 | 41244778 | 0.376 | BRCA1 |
| chr17 | 41244766 | 41245013 | 0.387 | BRCA1 |
| chr17 | 41245011 | 41245240 | 0.409 | BRCA1 |
| chr17 | 41245209 | 41245462 | 0.374 | BRCA1 |
| chr17 | 41245347 | 41245586 | 0.404 | BRCA1 |
| chr17 | 41245598 | 41245827 | 0.370 | BRCA1 |
| chr17 | 41245825 | 41246064 | 0.375 | BRCA1 |
| chr17 | 41246061 | 41246310 | 0.376 | BRCA1 |
| chr17 | 41246304 | 41246553 | 0.416 | BRCA1 |
| chr17 | 41246534 | 41246786 | 0.423 | BRCA1 |
| chr17 | 41246546 | 41246786 | 0.427 | BRCA1 |
| chr17 | 41246595 | 41246842 | 0.419 | BRCA1 |
| chr17 | 41246643 | 41246890 | 0.403 | BRCA1 |
| chr17 | 41246709 | 41246956 | 0.379 | BRCA1 |
| chr17 | 41246794 | 41247027 | 0.338 | BRCA1 |
| chr17 | 41247801 | 41248006 | 0.403 | BRCA1 |
| chr17 | 41249211 | 41249311 | 0.356 | BRCA1 |
| chr17 | 41251673 | 41251893 | 0.380 | BRCA1 |

-continued

| Chr. | Start | Stop | GC | Gene |
|---|---|---|---|---|
| chr17 | 41251732 | 41251945 | 0.397 | BRCA1 |
| chr17 | 37880017 | 37880264 | 0.528 | ERBB2 |
| chr17 | 37880031 | 37880255 | 0.524 | ERBB2 |
| chr17 | 37880061 | 37880274 | 0.505 | ERBB2 |
| chr17 | 37880069 | 37880274 | 0.500 | ERBB2 |
| chr17 | 37880955 | 37881196 | 0.595 | ERBB2 |
| chr17 | 37880969 | 37881216 | 0.589 | ERBB2 |
| chr17 | 37880974 | 37881216 | 0.593 | ERBB2 |
| chr17 | 37880983 | 37881227 | 0.592 | ERBB2 |
| chr17 | 37881166 | 37881380 | 0.609 | ERBB2 |
| chr17 | 37881201 | 37881450 | 0.584 | ERBB2 |
| chr17 | 37881273 | 37881520 | 0.573 | ERBB2 |
| chr17 | 37881304 | 37881521 | 0.573 | ERBB2 |
| chr17 | 37881453 | 37881652 | 0.595 | ERBB2 |
| chr17 | 37881465 | 37881668 | 0.598 | ERBB2 |
| chr17 | 37881510 | 37881737 | 0.601 | ERBB2 |
| chr17 | 37881598 | 37881798 | 0.632 | ERBB2 |
| chr17 | 41196311 | 41196511 | 0.393 | BRCA1 |
| chr17 | 41197220 | 41197464 | 0.429 | BRCA1 |
| chr17 | 41197314 | 41197566 | 0.419 | BRCA1 |
| chr17 | 41197571 | 41197819 | 0.550 | BRCA1 |
| chr17 | 41199637 | 41199729 | 0.559 | BRCA1 |
| chr17 | 41201055 | 41201304 | 0.476 | BRCA1 |
| chr17 | 41202997 | 41203243 | 0.449 | BRCA1 |
| chr17 | 41209041 | 41209195 | 0.445 | BRCA1 |
| chr17 | 41215338 | 41215577 | 0.433 | BRCA1 |
| chr17 | 41215806 | 41216045 | 0.375 | BRCA1 |
| chr17 | 41219623 | 41219726 | 0.337 | BRCA1 |
| chr17 | 41222828 | 41223088 | 0.402 | BRCA1 |
| chr17 | 41222835 | 41223088 | 0.406 | BRCA1 |
| chr17 | 41222885 | 41223141 | 0.444 | BRCA1 |
| chr17 | 41223090 | 41223269 | 0.494 | BRCA1 |
| chr17 | 41256181 | 41256358 | 0.315 | BRCA1 |
| chr17 | 41256830 | 41257034 | 0.376 | BRCA1 |
| chr17 | 41256884 | 41257140 | 0.339 | BRCA1 |
| chr17 | 41258410 | 41258681 | 0.324 | BRCA1 |
| chr17 | 41267598 | 41267807 | 0.371 | BRCA1 |
| chr17 | 41267602 | 41267807 | 0.369 | BRCA1 |
| chr17 | 41267603 | 41267794 | 0.354 | BRCA1 |
| chr17 | 41267603 | 41267834 | 0.371 | BRCA1 |
| chr17 | 41267630 | 41267779 | 0.353 | BRCA1 |
| chr17 | 41267645 | 41267836 | 0.391 | BRCA1 |
| chr17 | 41275961 | 41276197 | 0.312 | BRCA1 |
| chr17 | 46805588 | 46805837 | 0.672 | HOXB13 |
| chr17 | 47696239 | 47696485 | 0.453 | SPOP |
| chr17 | 47696300 | 47696545 | 0.455 | SPOP |
| chr17 | 47696324 | 47696565 | 0.442 | SPOP |
| chr17 | 47696359 | 47696607 | 0.422 | SPOP |
| chr17 | 47696424 | 47696669 | 0.415 | SPOP |
| chr17 | 47696450 | 47696669 | 0.405 | SPOP |
| chr17 | 47696450 | 47696689 | 0.413 | SPOP |
| chr17 | 47696486 | 47696715 | 0.387 | SPOP |
| chr17 | 56769976 | 56770175 | 0.590 | RAD51C |
| chr17 | 56772289 | 56772542 | 0.421 | RAD51C |
| chr17 | 56773994 | 56774243 | 0.404 | RAD51C |
| chr17 | 56780486 | 56780723 | 0.345 | RAD51C |
| chr17 | 56787247 | 56787446 | 0.365 | RAD51C |
| chr17 | 56787285 | 56787460 | 0.341 | RAD51C |
| chr17 | 56798102 | 56798172 | 0.352 | RAD51C |
| chr17 | 56801331 | 56801553 | 0.390 | RAD51C |
| chr17 | 56809830 | 56810049 | 0.382 | RAD51C |
| chr17 | 56811478 | 56811716 | 0.385 | RAD51C |
| chr17 | 59756779 | 59756979 | 0.313 | BRIP1 |
| chr17 | 59759726 | 59759955 | 0.252 | BRIP1 |
| chr17 | 59760615 | 59760854 | 0.308 | BRIP1 |
| chr17 | 59760809 | 59761044 | 0.335 | BRIP1 |
| chr17 | 59761001 | 59761201 | 0.353 | BRIP1 |
| chr17 | 59761265 | 59761494 | 0.413 | BRIP1 |
| chr17 | 59761395 | 59761636 | 0.343 | BRIP1 |
| chr17 | 59763229 | 59763449 | 0.357 | BRIP1 |
| chr17 | 59763460 | 59763660 | 0.338 | BRIP1 |
| chr17 | 59770816 | 59771046 | 0.307 | BRIP1 |
| chr17 | 59793106 | 59793349 | 0.316 | BRIP1 |
| chr17 | 59793137 | 59793367 | 0.338 | BRIP1 |
| chr17 | 59820379 | 59820551 | 0.393 | BRIP1 |
| chr17 | 59821796 | 59821945 | 0.373 | BRIP1 |
| chr17 | 59853687 | 59853887 | 0.353 | BRIP1 |

-continued

| Chr. | Start | Stop | GC | Gene |
|---|---|---|---|---|
| chr17 | 59857537 | 59857737 | 0.333 | BRIP1 |
| chr17 | 59858201 | 59858428 | 0.355 | BRIP1 |
| chr17 | 59861553 | 59861773 | 0.326 | BRIP1 |
| chr17 | 59870956 | 59871190 | 0.345 | BRIP1 |
| chr17 | 59876405 | 59876605 | 0.388 | BRIP1 |
| chr17 | 59876622 | 59876822 | 0.284 | BRIP1 |
| chr17 | 59878569 | 59878769 | 0.413 | BRIP1 |
| chr17 | 59878611 | 59878844 | 0.397 | BRIP1 |
| chr17 | 59885818 | 59886038 | 0.439 | BRIP1 |
| chr17 | 59886058 | 59886268 | 0.346 | BRIP1 |
| chr17 | 59924485 | 59924714 | 0.348 | BRIP1 |
| chr17 | 59926478 | 59926707 | 0.348 | BRIP1 |
| chr17 | 59934381 | 59934581 | 0.383 | BRIP1 |
| chr17 | 59937155 | 59937392 | 0.374 | BRIP1 |
| chr17 | 59938714 | 59938914 | 0.333 | BRIP1 |
| chr17 | 59940627 | 59940827 | 0.577 | BRIP1 |
| chr17 | 59940844 | 59941054 | 0.592 | BRIP1 |
| chr18 | 48556368 | 48556604 | 0.692 | SMAD4 |
| chr18 | 48556368 | 48556608 | 0.689 | SMAD4 |
| chr18 | 48556413 | 48556612 | 0.680 | SMAD4 |
| chr18 | 48556414 | 48556616 | 0.675 | SMAD4 |
| chr18 | 48573249 | 48573492 | 0.328 | SMAD4 |
| chr18 | 48573500 | 48573738 | 0.364 | SMAD4 |
| chr18 | 48575147 | 48575346 | 0.340 | SMAD4 |
| chr18 | 48575524 | 48575724 | 0.294 | SMAD4 |
| chr18 | 48581203 | 48581433 | 0.455 | SMAD4 |
| chr18 | 48581249 | 48581498 | 0.428 | SMAD4 |
| chr18 | 48584399 | 48584599 | 0.443 | SMAD4 |
| chr18 | 48584673 | 48584893 | 0.439 | SMAD4 |
| chr18 | 48586106 | 48586306 | 0.308 | SMAD4 |
| chr18 | 48591791 | 48592035 | 0.408 | SMAD4 |
| chr18 | 48593378 | 48593608 | 0.407 | SMAD4 |
| chr18 | 48602902 | 48603166 | 0.430 | SMAD4 |
| chr18 | 48602922 | 48603132 | 0.445 | SMAD4 |
| chr18 | 48603000 | 48603249 | 0.424 | SMAD4 |
| chr18 | 48603132 | 48603332 | 0.289 | SMAD4 |
| chr18 | 48604566 | 48604815 | 0.488 | SMAD4 |
| chr18 | 48604617 | 48604861 | 0.490 | SMAD4 |
| chr18 | 48604640 | 48604881 | 0.492 | SMAD4 |
| chr18 | 48604711 | 48604957 | 0.421 | SMAD4 |
| chr18 | 48605303 | 48605503 | 0.294 | SMAD4 |
| chr18 | 48605551 | 48605798 | 0.351 | SMAD4 |
| chr18 | 48605981 | 48606181 | 0.318 | SMAD4 |
| chr18 | 48606203 | 48606477 | 0.349 | SMAD4 |
| chr18 | 48606469 | 48606712 | 0.357 | SMAD4 |
| chr18 | 48607311 | 48607586 | 0.326 | SMAD4 |
| chr18 | 48607638 | 48607926 | 0.412 | SMAD4 |
| chr18 | 48608009 | 48608208 | 0.375 | SMAD4 |
| chr18 | 48608225 | 48608485 | 0.368 | SMAD4 |
| chr18 | 48608754 | 48608904 | 0.450 | SMAD4 |
| chr18 | 48609535 | 48609685 | 0.470 | SMAD4 |
| chr18 | 48609670 | 48609869 | 0.355 | SMAD4 |
| chr18 | 48610653 | 48610803 | 0.358 | SMAD4 |
| chr18 | 48610833 | 48611078 | 0.488 | SMAD4 |
| chr18 | 48611097 | 48611339 | 0.490 | SMAD4 |
| chr18 | 48611405 | 48611605 | 0.353 | SMAD4 |
| chr19 | 1206543 | 1206797 | 0.643 | STK11 |
| chr19 | 1206613 | 1206843 | 0.558 | STK11 |
| chr19 | 1206770 | 1207017 | 0.560 | STK11 |
| chr19 | 1206962 | 1207206 | 0.596 | STK11 |
| chr19 | 1218302 | 1218502 | 0.532 | STK11 |
| chr19 | 1219161 | 1219399 | 0.653 | STK11 |
| chr19 | 1220251 | 1220492 | 0.632 | STK11 |
| chr19 | 1220276 | 1220492 | 0.636 | STK11 |
| chr19 | 1220475 | 1220701 | 0.705 | STK11 |
| chr19 | 1220502 | 1220701 | 0.715 | STK11 |
| chr19 | 1220681 | 1220938 | 0.647 | STK11 |
| chr19 | 1220681 | 1220941 | 0.648 | STK11 |
| chr19 | 1221151 | 1221351 | 0.582 | STK11 |
| chr19 | 1221821 | 1222071 | 0.685 | STK11 |
| chr19 | 1222984 | 1223224 | 0.643 | STK11 |
| chr19 | 1226453 | 1226708 | 0.715 | STK11 |
| chr19 | 1226464 | 1226754 | 0.704 | STK11 |
| chr19 | 1226465 | 1226707 | 0.716 | STK11 |
| chr19 | 1228261 | 1228461 | 0.547 | STK11 |
| chr19 | 3114798 | 3115046 | 0.683 | GNA11 |
| chr19 | 3114798 | 3115049 | 0.683 | GNA11 |

-continued

| Chr. | Start | Stop | GC | Gene |
|---|---|---|---|---|
| chr19 | 3114839 | 3115040 | 0.688 | GNA11 |
| chr19 | 3114841 | 3115040 | 0.685 | GNA11 |
| chr19 | 3118772 | 3118996 | 0.622 | GNA11 |
| chr19 | 3118795 | 3119044 | 0.620 | GNA11 |
| chr19 | 3118818 | 3119047 | 0.613 | GNA11 |
| chr19 | 3118863 | 3119109 | 0.636 | GNA11 |
| chr19 | 10600276 | 10600491 | 0.588 | KEAP1 |
| chr19 | 10600284 | 10600528 | 0.592 | KEAP1 |
| chr19 | 10600284 | 10600532 | 0.594 | KEAP1 |
| chr19 | 10602242 | 10602441 | 0.645 | KEAP1 |
| chr19 | 10602423 | 10602671 | 0.691 | KEAP1 |
| chr19 | 10602539 | 10602747 | 0.632 | KEAP1 |
| chr19 | 10602539 | 10602753 | 0.628 | KEAP1 |
| chr19 | 10602653 | 10602854 | 0.609 | KEAP1 |
| chr19 | 10610056 | 10610289 | 0.585 | KEAP1 |
| chr19 | 10610069 | 10610306 | 0.576 | KEAP1 |
| chr19 | 10610081 | 10610306 | 0.580 | KEAP1 |
| chr19 | 10610083 | 10610306 | 0.580 | KEAP1 |
| chr19 | 11094768 | 11095038 | 0.697 | SMARCA4 |
| chr19 | 11095950 | 11096150 | 0.592 | SMARCA4 |
| chr19 | 11096820 | 11097078 | 0.625 | SMARCA4 |
| chr19 | 11097475 | 11097685 | 0.645 | SMARCA4 |
| chr19 | 11098265 | 11098553 | 0.706 | SMARCA4 |
| chr19 | 11098298 | 11098538 | 0.726 | SMARCA4 |
| chr19 | 11098376 | 11098606 | 0.732 | SMARCA4 |
| chr19 | 11099901 | 11100111 | 0.607 | SMARCA4 |
| chr19 | 11101757 | 11101957 | 0.612 | SMARCA4 |
| chr19 | 11105466 | 11105666 | 0.522 | SMARCA4 |
| chr19 | 11106694 | 11106939 | 0.557 | SMARCA4 |
| chr19 | 11107143 | 11107352 | 0.476 | SMARCA4 |
| chr19 | 11113645 | 11113845 | 0.592 | SMARCA4 |
| chr19 | 11113855 | 11114055 | 0.493 | SMARCA4 |
| chr19 | 11118483 | 11118683 | 0.587 | SMARCA4 |
| chr19 | 11120977 | 11121177 | 0.557 | SMARCA4 |
| chr19 | 11123551 | 11123751 | 0.592 | SMARCA4 |
| chr19 | 11129571 | 11129781 | 0.555 | SMARCA4 |
| chr19 | 11130134 | 11130372 | 0.619 | SMARCA4 |
| chr19 | 11130167 | 11130367 | 0.612 | SMARCA4 |
| chr19 | 11130245 | 11130468 | 0.585 | SMARCA4 |
| chr19 | 11130248 | 11130473 | 0.584 | SMARCA4 |
| chr19 | 11132367 | 11132587 | 0.611 | SMARCA4 |
| chr19 | 11132607 | 11132807 | 0.622 | SMARCA4 |
| chr19 | 11134126 | 11134326 | 0.557 | SMARCA4 |
| chr19 | 11134905 | 11135105 | 0.617 | SMARCA4 |
| chr19 | 11135986 | 11136186 | 0.602 | SMARCA4 |
| chr19 | 11136874 | 11137104 | 0.610 | SMARCA4 |
| chr19 | 11138402 | 11138674 | 0.502 | SMARCA4 |
| chr19 | 11138598 | 11138818 | 0.597 | SMARCA4 |
| chr19 | 11141332 | 11141532 | 0.637 | SMARCA4 |
| chr19 | 11141549 | 11141749 | 0.627 | SMARCA4 |
| chr19 | 11143924 | 11144134 | 0.621 | SMARCA4 |
| chr19 | 11144041 | 11144262 | 0.617 | SMARCA4 |
| chr19 | 11144868 | 11145108 | 0.618 | SMARCA4 |
| chr19 | 11145552 | 11145823 | 0.654 | SMARCA4 |
| chr19 | 11151919 | 11152129 | 0.616 | SMARCA4 |
| chr19 | 11151919 | 11152189 | 0.627 | SMARCA4 |
| chr19 | 11152171 | 11152371 | 0.572 | SMARCA4 |
| chr19 | 11168890 | 11169140 | 0.625 | SMARCA4 |
| chr19 | 11169359 | 11169619 | 0.644 | SMARCA4 |
| chr19 | 11170610 | 11170850 | 0.668 | SMARCA4 |
| chr19 | 11172452 | 11172706 | 0.498 | SMARCA4 |
| chr19 | 11172557 | 11172757 | 0.423 | SMARCA4 |
| chr19 | 11172753 | 11172953 | 0.493 | SMARCA4 |
| chr19 | 45854611 | 45854870 | 0.581 | ERCC2 |
| chr19 | 45854917 | 45855123 | 0.589 | ERCC2 |
| chr19 | 45855406 | 45855649 | 0.656 | ERCC2 |
| chr19 | 45855711 | 45855931 | 0.611 | ERCC2 |
| chr19 | 45855908 | 45856123 | 0.611 | ERCC2 |
| chr19 | 45855910 | 45856123 | 0.612 | ERCC2 |
| chr19 | 45855914 | 45856123 | 0.610 | ERCC2 |
| chr19 | 45855948 | 45856167 | 0.609 | ERCC2 |
| chr19 | 45855959 | 45856169 | 0.607 | ERCC2 |
| chr19 | 45856222 | 45856442 | 0.652 | ERCC2 |
| chr19 | 45857893 | 45858113 | 0.597 | ERCC2 |
| chr19 | 45860528 | 45860730 | 0.635 | ERCC2 |
| chr19 | 45860797 | 45861007 | 0.635 | ERCC2 |
| chr19 | 45864772 | 45864905 | 0.575 | ERCC2 |

-continued

| Chr. | Start | Stop | GC | Gene |
|---|---|---|---|---|
| chr19 | 45866937 | 45867137 | 0.706 | ERCC2 |
| chr19 | 45867119 | 45867343 | 0.724 | ERCC2 |
| chr19 | 45867124 | 45867373 | 0.716 | ERCC2 |
| chr19 | 45867329 | 45867584 | 0.684 | ERCC2 |
| chr19 | 45867491 | 45867711 | 0.656 | ERCC2 |
| chr19 | 45867506 | 45867746 | 0.660 | ERCC2 |
| chr19 | 45867566 | 45867806 | 0.618 | ERCC2 |
| chr19 | 45868096 | 45868344 | 0.635 | ERCC2 |
| chr19 | 45868149 | 45868349 | 0.637 | ERCC2 |
| chr19 | 45868154 | 45868396 | 0.626 | ERCC2 |
| chr19 | 45868287 | 45868486 | 0.600 | ERCC2 |
| chr19 | 45871786 | 45871991 | 0.524 | ERCC2 |
| chr19 | 45872064 | 45872264 | 0.582 | ERCC2 |
| chr19 | 45872211 | 45872411 | 0.562 | ERCC2 |
| chr19 | 45873397 | 45873585 | 0.661 | ERCC2 |
| chr19 | 45873421 | 45873651 | 0.675 | ERCC2 |
| chr19 | 45873436 | 45873665 | 0.687 | ERCC2 |
| chr19 | 45873632 | 45873861 | 0.700 | ERCC2 |
| chr19 | 45873636 | 45873901 | 0.684 | ERCC2 |
| chr19 | 45873726 | 45873936 | 0.645 | ERCC2 |
| chr19 | 45916987 | 45917191 | 0.571 | ERCC1 |
| chr19 | 45918047 | 45918240 | 0.619 | ERCC1 |
| chr19 | 45918047 | 45918243 | 0.619 | ERCC1 |
| chr19 | 45918048 | 45918243 | 0.622 | ERCC1 |
| chr19 | 45918053 | 45918243 | 0.628 | ERCC1 |
| chr19 | 45918060 | 45918235 | 0.625 | ERCC1 |
| chr19 | 45922222 | 45922436 | 0.567 | ERCC1 |
| chr19 | 45923506 | 45923678 | 0.607 | ERCC1 |
| chr19 | 45924445 | 45924632 | 0.638 | ERCC1 |
| chr19 | 45926611 | 45926815 | 0.615 | ERCC1 |
| chr19 | 50902097 | 50902336 | 0.650 | POLD1 |
| chr19 | 50902458 | 50902658 | 0.582 | POLD1 |
| chr19 | 50904960 | 50905171 | 0.656 | POLD1 |
| chr19 | 50905153 | 50905392 | 0.671 | POLD1 |
| chr19 | 50905436 | 50905665 | 0.683 | POLD1 |
| chr19 | 50905615 | 50905913 | 0.659 | POLD1 |
| chr19 | 50905899 | 50906137 | 0.665 | POLD1 |
| chr19 | 50906253 | 50906464 | 0.679 | POLD1 |
| chr19 | 50906723 | 50906971 | 0.622 | POLD1 |
| chr19 | 50906755 | 50906971 | 0.613 | POLD1 |
| chr19 | 50909485 | 50909773 | 0.640 | POLD1 |
| chr19 | 50910320 | 50910533 | 0.631 | POLD1 |
| chr19 | 50910334 | 50910578 | 0.629 | POLD1 |
| chr19 | 50910376 | 50910627 | 0.631 | POLD1 |
| chr19 | 50912042 | 50912281 | 0.617 | POLD1 |
| chr19 | 50912288 | 50912520 | 0.635 | POLD1 |
| chr19 | 50912795 | 50913010 | 0.667 | POLD1 |
| chr19 | 50916709 | 50916950 | 0.640 | POLD1 |
| chr19 | 50916970 | 50917221 | 0.623 | POLD1 |
| chr19 | 50917955 | 50918169 | 0.628 | POLD1 |
| chr19 | 50917960 | 50918169 | 0.624 | POLD1 |
| chr19 | 50918653 | 50918824 | 0.640 | POLD1 |
| chr19 | 50919033 | 50919269 | 0.692 | POLD1 |
| chr19 | 50919496 | 50919745 | 0.684 | POLD1 |
| chr19 | 50919683 | 50919957 | 0.691 | POLD1 |
| chr19 | 50919685 | 50919957 | 0.689 | POLD1 |
| chr19 | 50919770 | 50920048 | 0.699 | POLD1 |
| chr19 | 50919821 | 50920050 | 0.691 | POLD1 |
| chr19 | 50921104 | 50921313 | 0.576 | POLD1 |
| chr2 | 29443543 | 29443787 | 0.539 | ALK |
| chr2 | 29443549 | 29443783 | 0.545 | ALK |
| chr2 | 29443555 | 29443789 | 0.540 | ALK |
| chr2 | 29443585 | 29443816 | 0.500 | ALK |
| chr2 | 29445100 | 29445340 | 0.552 | ALK |
| chr2 | 29445107 | 29445340 | 0.556 | ALK |
| chr2 | 29445121 | 29445350 | 0.570 | ALK |
| chr2 | 29445121 | 29445367 | 0.571 | ALK |
| chr2 | 47600500 | 47600700 | 0.323 | EPCAM |
| chr2 | 47600912 | 47601112 | 0.473 | EPCAM |
| chr2 | 47601122 | 47601322 | 0.383 | EPCAM |
| chr2 | 47602199 | 47602445 | 0.328 | EPCAM |
| chr2 | 47604131 | 47604282 | 0.342 | EPCAM |
| chr2 | 47605987 | 47606187 | 0.249 | EPCAM |
| chr2 | 47606812 | 47606991 | 0.361 | EPCAM |
| chr2 | 47612268 | 47612488 | 0.398 | EPCAM |
| chr2 | 47613710 | 47613910 | 0.343 | EPCAM |
| chr2 | 47630105 | 47630305 | 0.652 | MSH2 |

-continued

| Chr. | Start | Stop | GC | Gene |
|---|---|---|---|---|
| chr2 | 47630152 | 47630400 | 0.643 | MSH2 |
| chr2 | 47630268 | 47630467 | 0.615 | MSH2 |
| chr2 | 47630315 | 47630515 | 0.667 | MSH2 |
| chr2 | 47630316 | 47630530 | 0.647 | MSH2 |
| chr2 | 47630384 | 47630615 | 0.690 | MSH2 |
| chr2 | 47630425 | 47630625 | 0.706 | MSH2 |
| chr2 | 47635539 | 47635709 | 0.339 | MSH2 |
| chr2 | 47637342 | 47637582 | 0.456 | MSH2 |
| chr2 | 47637389 | 47637594 | 0.442 | MSH2 |
| chr2 | 47639447 | 47639662 | 0.310 | MSH2 |
| chr2 | 47641283 | 47641487 | 0.327 | MSH2 |
| chr2 | 47643346 | 47643546 | 0.398 | MSH2 |
| chr2 | 47656945 | 47657096 | 0.388 | MSH2 |
| chr2 | 47672586 | 47672786 | 0.299 | MSH2 |
| chr2 | 47690076 | 47690276 | 0.303 | MSH2 |
| chr2 | 47693747 | 47693947 | 0.348 | MSH2 |
| chr2 | 47698159 | 47698397 | 0.326 | MSH2 |
| chr2 | 47702121 | 47702341 | 0.394 | MSH2 |
| chr2 | 47702174 | 47702413 | 0.388 | MSH2 |
| chr2 | 47703453 | 47703653 | 0.428 | MSH2 |
| chr2 | 47703663 | 47703863 | 0.363 | MSH2 |
| chr2 | 47705399 | 47705630 | 0.397 | MSH2 |
| chr2 | 47707788 | 47708018 | 0.424 | MSH2 |
| chr2 | 47709903 | 47710113 | 0.327 | MSH2 |
| chr2 | 47710107 | 47710336 | 0.287 | MSH2 |
| chr2 | 48010393 | 48010592 | 0.725 | MSH6 |
| chr2 | 48010420 | 48010619 | 0.740 | MSH6 |
| chr2 | 48010573 | 48010824 | 0.690 | MSH6 |
| chr2 | 48010575 | 48010781 | 0.725 | MSH6 |
| chr2 | 48017953 | 48018200 | 0.419 | MSH6 |
| chr2 | 48018205 | 48018415 | 0.431 | MSH6 |
| chr2 | 48023040 | 48023272 | 0.455 | MSH6 |
| chr2 | 48023105 | 48023304 | 0.430 | MSH6 |
| chr2 | 48025749 | 48025949 | 0.428 | MSH6 |
| chr2 | 48025933 | 48026201 | 0.476 | MSH6 |
| chr2 | 48026177 | 48026376 | 0.460 | MSH6 |
| chr2 | 48026340 | 48026558 | 0.457 | MSH6 |
| chr2 | 48026511 | 48026711 | 0.458 | MSH6 |
| chr2 | 48026765 | 48026965 | 0.383 | MSH6 |
| chr2 | 48027019 | 48027219 | 0.438 | MSH6 |
| chr2 | 48027273 | 48027473 | 0.438 | MSH6 |
| chr2 | 48027527 | 48027727 | 0.398 | MSH6 |
| chr2 | 48027746 | 48028017 | 0.426 | MSH6 |
| chr2 | 48028124 | 48028364 | 0.415 | MSH6 |
| chr2 | 48030536 | 48030736 | 0.433 | MSH6 |
| chr2 | 48030729 | 48031008 | 0.371 | MSH6 |
| chr2 | 48031952 | 48032152 | 0.443 | MSH6 |
| chr2 | 48032026 | 48032237 | 0.420 | MSH6 |
| chr2 | 48032772 | 48032971 | 0.315 | MSH6 |
| chr2 | 48033358 | 48033554 | 0.365 | MSH6 |
| chr2 | 48033416 | 48033655 | 0.367 | MSH6 |
| chr2 | 48033581 | 48033782 | 0.401 | MSH6 |
| chr2 | 48034024 | 48034264 | 0.307 | MSH6 |
| chr2 | 58386432 | 58386632 | 0.333 | FANCL |
| chr2 | 58386777 | 58386929 | 0.307 | FANCL |
| chr2 | 58387189 | 58387389 | 0.338 | FANCL |
| chr2 | 58388496 | 58388732 | 0.346 | FANCL |
| chr2 | 58389905 | 58390169 | 0.328 | FANCL |
| chr2 | 58390005 | 58390214 | 0.352 | FANCL |
| chr2 | 58390571 | 58390773 | 0.379 | FANCL |
| chr2 | 58392779 | 58392979 | 0.398 | FANCL |
| chr2 | 58431158 | 58431358 | 0.363 | FANCL |
| chr2 | 58448972 | 58449172 | 0.323 | FANCL |
| chr2 | 58453736 | 58453936 | 0.308 | FANCL |
| chr2 | 58456824 | 58457044 | 0.285 | FANCL |
| chr2 | 58459138 | 58459342 | 0.351 | FANCL |
| chr2 | 58468279 | 58468479 | 0.592 | FANCL |
| chr2 | 128014784 | 128015047 | 0.394 | ERCC3 |
| chr2 | 128015087 | 128015289 | 0.522 | ERCC3 |
| chr2 | 128016793 | 128017023 | 0.541 | ERCC3 |
| chr2 | 128018729 | 128018934 | 0.476 | ERCC3 |
| chr2 | 128028846 | 128029046 | 0.493 | ERCC3 |
| chr2 | 128030334 | 128030534 | 0.488 | ERCC3 |
| chr2 | 128036695 | 128036895 | 0.413 | ERCC3 |
| chr2 | 128037952 | 128038168 | 0.535 | ERCC3 |
| chr2 | 128044271 | 128044501 | 0.580 | ERCC3 |
| chr2 | 128044494 | 128044693 | 0.500 | ERCC3 |

-continued

| Chr. | Start | Stop | GC | Gene |
|---|---|---|---|---|
| chr2 | 128046183 | 128046383 | 0.502 | ERCC3 |
| chr2 | 128046840 | 128047040 | 0.468 | ERCC3 |
| chr2 | 128047177 | 128047377 | 0.522 | ERCC3 |
| chr2 | 128047669 | 128047869 | 0.448 | ERCC3 |
| chr2 | 128050206 | 128050419 | 0.514 | ERCC3 |
| chr2 | 128051102 | 128051343 | 0.566 | ERCC3 |
| chr2 | 128051633 | 128051852 | 0.655 | ERCC3 |
| chr2 | 128051746 | 128051946 | 0.577 | ERCC3 |
| chr2 | 209112977 | 209113230 | 0.394 | IDH1 |
| chr2 | 209113091 | 209113340 | 0.444 | IDH1 |
| chr2 | 212288833 | 212289075 | 0.366 | ERBB4 |
| chr2 | 212288836 | 212289075 | 0.367 | ERBB4 |
| chr2 | 212288849 | 212289089 | 0.378 | ERBB4 |
| chr2 | 212288867 | 212289111 | 0.376 | ERBB4 |
| chr2 | 212483732 | 212483976 | 0.327 | ERBB4 |
| chr2 | 212483745 | 212483975 | 0.338 | ERBB4 |
| chr2 | 212483745 | 212483989 | 0.343 | ERBB4 |
| chr2 | 212483745 | 212483992 | 0.347 | ERBB4 |
| chr2 | 212529983 | 212530215 | 0.468 | ERBB4 |
| chr2 | 212529983 | 212530219 | 0.468 | ERBB4 |
| chr2 | 212530006 | 212530255 | 0.444 | ERBB4 |
| chr2 | 212530049 | 212530293 | 0.420 | ERBB4 |
| chr2 | 212587102 | 212587341 | 0.379 | ERBB4 |
| chr2 | 212587102 | 212587342 | 0.378 | ERBB4 |
| chr2 | 212587104 | 212587343 | 0.379 | ERBB4 |
| chr2 | 215591713 | 215591913 | 0.348 | BARD1 |
| chr2 | 215592049 | 215592249 | 0.313 | BARD1 |
| chr2 | 215592385 | 215592585 | 0.318 | BARD1 |
| chr2 | 215592721 | 215592921 | 0.284 | BARD1 |
| chr2 | 215593393 | 215593593 | 0.458 | BARD1 |
| chr2 | 215593464 | 215593712 | 0.482 | BARD1 |
| chr2 | 215595070 | 215595319 | 0.348 | BARD1 |
| chr2 | 215609774 | 215610018 | 0.331 | BARD1 |
| chr2 | 215610357 | 215610557 | 0.368 | BARD1 |
| chr2 | 215617201 | 215617402 | 0.322 | BARD1 |
| chr2 | 215617244 | 215617478 | 0.315 | BARD1 |
| chr2 | 215632137 | 215632347 | 0.398 | BARD1 |
| chr2 | 215632347 | 215632547 | 0.299 | BARD1 |
| chr2 | 215633841 | 215634041 | 0.348 | BARD1 |
| chr2 | 215645283 | 215645483 | 0.418 | BARD1 |
| chr2 | 215645568 | 215645768 | 0.398 | BARD1 |
| chr2 | 215645789 | 215646022 | 0.385 | BARD1 |
| chr2 | 215645997 | 215646196 | 0.405 | BARD1 |
| chr2 | 215646018 | 215646167 | 0.413 | BARD1 |
| chr2 | 215656994 | 215657164 | 0.421 | BARD1 |
| chr2 | 215661815 | 215662059 | 0.355 | BARD1 |
| chr2 | 215674040 | 215674299 | 0.662 | BARD1 |
| chr2 | 215674057 | 215674299 | 0.671 | BARD1 |
| chr2 | 215674060 | 215674299 | 0.675 | BARD1 |
| chr2 | 215674115 | 215674321 | 0.681 | BARD1 |
| chr20 | 57484302 | 57484538 | 0.439 | GNAS |
| chr21 | 36252718 | 36252963 | 0.427 | RUNX1 |
| chr21 | 36252753 | 36253001 | 0.454 | RUNX1 |
| chr21 | 36252796 | 36253037 | 0.471 | RUNX1 |
| chr21 | 36252819 | 36253063 | 0.469 | RUNX1 |
| chr22 | 29092793 | 29093014 | 0.383 | CHEK2 |
| chr22 | 29095766 | 29095985 | 0.468 | CHEK2 |
| chr22 | 29099378 | 29099614 | 0.354 | CHEK2 |
| chr22 | 29105946 | 29106126 | 0.243 | CHEK2 |
| chr22 | 29105988 | 29106140 | 0.288 | CHEK2 |
| chr22 | 29107796 | 29107996 | 0.373 | CHEK2 |
| chr22 | 29115374 | 29115613 | 0.292 | CHEK2 |
| chr22 | 29120968 | 29121207 | 0.358 | CHEK2 |
| chr22 | 29121185 | 29121429 | 0.376 | CHEK2 |
| chr22 | 29130538 | 29130762 | 0.556 | CHEK2 |
| chr22 | 29130552 | 29130805 | 0.508 | CHEK2 |
| chr22 | 29137634 | 29137834 | 0.547 | CHEK2 |
| chr3 | 10070202 | 10070402 | 0.383 | FANCD2 |
| chr3 | 10074431 | 10074641 | 0.303 | FANCD2 |
| chr3 | 10076444 | 10076673 | 0.430 | FANCD2 |
| chr3 | 10076732 | 10076932 | 0.323 | FANCD2 |
| chr3 | 10077981 | 10078130 | 0.313 | FANCD2 |
| chr3 | 10080961 | 10081110 | 0.367 | FANCD2 |
| chr3 | 10081391 | 10081592 | 0.510 | FANCD2 |
| chr3 | 10083255 | 10083471 | 0.433 | FANCD2 |
| chr3 | 10116194 | 10116415 | 0.405 | FANCD2 |
| chr3 | 10119764 | 10119916 | 0.523 | FANCD2 |

-continued

| Chr. | Start | Stop | GC | Gene |
|---|---|---|---|---|
| chr3 | 10122693 | 10122903 | 0.422 | FANCD2 |
| chr3 | 10122903 | 10123103 | 0.378 | FANCD2 |
| chr3 | 10123144 | 10123344 | 0.358 | FANCD2 |
| chr3 | 10127494 | 10127703 | 0.433 | FANCD2 |
| chr3 | 10128659 | 10128873 | 0.414 | FANCD2 |
| chr3 | 10130055 | 10130255 | 0.448 | FANCD2 |
| chr3 | 10130418 | 10130618 | 0.398 | FANCD2 |
| chr3 | 10131860 | 10132052 | 0.461 | FANCD2 |
| chr3 | 10133776 | 10133976 | 0.418 | FANCD2 |
| chr3 | 10134833 | 10135033 | 0.448 | FANCD2 |
| chr3 | 10135971 | 10136220 | 0.484 | FANCD2 |
| chr3 | 10136796 | 10137016 | 0.425 | FANCD2 |
| chr3 | 10137928 | 10138128 | 0.398 | FANCD2 |
| chr3 | 10140403 | 10140603 | 0.448 | FANCD2 |
| chr3 | 10140685 | 10140895 | 0.322 | FANCD2 |
| chr3 | 10183302 | 10183451 | 0.653 | VHL |
| chr3 | 10183681 | 10183874 | 0.706 | VHL |
| chr3 | 10188234 | 10188438 | 0.390 | VHL |
| chr3 | 10191445 | 10191700 | 0.484 | VHL |
| chr3 | 10191721 | 10191932 | 0.392 | VHL |
| chr3 | 10192245 | 10192450 | 0.350 | VHL |
| chr3 | 12645599 | 12645838 | 0.504 | RAF1 |
| chr3 | 12645599 | 12645843 | 0.502 | RAF1 |
| chr3 | 12645599 | 12645844 | 0.500 | RAF1 |
| chr3 | 12645603 | 12645844 | 0.504 | RAF1 |
| chr3 | 14186692 | 14186898 | 0.319 | XPC |
| chr3 | 14186863 | 14187104 | 0.521 | XPC |
| chr3 | 14187085 | 14187334 | 0.532 | XPC |
| chr3 | 14187312 | 14187552 | 0.589 | XPC |
| chr3 | 14187523 | 14187722 | 0.570 | XPC |
| chr3 | 14188679 | 14188879 | 0.552 | XPC |
| chr3 | 14189299 | 14189509 | 0.583 | XPC |
| chr3 | 14189991 | 14190191 | 0.597 | XPC |
| chr3 | 14190286 | 14190496 | 0.578 | XPC |
| chr3 | 14193741 | 14194025 | 0.596 | XPC |
| chr3 | 14197850 | 14198050 | 0.483 | XPC |
| chr3 | 14199573 | 14199852 | 0.543 | XPC |
| chr3 | 14199862 | 14200062 | 0.582 | XPC |
| chr3 | 14200146 | 14200394 | 0.522 | XPC |
| chr3 | 14206322 | 14206487 | 0.434 | XPC |
| chr3 | 14206933 | 14207089 | 0.522 | XPC |
| chr3 | 14208699 | 14208911 | 0.474 | XPC |
| chr3 | 14209663 | 14209863 | 0.517 | XPC |
| chr3 | 14211839 | 14212049 | 0.384 | XPC |
| chr3 | 14214355 | 14214600 | 0.476 | XPC |
| chr3 | 14220004 | 14220204 | 0.682 | XPC |
| chr3 | 37034589 | 37034809 | 0.570 | EPM2AIP1 |
| chr3 | 37034790 | 37035063 | 0.544 | EPM2AIP1 |
| chr3 | 37035069 | 37035306 | 0.622 | MLH1 |
| chr3 | 37038000 | 37038200 | 0.368 | MLH1 |
| chr3 | 37042434 | 37042645 | 0.354 | MLH1 |
| chr3 | 37045773 | 37045973 | 0.418 | MLH1 |
| chr3 | 37048411 | 37048645 | 0.353 | MLH1 |
| chr3 | 37050230 | 37050436 | 0.377 | MLH1 |
| chr3 | 37053207 | 37053427 | 0.335 | MLH1 |
| chr3 | 37053528 | 37053730 | 0.340 | MLH1 |
| chr3 | 37055893 | 37056093 | 0.373 | MLH1 |
| chr3 | 37058865 | 37059114 | 0.424 | MLH1 |
| chr3 | 37061804 | 37062039 | 0.542 | MLH1 |
| chr3 | 37067171 | 37067392 | 0.500 | MLH1 |
| chr3 | 37067236 | 37067492 | 0.514 | MLH1 |
| chr3 | 37070194 | 37070394 | 0.408 | MLH1 |
| chr3 | 37070355 | 37070605 | 0.462 | MLH1 |
| chr3 | 37081625 | 37081777 | 0.438 | MLH1 |
| chr3 | 37083681 | 37083889 | 0.354 | MLH1 |
| chr3 | 37088877 | 37089113 | 0.468 | MLH1 |
| chr3 | 37088933 | 37089152 | 0.473 | MLH1 |
| chr3 | 37089899 | 37090099 | 0.468 | MLH1 |
| chr3 | 37090327 | 37090527 | 0.428 | MLH1 |
| chr3 | 37091892 | 37092087 | 0.480 | MLH1 |
| chr3 | 37091894 | 37092142 | 0.466 | MLH1 |
| chr3 | 41265974 | 41266223 | 0.464 | CTNNB1 |
| chr3 | 41266013 | 41266252 | 0.488 | CTNNB1 |
| chr3 | 41266021 | 41266268 | 0.476 | CTNNB1 |
| chr3 | 41266036 | 41266265 | 0.474 | CTNNB1 |
| chr3 | 52435062 | 52435320 | 0.583 | BAP1 |
| chr3 | 52435350 | 52435631 | 0.543 | BAP1 |

-continued

| Chr. | Start | Stop | GC | Gene |
|---|---|---|---|---|
| chr3 | 52435934 | 52436211 | 0.561 | BAP1 |
| chr3 | 52436217 | 52436465 | 0.647 | BAP1 |
| chr3 | 52436552 | 52436790 | 0.552 | BAP1 |
| chr3 | 52436807 | 52437063 | 0.572 | BAP1 |
| chr3 | 52437127 | 52437370 | 0.574 | BAP1 |
| chr3 | 52437447 | 52437693 | 0.599 | BAP1 |
| chr3 | 52437754 | 52437978 | 0.556 | BAP1 |
| chr3 | 52438443 | 52438682 | 0.575 | BAP1 |
| chr3 | 52439130 | 52439357 | 0.583 | BAP1 |
| chr3 | 52439752 | 52440014 | 0.544 | BAP1 |
| chr3 | 52440273 | 52440505 | 0.618 | BAP1 |
| chr3 | 52440695 | 52440946 | 0.552 | BAP1 |
| chr3 | 52441181 | 52441475 | 0.576 | BAP1 |
| chr3 | 52441983 | 52442230 | 0.532 | BAP1 |
| chr3 | 52442460 | 52442693 | 0.500 | BAP1 |
| chr3 | 52443505 | 52443740 | 0.602 | BAP1 |
| chr3 | 138374171 | 138374400 | 0.400 | PIK3CB |
| chr3 | 138374183 | 138374428 | 0.386 | PIK3CB |
| chr3 | 138374197 | 138374427 | 0.398 | PIK3CB |
| chr3 | 138374204 | 138374443 | 0.408 | PIK3CB |
| chr3 | 138409848 | 138410087 | 0.375 | PIK3CB |
| chr3 | 138409848 | 138410097 | 0.380 | PIK3CB |
| chr3 | 138409872 | 138410116 | 0.380 | PIK3CB |
| chr3 | 138409872 | 138410118 | 0.385 | PIK3CB |
| chr3 | 138417690 | 138417920 | 0.390 | PIK3CB |
| chr3 | 138417690 | 138417924 | 0.383 | PIK3CB |
| chr3 | 138417696 | 138417915 | 0.391 | PIK3CB |
| chr3 | 138417697 | 138417916 | 0.395 | PIK3CB |
| chr3 | 138665132 | 138665361 | 0.600 | FOXL2 |
| chr3 | 138665147 | 138665396 | 0.600 | FOXL2 |
| chr3 | 138665151 | 138665396 | 0.602 | FOXL2 |
| chr3 | 138665170 | 138665409 | 0.613 | FOXL2 |
| chr3 | 178916725 | 178916970 | 0.362 | PIK3CA |
| chr3 | 178916766 | 178917010 | 0.351 | PIK3CA |
| chr3 | 178916782 | 178917028 | 0.356 | PIK3CA |
| chr3 | 178916822 | 178917068 | 0.336 | PIK3CA |
| chr3 | 178917417 | 178917566 | 0.320 | PIK3CA |
| chr3 | 178917417 | 178917618 | 0.347 | PIK3CA |
| chr3 | 178917420 | 178917590 | 0.345 | PIK3CA |
| chr3 | 178917420 | 178917604 | 0.351 | PIK3CA |
| chr3 | 178921331 | 178921578 | 0.367 | PIK3CA |
| chr3 | 178921339 | 178921585 | 0.372 | PIK3CA |
| chr3 | 178921347 | 178921596 | 0.368 | PIK3CA |
| chr3 | 178921364 | 178921608 | 0.351 | PIK3CA |
| chr3 | 178927888 | 178928114 | 0.339 | PIK3CA |
| chr3 | 178927898 | 178928114 | 0.346 | PIK3CA |
| chr3 | 178927910 | 178928144 | 0.323 | PIK3CA |
| chr3 | 178927974 | 178928182 | 0.354 | PIK3CA |
| chr3 | 178935873 | 178936102 | 0.313 | PIK3CA |
| chr3 | 178935930 | 178936133 | 0.353 | PIK3CA |
| chr3 | 178935944 | 178936197 | 0.335 | PIK3CA |
| chr3 | 178935995 | 178936197 | 0.365 | PIK3CA |
| chr3 | 178936030 | 178936279 | 0.320 | PIK3CA |
| chr3 | 178951914 | 178952159 | 0.382 | PIK3CA |
| chr3 | 178951915 | 178952140 | 0.385 | PIK3CA |
| chr3 | 178951921 | 178952140 | 0.386 | PIK3CA |
| chr3 | 178951921 | 178952159 | 0.381 | PIK3CA |
| chr3 | 178951948 | 178952109 | 0.389 | PIK3CA |
| chr3 | 178952004 | 178952152 | 0.389 | PIK3CA |
| chr3 | 178952010 | 178952109 | 0.390 | PIK3CA |
| chr3 | 178952109 | 178952152 | 0.386 | PIK3CA |
| chr4 | 55151865 | 55152127 | 0.513 | PDGFRA |
| chr4 | 55593487 | 55593733 | 0.389 | KIT |
| chr4 | 55593505 | 55593749 | 0.400 | KIT |
| chr4 | 55593514 | 55593765 | 0.397 | KIT |
| chr4 | 55593530 | 55593778 | 0.390 | KIT |
| chr4 | 55594116 | 55594365 | 0.416 | KIT |
| chr4 | 55594125 | 55594365 | 0.411 | KIT |
| chr4 | 55594139 | 55594380 | 0.401 | KIT |
| chr4 | 55594139 | 55594385 | 0.401 | KIT |
| chr4 | 55599168 | 55599408 | 0.365 | KIT |
| chr4 | 55599173 | 55599417 | 0.367 | KIT |
| chr4 | 55599207 | 55599435 | 0.384 | KIT |
| chr4 | 55602645 | 55602892 | 0.423 | KIT |
| chr4 | 55602657 | 55602888 | 0.422 | KIT |
| chr4 | 55602657 | 55602892 | 0.424 | KIT |
| chr4 | 153244069 | 153244316 | 0.464 | FBXW7 |

-continued

| Chr. | Start | Stop | GC | Gene |
|---|---|---|---|---|
| chr4 | 153244075 | 153244315 | 0.465 | FBXW7 |
| chr4 | 153244085 | 153244324 | 0.454 | FBXW7 |
| chr4 | 153244106 | 153244353 | 0.427 | FBXW7 |
| chr4 | 153245291 | 153245531 | 0.398 | FBXW7 |
| chr4 | 153245297 | 153245541 | 0.400 | FBXW7 |
| chr4 | 153245312 | 153245560 | 0.406 | FBXW7 |
| chr4 | 153245328 | 153245572 | 0.396 | FBXW7 |
| chr4 | 153247109 | 153247353 | 0.433 | FBXW7 |
| chr4 | 153247122 | 153247369 | 0.448 | FBXW7 |
| chr4 | 153247150 | 153247399 | 0.456 | FBXW7 |
| chr4 | 153249264 | 153249512 | 0.414 | FBXW7 |
| chr4 | 153249285 | 153249525 | 0.419 | FBXW7 |
| chr4 | 153249290 | 153249529 | 0.417 | FBXW7 |
| chr4 | 153249303 | 153249551 | 0.414 | FBXW7 |
| chr4 | 153250763 | 153251006 | 0.340 | FBXW7 |
| chr4 | 153250791 | 153251017 | 0.348 | FBXW7 |
| chr4 | 153250791 | 153251031 | 0.349 | FBXW7 |
| chr4 | 153250808 | 153251047 | 0.342 | FBXW7 |
| chr4 | 153251774 | 153252018 | 0.380 | FBXW7 |
| chr4 | 153251789 | 153252028 | 0.388 | FBXW7 |
| chr4 | 153251792 | 153252040 | 0.382 | FBXW7 |
| chr4 | 153251832 | 153252071 | 0.379 | FBXW7 |
| chr4 | 153258843 | 153259092 | 0.356 | FBXW7 |
| chr4 | 153258850 | 153259097 | 0.355 | FBXW7 |
| chr4 | 153258888 | 153259137 | 0.344 | FBXW7 |
| chr4 | 153258953 | 153259199 | 0.368 | FBXW7 |
| chr4 | 153268077 | 153268219 | 0.517 | FBXW7 |
| chr4 | 153268078 | 153268219 | 0.514 | FBXW7 |
| chr4 | 153268079 | 153268219 | 0.518 | FBXW7 |
| chr5 | 56161075 | 56161306 | 0.328 | MAP3K1 |
| chr5 | 56161096 | 56161325 | 0.330 | MAP3K1 |
| chr5 | 56161113 | 56161321 | 0.349 | MAP3K1 |
| chr5 | 56161178 | 56161386 | 0.321 | MAP3K1 |
| chr5 | 56161545 | 56161787 | 0.346 | MAP3K1 |
| chr5 | 56161548 | 56161797 | 0.348 | MAP3K1 |
| chr5 | 56161563 | 56161807 | 0.355 | MAP3K1 |
| chr5 | 56161577 | 56161806 | 0.365 | MAP3K1 |
| chr5 | 56180437 | 56180676 | 0.363 | MAP3K1 |
| chr5 | 56180457 | 56180659 | 0.389 | MAP3K1 |
| chr5 | 56180502 | 56180707 | 0.369 | MAP3K1 |
| chr5 | 56181614 | 56181861 | 0.335 | MAP3K1 |
| chr5 | 56181627 | 56181876 | 0.332 | MAP3K1 |
| chr5 | 56181632 | 56181871 | 0.338 | MAP3K1 |
| chr5 | 56181648 | 56181887 | 0.346 | MAP3K1 |
| chr5 | 56183135 | 56183374 | 0.429 | MAP3K1 |
| chr5 | 56183138 | 56183347 | 0.429 | MAP3K1 |
| chr5 | 56183138 | 56183361 | 0.429 | MAP3K1 |
| chr5 | 56183176 | 56183375 | 0.455 | MAP3K1 |
| chr5 | 112043137 | 112043364 | 0.649 | APC |
| chr5 | 112043137 | 112043365 | 0.651 | APC |
| chr5 | 112043186 | 112043431 | 0.663 | APC |
| chr5 | 112043190 | 112043431 | 0.661 | APC |
| chr5 | 112043201 | 112043471 | 0.672 | APC |
| chr5 | 112043206 | 112043428 | 0.668 | APC |
| chr5 | 112073451 | 112073699 | 0.639 | APC |
| chr5 | 112073948 | 112074148 | 0.488 | APC |
| chr5 | 112090491 | 112090691 | 0.373 | APC |
| chr5 | 112102006 | 112102208 | 0.330 | APC |
| chr5 | 112102893 | 112103093 | 0.433 | APC |
| chr5 | 112111368 | 112111578 | 0.289 | APC |
| chr5 | 112116375 | 112116639 | 0.340 | APC |
| chr5 | 112128134 | 112128341 | 0.332 | APC |
| chr5 | 112128152 | 112128420 | 0.309 | APC |
| chr5 | 112136780 | 112137014 | 0.404 | APC |
| chr5 | 112151086 | 112151286 | 0.368 | APC |
| chr5 | 112154610 | 112154859 | 0.424 | APC |
| chr5 | 112154826 | 112155071 | 0.504 | APC |
| chr5 | 112157485 | 112157695 | 0.341 | APC |
| chr5 | 112162781 | 112162991 | 0.379 | APC |
| chr5 | 112163441 | 112163655 | 0.288 | APC |
| chr5 | 112163452 | 112163681 | 0.309 | APC |
| chr5 | 112164471 | 112164655 | 0.319 | APC |
| chr5 | 112170600 | 112170800 | 0.393 | APC |
| chr5 | 112170810 | 112171010 | 0.289 | APC |
| chr5 | 112173249 | 112173449 | 0.383 | APC |
| chr5 | 112173471 | 112173712 | 0.405 | APC |
| chr5 | 112173688 | 112173932 | 0.404 | APC |

-continued

| Chr. | Start | Stop | GC | Gene |
|---|---|---|---|---|
| chr5 | 112173840 | 112174071 | 0.466 | APC |
| chr5 | 112174070 | 112174313 | 0.361 | APC |
| chr5 | 112174297 | 112174537 | 0.353 | APC |
| chr5 | 112174544 | 112174783 | 0.392 | APC |
| chr5 | 112174788 | 112175027 | 0.400 | APC |
| chr5 | 112174985 | 112175185 | 0.378 | APC |
| chr5 | 112175164 | 112175405 | 0.459 | APC |
| chr5 | 112175413 | 112175652 | 0.471 | APC |
| chr5 | 112175519 | 112175768 | 0.460 | APC |
| chr5 | 112175523 | 112175780 | 0.461 | APC |
| chr5 | 112175853 | 112176053 | 0.333 | APC |
| chr5 | 112175867 | 112176116 | 0.380 | APC |
| chr5 | 112175900 | 112176040 | 0.326 | APC |
| chr5 | 112176145 | 112176391 | 0.449 | APC |
| chr5 | 112176384 | 112176633 | 0.412 | APC |
| chr5 | 112176631 | 112176875 | 0.322 | APC |
| chr5 | 112176860 | 112177104 | 0.396 | APC |
| chr5 | 112176995 | 112177234 | 0.400 | APC |
| chr5 | 112177404 | 112177650 | 0.385 | APC |
| chr5 | 112177589 | 112177789 | 0.408 | APC |
| chr5 | 112177796 | 112178080 | 0.389 | APC |
| chr5 | 112178130 | 112178379 | 0.456 | APC |
| chr5 | 112178293 | 112178573 | 0.391 | APC |
| chr5 | 112178510 | 112178755 | 0.407 | APC |
| chr5 | 112178763 | 112179036 | 0.449 | APC |
| chr5 | 112179030 | 112179324 | 0.380 | APC |
| chr5 | 112179325 | 112179525 | 0.423 | APC |
| chr5 | 112179582 | 112179827 | 0.472 | APC |
| chr5 | 112180193 | 112180393 | 0.338 | APC |
| chr5 | 112181061 | 112181261 | 0.398 | APC |
| chr5 | 112181929 | 112182129 | 0.313 | APC |
| chr5 | 131892606 | 131892857 | 0.718 | RAD50 |
| chr5 | 131892983 | 131893197 | 0.474 | RAD50 |
| chr5 | 131892984 | 131893223 | 0.463 | RAD50 |
| chr5 | 131893020 | 131893223 | 0.466 | RAD50 |
| chr5 | 131893049 | 131893292 | 0.492 | RAD50 |
| chr5 | 131894808 | 131895037 | 0.252 | RAD50 |
| chr5 | 131911382 | 131911618 | 0.376 | RAD50 |
| chr5 | 131915004 | 131915223 | 0.382 | RAD50 |
| chr5 | 131915567 | 131915717 | 0.364 | RAD50 |
| chr5 | 131923251 | 131923500 | 0.312 | RAD50 |
| chr5 | 131923517 | 131923757 | 0.328 | RAD50 |
| chr5 | 131924402 | 131924651 | 0.364 | RAD50 |
| chr5 | 131925323 | 131925552 | 0.343 | RAD50 |
| chr5 | 131926850 | 131927094 | 0.363 | RAD50 |
| chr5 | 131927570 | 131927750 | 0.354 | RAD50 |
| chr5 | 131930491 | 131930738 | 0.323 | RAD50 |
| chr5 | 131931278 | 131931508 | 0.442 | RAD50 |
| chr5 | 131939061 | 131939291 | 0.377 | RAD50 |
| chr5 | 131939553 | 131939789 | 0.350 | RAD50 |
| chr5 | 131940409 | 131940654 | 0.346 | RAD50 |
| chr5 | 131944351 | 131944557 | 0.261 | RAD50 |
| chr5 | 131944387 | 131944597 | 0.251 | RAD50 |
| chr5 | 131944873 | 131945090 | 0.271 | RAD50 |
| chr5 | 131951603 | 131951803 | 0.323 | RAD50 |
| chr5 | 131951820 | 131952020 | 0.294 | RAD50 |
| chr5 | 131953730 | 131953966 | 0.333 | RAD50 |
| chr5 | 131972864 | 131973090 | 0.454 | RAD50 |
| chr5 | 131973728 | 131973957 | 0.443 | RAD50 |
| chr5 | 131976168 | 131976417 | 0.520 | RAD50 |
| chr5 | 131977815 | 131978052 | 0.378 | RAD50 |
| chr5 | 131978075 | 131978308 | 0.372 | RAD50 |
| chr5 | 131978265 | 131978518 | 0.417 | RAD50 |
| chr5 | 131978882 | 131979101 | 0.486 | RAD50 |
| chr5 | 170837389 | 170837646 | 0.318 | NPM1 |
| chr5 | 170837423 | 170837672 | 0.316 | NPM1 |
| chr6 | 35419950 | 35420204 | 0.710 | FANCE |
| chr6 | 35420484 | 35420712 | 0.677 | FANCE |
| chr6 | 35423523 | 35423753 | 0.610 | FANCE |
| chr6 | 35423747 | 35423980 | 0.568 | FANCE |
| chr6 | 35423937 | 35424160 | 0.500 | FANCE |
| chr6 | 35425325 | 35425579 | 0.541 | FANCE |
| chr6 | 35425576 | 35425862 | 0.516 | FANCE |
| chr6 | 35425990 | 35426190 | 0.602 | FANCE |
| chr6 | 35427014 | 35427214 | 0.443 | FANCE |
| chr6 | 35427343 | 35427543 | 0.552 | FANCE |
| chr6 | 35428293 | 35428492 | 0.560 | FANCE |

-continued

| Chr. | Start | Stop | GC | Gene |
|---|---|---|---|---|
| chr6 | 35433986 | 35434203 | 0.550 | FANCE |
| chr6 | 35434173 | 35434385 | 0.493 | FANCE |
| chr6 | 43544117 | 43544321 | 0.459 | POLH |
| chr6 | 43550014 | 43550163 | 0.420 | POLH |
| chr6 | 43550754 | 43550953 | 0.415 | POLH |
| chr6 | 43554978 | 43555223 | 0.476 | POLH |
| chr6 | 43565476 | 43565625 | 0.467 | POLH |
| chr6 | 43568621 | 43568821 | 0.448 | POLH |
| chr6 | 43571533 | 43571733 | 0.423 | POLH |
| chr6 | 43572382 | 43572582 | 0.433 | POLH |
| chr6 | 43572829 | 43573058 | 0.374 | POLH |
| chr6 | 43578220 | 43578420 | 0.507 | POLH |
| chr6 | 43581333 | 43581514 | 0.407 | POLH |
| chr6 | 43581613 | 43581843 | 0.433 | POLH |
| chr6 | 43581852 | 43582085 | 0.517 | POLH |
| chr6 | 43582072 | 43582231 | 0.475 | POLH |
| chr6 | 43587356 | 43587593 | 0.361 | POLH |
| chr6 | 43587578 | 43587778 | 0.393 | POLH |
| chr6 | 43587842 | 43588084 | 0.444 | POLH |
| chr6 | 152265305 | 152265551 | 0.555 | ESR1 |
| chr6 | 152265322 | 152265569 | 0.556 | ESR1 |
| chr6 | 152265335 | 152265582 | 0.548 | ESR1 |
| chr6 | 152265349 | 152265597 | 0.562 | ESR1 |
| chr6 | 152332663 | 152332910 | 0.444 | ESR1 |
| chr6 | 152332707 | 152332937 | 0.463 | ESR1 |
| chr6 | 152332732 | 152332961 | 0.483 | ESR1 |
| chr6 | 152415449 | 152415694 | 0.553 | ESR1 |
| chr6 | 152415449 | 152415729 | 0.555 | ESR1 |
| chr6 | 152415452 | 152415694 | 0.556 | ESR1 |
| chr6 | 152415469 | 152415763 | 0.542 | ESR1 |
| chr6 | 152419792 | 152420036 | 0.576 | ESR1 |
| chr6 | 152419822 | 152420047 | 0.575 | ESR1 |
| chr6 | 152419877 | 152420111 | 0.591 | ESR1 |
| chr7 | 6029374 | 6029583 | 0.367 | PMS2 |
| chr7 | 6035119 | 6035348 | 0.387 | PMS2 |
| chr7 | 6036912 | 6037112 | 0.378 | PMS2 |
| chr7 | 6038718 | 6039008 | 0.430 | PMS2 |
| chr7 | 55241468 | 55241710 | 0.564 | EGFR |
| chr7 | 55241542 | 55241789 | 0.565 | EGFR |
| chr7 | 55241576 | 55241746 | 0.526 | EGFR |
| chr7 | 55241613 | 55241853 | 0.531 | EGFR |
| chr7 | 55242269 | 55242500 | 0.509 | EGFR |
| chr7 | 55242271 | 55242505 | 0.506 | EGFR |
| chr7 | 55242272 | 55242520 | 0.506 | EGFR |
| chr7 | 55242280 | 55242532 | 0.506 | EGFR |
| chr7 | 55242319 | 55242558 | 0.496 | EGFR |
| chr7 | 55242332 | 55242584 | 0.490 | EGFR |
| chr7 | 55248852 | 55249080 | 0.585 | EGFR |
| chr7 | 55248896 | 55249120 | 0.622 | EGFR |
| chr7 | 55248933 | 55249182 | 0.600 | EGFR |
| chr7 | 55248937 | 55249187 | 0.598 | EGFR |
| chr7 | 55248961 | 55249208 | 0.597 | EGFR |
| chr7 | 55259335 | 55259571 | 0.523 | EGFR |
| chr7 | 55259337 | 55259586 | 0.532 | EGFR |
| chr7 | 55259356 | 55259602 | 0.534 | EGFR |
| chr7 | 55259368 | 55259570 | 0.537 | EGFR |
| chr7 | 55259391 | 55259640 | 0.544 | EGFR |
| chr7 | 116411722 | 116411963 | 0.417 | MET |
| chr7 | 116411832 | 116412076 | 0.424 | MET |
| chr7 | 116411854 | 116412102 | 0.410 | MET |
| chr7 | 116411942 | 116412183 | 0.347 | MET |
| chr7 | 140453006 | 140453257 | 0.381 | BRAF |
| chr7 | 140453042 | 140453283 | 0.364 | BRAF |
| chr7 | 140453060 | 140453259 | 0.385 | BRAF |
| chr7 | 140453085 | 140453319 | 0.336 | BRAF |
| chr7 | 140453086 | 140453335 | 0.340 | BRAF |
| chr7 | 140453105 | 140453353 | 0.329 | BRAF |
| chr7 | 140481224 | 140481471 | 0.355 | BRAF |
| chr7 | 140481234 | 140481475 | 0.360 | BRAF |
| chr7 | 140481251 | 140481496 | 0.358 | BRAF |
| chr7 | 140481263 | 140481507 | 0.363 | BRAF |
| chr8 | 90947700 | 90947947 | 0.319 | NBN |
| chr8 | 90949123 | 90949343 | 0.326 | NBN |
| chr8 | 90955446 | 90955690 | 0.351 | NBN |
| chr8 | 90958290 | 90958510 | 0.321 | NBN |
| chr8 | 90959971 | 90960119 | 0.329 | NBN |
| chr8 | 90965407 | 90965703 | 0.347 | NBN |

-continued

| Chr. | Start | Stop | GC | Gene |
|---|---|---|---|---|
| chr8 | 90965709 | 90965960 | 0.333 | NBN |
| chr8 | 90967522 | 90967722 | 0.388 | NBN |
| chr8 | 90967762 | 90967962 | 0.299 | NBN |
| chr8 | 90970951 | 90971177 | 0.414 | NBN |
| chr8 | 90976592 | 90976816 | 0.324 | NBN |
| chr8 | 90976592 | 90976817 | 0.323 | NBN |
| chr8 | 90982598 | 90982805 | 0.385 | NBN |
| chr8 | 90983304 | 90983514 | 0.308 | NBN |
| chr8 | 90990344 | 90990544 | 0.318 | NBN |
| chr8 | 90992886 | 90993086 | 0.323 | NBN |
| chr8 | 90993103 | 90993303 | 0.284 | NBN |
| chr8 | 90993522 | 90993742 | 0.321 | NBN |
| chr8 | 90994780 | 90995004 | 0.347 | NBN |
| chr8 | 90996593 | 90996859 | 0.678 | NBN |
| chr9 | 5073651 | 5073873 | 0.354 | JAK2 |
| chr9 | 21968200 | 21968432 | 0.545 | CDKN2A |
| chr9 | 21970919 | 21971216 | 0.721 | CDKN2A |
| chr9 | 21970920 | 21971216 | 0.721 | CDKN2A |
| chr9 | 21973486 | 21973718 | 0.365 | CDKN2A |
| chr9 | 21974363 | 21974602 | 0.500 | CDKN2A |
| chr9 | 21994083 | 21994336 | 0.654 | CDKN2A |
| chr9 | 21994085 | 21994334 | 0.656 | CDKN2A |
| chr9 | 35073773 | 35074045 | 0.432 | FANCG |
| chr9 | 35074052 | 35074258 | 0.517 | FANCG |
| chr9 | 35074248 | 35074484 | 0.565 | FANCG |
| chr9 | 35074847 | 35075072 | 0.535 | FANCG |
| chr9 | 35075125 | 35075335 | 0.493 | FANCG |
| chr9 | 35075354 | 35075564 | 0.531 | FANCG |
| chr9 | 35075451 | 35075651 | 0.562 | FANCG |
| chr9 | 35075668 | 35075868 | 0.587 | FANCG |
| chr9 | 35075897 | 35076097 | 0.557 | FANCG |
| chr9 | 35076388 | 35076632 | 0.494 | FANCG |
| chr9 | 35076699 | 35076959 | 0.529 | FANCG |
| chr9 | 35076908 | 35077108 | 0.537 | FANCG |
| chr9 | 35077204 | 35077404 | 0.517 | FANCG |
| chr9 | 35078145 | 35078385 | 0.593 | FANCG |
| chr9 | 35078512 | 35078712 | 0.522 | FANCG |
| chr9 | 35079068 | 35079268 | 0.587 | FANCG |
| chr9 | 35079437 | 35079667 | 0.671 | FANCG |
| chr9 | 35079767 | 35079970 | 0.667 | FANCG |
| chr9 | 35079828 | 35080069 | 0.702 | FANCG |
| chr9 | 35079839 | 35080069 | 0.706 | FANCG |
| chr9 | 35079923 | 35080159 | 0.667 | FANCG |
| chr9 | 80336120 | 80336372 | 0.478 | GNAQ |
| chr9 | 80336121 | 80336372 | 0.476 | GNAQ |
| chr9 | 80336223 | 80336472 | 0.500 | GNAQ |
| chr9 | 80336253 | 80336500 | 0.484 | GNAQ |
| chr9 | 80336259 | 80336500 | 0.483 | GNAQ |
| chr9 | 80409367 | 80409598 | 0.353 | GNAQ |
| chr9 | 80409379 | 80409628 | 0.352 | GNAQ |
| chr9 | 97863312 | 97863512 | 0.572 | FANCC |
| chr9 | 97863840 | 97864111 | 0.548 | FANCC |
| chr9 | 97869338 | 97869594 | 0.595 | FANCC |
| chr9 | 97872619 | 97872829 | 0.308 | FANCC |
| chr9 | 97872955 | 97873165 | 0.398 | FANCC |
| chr9 | 97873179 | 97873409 | 0.494 | FANCC |
| chr9 | 97873711 | 97873957 | 0.587 | FANCC |
| chr9 | 97876827 | 97877027 | 0.517 | FANCC |
| chr9 | 97879613 | 97879852 | 0.404 | FANCC |
| chr9 | 97887262 | 97887462 | 0.403 | FANCC |
| chr9 | 97888682 | 97888882 | 0.423 | FANCC |
| chr9 | 97897551 | 97897761 | 0.417 | FANCC |
| chr9 | 97897761 | 97897961 | 0.313 | FANCC |
| chr9 | 97912208 | 97912455 | 0.456 | FANCC |
| chr9 | 97933298 | 97933498 | 0.363 | FANCC |
| chr9 | 97934219 | 97934419 | 0.333 | FANCC |
| chr9 | 98002823 | 98003043 | 0.321 | FANCC |
| chr9 | 98009694 | 98009940 | 0.328 | FANCC |
| chr9 | 98011375 | 98011575 | 0.418 | FANCC |
| chr9 | 98011585 | 98011785 | 0.433 | FANCC |
| chr9 | 98079868 | 98080148 | 0.669 | FANCC |
| chr9 | 100437190 | 100437390 | 0.428 | XPA |
| chr9 | 100437359 | 100437558 | 0.475 | XPA |
| chr9 | 100437525 | 100437765 | 0.299 | XPA |
| chr9 | 100437793 | 100437993 | 0.383 | XPA |
| chr9 | 100444474 | 100444677 | 0.397 | XPA |
| chr9 | 100447108 | 100447308 | 0.348 | XPA |

-continued

| Chr. | Start | Stop | GC | Gene |
|---|---|---|---|---|
| chr9 | 100449321 | 100449540 | 0.309 | XPA |
| chr9 | 100451744 | 100451944 | 0.323 | XPA |
| chr9 | 100455831 | 100456031 | 0.328 | XPA |
| chr9 | 100459275 | 100459499 | 0.720 | XPA |
| chr9 | 100459396 | 100459601 | 0.728 | XPA |
| chr9 | 100459482 | 100459691 | 0.724 | XPA |
| chr9 | 100459482 | 100459695 | 0.720 | XPA |
| chr9 | 100459482 | 100459721 | 0.721 | XPA |
| chrX | 14861796 | 14861980 | 0.416 | FANCB |
| chrX | 14861961 | 14862165 | 0.322 | FANCB |
| chrX | 14862588 | 14862788 | 0.368 | FANCB |
| chrX | 14862805 | 14863005 | 0.294 | FANCB |
| chrX | 14862977 | 14863177 | 0.358 | FANCB |
| chrX | 14863227 | 14863447 | 0.403 | FANCB |
| chrX | 14868691 | 14868896 | 0.306 | FANCB |
| chrX | 14871130 | 14871330 | 0.313 | FANCB |
| chrX | 14875743 | 14875993 | 0.307 | FANCB |
| chrX | 14877225 | 14877425 | 0.313 | FANCB |
| chrX | 14877435 | 14877635 | 0.274 | FANCB |
| chrX | 14882681 | 14882881 | 0.393 | FANCB |
| chrX | 14882885 | 14883085 | 0.328 | FANCB |
| chrX | 14883089 | 14883289 | 0.383 | FANCB |
| chrX | 14883275 | 14883501 | 0.291 | FANCB |
| chrX | 14883493 | 14883735 | 0.350 | FANCB |
| chrX | 14887070 | 14887270 | 0.323 | FANCB |
| chrX | 14890941 | 14891170 | 0.578 | FANCB |
| chrX | 47426013 | 47426262 | 0.636 | ARAF |
| chrX | 47426015 | 47426263 | 0.635 | ARAF |
| chrX | 47426016 | 47426262 | 0.640 | ARAF |
| chrX | 47426063 | 47426266 | 0.627 | ARAF |
| chrX | 66765925 | 66766173 | 0.635 | AR |
| chrX | 66765934 | 66766173 | 0.638 | AR |
| chrX | 66766002 | 66766226 | 0.671 | AR |
| chrX | 66766013 | 66766226 | 0.682 | AR |
| chrX | 66931238 | 66931486 | 0.522 | AR |
| chrX | 66931245 | 66931461 | 0.525 | AR |
| chrX | 66931245 | 66931492 | 0.524 | AR |
| chrX | 66931246 | 66931484 | 0.523 | AR |
| chrX | 66937264 | 66937498 | 0.536 | AR |
| chrX | 66937327 | 66937559 | 0.532 | AR |
| chrX | 66937327 | 66937576 | 0.524 | AR |
| chrX | 66943491 | 66943695 | 0.468 | AR |
| chrX | 66943494 | 66943696 | 0.473 | AR |
| chrX | 66943515 | 66943684 | 0.476 | AR |
| chrX | 66943534 | 66943689 | 0.474 | AR |

DETAILED DESCRIPTION

The invention pertains to a method for analyzing tumor biomarker sequences that involves hybridization-based enrichment of selected target regions across the human genome in a multiplexed panel assay, followed by quantification, coupled with a novel bioinformatics and mathematical analysis pipeline. An overview of the method is shown schematically in FIG. 1.

Figure 3:
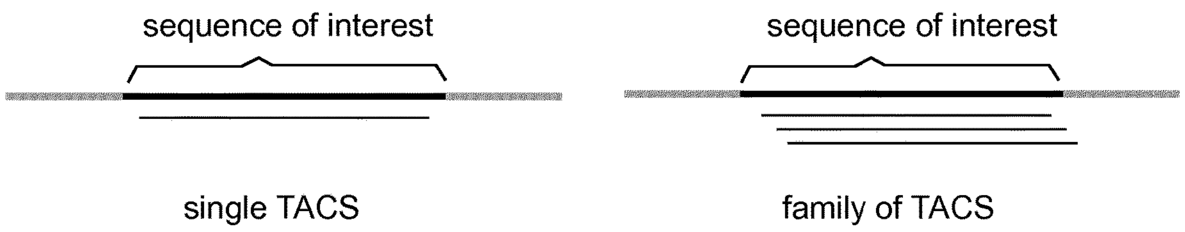
FIG. 3 is a schematic diagram of TACS-based enrichment of a sequence of interest (bold line) using a single TACS (left) versus TACS-based enrichment using a family of TACS (right).

In-solution hybridization enrichment has been used in the past to enrich specific regions of interest prior to sequencing (see e.g., Meyer, M and Kirchner, M. (2010) *Cold Spring Harb. Protoc.* 2010 (6): pdbprot5448; Liao, G. J. et al. (2012) *PLOS One* 7: e38154; Maricic, T. et al. (2010) *PLOS One* 5: e14004; Tewhey, R. et al. (2009) *Genome Biol.* 10: R116; Tsangaras, K. et al. (2014) *PLOS One* 9: e109101; PCT Publication WO 2016/189388; US Patent Publication 2016/0340733; Koumbaris, G. et al. (2016) *Clinical chemistry,* 62 (6), pp. 848-855). However, for the methods of the invention, the target sequences (referred to as TArget Capture Sequences, or TACS) used to enrich for specific regions of interest have been optimized for maximum efficiency, specificity and accuracy and, furthermore, in certain embodiments are used in families of TACS, comprising a plurality of members that bind to the same tumor biomarker sequence but with differing start and/or stop positions, such that enrichment of the tumor biomarker sequences of interest is significantly improved compared to use of a single TACS binding to the genomic sequence. An example of a configuration of such families of TACS is illustrated schematically in FIG. 3, showing that the different start and/or stop positions of the members of the TACS family when bound to the genomic sequence of interest results in a staggered binding pattern for the family members.

The use of families of TACS with the TACS pool that bind to each target sequence of interest, as compared to use of a single TACS within the TACS pool that binds to each target sequence of interest, significantly increases enrichment for the target sequences of interest, as evidenced by a greater than 50% average increase in read-depth for the family of TACS versus a single TACS. Comparison of use of a family of TACS versus a single TACS, and the significantly improved read-depth that was observed, is described in detail in Example 5.

Tumor Biomarker Detection

The methods and kits of the disclosure are used in the analysis of tumor biomarkers in biological samples. As described in detail in Examples 6-9, the methods of the invention can used for the detection of large panels of tumor biomarkers at tumor loads as low as 0.1% and can detect tumor biomarkers in both tumor tissue and in liquid biopsy samples from tumor patients. Accordingly, in one aspect, the invention pertains to a method of detecting one or more tumor biomarkers in a DNA sample from a subject having or suspected of having a tumor, the method comprising:

(a) preparing a sequencing library from the DNA sample;
(b) hybridizing the sequencing library to a pool of double-stranded TArget Capture Sequences (TACS) that bind to one or more tumor biomarker sequences of interest, wherein:
 (i) each member sequence within the pool of TACS is between 100-500 base pairs in length, each member sequence having a 5' end and a 3' end;
 (ii) preferably each member sequence binds to the tumor biomarker sequence of interest at least 50 base pairs away, on both the 5' end and the 3' end, from regions harboring Copy Number Variations (CNVs), Segmental duplications or repetitive DNA elements; and
 (iii) the GC content of the pool of TACS is between 19% and 80%, as determined by calculating the GC content of each member within the pool of TACS;
(c) isolating members of the sequencing library that bind to the pool of TACS to obtain an enriched library;
(d) amplifying and sequencing the enriched library; and
(e) performing statistical analysis on the enriched library sequences, optionally utilizing only fragments of a specific size range, to thereby detect the tumor biomarker(s) in the DNA sample.

In one embodiment, the pool of TACS comprises a plurality of TACS families, wherein each member of a TACS family binds to the same tumor biomarker sequence of interest but with different start and/or stop positions on the sequence with respect to a reference coordinate system (i.e., binding of TACS family members to the target sequence is staggered) to thereby enrich for target sequences of interest, followed by massive parallel sequencing and statistical analysis of the enriched population. Typically, the reference coordinate system that is used for analyzing human genomic DNA is the human reference genome built hg19, which is publically available in the art, although other versions may be used. Alternatively, the reference coordinate system can be an artificially created genome based on built hg19 that contains only the genomic sequences of interest. Exemplary non-limiting examples of start/stop positions for TACS that bind to chromosome 13, 18, 21, X or Y are shown in FIG. 2. Exemplary non-limiting examples of start/stop positions for TACS that bind to NRAS on chromosome 1, PI3KCA on chromosome 3, EGFR on chromosome 7 or KRAS on chromosome 12 (as non-limiting examples of tumor biomarkers) are shown in FIG. 10.

Accordingly, in another aspect, the invention pertains to a method of detecting one or more tumor biomarkers in a DNA sample from a subject having or suspected of having a tumor, the method comprising:

(a) preparing a sequencing library from the DNA sample;
(b) hybridizing the sequencing library to a pool of double-stranded TArget Capture Sequences (TACS) that bind to one or more tumor biomarker sequences of interest, wherein the pool of TACS comprises a plurality of TACS families, wherein each member of a TACS family binds to the same tumor biomarker sequence of interest but with different start and/or stop positions on the sequence with respect to a reference coordinate system, and further wherein:
  (i) each member sequence within the pool of TACS is between 100-500 base pairs in length, each member sequence having a 5' end and a 3' end;
  (ii) preferably each member sequence binds to the tumor biomarker sequence of interest at least 50 base pairs away, on both the 5' end and the 3' end, from regions harboring Copy Number Variations (CNVs), Segmental duplications or repetitive DNA elements; and
  (iii) the GC content of the pool of TACS is between 19% and 80%, as determined by calculating the GC content of each member within the pool of TACS;
(c) isolating members of the sequencing library that bind to the pool of TACS to obtain an enriched library;
(d) amplifying and sequencing the enriched library; and:
(e) performing statistical analysis on the enriched library sequences, optionally utilizing only fragments of a specific size range, to thereby detect the tumor biomarker(s) in the DNA sample.

The TACS-enrichment based method of the disclosure can be used in the detection of a wide variety of genetic abnormalities. In one embodiment, the genetic abnormality is a chromosomal aneuploidy (such as a trisomy, a partial trisomy or a monosomy). In other embodiments, the genomic abnormality is a structural abnormality, including but not limited to copy number changes including microdeletions and microduplications, insertions, translocations, inversions and small-size mutations including point mutations and mutational signatures. In another embodiment, the genetic abnormality is a chromosomal mosaicism.

Further aspects and features of the methods of the disclosure are described in the subsections below.

TArget Capture Sequence Design

As used herein, the term "TArget Capture Sequences" or "TACS" refers to short DNA sequences that are complementary to the region(s) of interest on a genomic sequence(s) of interest (e.g., chromosome(s) of interest) and which are used as "bait" to capture and enrich the region of interest from a large library of sequences, such as a whole genomic sequencing library prepared from a biological sample. In addition to the features of the families of TACS described above (e.g., staggered binding to the genomic sequence of interest), a pool of TACS is used for enrichment wherein the sequences within the pool have been optimized with regard to: (i) the length of the sequences; (ii) the distribution of the TACS across the region(s) of interest; and (iii) the GC content of the TACS. The number of sequences within the TACS pool (pool size) has also been optimized.

It has been discovered that TACS having a length of 100-500 base pairs are optimal to maximize enrichment efficiency. In various other embodiments, each sequence within the pool of TACS is between 150-260 base pairs, 100-200 base pairs, 200-260 base pairs, 100-350 bp in length, or 100-500 bp in length. In preferred embodiments, the length of the TACS within the pool is at least 250 base pairs, or is 250 base pairs or is 260 base pairs or is 280 base pairs. It will be appreciated by the ordinarily skilled artisan that a slight variation in TACS size typically can be used without altering the results (e.g., the addition or deletion of a few base pairs on either end of the TACS); accordingly, the base pair lengths given herein are to be considered "about" or "approximate", allowing for some slight variation (e.g., 1-5%) in length. Thus, for example, a length of "250 base pairs" is intended to refer to "about 250 base pairs" or "approximately 250 base pairs", such that, for example, 248 or 252 base pairs is also encompassed.

The distribution of the TACS across each region or chromosome of interest has been optimized to avoid, if applicable, high copy repeats, low copy repeats and copy number variants, while at the same time also being able to target informative single nucleotide polymorphisms (SNPs) in order to enable both aneuploidy, or structural copy number change detection, and fraction of interest estimation. Accordingly, each sequence within the TACS pool is designed such that the 5' end and the 3' end are each at least 50 base pairs away from regions in the genome that are known to harbor one or more of the following genomic elements: Copy Number Variations (CNVs), Segmental duplications and/or repetitive DNA elements (such as transposable elements or tandem repeat areas). In various other embodiments, each sequence within the TACS pool is designed such that the 5' end and the 3' end are each at least 50, 100, 150, 200, 250, 300, 400 or 500 base pairs away from regions in the genome that are known to harbor one or more of the aforementioned elements.

The term "Copy Number Variations" is a term of art that refers to a form of structural variation in the human genome in which there can be alterations in the DNA of the genome in different individuals that can result in a fewer or greater than normal number of a section(s) of the genome in certain individuals. CNVs correspond to relatively large regions of the genome that may be deleted (e.g., a section that normally is A-B-C-D can be A-B-D) or may be duplicated (e.g., a section that normally is A-B-C-D can be A-B-C-C-D). CNVs account for roughly 13% of the human genome, with each variation ranging in size from about 1 kilobase to several megabases in size.

The term "Segmental duplications" (also known as "low-copy repeats") is also a term of art that refers to blocks of DNA that range from about 1 to 400 kilobases in length that occur at more than one site within the genome and typically share a high level (greater than 90%) of sequence identity. Segmental duplications are reviewed in, for example, Eichler. E.E. (2001) *Trends Genet.* 17:661-669.

The term "repetitive DNA elements" (also known as "repeat DNA" or "repeated DNA") is also a term of art that refers to patterns of DNA that occur in multiple copies throughout the genome. The term "repetitive DNA element" encompasses terminal repeats, tandem repeats and interspersed repeats, including transposable elements. Repetitive DNA elements in NGS is discussed further in, for example, Todd, J. et al. (2012) *Nature Reviews Genet.* 13:36-46.

The TACS are designed with specific GC content characteristics in order to minimize data GC bias and to allow a custom and innovative data analysis pipeline. It has been determined that TACS with a GC content of 19-80% achieve optimal enrichment and perform best with cell free DNA. Within the pool of TACS, different sequences can have different % GC content, although to be selected for inclusion with the pool, the % GC content of each sequence is chosen as between 19-80%, as determined by calculating the GC content of each member within each family of TACS. That is, every member within each family of TACS has a % GC content within the given percentage range (e.g., between 19-80% GC content).

In some instances, the pool of TACS (i.e., each member within each family of TACS) may be chosen so as to define a different % GC content range, deemed to be more suitable for the assessment of specific genetic abnormalities. Non-limiting examples of various % GC content ranges, can be between 19% and 80%, or between 19% and 79%, or between 19% and 78%, or between 19% and 77%, or between 19% and 76%, or between 19% and 75%, or between 19% and 74%, or between 19% and 73%, or between 19% and 72%, or between 19% and 71%, or between 19% and 70%, or between 19% and 69%, or between 19% and 68%, or between 19% and 67%, or between 19% and 66%, or between 19% and 65%, or between 19% and 64%, or between 19% and 63%, or between 19% and 62%, or between 19% and 61%, or between 19% and 60%, or between 19% and 59%, or between 19% and 58%, or between 19% and 57%, or between 19% and 56%, or between 19% and 55%, or between 19% and 54%, or between 19% and 53%, or between 19% and 52%, or between 19% and 51%, or between 19% and 50%, or between 19% and 49%, or between 19% and 48%, or between 19% and 47%, or between 19% and 46%, or between 19% and 45%, or between 19% and 44%, or between 19% and 43%, or between 19% and 42%, or between 19% and 41%, or between 19% and 40%.

As described in further detail below with respect to one embodiment of the data analysis, following amplification and sequencing of the enriched sequences, the test loci and reference loci can then be "matched" or grouped together according to their % GC content (e.g., test loci with a % GC content of 40% is matched with reference loci with a % GC content of 40%). It is appreciated that the % GC content matching procedure may allow slight variation in the allowed matched % GC range. A non-limiting instance, and with reference to the previously described example in text, a test locus with % GC content of 40% could be matched with reference loci of % GC ranging from 39-41%, thereby encompassing the test locus % GC within a suitable range.

To prepare a pool of TACS having the optimized criteria set forth above with respect to size, placement within the human genome and % GC content, both manual and computerized analysis methods known in the art can be applied to the analysis of the human reference genome. In one embodiment, a semi-automatic method is implemented where regions are firstly manually designed based on the human reference genome build 19 (hg19) ensuring that, if applicable, the aforementioned repetitive regions are avoided and subsequently are curated for GC-content using software that computes the % GC-content of each region based on its coordinates on the human reference genome build 19 (hg19). In another embodiment, custom-built software is used to analyses the human reference genome in order to identify suitable TACS regions that fulfill certain criteria, such as but not limited to, % GC content, proximity to repetitive regions and/or proximity to other TACS.

The number of TACS in the pool has been carefully examined and adjusted to achieve the best balance between result robustness and assay cost/throughput. The pool typically contains at least 800 or more TACS, but can include more, such as 1500 or more TACS, 2000 or more TACS or 2500 or more TACS or 3500 or more TACS or 5000 or more TACS. It has been found that an optimal number of TACS in the pool is 5000. It will be appreciated by the ordinarily skilled artisan that a slight variation in pool size typically can be used without altering the results (e.g., the addition or removal of a small number of TACS); accordingly, the number sizes of the pool given herein are to be considered "about" or "approximate", allowing for some slight variation (e.g., 1-5%) in size. Thus, for example, a pool size of "1600 sequences" is intended to refer to "about 1600 sequences" or "approximately 1600 sequences", such that, for example, 1590 or 1610 sequences is also encompassed.

In view of the foregoing, in another aspect, the invention provides a method for preparing a pool of TACS for use in the method of the invention for detecting risk of a chromosomal and/or other genetic abnormality, wherein the method for preparing the pool of TACS comprises: selecting regions in one or more chromosomes of interest having the criteria set forth above (e.g., at least 50 base pairs away on either end from the aforementioned repetitive sequences and a GC content of between 19% and 80%, as determined by calculating the GC content of each member within each family of TACS), preparing primers that amplify sequences that hybridize to the selected regions, and amplifying the sequences, wherein each sequence is 100-500 base pairs in length.

For use in the methods of the disclosure, the pool of TACS typically is fixed to a solid support, such as beads (such as magnetic beads) or a column. In one embodiment, the pool of TACS are labeled with biotin and are bound to magnetic beads coated with a biotin-binding substance, such as streptavidin or avidin, to thereby fix the pool of TACS to a solid support. Other suitable binding systems for fixing the pool of TACS to a solid support (such as beads or column) are known to the skilled artisan and readily available in the art. When magnetic beads are used as the solid support, sequences that bind to the TACS affixed to the beads can be separated magnetically from those sequences that do not bind to the TACS.

Families of TACS

In one embodiment, the pool of TACS comprises a plurality of TACS families directed to different tumor biomarker sequences of interest. Each TACS family comprises a plurality of members that bind to the same tumor biomarker sequence of interest but having different start and/or stop positions with respect to a reference coordinate system for the genomic sequence of interest. Typically, the reference coordinate system that is used for analyzing human genomic DNA is the human reference genome built hg19, which is publically available in the art, but other coordinate systems may also be used. Alternatively, the reference coordinate system can be an artificially created genome based on publically available coordinate systems, such as for example built hg19 of the human genome, that contains only the genomic sequences of interest. Exemplary non-limiting examples of start/stop positions for TACS that bind to chromosome 13, 18, 21, X or Y are shown in FIG. 2.

Each TACS family comprises at least 2 members that bind to the same genomic sequence of interest. In various embodiments, each TACS family comprises at least 2 member sequences, or at least 3 member sequences, or at least 4 member sequences, or at least 5 member sequences, or at least 6 member sequences, or at least 7 member sequences, or at least 8 member sequence, or at least 9 member sequences, or at least 10 member sequences. In various embodiments, each TACS family comprises 2 member sequences, or 3 member sequences, or 4 member sequences, or 5 member sequences, or 6 member sequences, or 7 member sequences, or 8 member sequences, or 9 member sequences, or 10 member sequences. In various embodiments, the plurality of TACS families comprises different families having different numbers of member sequences. For example, a pool of TACS can comprise one TACS family that comprises 3 member sequences, another TACS family that comprises 4 member sequences, and yet another TACS family that comprises 5 member sequences, and the like. In one embodiment, a TACS family comprises 3-5 member sequences. In another embodiment, the TACS family comprises 4 member sequences.

The pool of TACS comprises a plurality of TACS families. Thus, a pool of TACS comprises at least 2 TACS families. In various embodiments, a pool of TACS comprises at least 3 different TACS families, or at least 5 different TACS families, or at least 10 different TACS families, or at least 50 different TACS families, or at least 100 different TACS families, or at least 500 different TACS families, or at least 1000 different TACS families, or at least 2000 TACS families, or at least 4000 TACS families, or at least 5000 TACS families.

Each member within a family of TACS binds to the same genomic region of interest but with different start and/or stop positions, with respect to a reference coordinate system for the genomic sequence of interest, such that the binding pattern of the members of the TACS family is staggered (for example see FIG. 3). In various embodiments, the start and/or stop positions are staggered by at least 3 base pairs, or at least 4 base pairs, or at least 5 base pairs, or at least 6 base pairs, or at least 7 base pairs, or at least 8 base pairs, or at least 9 base pairs, or at least 10 base pairs, or at least 15 base pairs, or at least 20 base pairs, or at least 25 base pairs. Typically, the start and/or stop positions are staggered by 5-10 base pairs. In one embodiment, the start and/or stop positions are staggered by 5 base pairs. In another embodiment, the start and/or stop positions are staggered by 10 base pairs.

Sample Collection and Preparation

The methods of the invention can be used with a variety of biological samples. Essentially any biological sample containing DNA, and in particular cell-free DNA (cfDNA), can be used as the sample in the methods, allowing for genetic analysis of the DNA therein. For example, a peripheral whole blood sample can be obtained from a subject and plasma can be obtained from the whole blood sample by standard methods. Total cell free DNA can then be extracted from the sample using standard techniques, non-limiting examples of which include a Qiasymphony protocol (Qiagen) suitable for cell free DNA isolation or any other manual or automated extraction method suitable for cell free DNA isolation.

For tumor biomarker detection, the sample is a biological sample obtained from a patient having or suspected of having a tumor. In one embodiment, the DNA sample comprises cell free tumor DNA (cftDNA). In one embodiment, the oncology sample is a sample of tissue (e.g., from a tumor biopsy). In another embodiment the sample is a patient's urine, sputum, ascites, cerebrospinal fluid or pleural effusion. In another embodiment, the oncology sample is a patient plasma sample, prepared from patient peripheral blood. Thus, the sample can be a liquid biopsy sample that is obtained non-invasively from a patient's blood sample, thereby potentially allowing for early detection of cancer prior to development of a detectable or palpable tumor, or can be from a tissue that has or is suspected of having cancer. In another embodiment, the oncology sample is a patient's healthy tissue such as buffy coat, prepared from patient peripheral blood, or buccal swab or healthy tissue adjacent to the tumor or another source of healthy cells. Thus, the healthy cells can provide a source of DNA that allows for detection of germline mutations and comparison with tumor DNA.

For the biological sample preparation, typically cells are lysed and DNA is extracted using standard techniques known in the art, a non-limiting example of which is the Qiagen DNeasy Blood and Tissue protocol. In another embodiment, cell free DNA is isolated from plasma using standard techniques, a non-limiting example of which is the Qiasymphony (Qiagen) protocol.

Following isolation, the cell free DNA of the sample is used for sequencing library construction to make the sample compatible with a downstream sequencing technology, such as Next Generation Sequencing. Typically this involves ligation of adapters onto the ends of the cell free DNA fragments, followed by amplification. Sequencing library preparation kits are commercially available. A non-limiting exemplary protocol for sequencing library preparation is described in detail in Example 1. In another embodiment, nuclear DNA (a non-limiting example of which is DNA extracted from tissue of buffy coat) is fragmented using standard techniques. A non-limiting example of DNA fragmentation is sonication. Fragmented nuclear DNA is then subjected to the same downstream procedures for cell free DNA described in this paragraph.

Enrichment by TACS Hybridization

The region(s) of interest on the chromosome(s) of interest (e.g., tumor biomarker sequences) is enriched by hybridizing the pool of TACS to the sequencing library, followed by isolation of those sequences within the sequencing library that bind to the TACS. To facilitate isolation of the desired, enriched sequences, typically the TACS sequences are modified in such a way that sequences that hybridize to the TACS can be separated from sequences that do not hybridize to the TACS. Typically, this is achieved by fixing the TACS to a solid support. This allows for physical separation of those sequences that bind the TACS from those sequences that do not bind the TACS. For example, each sequence within the pool of TACS can be labeled with biotin and the pool can then be bound to beads coated with a biotin-binding substance, such as streptavidin or avidin. In a preferred embodiment, the TACS are labeled with biotin and bound to streptavidin-coated magnetic beads. The ordinarily skilled artisan will appreciate, however, that other affinity binding systems are known in the art and can be used instead of biotin-streptavidin/avidin. For example, an antibody-based system can be used in which the TACS are labeled with an antigen and then bound to antibody-coated beads. Moreover, the TACS can incorporate on one end a sequence tag and can be bound to a solid support via a complementary sequence on the solid support that hybridizes to the sequence tag. Furthermore in addition to magnetic beads, other types of solid supports can be used, such as polymer beads and the like.

In certain embodiments, the members of the sequencing library that bind to the pool of TACS are fully complementary to the TACS. In other embodiments, the members of the sequencing library that bind to the pool of TACS are partially complementary to the TACS. For example, in certain circumstances it may be desirable to utilize and analyze data that are from DNA fragments that are products of the enrichment process but that do not necessarily belong to the genomic regions of interest (i.e. such DNA fragments could bind to the TACS because of part homologies (partial complementarity) with the TACS and when sequenced would produce very low coverage throughout the genome in non-TACS coordinates).

Following enrichment of the sequence(s) of interest using the TACS, thereby forming an enriched library, the members of the enriched library are eluted from the solid support and are amplified and sequenced using standard methods known in the art. Next Generation Sequencing is typically used, although other sequencing technologies can also be employed, which provides very accurate counting in addition to sequence information. To detect genetic abnormalities, such as but not limited to, aneuploidies or structural copy number changes requires very accurate counting and NGS is a type of technology that enables very accurate counting. Accordingly, for the detection of genetic abnormalities, such as but not limited to, aneuploidies or structural copy number changes, other accurate counting methods, such as digital PCR and microarrays can also be used instead of NGS. Non-limiting exemplary protocols for amplification and sequencing of the enriched library are described in detail in Example 3.

Data Analysis

The information obtained from the sequencing of the enriched library can be analyzed using an innovative biomathematical/biostatistical data analysis pipeline. Details of an exemplary analysis using this pipeline are described in depth in Example 4, and in further detail below. Alternative data analysis approaches for different purposes are also provided herein. For example, data analysis approaches for analyzing oncology samples are described in detail in Example 6-9 and in the oncology section below.

The analysis pipeline described in Example 4 exploits the characteristics of the TACS, and the high-efficiency of the target capture enables efficient detection of aneuploidies or structural copy number changes, as well as other types of genetic abnormalities. In the analysis, first the sample's sequenced DNA fragments are aligned to the human reference genome. QC metrics are used to inspect the aligned sample's properties and decide whether the sample is suitable to undergo classification. These QC metrics can include, but are not limited to, analysis of the enrichment patterns of the loci of interest, such as for example the overall sequencing depth of the sample, the on-target sequencing output of the sample, TACS performance, GC bias expectation, fraction of interest quantification. For determining the risk of a chromosomal abnormality in the DNA of the sample, an innovative algorithm is applied. The steps of the algorithm include, but are not limited to, removal of inadequately sequenced loci, read-depth and fragment-size information extraction at TACS-specific coordinates, genetic (GC-content) bias alleviation and ploidy status classification.

Ploidy status determination can be achieved using one or more statistical methods, non-limiting examples of which include a t-test method, a bootstrap method, a permutation test and/or a binomial test of proportions and/or segmentation-based methods and/or combinations thereof. It will be appreciated by the ordinarily skilled artisan that the selection and application of tests to be included in ploidy status determination is based on the number of data points available. As such, the suitability of each test is determined by various factors such as, but not limited to, the number of TACS utilized and the respective application for GC bias alleviation, if applicable. Thus, the aforementioned methods are to be taken as examples of the types of statistical analysis that may be employed and are not the only methods suitable for the determination of ploidy status. Typically, the statistical method results in a score value for the mixed sample and risk of the chromosomal abnormality in the DNA is detected when the score value for the mixed sample is above a reference threshold value.

In particular, one aspect of the statistical analysis involves quantifying and alleviating GC-content bias. In addition to the challenge of detecting small signal changes in DNA in the mixed sample, and/or other components of DNA of interest part of a mixed sample (for example, but not limited to, additional or less genetic material from certain chromosomal regions), the sequencing process itself introduces certain biases that can obscure signal detection. One such bias is the preferential sequencing/amplification of genetic regions based on their GC-content. As such, certain detection methods, such as but not limited to, read-depth based methods, need to account for such bias when examining sequencing data. Thus, the bias in the data needs to be quantified and, subsequently, suitable methods are applied to account for it such that genetic context dependencies cannot affect any statistical methods that may be used to quantify genetic abnormality risk.

For example, one method of quantifying the GC-content bias is to use a locally weighted scatterplot smoothing (LOESS) technique on the sequencing data. Each targeted locus may be defined by its sequencing read-depth output and its' GC-content. A line of best fit through these two variables, for a large set of loci, provides an estimate of the expected sequencing read-depth given the GC-content. Once this GC-bias quantification step is completed, the next step is to use this information to account for possible biases in the data. One method is to normalize the read-depth of all loci by their expected read-depth (based on each locus' GC-content). In principle, this unlinks the read-depth data from their genetic context and makes all data comparable. As such, data that are retrieved from different GC-content regions, such as for example, but not limited, to different chromosomes, can now be used in subsequent statistical tests for detection of any abnormalities. Thus, using the LOESS procedure, the GC bias is unlinked from the data prior to statistical testing. In one embodiment, the statistical analysis of the enriched library sequences comprises alleviating GC bias using a LOESS procedure.

In an alternative embodiment, the GC-content bias is quantified and alleviated by grouping together loci of similar (matching) GC-content. Thus, conceptually this method for alleviating GC-content bias comprises of three steps, as follows:

1) identification and calculation of GC-content in the TACS;
2) alleviation/accounting of GC-content bias using various matching/grouping procedures of the TACS; and
3) calculation of risk of any genetic abnormalities that may be present in the fetus utilizing statistical and mathematical methods on datasets produced from step 2.

For the t-test method, the dataset is split into two groups; the test loci and the reference loci. For each group, subsets of groups are created where loci are categorized according to their GC-content as illustrated in a non-limiting example in the sample Table 1 below:

TABLE 1

| GC | Reference loci read-depth | Test loci read-depth |
|---|---|---|
| 40% | $x_1^{40}, x_2^{40}, \ldots, x_{nx40}^{40}$ | $y_1^{40}, y_2^{40}, \ldots, y_{ny40}^{40}$ |
| 41% | $x_1^{41}, x_2^{41}, \ldots, x_{nx41}^{41}$ | $y_1^{41}, y_2^{41}, \ldots, y_{ny41}^{41}$ |
| 42% | $x_1^{42}, x_2^{42}, \ldots, x_{nx42}^{42}$ | $y_1^{42}, y_2^{42}, \ldots, y_{ny42}^{42}$ |
| . . . | . . . | . . . |

It is appreciated by the ordinarily skilled artisan that subgroup creation may involve encompassing a range of appropriate GC-content and/or a subset of loci that are defined by a given GC-content and/or GC-content range. Accordingly, the % GC content given in the non-limiting example of Table 1 are to be considered "about" or "approximate", allowing for some slight variation (e.g., 1-2%). Thus, for example, a % GC content of "40%" is intended to refer to "about 40%" or "approximately 40%", such that, for example, "39%-41%" GC-content loci may also be encompassed if deemed appropriate.

Hence, when referring to a particular GC-content it is understood that the reference and test loci subgroups may comprise of any number of loci related to a particular % GC content and/or range.

ence-test pair is recorded, say E1. The loci are then replaced to their respective groups. This process is repeated until a bootstrap sample of the same size as the number of test TACS present is created. A representative read-depth of the bootstrap sample is estimated, say E_mu, and recorded. A number of methods may be utilized to do so, such as but not limited to, the mean, mode or median value of the vector, and/or multiples thereof.

The process described above is repeated as many times as necessary and a distribution of E_mu is created. The sample is then attributed a score that corresponds to a percentile of this distribution.

For statistical analysis using a permutation test, the dataset is sorted firstly into two groups, the test-loci and the reference loci. For each group, subsets of groups are created, where loci are categorized according to their GC-content similarity (see columns 2 and 3 of the non-limiting sample Table 2 below). The number of loci present in each test subgroup is also recorded. The loci of the test group are utilized to calculate an estimate of the test-group's read-depth, say Yobs. A representative number from each GC-content subgroup may be selected to do so. Any number of methods may be used to provide a read-depth estimate, such as but not limited to, the mean, median or mode of the chosen loci.

TABLE 2

| GC | Reference loci read-depth | Test loci read-depth | test loci | Merging of loci |
|---|---|---|---|---|
| 40% | $x_1^{40}, x_2^{40}, \ldots, x_{nx40}^{40}$ | $y_1^{40}, y_2^{40}, \ldots, y_{ny40}^{40}$ | ny40 | $x_1^{40}, \ldots, x_{nx40}^{40}, y_1^{40}, \ldots, y_{ny40}^{40}$ |
| 41% | $x_1^{41}, x_2^{41}, \ldots, x_{nx41}^{41}$ | $y_1^{41}, y_2^{41}, \ldots, y_{ny41}^{41}$ | ny41 | $x_1^{41}, \ldots, x_{nx41}^{41}, y_1^{41}, \ldots, y_{ny41}^{41}$ |
| 42% | $x_1^{42}, x_2^{42}, \ldots, x_{nx42}^{42}$ | $y_1^{42}, y_2^{42}, \ldots, y_{ny42}^{42}$ | ny42 | $x_1^{42}, \ldots, x_{nx42}^{42}, y_1^{42}, \ldots, y_{ny42}^{42}$ |
| . . . | . . . | . . . | . . . | . . . |

Subsequently, for each GC-content subgroup, a representative read-depth is calculated. A number of methods may be utilized to choose this such as, but not limited to, the mean, median or mode of each set. Thus, two vectors of representative read-depth are created where one corresponds to the reference loci and the other to the test loci (e.g., Xm, Ym). In one embodiment, the two vectors may be tested against each other to identify significant differences in read-depth. In another embodiment, the difference of the two vectors may be used to assess if there are significant discrepancies between the test and reference loci. The sample is attributed the score of the test.

For statistical analysis using a bootstrap approach, the dataset is split into two groups, the test loci and the reference loci. The GC-content of each locus is then calculated. Then the following procedure is performed:

A random locus is selected from the reference loci; its read-depth and GC-content are recorded. Subsequently, a random locus from the test loci is selected, with the only condition being that its' GC-content is similar to that of the reference locus. Its read-depth is recorded. It is appreciated by the ordinarily skilled artisan that GC-content similarity may encompass a range of suitable GC-content. As such, referral to a specific % GC content may be considered as "approximate" or "proximal" or "within a suitable range" (e.g., 1%-2%) encompassing the specific % GC content under investigation. Thus, a reference-test locus pair of similar GC-content is created. The difference of the refer- A distribution to test Yobs is then built utilizing loci irrespective of their test or reference status as follows. The test and reference loci of each GC-content subgroup (see last column of sample Table 2) are combined to allow for calculation of a new read-depth estimate. From each merged subgroup a number of loci are chosen at random, where this number is upper-bounded by the number of test-loci utilized in the original calculation of Yobs (e.g., for GC content 40%, and in the context of the non-limiting sample Table 2, this number of loci may be in the range [1,ny40]). The new read-depth estimate is calculated from all the chosen loci. The procedure is iterated as many times as necessary in order to build a distribution of observed means. A sample is then attributed a score that corresponds to the position of Yobs in this distribution using a suitable transformation that accounts for the moments of the built distribution. As with the already described methods, it is appreciated that slight variation in % GC content is allowed (e.g., 1%-2%), if deemed appropriate. Hence, reference to a specific GC-content could be taken as "about" or "approximate", so that for example when referring to a 40% GC-content, loci that are "approximately" or "about" 40% (e.g., 39%-41%) may be utilized in the method.

For statistical analysis using a binomial test of proportions, fragment-sizes aligned to TACS-specific genomic coordinates are used. There is evidence from the literature that specific types of cancer can be characterized by and/or associated with fragments in the plasma having a smaller size than the expected size of fragments originating from healthy tissues (Jiang et al, (2015), *Proceedings of the National Academy of Sciences,* 112 (11), ppE1317-E1325). The same hypothesis holds true for fragments originating from the placenta/fetus. Specifically, it has been shown that fragments of cell free genetic material originating from the placenta tend to be smaller in length when compared to other cell free genetic material (Chan, K. C. (2004) *Clin. Chem.* 50:88-92). Hence, the statistic of interest is whether the proportion of small-size fragments aligned to a TACS-specific test-region deviates significantly from what is expected when comparing it to the respective proportion of other TACS-specific reference-regions, as this would indicate fetal genetic abnormalities.

Thus, fragment-sizes are assigned into two groups. Sizes related to the test loci are assigned to one group and fragment-sizes related to the reference loci are assigned to the other group. Subsequently, in each group, fragment sizes are distributed into two subgroups, whereby small-size fragments are assigned into one subgroup and all remaining fragments are designated to the remaining subgroup. The last step computes the proportion of small-sized fragments in each group and uses these quantities in a binomial test of proportions. The score of the test is attributed to the sample under investigation.

The final result of a sample may be given by combining one or more scores derived from the different statistical methods, non-limiting examples of which are given in Example 4.

For statistical analysis using segmentation methods, the read-depth and sequence composition of non-overlapping genomic regions of interest of fixed-size is obtained. On the obtained dataset, GC-content read-depth bias alleviation may be performed, but is not limited to, using a local polynomial fitting method in order to estimate the expected read-depth of regions based on their GC content. The expected value, dependent on GC-content, is then used to normalize regions using suitable methods known to those skilled in the art. The normalized dataset is subsequently processed using one or more segmentation-based classification routines. To do so the algorithms process consecutive data points to detect the presence of read-depth deviations which manifest in the form of a “jump/drop” from their surrounding data points. Depending on the segmentation routine used, data points are given a score which is used towards assigning membership into segments of similar performing read-depths. For example, consecutive data points with score values within a suitable range may be classified as one segment, whereas consecutive data points with score values which exceed the set thresholds may be assigned to a different segment.

Kits of the Invention

In another aspect, the invention provides kits for carrying out the methods of the disclosure. In one embodiment, the kit comprises a container consisting of the pool of TACS and instructions for performing the method. In one embodiment, the TACS are provided in a form that allows them to be bound to a solid support, such as biotinylated TACS. In another embodiment, the TACS are provided together with a solid support, such as biotinylated TACS provided together with streptavidin-coated magnetic beads.

In one embodiment, the kit comprises a container comprising the pool of TACS and instructions for performing the method, wherein the pool of TACS comprises a plurality of TACS families, wherein each TACS family comprises a plurality of member sequences, wherein each member sequence binds to the same genomic sequence of interest (e.g., tumor biomarker sequence of interest) but has different start and/or stop positions with respect to a reference coordinate system for the genomic sequence of interest, and further wherein:

(i) each member sequence within each TACS family is between 100-500 base pairs in length, each member sequence having a 5' end and a 3' end;

(ii) preferably each member sequence binds to the same genomic sequence of interest, and if applicable at least 50 base pairs away, on both the 5' end and the 3' end, from regions harboring Copy Number Variations (CNVs), Segmental duplications or repetitive DNA elements; and (iii) the GC content of the pool of TACS is between 19% and 80%, as determined by calculating the GC content of each member within each family of TACS.

Furthermore, any of the various features described herein with respect to the design and structure of the TACS can be incorporated into the TACS that are included in the kit.

In various other embodiments, the kit can comprise additional components for carrying out other aspects of the method. For example, in addition to the pool of TACS, the kit can comprise one or more of the following (i) one or more components for isolating cell free DNA or nucleated DNA from a biological sample (e.g., as described in Example 1);

(ii) one or more components for preparing the sequencing library (e.g., primers, adapters, buffers, linkers, restriction enzymes, ligation enzymes, polymerase enzymes and the like as described in detail in Example 1); (iii) one or more components for amplifying and/or sequencing the enriched library (e.g., as described in Example 3); and/or (iv) software for performing statistical analysis (e.g., as described in Examples 4 and 6-11).

Oncology Uses

In various embodiments, the TACS-based enrichment method of the disclosure can be used for a variety of purposes in the oncology field. As described in detail in Examples 6-9, the method allows for detection of tumor biomarkers (including cancer related-germline mutations) in biological samples. The method can be applied to the analysis of essentially any known tumor biomarker. An extensive catalogue of known cancer-associated mutations is known in the art, referred to as COSMIC (Catalogue of Somatic Mutations in Cancer), described in, for example, Forbes, S. A. et al. (2016) *Curr. Protocol Hum. Genetic* 91:10.11.1-10.11.37; Forbes, S. A. et al. (2017) *Nucl. Acids Res.* 45: D777-D783; and Prior et al. (2012) *Cancer Res.* 72:2457-2467. The COSMIC database is publically available at www.cancer.sanger.ac.uk. The database includes oncogenes that have been associated with cancers, any of which can be analyzed using the method of the disclosure. In addition to the COSMIC catalogue, other compilations of tumor biomarker mutations have been described in the art, non limiting examples of which include the ENCODE Project, which describes mutations in the regulatory sites of oncogenes (see e.g., Shar, N. A. et al. (2016) *Mol. Canc.* 15:76) and ClinVar, a National Center for Biotechnology Information (NCBI) database for genomic variations associated with human health. The ClinVar database is publicly available at www.ncbi.nlm.nih.gov/clinvar.

The methods of the invention can be used to simultaneously analyze a large panel of tumor biomarkers in a single biological sample. For example, in various embodiments, the pool of TACS used in the method detects at least 5, or at least 10, or at least 15, or at least 20, or at least 25, or at least 30, or at least 35, or at least 40, or at least 45 or at least 50 different tumor biomarkers.

For detection of tumor biomarkers, TACS are designed based on the design criteria described herein and the known sequences of tumor biomarker genes and genetic mutations therein associated with cancer. In one embodiment, a plurality of TACS families used in the method bind to a plurality of tumor biomarker sequences of interest selected from the group comprising of ABL, AKT, AKT1, ALK, APC, AR, ARAF, ATM, BAP1, BARD1, BCL, BMPR1A, BRAF, BRCA, BRCA1, BRCA2, BRIP1, CDH1, CDKN, CHEK2, CTNNB1, DDB2, DDR2, DICER1, EGFR, EPCAM, ErbB, ErcC, ESR1, FANCA, FANCB, FANCC, FANCD2, FANCE, FANCF, FANCG, FANCI, FANCL, FANCM, FBXW7, FGFR, FLT, FLT3, FOXA1, FOXL2, GATA3, GNA11, GNAQ, GNAS, GREM1, HOX, HOXB13, HRAS, IDH1, JAK, JAK2, KEAP1, KIT, KRAS, MAP2Ks, MAP3Ks, MET, MLH1, MPL, MRE11A, MSH2, MSH6, MTOR, MUTYH, NBN, NPM1, NRAS, NTRK1, PALB2, PDGFRs, PI3KCs, PMS2, POLD1, POLE, POLH, PTEN, RAD50, RAD51C, RAD51D, RAF1, RB1, RET, RUNX1, SLX4, SMAD, SMAD4, SMARCA4, SPOP, STAT, STK11, TP53, VHL, XPA and XPC, and combinations thereof.

In one embodiment, the plurality of TACS families used in the method bind to a plurality of tumor biomarker sequences of interest selected from the group consisting of, but not limited to, EGFR_6240, KRAS_521, EGFR_6225, NRAS_578, NRAS_580, PIK3CA_763, EGFR_13553, EGFR_18430, BRAF_476, KIT_1314, NRAS_584, EGFR_12378, and combinations thereof.

Representative, exemplary and non-limiting examples of chromosomal start and stop positions for amplifying TACS that bind to exemplary, non-limiting tumor biomarker genes are shown in FIG. 10, for NRAS on chromosome 1, for PI3KCA on chromosome 3, for EGFR on chromosome 7 and for KRAS on chromosome 12. Alternative suitable chromosomal start and stop positions, for these oncogenes and/or for other oncogenes, for amplifying TACS are readily identifiable by one of ordinary skill in the art based on the teachings herein.

In one embodiment of the method, following sequencing of the library preparation and enrichment for the sequences of interest through TACS hybridization, the subsequent step of amplifying the enriched library is performed in the presence of blocking sequences that inhibit amplification of wild-type sequences. Thus, amplification is biased toward amplification of the mutant tumor biomarker sequences.

The pool of TACS and families of TACS used in the method of detecting tumor biomarkers can include any of the design features described herein with respect to the design of the TACS. For example, in various embodiments, each TACS family comprises at least 2, at least 3, at least 4 or at least 5 different member sequences. In one embodiment, each TACS family comprises 4 different member sequences. In various embodiments, the start and/or stop positions for the member sequences within a TACS family, with respect to a reference coordinate system for the genomic sequence of interest, are staggered by at least 5 base pairs, or at least 10 base pairs, or by 5-10 base pairs. In various embodiments, the pool of TACS comprises at least 5, or at least 10 or at least 50 or at least 100 different TACS families, or more.

Suitable statistical analysis approaches for use with oncology samples and detection of tumor biomarkers are described further in Examples 6-9.

The method for detecting tumor biomarkers can be used in a variety of different clinical circumstances in the oncology field. For example, the method can be used for making an initial cancer diagnosis in a subject suspected of having cancer. Accordingly in one embodiment, the method further comprises making a diagnosis of the subject based on detection of at least one tumor biomarker sequence.

Additionally, the method can be used to select an appropriate treatment regimen for a patient diagnosed with cancer, wherein the treatment regimen is designed to be effective against a tumor having the tumor biomarkers detected in the patient's tumor (i.e., known in the art as personalized medicine). Accordingly, in another embodiment, the method further comprises selecting a therapeutic regimen for the subject based on detection of at least one tumor biomarker sequence.

Still further, the method can be used to monitor the efficacy of a therapeutic regiment, wherein changes in tumor biomarker detection are used as an indicator of treatment efficacy. Accordingly, in another embodiment, the method further comprises monitoring treatment efficacy of a therapeutic regimen in the subject based on detection of at least one tumor biomarker sequence.

Moreover, the method can be used to detect relapse and minimal residual disease (MRD), wherein detection of at least one tumor biomarker are used as an indicator of remaining tumor cells in a patient after treatment or tumor recurrence. Accordingly in another embodiment, the method further informs of MRD and disease relapse.

Also, the method can be used to detect cancer-related germline (hereditary) mutations in patients with cancer or individuals suspected of a cancer pre-disposing syndrome wherein detection of at least one germline mutation is used as an indicator for having a cancer pre-disposing syndrome. Accordingly, in another embodiment, the method further comprises diagnosing a patient or an individual with a hereditary cancer pre-disposing syndrome that can inform the clinician to allow for early medical intervention, treatment selection and close monitoring.

Fragment-Based Analysis

In another aspect, the invention pertains to fragment based analysis of samples, described further in Example 9. There is evidence from the literature that specific types of cancer can be characterized by and/or associated with fragments in the plasma having a smaller size than the expected size of fragments originating from healthy tissues (Jiang et al, (2015), *Proceedings of the National Academy of Sciences,* 112 (11), ppE1317-E1325). The same hypothesis holds true for fragments originating from the placenta/fetus. Specifically, placenta derived fragments are generally of smaller size when compared to fragments originating from maternal tissues/cells. Accordingly, a fragment size-based test was developed and assessed, demonstrating its ability to identify samples harboring chromosomal abnormalities.

Thus, the fragments-based detection may be used to detect abnormalities in mixed samples with low signal-to-noise ratio (e.g., as is the case in detection of cancer).

Accordingly, in one embodiment, a fragments-based test is utilized to detect the presence of somatic copy number aberrations in a sample from a patient suspected of having cancer. For example, a binomial test of proportions, as described Example 4 and Example 9, can be used for the detection of increased presence of nucleic acid material originating from non-healthy tissue (e.g., tumor tissue) based on fragment size. In particular, under the null hypothesis that the distribution of fragment sizes originating from both healthy and cancerous cells is the same, a binomial test for proportions (as described in Example 4 and Example 9) using continuity correction can be utilized to quantify any evidence against it.

EXAMPLES

The present invention is further illustrated by the following examples, which should not be construed as further limiting. The contents of all references, appendices, Genbank entries, patents and published patent applications cited throughout this application are expressly incorporated herein by reference in their entirety.

Example 1: Sample Collection and Library Preparation

The general methodology for the TACS-based multiplexed parallel analysis approach for genetic assessment is shown schematically in FIG. 1. In this example, methods for collecting and processing a maternal plasma sample (containing maternal and fetal DNA), followed by sequencing library preparation for use in the methodology of FIG. 1 are described. The DNA sample and library preparation described herein can similarly be used with DNA samples from tumors for tumor biomarker detection (see Example 6-9).

Sample Collection

Plasma samples were obtained anonymously from pregnant women after the 10th week of gestation. Protocols used for collecting samples for our study were approved by the Cyprus National Bioethics Committee, and informed consent was obtained from all participants.

Sample Extraction

Cell Free DNA was extracted from 2-4 ml plasma from each individual using a manual or automated extraction method suitable for cell free DNA isolation such as for example, but not limited to, Qiasymphony protocol suitable for cell free fetal DNA isolation (Qiagen) (Koumbaris, G. et al. (2016) *Clinical chemistry,* 62 (6), pp. 848-855).

Sequencing Library Preparation

Extracted DNA from maternal plasma samples was used for sequencing library construction. Standard library preparation methods were used with the following modifications. A negative control extraction library was prepared separately to monitor any contamination introduced during the experiment. During this step, 5' and 3' overhangs were filled-in, by adding 12 units of T4 polymerase (NEB) while 5' phosphates were attached using 40 units of T4 polynucleotide kinase (NEB) in a 100 μl reaction and subsequent incubation at 25° C. for 15 minutes and then 12° C. for 15 minutes. Reaction products were purified using the MinElute kit (Qiagen). Subsequently, adaptors P5 and P7 (see adaptor preparation) were ligated at 1:10 dilution to both ends of the DNA using 5 units of T4 DNA ligase (NEB) in a 40 μl reaction for 20 minutes at room temperature, followed by purification using the MinElute kit (Qiagen). Nicks were removed in a fill-in reaction with 16 units of Bst polymerase (NEB) in a 40 μl reaction with subsequent incubation at 65° C. for 25 minutes and then 12° C. for 20 minutes. Products were purified using the MinElute kit (Qiagen). Library amplification was performed using a Fusion polymerase (Herculase II Fusion DNA polymerase (Agilent Technologies) or Pfusion High Fidelity Polymerase (NEB)) in 50 μl reactions and with the following cycling conditions, 95° C. for 3 minutes; followed by 10 cycles at 95° C. for 30 seconds, 60° C. for 30 seconds, 72° C. for 30 seconds and finally 72° C. for 3 minutes (Koumbaris, G. et al. (2016) *Clinical chemistry,* 62 (6), pp. 848-855). The final library products were purified using the MinElute Purification Kit (Qiagen) and measured by spectrophotometry.

Adaptor Preparation

Hybridization mixtures for adapter P5 and P7 were prepared separately and incubated for 10 seconds at 95° C. followed by a ramp from 95° C. to 12° C. at a rate of 0.1° C./second. P5 and P7 reactions were combined to obtain a ready-to-use adapter mix (100 μM of each adapter). Hybridization mixtures were prepared as follows: P5 reaction mixture contained adaptor P5_F (500 UM) at a final concentration of 200 μM, adaptor P5+P7_R (500 UM) at a final concentration of 200 μM with 1× oligo hybridization buffer. In addition, P7 reaction mixture contained adaptor P7_F (500 μM) at a final concentration of 200 μM, adapter P5+P7_R (500 μM) at a final concentration of 200 μM with 1× oligo hybridization buffer (Koumbaris, G. et al. (2016) *Clinical chemistry,* 62 (6), pp. 848-855.). Sequences were as follows, wherein *=a phosphorothioate bond (PTO) (Integrated DNA Technologies):

```
adaptor P5_F:
                                        (SEQ ID NO: XX)
A*C*A*C*TCTTTCCCTACACGACGCTCTTCCG*A*T*C*T

adaptor P7_F:
                                        (SEQ ID NO: YY)
G*T*G*A*CTGGAGTTCAGACGTGTGCTCTTCCG*A*T*C*T,

adaptor_P5+P7_R:
                                        (SEQ ID NO: ZZ)
A*G*A*T*CGGAA*G*A*G*C.
```

Example 2: TArget Capture Sequences (TACS) Design and Preparation

This example describes preparation of custom TACS for the detection of whole or partial chromosomal abnormalities for chromosomes 13, 18, 21, X, Y or any other chromosome, as well as other genetic abnormalities, such as but not limited to, microdeletion/microduplication syndromes, translocations, inversions, insertions, and other point or small size mutations. The genomic target-loci used for TACS design were selected based on their GC content and their distance from repetitive elements (minimum 50 bp away). TACS size can be variable. In one embodiment of the method the TACS range from 100-500 bp in size and are generated through a PCR-based approach as described below. The TACS were prepared by simplex polymerase chain reaction using standard Taq polymerase, primers designed to amplify the target-loci, and normal DNA used as template. The chromosomal regions used to design primers to amplify suitable loci on chromosomes 13, 18, 21 and X, to thereby prepare the pool of TACS for analysis of chromosomes 13, 18, 21 and X, are shown in FIG. 2.

All custom TACS were generated using the following cycling conditions: 95° C. for 3 minutes; 40 cycles at 95° C. for 15 seconds, 60° C. for 15 seconds, 72° C. for 12 seconds; and 72° C. for 12 seconds, followed by verification via agarose gel electrophoresis and purification using standard PCR clean up kits such as the Qiaquick PCR Purification Kit (Qiagen) or the NucleoSpin 96 PCR clean-up (Mackerey Nagel) or the Agencourt AMPure XP for PCR Purification (Beckman Coulter). Concentration was measured by Nanodrop (Thermo Scientific).

Example 3: TACS Hybridization and Amplification

This example describes the steps schematically illustrated in FIG. 1 of target capture by hybridization using TACS, followed by quantitation of captured sequences by Next Generation Sequencing (NGS).

TACS Biotinylation

TACS were prepared for hybridization, as previously described (Koumbaris, G. et al. (2016) *Clinical chemistry,* 62 (6), pp. 848-855), starting with blunt ending with the Quick Blunting Kit (NEB) and incubation at room temperature for 30 minutes. Reaction products were subsequently purified using the MinElute kit (Qiagen) and were ligated with a biotin adaptor using the Quick Ligation Kit (NEB) in a 40 µl reaction at RT for 15 minutes. The reaction products were purified with the MinElute kit (Qiagen) and were denatured into single stranded DNA prior to immobilization on streptavidin coated magnetic beads (Invitrogen).

TACS Hybridization

Amplified libraries were mixed with blocking oligos (Koumbaris, G. et al. (2016) *Clinical chemistry,* 62 (6), pp. 848-855) (200 µM), 5 µg of Cot-1 DNA (Invitrogen), 50 µg of Salmon Sperm DNA (Invitrogen), Agilent hybridization buffer 2×, Agilent blocking agent 10×, and were heated at 95° C. for 3 minutes to denature the DNA strands. Denaturation was followed by 30 minute incubation at 37° C. to block repetitive elements and adaptor sequences. The resulting mixture was then added to the biotinylated TACS. All samples were incubated in a rotating incubator for 12-48 hours at 66° C. After incubation, the beads were washed as described previously and DNA was eluted by heating (Koumbaris, G. et al. (2016) *Clinical chemistry,* 62 (6), pp. 848-855). Eluted products were amplified using outer-bound adaptor primers. Enriched amplified products were pooled equimolarly and sequenced on a suitable platform.

If appropriate, amplification may be biased toward amplification of specific/desired sequences. In one embodiment of the method, this is performed when amplification is performed in the presence of sequences that hybridize to the undesired sequence of interest, and as such block the action of the polymerase enzyme during the process. Hence, the action of the amplification enzyme is directed toward the sequence of interest during the process.

Example 4: Bioinformatics Sample Analysis

This example describes representative statistical analysis approaches for use in the methodology illustrated in FIG. 1 ("analysis pipeline" in FIG. 1).

Human Genome Alignment

For each sample, the bioinformatic pipeline routine described below was applied in order to align the sample's sequenced DNA fragments to the human reference genome. Targeted paired-end read fragments obtained from NGS results were processed to remove adaptor sequences and poor quality reads (Q-score<25) using the cutadapt software (Martin, M. et al. (2011) EMB.netJournal 17.1). The quality of the raw and/or processed reads as well as any descriptive statistics which aid in the assessment of quality check of the sample's sequencing output were obtained using the FastQC software (Babraham Institute (2015) FastQC) and/or other custom-built software. Processed reads which were at least 25 bases long were aligned to the human reference genome built hg19 (UCSC Genome Bioinformatics) using the Burrows-Wheel Alignment algorithm (Li, H. and Durbin, R. (2009) Bioinformatics 25:1754-1760) but other algorithms known to those skilled in the art may be used as well. If relevant, duplicate reads were removed post-alignment. Where applicable, sequencing output pertaining to the same sample but processed on separate sequencing lanes, was merged to a single sequencing output file. The removal of duplicates and merging procedures were performed using the Picard tools software suite (Broad Institute (2015) Picard) and/or the Sambamba tools software suite (Tarasov, Artem, et al. "Sambamba: fast processing of NGS alignment formats." Bioinformatics 31.12 (2015): 2032-2034.). A realignment procedure, using tools known to those in the art, may also be performed.

The above software analysis resulted in a final aligned version of a sequenced sample against the human reference genome and all subsequent steps were based on this aligned version. Information in terms of Short Nucleotide Polymorphisms (SNPs) at loci of interest was obtained using bcftools from the SAMtools software suite (Li, H. et al. (2009) *Bioinformatics* 25:2078-2079) and/or other software known to those skilled in the art. The read-depth per base, at loci of interest, was obtained using the mpileup option of the SAMtools software suite, from here on referred to as the mpileup file. Information pertaining to the size of the aligned fragments was obtained using the view option of the SAMtools software suite, from here on referred to as the fragment-sizes file and/or other software known to those skilled in the art.

The mpileup file and the fragment-sizes file were processed using custom-build application programming interfaces (APIs) written in the Python and R programming languages (Python Software Foundation (2015) *Python*; The R Foundation (2015) *The R Project for Statistical Computing*). The APIs were used to determine the ploidy state of chromosomes of interest, and/or other genetic abnormalities in regions of interest across the human genome, using a series of steps (collectively henceforth referred to as the "algorithm") and to also collect further descriptive statistics to be used as quality check metrics, such as but not limited to fetal fraction and/or fraction of interest quantification (collectively henceforth referred to as the "QC metrics"). The APIs can also be used for the assessment of genetic abnormalities from data generated when applying the described method in cases of multiple gestation pregnancies, as well as other genetic abnormalities such as, but not limited to, microdeletions, microduplications, copy number variations, translocations, inversions, insertions, point mutations and mutational signatures.

QC Metrics:

QC metrics were used to inspect an aligned sample's properties and decide whether the sample was suitable to undergo classification. These metrics were, but are not limited to:

(a) The enrichment of a sample. The patterns of enrichment are indicative of whether a sample has had adequate enrichment across loci of interest in a particular sequencing experiment (herein referred to as a "run"). To assess this, various metrics are assessed, non-limiting examples of which are:
   (i) overall sample on-target read depth,
   (ii) sample on-target sequencing output with respect to total mapped reads,
   (iii) individual TACS performance in terms of achieved read-depth,
   (iv) kurtosis and skewness of individual TACS enrichment,
   (v) kurtosis and skewness moments that arise from all TACS,
   (vi) fragment size distribution,
   (vii) percentage of duplication,
   (viii) percentage of paired reads and,
   (ix) percentage of aligned reads, if applicable.

The above checks are also taken into consideration with regards to GC-bias enrichment. Samples that fail to meet one or more of the criteria given above are flagged for further inspection, prior to classification.

(b) A sample's fetal fraction or fraction of interest. Samples with an estimated fetal fraction, or fraction of interest, that is below a specific threshold are not classified. Furthermore, if applicable the fraction of interest may be calculated using more than one method and concordance of results between estimation methods may be used as an additional QC prior to classification.

The Algorithm

The algorithm is a collection of data processing, mathematical and statistical model routines arranged as a series of steps. The algorithm's steps aim in deciding the relative ploidy state of a chromosome of interest with respect to all other chromosomes of the sequenced sample and is used for the detection of whole or partial chromosomal abnormalities for chromosomes 13, 18, 21, X, Y or any other chromosome, as well as other genetic abnormalities such as, but not limited to, microdeletion/microduplication syndromes and other point or small size mutations. As such the algorithm can be used, but is not limited to, the detection of whole or partial chromosomal abnormalities for chromosomes 13, 18, 21, X,Y or any other chromosome, as well as other genetic abnormalities such as, but not limited to, microdeletions, microduplications, copy number variations, translocations, inversions, insertions, point mutations and other mutational signatures. The algorithm carries out, but is not limited to, two types of assessments, one pertaining to the read-depth information of each sample and the other to the distribution of fragment-sizes, across TACS-specific regions. One or more statistical tests may be associated with each type of assessment, non-limiting examples of which are given in the statistical methods described herein.

In the case of read-depth associated tests, the algorithm compares sequentially the read-depth of loci from each chromosome of interest (herein referred to as the test chromosome) against the read-depth of all other loci (herein referred to as the reference loci) to classify its ploidy state. For each sample, these steps were, but are not limited to:

(a) Removal of inadequately sequenced loci. The read-depth of each locus was retrieved. Loci that have not achieved a minimum number of reads, were considered as inadequately enriched and were removed prior to subsequent steps.

(b) Genetic (GC-content) bias alleviation. The sequencing procedure may introduce discrepancies in read-depth across the loci of interest depending on their GC content. To account for such bias, a novel sequence-matching approach that increases both sensitivity and specificity to detect chromosomal aneuploidies was employed. The GC content of each locus on the test chromosome was identified and similar genetic loci were grouped together to form genetically matched groups. The procedure was repeated for the reference loci. Then, genetically matched groups from the test chromosome were conditionally paired with their genetically matched group counterparts on the reference chromosome(s). The groups may have any number of members. The conditionally matched groups were then used to assess the ploidy status of test chromosomes.

(c) Genetic abnormality determination. Ploidy status determination, or other genetic abnormalities of interest such as but not limited to microdeletions, microduplications, copy number variations, translocations, inversions, insertions, point mutations and other mutational signatures was achieved using a single statistical method and/or a weighted score approach on the result from the following, but not limited to, statistical methods:

Statistical Method 1: The differences in read-depth of the conditionally paired groups were tested for statistical significance using the t-test formula:

$$t = \frac{\hat{x} - \mu}{s/\sqrt{n}}$$

where t is the result of the t-test, $\hat{x}$ is the average of the differences of the conditionally paired groups, μ is the expected read-depth and is set to a value that represents insignificant read-depth differences between the two groups, s the standard deviation of the differences of the conditionally paired groups and n the length of the vector of the conditionally paired differences. The magnitude of the t-score was then used to identify evidence, if any, against the null hypothesis of same ploidy between reference and test chromosomes. Specifically, t>=c1 (where c1 is a predefined threshold belonging to the set of all positive numbers) shows evidence against the null hypothesis of no difference.

Statistical Method 2: Bivariate nonparametric bootstrap. The bootstrap method depends on the relationship between the random variables X (read-depth of reference loci) and Y (read-depth of test loci). Here, the read depth of baits on the reference group (random variable denoted by X) were treated as the independent covariate. The first step of the iterative procedure involved random sampling with replacement (bootstrapping) of the read-depths of loci on the reference chromosomes, i.e. (x1,g1), . . . , (xn,gn), where the parameter g is known and denotes the GC-content of the chosen bait. Then, for each randomly selected reference bait (xi,gi), a corresponding read depth was generated for a genetically matched locus i.e., (y1,g1), . . . , (yn,gn). Thus, the bivariate data (x1,y1), (x2,y2), . . . , (xn,yn) was arrived at, which was conditionally matched on their GC-content (parameter gi). The differences between the read depths of the genetically matched bootstrapped values xi and yi were used to compute the statistic of interest in each iteration. In one embodiment this statistical measure can be, but is not limited to, the mode, mean or median of the recorded differences, and/or multiples thereof. The procedure was repeated as necessary to build up the distribution of the statistic of interest from these differences. The sample was assigned a score that corresponds to a specific percentile of the built distribution (e.g. 5th percentile). Under the null hypothesis the ploidy between chromosomes in the reference and test groups is not different. As such, samples whose score for a particular chromosome, was greater than a predefined threshold, say c2, were classified as statistically unlikely to have the same ploidy. Other statistical measures may be employed.

Statistical Method 3: Stratified permutation test. The statistic of interest is the read-depth estimate of the test chromosome, denoted by $\hat{Y}_{obs}$, which is calculated using all loci of the test chromosome's genetically matched groups as follows:

$$\hat{Y}_{obs} = \frac{\sum_{j=1}^{j=T} \sum_{i=1}^{i=Nj} y_{ij}}{\sum_{j=1}^{j=T} Nj}$$

where $y_{ij}$ is the read-depth of locus i part of the genetically matched group j (i.e., loci belonging to a specific group based on their GC-content), Nj is the number of test loci part of the genetically matched group j and T the number of genetically matched groups.

Subsequently, a null distribution to test $\hat{Y}_{obs}$ was built. To do so, for each group j, the test and reference loci were combined (exchangeability under the null hypothesis), and each group j was sampled randomly up to Nj times without replacement (stratified permutation). This created a vector of values, say yi, and from this the vector's average value, say $\acute{y}_i$, was calculated. The procedure was repeated as necessary to build the null distribution. Finally $\hat{Y}_{obs}$, was studentized against the null distribution using the formula:

$$Z_{Yobs} = \frac{\hat{Y_{obs}} - \hat{Y}}{\sigma_Y}$$

where $\hat{Y}$ and $\sigma_Y$ are the first and square root of the second moment of all permuted $\acute{y}_i$ statistic values. Samples whose $Z_{Yobs}$ was greater than a predefined threshold, say c3, were statistically less likely to have the same ploidy in the reference and test groups.

In the case of fragment-size associated tests, the algorithm computes the proportion of small-size fragments found in test-loci and compares it with the respective proportion in reference-loci as described in Statistical Method 4 below.

Statistical Method 4: Fragment Size Proportions. For each sample the number and size of fragments aligned onto the human reference genome at the corresponding TACS coordinates, is extracted. The data is subsequently filtered so as to remove fragment-sizes considered statistical outliers using the median outlier detection method. Specifically, outliers are defined as those fragments whose size is above or below the thresholds, $F_{thr}$, set by equation:

$$F_{thr} = F_{median} \pm (X \times \text{IQR})$$

where $F_{median}$ is the median fragment-size of all fragments of a sample, X is a variable that can take values from the set of R+, and IQR is the interquartile range of fragment sizes. Thereafter, a binomial test of proportions is carried out to test for supporting evidence against the null hypothesis, H0, where this is defined as:

H0: The proportion of small fragments of the test-region is not different from the proportion of small-fragments of the reference region.

In various embodiments of the invention, small fragments are defined as those fragments whose size is less than or equal to a subset of Z+, that is upper-bounded by 160 bp. If the set of all TACS are defined as T, then the test region can be any proper subset S which defines the region under investigation, and the reference region is the relative complement of S in T. For example, in one embodiment of the invention, the set S is defined by all TACS-captured sequences of chromosome 21 and thus the reference set is defined by all TACS-captured fragments on the reference chromosomes, and/or other reference loci The alternative hypothesis, H1, is defined as:

H1: The proportion of small fragments of the test-region is not equal to the proportion of test fragments of the reference region.

As such, and taking into account continuity correction, the following score is computed (Brown et. al, Harrel):

$$W_{test} = \left(\acute{p} - p_{ref}\right) \Big/ \sqrt{\frac{\acute{p}\left(1 - \acute{p}\right)}{N_{test}}}$$

where $$\acute{p} = \frac{\left(\acute{F} + 0.5\right)}{(N_{test} + 1)}$$

$$p_{ref} = \frac{(F_{ref} + 0.5)}{(N_{ref} + 1)}$$

$\acute{F}$ is the number of small-size fragments on the test-region, $F_{ref}$ the number of small size fragments on the reference region, $N_{test}$ the number of all fragments on the test region and $N_{ref}$ the number of all fragments on the reference region.

For each sample, the algorithm tests sequentially the proportion of fragment sizes of regions under investigation (for example, but not limited to, chromosome 21, chromosome 18, chromosome 13 or other (sub) chromosomal regions of interest) against reference regions; those not under investigation at the time of testing. For each sample a score is assigned for each test. Scores above a set-threshold, say c4, provide evidence against the null hypothesis.

Weighted Score method 1: In one embodiment of the method, a weighted score was attributed to each sample s, computed as a weighted sum of all statistical methods using the formula:

$$V_s(R,F) = z_1 \max\{R_s, F_s\} + (1 - z_1)\text{Min}\{R_s, F_s\}$$

where $R_s$ is the run-specific corrected score arising from a weighted contribution of each read-depth related statistical method for sample s and is defined as:

$$R_s = \frac{\left(\Sigma_i w_i S_{is} - \acute{R}_r\right)}{\sigma_r}$$

and $\acute{R}_r$ is the run-specific median value calculated from the vector of all unadjusted read-depth related weighted scores that arise from a single sequencing run, and $\sigma_r$ is a multiple of the standard deviation of R scores calculated from a reference set of 100 euploid samples. The terms max $\{R_s, F_s\}$ and min $\{R_s, F_s\}$ denote the maximum and minimum values of the bracketed set, respectively.

$F_s$ is the run-specific corrected score arising from the fragment-size related statistical method and is defined as:

$$F_s = \frac{\left(W_{test} - \acute{R}_f\right)}{\sigma_f}$$

where $W_{test}$ is as defined earlier, $\acute{R}_f$ is the run specific median calculated from the vector of all unadjusted fragment-related statistical scores that arise from a single sequencing run, and $\sigma_f$ is a multiple of the standard deviation of F scores calculated from a reference set of 100 euploid samples.

A unique classification score of less than a predefined value indicates that there is no evidence from the observed data that a sample has a significant risk of aneuploidy.

Weighted Score method 2: In another embodiment of the method, the weighted score arising from the statistical methods described above was used to assign each sample a unique genetic abnormality risk score using the formula:

$$R(t, c) = \sum_{j=0}^{j=N} w_j \frac{t_j}{c_j}$$

where R is the weighted score result, $w_j$ the weight assigned to method j, $t_j$ the observed score resulting from method j, and $c_j$ the threshold of method j.

A unique classification score of less than a predefined value indicates that there is no evidence from the observed data that a sample has a significant risk of aneuploidy.

Since all read depths from baits in the reference group were assumed to be generated from the same population, and in order to have a universal threshold, run-specific adjustments were also employed to alleviate run-specific biases.

The aforementioned method(s), are also suitable for the detection of other genetic abnormalities, such as but not limited to, subchromosomal abnormalities. A non-limiting example is the contiguous partial loss of chromosomal material leading to a state of microdeletion, or the contiguous partial gain of chromosomal material leading to a state of microduplication. A known genetic locus subject to both such abnormalities is 7q11.23. In one embodiment of statistical method 1, synthetic plasma samples of 5%, 10% and 20% fetal material were tested for increased risk of microdeletion and/or microduplication states for the genetic locus 7q11.23.

For point mutations various binomial tests are carried out that take into consideration the fetal fraction estimate of the sample, f, the read-depth of the minor allele, r, and the total read-depth of the sequenced base, n. Two frequent, yet non-limiting examples involve assessment of the risk when the genetic abnormality is a recessive point mutation or a dominant point mutation.

In the non-limiting example of a recessive point mutation the null hypothesis tested is that both the mother and the fetus are heterozygous (minor allele frequency is 0.5) against the alternative in which the fetus is homozygous (minor allele frequency is 0.5-f/2). A small p-value from the corresponding likelihood ratio test would indicate evidence against the null. In the non-limiting example of a dominant point mutation the null hypothesis tested is that the mother and fetus are homozygous at the given position against the alternative in which only the fetus is heterozygous for the given position. A small p-value from the corresponding likelihood ratio test would indicate evidence against the null.

In addition to the above, fetal sex determination methods were also developed, with non-limiting examples given below. In one embodiment of the invention, fetal sex was assigned to a sample using a Poisson test using the formula:

$$Pr(r_y \leq k) = e^{-\lambda} \sum_{i=0}^{i=k} \frac{\lambda^i}{i!}$$

where $$\lambda = \frac{f B \mu}{2}$$

and f is the fetal fraction estimate of the sample, B is the number of target sequences on chromosome Y, μ is the read-depth of the sample and k is the sum of reads obtained from all targets B. The null hypothesis of the Poisson test was that the sample is male. A value of $Pr(r_y)$ less than a threshold cy was considered as enough evidence to reject the null hypothesis, i.e. the sample is not male. If any of the terms for computing $Pr(r_y)$ were unavailable, then the sample's sex was classified as NA (not available).

In another embodiment of the invention, fetal sex was assigned using the average read-depth of target sequences on chromosome Y. If the average read-depth of the target-sequences was over a predefined threshold, where such threshold may be defined using other sample-specific characteristics such as read-depth and fetal-fraction estimate, the fetal sex was classified as male. If the average read-depth was below such threshold then the sample was classified as female.

Fetal Fraction Estimation/Fraction of Interest Estimation

Several methods have been developed to estimate fetal fraction that can be applied to singleton and/or to multiple gestation pregnancies. As such, and dependent on the type of pregnancy, . . . the fetal fraction estimate can be obtained from either method or as a weighted estimate from a subset and/or all developed methods. Some non-limiting examples are given below.

In one embodiment, a machine learning technique has been developed based on Bayesian inference to compute the posterior distribution of fetal DNA fraction using allelic counts at heterozygous loci in maternal plasma of singleton pregnancies. Three possible informative combinations of maternal/fetal genotypes were utilized within the model to identify those fetal DNA fraction values that get most of the support from the observed data.

Let f denote the fetal DNA fraction. If the mother is heterozygous at a given genomic locus, the fetal genotype can be either heterozygous or homozygous resulting in expected minor allele frequencies at 0.5 and 0.5−f/2, respectively. If the mother is homozygous and the fetus is heterozygous then the expected minor allele frequency will be f/2. A Markov chain Monte Carlo method (a Metropolis-Hastings algorithm) (The R Foundation (2015) *The R Project for Statistical Computing*) was used with either a non-informative or an informative prior (i.e. incorporate additional information such as gestational age, maternal weight etc.) to obtain a sequence of random samples from the posterior probability distribution of fetal DNA fraction that is based on a finite mixture model.

In another embodiment, the fetal fraction estimate is computed only from the fetus-specific minor allele frequency (MAF) cluster, i.e. the cluster formed when the mother is homozygous and the fetus is heterozygous for a given genomic locus. It is assumed that the mean value of the fetal fraction estimate is normally distributed as $N(2\acute{x}, \sigma_{\acute{x}})$, where $\acute{x}$ is the mean of the fetus-specific MAF, and $\sigma_{\acute{x}}$ is the standard deviation of the fetus-specific MAF. The fetal fraction estimate is then obtained from percentiles of the computed distribution, $N(2\acute{x}, \sigma_{\acute{x}})$.

For multiple gestation pregnancies, non-limiting examples of which include monozygotic and dizygotic twin pregnancies, triplet pregnancies and various egg and/or sperm donor cases, the fetal fraction can be estimated using information obtained from heterozygous genetic loci whose MAF value is less than a threshold, say $M_{thresh}$, and derived from potential fetus-specific SNPs. The ordinarily skilled artisan will appreciate that fetus specific SNPs can originate from any fetus, or from any possible combination of the fetuses or from all the fetuses of the gestation. As such, an algorithm that estimates the fetal fraction of the fetus with the smallest contribution to the total fetal content, by taking into account the combinatorial contribution of each fetus to the MAF values that define fetus-specific SNPs, and also allows for inhomogeneous contribution of fetal material to the total fetal content of plasma derived material has been developed. To this effect, a two-step approach is employed by the algorithm.

In one embodiment of the algorithm, the multiple gestation pregnancy under consideration is a dizygotic twin pregnancy. As a first step, the algorithmic implementation of the model utilizes all informative SNPs and allows for inhomogeneous fetal contribution that can be explained with a fold-difference in fetal fraction estimates of a set threshold, say cf. Specifically, if f1 and f2 represent the fetal fractions of fetus one and fetus two, and f1<=f2, then the assumption is that f2<=cf f1, with cf being a positive real number greater than or equal to 1. Under this assumption, the observed data D, defined as counts of the alternate and reference alleles at informative SNP loci, are believed to be generated from a mixture distribution of three Binomials (defined by parameters, f1/2, f2/2 and (f1+f2)/2), with the posterior distribution p (f1,f2 | D) being proportional to the observational model which can be written as p (f1 |f2,D) p (f2|D). The posterior distribution p (f1,f2 |D) is sampled with an MCMC Metropolis-Hastings algorithm using a uniform prior. The empirical quantile approach is performed on the generated data array to infer the fetal fractions.

As a second step, the algorithm runs a model-based clustering algorithm (Finite Gaussian mixture modeling fitted via EM algorithm; R-package: mclust) to identify whether there exists a separate outlier SNP cluster which is believed to be centered around f1/2. Existence of such a cluster with a mean invalidating the cf >=f2/f1 assumption, leads to estimation of f1 using only SNPs part of the identified cluster.

The methods described above are suited to the determination of the fraction of any component of interest part of a mixed sample. As such, the methods are not to be understood as applicable only to the application of fetal fraction estimation and can be applied to the estimation of any component of interest part of a mixed sample, as outlined in Example 6.

Example 5: Target Enrichment Using Families of TACS

In this example, a family of TACS, containing a plurality of members that all bind to the same target sequence of interest, was used for enrichment, compared to use of a single TACS binding to a target sequence of interest. Each member of the family of TACS bound to the same target sequence of interest but had different start/stop coordinates with respect to a reference coordinate system for that target sequence (e.g., the human reference genome, built hg19). Thus, when aligned to the target sequence, the family of TACS exhibit a staggered binding pattern, as illustrated in FIG. 3. Typically, the members of a TACS family were staggered approximately 5-10 base pairs.

A family of TACS containing four members (i.e., four sequences that bound to the same target sequence but having different start and/or stop positions such that the binding of the members to the target sequence was staggered) was prepared. Single TACS hybridization was also prepared as a control. The TACS were fixed to a solid support by labelling with biotin and binding to magnetic beads coated with a biotin-binding substance (e.g., streptavidin or avidin) as described in Example 3. The family of TACS and single TACS were then hybridized to a sequence library, bound sequences were eluted and amplified, and these enriched amplified products were then pooled equimolarly and sequenced on a suitable sequencing platform, as described in Example 3.

Figure 4A:
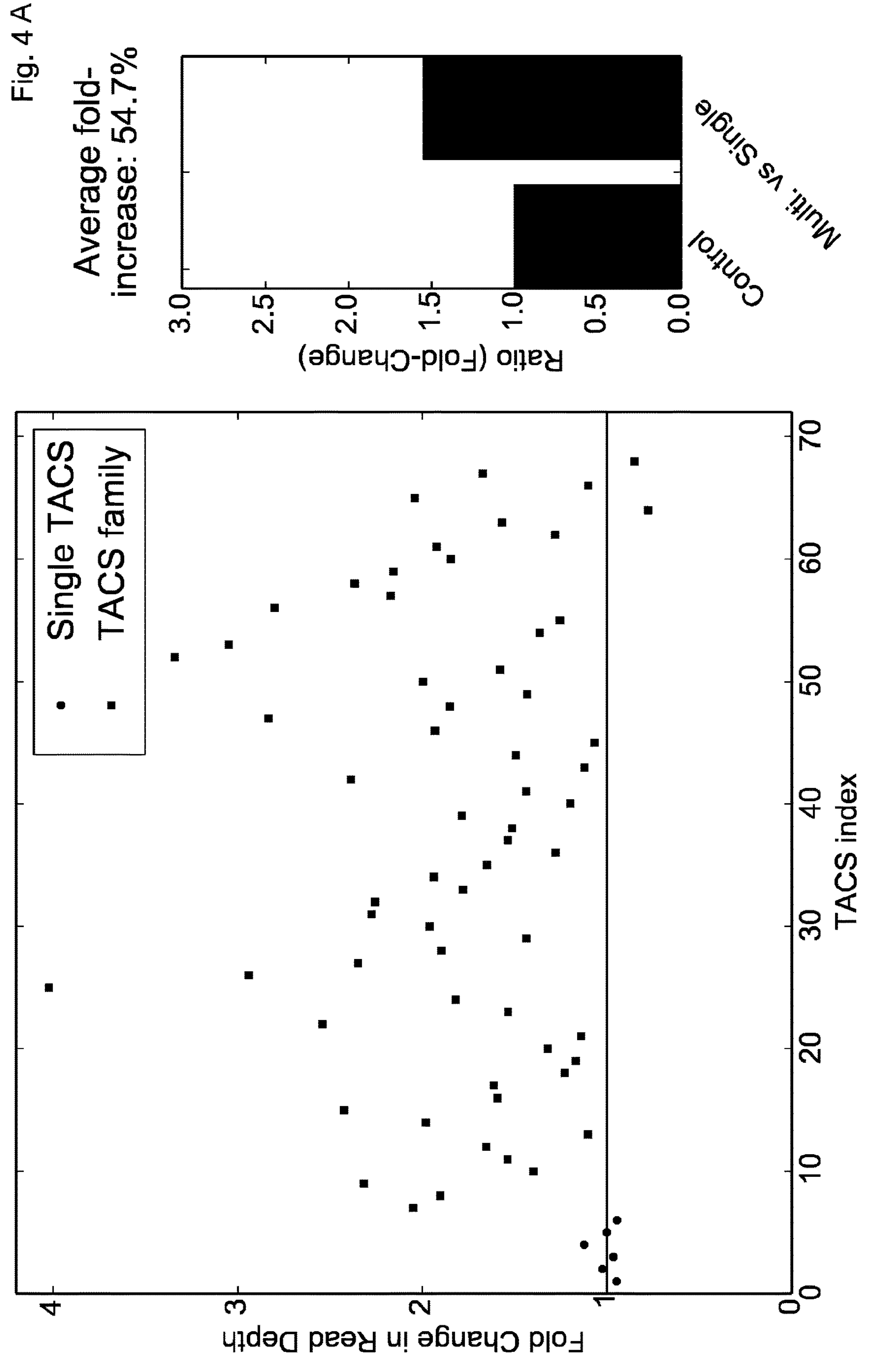
FIGS. 4A-4B are graphs showing enrichment using families of TACS versus a single TACS, as illustrated by increase in the average read-depth.
Figure 4B:
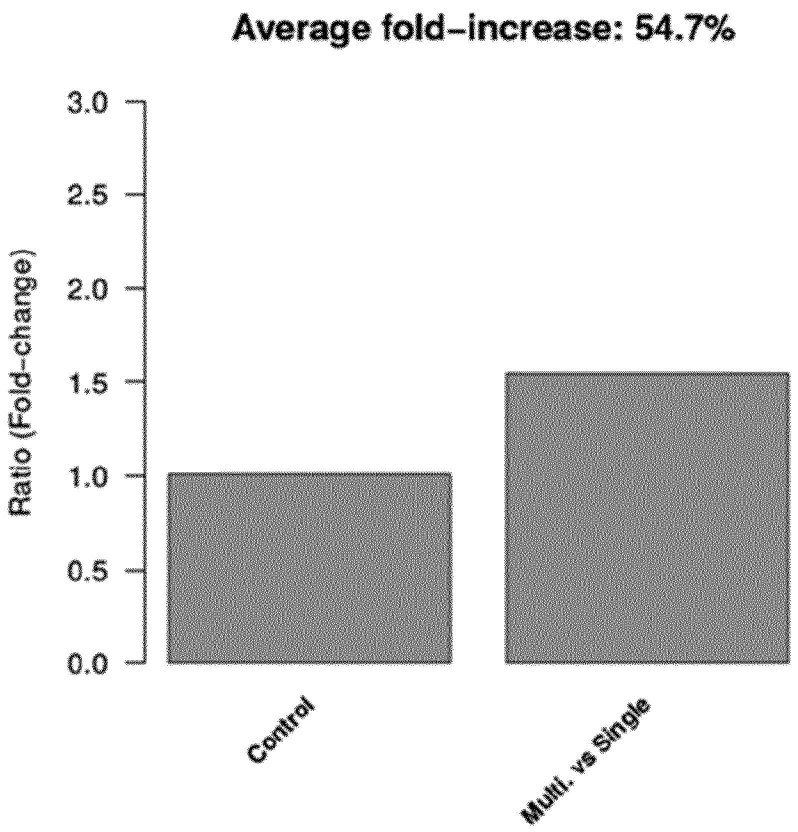

The enriched sequences from the family of TACS sample and the single TACS sample were analyzed for read-depth. The results are shown in FIGS. 4A and 4B. As shown in FIG. 4A, target sequences of interest enriched using the family of four TACS (red dots) exhibited a fold-change in read-depth when compared to control sequences that were subjected to enrichment using only a single TACS (blue dots). Fold-change was assessed by normalizing the read-depth of each locus by the average read-depth of a sample, wherein the average read-depth was calculated from all loci enriched with a single TACS. As shown in FIG. 4B, an overall 54.7% average increase in read-depth was observed using the family of four TACS.

This example demonstrates that use of a family of TACS, as compared to a single TACS, results in significantly improved enrichment of a target sequence of interest resulting in significantly improved read-depth of that sequence.

Example 6: Tumor Biomarker Detection in Reference Material

In this example, the TACS methodology, illustrated in FIG. 1, was used for the detection of tumor biomarkers in certified reference material known to harbor particular genetic mutations that are tumor biomarkers. For detection of the tumor biomarker sequences of interest, families of TACS, as described in Example 5, were used.

A sample of certified reference material harboring known tumor-associated genetic mutations was commercially obtained and samples were prepared to simulate tumor loads of 0.1%, 1.0% and 5.0%.

The samples were subjected to the TACS methodology illustrated in FIG. 1 using families of TACS that bound to the following tumor-associated genetic mutations: EGFR_6240, KRAS_521, EGFR_6225, NRAS_578, NRAS_580, PIK3CA_763, EGFR_13553, EGFR_18430.

Following amplification and sequence of the TACS-enriched products, data analysis was performed as follows. Sequencing products were processed to remove adaptor sequences and poor quality reads. Reads whose length was at least 25 bases long post adaptor-removal were aligned to either:

(a) the human reference genome built hg19, or (b) an artificially created genome based on built hg19 which contains only sequences of interest.

If relevant, duplicate reads were removed post-alignment. Where applicable, sequencing output pertaining to the same sample but processed on separate sequencing lanes was merged to a single sequencing output file. Local realignment of the data, using tools known in the art, may also be performed. The above software analysis provided a final aligned version of a sequenced sample against the reference genome, defined here as the final BAM file, where information can be extracted from it in terms of Short Nucleotide Polymorphisms (SNPs), Single Nucleotide Variants (SNVs) and other genetic variations with respect to a reference sequence at loci of interest, read-depth per base and the size of aligned fragments. Various available tools known to those skilled in the art, such as but not limited to bcftools, which is part of the samtools software suite, or varDict can be used to collect SNP information from the final BAM file. Such information concerns the sequence and number of times each variant is present in a sequenced sample was detected and was used to (a) infer the presence of a genetic mutation, and (b) to estimate the tumor load using the fetal-fraction estimation/fraction of interest estimation method described in Example 4.

In addition to the detection of the genetic mutation, statistical confidence was ascribed to a detected mutation using the estimated tumor load of the sample and the read-depth of each of the detected variants at a given position using binomial statistics. More than one test may be employed from which one can compute the probability of obtaining the sequenced information, or obtain a 95% confidence interval which describes a range of possible read-depths for the genetic mutation, or whether the obtained proportion of reads which can be ascribed to the genetic mutation is consistent with what would be expected at the given tumor load. A suitable binomial test of proportions is described in Example 4 (in the context of classification of chromosomal abnormalities).

Figure 5:
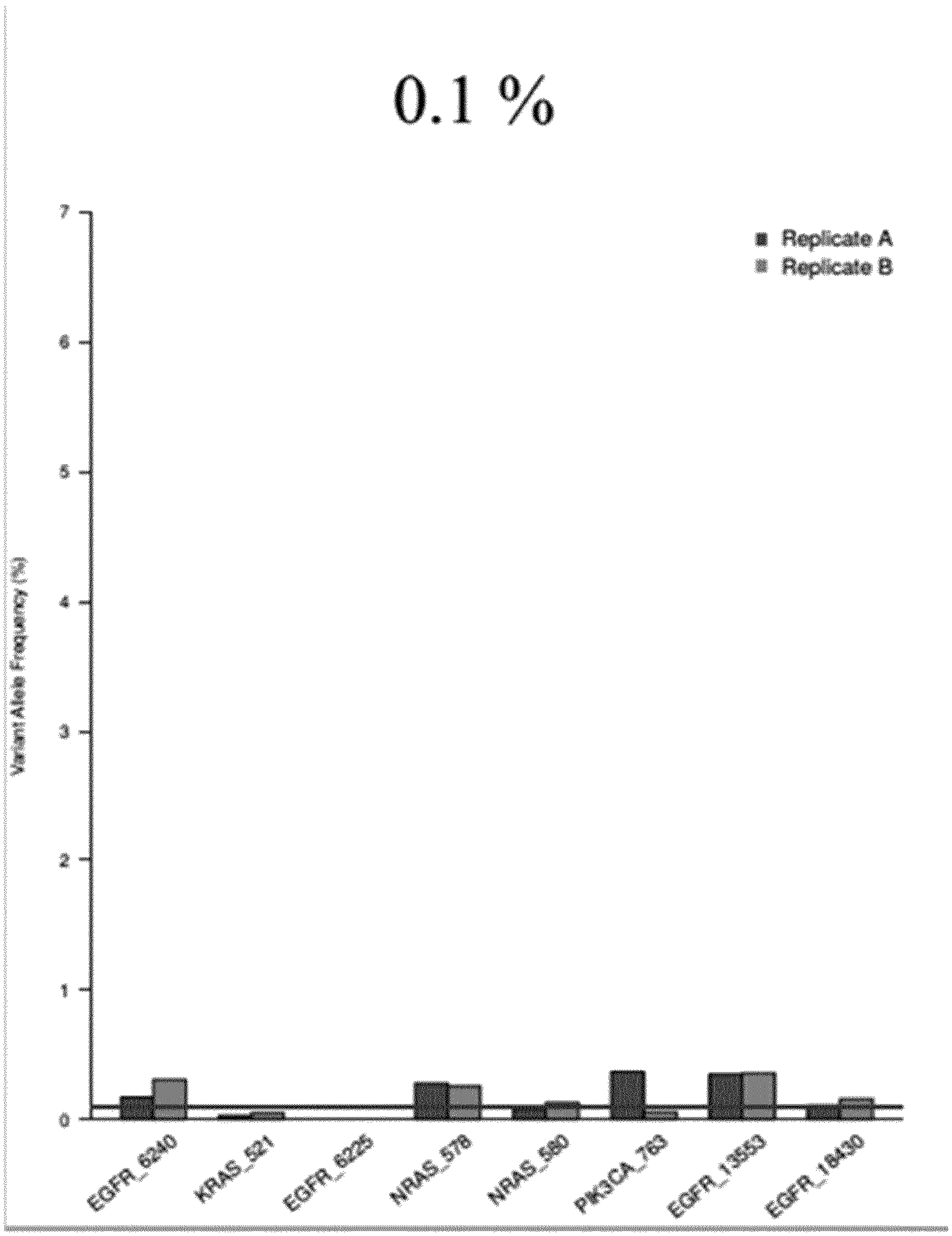
FIG. 5 shows bar graphs illustrating detection of known genetic mutations that are tumor biomarkers in certified reference material harboring the mutations. Two replicates of the reference material are shown. The line illustrates the expected minor allele frequency (MAF) for each of the assessed tumor loads. The bars (x-axis) illustrate the detected MAF (y-axis) for the indicated genetic mutations in the certified reference material.
Figure 5:
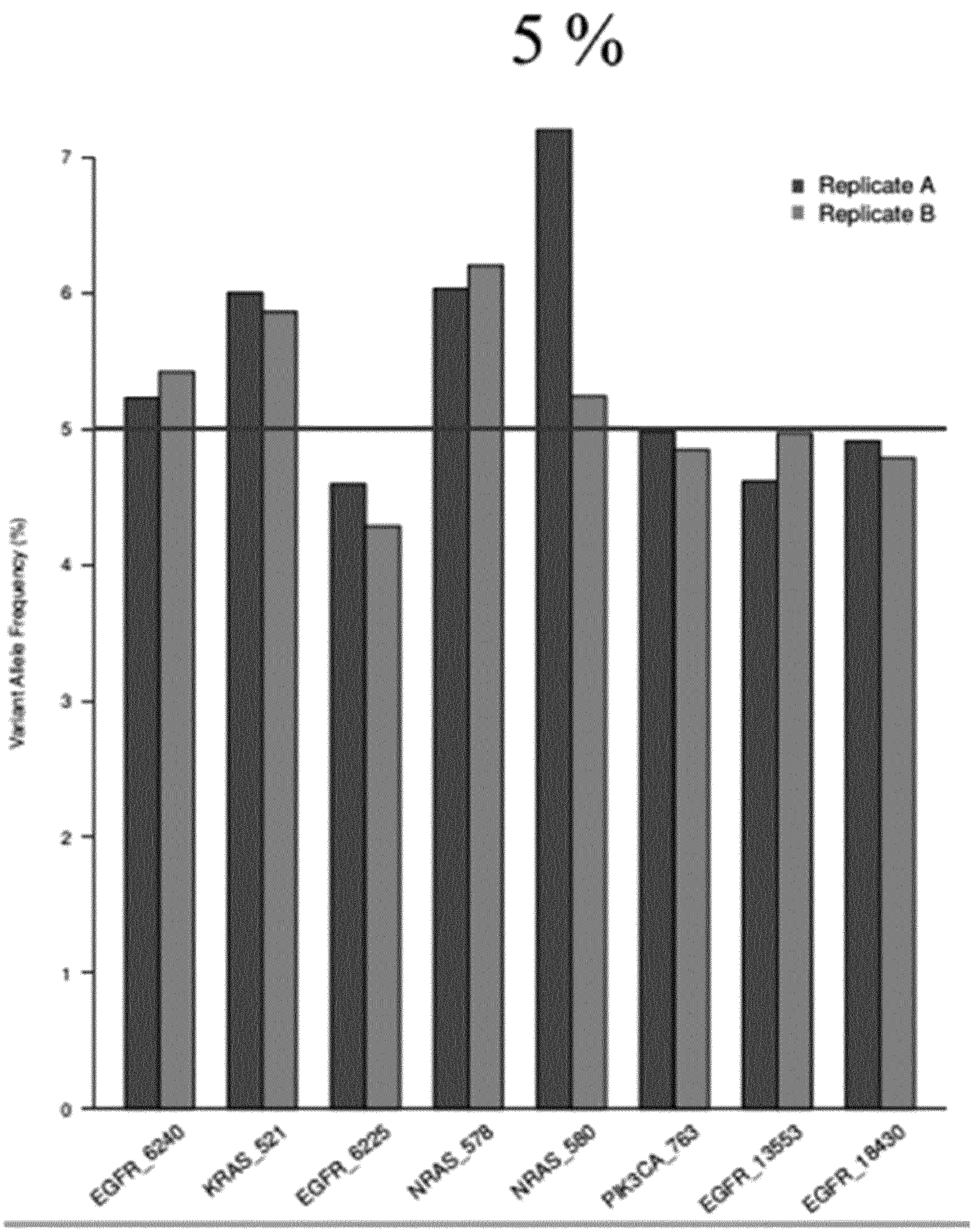

The results are shown in FIG. 5. The line illustrates the expected minor allele frequency (MAF) for each percent (%) tumor load. The bars (x-axis) illustrate the detected MAF (y-axis) for each sample for the indicated genetic mutations. Two technical replicates are shown for the reference material.

The data demonstrates that the TACS methodology successfully detected the tumor-associated genetic mutations EGFR_6240, KRAS_521, EGFR_6225, NRAS_578, NRAS_580, PIK3CA_763, EGFR_13553 and EGFR_18430 at the expected tumor loads of 1.0% and 5.0%. Mutations EGFR_6240, NRAS_578, PIK3CA_763, EGFR_13553 and EFGR_18430 were also successfully detected at 0.1% tumor load.

Accordingly, this example demonstrates the successful detection of a large panel of different tumor biomarkers using the TACS methodology at tumor loads as low as 0.1%.

Example 7: Tumor Biomarker Detection in Patient Samples

In this example, the TACS methodology, illustrated in FIG. 1, was used for the detection of tumor biomarkers in tumor tissue and blood plasma samples from untreated cancer patients with confirmed diagnosis. For detection of the tumor biomarker sequences of interest, families of TACS, as described in Example 5, were used.

Matched pairs of peripheral blood and tumor tissue samples from untreated cancer patients were used to further validate the performance of the TACS methodology for tumor biomarker detection for a patient harboring mutation PIK3CA E545K (Patient 1) and for a patient harboring mutation TP53 K139 (Patient 2). The results are shown in FIG. 6.

Figure 6:
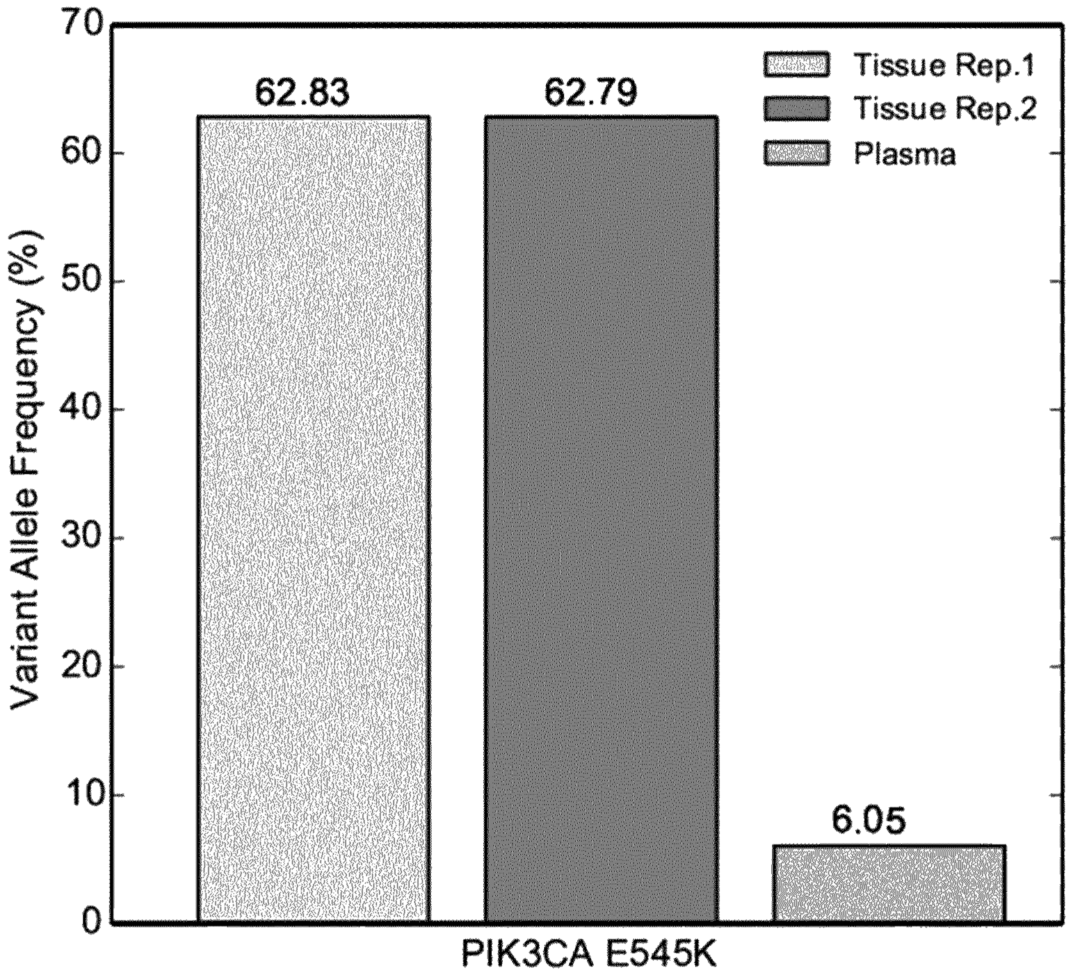
FIG. 6 shows bar graphs illustrating detection of tumor biomarkers in cancer patient samples. Results are shown for two patients, one harboring mutation PIK3CA E545K (top bars) and one harboring mutation TP53 K139 (bottom bars). Both tumor tissue samples ("Tissue Rep. 1" and "Tissue Rep. 2") and plasma samples ("Plasma") are shown. The y-axis shows % variant allele frequency (VAF) detected in the samples.
Figure 6:
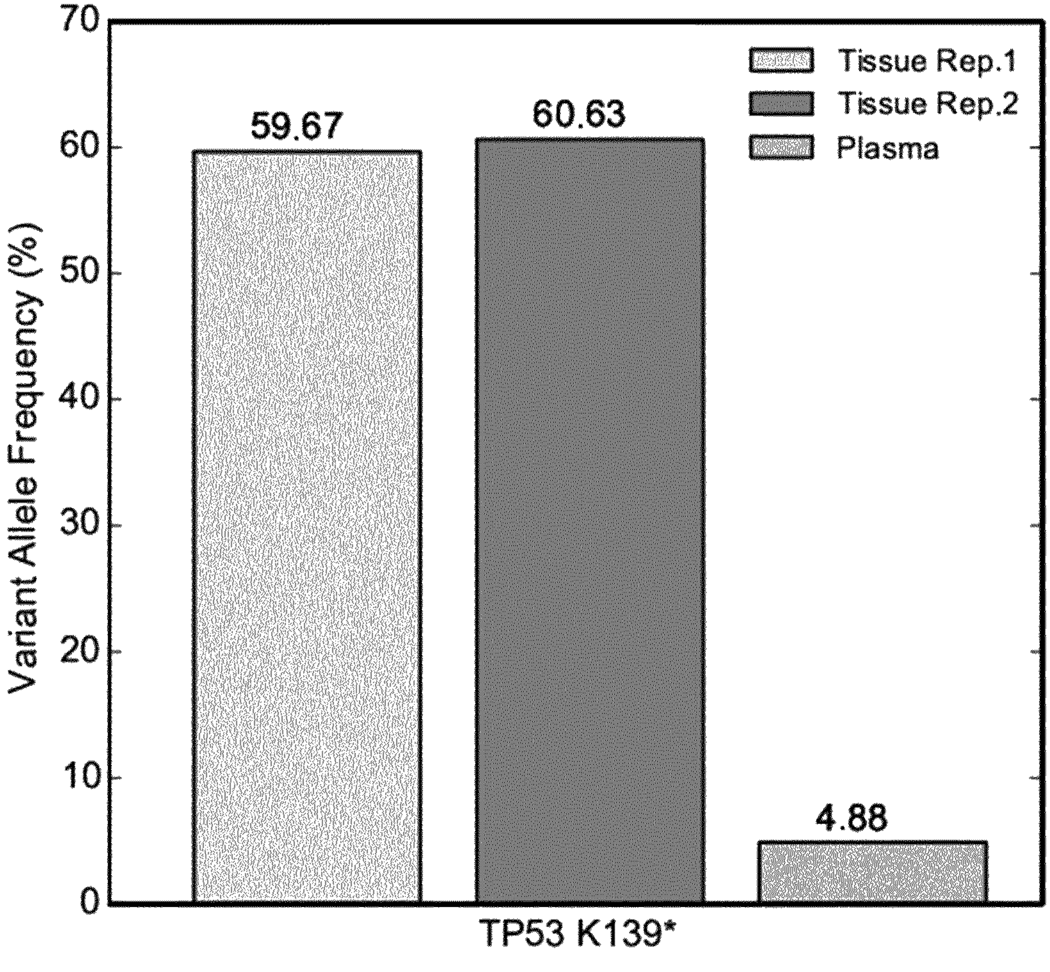

As shown in FIG. 6, application of the TACS methodology to a tissue sample obtained from Patient 1 harboring mutation PIK3CA E545K (top bars) provided a variant allele frequency (VAF) percentage (i.e., the percentage that the genetic mutation is present instead of the normal allele) of ~62%. Plasma obtained from peripheral blood of Patient 1 was processed according to the method described in Example 1 and provided a 6.05% VAF. Similarly, application of the TACS methodology to samples obtained from Patient 2 harboring mutation TP53 K139 (bottom bars) provided a VAF of ~60% for tumor tissue and a VAF of 4.88% for plasma obtained from a peripheral blood sample.

Accordingly, this example demonstrates the successful detection of tumor biomarkers in cancer patient samples, in both tumor tissue samples and plasma samples, thereby demonstrating the suitability of the TACS methodology for tissue biopsy and for non-invasive tumor biomarker detection using liquid biopsy.

Example 8: Detection of Mutational Profiles

Given the ability of the TACS methodology illustrated in FIG. 1 to detect a number of somatic single nucleotide variations (SNVs), these can be examined in the context of motifs, also referred to as mutational profiles. Most somatic mutations in tumors can be considered as passengers and may not be associated with pathogenesis if examined individually. Nonetheless, examining the profile of detected mutations as a whole can be useful in determining and/or detecting a pathogenesis-associated mutational profile. Various algorithms have been developed to decompose known mutational motifs operative in many cancer types. Alternatively, other metrics utilizing specific characteristics such as the type of mutations detected in the context of their neighboring bases can be utilized to this effect. The developed algorithms can infer the most likely scenario(s) that explain the observed data. Decomposition of the number and types of known mutational patterns/signatures that have, most likely, generated the observed mutational profile has been achieved using, but not limited to, the Lawson-Hanson non-negative least squares algorithm.

Figure 7:
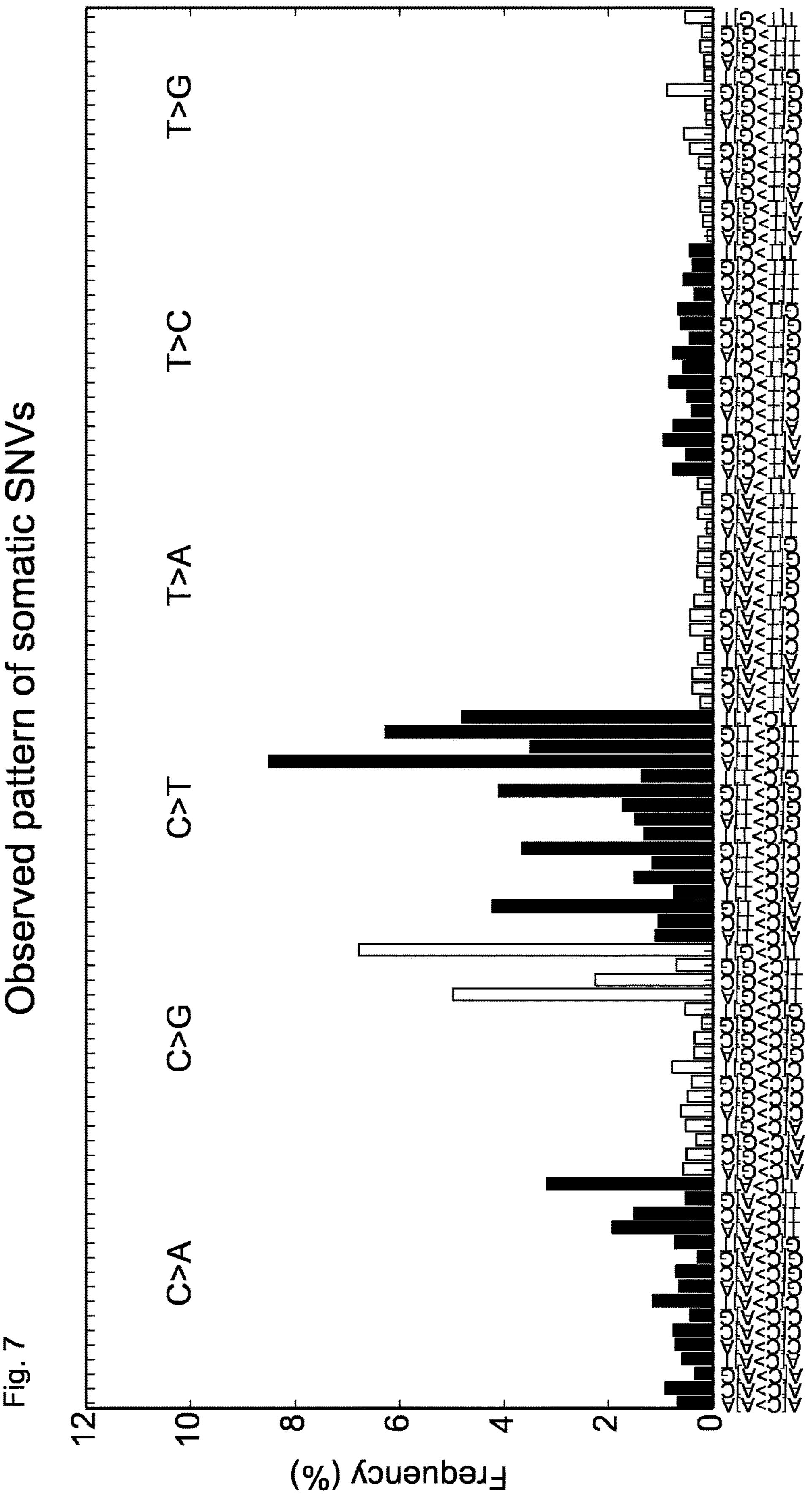
FIG. 7 is a bar graph showing the observed pattern of somatic SNVs in breast cancer, as found in the COSMIC database. The x-axis shows a single base mutation observed in cancer in the context of its neighboring sequences. For example A [C>A]T describes the mutation of Cytosine (C) to Adenine (A) where the upstream sequence is Adenine and the downstream sequence is Thymine. The y-axis shows the frequency of occurrence of this mutation in breast cancer.

FIG. 7 shows the observed pattern of somatic SNVs for breast cancer using data downloaded from the COSMIC database. The x-axis shows a single base mutation observed in cancer in the context of its neighboring sequences. For example A[C>A] T describes the mutation of Cytosine (C) to Adenine (A) where the upstream sequence is Adenine and the downstream sequence is Thymine. The y-axis shows the frequency of occurrence of this mutation in breast cancer.

Figure 8:
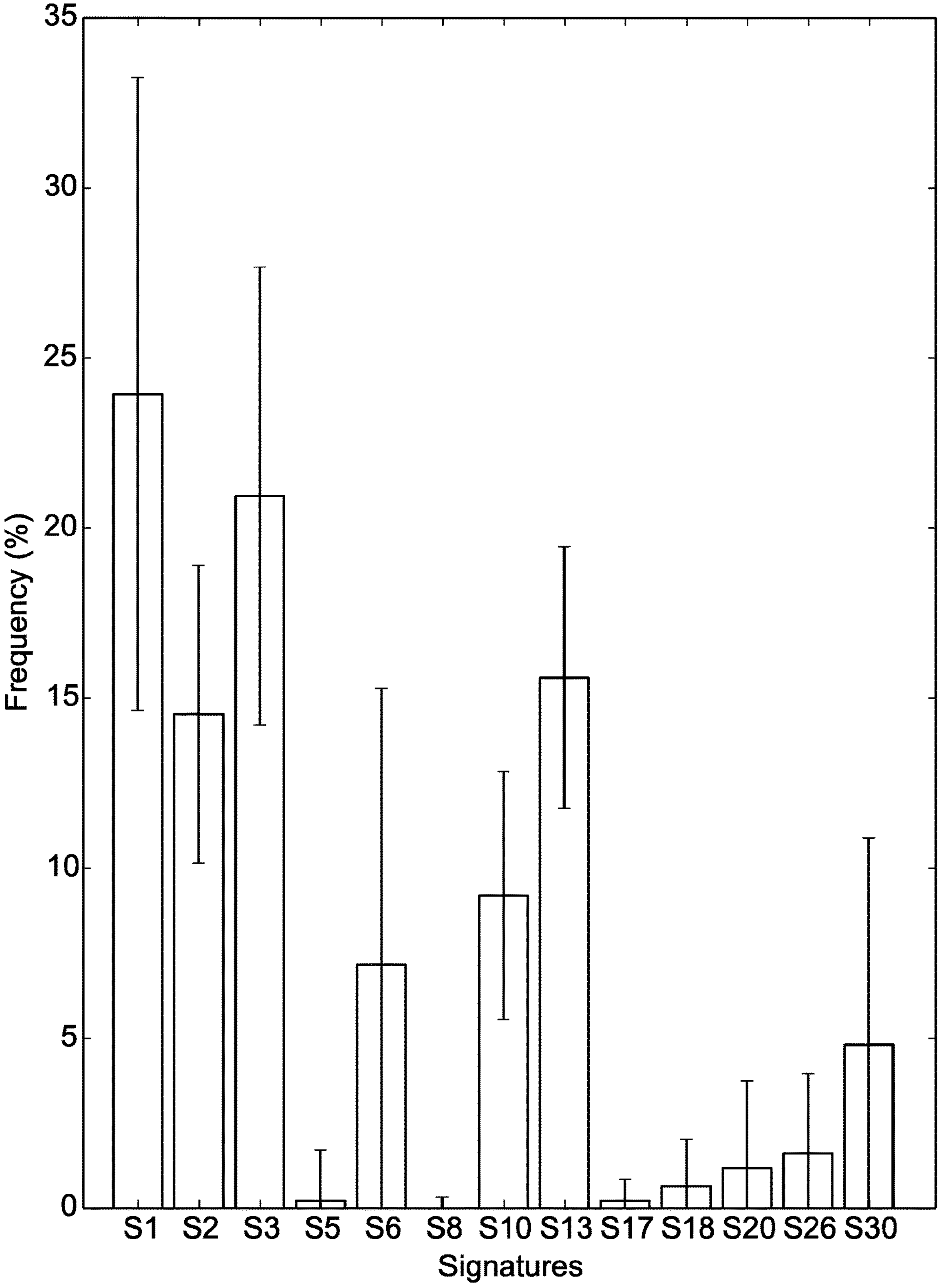
FIG. 8 is a bar graph showing results of a simulations study where simulated sequencing data includes mutational motifs. The data were subjected to mutational motif detection. The bars indicate the average estimated frequency of the known mutational breast cancer motifs computed from a data set of 10000 simulations. Results illustrate that detection of mutational motifs is possible using the developed algorithm.

FIG. 8 illustrates the results of a simulations study where mutational profiles were randomly generated by sampling a subset of SNVs each time, from data available in the COSMIC database, thereby simulating individuals. The simulated data were then subjected to the decomposition algorithms described above in order to detect the likely underlying mutational motifs. The bars indicate the average estimated frequency of the known mutational breast signatures computed from a data set of 10000 simulations. The developed algorithm shows evidence of detection of the mutational profiles, thereby demonstrating that detection of mutational profiles, or motifs, is possible using the developed algorithms.

Example 9: Fragment Size Based Tests

There is evidence from the literature that specific types of cancer can be characterized by and/or associated with fragments in the plasma having a smaller size than the expected size of fragments originating from healthy tissues (Jiang et al, (2015), *Proceedings of the National Academy of Sciences,* 112 (11), ppE1317-E1325). Thus, a fragments-size based test can be utilized to detect the presence of somatic copy number variations in individuals suspected of having cancer. To this effect, a binomial test of proportions, as described Example 4, can be used for the detection of increased presence of nucleic acid material originating from non-healthy tissue (e.g., tumor tissue) based on fragment size. In particular, under the null hypothesis that the distribution of fragment sizes originating from both healthy and non-healthy cells (for example, but not limited to cancerous cells) is the same, a binomial test for proportions (as described in Example 4) using continuity correction can be utilized to quantify any evidence against it.

The same hypothesis holds true for fragments originating from the placenta/fetus. Specifically, placenta derived fragments are generally of smaller size when compared to fragments originating from maternal tissues/cells. Accordingly, assessment of the fragment size-based test was performed using maternal plasma samples (i.e., mixed samples where cell free DNA is of maternal and fetal origin). The size of fragments that have aligned to TACS-enriched regions can be obtained from the aligned data. Subsequently, the proportion of fragments under a specific threshold from a test region is compared respective proportion of fragments from a reference region for evidence against the null hypothesis H0, H0: The proportion of small fragments of the test-region is not different from the proportion of small-fragments of the reference region.

Figure 9:
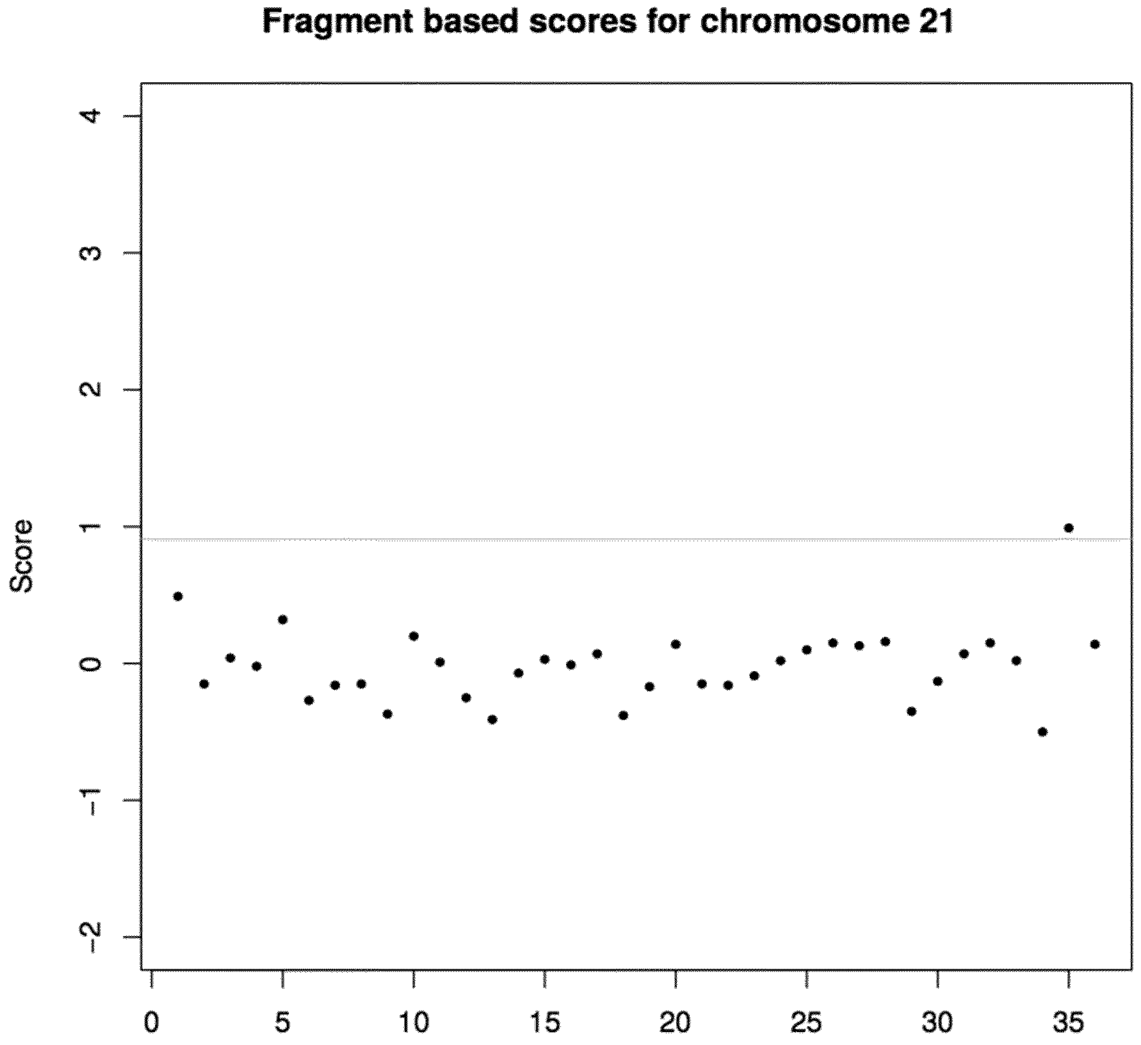
FIG. 9 is a dot plot graph showing results of a fragments-based test for detecting increased numbers of smaller-size fragments in a mixed sample. An abnormal, aneuploid sample, with an estimated fetal fraction of 2.8%, was correctly detected using this method. The black dots are individual samples. The x-axis shows the sample index. The y-axis shows the score result of the fragments-size based method. A score result greater than the threshold shown by the grey line indicates a deviation from the expected size of fragments illustrating the presence of aneuploidy.

FIG. 9 shows results when applying the fragment sizes method to the mixed sample containing maternal and fetal DNA. The black dots are individual samples. The x-axis shows the sample index. The y-axis shows the score result of the fragments-based method. A score result greater than the one indicated by the threshold, illustrated as a grey line, indicates a deviation from the expected size of fragments illustrating the presence of aneuploidy. The results demonstrate that an aneuploid sample, having an estimated fetal fraction equal to 2.8%, was correctly identified, illustrating that fragments-based detection may be used to detect abnormalities in mixed samples with low signal-to-noise ratio (e.g., as is the case in detection of cancer).

Accordingly, this example demonstrates the successful ability of the fragments-based detection method in detecting genetic abnormalities in mixed samples with low signal-to-noise ratios, thereby demonstrating the suitability of the fragments-based test for analysis of either cancer samples for oncology purposes or maternal samples for NIPT.

Since small-sized fragments are associated with fragments from non-healthy tissues (Jiang et al, (2015), *Proceedings of the National Academy of Sciences,* 112 (11), ppE1317-E1325) they can also be leveraged for the detection of small-sized mutations, such as point mutations and mutational signatures. For example, one may only use small-sized fragments in Variant Allele Frequency estimation as described in examples 6-9, thereby increasing the signal-to-noise ratio.

Example 10: Use of the Method for Tissue Biopsies

Five FFPE samples from Breast carcinoma and 13 tissue samples (fresh/frozen and FFPE) from lung adenocarcinoma were subjected to the method and the mutational status was successfully detected. The data are presented below.

Breast Carcinoma:

| Type of specimen | Patient ID | Gene | CDS mutation | AA change | COMSIC ID | MAF % |
|---|---|---|---|---|---|---|
| FFPE | BCa1 | TP53 | c.569delC | p.190fs*57 | COSM100030 | 17.39 |
| | | TP53 | c.559 + 25G > A | intronic | COSM45841 | 22.22 |
| FFPE | BCa2 | PIK3CA | c.1624G > A | P.E542K | COSM760 | 32.15 |
| | | FLT3 | c.2501G > A | P.R834Q | COSM28047 | 2.01 |
| FFPE | BCa3 | ALK | C.3515 + 18C > T | intronic | COSM28496 | 49.43 |
| FFPE | BCa4 | AKT1 | c.49G > A | p.E17K | COSM33765 | 42.86 |
| FFPE | BCa5 | PIK3CA | c.1633G > A | E545K | COSM763 | 62.79 |
| | | PTEN | C.1-9C > G | intronic | COSM5915 | 26.19 |
| | | TP53 | c.415A > T | p.K139* | COSM44678 | 60.63 |

Lung Adenocarcinoma:

| Type of specimen | Sample ID | COSMIC ID | NIPD method | Independent method |
|---|---|---|---|---|
| Fresh/frozen | LCA1 | COSM459 | 0.0245 | 0.0261 |
| | | COSM527 | 0.036 | 0.0378 |
| Fresh/frozen | LCA2 | COSM763 | 0.1427 | 0.1558 |
| Fresh/frozen | LCA3 | COSM522 | 0.3815 | 0.3492 |
| Fresh/frozen | LCA4 | COSM521 | 0.106 | 0.0923 |
| Fresh/frozen | LCA6 | COSM3675521 | 0.1387 | 0.1026 |
| Fresh/frozen | LCA13 | MET c.3028 + 1G > T | 0.0126 | Not covered |
| Fresh/frozen | LCA15 | COSM27887 | 0.1352 | Not covered |
| | | COSM521 | 0.2871 | 0.3185 |
| Fresh/frozen | LCA21 | COSM763 | 0.2798 | 0.3128 |
| FFPE | LCA36 | COSM6224 | 0.2431 | 0.1847 |
| FFPE | LCA40 | COSM6225 | 0.08 | 0.1148 |
| FFPE | LCA45 | COSM6223 | 0.2098 | 0.2456 |
| FFPE | LCA47 | COSM12370 | 0.6295 | 0.5719 |
| FFPE | LCA48 | COSM522 | 0.2649 | 0.4032 |

For the lung cancer data, results were compared with data obtained for the same tissue samples with an independent method. For the genomic regions covered by both methods we observed 100% concordance.

The invention claimed is:

1. A method of detecting one or more tumor biomarkers in a DNA sample from a subject having or suspected of having a tumor, the method comprising:

(a) preparing a sequencing library from the DNA sample;

(b) hybridizing the sequencing library to a pool of double-stranded TArget Capture Sequences (TACS) that bind to one or more tumor biomarker sequences of interest, wherein:

(i) each member sequence within the pool of TACS is between 100-500 base pairs in length, each member sequence having a 5' end and a 3' end;

(ii) each member sequence binds to the one or more tumor biomarker sequences of interest at least 50 base pairs away, on both the 5' end and the 3' end, from regions harboring Copy Number Variations (CNVs), Segmental duplications or repetitive DNA elements; and (iii) the GC content of the pool of TACS is between 19% and 80%, as determined by calculating the GC content of each member within the pool of TACS;

(c) isolating members of the sequencing library that bind to the pool of TACS to obtain an enriched library;

(d) amplifying and sequencing the enriched library; and (e) selecting one or more fragments from the enriched library, the one or more fragments being at most 160 bp in length, and comparing the one or more fragments from the enriched library with fragments from a reference region, to assign a score value, wherein the score value above a threshold is indicative of the presence of the one or more tumor biomarker(s) in the DNA sample, wherein the pool of TACS comprises a plurality of TACS families each directed to a different tumor biomarker sequence of interest, wherein each TACS family comprises a plurality of member sequences, wherein each member sequence binds to the same one or more tumor biomarker sequences of interest but has different start and/or stop positions with respect to a reference coordinate system for the one or more tumor biomarker sequences of interest, wherein the start and/or stop positions for each member sequence within a TACS family, with respect to a reference coordinate system for the one or more tumor biomarker sequences of interest, are staggered by 5-10 base pairs.

2. The method of claim 1, wherein the pool of TACS comprises at least 5 different TACS families, or wherein each TACS family comprises at least 3 member sequences.

3. The method of claim 1, wherein members of the sequencing library that bind to the pool of TACS are partially complementary to the TACS.

4. The method of claim 1, wherein the pool of TACS is fixed to a solid support, wherein the TACS are biotinylated and are bound to streptavidin-coated magnetic beads.

5. The method of claim 1, wherein the DNA sample comprises cell free tumor DNA (cftDNA).

6. The method of claim 1, wherein the DNA sample is selected from a group comprising of a plasma sample, a urine sample, a sputum sample, a cerebrospinal fluid sample, an ascites sample and a pleural effusion sample from subject having or suspected of having a tumor.

7. The method of claim 1, wherein the DNA sample is from a tissue sample from a subject having or suspected of having a tumor.

8. The method of claim 1, wherein the statistical analysis comprises a segmentation algorithm.

9. The method of claim 1, wherein the statistical analysis comprises a score-based classification system.

10. The method of claim 1, wherein the pool of TACS binds to a plurality of tumor biomarker sequences of interest selected from a group comprising AKT1, ALK, APC, AR, ARAF, ATM, BAP1, BARD1, BMPR1A, BRAF, BRCA1, BRCA2, BRIP1, CDH1, CDK4, CDKN2A (p14ARF), CDKN2A (p16INK4a), CHEK2, CTNNB1, DDB2, DDR2, DICER1, EGFR, EPCAM, ERBB2, ERBB3, ERBB4, ERCC1, ERCC2, ERCC3, ERCC4, ERCC5, ESR1, FANCA, FANCB, FANCC, FANCD2, FANCE, FANCF, FANCG, FANCI, FANCL, FANCM, FBXW7, FGFR1, FGFR2, FLT3, FOXA1, FOXL2, GATA3, GNA11, GNAQ, GNAS, GREM1, HOXB13, IDH1, IDH2, JAK2, KEAP1, KIT, KRAS, MAP2K1, MAP3K1, MEN1, MET, MLH1, MPL, MRE11A, MSH2, MSH6, MTOR, MUTYH, MYC, MYCN, NBN, NPM1, NRAS, NTRK1, PALB2, PDGFRA, PIK3CA, PIK3CB, PMS2, POLD1, POLE, POLH, PTEN, RAD50, RAD51C, RAD51D, RAF1, RB1, RET, ROS1, RUNX1, SDHA, SDHAF2, SDHB, SDHC, SDHD, SLX4, SMAD4, SMARCA4, SPOP, STAT, STK11, TMPRSS2, TP53, VHL, XPA, XPC, and combinations thereof.

11. The method of claim 1, wherein the pool of TACS binds to a plurality of tumor biomarker sequences of interest selected from a group comprising EGFR_6240, KRAS_521, EGFR_6225, NRAS_578, NRAS_580, PIK3CA_763, EGFR_13553, EGFR_18430, BRAF_476, KIT_1314, NRAS_584, EGFR_12378, and combinations thereof.

12. The method of claim 1, which further comprises making a diagnosis of the subject based on detection of at least one tumor biomarker sequence.

13. The method of claim 1, which further comprises selecting a therapeutic regimen for the subject based on detection of at least one tumor biomarker sequence.

14. The method of claim 1, which further comprises monitoring treatment efficacy of a therapeutic regimen in the subject based on detection of at least one tumor biomarker sequence.

* * * * *